US012637451B2

(12) United States Patent
Bruno et al.

(10) Patent No.: US 12,637,451 B2
(45) **Date of Patent: *May 26, 2026**

(54) AMINO QUINAZOLINE DERIVATIVES AS $P2X_3$ INHIBITORS

(71) Applicant: CHIESI FARMACEUTICI S.p.A., Parma (IT)

(72) Inventors: Paolo Bruno, Parma (IT); Matteo Biagetti, Parma (IT); Claudio Fiorelli, Parma (IT); Daniela Pizzirani, Parma (IT); Daniele Pala, Parma (IT); Paolo Ronchi, Parma (IT); Charles Baker-Glenn, Parma (IT); Hervè Van De Poël, Parma (IT); Kim Louise Hirst, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 862 days.

This patent is subject to a terminal disclaimer.

(21) Appl. No.: 17/615,056

(22) PCT Filed: May 28, 2020

(86) PCT No.: PCT/EP2020/064913

§ 371 (c)(1),
(2) Date: Nov. 29, 2021

(87) PCT Pub. No.: WO2020/239951

PCT Pub. Date: Dec. 3, 2020

(65) Prior Publication Data

US 2023/0092892 A1 Mar. 23, 2023

(30) Foreign Application Priority Data

May 31, 2019 (EP) .................................... 19177604
Oct. 2, 2019 (EP) .................................... 19201168

(51) Int. Cl.

| | |
|---|---|
| ***C07D 417/12*** | (2006.01) |
| ***C07D 239/94*** | (2006.01) |
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 405/14*** | (2006.01) |
| ***C07D 409/12*** | (2006.01) |
| ***C07D 409/14*** | (2006.01) |
| ***C07D 413/12*** | (2006.01) |
| ***C07D 413/14*** | (2006.01) |
| ***C07D 417/14*** | (2006.01) |
| ***C07D 487/04*** | (2006.01) |
| ***C07F 5/02*** | (2006.01) |

(52) U.S. Cl.

CPC ......... *C07D 417/12* (2013.01); *C07D 239/94* (2013.01); *C07D 401/12* (2013.01); *C07D 401/14* (2013.01); *C07D 403/12* (2013.01); *C07D 403/14* (2013.01); *C07D 405/14* (2013.01); *C07D 409/12* (2013.01); *C07D 409/14* (2013.01); *C07D 413/12* (2013.01); *C07D 413/14* (2013.01); *C07D 417/14* (2013.01); *C07D 487/04* (2013.01); *C07F 5/02* (2013.01)

(58) Field of Classification Search

CPC ........................... C07D 239/94; C07D 417/12
USPC ........................................................ 514/210
See application file for complete search history.

(56) References Cited

U.S. PATENT DOCUMENTS

| | | | |
|---|---|---|---|
| 5,707,998 | A | 1/1998 | Takase et al. |
| 2012/0122838 | A1 | 5/2012 | Ren et al. |
| 2016/0115151 | A1 | 4/2016 | Kai |
| 2018/0311240 | A1 | 11/2018 | Broka et al. |

FOREIGN PATENT DOCUMENTS

| | | | | |
|---|---|---|---|---|
| JP | 4342007 | B2 | 10/2009 | |
| WO | WO-03040109 | A2 * | 5/2003 | ........... C07D 409/14 |
| WO | WO-2003040109 | A2 | 5/2003 | |
| WO | WO-2005095359 | A1 | 10/2005 | |
| WO | WO-2006119504 | A2 | 11/2006 | |
| WO | WO-2008000645 | A1 | 1/2008 | |
| WO | WO-2008123963 | A1 | 10/2008 | |
| WO | WO-2008130481 | A1 | 10/2008 | |

(Continued)

OTHER PUBLICATIONS

Stevens et al., A New Synthesis of Aminoquinazolines, Jan. 1969, Angewandte Chemie International Edition, vol. 8, Issue 1, pp. 73-74 (Year: 1969).*

Kabri et al., Efficient Access to 2,6,8-trisubstituted 4-aminoquinazolines through microwave-assisted one-pot chemoselective tris-Suzuki-Miyaura or SNAr/bis-Suzuki-Miyaura reaction in water, Eur. J. Org. Chem., 2015, vol. 17, pp. 3806-3817 (Year: 2015).*

Antonov et al., "Tautomerism: Introduction, History, and Recent Developments in Experimental and Theoretical Methods." Tautomerism: Methods and Theories, Wiley-VCH, 2014, pp. 1-24 (Year: 2014).*

Rosen, Chronic Cough Due to Tuberculosis and Other Infections, Chest, 2006, vol. 129(1), pp. 197S-201S (Year: 2006).*

(Continued)

*Primary Examiner* — Jeffrey H Murray
*Assistant Examiner* — Rilla Marie Samsell
(74) *Attorney, Agent, or Firm* — STERNE, KESSLER, GOLDSTEIN & FOX P.L.L.C.

(57) ABSTRACT

The present invention relates to compounds of formula I inhibiting P2X purinoceptor 3; particularly the invention relates to compounds that are amino quinazoline derivatives, methods of preparing such compounds, pharmaceutical compositions containing them and therapeutic use thereof. The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

11 Claims, No Drawings

(56) References Cited

FOREIGN PATENT DOCUMENTS

| | | | | |
|---|---|---|---|---|
| WO | WO-2009110985 A2 | | 9/2009 | |
| WO | WO-2010033168 A2 | | 3/2010 | |
| WO | WO-2010111060 A1 | | 9/2010 | |
| WO | WO-2014102233 A1 | * | 7/2014 | ............. A61P 43/00 |
| WO | WO-2015027212 A1 | | 2/2015 | |
| WO | WO-2016053794 A1 | | 4/2016 | |
| WO | WO-2016084922 A1 | | 6/2016 | |
| WO | WO-2016088838 A1 | | 6/2016 | |
| WO | WO-2016091776 A1 | | 6/2016 | |
| WO | WO-2017011729 A1 | | 1/2017 | |
| WO | WO-2017058645 A1 | | 4/2017 | |
| WO | WO-2017091661 A1 | | 6/2017 | |
| WO | WO-2018005435 A1 | * | 1/2018 | ................ A61P 1/04 |
| WO | WO-2018035061 A1 | | 2/2018 | |
| WO | WO-2018064135 A1 | | 4/2018 | |
| WO | WO-2018115380 A1 | | 6/2018 | |
| WO | WO-2018134685 A2 | | 7/2018 | |
| WO | WO-2018172250 A1 | | 9/2018 | |
| WO | WO-2018204775 A1 | | 11/2018 | |
| WO | WO-2020239951 A1 | | 12/2020 | |
| WO | WO-2020239952 A1 | | 12/2020 | |
| WO | WO-2020239953 A1 | | 12/2020 | |

OTHER PUBLICATIONS

Saez-Orellana et al., Modulation of the neuronal network activity by P2X receptors and their involvement in neurological disorders, Pharmacological Research, 2015, vol. 101, pp. 109-115 (Year: 2015).*

Kabri et al., Efficient Access to 2,6,8-Trisubstituted 4-Aminoquinazolines through Microwave-Assisted One-Pot Chemoselective Tris-Suzuki-Miyaura or SNAr.Bis-Suzuki-Miyaura Reactions in Water, European Journal of Organic Chemistry, 2015, vol. 2015(17), pp. 3806-3817 (Year: 2015).*

Kabri et al., Efficient Access to 2,6,8-Trisubstituted 4-Aminoquinazolines through Microwave-Assisted One-Pot Chemoselective Tris-Suzuki-Miyaura SNAr Bis-Suzuki-Miyaura Reactions in Water, European Journal of Organic Chemistry, 2015, vol. 2015 (17), pp. 3806-3817. (Year: 2015).*

Kabri, Y., et al., "Efficient Access to 2,6,8-Trisubstituted 4-Aminoquinazolines through Microwave-Assisted One-Pot Chemoselective Tris-Suzuki-Miyaura or SNAr/Bis-Suzuki-Miyaura Reactions in Water," Eur. J. Org. Chem. 2015(17):3806-3817, European Chemical Societies Publishing, United Kingdom (Jun. 2015).

Abdulqawi, R., et al., "P2X3 receptor antagonist (AF-219) in refractory chronic cough: a randomised, double-blind, placebo-controlled phase 2 study," Lancet 385(9974):1198-205, Elsevier Ltd., United Kingdom (2015).

Basoglu, O. K., et al., "Effects of aerosolized adenosine 5'-triphosphate vs adenosine 5'- monophosphate on dyspnea and airway caliber in healthy nonsmokers and patients with asthma," Chest 128(4):1905-1909, Elsevier, Netherlands (2005).

Bo, X., et al., "Localization of ATP-gated P2X2 and P2X3 receptor immunoreactive nerves in rat taste buds," NeuroReport 10(5):1107-11, Lippincott Williams and Wilkins Ltd., United States (1999).

Canda, A. E., et al., "Physiology and pharmacology of the human ureter: basis for current and future treatments," Urol Int 78(4):289-298, S. Karger AG, Switzerland (2007).

Cheung, K.-K., and Burnstock, G., "Localization of P2X3 receptors and coexpression with P2X2 receptors during rat embryonic neurogenesis," J Comp Neurol 443(4):368-386, Wiley-Liss, United States (2002).

Finlay, H. J., et al., "Discovery of 5-Phenyl-N-(pyridin-2-ylmethyl)-2-(pyrimidin-5-yl)quinazolin-4-amine as a Potent I Kur Inhibitor," ACS Med Chem Lett 7(9):831-834, American Chemical Society, United States (2016).

Ford, A. P., "In pursuit of P2X3 antagonists: novel therapeutics for chronic pain and afferent sensitization," Purinergic Signal 8(Suppl 1):3-26, Springer, Netherlands (2012).

Ford, A. P., and Undem, B. J., "The therapeutic promise of ATP antagonism at P2X3 receptors in respiratory and urological disorders," Front Cell Neurosci 7:267, 10 pages, Frontiers Media S.A., Switzerland (2013).

Garcia-Guzman, M., et al., "Molecular characterization and pharmacological properties of the human P2X3 purinoceptor," Brain Res Mol Brain Res 47(1-2):59-66, Elsevier, Netherlands (1997).

Guo, J., et al., "Contributions of purinergic P2X3 receptors within the midbrain periaqueductal gray to diabetes-induced neuropathic pain," J Physiol Sci 65(1):99-104, BioMed Central Ltd., United Kingdom (2015).

Haffner, C. D., et al., "Discovery, Synthesis, and Biological Evaluation of Thiazoloquin(az)olin(on)es as Potent CD38 Inhibitors," J Med Chem 58(8):3548-3571, American Chemical Society, United States (2015).

Huang, H.-C., et al., "A novel one-pot conversion of methyl sulfones to sulfonamides," Tetrahedron Letters 35(39):7201-7204, Elsevier, Netherlands (1994).

Kaczmarek-Hajek, K., et al., "Molecular and functional properties of P2X receptors—recent progress and persisting challenges," Purinergic Signal 8(3):375-417, Springer, Netherlands (2012).

Kamei, J., and Takahashi, Y., "Involvement of ionotropic purinergic receptors in the histamine-induced enhancement of the cough reflex sensitivity in guinea pigs," Eur J Pharmacol 547(1-3):160-164, Elsevier, Netherlands (2006).

Li, C.-L., et al., "Effects of intracavernous injection of P2X3 and NK1 receptor antagonists on erectile dysfunction induced by spinal cord transection in rats," Andrologia 47(1):25-29, Wiley-Blackwell Publishing Ltd., United Kingdom (2015).

Lloyd, R. F., et al., "4-(Substituted)pteridines, analogues of kinetin," Canadian Journal of Chemistry 45(19):2213-2216, 4 pages, NRC Research Press, Canada (1967).

Maynard, J. P., et al., "P2X3 purinergic receptor overexpression is associated with poor recurrence-free survival in hepatocellular carcinoma patients," Oncotarget 6(38):41162-41179, Impact Journals LLC, United States (2015).

North, R. A., "Molecular physiology of P2X receptors," Physiol Rev 82(4):1013-1067, The American Physiological Society, United States (2002).

North, R. A., and Jarvis, M. F., "P2X receptors as drug targets," Mol Pharmacol 83(4):759-69, American Society for Pharmacology and Experimental Therapeutics, United States (2013).

Pan, Y., et al., "Pharmacophore and 3D-QSAR characterization of 6-arylquinazolin-4-amines as Cdc2-like kinase 4 (Clk4) and dual specificity tyrosine-phosphorylation-regulated kinase 1A (Dyrk1A) inhibitors ," J Chem Inf Model 53(4):938-947, American Chemical Society, United States (2013).

Registry Nov. 16, 1984 (Nov. 16, 1984), Database accession No. RN 74173-76-5, RN 26850-60-2, RN 20028-68-6 Retrieved from the Internet: URL:Chemical Abstracts Service, Columbus, Ohio, US XP002796884.

Registry May 26, 1986 (May 26, 1986), Database accession No. RN 102393-82-8 Retrieved from the Internet: URL:Chemical Abstracts Service, Columbus, Ohio, US XP002796887.

Registry Dec. 17, 2007 (Dec. 17, 2007), Database accession No. RN 958360-30-0 Retrieved from the Internet: URL:Chemical Abstracts Service, Columbus, Ohio, US XP002796883.

Registry Jul. 28, 2008 (Jul. 28, 2008), Database accession No. RN 1036738-12-1 Retrieved from the Internet: URL:Chemical Abstracts Service, Columbus, Ohio, US XP002796882.

Registry Apr. 27, 2010 (Apr. 27, 2010), Database accession No. RN 1220518-09-1 Retrieved from the Internet: URL:Chemical Abstracts Service, Columbus, Ohio, US XP002796881.

Registry Aug. 3, 2010 (Aug. 3, 2010), Database accession No. RN 1234616-70-6 Retrieved from the Internet: URL:Chemical Abstracts Service, Columbus, Ohio, US XP002796880.

Registry Jan. 27, 2011 (Jan. 27, 2011), Database accession No. RN 1260665-43-7 Retrieved from the Internet: URL:Chemical Abstracts Service, Columbus, Ohio, US XP002796879.

Registry Nov. 17, 2017 (Nov. 17, 2017), Database accession No. RN 2143878-49-1 Retrieved from the Internet: URL:Chemical Abstracts Service, Columbus, Ohio, US XP002796469.

(56) References Cited

OTHER PUBLICATIONS

Registry Jun. 28, 1991 (Jun. 28, 1991), Database accession No. RN 2379641-82-2 Retrieved from the Internet: URL:Chemical Abstracts Service, Columbus, Ohio, US XP002796886.
Registry Oct. 21, 2014 (Oct. 21, 2014), Database accession No. RN 2387320-34-3 Retrieved from the Internet: URL:Chemical Abstracts Service, Columbus, Ohio, US XP002796885.
Spulák, M., et al., "Novel bronchodilatory quinazolines and quinoxalines: synthesis and biological evaluation," Eur J Med Chem 74:65-72, Elsevier, Netherlands (2014).
Szántó, G., et al., "New P2X3 receptor antagonists. Part 2: Identification and SAR of quinazolinones," Bioorg Med Chem Lett 26(16):3905-3912, Elsevier, Netherlands (2016).
Teixeira, J. M., et al., "P2X3 and P2X2/3 Receptors Play a Crucial Role in Articular Hyperalgesia Development Through Inflammatory Mechanisms in the Knee Joint Experimental Synovitis," Mol Neurobiol 54(8):6174-6186, Springer Science+Business Media, Germany (2017).
Undem, B. J., and Nassenstein, C., "Airway nerves and dyspnea associated with inflammatory airway disease," Respir Physiol Neurobiol 167(1):36-44, Elsevier, Netherlands (2009).
Vandenbeuch, A., et al., "Role of the ectonucleotidase NTPDase2 in taste bud function," Proc Natl Acad Sci USA 110(36):14789-94, National Academy of Sciences, United States (2013).
Zhang, Q., et al., "Design, synthesis and biological evaluation of novel histone deacetylase inhibitors incorporating 4-aminoquinazolinyl systems as capping groups," Bioorg Med Chem Lett 27(21):4885-4888, Elsevier, Netherlands (2017).
International Search Report and Written Opinion for International Application No. PCT/EP2020/064913, European Patent Office, Netherlands, mailed on Jun. 23, 2020 14 pages.
Co-pending Application, U.S. Appl. No. 17/615,012, inventors Bruno, P., et al., international filing date: May 28, 2020 (Not yet Published).
Co-pending Application, U.S. Appl. No. 17/615,017, inventors Bruno, P., et al., international filing date: May 28, 2020 (Not yet Published).
Registry May 7, 2015 (May 7, 2015), Database accession No. RN 1700636-78-7 Retrieved from the Internet: URL:Chemical Abstracts Service, Columbus, Ohio, US XP002796590.
Registry Jul. 24, 2014 (Jul. 24, 2014), Database accession No. RN 1616828-53-5 Retrieved from the Internet: URL:Chemical Abstracts Service, Columbus, Ohio, US XP002796899.
Registry May 11, 2014 (May 11, 2014), Database accession No. RN 1602300-56-0 Retrieved from the Internet: URL:Chemical Abstracts Service, Columbus, Ohio, US XP002796900.
Registry Mar. 12, 2014 (Mar. 12, 2014), Database accession No. RN 1566729-83-6 Retrieved from the Internet: URL:Chemical Abstracts Service, Columbus, Ohio, US XP002796901.
Registry Mar. 11, 2014 (Mar. 11, 2014), Database accession No. RN 1566199-66-3 Retrieved from the Internet: URL:Chemical Abstracts Service, Columbus, Ohio, US XP002796902.
Registry Jan. 24, 1987 (Jan. 24, 1987), Database accession No. RN 106319-77-1, RN 106319-93-1 Retrieved from the Internet: URL:Chemical Abstracts Service, Columbus, Ohio, US XP002796903.
Registry Mar. 22, 1986 (Mar. 22, 1986), Database accession No. RN 100949-33-5, RN 100948-96-7 Retrieved from the Internet: Url:Chemical Abstracts Service, Columbus, Ohio, US XP002796904.
Registry Nov. 16, 1984 (Nov. 16, 1984), Database accession No. RN 19815-13-5 Retrieved from the Internet: URL:Chemical Abstracts Service, Columbus, Ohio, US XP002796905.

* cited by examiner

AMINO QUINAZOLINE DERIVATIVES AS $P2X_3$ INHIBITORS

FIELD OF THE INVENTION

The present invention relates to compounds inhibiting P2X purinoceptor 3 (hereinafter $P2X_3$ inhibitors); particularly the invention relates to compounds that are amino quinazoline derivatives, methods of preparing such compounds, pharmaceutical compositions containing them and therapeutic use thereof.

The compounds of the invention may be useful in the treatment of many disorders associated with $P2X_3$ receptors mechanisms, such as respiratory diseases including cough, asthma, idiopathic pulmonary fibrosis (IPF) and chronic obstructive pulmonary disease (COPD).

BACKGROUND OF THE INVENTION

P2X receptors are cell surface ion channels activated by extracellular Adenosine 5-TriPhosphate (ATP). P2X receptor family are trimeric assemblies composed of seven distinct subunit subtypes (P2X1-7) that assemble as homomeric and heteromeric channels. All subunits share a common topology containing intracellular termini, two transmembrane helices forming the ion channels and a large extracellular domain containing the ATP binding site. Homomeric $P2X_1$, $P2X_2$, $P2X_3$, $P2X_4$, $P2X_5$, and $P2X_7$ channels and heteromeric $P2X_{2/3}$ and $P2X_{1/5}$ channels have been fully characterized following heterologous expression. P2X receptors are abundantly distributed, and functional responses are seen in neurons, glia, epithelia, endothelia, bone, muscle, and hemopoietic tissues. On smooth muscles, P2X receptors respond to ATP released from sympathetic motor nerves (e.g., in ejaculation). On sensory nerves, they are involved in the initiation of afferent signals in several viscera (e.g., bladder, intestine) and play a key role in sensing tissue-damaging and inflammatory stimuli. Paracrine roles for ATP signaling through P2X receptors are likely in neurohypophysis, ducted glands, airway epithelia, kidney, bone and hemopoietic tissues. (R A. North: Molecular Physiology of P2X Receptors; Physiol Rev, Vol 82, October 2002). All P2X receptors are non-selective cation channels permeable to Na+ and Ca+ ions and are activated by ATP; however, the pharmacology of the receptor subtypes varies with respect to sensitivity to ATP and to small molecules antagonists. (K Kaczmarek-Hajek et al: Molecular and functional properties of P2X receptors—recent progress and persisting challenges; Purinergic Signalling 8:375-417, 2012)

In humans, the $P2X_3$ receptor has been reported in heart and spinal cord at the mRNA level and in DRG, intestine (myenteric plexus neurons), urinary bladder (urothelium and suburothelium), and dental pulp at the protein level (Garcia-Guzman M et al: Molecular characterization and pharmacological properties of the human $P2X_3$ purinoceptor: Brain Res Mol Brain Res. 1997; 47(1-2):59-66).

The neurophysiological role of $P2X_3$ receptors in sensory nerve function in the airways is similar to that mediating somatic nociception (Undem B J and Nassenstein C: Airway nerves and dyspnea associated with inflammatory airway disease, Respir Physiol Nerobiol 167: 36-44, 2009). This similarity has driven hypotheses concerning the involvement of $P2X_3$ receptors in the symptoms of airway dysfunction including cough and bronchial hyper-reactivity (Ford A P: In pursuit of $P2X_3$ antagonists: novel therapeutics for chronic pain and afferent sensitization, Purinergic signal 8 (suppl 1):3-26, 2012; North R A, Jarvis M F P2X Receptors as Drug Targets; Mol Pharmacol, 83:759-769, 2013). $P2X_3$ subunits are also co-localized in many neurons, particularly within DRG, nodose ganglia, nucleus tractus solitarius, and taste buds (Cheung K K, Burnstock G: Localization of $P2X_3$ receptors and coexpression with P2X2 receptors during rat embryonic neurogenesis. J Comp Neurol 443(4):368-382 2002)

$P2X_3$ antagonists have been proposed for the treatment of diabetic neuropathic pain (Guo J et al: Contributions of purinergic $P2X_3$ receptors within the midbrain periaqueductal gray to diabetes-induced neuropathic pain, J Physiol Sci January; 65(1):99-104 2015).

$P2X_3$ and $P2X_{2/3}$ channels play an important role in the development of articular hyperalgesia of arthritic joints (Teixeira J M et al: $P2X_3$ and $P2X_{2/3}$ Receptors Play a Crucial Role in Articular Hyperalgesia Development Through Inflammatory Mechanisms in the Knee Joint Experimental Synovitis, Mol Neurobiol October; 54(8): 6174-6186, 2017).

$P2X_3$ are also a potential target for therapeutic treatment of bladder pain. They were also proposed to be analgesic targets to treat ureteral colicky pain and to facilitate ureteral stone passage (Canda A E et al: Physiology and pharmacology of the human ureter: basis for current and future treatments, Urol Int. 78(4):289-98, 2007).

$P2X_3$ over-expression is involved in poor recurrence-free survival in hepatocellular carcinoma patients and identifies the $P2X_3$ as a potential therapeutic target (Maynard J P et al: $P2X_3$ purinergic receptor overexpression is associated with poor recurrence-free survival in hepatocellular carcinoma patients Oncotarget December 1; 6(38):41162-79, 2015).

It has been suggested that $P2X_3$ antagonists may improve recovery of erectile function (Li C L et al: Effects of intracavernous injection of $P2X_3$ and NK1 receptor antagonists on erectile dysfunction induced by spinal cord transection in rats, Andrologia. February; 47(1):25-9, 2015).

ATP enhances citric acid-evoked and histamine-evoked cough in preclinical models, effects that can be attenuated by $P2X_3$ selective antagonists (Kamei J and Takahashi Y: Involvement of ionotropic purinergic receptors in the histamine-induced enhancement of the cough reflex sensitivity in guinea pigs, October 10; 547(1-3):160-4, 2006). In humans, local delivery of ATP initiates cough and bronchospasm (Basoglu O K et al: Effects of aerosolized adenosine 5'-triphosphate vs adenosine 5'-monophosphate on dyspnea and airway caliber in healthy nonsmokers and patients with asthma, Chest. October; 128(4): 1905-9, 2005).

The therapeutic promise of $P2X_3$ antagonists for the treatment of chronic cough was first recognized by Ford and Undem (Ford A P, Undem B J: The therapeutic promise of ATP antagonism at $P2X_3$ receptors in respiratory and urological disorders, Front Cell Neurosci, December 19; 7:267, 2013). $P2X_3$ are expressed by airway afferent nerves and mediate hypersensitivity of the cough reflex, which is dramatically reduced by the oral $P2X_3$ antagonist, AF-219 (Abdulqawi et al: $P2X_3$ receptor antagonist (AF-219) in refractory chronic cough: a randomised, double-blind, placebo-controlled phase 2 study, Lancet 385, 1198-205, 2015).

ATP is a key neurotransmitter in the taste system, acting largely via $P2X_{2/3}$ heteromultimer receptors. Consequently, disruption of taste function may be an unintentional consequence of therapeutic trials of pain, chronic cough and other conditions using purinergic $P2X_3$ antagonists (Vandenbeuch A et al: Role of the ectonucleotidase NTPDase2 in taste bud function, Proc Natl Acad Sci USA, September 3; 110(36): 14789-94, 2013. Bo X et al: Localization of ATP-gated P2X2 and $P2X_3$ receptor immunoreactive nerves in rat taste buds, Neuroreport, 10(5):1107-11, 1999).

Various compounds have been described in the literature as $P2X_3$ and/or $P2X_{2/3}$ Inhibitors.

WO2017058645 (Afferent Pharmaceuticals INC) discloses the use of diaminopyrimidine $P2X_3$/$P2X_{2/3}$ antagonists for the treatment of disorders including cough, chronic cough and urge to cough, including cough associated with a respiratory disease or disorder, administering an efficacious amount of the compound disclosed. However, amino quinazoline derivatives are not disclosed.

WO2017011729 (Patara Pharma LLC), discloses the use of cromolyn or a pharmaceutically acceptable salt thereof and $P2X_3$ and/or a $P2X_{2/3}$ receptor antagonist as antitussive agent, for the treatment of lung diseases and conditions.

WO2016091776, (Evotec AG), discloses 1,3-thiazol-2-yl substituted benzamide compounds that inhibit $P2X_3$ receptor and to pharmaceutical compositions containing such compounds, and the use of compounds for the treatment of several disorders, including the respiratory diseases.

WO2016088838 (Shionogi), discloses purine derivatives compounds having a novel $P2X_3$ and/or $P2X_{2/3}$ receptor antagonizing effect.

WO2016084922, (Shionogi), discloses triazine derivatives compounds having a novel $P2X_3$ and/or $P2X_{2/3}$ receptor antagonizing effect WO2008123963 (Renovis) relates to fused heterocyclic compounds of the class tetrahydropyrido[4,3-d]pyrimidines and pharmaceutical compositions comprising such compounds. Also provided are methods for preventing and/or treating several disorders, such as neurodegenerative disorders, pain, asthma, autoimmune disorders administering the disclosed compounds.

WO2008130481 (Renovis) discloses 2-cyanophenyl fused heterocyclic compounds of the class tetrahydropyrido [4,3-d]pyrimidines and pharmaceutical compositions comprising such compounds.

WO2010033168 (Renovis) discloses a series of benzamides substituted with phenyl or pyridyl which are stated to be useful for treatment of diseases associated with P2X purinergic receptors, and more particularly to $P2X_3$ receptor and/or $P2X_{2/3}$ receptor antagonists. However, amino quinazoline derivatives are not disclosed.

WO2009110985 (Renovis) relates to phenyl- and pyridyl-substituted benzamide compounds and pharmaceutical compositions comprising such compounds, but not thiazole-substituted benzamides, rendering said compounds different from the compounds of the present invention.

WO2008000645 (Roche) discloses tetrazole substituted arylamides compounds antagonists of $P2X_3$ and/or $P2X_{2/3}$ receptors, useful for the treatment of genitourinary, pain, gastrointestinal and respiratory diseases, conditions and disorders.

Despite the above cited prior art, there is still the need of novel amino quinazoline compounds for treatment of diseases associated with $P2X_3$ receptors in many therapeutic areas such as in particular the respiratory diseases, preferably having a selective action on the $P2X_3$ receptor.

Of note, the state of the art does not describe or suggest amino quinazoline derivatives compounds of general formula (I) of the present invention which represent a solution to the aforementioned need.

SUMMARY OF THE INVENTION

The present invention refers to compounds of formula (I)

(I)

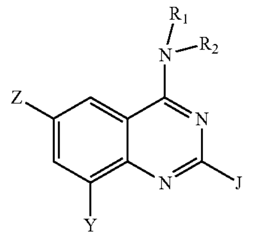

wherein

Z is selected from the group consisting of $(C_3-C_8)$heterocycloalkyl, $(R^AR^B)N$—, heteroaryl, aryl, wherein any of such alkyl, heteroaryl, heterocycloalkyl and aryl may be optionally substituted by one or more groups selected from $(C_1-C_3)$alkyl-, halo, CN, $(R^AR^B)NC(O)$—, $(C_1-C_6)$haloalkyl-, $R^AO$—, $(R^AR^B)N(C_1-C_6)$alkylene-, $(C_3-C_7)$cycloalkyl-, $R^CSO_2$—, $(R^AR^B)N$—;

$R_1$ is H or $(C_1-C_4)$alkyl;

$R_2$ is selected from the group consisting of $(C_1-C_6)$alkyl-, heteroaryl$(C_1-C_4)$alkyl-, $(C_3-C_8)$heterocycloalkyl-$(C_1-C_6)$alkyl-, heteroaryl-$(C_1-C_6)$hydroxyalkyl-, $(C_3-C_8)$heterocycloalkyl, $(C_3-C_8)$cycloalkyl-$(C_1-C_6)$alkyl-, aryl-$(C_1-C_4)$alkyl-, $(R^AR^B)N(C_1-C_6)$alkylene-, $(R^AR^B)N(O)C(C_1-C_4)$alkylene-, $R^AO(C_1-C_4)$alkylene-wherein any of such alkyl, alkylene, aryl, heteroaryl and heterocycloalkyl may be optionally substituted by one or more groups selected from $(C_1-C_3)$alkyl, $R^AO(C_1-C_4)$alkylene-, $(C_1-C_6)$haloalkyl, halo, oxo, $R^AO$—, $(C_3-C_8)$heterocycloalkyl-$(C_1-C_6)$alkyl-, heteroaryl, $(R^AR^B)N$—, —NHC(O)$R^C$, —C(O)N$(R^AR^B)$, —$SO_2N(R^AR^B)$, —O$(C_1-C_4)$alkylene-N$(R^AR^B)$, aryl optionally substituted by halo, —$OR^C$, aryl-$(C_1-C_4)$alkyl-, —C(O)$R^A$;

$R^A$ and $R^B$ are at each occurrence independently H or selected from the group consisting of $(C_1-C_4)$alkyl-, $(C_3-C_8)$cycloalkyl, $(C_1-C_6)$ haloalkyl, or $R^A$ and $R^B$ may form together with the nitrogen atom to which they are attached a 5 or 6 membered saturated heterocyclic monocyclic ring system optionally containing a further heteroatom which is nitrogen or oxygen, which may be optionally substituted by one or more groups selected $(C_1-C_4)$alkyl and oxo;

$R^C$ is at each occurrence H or selected from the group consisting of $(C_1-C_6)$alkyl, $(R^AR^B)N$—, aryl-$(C_1-C_4)$alkyl-;

Y is selected from the group consisting of H, —$OR^D$, $R^CSO_2$, halo, —$NHSO_2R^C$, heteroaryl, $(C_3-C_8)$heterocycloalkyl, wherein any of such heteroaryl and heterocycloalkyl may be optionally substituted by one or more groups selected from $(C_1-C_3)$alkyl and —C(O)N$(R^AR^B)$;

$R^D$ is selected from the group consisting of H, $(C_1-C_6)$alkyl, $(C_3-C_8)$heterocycloalkyl-$(C_1-C_6)$alkyl-, $R^COC(O)(C_1-C_4)$alkylene-, $(R^AR^B)N(C_1-C_6)$alkylene-, $(C_3-C_8)$heterocycloalkyl, $(C_3-C_8)$cycloalkyl-$(C_1-C_6)$alkyl-, $R^CO(C_1-C_4)$alkylene-, $(R^AR^B)N(O)C(C_1-C_4)$alkylene-, wherein any of such heterocycloalkyl may be optionally substituted by one or more groups selected from $(C_1-C_3)$alkyl;

J is H or selected from the group consisting of ($C_1$-$C_6$) alkyl, ($R^AR^B$)N—, ($C_1$-$C_6$) haloalkyl, —$OR^C$ and halo.

In a second aspect, the invention refers to a pharmaceutical composition comprising a compound of formula (I) or pharmaceutically acceptable salt thereof, either alone or in combination with another one or more active ingredient, in admixture with one or more pharmaceutically acceptable carrier or excipient.

In a third aspect, the invention provides a compound of formula (I) for the use as a medicament.

In a further aspect, the invention provides the use of a compound of formula (I) for use in treatment of any disease wherein the $P2X_3$ receptors are involved.

In a further aspect, the invention refers to a compound of formula (I) for use in the prevention and/or treatment of respiratory diseases including cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

In a further aspect, the invention refers to a compound of formula Ib (Ib)

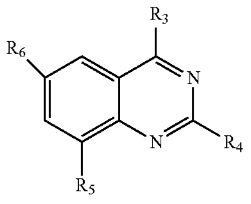

wherein $R_3$ is OH or halo, $R_4$ is H or OH, $R_5$ is halo or —OMe, $R_6$ is halo or Z, Z is as defined above.

In a further aspect, the invention refers to the use of compound of formula (Ib) as intermediate in the preparation of compounds of formula (I).

DETAILED DESCRIPTION OF THE INVENTION

The invention relates to a compound of formula (I)

(I)

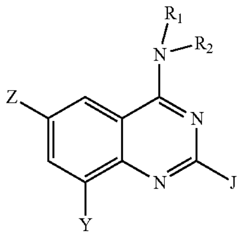

wherein

Z is selected from the group consisting of ($C_3$-$C_8$)heterocycloalkyl, ($R^AR^B$)N—, heteroaryl, aryl, wherein any of such alkyl, heteroaryl, heterocycloalky and aryl may be optionally substituted by one or more groups selected from ($C_1$-$C_3$)alkyl-, halo, CN, ($R^AR^B$)NC(O)—, ($C_1$-$C_6$)haloalkyl-, $R^A$O—, ($R^AR^B$)N($C_1$-$C_6$)alkylene-, ($C_3$-$C_7$)cycloalkyl-, $R^C$$SO_2$—, ($R^AR^B$)N—;

$R_1$ is H or ($C_1$-$C_4$)alkyl;

$R_2$ is selected from the group consisting of ($C_1$-$C_6$)alkyl-, heteroaryl($C_1$-$C_4$)alkyl-, ($C_3$-$C_8$)heterocycloalkyl-($C_1$-$C_6$)alkyl-, heteroaryl-($C_1$-$C_6$)hydroxyalkyl-, ($C_3$-$C_8$) heterocycloalkyl, ($C_3$-$C_8$)cycloalkyl-($C_1$-$C_6$)alkyl-, aryl-($C_1$-$C_4$)alkyl-, ($R^AR^B$)N($C_1$-$C_6$)alkylene-, ($R^AR^B$)N(O)C($C_1$-$C_4$)alkylene-, RAO($C_1$-$C_4$)alkylene- wherein any of such alkyl, alkylene, aryl, heteroaryl and heterocycloalkyl may be optionally substituted by one or more groups selected from ($C_1$-$C_3$)alkyl, $R^A$O($C_1$-$C_4$)alkylene-, ($C_1$-$C_6$)haloalkyl, halo, oxo, $R^A$O—, ($C_3$-$C_8$)heterocycloalkyl-($C_1$-$C_6$)alkyl-, heteroaryl, ($R^AR^B$)N—, —NHC(O)$R^C$, —C(O)N($R^AR^B$), —$SO_2$N($R^AR^B$), —O($C_1$-$C_4$)alkylene-N($R^AR^B$), aryl optionally substituted by halo, —$OR^C$, aryl-($C_1$-$C_4$)alkyl-, —C(O)$R^A$;

$R^A$ and $R^B$ are at each occurrence independently H or selected from the group consisting of ($C_1$-$C_4$)alkyl-, ($C_3$-$C_8$)cycloalkyl, ($C_1$-$C_6$) haloalkyl, or $R^A$ and $R^B$ may form together with the nitrogen atom to which they are attached a 5 or 6 membered saturated heterocyclic monocyclic ring system optionally containing a further heteroatom which is nitrogen or oxygen, which may be optionally substituted by one or more groups selected ($C_1$-$C_4$)alkyl and oxo;

$R^C$ is at each occurrence H or selected from the group consisting of ($C_1$-$C_6$)alkyl, ($R^AR^B$)N—, aryl-($C_1$-$C_4$) alkyl-; Y is selected from the group consisting of H, —$OR^D$, $R^C$$SO_2$, halo, —$NHSO_2R^C$, heteroaryl, ($C_3$-$C_8$)heterocycloalkyl, wherein any of such heteroaryl and heterocycloalkyl may be optionally substituted by one or more groups selected from ($C_1$-$C_3$)alkyl and —C(O)N($R^AR^B$);

$R^D$ is selected from the group consisting of H, ($C_1$-$C_6$) alkyl, ($C_3$-$C_8$)heterocycloalkyl-($C_1$-$C_6$)alkyl-, $R^C$OC(O)($C_1$-$C_4$)alkylene-, ($R^AR^B$)N($C_1$-$C_6$)alkylene-, ($C_3$-$C_8$)heterocycloalkyl, ($C_3$-$C_8$)cycloalkyl-($C_1$-$C_6$)alkyl-, $R^C$O($C_1$-$C_4$)alkylene-, ($R^AR^B$)N(O)C($C_1$-$C_4$)alkylene-, wherein any of such heterocycloalkyl may be optionally substituted by one or more groups selected from ($C_1$-$C_3$)alkyl;

J is H or selected from the group consisting of ($C_1$-$C_6$) alkyl, ($R^AR^B$)N—, ($C_1$-$C_6$) haloalkyl, —$OR^C$ and halo.

Definitions

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen" or "halogen atoms" as used herein includes fluorine, chlorine, bromine, and iodine atom, preferably chlorine or fluorine.

The term "($C_x$-$C_y$) alkyl" wherein x and y are integers, refers to a straight or branched chain alkyl radical having from x to y carbon atoms. Thus, when x is 1 and y is 6, for example, the term includes methyl, ethyl, n-propyl, isopropyl, n-butyl, isobutyl, sec-butyl, t-butyl, n-pentyl and n-hexyl.

As used herein, the term "($C_x$-$C_y$)alkylene" wherein x and y are integers, refers to a $C_x$-$C_y$alkyl radical having in total two unsatisfied valencies, such as a divalent methylene radical.

The expressions "($C_x$-$C_y$) haloalkyl" wherein x and y are integers, refer to the above defined "$C_x$-$C_y$alkyl" groups wherein one or more hydrogen atoms are replaced by one or more halogen atoms, which can be the same or different.

Examples of said "($C_x$-$C_y$) haloalkyl" groups may thus include halogenated, poly-halogenated and fully halogenated alkyl groups wherein all of the hydrogen atoms are replaced by halogen atoms, e.g. trifluoromethyl or difluoro methyl, trifluoroethyl groups.

By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively. Examples include respectively hydroxymethyl, aminomethyl, dimethylaminopropyl and the like.

In the present description, unless otherwise provided, the aminoalkyl encompasses alkyl groups (i.e. "($C_1$-$C_6$) alkyl" groups) substituted by one or more amino group (—$NR^AR^B$). Thus, an example of aminoalkyl is a mono-aminoalkyl group such as $R^AR^BN$—($C_1$-$C_6$) alkyl.

With reference to the substituent $R^A$ and $R^B$ as defined above and below, when $R^A$ and $R^B$ are taken together with the nitrogen atom they are linked to form 5 to 6 membered heterocyclic radical, at least one further ring carbon atom in the said heterocyclic radical is optionally replaced by at least one heteroatom (e.g. N, S or O) and/or may bear -oxo (═O) substituent groups. It is understood that the said heterocyclic radical might be further optionally substituted on any available position in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Examples of said heterocycle radicals are 1-pyrrolidinyl, 1-piperidinyl, 1-piperazinyl, 4-methylpiperazinyl, piperazin-4yl-2-one, 4-morpholinyl, morpholinyl-3-one, 1-(piperazin-1-yl)ethenone.

The term "($C_x$-$C_y$) cycloalkyl" wherein x and y are integers, refers to saturated cyclic hydrocarbon groups containing the indicated number of ring carbon atoms. Examples include cyclopropyl, cyclobutyl, cyclopentyl, cyclohexyl, cycloheptyl.

The term "aryl" refers to mono cyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic radical containing one or more heteroatoms selected from S, N and O, and includes radicals having two such monocyclic rings, or one such monocyclic ring and one monocyclic aryl ring, which are fused through a common bond. Examples of suitable 5,6-membered heteroaryl are: are thienyl, furyl, pyrrolyl, imidazolyl, thiazolyl, isothiazolyl, pyrazolyl, oxazolyl, isoxazolyl, isothiazolyl, triazolyl, thiadiazolyl, oxadiazolyl, pyridinyl, pyridazinyl, pyrimidinyl, pyrazinyl, tetrazolyl and triazinyl.

The term "heterocyclyl" or "heterocyclic" relate to a saturated mono-, bi- or tri-cyclic non-aromatic radical containing one or more heteroatoms selected from S, N and O. In the case of bicyclic heterocyclic systems, included within the scope of the term are fused, spiro and bridged bicyclic systems.

The term "($C_x$-$C_y$) heterocycloalkyl" wherein x and y are integers, refers to saturated or partially unsaturated monocyclic ($C_x$-$C_y$) cycloalkyl groups in which at least one ring carbon atom is replaced by at least one heteroatom (e.g. N, S or O) or may bear an -oxo (═O) substituent group. Said heterocycloalkyl (i.e. heterocyclic radical or group) may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring. Examples of ($C_x$-$C_y$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydrothiophenyl, azetidinyl, oxetanyl, tetrahydropyranyl, pyranyl, 2H- or 4H-pyranyl, dihydro- or tetrahydrofuranyl, dihydroisoxazolyl, pyrrolidin-2-one-yl, dihydropyrrolyl radicals and the like.

Specific examples of said heterocycle radicals are tetrahydrothiophene 1,1-dioxide, 3,3-difluoropyrrolidinyl, 1-pyrrolidinyl, 1-methyl-2-pyrrolidinyl, 1-piperidinyl, 1-piperazinyl, 4-morpholinyl.

The expressions "Aryloxyl" and "Aryl ($C_1$-$C_6$) alkoxyl" likewise "heteroAryloxyl" and "Heteroaryl ($C_1$-$C_6$) alkoxyl" refer to Aryl or Heteroaryl groups attached through an oxygen bridge and chained Aryl-alkoxyl or HeteroAryl-alkoxyl groups. Examples of such groups are phenyloxy, benzyloxy and pyridinyloxy respectively.

The term "aryl ($C_1$-$C_6$) alkyl" refers to an aryl ring linked to a straight-chained or branched alkyl groups wherein the number of carbon atoms is from 1 to 6, e.g. phenylmethyl (i.e. benzyl), phenylethyl or phenylpropyl.

The term ($C_z$-$C_k$)heterocycloalkyl-($C_x$-$C_y$)alkyl wherein z and k are integers, refers to an heterocyclic ring linked to a straight-chained or branched alkyl groups having from x to y carbon atoms.

Likewise, the term "heteroaryl ($C_x$-$C_y$)alkyl" or "aryl ($C_x$-$C_y$)alkyl" refers to an heteroaryl or aryl ring linked to a straight-chained or branched alkyl groups having from x to y carbon atoms.

The expression "ring system" refers to mono- or bicyclic or polycyclic ring systems which may be saturated, partially unsaturated or unsaturated, such as aryl, ($C_3$-$C_{10}$) cycloalkyl, ($C_3$-$C_6$) heterocycloalkyl or heteroaryl.

The terms "group", "radical" or "fragment" or "substituent" are synonymous and are intended to indicate functional groups or fragments of molecules attachable to a bond or other fragments or molecules. Thus, as an example, a "heterocyclic radical" herein refers to a mono- or bi-cyclic saturated or partially saturated heterocyclic moiety (group, radical), preferably a 4 to 11 membered monocyclic radical, at least one further ring carbon atom in the said heterocyclic radical is optionally replaced by at least one further heteroatom independently selected from N, S or O and/or may bear an -oxo (═O) substituent group, said heterocyclic radical is further optionally including spiro disubstitution as well as substitution on two adjacent or vicinal atoms forming an additional 5 to 6 membered cyclic or heterocyclic, saturated, partially saturated or aromatic ring. Examples of said heterocycle radicals are 1-pyrrolidinyl, 1-piperidinyl, 1-piperazinyl, 4-morpholinyl and the like.

A dash ("—") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

An oxo moiety is represented by (O) as an alternative to the other common representation, e.g. (=O). Thus, in terms of general formula, the carbonyl group is herein represented as —C(O)—, in general, the bracketed group is a lateral group, not included into the chain, and brackets are used, when deemed useful, to help disambiguating linear chemical formulas; e.g. the sulfonyl group $—SO_2—$ might be also represented as $—S(O)_2—$ to disambiguate e.g. with respect to the sulfinic group —S(O)O—.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

It will be apparent that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. All such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

The invention further concerns the corresponding deuterated derivatives of compounds of formula (I).

All preferred groups or embodiments described above and herebelow for compounds of formula I may be combined among each other and apply as well mutatis mutandis.

In a preferred embodiment, the invention is directed to compounds of formula (I) as defined above (I)

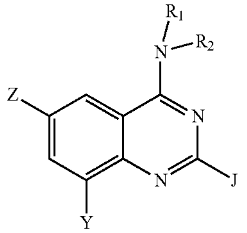

wherein

Z is selected from the group consisting of heteroaryl, aryl, $(R^AR^B)N—$, $(C_3-C_8)$heterocycloalkyl, wherein any of such heteroaryl, aryl and heterocycloalkyl may be optionally substituted by one or more groups selected from $(C_1-C_3)$alkyl, halo, CN, $(R^AR^B)NC(O)—$;

$R_1$ is H or $(C_1-C_4)$alkyl;

$R_2$ is selected from the group consisting of heteroaryl$(C_1-C_4)$alkyl-, $(R^AR^B)N(O)C(C_1-C_4)$alkylene-, wherein any of such heteroaryl may be optionally substituted by one or more groups selected from $(C_1-C_3)$alkyl, halo, $(C_1-C_6)$ haloalkyl;

$R^A$ and $R^B$ are at each occurrence independently H, $(C_1-C_4)$alkyl- and $(C_3-C_8)$cycloalkyl-, or $R^A$ and $R^B$ may form together with the nitrogen atom to which they are attached a 5 or 6 membered saturated heterocyclic monocyclic ring system optionally containing a further heteroatom which is oxygen or nitrogen, which may be optionally substituted by one or more groups selected from oxo, $(C_1-C_4)$alkyl;

Y is H;

J is H or selected from the group consisting of $(C_1-C_4)$ alkyl, $(R^AR^B)N—$, halo, $(C_1-C_6)$haloalkyl.

In another preferred embodiment, the invention refers to compounds of formula (I) wherein is selected from the group consisting of heteroaryl and aryl, wherein any of such heteroaryl and aryl may be optionally substituted by one or more groups selected from $(C_1-C_3)$alkyl and halo;

$R_1$ is H;

$R_2$ is selected from the group consisting of $(C_3-C_8)$ heterocycloalkyl-$(C_1-C_6)$alkyl-, preferably (piperidinyl)methyl; heteroaryl$(C_1-C_4)$alkyl-, preferably (pyridinyl)methyl, (pyridinyl)ethyl, (pyridazinyl) methyl, (pyridazinyl)ethyl (pyrimidinyl)methyl, (pyrimidinyl)ethyl, (oxadiazolyl)ethyl, (thiadiazolyl)ethyl ([1,2,4]triazolo[4,3-a]pyrimidin-3-yl)methyl, and Wherein any of such alkyl, heteroaryl and heterocycloalkyl may be optionally substituted by one or more groups selected from $(C_1-C_3)$alkyl, $(C_1-C_6)$haloalkyl and —OH;

Y is selected from the group consisting of H and $—OR^D$, $R^D$ is at each occurrence selected from the group consisting of $(C_1-C_6)$alkyl, preferably methyl, $(C_3-C_8)$heterocycloalkyl-$(C_1-C_6)$alkyl-, preferably (oxetanyl)methyl, (morpholinyl)methyl, $R^COC(O)(C_1-C_4)$alkylene-, preferably $—CH_2C(O)OH$;

$(C_3-C_8)$heterocycloalkyl, preferably tetrahydropyranyl, pyrrolidinyl, and $R^CO(C_1-C_4)$alkylene-, preferably methoxyethyl;

J is at each occurrence selected from the group consisting of H and $—OR^C$, preferably is H or —OH;

$R^C$ is at each occurrence selected from the group consisting of H and $(C_1-C_6)$alkyl.

According to a preferred embodiment, the invention refers to at least one of the compounds listed in the Table 1 below and pharmaceutical acceptable salts thereof.

TABLE 1

| List of preferred compounds having Formula (I) | | |
|---|---|---|
| Ex. N. | Structure | Chemical Name |
| Example 4 | 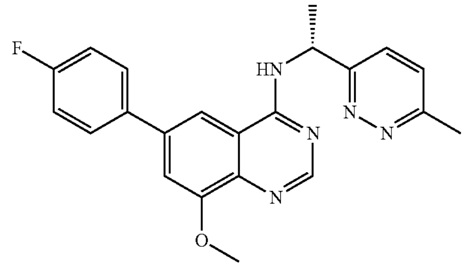 | (R)-6-(4-Fluorophenyl)-8-methoxy-N-(1-(6-methylpyridazin-3-yl)ethyl)quinazolin-4-amine |
| Example 19 | 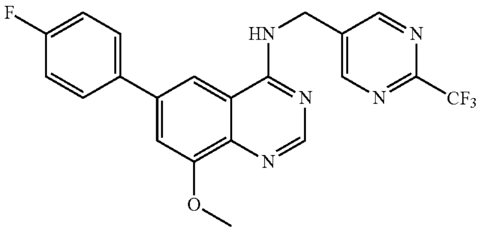 [SMILES: COc1cc(-c2ccc(F)cc2)cc2c(NCc3cnc(C(F)(F)F)nc3)ncnc12] | 6-(4-Fluorophenyl)-8-methoxy-N-((2-(trifluoromethyl)pyrimidin-5-yl)methyl)quinazolin-4-amine |
| Example 28 | 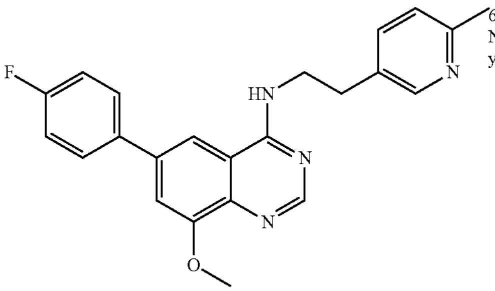 | 6-(4-Fluorophenyl)-8-methoxy-N-(2-(6-methylpyridin-3-yl)ethyl)quinazolin-4-amine |
| Example 48 | 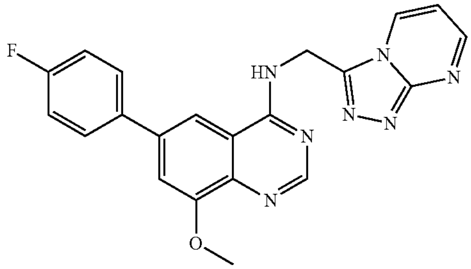 [SMILES: COc1cc(-c2ccc(F)cc2)cc2c(NCc3nnc4ncccn34)ncnc12] | N-([1,2,4]Triazolo[4,3-a]pyrimidin-3-ylmethyl)-6-(4-fluorophenyl)-8-methoxyquinazolin-4-amine |
| Example 65 | 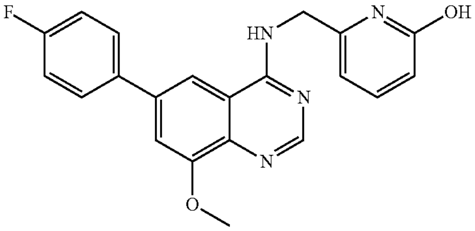 | 6-[[[6-(4-Fluorophenyl)-8-methoxy-quinazolin-4-yl]amino]methyl]-1H-pyridin-2-one |
| Example 110 | 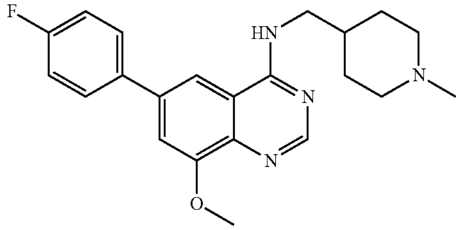 [SMILES: COc1cc(-c2ccc(F)cc2)cc2c(NCC3CCN(C)CC3)ncnc12] | 6-(4-Fluorophenyl)-8-methoxy-N-[(1-methyl-4-piperidyl)methyl]quinazolin-4-amine |

TABLE 1-continued

| List of preferred compounds having Formula (I) | | |
|---|---|---|
| Ex. N. | Structure | Chemical Name |
| Example 112 | 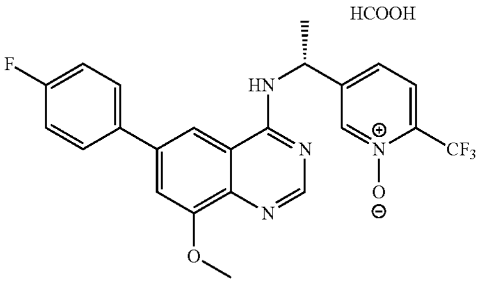 [SMILES: COc1cc(-c2ccc(F)cc2)cc2c(N[C@H](C)c3ccc(C(F)(F)F)[n+]([O-])c3)ncnc12 ; "HCOOH"] | (R)-5-(1-((6-(4-fluorophenyl)-8-methoxyquinazolin-4-yl)amino)ethyl)-2-(trifluoromethyl)pyridine 1-oxide formate |
| Example 116 | 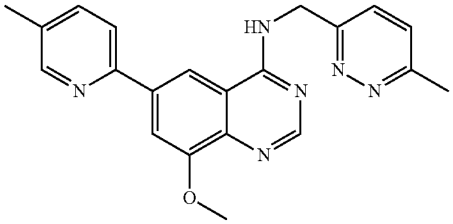 | 8-Methoxy-N-((6-methylpyridazin-3-yl)methyl)-6-(5-methylpyridin-2-yl)quinazolin-4-amine |
| Example 134 | 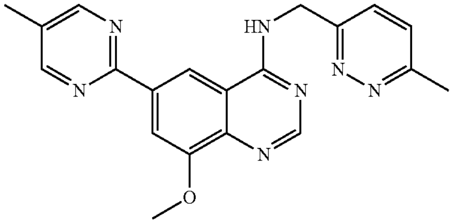 | 8-Methoxy-N-[(6-methylpyridazin-3-yl)methyl]-6-(5-methylpyrimidin-2-yl)quinazolin-4-amine |
| Example 140 | 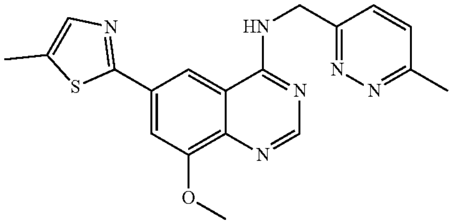 | 8-Methoxy-N-((6-methylpyridazin-3-yl)methyl)-6-(5-methylthiazol-2-yl)quinazolin-4-amine |
| Example 145 | 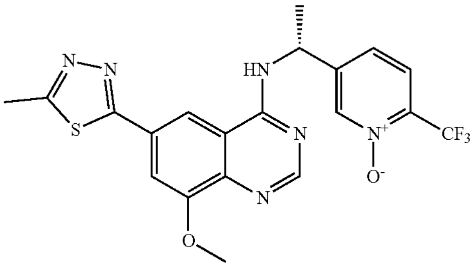 [SMILES: COc1cc(-c2nnc(C)s2)cc2c(N[C@H](C)c3ccc(C(F)(F)F)[n+]([O-])c3)ncnc12] | (R)-5-(1-((8-Methoxy-6-(5-methyl-1,3,4-thiadiazol-2-yl)quinazolin-4-yl)amino)ethyl)-2-(trifluoromethyl)pyridine 1-oxide |
| Example 148 | 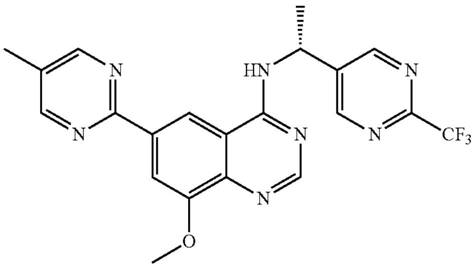 [SMILES: COc1cc(-c2ncc(C)cn2)cc2c(N[C@H](C)c3cnc(C(F)(F)F)nc3)ncnc12] | 8-Methoxy-6-(5-methylpyrimidin-2-yl)-N-[(1R)-1-[2-(trifluoromethyl)pyrimidin-5-y]ethyl]quinazolin-4-amine |

TABLE 1-continued

| List of preferred compounds having Formula (I) | | |
|---|---|---|
| Ex. N. | Structure | Chemical Name |
| Example 149 | 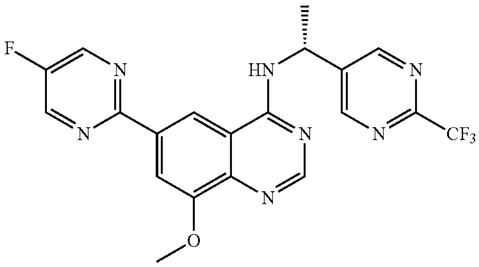 [SMILES: COc1cc(-c2ncc(F)cn2)cc2c(N[C@H](C)c3cnc(C(F)(F)F)nc3)ncnc12] | 6-(5-Fluoropyrimidin-2-yl)-8-methoxy-N-[(1R)-1-[2-(trifluoromethyl)pyrimidin-5-yl]ethyl]quinazolin-4-amine |
| Example 150 | 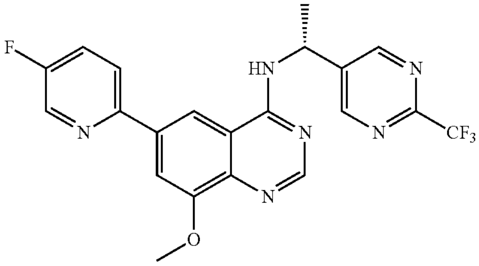 [SMILES: COc1cc(-c2ccc(F)cn2)cc2c(N[C@H](C)c3cnc(C(F)(F)F)nc3)ncnc12] | 6-(5-Fluoro-2-pyridyl)-8-methoxy-N-[(1R)-1-[2-(trifluoromethyl)pyrimidin-5-yl]ethyl]quinazolin-4-amine |
| Example 151 | 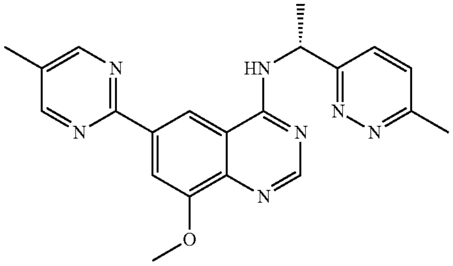 | 8-Methoxy-N-[(1R)-1-(6-methylpyridazin-3-yl)ethyl]-6-(5-methylpyrimidin-2-yl)quinazolin-4-amine |
| Example 152 | 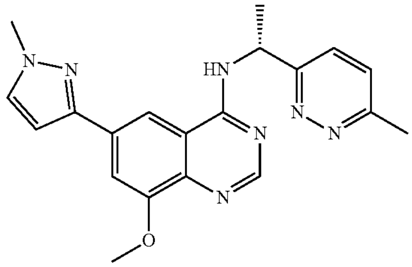 [SMILES: COc1cc(-c2ccn(C)n2)cc2c(N[C@H](C)c3ccc(C)nn3)ncnc12] | 8-Methoxy-6-(1-methylpyrazol-3-yl)-N-[(1R)-1-(6-methylpyridazin-3-yl)ethyl]quinazolin-4-amine |
| Example 155 | 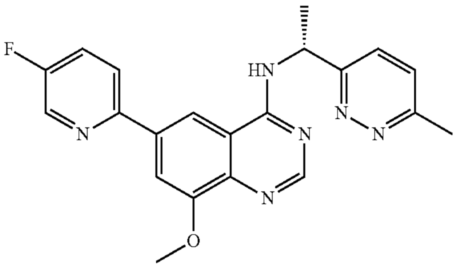 [SMILES: COc1cc(-c2ccc(F)cn2)cc2c(N[C@H](C)c3ccc(C)nn3)ncnc12] | 6-(5-Fluoro-2-pyridyl)-8-methoxy-N-[(1R)-1-(6-methylpyridazin-3-yl)ethyl]quinazolin-4-amine |

TABLE 1-continued

List of preferred compounds having Formula (I)

| Ex. N. | Structure | Chemical Name |
|---|---|---|
| Example 175 | 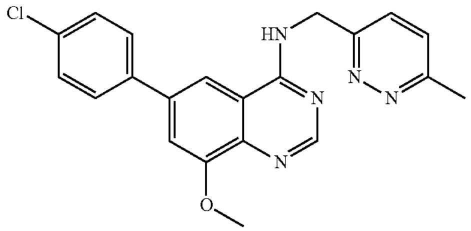 [SMILES: COc1cc(-c2ccc(Cl)cc2)cc2c(NCc3ccc(C)nn3)ncnc12] | 6-(4-chlorophenyl)-8-methoxy-N-((6-methylpyridazin-3-yl)methyl)quinazolin-4-amine |
| Example 181 | 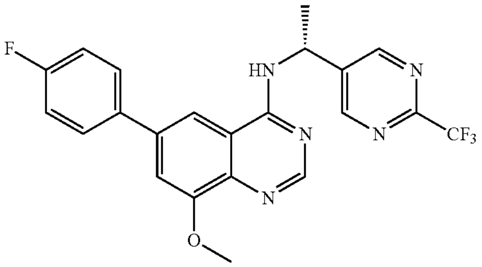 [SMILES: COc1cc(-c2ccc(F)cc2)cc2c(N[C@H](C)c3cnc(C(F)(F)F)nc3)ncnc12] | (R)-6-(4-fluorophenyl)-8-methoxy-N-(1-(2-(trifluoromethyl)pyrimidin-5-yl)ethyl)quinazolin-4-amine |
| Example 182 | 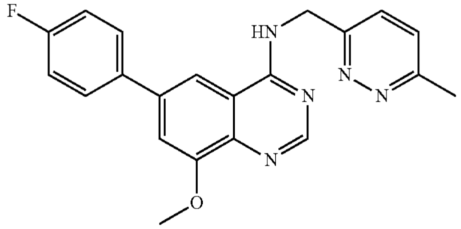 [SMILES: COc1cc(-c2ccc(F)cc2)cc2c(NCc3ccc(C)nn3)ncnc12] | 6-(4-fluorophenyl)-8-methoxy-N-((6-methylpyridazin-3-yl)methyl)quinazolin-4-amine |
| Example 184 | 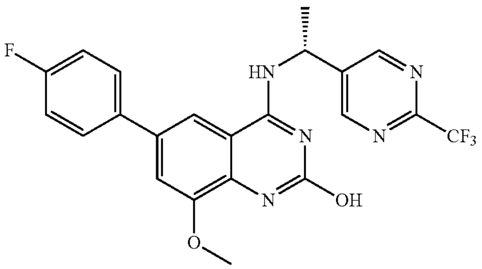 | (R)-6-(4-Fluorophenyl)-8-methoxy-4-((1-(2-(trifluoromethyl)pyrimidin-5-yl)ethyl)-amino)-quinazolin-2-ol |
| Example 206 | 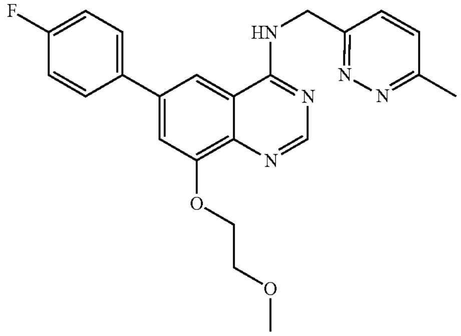 [SMILES: COCCOc1cc(-c2ccc(F)cc2)cc2c(NCc3ccc(C)nn3)ncnc12] | 6-(4-fluorophenyl)-8-(2-methoxyethoxy)-N-[(6-methylpyridazin-3-yl)methyl]quinazolin-4-amine |

TABLE 1-continued

List of preferred compounds having Formula (I)

| Ex. N. | Structure | Chemical Name |
|---|---|---|
| Example 207 | 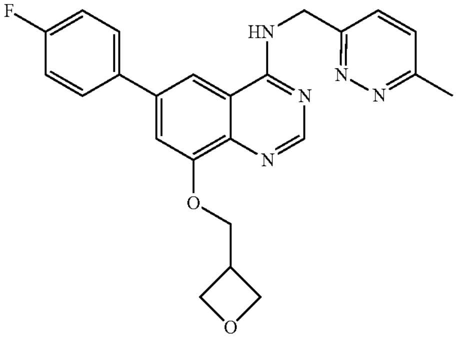 [SMILES: Cc1ccc(CNc2ncnc3c(OCC4COC4)cc(-c4ccc(F)cc4)cc23)nn1] | 6-(4-fluorophenyl)-N-[(6-methylpyridazin-3-yl)methyl]-8-(oxetan-3-ylmethoxy)quinazolin-4-amine |
| Example 208 | 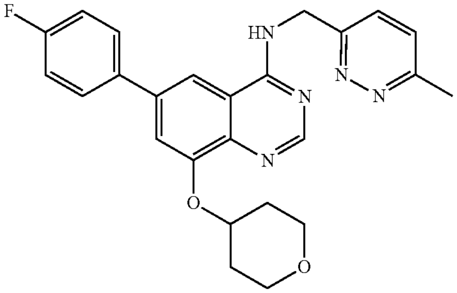 [SMILES: Cc1ccc(CNc2ncnc3c(OC4CCOCC4)cc(-c4ccc(F)cc4)cc23)nn1] | 6-(4-fluorophenyl)-N-[(6-methylpyridazin-3-yl)methyl]-8-tetrahydropyran-4-yloxy-quinazolin-4-amine |
| Example 214 | 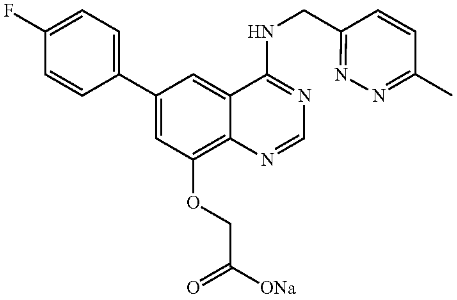 | 2-[6-(4-fluorophenyl)-4-[(6-methylpyridazin-3-yl)methylamino]quinazolin-8-yl]oxyacetic acid, sodium salt |
| Example 216 | 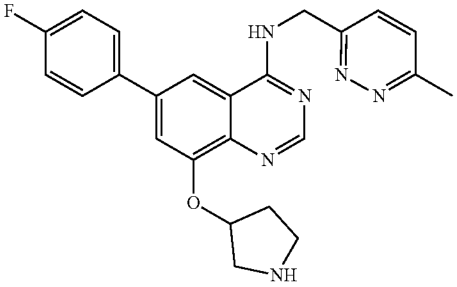 [SMILES: Cc1ccc(CNc2ncnc3c(OC4CCNC4)cc(-c4ccc(F)cc4)cc23)nn1] | 6-(4-fluorophenyl)-N-[(6-methylpyridazin-3-yl)methyl]-8-pyrrolidin-3-yloxy-quinazolin-4-amine |

TABLE 1-continued

| List of preferred compounds having Formula (I) | | |
|---|---|---|
| Ex. N. | Structure | Chemical Name |
| Example 217 | 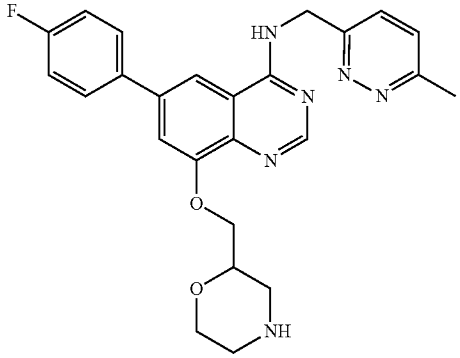 [SMILES: Cc1ccc(CNc2ncnc3c(OCC4CNCCO4)cc(-c4ccc(F)cc4)cc23)nn1] | 6-(4-fluorophenyl)-N-[(6-methylpyridazin-3-yl)methyl]-8-(morpholin-2-ylmethoxy)quinazolin-4-amine |
| Example 228 | 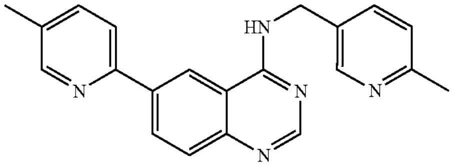 | 6-(5-methylpyridin-2-yl)-N-((6-methylpyridin-3-yl)methyl)quinazolin-4-amine |
| Example 231 | 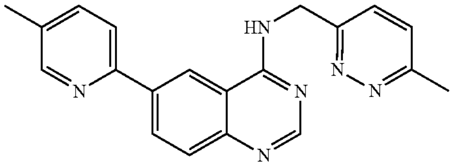 | N-((6-methylpyridazin-3-yl)methyl)-6-(5-methylpyridin-2-yl)quinazolin-4-amine |
| Example 240 | 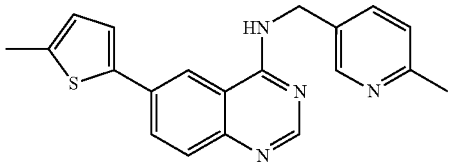 | N-((6-methylpyridin-3-yl)methyl)-6-(5-methylthiophen-2-yl)quinazolin-4-amine |
| Example 241 | 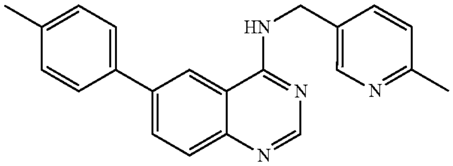 | N-((6-methylpyridin-3-yl)methyl)-6-(p-tolyl)quinazolin-4-amine |
| Example 243 | 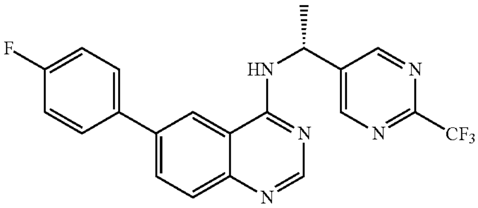 [SMILES: C[C@@H](Nc1ncnc2ccc(-c3ccc(F)cc3)cc12)c1cnc(C(F)(F)F)nc1] | (R)-6-(4-fluorophenyl)-N-(1-(2-(trifluoromethyl)pyrimidin-5-yl)ethyl)quinazolin-4-amine |
| Example 244 | 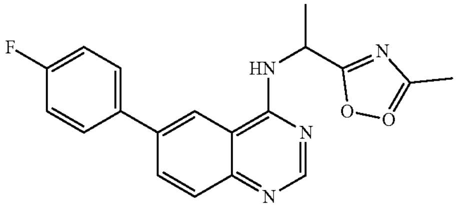 | 6-(4-fluorophenyl)-N-(1-(3-methyl-1,2,4-oxadiazol-5-yl)ethyl)quinazolin-4-amine |

TABLE 1-continued

| List of preferred compounds having Formula (I) | | |
|---|---|---|
| Ex. N. | Structure | Chemical Name |
| Example 247 | 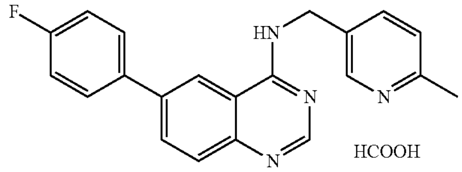 [SMILES: Cc1ccc(CNc2ncnc3ccc(-c4ccc(F)cc4)cc23)cn1 ; "HCOOH"] | 6-(4-fluorophenyl)-N-((6-methylpyridin-3-yl)methyl)quinazolin-4-amine formate |
| Example 257 | 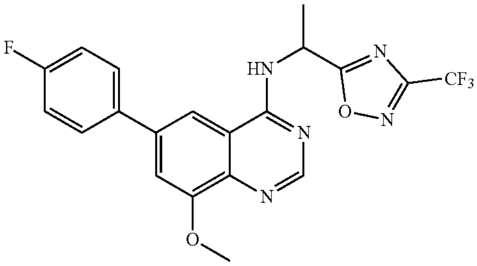 [SMILES: COc1cc(-c2ccc(F)cc2)cc2c(NC(C)c3nc(C(F)(F)F)no3)ncnc12] | Single enantiomer 1 of 6-(4-fluorophenyl)-8-methoxy-N-(1-(3-(trifluoromethyl)-1,2,4-oxadiazol-5-yl)ethyl)quinazolin-4-amine |
| Example 258 | 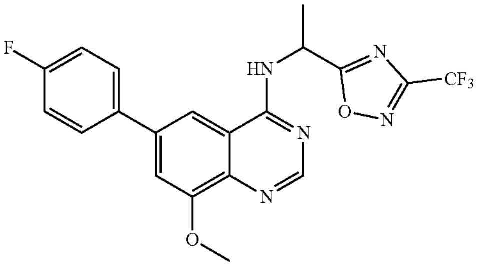 [SMILES: COc1cc(-c2ccc(F)cc2)cc2c(NC(C)c3nc(C(F)(F)F)no3)ncnc12] | Single enantiomer 2 of 6-(4-fluorophenyl)-8-methoxy-N-(1-(3-(trifluoromethyl)-1,2,4-oxadiazol-5-yl)ethyl)quinazolin-4-amine |
| Example 267 | 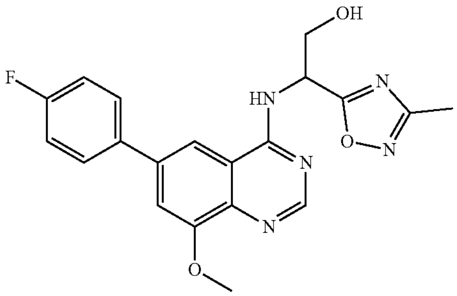 [SMILES: COc1cc(-c2ccc(F)cc2)cc2c(NC(CO)c3nc(C)no3)ncnc12] | Single enantiomer 1 of 2-((6-(4-fluorophenyl)-8-methoxyquinazolin-4-yl)amino)-2-(3-methyl-1,2,4-oxadiazol-5-yl)ethan-1-ol |
| Example 268 | 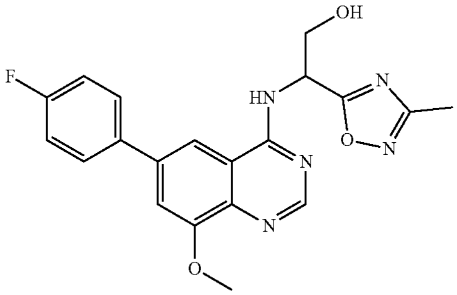 [SMILES: COc1cc(-c2ccc(F)cc2)cc2c(NC(CO)c3nc(C)no3)ncnc12] | Single enantiomer 2 of 2-((6-(4-fluorophenyl)-8-methoxyquinazolin-4-yl)amino)-2-(3-methyl-1,2,4-oxadiazol-5-yl)ethan-1-ol |

TABLE 1-continued

| List of preferred compounds having Formula (I) | | |
|---|---|---|
| Ex. N. | Structure | Chemical Name |
| Example 281 | 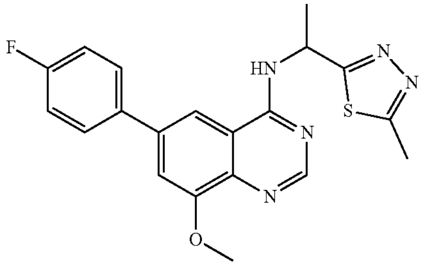 [SMILES: COc1cc(-c2ccc(F)cc2)cc2c(NC(C)c3nnc(C)s3)ncnc12] | Single enantiomer 1 of 6-(4-fluorophenyl)-8-methoxy-N-(1-(5-methyl-1,3,4-thiadiazol-2-yl)ethyl)quinazolin-4-amine |
| Example 282 | 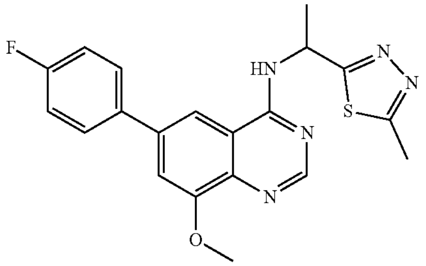 | Single enantiomer 2 of 6-(4-fluorophenyl)-8-methoxy-N-(1-(5-methyl-1,3,4-thiadiazol-2-yl)ethyl)quinazolin-4-amine |
| Example 296 | 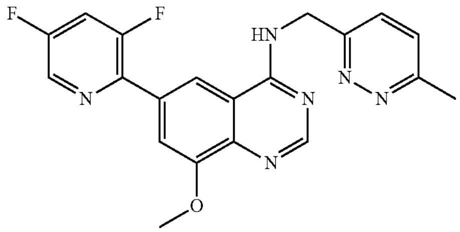 [SMILES: COc1cc(-c2ncc(F)cc2F)cc2c(NCc3ccc(C)nn3)ncnc12] | 6-(3,5-Difluoropyridin-2-yl)-8-methoxy-N-((6-methylpyridazin-3-yl)methyl)quinazolin-4-amine |
| Example 297 | 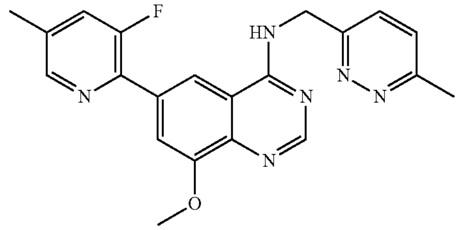 | 6-(3-Fluoro-5-methyl-2-pyridyl)-8-methoxy-N-[(6-methylpyridazin-3-yl)methyl]quinazolin-4-amine |
| Example 298 | 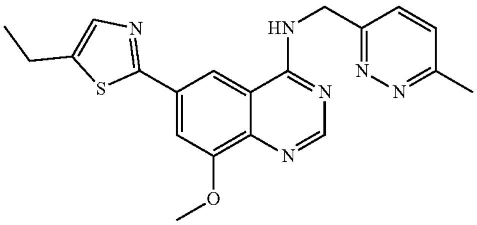 [SMILES: CCc1cnc(-c2cc(OC)c3ncnc(NCc4ccc(C)nn4)c3c2)s1] | 6-(5-Ethylthiazol-2-yl)-8-methoxy-N-[(6-methylpyridazin-3-yl)methyl]quinazolin-4-amine |
| Example 299 | 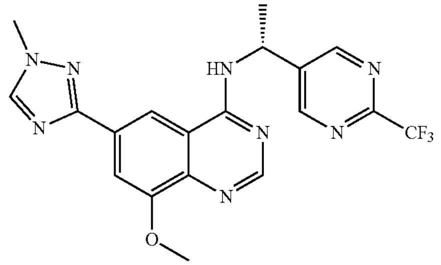 [SMILES: COc1cc(-c2ncn(C)n2)cc2c(N[C@H](C)c3cnc(C(F)(F)F)nc3)ncnc12] | (R)-8-methoxy-6-(1-methyl-1H-1,2,4-triazol-3-yl)-N-(1-(2-(trifluoromethyl)pyrimidin-5-yl)ethyl)quinazolin-4-amine |

TABLE 1-continued

| List of preferred compounds having Formula (I) | | |
|---|---|---|
| Ex. N. | Structure | Chemical Name |
| Example 300 | 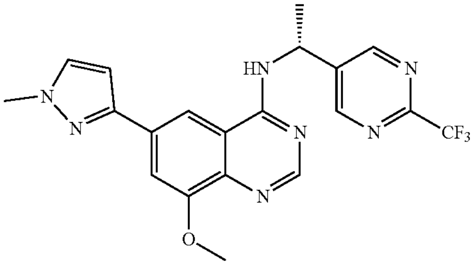 [SMILES: COc1cc(-c2ccn(C)n2)cc2c(N[C@H](C)c3cnc(C(F)(F)F)nc3)ncnc12] | (R)-8-methoxy-6-(1-methyl-1H-pyrazol-3-yl)-N-(1-(2-(trifluoromethyl)pyrimidin-5-yl)ethyl)quinazolin-4-amine |
| Example 301 | 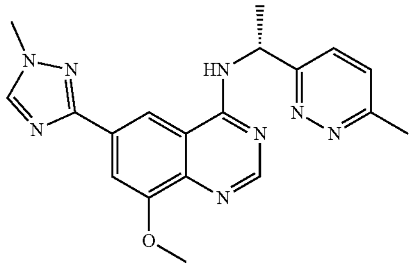 [SMILES: COc1cc(-c2ncn(C)n2)cc2c(N[C@H](C)c3ccc(C)nn3)ncnc12] | (R)-8-methoxy-6-(1-methyl-1H-1,2,4-triazol-3-yl)-N-(1-(6-methylpyridazin-3-yl)ethyl)quinazolin-4-amine |
| Example 315 | 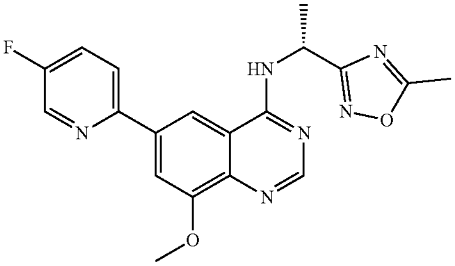 [SMILES: COc1cc(-c2ccc(F)cn2)cc2c(N[C@H](C)c3noc(C)n3)ncnc12] | (R)-6-(5-fluoropyridin-2-yl)-8-methoxy-N-(1-(5-methyl-1,2,4-oxadiazol-3-yl)ethyl)quinazolin-4-amine |
| Example 316 | 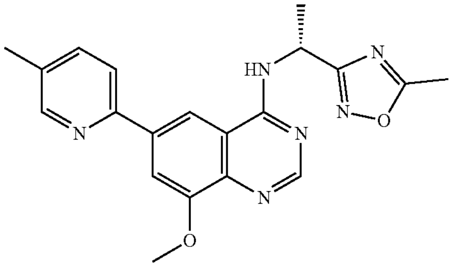 | (R)-8-methoxy-N-(1-(5-methyl-1,2,4-oxadiazol-3-yl)ethyl)-6-(5-methylpyridin-2-yl)quinazolin-4-amine |
| Example 317 | 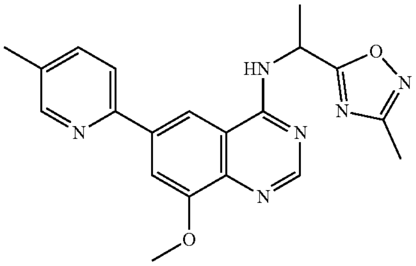 [SMILES: COc1cc(-c2ccc(C)cn2)cc2c(NC(C)c3nc(C)no3)ncnc12] | 8-Methoxy-N-[1-(3-methyl-1,2,4-oxadiazol-5-yl)ethyl]-6-(5-methyl-2-pyridyl)quinazolin-4-amine |

TABLE 1-continued

| List of preferred compounds having Formula (I) | | |
|---|---|---|
| Ex. N. | Structure | Chemical Name |
| Example 318 | 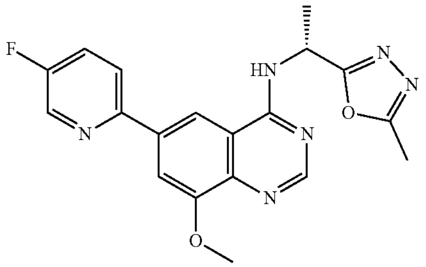 [SMILES: COc1cc(-c2ccc(F)cn2)cc2c(N[C@H](C)c3nnc(C)o3)ncnc12] | 6-(5-fluoro-2-pyridyl)-8-methoxy-N-[(1R)-1-(5-methyl-1,3,4-oxadiazol-2-yl)ethyl]quinazolin-4-amine |
| Example 319 | 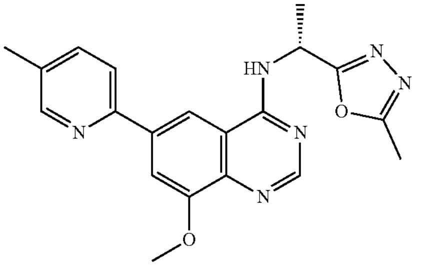 [SMILES: COc1cc(-c2ccc(C)cn2)cc2c(N[C@H](C)c3nnc(C)o3)ncnc12] | 8-methoxy-N-[(1R)-1-(5-methyl-1,3,4-oxadiazol-2-yl)ethyl]-6-(5-methyl-2-pyridyl)quinazolin-4-amine |
| Example 321 | 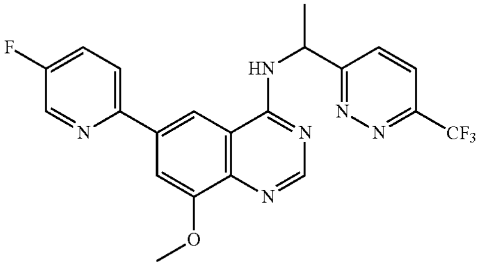 [SMILES: COc1cc(-c2ccc(F)cn2)cc2c(NC(C)c3ccc(C(F)(F)F)nn3)ncnc12] | 6-(5-fluoro-2-pyridyl)-8-methoxy-N-[1-[6-(trifluoromethyl)pyridazin-3-yl]ethyl]quinazolin-4-amine |
| Example 322 | 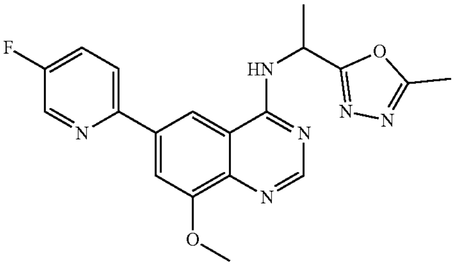 [SMILES: COc1cc(-c2ccc(F)cn2)cc2c(NC(C)c3nnc(C)o3)ncnc12] | 6-(5-fluoropyridin-2-yl)-8-methoxy-N-(1-(5-methyl-1,3,4-oxadiazol-2-yl)ethyl)quinazolin-4-amine |
| Example 323 | 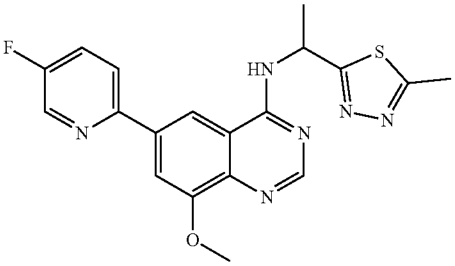 [SMILES: COc1cc(-c2ccc(F)cn2)cc2c(NC(C)c3nnc(C)s3)ncnc12] | 6-(5-fluoropyridin-2-yl)-8-methoxy-N-(1-(5-methyl-1,3,4-thiadiazol-2-yl)ethyl)quinazolin-4-amine |

TABLE 1-continued

List of preferred compounds having Formula (I)

| Ex. N. | Structure | Chemical Name |
|---|---|---|
| Example 324 | 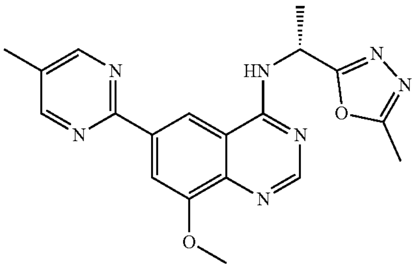 [SMILES: COc1cc(-c2ncc(C)cn2)cc2c(N[C@H](C)c3nnc(C)o3)ncnc12] | 8-methoxy-N-[(1R)-1-(5-methyl-1,3,4-oxadiazol-2-yl)ethyl]-6-(5-methylpyrimidin-2-yl)quinazolin-4-amine |
| Example 325 | 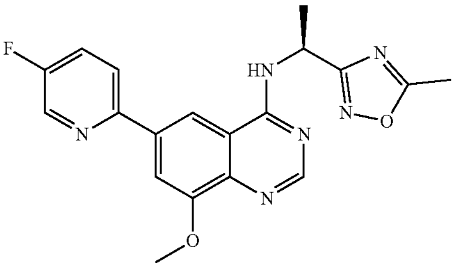 [SMILES: COc1cc(-c2ccc(F)cn2)cc2c(N[C@@H](C)c3noc(C)n3)ncnc12] | (S)-6-(5-fluoropyridin-2-yl)-8-methoxy-N-(1-(5-methyl-1,2,4-oxadiazol-3-yl)ethyl)quinazolin-4-amine |
| Example 326 | 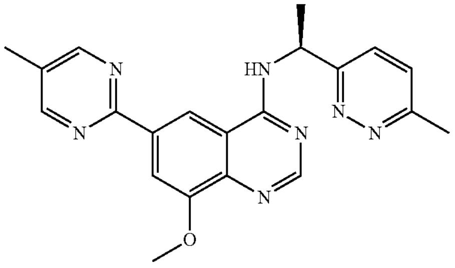 | 8-Methoxy-N-[(1S)-1-(6-methylpyridazin-3-yl)ethyl]-6-(5-methylpyrimidin-2-yl)quinazolin-4-amine |

In a further preferred embodiment, the invention refers to compound of formula (I) wherein Z is selected from the group consisting of heteroaryl, preferably pyrimidinyl, thiazolyl, pyridinyl, thiophenyl, aryl, preferably phenyl, $(R^AR^B)N$—, wherein $R^A$ and $R^B$ form together with the nitrogen atom to which they are attached a 5 or 6 membered saturated heterocyclic monocyclic ring system containing a further heteroatom which is oxygen or nitrogen, said heterocyclic radical being optionally in its turn further substituted with one or more oxo, methyl and fluorine; any of such heteroaryl and aryl is further optionally substituted by one or more groups selected from methyl, fluorine, $R^CSO_2$— wherein $R^C$ is selected form the group consisting of fluorine, —OH and $(R^AR^B)N$— wherein $R^A$ and $R^B$ are H,

CN, $(R^AR^B)NC(O)$— wherein $R^A$ and $R^B$ are H, $R_1$ is H or methyl;

$R_2$ is selected from the group consisting of heteroaryl(C1-C4)alkyl-, preferably (pyridinyl)methyl, (pyridazyl)methyl, (pyrimidinyl)ethyl, (oxadiazolyl) ethyl $(R^AR^B)N(O)C(C_1\text{-}C_4)$alkylene-, preferably $R^AR^B$ are H, cyclopropyl;

any of said heteroaryl may be optionally substituted by one or more groups selected from methyl, fluorine, and trifluoromethyl.

Y is H;

J is H or selected from the group consisting of halo, preferably chlorine, $(C_1\text{-}C_4)$alkyl, preferably methyl, $(C_1\text{-}C_6)$haloalkyl preferably trifluoromethyl, $(R^AR^B)N$— wherein $R^A$ and $R^B$ are at each occurrence independently H, cyclopropyl and methyl or, in alternative, $R^A$ and $R^B$ form together with the nitrogen atom to which they are attached a 6 membered saturated heterocyclic monocyclic ring system containing a further heteroatom which is oxygen.

According to a preferred embodiment, the invention refers to at least one of the compounds listed in the Table 2 below and pharmaceutical acceptable salts thereof.

TABLE 2

List of preferred compounds having Formula (I)

| Ex. N. | Structure | Chemical Name |
| --- | --- | --- |
| Example 228 | 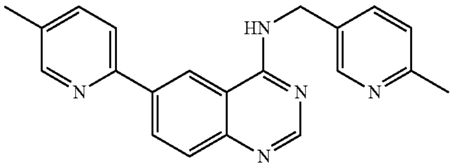 | 6-(5-methylpyridin-2-yl)-N-((6-methylpyridin-3-yl)methyl)quinazolin-4-amine |
| Example 229 | 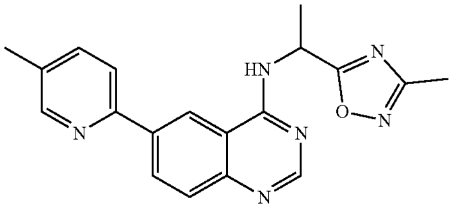 | N-(1-(3-methyl-1,2,4-oxadiazol-5-yl)ethyl)-6-(5-methylpyridin-2-yl)quinazolin-4-amine |
| Example 230 | 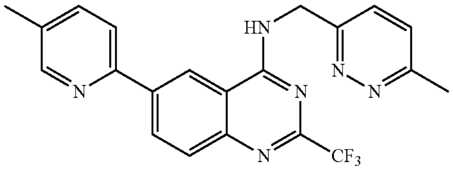 | N-((6-methylpyridazin-3-yl)methyl)-6-(5-methylpyridin-2-yl)-2-(trifluoromethyl)quinazolin-4-amine |
| Example 231 | 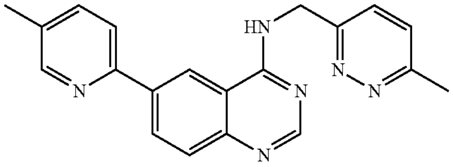 | N-((6-methylpyridazin-3-yl)methyl)-6-(5-methylpyridin-2-yl)quinazolin-4-amine |
| Example 232 | 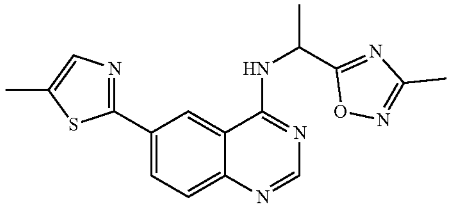 | N-(1-(3-methyl-1,2,4-oxadiazol-5-yl)ethyl)-6-(5-methylthiazol-2-yl)quinazolin-4-amine |
| Example 233 | 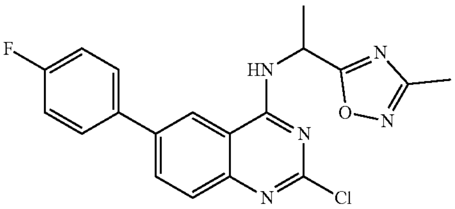 [SMILES: Cc1noc(C(C)Nc2nc(Cl)nc3ccc(-c4ccc(F)cc4)cc23)n1] | 2-chloro-6-(4-fluorophenyl)-N-methyl-1,2,4-oxadiazol-5-yl)ethyl)quinazolin-4-amine |
| Example 234 | 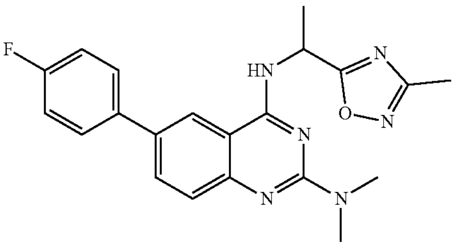 [SMILES: Cc1noc(C(C)Nc2nc(N(C)C)nc3ccc(-c4ccc(F)cc4)cc23)n1] | 6-(4-fluorophenyl)-N2,N2-dimethyl-N4-(1-(3-methyl-1,2,4-oxadiazol-5-yl)ethyl)quinazoline-2,4-diamine |

TABLE 2-continued

| List of preferred compounds having Formula (I) | | |
|---|---|---|
| Ex. N. | Structure | Chemical Name |
| Example 235 | 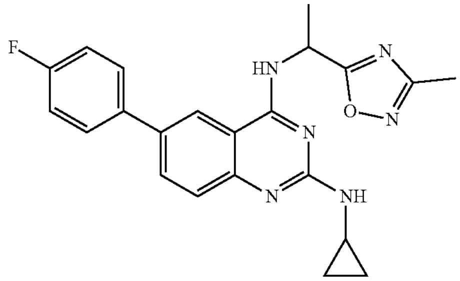 [SMILES: Cc1noc(C(C)Nc2nc(NC3CC3)nc3ccc(-c4ccc(F)cc4)cc23)n1] | N2-cyclopropyl-6-(4-fluorophenyl)-N4-(1-(3-methyl-1,2,4-oxadiazol-5-yl)ethyl)quinazoline-2,4-diamine |
| Example 236 | 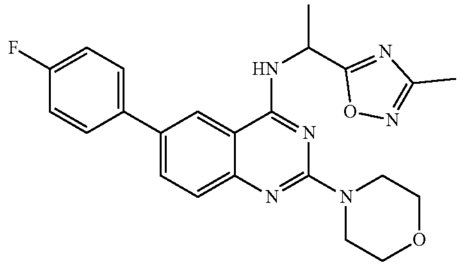 [SMILES: Cc1noc(C(C)Nc2nc(N3CCOCC3)nc3ccc(-c4ccc(F)cc4)cc23)n1] | 6-(4-fluorophenyl)-N-(1-(3-methyl-1,2,4-oxadiazol-5-yl)ethyl)-2-morpholinoquinazolin-4-amine |
| Example 237 | 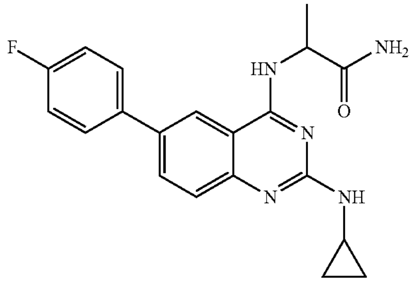 [SMILES: CC(Nc1nc(NC2CC2)nc2ccc(-c3ccc(F)cc3)cc12)C(N)=O] | 2-((2-(cyclopropylamino)-6-(4-fluorophenyl)quinazolin-4-yl)amino)propanamide |
| Example 238 | 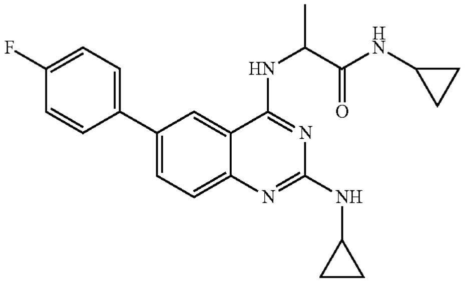 [SMILES: CC(Nc1nc(NC2CC2)nc2ccc(-c3ccc(F)cc3)cc12)C(=O)NC1CC1] | N-cyclopropyl-2-((2-(cyclopropylamino)-6-(4-fluorophenyl)quinazolin-4-yl)amino)propanamide |
| Example 239 | 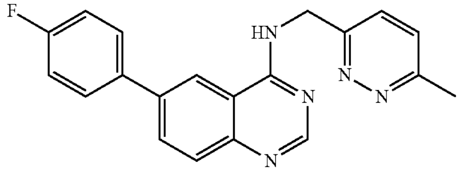 [SMILES: Cc1ccc(CNc2ncnc3ccc(-c4ccc(F)cc4)cc23)nn1] | 6-(4-fluorophenyl)-2-methyl-N-((6-methylpyridazin-3-yl)methyl)quinazolin-4-amine |
| Example 240 | 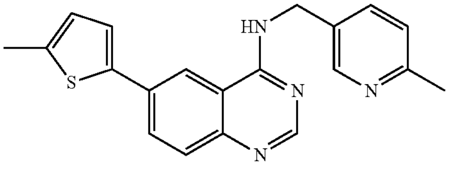 | N-((6-methylpyridin-3-yl)methyl)-6-(5-methylthiophen-2-yl)quinazolin-4-amine |

TABLE 2-continued

List of preferred compounds having Formula (I)

| Ex. N. | Structure | Chemical Name |
|---|---|---|
| Example 241 | 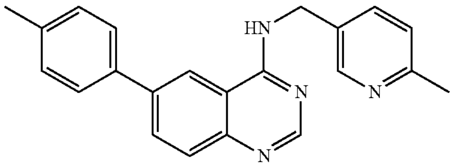 | N-((6-methylpyridin-3-yl)methyl)-6-(p-tolyl)quinazolin-4-amine |
| Example 242 | 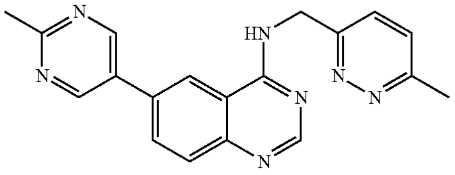 | N-((6-methylpyridazin-3-yl)methyl)-6-(2-methylpyrimidin-5-yl)quinazolin-4-amine |
| Example 243 | 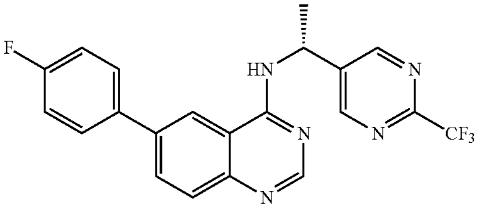 [SMILES: C[C@@H](Nc1ncnc2ccc(-c3ccc(F)cc3)cc12)c1cnc(C(F)(F)F)nc1] | (R)-6-(4-fluorophenyl)-N-(1-(2-(trifluoromethyl)pyrimidin-5-yl)ethyl)quinazolin-4-amine |
| Example 244 | 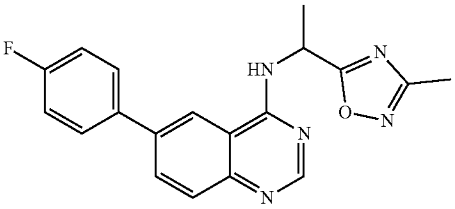 [SMILES: Cc1noc(C(C)Nc2ncnc3ccc(-c4ccc(F)cc4)cc23)n1] | 6-(4-fluorophenyl)-N-(1-(3-methyl-1,2,4-oxadiazol-5-yl)ethyl)quinazolin-4-amine |
| Example 245 | 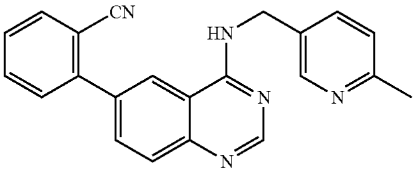 [SMILES: Cc1ccc(CNc2ncnc3ccc(-c4ccccc4C#N)cc23)cn1] | 2-(4-(((6-methylpyridin-3-yl)methyl)amino)quinazolin-6-yl)benzonitrile |
| Example 246 | 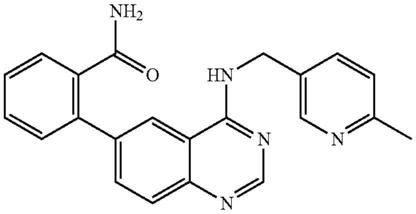 [SMILES: Cc1ccc(CNc2ncnc3ccc(-c4ccccc4C(N)=O)cc23)cn1] | 2-(4-(((6-methylpyridin-3-yl)methyl)amino)quinazolin-6-yl)benzamide |
| Example 247 | 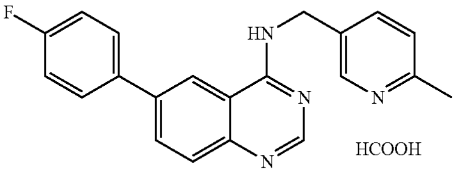 [SMILES: Cc1ccc(CNc2ncnc3ccc(-c4ccc(F)cc4)cc23)cn1 ; "HCOOH"] HCOOH | 6-(4-fluorophenyl)-N-((6-methylpyridin-3-yl)methyl)quinazolin-4-amine formate |
| Example 248 | 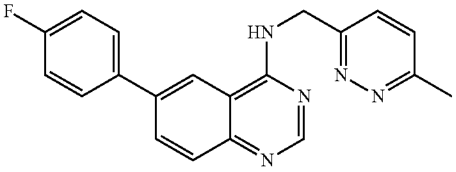 [SMILES: Cc1ccc(CNc2ncnc3ccc(-c4ccc(F)cc4)cc23)nn1] | 6-(4-fluorophenyl)-N-((6-methylpyridazin-3-yl)methyl)quinazolin-4-amine |

TABLE 2-continued

| List of preferred compounds having Formula (I) | | |
|---|---|---|
| Ex. N. | Structure | Chemical Name |
| Example 249 | 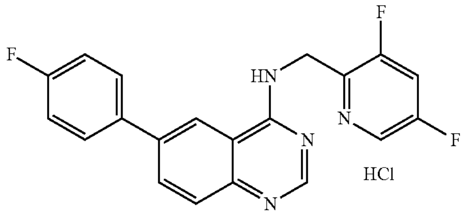 [SMILES: Fc1ccc(-c2ccc3ncnc(NCc4ncc(F)cc4F)c3c2)cc1 ; Cl] | N-((3,5-difluoropyridin-2-yl)methyl)-6-(4-fluorophenyl)quinazolin-4-amine hydrochloride |
| Example 250 | 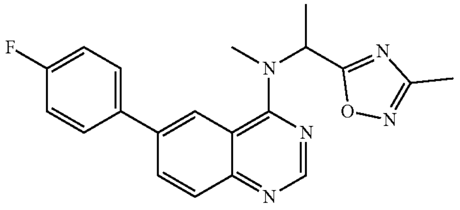 [SMILES: Cc1noc(C(C)N(C)c2ncnc3ccc(-c4ccc(F)cc4)cc23)n1] | 6-(4-fluorophenyl)-N-methyl-N-(1-(3-methyl-1,2,4-oxadiazol-5-yl)ethyl) quinazolin-4-amine |
| Example 251 | 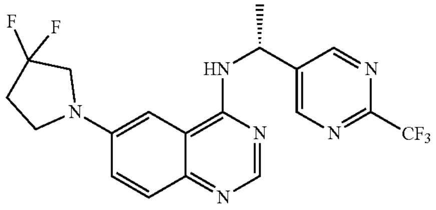 [SMILES: C[C@@H](Nc1ncnc2ccc(N3CCC(F)(F)C3)cc12)c1cnc(C(F)(F)F)nc1] | (R)-6-(3,3 difluoropyrrolidin-1-yl)-N-(1-(2-(trifluoromethyl)pyrimidin-5-yl)ethyl)quinazolin-4-amine |
| Example 252 | 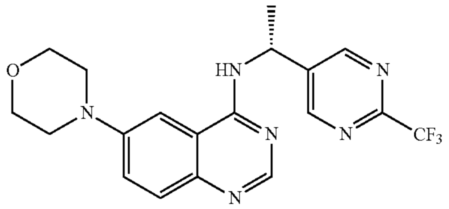 [SMILES: C[C@@H](Nc1ncnc2ccc(N3CCOCC3)cc12)c1cnc(C(F)(F)F)nc1] | (R)-6-morpholino-N-(1-(2-(trifluoromethyl)pyrimidin-5-yl)ethyl)quinazolin-4-amine |
| Example 253 | 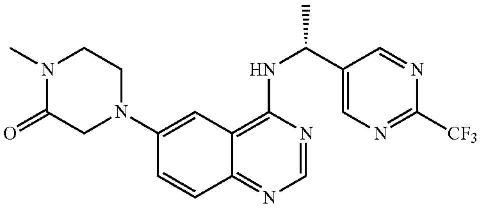 [SMILES: C[C@@H](Nc1ncnc2ccc(N3CCN(C)C(=O)C3)cc12)c1cnc(C(F)(F)F)nc1] | (R)-1-methyl-4-(4-((1-(2-(trifluoromethyl)pyrimidin-5-yl)ethyl)amino) quinazolin-6-yl)piperazin-2-one |
| Example 254 | 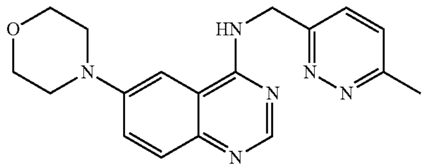 [SMILES: Cc1ccc(CNc2ncnc3ccc(N4CCOCC4)cc23)nn1] | N-((6-methylpyridazin-3-yl)methyl)-6-morpholinoquinazolin-4-amine |
| Example 283 | 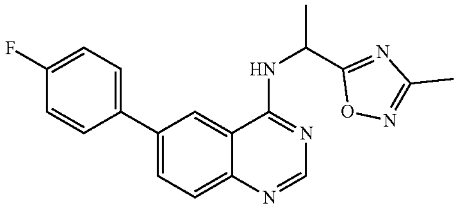 [SMILES: Cc1noc(C(C)Nc2ncnc3ccc(-c4ccc(F)cc4)cc23)n1] | Single enantiomer 1 of 6-(4-fluorophenyl)-N-[1-(3-methyl-1,2,4-oxadiazol-5-yl)ethyl]quinazolin-4-amine |

TABLE 2-continued

| List of preferred compounds having Formula (I) | | |
|---|---|---|
| Ex. N. | Structure | Chemical Name |
| Example 284 | 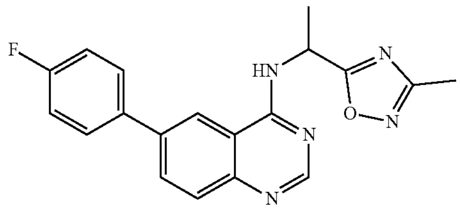 [SMILES: Cc1noc(C(C)Nc2ncnc3ccc(-c4ccc(F)cc4)cc23)n1] | Single enantiomer 2 of 6-(4-fluorophenyl)-N-[1-(3-methyl-1,2,4-oxadiazol-5-yl)ethyl]quinazolin-4-amine |
| Example 285 | 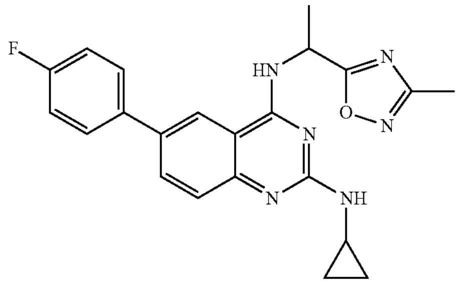 [SMILES: Cc1noc(C(C)Nc2nc(NC3CC3)nc3ccc(-c4ccc(F)cc4)cc23)n1] | Single enantiomer 1 of N2-cyclopropyl-6-(4-fluorophenyl)-N4-[1-(3-methyl-1,2,4-oxadiazol-5-yl)ethyl]quinazoline-2,4-diamine |
| Example 286 | 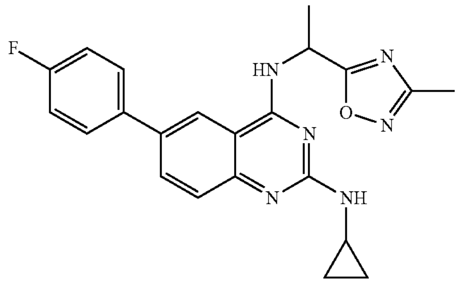 [SMILES: Cc1noc(C(C)Nc2nc(NC3CC3)nc3ccc(-c4ccc(F)cc4)cc23)n1] | Single enantiomer 2 of N2-cyclopropyl-6-(4-fluorophenyl)-N4-[1-(3-methyl-1,2,4-oxadiazol-5-yl)ethyl]quinazoline-2,4-diamine |
| Example 287 | 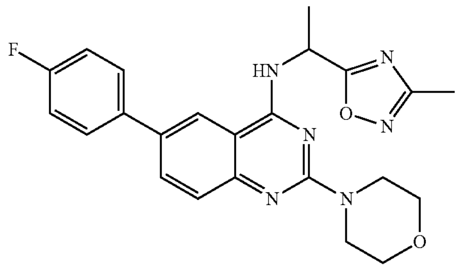 [SMILES: Cc1noc(C(C)Nc2nc(N3CCOCC3)nc3ccc(-c4ccc(F)cc4)cc23)n1] | Single enantiomer 1 of 6-(4-fluorophenyl)-N-[1-(3-methyl-1,2,4-oxadiazol-5-yl)ethyl]-2-morpholino-quinazolin-4-amine |
| Example 288 | 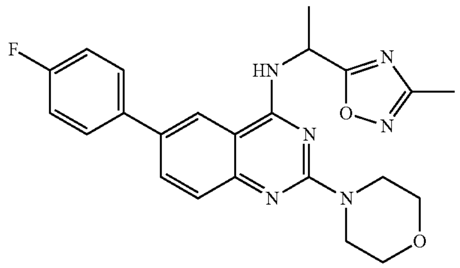 [SMILES: Cc1noc(C(C)Nc2nc(N3CCOCC3)nc3ccc(-c4ccc(F)cc4)cc23)n1] | Single enantiomer 2 of 6-(4-fluorophenyl)-N-[1-(3-methyl-1,2,4-oxadiazol-5-yl)ethyl]-2-morpholino-quinazolin-4-amine |

TABLE 2-continued

| List of preferred compounds having Formula (I) | | |
|---|---|---|
| Ex. N. | Structure | Chemical Name |
| Example 289 | 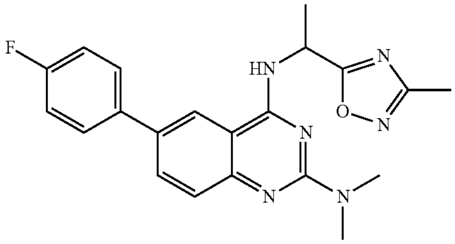 [SMILES: Cc1noc(C(C)Nc2nc(N(C)C)nc3ccc(-c4ccc(F)cc4)cc23)n1] | Single enantiomer of 6-(4-fluorophenyl)-N2,N2-dimethyl-N4-[1-(3-methyl-1,2,4-oxadiazol-5-yl)ethyl]quinazoline-2,4-diamine |
| Example 290 | 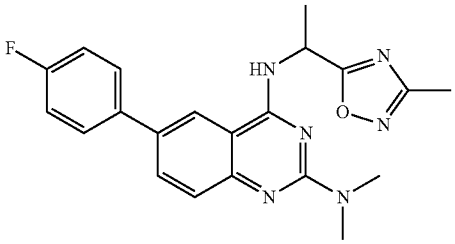 [SMILES: Cc1noc(C(C)Nc2nc(N(C)C)nc3ccc(-c4ccc(F)cc4)cc23)n1] | Single enantiomer of 6-(4-fluorophenyl)-N2,N2-dimethyl-N4-[1-(3-methyl-1,2,4-oxadiazol-5-yl)ethyl]quinazoline-2,4-diamine |

In a further preferred embodiment, the invention is addressed to compound of formula (I) wherein Z is H or selected from the group consisting of heteroaryl and aryl, wherein any of such heteroaryl and aryl may be optionally substituted by one or more groups selected from ($C_1$-$C_3$)alkyl and halo;

R1 is H;

R2 is selected from the group consisting of heteroaryl (C1-C4)alkyl-, wherein any of such heteroaryl may be optionally substituted by one or more groups selected from ($C_1$-$C_3$)alkyl and ($C_1$-$C_6$) haloalkyl;

Y is H;

J is H or halo.

According to a preferred embodiment, the invention refers to at least one compound of Table 3, selected from:

TABLE 3

| List of preferred compounds having Formula (I) | | |
|---|---|---|
| Ex. N. | Structure | Chemical Name |
| Example 228 | 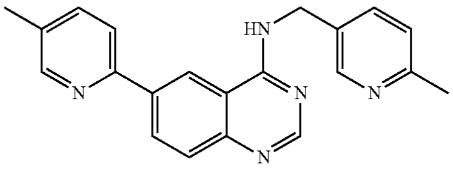 | 6-(5-methylpyridin-2-yl)-N-((6-methylpyridin-3-yl)methyl)quinazolin-4-amine |
| Example 229 | 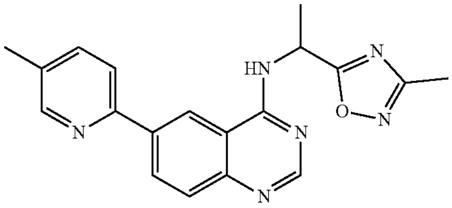 | N-(1-(3-methyl-1,2,4-oxadiazol-5-yl)ethyl)-6-(5-methylpyridin-2-yl)quinazolin-4-amine |
| Example 231 | 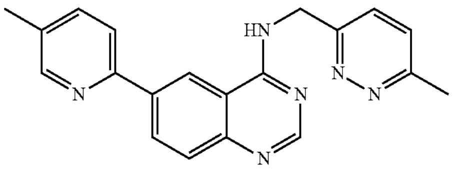 | N-((6-methylpyridazin-3-yl)methyl)-6-(5-methylpyridin-2-yl)quinazolin-4-amine |

TABLE 3-continued

List of preferred compounds having Formula (I)

| Ex. N. | Structure | Chemical Name |
|---|---|---|
| Example 232 | 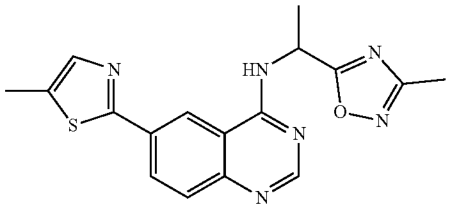 | N-(1-(3-methyl-1,2,4-oxadiazol-5-yl)ethyl)-6-(5-methylthiazol-2-yl)quinazolin-4-amine |
| Example 233 | 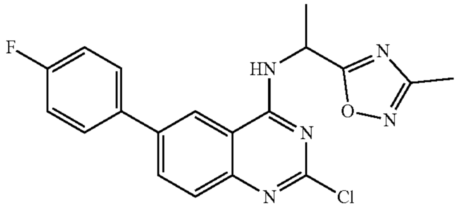 [SMILES: Cc1noc(C(C)Nc2nc(Cl)nc3ccc(-c4ccc(F)cc4)cc23)n1] | 2-chloro-6-(4-fluorophenyl)-N-(1-(3-methyl-1,2,4-oxadiazol-5-yl)ethyl)quinazolin-4-amine |
| Example 240 | 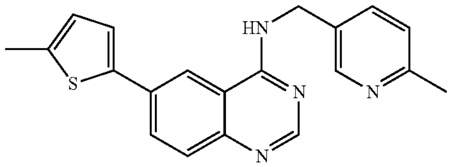 | N-((6-methylpyridin-3-yl)methyl)-6-(5-methylthiophen-2-yl)quinazolin-4-amine |
| Example 241 | 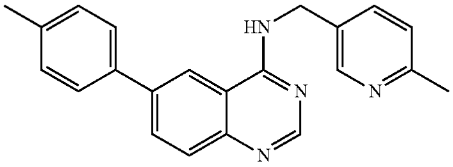 | N-((6-methylpyridin-3-yl)methyl)-6-(p-tolyl)quinazolin-4-amine |
| Example 243 | 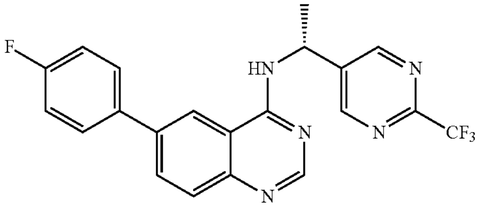 [SMILES: C[C@@H](Nc1ncnc2ccc(-c3ccc(F)cc3)cc12)c1cnc(C(F)(F)F)nc1] | (R)-6-(4-fluorophenyl)-N-(1-(2-(trifluoromethyl)pyrimidin-5-yl)ethyl)quinazolin-4-amine |
| Example 244 | 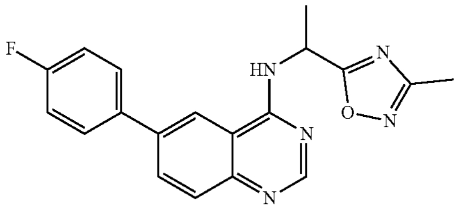 [SMILES: Cc1noc(C(C)Nc2ncnc3ccc(-c4ccc(F)cc4)cc23)n1] | 6-(4-fluorophenyl)-N-( 1-(3-methyl-1,2,4-oxadiazol-5-yl)ethyl)quinazolin-4-amine |
| Example 247 | 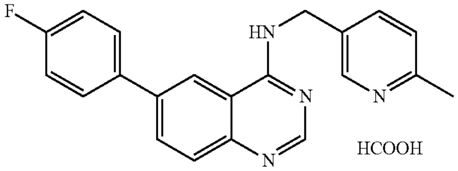 [SMILES: Cc1ccc(CNc2ncnc3ccc(-c4ccc(F)cc4)cc23)cn1 ; "HCOOH"] HCOOH | 6-(4-fluorophenyl)-N-((6-methylpyridin-3-yl)methyl)quinazolin-4-amine formate |

TABLE 3-continued

| Ex. N. | Structure | Chemical Name |
|---|---|---|
| | List of preferred compounds having Formula (I) | |
| Example 248 | 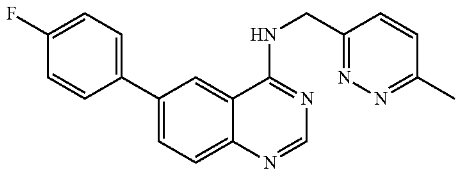 [SMILES: Cc1ccc(CNc2ncnc3ccc(-c4ccc(F)cc4)cc23)nn1] | 6-(4-fluorophenyl)-N-((6-methylpyridazin-3-yl)methyl)quinazolin-4-amine |
| Example 283 | 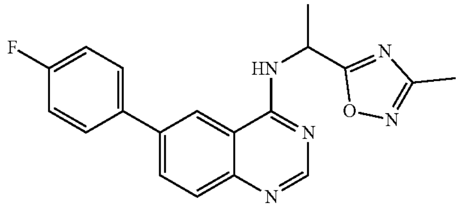 [SMILES: Cc1noc(C(C)Nc2ncnc3ccc(-c4ccc(F)cc4)cc23)n1] | Single enantiomer 1 of 6-(4-fluorophenyl)-N-[1-(3-methyl-1,2,4-oxadiazol-5-yl)ethyl]quinazolin-4-amine |
| Example 284 | 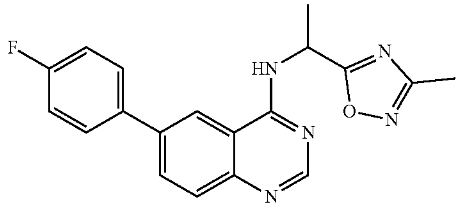 [SMILES: Cc1noc(C(C)Nc2ncnc3ccc(-c4ccc(F)cc4)cc23)n1] | Single enantiomer 2 of 6-(4-fluorophenyl)-N-[1-(3-methyl-1,2,4-oxadiazol-5-yl)ethyl]quinazolin-4-amine |

In a preferred embodiment, the invention refers to a compound of formula (I)

(I)

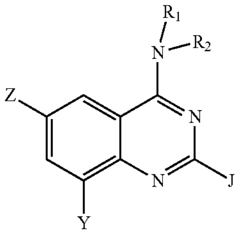

wherein

Z is selected from the group consisting of heteroaryl and aryl, wherein any of such heteroaryl and aryl may be optionally substituted by one or more groups selected from $(C_1-C_3)$ alkyl, halo, CN, $(R^AR^B)NC(O)$—, $(C_1-C_6)$haloalkyl, $R^AO$—, $(R^AR^B)N(C_1-C_6)$alkylene-, $(C_3-C_7)$cycloalkyl-, $R^CSO_2$—, $(R^AR^B)N$—;

$R_1$ is H or $(C_1-C_4)$alkyl, $R_2$ is selected from the group consisting of $(C_1-C_6)$alkyl, heteroaryl$(C_1-C_4)$alkyl-, $(C_3-C_8)$heterocycloalkyl-$(C_1-C_6)$alkyl, heteroaryl-$(C_1-C_6)$hydroxyalkyl, aryl-$(C_1-C_4)$alkyl-, $(C_3-C_8)$heterocycloalkyl, $(C_3-C_8)$cycloalkyl-$(C_1-C_6)$alkyl-, $(R^AR^B)N(C_1-C_6)$alkylene-; $R^AO(C_1-C_4)$ alkylene, wherein any of such alkyl, alkylene, aryl, heteroaryl, cycloalkyl and heterocycloalkyl may be optionally substituted by one or more groups selected from $(C_1-C_3)$alkyl, $R^AO(C_1-C_4)$alkylene, $(C_1-C_6)$haloalkyl, oxo, $R^AO$—, $(C_3-C_8)$heterocycloalkyl-$(C_1-C_6)$alkyl, heteroaryl, aryl optionally substituted by halo, $R^CO$—, $(R^AR^B)N$—, —NHC(O)$R^C$, —C(O)N$(R^AR^B)$, halo, —$SO_2N(R^AR^B)$, —O$(R^AO(C_1-C_4)$alkylene-N$(R^AR^B)$, aryl-$(C_1-C_4)$alkyl-, —C(O)$R^A$, $R^A$ and $R^B$ are at each occurrence independently H or selected from the group consisting of $(C_1-C_4)$alkyl-, aryl, $(C_1-C_6)$ haloalkyl, or $R^A$ and $R^B$ may form together with the nitrogen atom to which they are attached a 6 membered saturated heterocyclic monocyclic ring system optionally containing a further heteroatom which is nitrogen or oxygen, which may be optionally substituted by $(C_1-C_4)$alkyl- and oxo;

$R^C$ is H or selected from the group consisting of $(C_1-C_6)$ alkyl, $(R^AR^B)N$—, aryl-$(C_1-C_4)$alkyl-, Y is selected from the group consisting of —$OR^D$, $R^CSO_2$—, halo, —$NHSO_2R^C$, heteroaryl, $(C_3-C_8)$heterocycloalkyl, wherein any of such heteroaryl and heterocycloalkyl may be optionally substituted by one or more groups selected from $(C_1-C_3)$alkyl, —C(O)N$(R^AR^B)$;

J is H or selected from the group consisting of $(C_1-C_6)$ alkyl, —$OR^C$, $R^D$ is H or $(C_1-C_6)$alkyl.

In a still preferred embodiment, the invention refers to a compound of formula (I) as defined above (I)

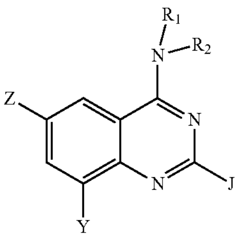

wherein

Z is selected from the group consisting of heteroaryl and aryl, wherein any of such heteroaryl and aryl may be optionally substituted by one or more groups selected from $(C_1$-$C_3)$alkyl, halo, CN, $(R^AR^B)NC(O)$—, $(C_1$-$C_6)$ haloalkyl, $R^AO$—, $(R^AR^B)N(C_1$-$C_6)$alkylene-, $(C_3$-$C_7)$ cycloalkyl-, $R^CSO_2$—, $(R^AR^B)N$—;

$R_1$ is H;

$R_2$ is selected from the group consisting of $(C_1$-$C_6)$alkyl, heteroaryl$(C_1$-$C_4)$alkyl-, $(C_3$-$C_8)$heterocycloalkyl-$(C_1$-$C_6)$alkyl, heteroaryl-$(C_1$-$C_6)$hydroxyalkyl, $(C_3$-$C_8)$heterocycloalkyl, $(C_3$-$C_8)$cycloalkyl-$(C_1$-$C_6)$alkyl-, $(R^AR^B)N(C_1$-$C_6)$alkylene-; $R^AO(C_1$-$C_4)$alkylene, wherein any of such alkyl, alkylene, aryl, heteroaryl, cycloalkyl and heterocycloalkyl may be optionally substituted by one or more groups selected from $(C_1$-$C_3)$ alkyl, $R^AO(C_1$-$C_4)$alkylene-, $(C_1$-$C_6)$haloalkyl, oxo, $R^AO$—, $(C_3$-$C_8)$heterocycloalkyl-$(C_1$-$C_6)$alkyl, heteroaryl, aryl optionally substituted by halo, $R^CO$—, $(R^AR^B)N$—, —$NHC(O)R^C$, —$C(O)N(R^AR^B)$, halo, —$SO_2N(R^AR^B)$, —$O(R^AO(C_1$-$C_4)$alkylene-$N(R^AR^B)$, aryl-$(C_1$-$C_4)$alkyl-, —$C(O)R^A$;

$R^A$ and $R^B$ are at each occurrence independently H or selected from the group consisting of $(C_1$-$C_4)$alkyl-, aryl, $(C_1$-$C_6)$ haloalkyl, or $R^A$ and $R^B$ may form together with the nitrogen atom to which they are attached a 6 membered saturated heterocyclic monocyclic ring system optionally containing a further heteroatom which is nitrogen or oxygen, which may be optionally substituted by $(C_1$-$C_4)$alkyl- and oxo;

$R^C$ is H or selected from the group consisting of $(C_1$-$C_6)$ alkyl, $(R^AR^B)N$—, $C_4)$alkyl-, Y is selected from the group consisting of —$OR^D$, $R^CSO_2$, halo, —$NHSO_2R^C$, heteroaryl, $(C_3$-$C_8)$heterocycloalkyl, wherein any of such heteroaryl and heterocycloalkyl may be optionally substituted by one or more groups selected from $(C_1$-$C_3)$alkyl, —$C(O)N(R^AR^B)$;

J is H or selected from the group consisting of $(C_1$-$C_6)$ alkyl, $OR^C$;

$R^D$ is H or $(C_1$-$C_6)$alkyl.

In a further preferred embodiment, the invention is addressed to compound of formula (I) wherein Z is H or selected from the group consisting of $(R^AR^B)N$—, heteroaryl, preferably thiadiazolyl, thiazolyl, pyrazolyl, pyridazyl, oxadiazolyl, pyridinyl, pyrimidinyl, aryl, preferably phenyl, $R^AO$—, wherein $R^A$ is H, each of said heteroaryl and aryl may be optionally substituted by one or more groups selected from methyl, halo, preferably fluorine and chlorine,

CN, $(R^AR^B)NC(O)$—, wherein $R^A$ and $R^B$ are at each occurrence independently H or methyl, $C_1$-$C_6)$haloalkyl, preferably trifluoromethyl and difluoromethyl, $R^AO$—, wherein $R^A$ is H or selected from methyl, trifluoromethyl and difluoromethyl, $(R^AR^B)N(C_1$-$C_6)$alkylene-, wherein $R^A$ and $R^B$ are methyl, cyclopropyl, $R^CSO_2$—, wherein $R^C$ is methyl, $(R^AR^B)N$— wherein $R^A$ and $R^B$ are independently H and methyl;

$R_1$ is H;

$R_2$ is selected from the group consisting of heteroaryl$(C_1$-$C_4)$alkyl-, preferably ([1,2,4]triazolo[4,3-a]pyrimidin-3-yl)methyl, (triazolyl)methyl, (triazolyl)ethyl, (imidazo[1,2-a]pyrimidinyl)methyl, (pyrimidinyl)ethyl, (pyrimidinyl)methyl, (pyrazolyl) methyl, (pyridazinyl)methyl, (pyridazinyl)ethyl (oxadiazolyl)methyl, (oxadiazolyl)propyl, (pyridinyl)methyl, (pyridinyl)ethyl, (oxadiazolyl)ethyl, $(C_3$-$C_8)$heterocycloalkyl-$(C_1$-$C_6)$alkyl, preferably (piperidinyl)methyl, (tetrazolyl)methyl, (morpholinyl) ethyl, heteroaryl$(C_1$-$C_6)$hydroxyalkyl-, preferably (oxadiazolyl)methanol, $(C_3$-$C_8)$cycloalkyl$(C_1$-$C_6)$alkyl-, preferably (cyclopropyl)methyl, aryl-$(C_1$-$C_4)$alkyl-, preferably (phenyl)methyl, $(R^AR^B)N(C_1$-$C_6)$alkylene-, preferably dimethylaminobuthyl, dimethylaminopropyl, each of said aryl, heteroaryl, cycloalkyl and heterocycloalkyl is optionally further substituted by one or more groups selected from $(C_1$-$C_3)$alkyl, preferably methyl and ethyl, trifluoromethyl, oxo, chlorine, $R^AO$—, wherein $R^A$ is selected from the group of trifluoroethyl, difluoroethyl, methyl and ethyl, $(C_3$-$C_8)$heterocycloalkyl-$(C_1$-$C_6)$alkyl-, preferably (piperidinyl)methyl, $(C_3$-$C_8)$heterocycloalkyl, preferably piperazinyl optionally further substituted by methyl, heteroaryl, preferably pyridinyl, —$NHC(O)R^C$, wherein $R^C$ is methyl, $(R^AR^B)N$—, wherein $R^A$ and $R^B$ are methyl, $R^CO$—, wherein $R^C$ is methyl, —$C(O)N(R^AR^B)$; wherein $R^A$ is H and $R^B$ is methyl;

Y is selected from the group consisting of —$OR^D$, $R^CSO_2$, halo, —$NHSO_2R^C$, heteroaryl wherein any of such heteroaryl may be optionally substituted by one or more groups selected from $(C_1$-$C_3)$alkyl, —$C(O)N(R^AR^B)$;

$R^D$ is $(C_1$-$C_6)$alkyl, preferably methyl;

J is selected from the group consisting of $(C_1$-$C_6)$alkyl, preferably methyl, —$OR^C$ wherein $R^C$ is H or $(C_1$-$C_6)$alkyl, preferably methyl.

According to specific embodiments, the invention refers to at least one compound as listed in the Table 4 below and pharmaceutical acceptable salts thereof.

TABLE 4

| List of preferred compounds having Formula (I) | | |
|---|---|---|
| Ex. N. | Structure | Chemical Name |
| Example 183 | 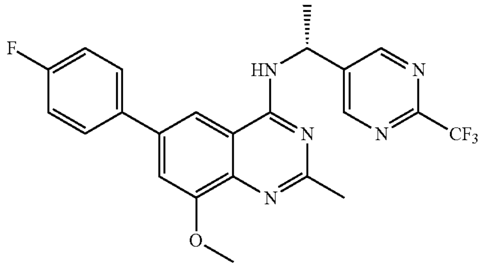 [SMILES: COc1cc(-c2ccc(F)cc2)cc2c(N[C@H](C)c3cnc(C(F)(F)F)nc3)nc(C)nc12] | (R)-6-(4-Fluorophenyl)-8-methoxy-2-methyl-N-(1-(2-(trifluoromethyl)pyrimidin-5 yl)ethyl)quinazolin-4-amine |
| Example 184 | 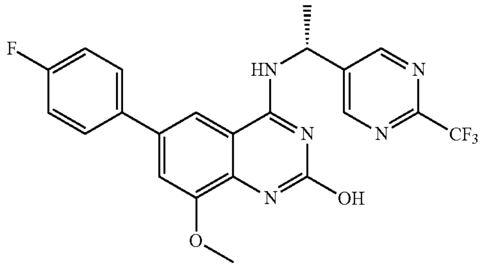 [SMILES: COc1cc(-c2ccc(F)cc2)cc2c(N[C@H](C)c3cnc(C(F)(F)F)nc3)nc(O)nc12] | (R)-6-(4-Fluorophenyl)-8-methoxy-4-((1-(2-(trifluoromethyl)pyrimidin-5-yl)ethyl)-amino)-quinazolin-2-ol |
| Example 185 | 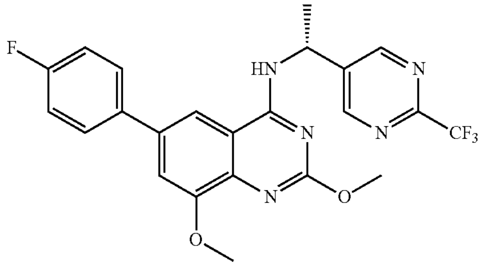 [SMILES: COc1nc(N[C@H](C)c2cnc(C(F)(F)F)nc2)c2cc(-c3ccc(F)cc3)cc(OC)c2n1] | (R)-6-(4-Fluorophenyl)-2,8-dimethoxy-N-(1-(2-(trifluoromethyl)pyrimidin-5-yl)ethyl)quinazolin-4-amine |
| Example 1 | 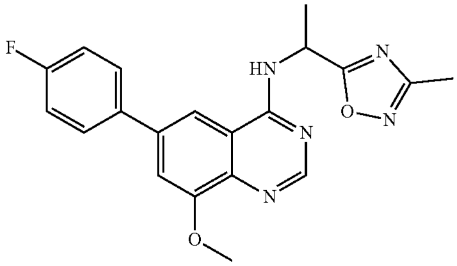 [SMILES: COc1cc(-c2ccc(F)cc2)cc2c(NC(C)c3nc(C)no3)ncnc12] | 6-(4-Fluorophenyl)-8-methoxy-N-(1-(3-methyl-1,2,4-oxadiazol-5-yl)ethyl)quinazolin-4-amine |
| Example 2 | 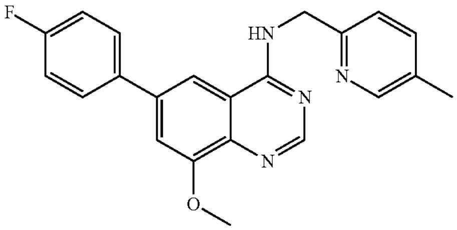 [SMILES: COc1cc(-c2ccc(F)cc2)cc2c(NCc3ccc(C)cn3)ncnc12] | 6-(4-Fluorophenyl)-8-methoxy-N-((5-methylpyridin-2-yl)methyl)quinazolin-4-amine |
| Example 3 | 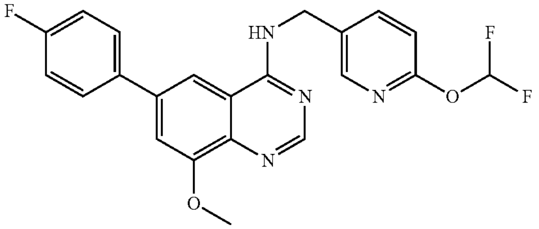 [SMILES: COc1cc(-c2ccc(F)cc2)cc2c(NCc3ccc(OC(F)F)nc3)ncnc12] | N-((6-(Difluoromethoxy)pyridin-3-yl)methyl)-6-(4-fluorophenyl)-8-methoxyquinazolin-4-amine |

TABLE 4-continued

List of preferred compounds having Formula (I)

| Ex. N. | Structure | Chemical Name |
|---|---|---|
| Example 4 | 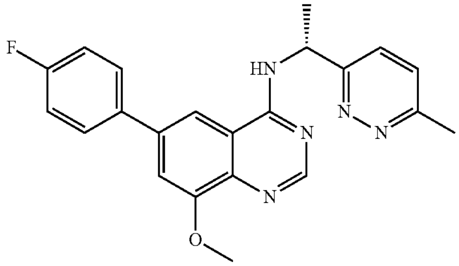 [SMILES: COc1cc(-c2ccc(F)cc2)cc2c(N[C@H](C)c3ccc(C)nn3)ncnc12] | (R)-6-(4-Fluorophenyl)-8-methoxy-N-(1-(6-methylpyridazin-3-yl)ethyl)quinazolin-4-amine |
| Example 5 | 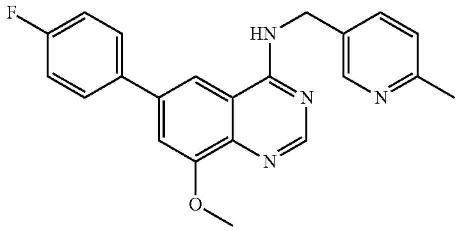 [SMILES: COc1cc(-c2ccc(F)cc2)cc2c(NCc3ccc(C)nc3)ncnc12] | 6-(4-Fluorophenyl)-8-methoxy-N-((6-methylpyridin-3-yl)methyl)quinazolin-4-amine |
| Example 6 | 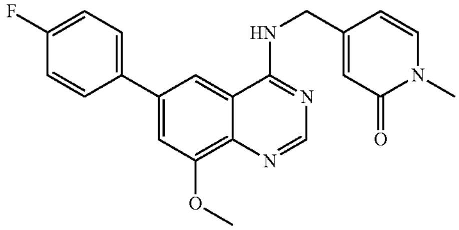 [SMILES: COc1cc(-c2ccc(F)cc2)cc2c(NCc3ccn(C)c(=O)c3)ncnc12] | 4-(((6-(4-Fluorophenyl)-8-methoxyquinazolin-4-yl)amino)methyl)-1-methylpyridin-2(1H)-one |
| Example 7 | 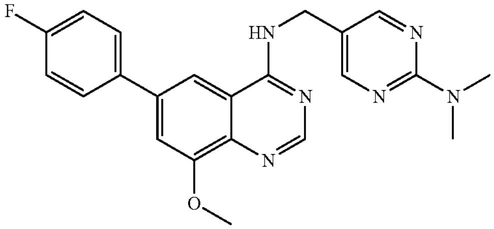 [SMILES: COc1cc(-c2ccc(F)cc2)cc2c(NCc3cnc(N(C)C)nc3)ncnc12] | N-((2-(Dimethylamino)pyrimidin-5-yl)methyl)-6-(4-fluorophenyl)-8-methoxyquinazolin-4-amine |
| Example 8 | 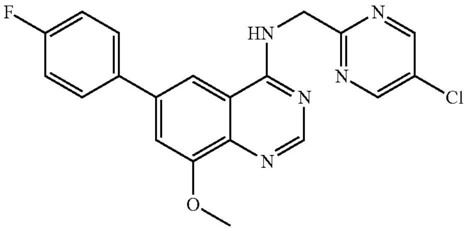 [SMILES: COc1cc(-c2ccc(F)cc2)cc2c(NCc3ncc(Cl)cn3)ncnc12] | N-((5-Chloropyrimidin-2-yl)methyl)-6-(4-fluorophenyl)-8-methoxyquinazolin-4-amine |
| Example 9 | 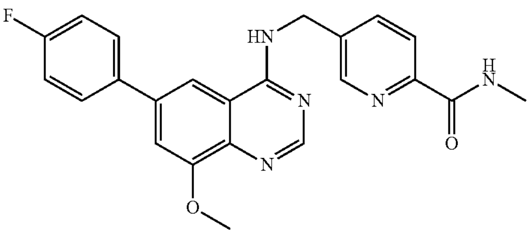 [SMILES: CNC(=O)c1ccc(CNc2ncnc3c(OC)cc(-c4ccc(F)cc4)cc23)cn1] | 5-(((6-(4-Fluorophenyl)-8-methoxyquinazolin-4-yl)amino)methyl)-N-methylpicolinamide |

TABLE 4-continued

List of preferred compounds having Formula (I)

| Ex. N. | Structure | Chemical Name |
| --- | --- | --- |
| Example 10 | 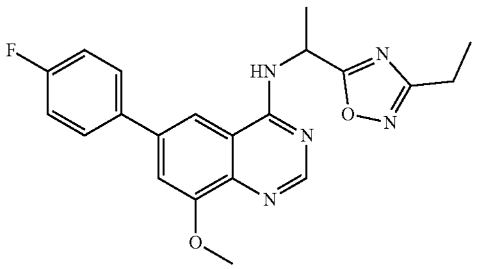 [SMILES: CCc1noc(C(C)Nc2ncnc3c(OC)cc(-c4ccc(F)cc4)cc23)n1] | N-(1-(3-Ethyl-1,2,4-oxadiazol-5-yl)ethyl)-6-(4-fluorophenyl)-8-methoxyquinazolin-4-amine |
| Example 11 | 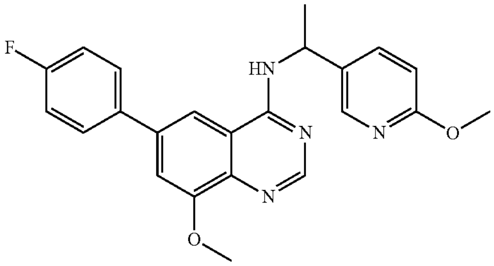 [SMILES: COc1ccc(C(C)Nc2ncnc3c(OC)cc(-c4ccc(F)cc4)cc23)cn1] | 6-(4-Fluorophenyl)-8-methoxy-N-(1-(6-methoxypyridin-3-yl)ethyl)quinazolin-4-amine |
| Example 12 | 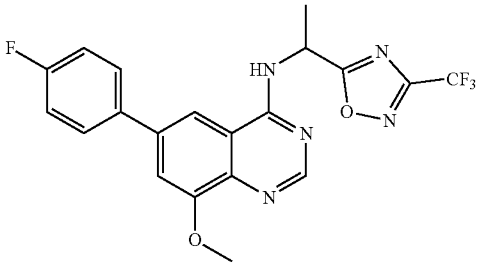 [SMILES: COc1cc(-c2ccc(F)cc2)cc2c(NC(C)c3nc(C(F)(F)F)no3)ncnc12] | 6-(4-Fluorophenyl)-8-methoxy-N-(1-(3-(trifluoromethyl)-1,2,4-oxadiazol-5-yl)ethyl)quinazolin-4-amine |
| Example 13 | 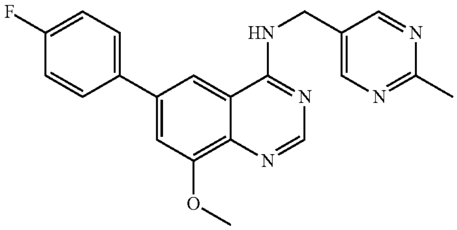 [SMILES: COc1cc(-c2ccc(F)cc2)cc2c(NCc3cnc(C)nc3)ncnc12] | 6-(4-Fluorophenyl)-8-methoxy-N-((2-methylpyrimidin-5-yl)methyl)quinazolin-4- |
| Example 14 | 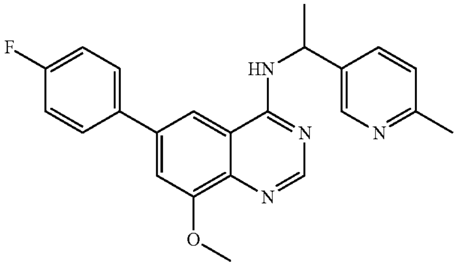 [SMILES: COc1cc(-c2ccc(F)cc2)cc2c(NC(C)c3ccc(C)nc3)ncnc12] | 6-(4-Fluorophenyl)-8-methoxy-N-(1-(6-methylpyridin-3-yl)ethyl)quinazolin-4-amine |

TABLE 4-continued

| List of preferred compounds having Formula (I) | | |
|---|---|---|
| Ex. N. | Structure | Chemical Name |
| Example 15 | 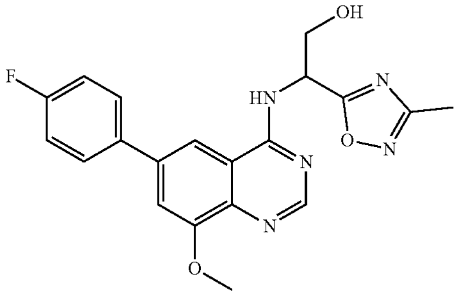 [SMILES: COc1cc(-c2ccc(F)cc2)cc2c(NC(CO)c3nc(C)no3)ncnc12] | 2-((6-(4-Fluorophenyl)-8-methoxyquinazolin-4-yl)amino)-2-(3-methyl-1,2,4-oxadiazol-5-yl)ethan-1-ol |
| Example 16 | 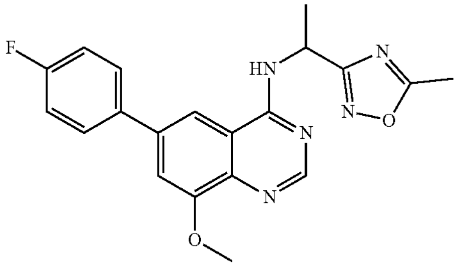 [SMILES: COc1cc(-c2ccc(F)cc2)cc2c(NC(C)c3noc(C)n3)ncnc12] | 6-(4-Fluorophenyl)-8-methoxy-N-(1-(5-methyl-1,2,4-oxadiazol-3-yl)ethyl)quinazolin-4-amine |
| Example 18 | 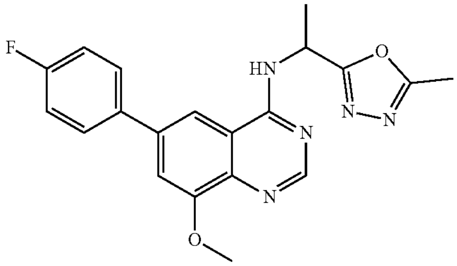 [SMILES: COc1cc(-c2ccc(F)cc2)cc2c(NC(C)c3nnc(C)o3)ncnc12] | 6-(4-Fluorophenyl)-8-methoxy-N-(1-(5-methyl-1,3,4-oxadiazol-2-yl)ethyl)quinazolin-4-amine |
| Example 17 | 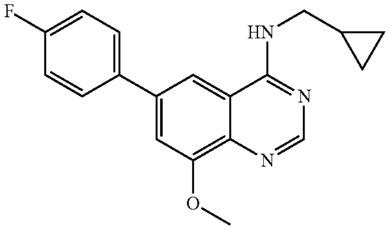 [SMILES: COc1cc(-c2ccc(F)cc2)cc2c(NCC3CC3)ncnc12] | N-(Cyclopropylmethyl)-6-(4-fluorophenyl)-8-methoxyquinazolin-4-amine |
| Example 19 | 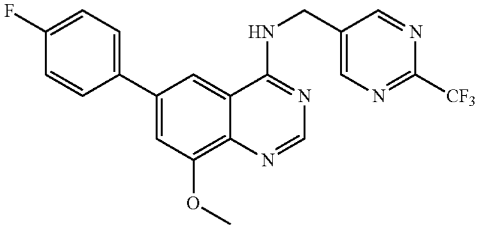 [SMILES: COc1cc(-c2ccc(F)cc2)cc2c(NCc3cnc(C(F)(F)F)nc3)ncnc12] | 6-(4-Fluorophenyl)-8-methoxy-N-((2-(trifluoromethyl)pyrimidin-5-yl)methyl)quinazolin-4-amine |
| Example 20 | 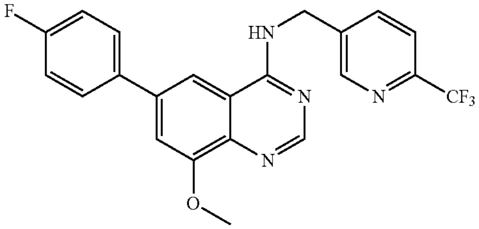 | 6-(4-Fluorophenyl)-8-methoxy-N-((6-(trifluoromethyl)pyridin-3-yl)methyl)quinazolin-4-amine |

TABLE 4-continued

| List of preferred compounds having Formula (I) | | |
|---|---|---|
| Ex. N. | Structure | Chemical Name |
| Example 21 | 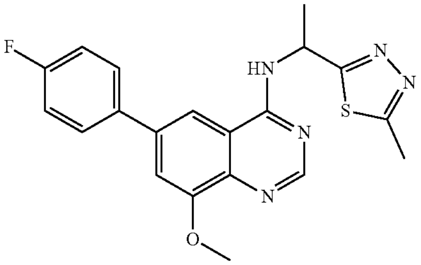 | 6-(4-Fluorophenyl)-8-methoxy-N-(1-(5-methyl-1,3,4-thiadiazol-2-yl)ethyl)quinazolin-4-amine |
| Example 22 | 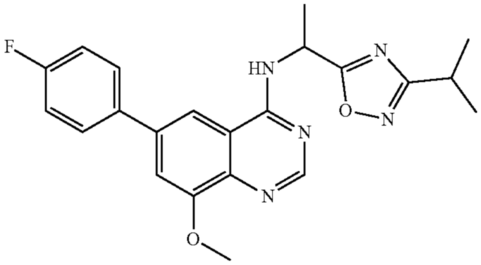 [SMILES: COc1cc(-c2ccc(F)cc2)cc2c(NC(C)c3nc(C(C)C)no3)ncnc12] | 6-(4-Fluorophenyl)-N-(1-(3-isopropyl-1,2,4-oxadiazol-5-yl)ethyl)-8-methoxyquinazolin-4-amine |
| Example 23 | 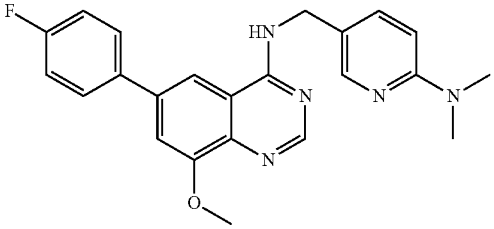 [SMILES: COc1cc(-c2ccc(F)cc2)cc2c(NCc3ccc(N(C)C)nc3)ncnc12] | N-((6-(Dimethylamino)pyridin-3-yl)methyl)-6-(4-fluorophenyl)-8-methoxyquinazolin-4-amine |
| Example 24 | 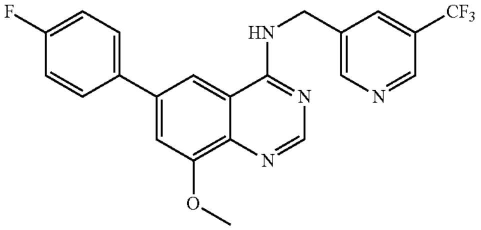 [SMILES: COc1cc(-c2ccc(F)cc2)cc2c(NCc3cncc(C(F)(F)F)c3)ncnc12] | 6-(4-Fluorophenyl)-8-methoxy-N-[[5-(trifluoromethyl)-3-pyridyl]methyl]quinazolin-4-amine |
| Example 25 | 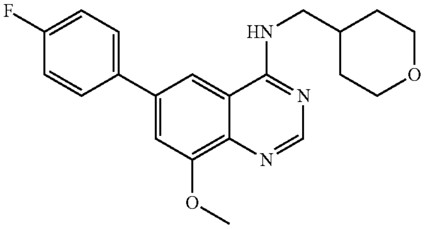 [SMILES: COc1cc(-c2ccc(F)cc2)cc2c(NCC3CCOCC3)ncnc12] | 6-(4-Fluorophenyl)-8-methoxy-N-((tetrahydro-2H-pyran-4-yl)methyl)quinazolin-4-amine |
| Example 26 | 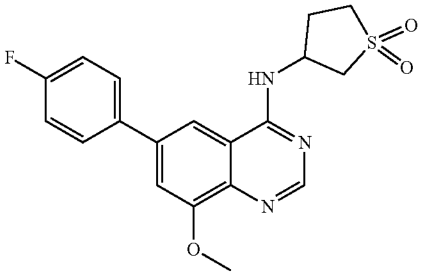 [SMILES: COc1cc(-c2ccc(F)cc2)cc2c(NC3CCS(=O)(=O)C3)ncnc12] | 3-((6-(4-Fluorophenyl)-8-methoxyquinazolin-4-yl)amino)tetrahydrothiophene 1,1-dioxide |

TABLE 4-continued

| List of preferred compounds having Formula (I) | | |
|---|---|---|
| Ex. N. | Structure | Chemical Name |
| Example 27 | 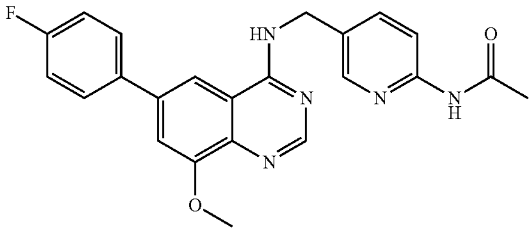 [SMILES: COc1cc(-c2ccc(F)cc2)cc2c(NCc3ccc(NC(C)=O)nc3)ncnc12] | N-(5-(((6-(4-Fluorophenyl)-8-methoxyquinazolin-4-yl)amino)methyl)pyridin-2-yl)acetamide |
| Example 28 | 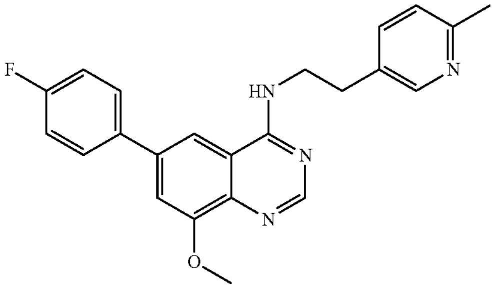 [SMILES: COc1cc(-c2ccc(F)cc2)cc2c(NCCc3ccc(C)nc3)ncnc12] | 6-(4-Fluorophenyl)-8-methoxy-N-(2-(6-methylpyridin-3-yl)ethylquinazolin-4-amine |
| Example 29 | 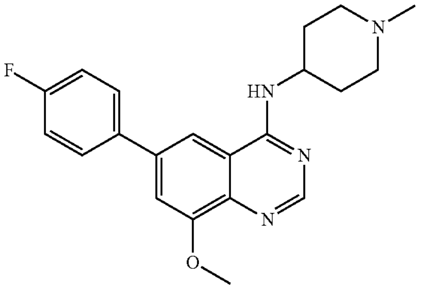 [SMILES: COc1cc(-c2ccc(F)cc2)cc2c(NC3CCN(C)CC3)ncnc12] | 6-(4-Fluorophenyl)-8-methoxy-N-(1-methylpiperidin-4-yl)quinazolin-4-amine |
| Example 30 | 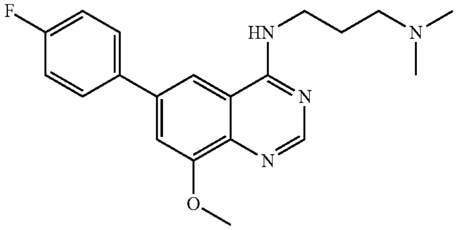 [SMILES: COc1cc(-c2ccc(F)cc2)cc2c(NCCCN(C)C)ncnc12] | N1-(6-(4-Fluorophenyl)-8-methoxyquinazolin-4-yl)-N3,N3-dimethylpropane-1,3-diamine |
| Example 31 | 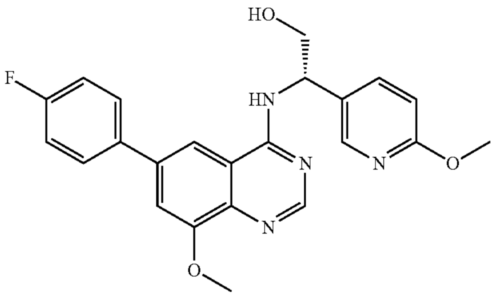 [SMILES: COc1ccc([C@@H](CO)Nc2ncnc3c(OC)cc(-c4ccc(F)cc4)cc23)cn1] | (S)-2-((6-(4-Fluorophenyl)-8-methoxyquinazolin-4-yl)amino)-2-(6-methoxypyridin-3-yl)ethan-1-ol |

TABLE 4-continued

| List of preferred compounds having Formula (I) | | |
|---|---|---|
| Ex. N. | Structure | Chemical Name |
| Example 32 | 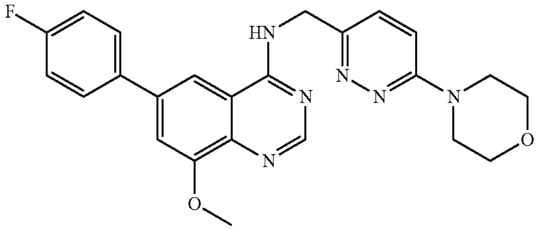 [SMILES: COc1cc(-c2ccc(F)cc2)cc2c(NCc3ccc(N4CCOCC4)nn3)ncnc12] | 6-(4-Fluorophenyl)-8-methoxy-N-((6-morpholinopyridazin-3-yl)methyl)quinazolin-4-amine |
| Example 33 | 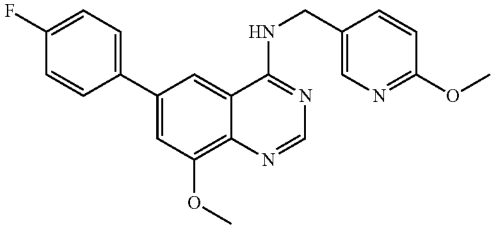 [SMILES: COc1ccc(CNc2ncnc3c(OC)cc(-c4ccc(F)cc4)cc23)cn1] | 6-(4-Fluorophenyl)-8-methoxy-N-((6-methoxypyridin-3-yl)methyl)quinazolin-4-amine |
| Example 34 | 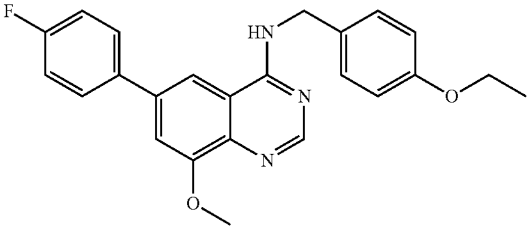 [SMILES: CCOc1ccc(CNc2ncnc3c(OC)cc(-c4ccc(F)cc4)cc23)cc1] | N-(4-ethoxybenzyl)-6-(4-fluorophenyl)-8-methoxyquinazolin-4-amine |
| Example 35 | 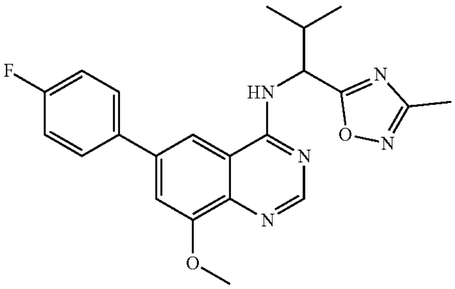 [SMILES: COc1cc(-c2ccc(F)cc2)cc2c(NC(c3nc(C)no3)C(C)C)ncnc12] | 6-(4-Fluorophenyl)-8-methoxy-N-(2-methyl-1-(3-methyl-1,2,4-oxadiazol-5-yl)propyl)quinazolin-4-amine |
| Example 36 | 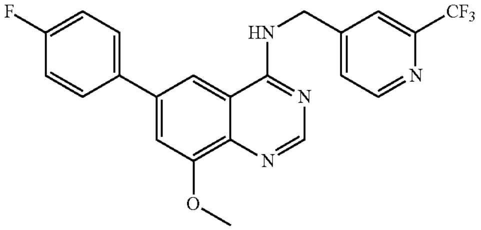 [SMILES: COc1cc(-c2ccc(F)cc2)cc2c(NCc3ccnc(C(F)(F)F)c3)ncnc12] | 6-(4-Fluorophenyl)-8-methoxy-N-[[2-(trifluoromethyl)-4-pyridyl]methyl]quinazolin-4-amine |
| Example 38 | 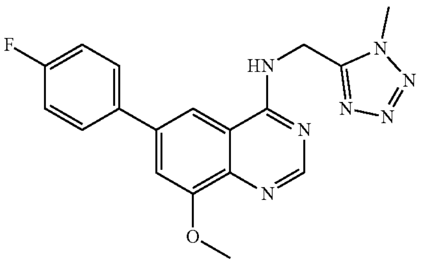 | 6-(4-Fluorophenyl)-8-methoxy-N-((1-methyl-1H-tetrazol-5-yl)methyl)quinazolin-4-amine |

TABLE 4-continued

| List of preferred compounds having Formula (I) | | |
|---|---|---|
| Ex. N. | Structure | Chemical Name |
| Example 39 | 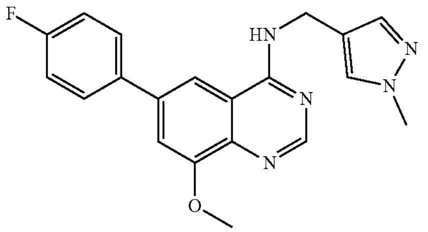 [SMILES: COc1cc(-c2ccc(F)cc2)cc2c(NCc3cnn(C)c3)ncnc12] | 6-(4-Fluorophenyl)-8-methoxy-N-((1-methyl-1H-pyrazol-4-yl)methyl)quinazolin-4-amine |
| Example 41 | 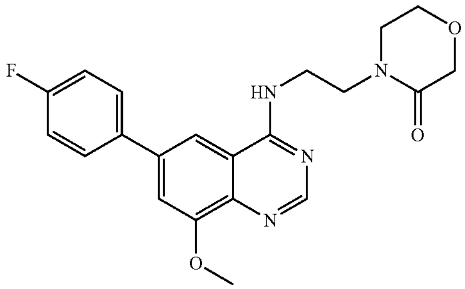 [SMILES: COc1cc(-c2ccc(F)cc2)cc2c(NCCN3CCOCC3=O)ncnc12] | 4-(2-((6-(4-Fluorophenyl)-8-methoxyquinazolin-4-yl)amino)ethyl)morpholin-3-one |
| Example 42 | 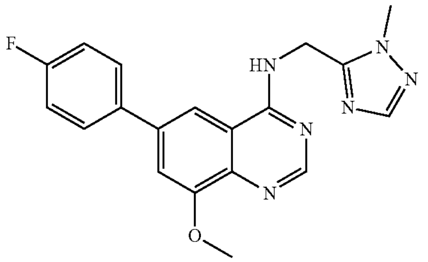 | 6-(4-Fluorophenyl)-8-methoxy-N-((1-methyl-1H-1,2,4-triazol-5-yl)methyl)quinazolin-4-amine |
| Example 43 | 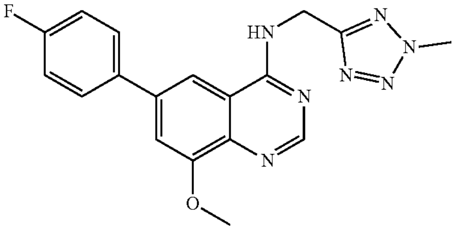 [SMILES: COc1cc(-c2ccc(F)cc2)cc2c(NCc3nnn(C)n3)ncnc12] | 6-(4-Fluorophenyl)-8-methoxy-N-((2-methyl-2H-tetrazol-5-yl)methyl)quinazolin-4-amine |
| Example 44 | 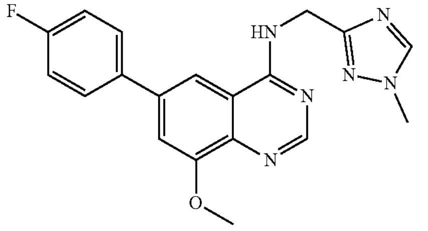 [SMILES: COc1cc(-c2ccc(F)cc2)cc2c(NCc3ncn(C)n3)ncnc12] | 6-(4-Fluorophenyl)-8-methoxy-N-((1-methyl-1H-1,2,4-triazol-3-yl)methyl)quinazolin-4-amine |
| Example 45 | 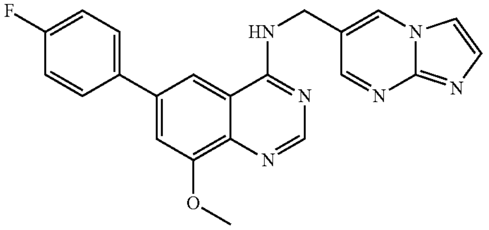 [SMILES: COc1cc(-c2ccc(F)cc2)cc2c(NCc3cnc4nccn4c3)ncnc12] | 6-(4-Fluorophenyl)-N-(imidazo[1,2-a]pyrimidin-6-ylmethyl)-8-methoxyquinazolin-4-amine |

TABLE 4-continued

List of preferred compounds having Formula (I)

| Ex. N. | Structure | Chemical Name |
| --- | --- | --- |
| Example 46 | 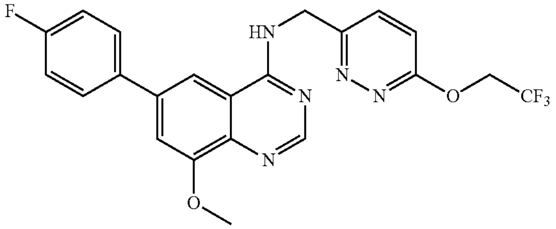 [SMILES: COc1cc(-c2ccc(F)cc2)cc2c(NCc3ccc(OCC(F)(F)F)nn3)ncnc12] | 6-(4-Fluorophenyl)-8-methoxy-N-((6-(2,2,2-trifluoroethoxy)pyridazin-3-yl)methyl)quinazolin-4-amine |
| Example 47 | 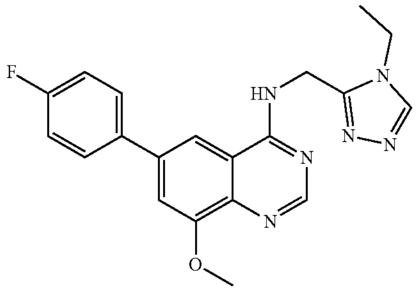 [SMILES: CCn1cnnc1CNc1ncnc2c(OC)cc(-c3ccc(F)cc3)cc12] | N-((4-Ethyl-4H-1,2,4-triazol-3-yl)methyl)-6-(4-fluorophenyl)-8-methoxyquinazolin-4-amine |
| Example 48 | 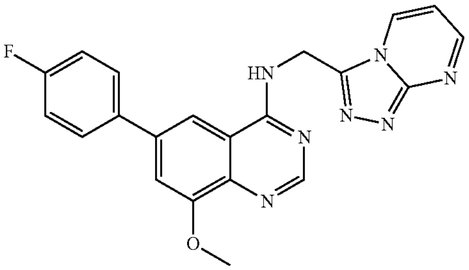 [SMILES: COc1cc(-c2ccc(F)cc2)cc2c(NCc3nnc4ncccn34)ncnc12] | N-([1,2,4]Triazolo[4,3-a]pyrimidin-3-ylmethyl)-6-(4-fluorophenyl)-8-methoxyquinazolin-4-amine |
| Example 49 | 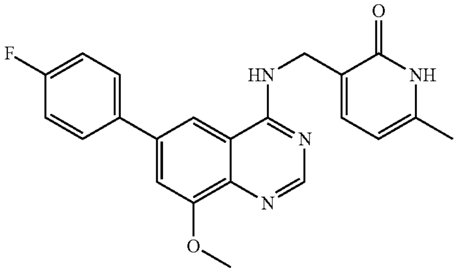 [SMILES: COc1cc(-c2ccc(F)cc2)cc2c(NCc3ccc(C)[nH]c3=O)ncnc12] | 3-(((6-(4-Fluorophenyl)-8-methoxyquinazolin-4-yl)amino)methyl)-6-methylpyridin-2(1H)-one |
| Example 50 | 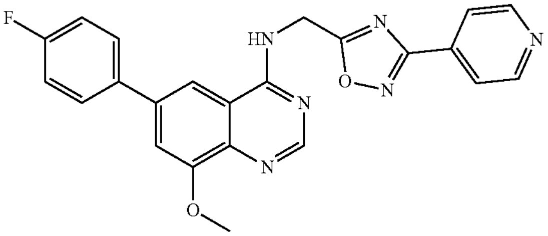 [SMILES: COc1cc(-c2ccc(F)cc2)cc2c(NCc3nc(-c4ccncc4)no3)ncnc12] | 6-(4-Fluorophenyl)-8-methoxy-N-((3-(pyridin-4-yl)-1,2,4-oxadiazol-5-yl)methyl)quinazolin-4-amine |
| Example 51 | 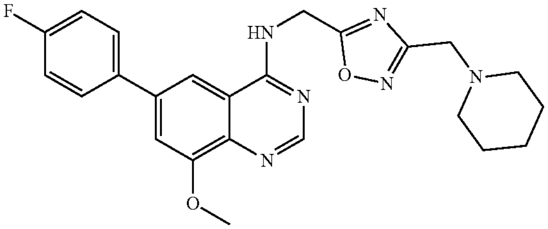 [SMILES: COc1cc(-c2ccc(F)cc2)cc2c(NCc3nc(CN4CCCCC4)no3)ncnc12] | 6-(4-Fluorophenyl)-8-methoxy-N-((3-(piperidin-1-ylmethyl)-1,2,4-oxadiazol-5-yl)methyl)quinazolin-4-amine |

TABLE 4-continued

| List of preferred compounds having Formula (I) | | |
|---|---|---|
| Ex. N. | Structure | Chemical Name |
| Example 52 | 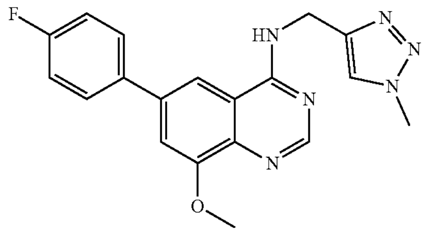 [SMILES: COc1cc(-c2ccc(F)cc2)cc2c(NCc3cn(C)nn3)ncnc12] | 6-(4-Fluorophenyl)-8-methoxy-N-((1-methyl-1H-1,2,3-triazol-4-yl)methyl)quinazolin-4-amine |
| Example 53 | 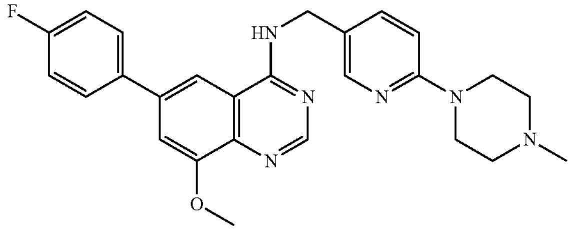 [SMILES: COc1cc(-c2ccc(F)cc2)cc2c(NCc3ccc(N4CCN(C)CC4)nc3)ncnc12] | 6-(4-Fluorophenyl)-8-methoxy-N-((6-(4-methylpiperazin-1-yl)pyridin-3-yl)methyl)quinazolin-4-amine |
| Example 54 | 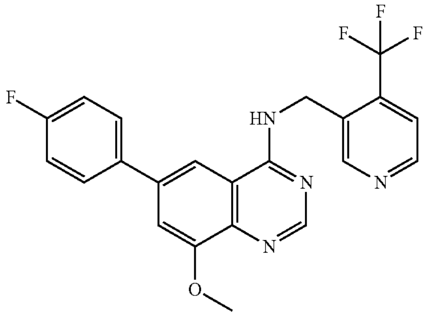 [SMILES: COc1cc(-c2ccc(F)cc2)cc2c(NCc3cnccc3C(F)(F)F)ncnc12] | 6-(4-Fluorophenyl)-8-methoxy-N-((4-(trifluoromethyl)pyridin-3-yl)methyl)quinazolin-4-amine |
| Example 55 | 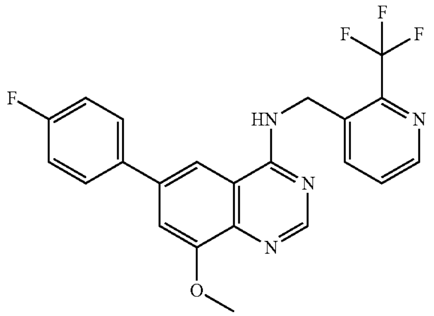 [SMILES: COc1cc(-c2ccc(F)cc2)cc2c(NCc3cccnc3C(F)(F)F)ncnc12] | 6-(4-Fluorophenyl)-8-methoxy-N-((2-(trifluoromethyl)pyridin-3-yl)methyl)quinazolin-4-amine |
| Example 56 | 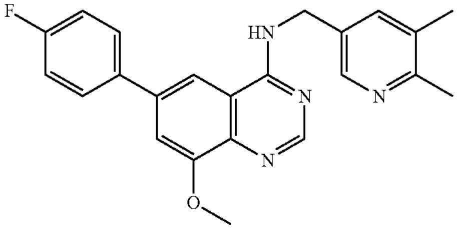 [SMILES: COc1cc(-c2ccc(F)cc2)cc2c(NCc3cnc(C)c(C)c3)ncnc12] | N-((5,6-Dimethylpyridin-3-yl)methyl)-6-(4-fluorophenyl)-8-methoxyquinazolin-4-amine |

TABLE 4-continued

List of preferred compounds having Formula (I)

| Ex. N. | Structure | Chemical Name |
|---|---|---|
| Example 57 | 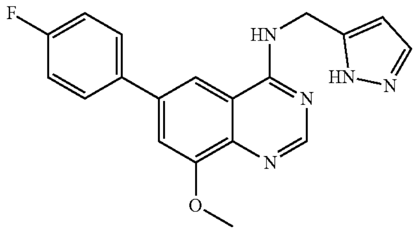 | 6-(4-Fluorophenyl)-8-methoxy-N-(2-methyl-1-(3-methyl-1,2,4-oxadiazol-5-yl)propyl)quinazolin-4-amine |
| Example 58 | 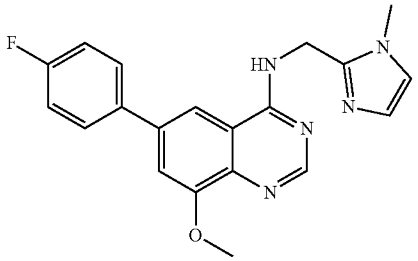 [SMILES: COc1cc(-c2ccc(F)cc2)cc2c(NCc3nccn3C)ncnc12] | 6-(4-Fluorophenyl)-8-methoxy-N-[(1-methylimidazol-2-yl)methyl]quinazolin-4-amine |
| Example 59 | 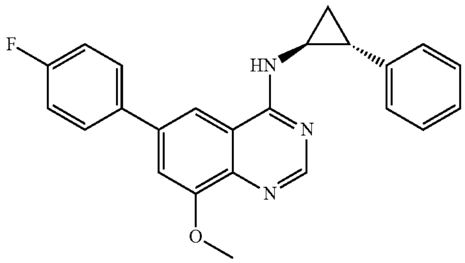 [SMILES: COc1cc(-c2ccc(F)cc2)cc2c(N[C@H]3C[C@@H]3c3ccccc3)ncnc12] | 6-(4-Fluorophenyl)-8-methoxy-N-(2-phenylcyclopropyl)quinazolin-4-amine |
| Example 60 | 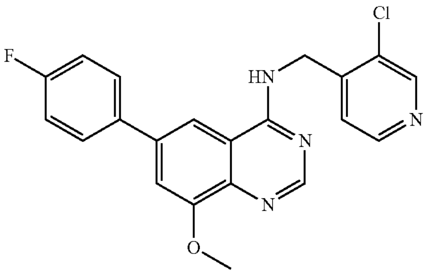 [SMILES: COc1cc(-c2ccc(F)cc2)cc2c(NCc3ccncc3Cl)ncnc12] | N-[(3-Chloro-4-pyridyl)methyl]-6-(4-fluorophenyl)-8-methoxy-quinazolin-4-amine |
| Example 61 | 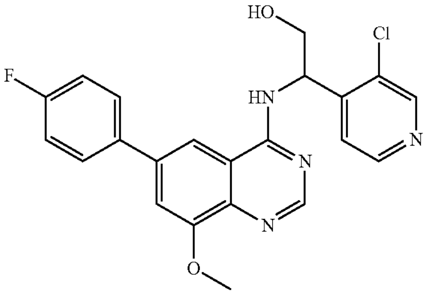 [SMILES: COc1cc(-c2ccc(F)cc2)cc2c(NC(CO)c3ccncc3Cl)ncnc12] | 2-(3-Chloro-4-pyridyl)-2-[[6-(4-fluorophenyl)-8-methoxy-quinazolin-4-yl]amino]ethanol |

TABLE 4-continued

| List of preferred compounds having Formula (I) | | |
|---|---|---|
| Ex. N. | Structure | Chemical Name |
| Example 62 | 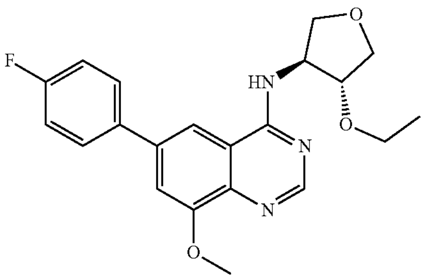 [SMILES: CCO[C@H]1COC[C@@H]1Nc1ncnc2c(OC)cc(-c3ccc(F)cc3)cc12] | N-[(3S,4R)-4-Ethoxytetrahydrofuran-3-yl]-6-(4-fluorophenyl)-8-methoxy-quinazolin-4-amine |
| Example 63 | 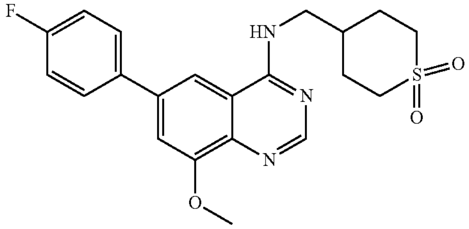 [SMILES: COc1cc(-c2ccc(F)cc2)cc2c(NCC3CCS(=O)(=O)CC3)ncnc12] | N-[(1,1-Dioxothian-4-yl)methyl]-6-(4-fluorophenyl)-8-methoxy-quinazolin-4-amine |
| Example 64 | 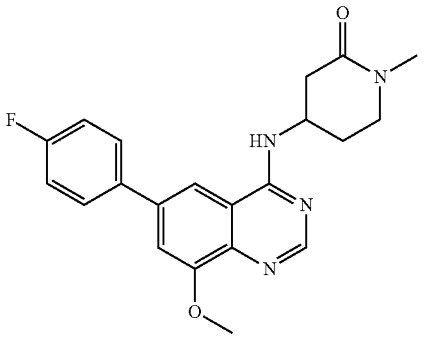 [SMILES: COc1cc(-c2ccc(F)cc2)cc2c(NC3CCN(C)C(=O)C3)ncnc12] | 4-[[6-(4-Fluorophenyl)-8-methoxy-quinazolin-4-yl]amino]-1-methyl-piperidin-2-one |
| Example 65 | 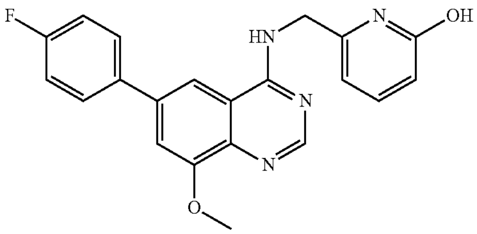 [SMILES: COc1cc(-c2ccc(F)cc2)cc2c(NCc3cccc(O)n3)ncnc12] | 6-[[[6-(4-Fluorophenyl)-8-methoxy-quinazolin-4-yl]amino]methyl]-1H-pyridin-2-one |
| Example 66 | 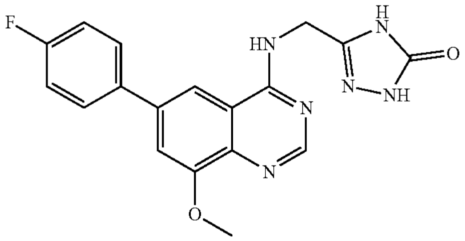 [SMILES: COc1cc(-c2ccc(F)cc2)cc2c(NCc3n[nH]c(=O)[nH]3)ncnc12] | 3-[[[6-(4-Fluorophenyl)-8-methoxy-quinazolin-4-yl]amino]methyl]-1,4-dihydro-1,2,4-triazol-5-one |

TABLE 4-continued

| List of preferred compounds having Formula (I) | | |
|---|---|---|
| Ex. N. | Structure | Chemical Name |
| Example 67 | 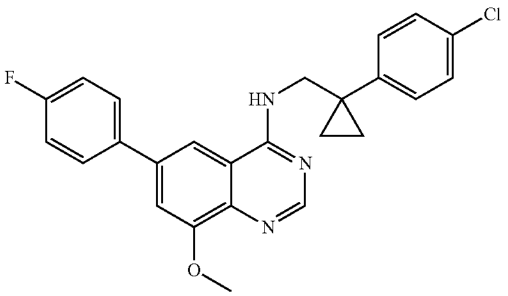 [SMILES: COc1cc(-c2ccc(F)cc2)cc2c(NCC3(c4ccc(Cl)cc4)CC3)ncnc12] | N-[[1-(4-Chlorophenyl)cyclopropyl]methyl]-6-(4-fluorophenyl)-8-methoxy-quinazolin-4-amine |
| Example 68 | 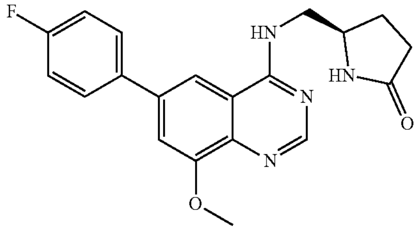 [SMILES: COc1cc(-c2ccc(F)cc2)cc2c(NC[C@H]3CCC(=O)N3)ncnc12] | (5R)-5-[[[6-(4-Fluorophenyl)-8-methoxy-quinazolin-4-yl]amino]methyl]pyrrolidin-2-one |
| Example 69 | 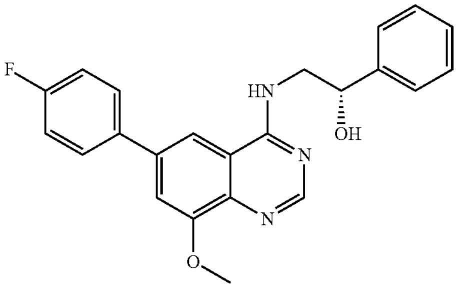 [SMILES: COc1cc(-c2ccc(F)cc2)cc2c(NC[C@@H](O)c3ccccc3)ncnc12] | (1S)-2-[[6-(4-Fluorophenyl)-8-methoxy-quinazolin-4-yl]amino]-1-phenyl-ethanol |
| Example 70 | 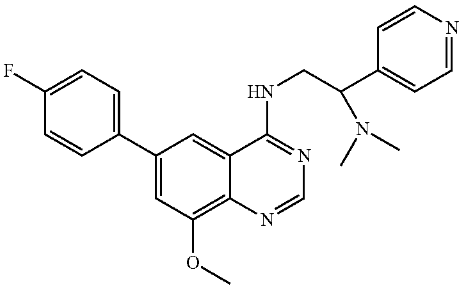 [SMILES: COc1cc(-c2ccc(F)cc2)cc2c(NCC(c3ccncc3)N(C)C)ncnc12] | N'-[6-(4-Fluorophenyl)-8-methoxy-quinazolin-4-yl]-N,N-dimethyl-1-(4-pyridyl)ethane-1,2-diamine |
| Example 71 | 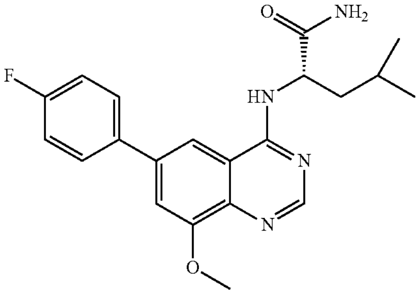 [SMILES: COc1cc(-c2ccc(F)cc2)cc2c(N[C@@H](CC(C)C)C(N)=O)ncnc12] | (2S)-2-[[6-(4-fluorophenyl)-8-methoxy-quinazolin-4-yl]amino]-4-methyl-pentanamide |

TABLE 4-continued

| List of preferred compounds having Formula (I) | | |
|---|---|---|
| Ex. N. | Structure | Chemical Name |
| Example 72 | 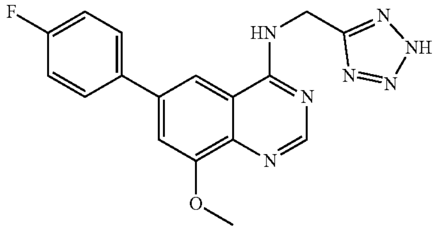 [SMILES: COc1cc(-c2ccc(F)cc2)cc2c(NCc3nn[nH]n3)ncnc12] | 6-(4-Fluorophenyl)-8-methoxy-N-(2H-tetrazol-5-ylmethyl)quinazolin-4-amine |
| Example 73 | 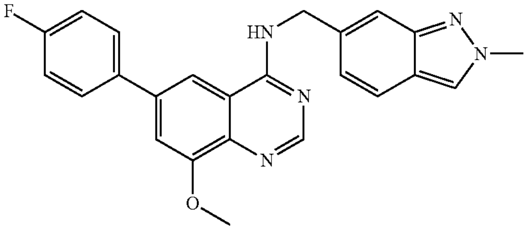 [SMILES: COc1cc(-c2ccc(F)cc2)cc2c(NCc3ccc4cn(C)nc4c3)ncnc12] | 6-(4-Fluorophenyl)-8-methoxy-N-[(2-methylindazol-6-yl)methyl]quinazolin-4-amine |
| Example 74 | 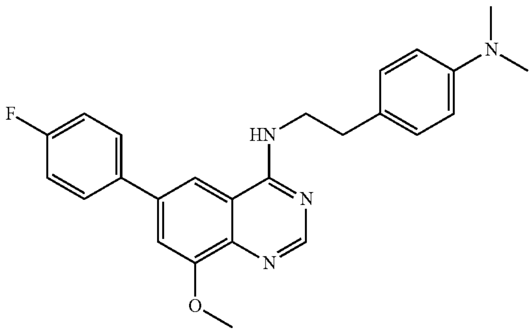 [SMILES: COc1cc(-c2ccc(F)cc2)cc2c(NCCc3ccc(N(C)C)cc3)ncnc12] | N-[2-[4-(Dimethylamino)phenyl]ethyl]-6-(4-fluorophenyl)-8-methoxy-quinazolin-4-amine |
| Example 75 | 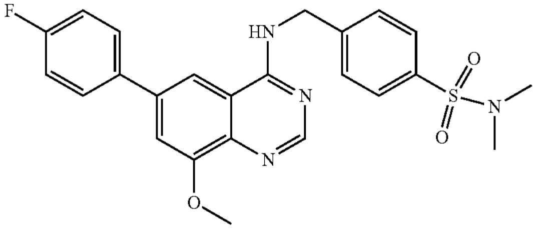 [SMILES: COc1cc(-c2ccc(F)cc2)cc2c(NCc3ccc(S(=O)(=O)N(C)C)cc3)ncnc12] | 4-[[[6-(4-Fluorophenyl)-8-methoxy-quinazolin-4-yl]amino]methyl]-N,N-dimethyl-benzenesulfonamide |
| Example 76 | 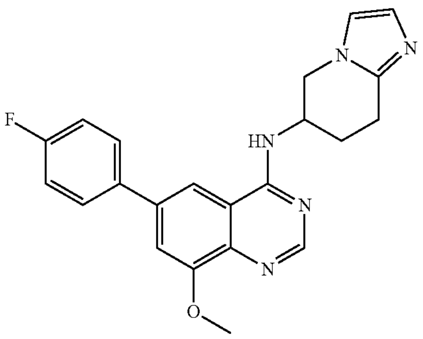 [SMILES: COc1cc(-c2ccc(F)cc2)cc2c(NC3CCc4nccn4C3)ncnc12] | 6-(4-Fluorophenyl)-8-methoxy-N-(5,6,7,8-tetrahydroimidazo[1,2-a]pyridin-6-yl)quinazolin-4-amine |

TABLE 4-continued

| List of preferred compounds having Formula (I) | | |
|---|---|---|
| Ex. N. | Structure | Chemical Name |
| Example 77 | 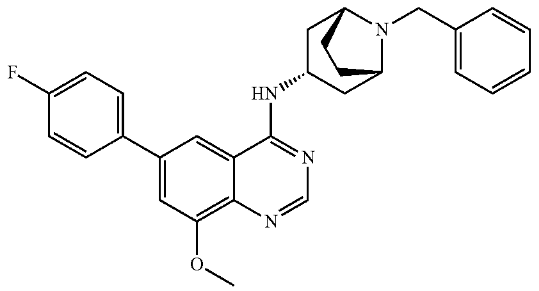 [SMILES: COc1cc(-c2ccc(F)cc2)cc2c(N[C@@H]3C[C@H]4CC[C@@H](C3)N4Cc3ccccc3)ncnc12] | N-[(1R,5S)-8-Benzyl-8-azabicyclo[3.2.1]octan-3-yl]-6-(4-fluorophenyl)-8-methoxy-quinazolin-4-amine |
| Example 78 | 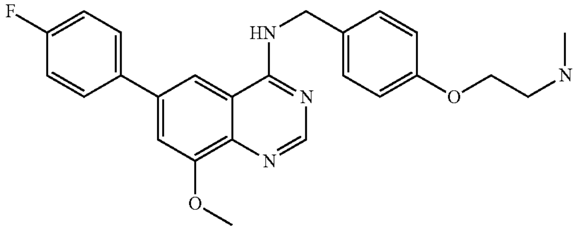 [SMILES: CNCCOc1ccc(CNc2ncnc3c(OC)cc(-c4ccc(F)cc4)cc23)cc1] | N-[[4-[2-(dimethylamino)ethoxy]phenyl]methyl]-6-(4-fluorophenyl)-8-methoxy-quinazolin-4-amine |
| Example 79 | 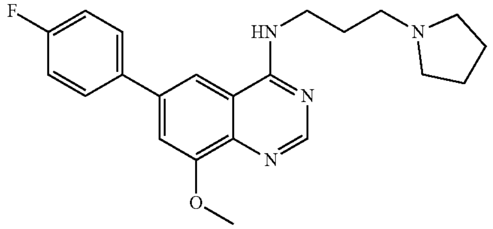 [SMILES: COc1cc(-c2ccc(F)cc2)cc2c(NCCCN3CCCC3)ncnc12] | 6-(4-Fluorophenyl)-8-methoxy-N-(3-pyrrolidin-1-ylpropyl)quinazolin-4-amine |
| Example 80 | 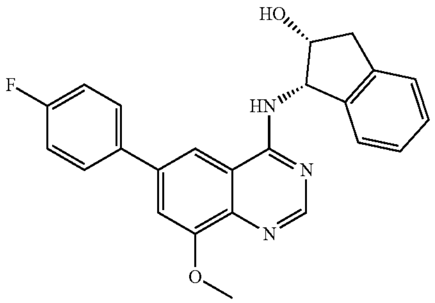 [SMILES: COc1cc(-c2ccc(F)cc2)cc2c(N[C@H]3c4ccccc4C[C@H]3O)ncnc12] | (1S,2R)-1-[[6-(4-Fluorophenyl)-8-methoxy-quinazolin-4-yl]amino]indan-2-ol |
| Example 81 | 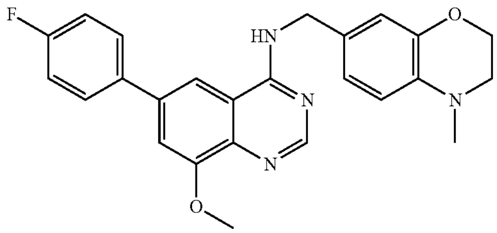 [SMILES: COc1cc(-c2ccc(F)cc2)cc2c(NCc3ccc4c(c3)OCCN4C)ncnc12] | 6-(4-Fluorophenyl)-8-methoxy-N-[(4-methyl-2,3-dihydro-1,4-benzoxazin-7-yl)methyl]quinazolin-4-amine |
| Example 82 | 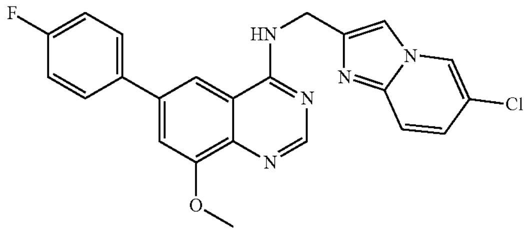 [SMILES: COc1cc(-c2ccc(F)cc2)cc2c(NCc3cn4cc(Cl)ccc4n3)ncnc12] | N-[(6-Chloroimidazo[1,2-a]pyridin-2-yl)methyl]-6-(4-fluorophenyl)-8-methoxy-quinazolin-4-amine |

TABLE 4-continued

List of preferred compounds having Formula (I)

| Ex. N. | Structure | Chemical Name |
| --- | --- | --- |
| Example 83 | 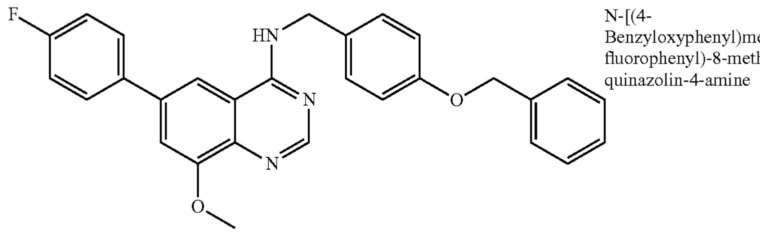 | N-[(4-Benzyloxyphenyl)methyl]-6-(4-fluorophenyl)-8-methoxy-quinazolin-4-amine |
| Example 84 | 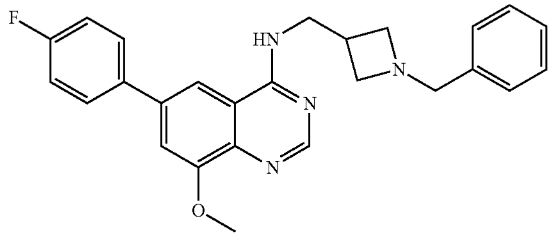 [SMILES: COc1cc(-c2ccc(F)cc2)cc2c(NCC3CN(Cc4ccccc4)C3)ncnc12] | N-[(1-Benzylazetidin-3-yl)methyl]-6-(4-fluorophenyl)-8-methoxy-quinazolin-4-amine |
| Example 85 | 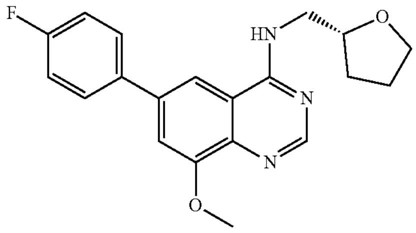 [SMILES: COc1cc(-c2ccc(F)cc2)cc2c(NC[C@H]3CCCO3)ncnc12] | 6-(4-Fluorophenyl)-8-methoxy-N-[[(2R)-tetrahydrofuran-2-yl]methyl]quinazolin-4-amine |
| Example 86 | 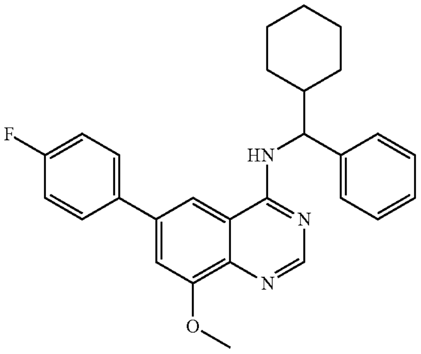 [SMILES: COc1cc(-c2ccc(F)cc2)cc2c(NC(c3ccccc3)C3CCCCC3)ncnc12] | N-[Cyclohexyl(phenyl)methyl]-6-(4-fluorophenyl)-8-methoxy-quinazolin-4-amine |
| Example 87 | 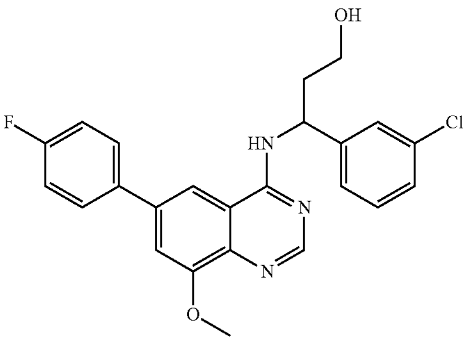 [SMILES: COc1cc(-c2ccc(F)cc2)cc2c(NC(CCO)c3cccc(Cl)c3)ncnc12] | 3-(3-Chlorophenyl)-3-[[6-(4-fluorophenyl)-8-methoxy-quinazolin-4-yl]amino]propan-1-ol |

TABLE 4-continued

| List of preferred compounds having Formula (I) | | |
|---|---|---|
| Ex. N. | Structure | Chemical Name |
| Example 88 | 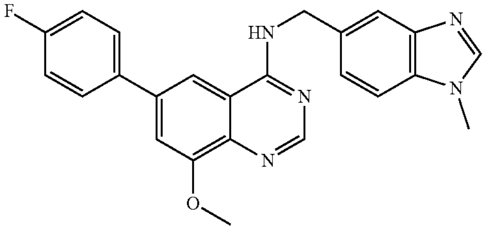 [SMILES: COc1cc(-c2ccc(F)cc2)cc2c(NCc3ccc4c(c3)ncn4C)ncnc12] | 6-(4-Fluorophenyl)-8-methoxy-N-[(1-methylbenzimidazol-5-yl)methyl]quinazolin-4-amine |
| Example 89 | 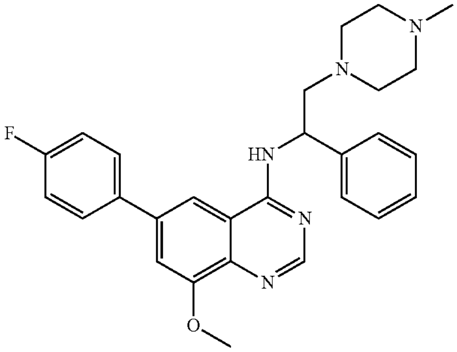 [SMILES: COc1cc(-c2ccc(F)cc2)cc2c(NC(CN3CCN(C)CC3)c3ccccc3)ncnc12] | 6-(4-Fluorophenyl)-8-methoxy-N-[2-(4-methylpiperazin-1-yl)-1-phenyl-ethyl]quinazolin-4-amine |
| Example 90 | 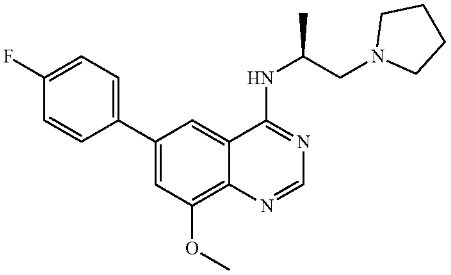 [SMILES: COc1cc(-c2ccc(F)cc2)cc2c(N[C@@H](C)CN3CCCC3)ncnc12] | 6-(4-Fluorophenyl)-8-methoxy-N-[(1S)-1-methyl-2-pyrrolidin-1-yl-ethyl]quinazolin-4-amine |
| Example 91 | 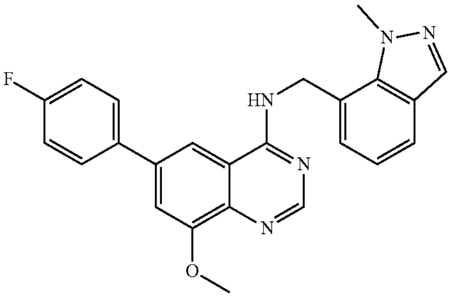 [SMILES: COc1cc(-c2ccc(F)cc2)cc2c(NCc3cccc4cnn(C)c34)ncnc12] | 6-(4-Fluorophenyl)-8-methoxy-N-[(1-methylindazol-7-yl)methyl]quinazolin-4-amine |
| Example 92 | 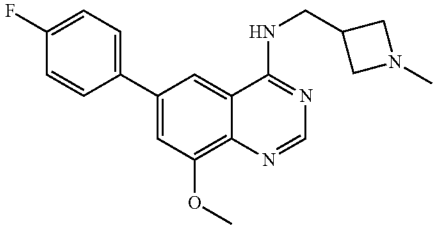 [SMILES: COc1cc(-c2ccc(F)cc2)cc2c(NCC3CN(C)C3)ncnc12] | 6-(4-Fluorophenyl)-8-methoxy-N-[(1-methylazetidin-3-yl)methyl]quinazolin-4-amine |

TABLE 4-continued

List of preferred compounds having Formula (I)

| Ex. N. | Structure | Chemical Name |
|---|---|---|
| Example 93 | 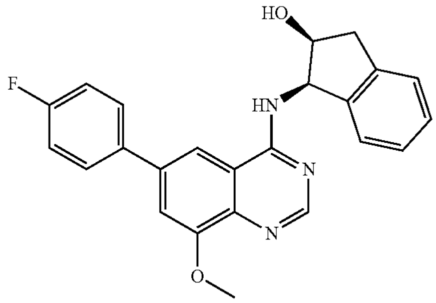 [SMILES: COc1cc(-c2ccc(F)cc2)cc2c(N[C@@H]3c4ccccc4C[C@@H]3O)ncnc12] | (1R,2S)-1-[[6-(4-Fluorophenyl)-8-methoxy-quinazolin-4-yl]amino]indan-2-ol |
| Example 94 | 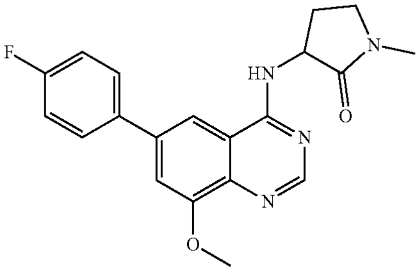 [SMILES: COc1cc(-c2ccc(F)cc2)cc2c(NC3CCN(C)C3=O)ncnc12] | 3-[[6-(4-Fluorophenyl)-8-methoxy-quinazolin-4-yl]amino]-1-methyl-pyrrolidin-2-one |
| Example 95 | 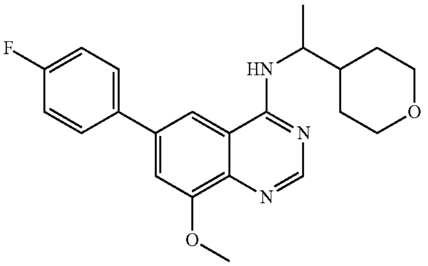 [SMILES: COc1cc(-c2ccc(F)cc2)cc2c(NC(C)C3CCOCC3)ncnc12] | 6-(4-Fluorophenyl)-8-methoxy-N-(1-tetrahydropyran-4-ylethyl)quinazolin-4-amine |
| Example 96 | 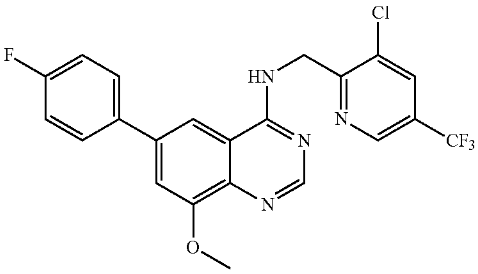 [SMILES: COc1cc(-c2ccc(F)cc2)cc2c(NCc3ncc(C(F)(F)F)cc3Cl)ncnc12] | N-[[3-Chloro-5-(trifluoromethyl)-2-pyridyl]methyl]-6-(4-fluorophenyl)-8-methoxy-quinazolin-4-amine |
| Example 97 | 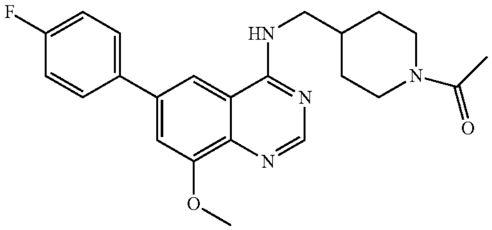 [SMILES: COc1cc(-c2ccc(F)cc2)cc2c(NCC3CCN(C(C)=O)CC3)ncnc12] | 1-[4-[[[6-(4-Fluorophenyl)-8-methoxy-quinazolin-4-yl]amino]methyl]-1-piperidyl]ethanone |

TABLE 4-continued

List of preferred compounds having Formula (I)

| Ex. N. | Structure | Chemical Name |
|---|---|---|
| Example 98 | 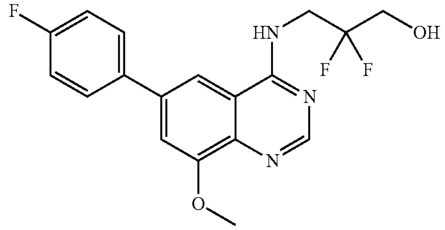 [SMILES: COc1cc(-c2ccc(F)cc2)cc2c(NCC(F)(F)CO)ncnc12] | 2,2-Difluoro-3-[[6-(4-fluorophenyl)-8-methoxy-quinazolin-4-yl]amino]propan-1-ol |
| Example 99 | 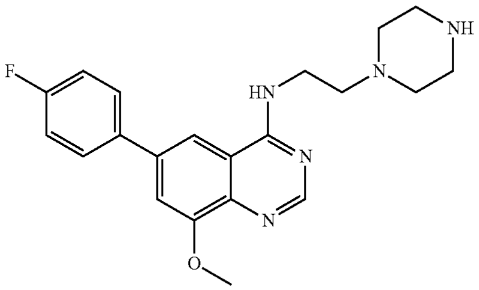 [SMILES: COc1cc(-c2ccc(F)cc2)cc2c(NCCN3CCNCC3)ncnc12] | 6-(4-Fluorophenyl)-8-methoxy-N-(2-piperazin-1-ylethyl)quinazolin-4-amine |
| Example 100 | 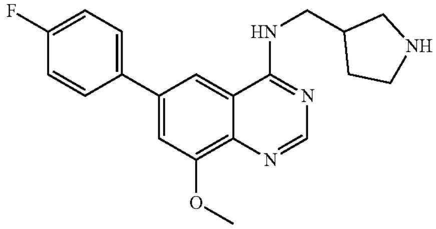 [SMILES: COc1cc(-c2ccc(F)cc2)cc2c(NCC3CCNC3)ncnc12] | 6-(4-Fluorophenyl)-8-methoxy-N-(pyrrolidin-3-ylmethyl)quinazolin-4-amine |
| Example 101 | 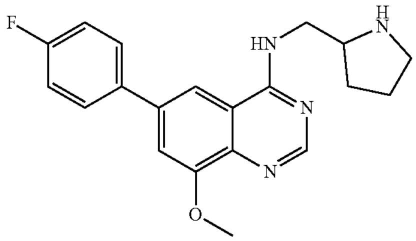 [SMILES: COc1cc(-c2ccc(F)cc2)cc2c(NCC3CCCN3)ncnc12] | 6-(4-Fluorophenyl)-8-methoxy-N-(pyrrolidin-2-ylmethyl)quinazolin-4-amine |
| Example 102 | 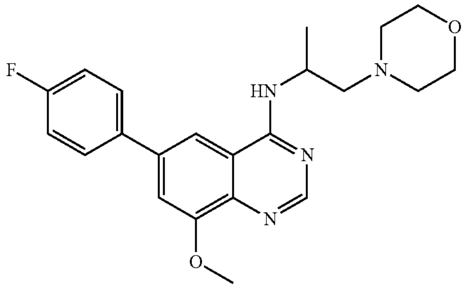 [SMILES: COc1cc(-c2ccc(F)cc2)cc2c(NC(C)CN3CCOCC3)ncnc12] | 6-(4-Fluorophenyl)-8-methoxy-N-(1-methyl-2-morpholino-ethyl)quinazolin-4-amine |
| Example 103 | 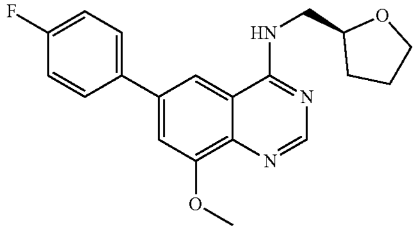 [SMILES: COc1cc(-c2ccc(F)cc2)cc2c(NC[C@@H]3CCCO3)ncnc12] | (S)-6-(4-Fluorophenyl)-8-methoxy-N-((tetrahydrofuran-2-yl)methyl)quinazolin-4-amine |

TABLE 4-continued

List of preferred compounds having Formula (I)

| Ex. N. | Structure | Chemical Name |
| --- | --- | --- |
| Example 104 | 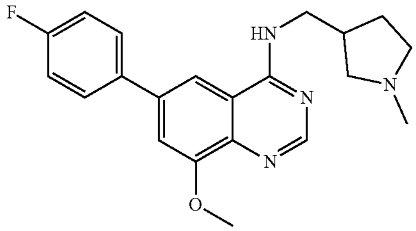 [SMILES: COc1cc(-c2ccc(F)cc2)cc2c(NCC3CCN(C)C3)ncnc12] | 6-(4-Fluorophenyl)-8-methoxy-N-((1-methylpyrrolidin-3-yl)methyl)quinazolin-4-amine |
| Example 105 | 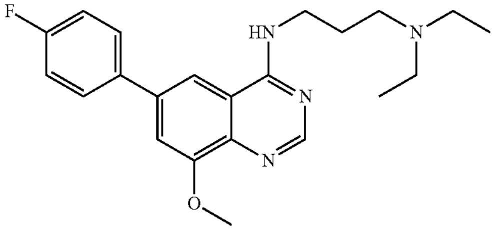 [SMILES: CCN(CC)CCCNc1ncnc2c(OC)cc(-c3ccc(F)cc3)cc12] | N1,N1-Diethyl-N3-(6-(4-fluorophenyl)-8-methoxyquinazolin-4-yl)propane-1,3-diamine |
| Example 106 | 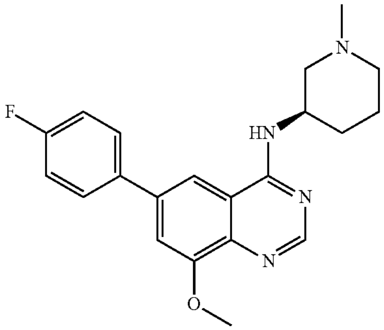 [SMILES: COc1cc(-c2ccc(F)cc2)cc2c(N[C@@H]3CCCN(C)C3)ncnc12] | (R)-6-(4-Fluorophenyl)-8-methoxy-N-(1-methylpiperidin-3-yl)quinazolin-4-amine |
| Example 107 | 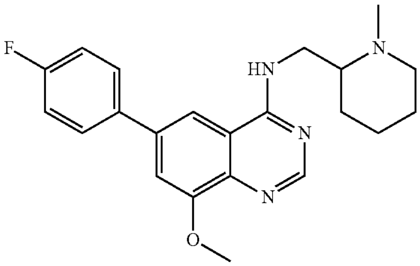 [SMILES: COc1cc(-c2ccc(F)cc2)cc2c(NCC3CCCCN3C)ncnc12] | 6-(4-Fluorophenyl)-8-methoxy-N-((1-methylpiperidin-2-yl)methyl)quinazolin-4-amine |
| Example 108 | 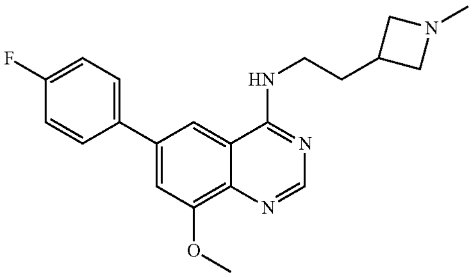 [SMILES: COc1cc(-c2ccc(F)cc2)cc2c(NCCC3CN(C)C3)ncnc12] | 6-(4-Fluorophenyl)-8-methoxy-N-(2-(1-methylazetidin-3-yl)ethyl)quinazolin-4-amine |

TABLE 4-continued

| List of preferred compounds having Formula (I) | | |
|---|---|---|
| Ex. N. | Structure | Chemical Name |
| Example 109 | 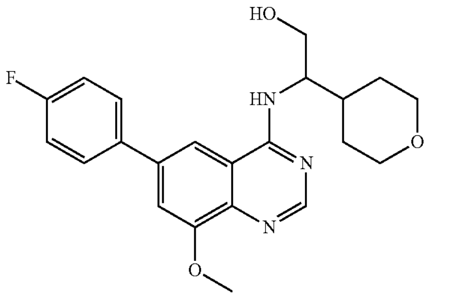 [SMILES: COc1cc(-c2ccc(F)cc2)cc2c(NC(CO)C3CCOCC3)ncnc12] | 2-[[6-(4-Fluorophenyl)-8-methoxy-quinazolin-4-yl]amino]-2-tetrahydropyran-4-yl-ethanol formate |
| Example 110 | 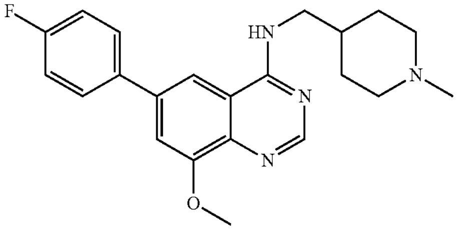 [SMILES: COc1cc(-c2ccc(F)cc2)cc2c(NCC3CCN(C)CC3)ncnc12] | 6-(4-Fluorophenyl)-8-methoxy-N-[(1-methyl-4-piperidyl)methyl]quinazolin-4-amine |
| Example 111 | 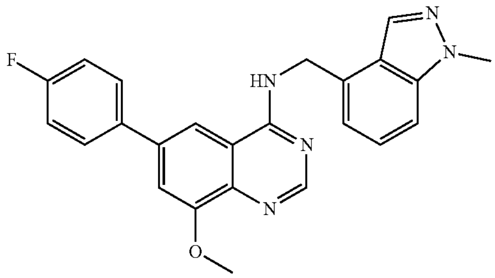 [SMILES: COc1cc(-c2ccc(F)cc2)cc2c(NCc3cccc4c3cnn4C)ncnc12] | 6-(4-Fluorophenyl)-8-methoxy-N-[(1-methylindazol-4-yl)methyl]quinazolin-4-amine |
| Example 112 | 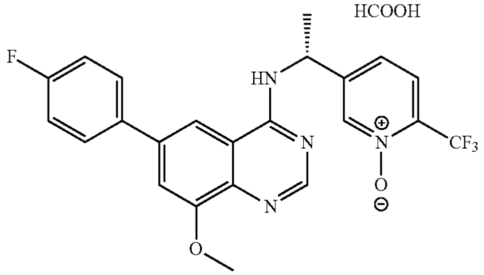 [SMILES: COc1cc(-c2ccc(F)cc2)cc2c(N[C@H](C)c3ccc(C(F)(F)F)[n+]([O-])c3)ncnc12 ; "HCOOH"] HCOOH | (R)-5-(1-((6-(4-fluorophenyl)-8-methoxyquinazolin-4-yl)amino)ethyl)-2-(trifluoromethyl)pyridine 1-oxide formate |
| Example 113 | 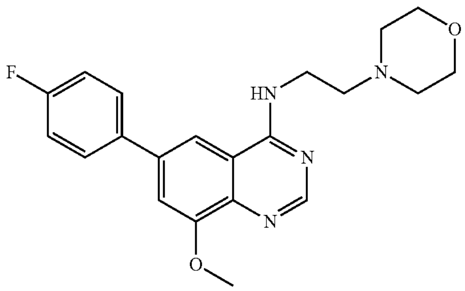 [SMILES: COc1cc(-c2ccc(F)cc2)cc2c(NCCN3CCOCC3)ncnc12] | 6-(4-fluorophenyl)-8-methoxy-N-(2-morpholinoethyl)quinazolin-4-amine |

TABLE 4-continued

| List of preferred compounds having Formula (I) | | |
|---|---|---|
| Ex. N. | Structure | Chemical Name |
| Example 114 | 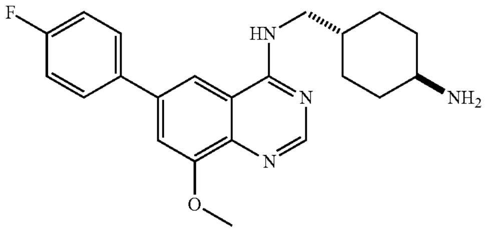 | N-(((1r,4r)-4-Aminocyclohexyl)methyl)-6-(4-fluorophenyl)-8-methoxyquinazolin-4-amine |
| Example 115 | 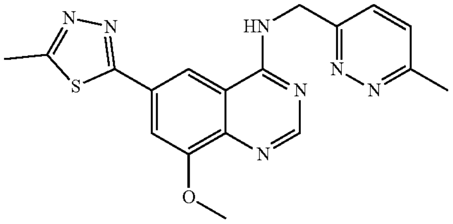 | 8-Methoxy-6-(5-methyl-1,3,4-thiadiazol-2-yl)-N-((6-methylpyridazin-3-yl)methyl)quinazolin-4-amine |
| Example 116 | 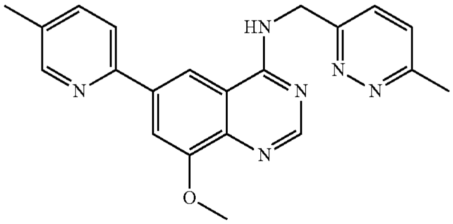 | 8-Methoxy-N-((6-methylpyridazin-3-yl)methyl)-6-(5-methylpyridin-2-yl)quinazolin-4-amine |
| Example 117 | 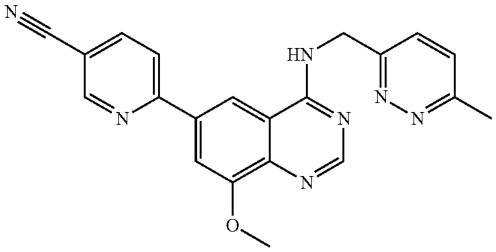 [SMILES: COc1cc(-c2ccc(C#N)cn2)cc2c(NCc3ccc(C)nn3)ncnc12] | 6-(8-Methoxy-4-(((6-methylpyridazin-3-yl)methyl)amino)quinazolin-6-yl)nicotinonitrile |
| Example 118 | 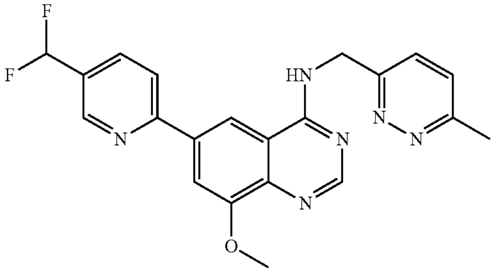 [SMILES: COc1cc(-c2ccc(C(F)F)cn2)cc2c(NCc3ccc(C)nn3)ncnc12] | 6-(5-(Difluoromethyl)pyridin-2-yl)-8-methoxy-N-((6-methylpyridazin-3-yl)methyl)quinazolin-4-amine |
| Example 119 | 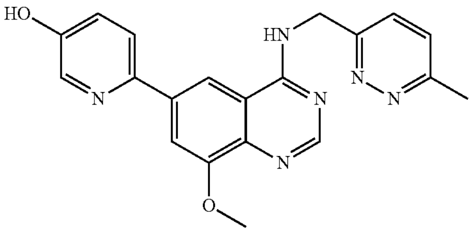 | 6-(8-Methoxy-4-(((6-methylpyridazin-3-yl)methyl)amino)quinazolin-6-yl)pyridin-3-ol |

TABLE 4-continued

| List of preferred compounds having Formula (I) | | |
|---|---|---|
| Ex. N. | Structure | Chemical Name |
| Example 120 | 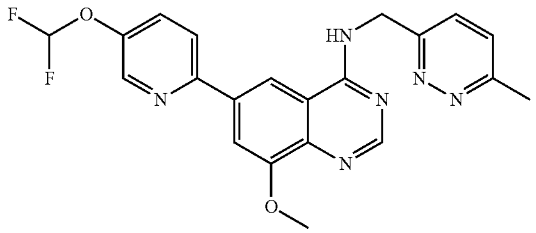 [SMILES: COc1cc(-c2ccc(OC(F)F)cn2)cc2c(NCc3ccc(C)nn3)ncnc12] | 6-(5-(Difluoromethoxy)pyridin-2-yl)-8-methoxy-N-((6-methylpyridazin-3-yl)methyl)quinazolin-4-amine |
| Example 121 | 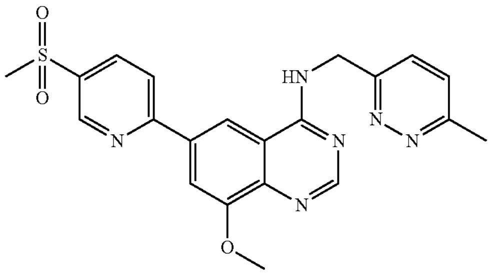 | 8-Methoxy-N-((6-methylpyridazin-3-yl)methyl)-6-(5-(methylsulfonyl)pyridin-2-yl)quinazolin-4-amine |
| Example 122 | 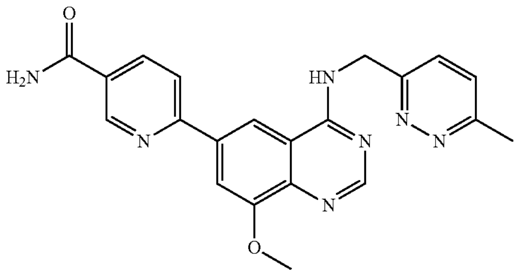 [SMILES: COc1cc(-c2ccc(C(N)=O)cn2)cc2c(NCc3ccc(C)nn3)ncnc12] | 6-(8-Methoxy-4-(((6-methylpyridazin-3-yl)methyl)amino)quinazolin-6-yl)nicotinamide |
| Example 123 | 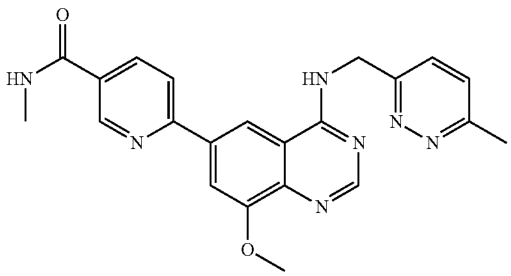 [SMILES: CNC(=O)c1ccc(-c2cc(OC)c3ncnc(NCc4ccc(C)nn4)c3c2)nc1] | 6-(8-Methoxy-4-(((6-methylpyridazin-3-yl)methyl)amino)quinazolin-6-yl)-N-methylnicotinamide |
| Example 124 | 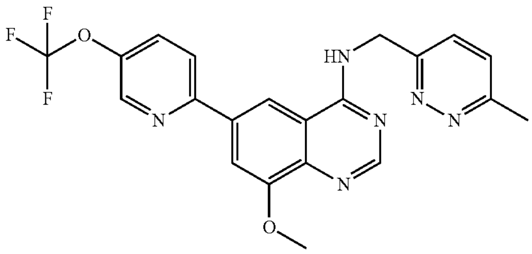 [SMILES: COc1cc(-c2ccc(OC(F)(F)F)cn2)cc2c(NCc3ccc(C)nn3)ncnc12] | 8-Methoxy-N-((6-methylpyridazin-3-yl)methyl)-6-(5-(trifluoromethoxy)pyridin-2-yl)quinazolin-4-amine |

TABLE 4-continued

List of preferred compounds having Formula (I)

| Ex. N. | Structure | Chemical Name |
|---|---|---|
| Example 125 | 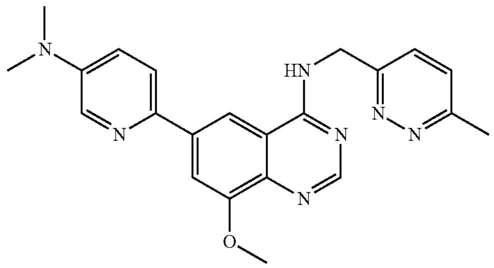 | 6-[5-(Dimethylamino)-2-pyridyl]-8-methoxy-N-[(6-methylpyridazin-3-yl)methyl]quinazolin-4-amine |
| Example 126 | 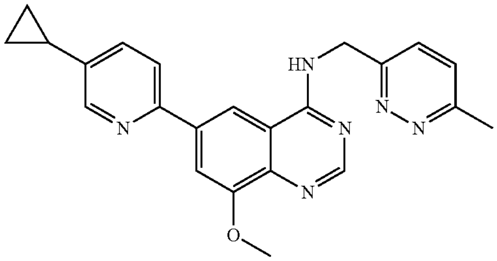 [SMILES: COc1cc(-c2ccc(C3CC3)cn2)cc2c(NCc3ccc(C)nn3)ncnc12] | 6-(5-Cyclopropylpyridin-2-yl)-8-methoxy-N-((6-methylpyridazin-3-yl)methyl)quinazolin-4-amine |
| Example 127 | 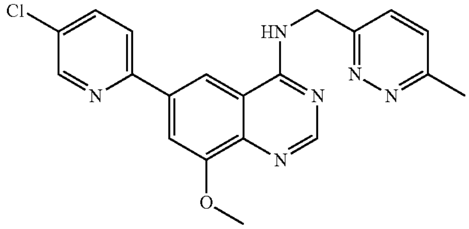 | 6-(5-Chloropyridin-2-yl)-8-methoxy-N-((6-methylpyridazin-3-yl)methyl)quinazolin-4-amine |
| Example 128 | 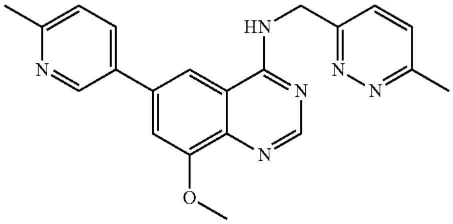 | 8-Methoxy-N-((6-methylpyridazin-3-yl)methyl)-6-(6-methylpyridin-3-yl)quinazolin-4-amine |
| Example 129 | 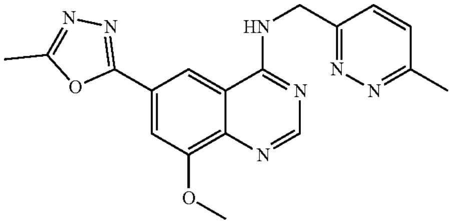 | 8-Methoxy-6-(5-methyl-1,3,4-oxadiazol-2-yl)-N-((6-methylpyridazin-3-yl)methyl)quinazolin-4-amine |
| Example 130 | 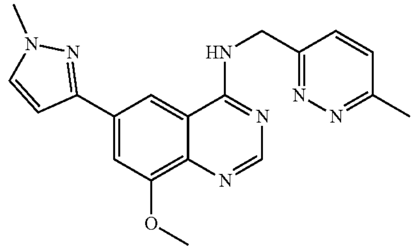 [SMILES: COc1cc(-c2ccn(C)n2)cc2c(NCc3ccc(C)nn3)ncnc12] | 8-Methoxy-6-(1-methyl-1H-pyrazol-3-yl)-N-((6-methylpyridazin-3-yl)methyl)quinazolin-4-amine |

TABLE 4-continued

| List of preferred compounds having Formula (I) | | |
|---|---|---|
| Ex. N. | Structure | Chemical Name |
| Example 131 | 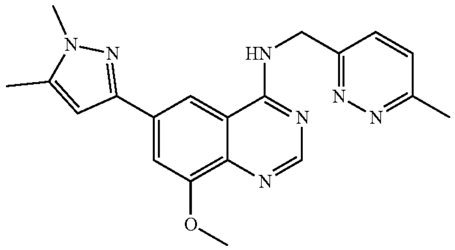 | 6-(1,5-Dimethyl-1H-pyrazol-3-yl)-8-methoxy-N-((6-methylpyridazin-3-yl)methyl)quinazolin-4-amine |
| Example 132 | 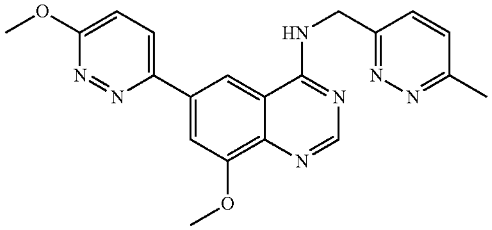 | 8-Methoxy-6-(6-methoxypyridazin-3-yl)-N-[(6-methylpyridazin-3-yl)methyl]quinazolin-4-amine |
| Example 133 | 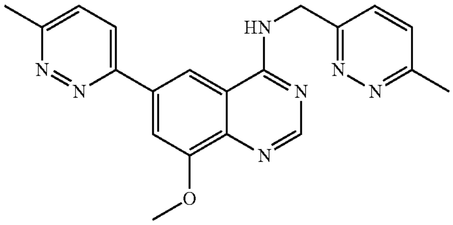 | 8-Methoxy-6-(6-methylpyridazin-3-yl)-N-[(6-methylpyridazin-3-yl)methyl]quinazolin-4-amine |
| Example 134 | 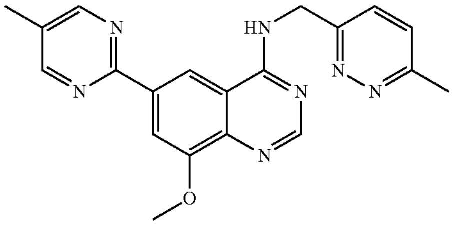 | 8-Methoxy-N-[(6-methylpyridazin-3-yl)methyl]-6-(5-methylpyrimidin-2-yl)quinazolin-4-amine |
| Example 135 | 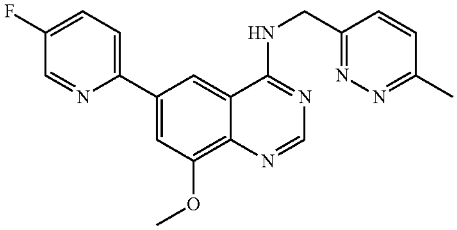 | 6-(5-Fluoro-2-pyridyl)-8-methoxy-N-[(6-methylpyridazin-3-yl)methyl]quinazolin-4-amine |
| Example 136 | 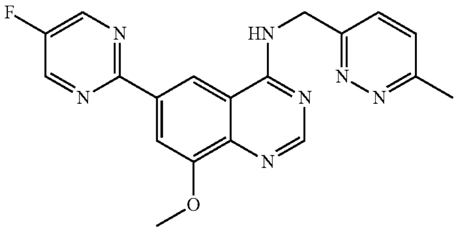 | 6-(5-Fluoropyrimidin-2-yl)-8-methoxy-N-[(6-methylpyridazin-3-yl)methyl]quinazolin-4-amine |

TABLE 4-continued

List of preferred compounds having Formula (I)

| Ex. N. | Structure | Chemical Name |
|---|---|---|
| Example 137 | 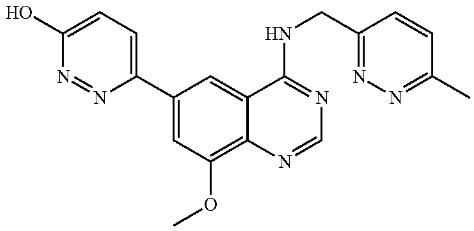 [SMILES: COc1cc(-c2ccc(O)nn2)cc2c(NCc3ccc(C)nn3)ncnc12] | 6-[8-Methoxy-4-[(6-methylpyridazin-3-yl)methylamino]quinazolin-6-yl]pyridazin-3-ol |
| Example 138 | 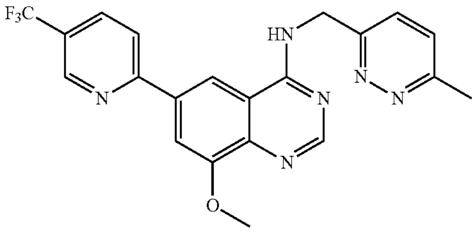 [SMILES: COc1cc(-c2ccc(C(F)(F)F)cn2)cc2c(NCc3ccc(C)nn3)ncnc12] | 8-Methoxy-N-((6-methylpyridazin-3-yl)methyl)-6-(5-(trifluoromethyl)pyridin-2-yl)quinazolin-4-amine |
| Example 139 | 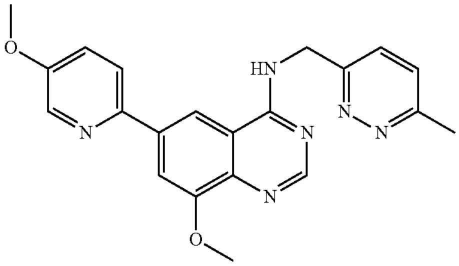 [SMILES: COc1ccc(-c2cc(OC)c3ncnc(NCc4ccc(C)nn4)c3c2)nc1] | 8-Methoxy-6-(5-methoxypyridin-2-yl)-N-((6-methylpyridazin-3-yl)methyl)quinazolin-4-amine |
| Example 140 | 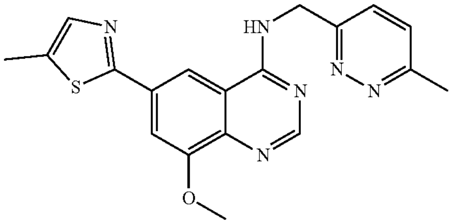 | 8-Methoxy-N-((6-methylpyridazin-3-yl)methyl)-6-(5-methylthiazol-2-yl)quinazolin-4-amine |
| Example 141 | 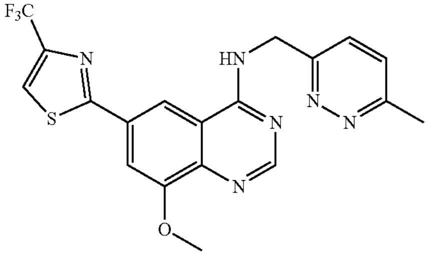 [SMILES: COc1cc(-c2nc(C(F)(F)F)cs2)cc2c(NCc3ccc(C)nn3)ncnc12] | 8-Methoxy-N-((6-methylpyridazin-3-yl)methyl)-6-(4-(trifluoromethyl)thiazol-2-yl)quinazolin-4-amine |
| Example 142 | 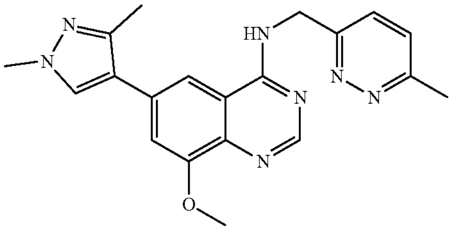 | 6-(1,3-Dimethyl-1H-pyrazol-4-yl)-8-methoxy-N-((6-methylpyridazin-3-yl)methyl)quinazolin-4-amine |

TABLE 4-continued

List of preferred compounds having Formula (I)

| Ex. N. | Structure | Chemical Name |
|---|---|---|
| Example 143 | 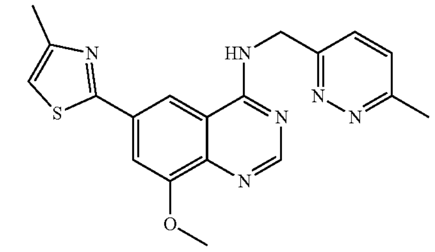 [SMILES: COc1cc(-c2nc(C)cs2)cc2c(NCc3ccc(C)nn3)ncnc12] | 8-Methoxy-N-((6-methylpyridazin-3-yl)methyl)-6-(4-methylthiazol-2-yl)quinazolin-4-amine |
| Example 144 | 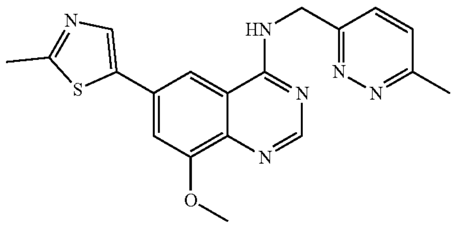 | 8-Methoxy-N-((6-methylpyridazin-3-yl)methyl)-6-(2-methylthiazol-5-yl)quinazolin-4-amine |
| Example 145 | 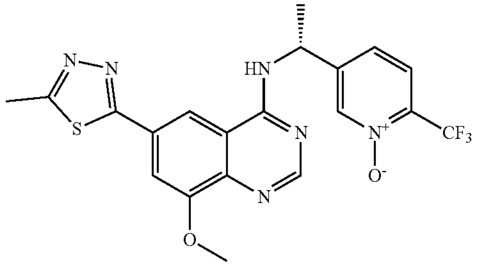 [SMILES: COc1cc(-c2nnc(C)s2)cc2c(N[C@H](C)c3ccc(C(F)(F)F)[n+]([O-])c3)ncnc12] | (R)-5-(1-((8-Methoxy-6-(5-methyl-1,3,4-thiadiazol-2-yl)quinazolin-4-yl)amino)ethyl)-2-(trifluoromethyl)pyridine 1-oxide |
| Example 146 | 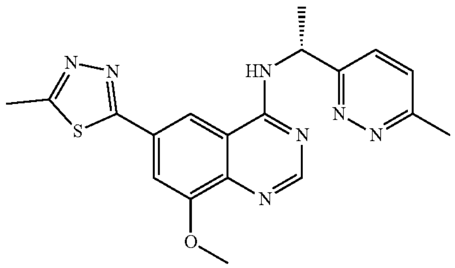 | (R)-8-Methoxy-6-(5-methyl-1,3,4-thiadiazol-2-yl)-N-(1-(6-methylpyridazin-3-yl)ethyl)quinazolin-4-amine |
| Example 147 | 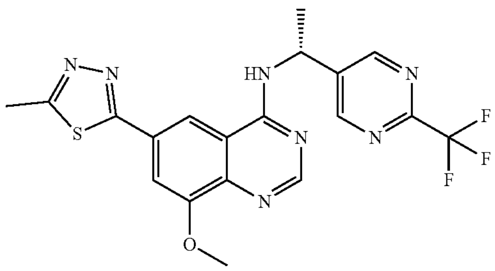 [SMILES: COc1cc(-c2nnc(C)s2)cc2c(N[C@H](C)c3cnc(C(F)(F)F)nc3)ncnc12] | (R)-8-Methoxy-6-(5-methyl-1,3,4-thiadiazol-2-yl)-N-(1-(2-(trifluoromethyl)pyrimidin-5-yl)ethyl)quinazolin-4-amine |

TABLE 4-continued

| List of preferred compounds having Formula (I) | | |
|---|---|---|
| Ex. N. | Structure | Chemical Name |
| Example 148 | 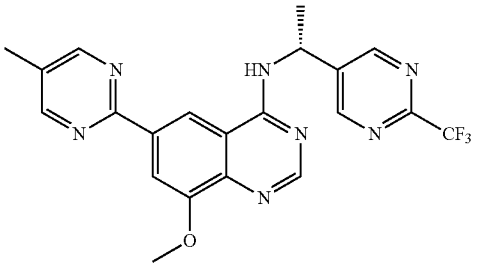 [SMILES: COc1cc(-c2ncc(C)cn2)cc2c(N[C@H](C)c3cnc(C(F)(F)F)nc3)ncnc12] | 8-Methoxy-6-(5-methylpyrimidin-2-yl)-N-[(1R)-1-[2-(trifluoromethyl)pyrimidin-5-yl]ethyl]quinazolin-4-amine |
| Example 149 | 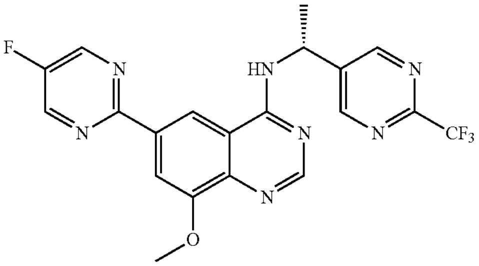 [SMILES: COc1cc(-c2ncc(F)cn2)cc2c(N[C@H](C)c3cnc(C(F)(F)F)nc3)ncnc12] | 6-(5-Fluoropyrimidin-2-yl)-8-methoxy-N-[(1R)-1-[2-(trifluoromethyl)pyrimidin-5-yl]ethyl]quinazolin-4-amine |
| Example 150 | 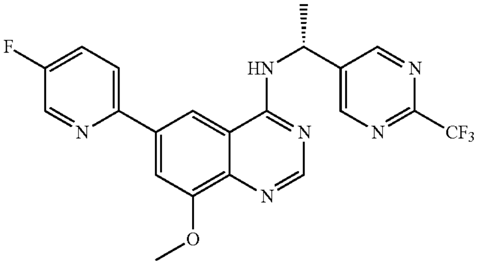 [SMILES: COc1cc(-c2ccc(F)cn2)cc2c(N[C@H](C)c3cnc(C(F)(F)F)nc3)ncnc12] | 6-(5-Fluoro-2-pyridyl)-8-methoxy-N-[(1R)-1-[2-(trifluoromethyl)pyrimidin-5-yl]ethyl]quinazolin-4-amine |
| Example 151 | 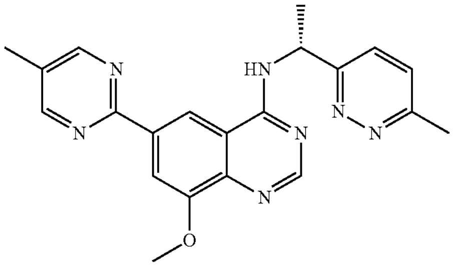 | 8-Methoxy-N-[(1R)-1-(6-methylpyridazin-3-yl)ethyl]-6-(5-methylpyrimidin-2-yl)quinazolin-4-amine |
| Example 152 | 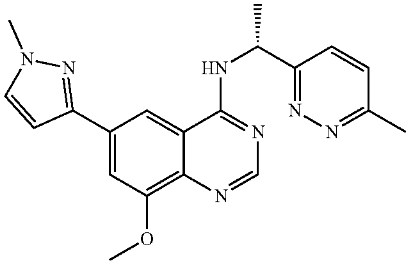 [SMILES: COc1cc(-c2ccn(C)n2)cc2c(N[C@H](C)c3ccc(C)nn3)ncnc12] | 8-Methoxy-6-(1-methylpyrazol-3-yl)-N-[(1R)-1-(6-methylpyridazin-3-yl)ethyl]quinazolin-4-amine |

TABLE 4-continued

| List of preferred compounds having Formula (I) | | |
|---|---|---|
| Ex. N. | Structure | Chemical Name |
| Example 153 | 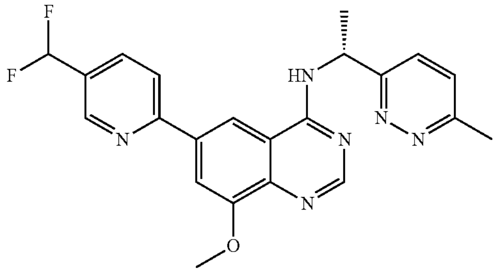 [SMILES: COc1cc(-c2ccc(C(F)F)cn2)cc2c(N[C@H](C)c3ccc(C)nn3)ncnc12] | 6-[5-(Difluoromethyl)-2-pyridyl]-8-methoxy-N-[(1R)-1-(6-methylpyridazin-3-yl)ethyl]quinazolin-4-amine |
| Example 154 | 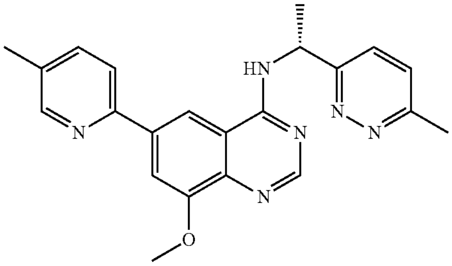 | 8-Methoxy-N-[(1R)-1-(6-methylpyridazin-3-yl)ethyl]-6-(5-methyl-2-pyridyl)quinazolin-4-amine |
| Example 155 | 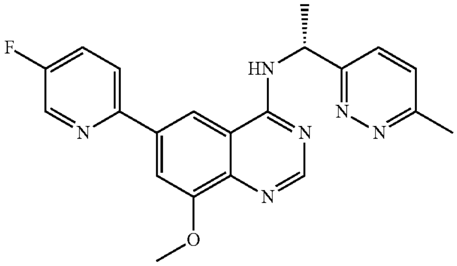 [SMILES: COc1cc(-c2ccc(F)cn2)cc2c(N[C@H](C)c3ccc(C)nn3)ncnc12] | 6-(5-Fluoro-2-pyridyl)-8-methoxy-N-[(1R)-1-(6-methylpyridazin-3-yl)ethyl]quinazolin-4-amine |
| Example 156 | 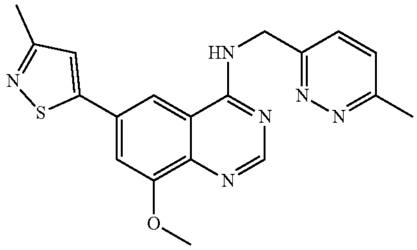 [SMILES: COc1cc(-c2cc(C)ns2)cc2c(NCc3ccc(C)nn3)ncnc12] | 8-Methoxy-6-(3-methylisothiazol-5-yl)-N-((6-methylpyridazin-3-yl)methyl)quinazolin-4-amine |
| Example 157 | 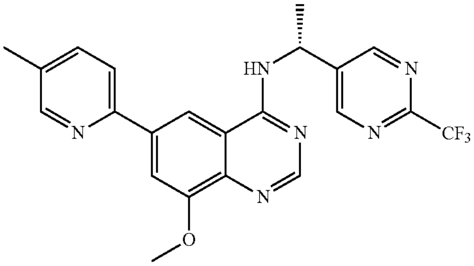 | (R)-8-methoxy-6-(5-methylpyridin-2-yl)-N-(1-(2-(trifluoromethyl)pyrimidin-5-yl)ethyl)quinazolin-4-amine |

TABLE 4-continued

List of preferred compounds having Formula (I)

| Ex. N. | Structure | Chemical Name |
|---|---|---|
| Example 158 | 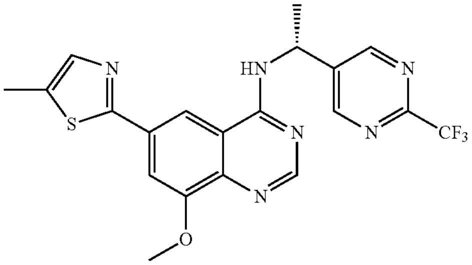 [SMILES: COc1cc(-c2ncc(C)s2)cc2c(N[C@H](C)c3cnc(C(F)(F)F)nc3)ncnc12] | (R)-8-methoxy-6-(5-methylthiazol-2-yl)-N-(1-(2-(trifluoromethyl)pyrimidin-5-yl)ethyl)quinazolin-4-amine |
| Example 159 | 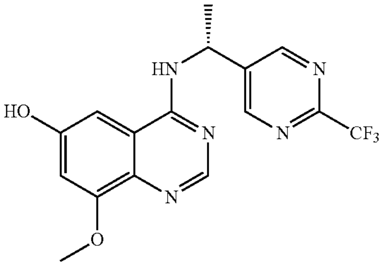 [SMILES: COc1cc(O)cc2c(N[C@H](C)c3cnc(C(F)(F)F)nc3)ncnc12] | (R)-8-methoxy-4-((1-(2-(trifluoromethyl)pyrimidin-5-yl)ethyl)amino)quinazolin-6-ol |
| Example 160 | 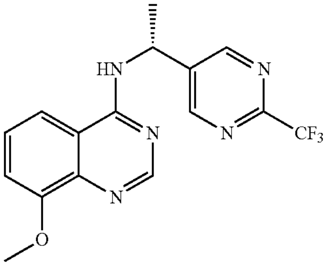 [SMILES: COc1cccc2c(N[C@H](C)c3cnc(C(F)(F)F)nc3)ncnc12] | (R)-8-methoxy-N-(1-(2-(trifluoromethyl)pyrimidin-5-yl)ethyl)quinazolin-4-amine |
| Example 161 | 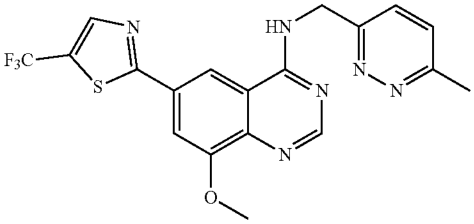 [SMILES: COc1cc(-c2ncc(C(F)(F)F)s2)cc2c(NCc3ccc(C)nn3)ncnc12] | 8-Methoxy-N-((6-methylpyridazin-3-yl)methyl)-6-(5-(trifluoromethyl)thiazol-2-yl)quinazolin-4-amine |
| Example 163 | 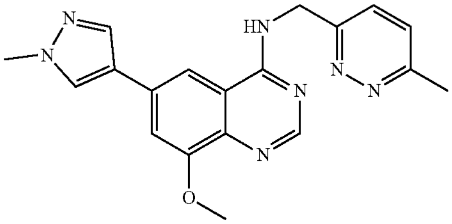 | 8-Methoxy-6-(1-methyl-1H-pyrazol-4-yl)-N-((6-methylpyridazin-3-yl)methyl)quinazolin-4-amine |
| Example 163a | 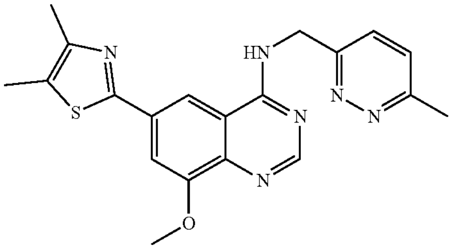 | 6-(4,5-Dimethylthiazol-2-yl)-8-methoxy-N-((6-methylpyridazin-3-yl)methyl)quinazolin-4-amine |

TABLE 4-continued

| List of preferred compounds having Formula (I) | | |
|---|---|---|
| Ex. N. | Structure | Chemical Name |
| Example 164 | 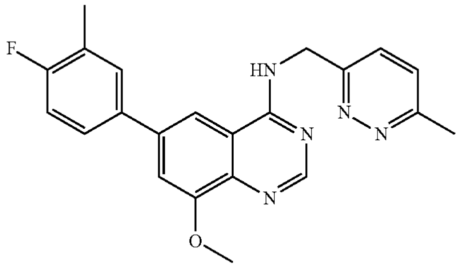 [SMILES: COc1cc(-c2ccc(F)c(C)c2)cc2c(NCc3ccc(C)nn3)ncnc12] | 6-(4-Fluoro-3-methylphenyl)-8-methoxy-N-((6-methylpyridazin-3-yl)methyl)quinazolin-4-amine |
| Example 165 | 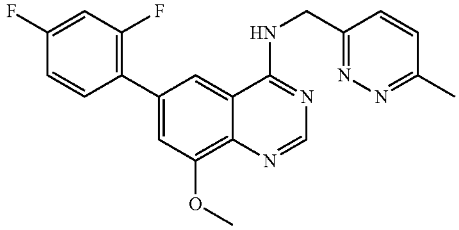 [SMILES: COc1cc(-c2ccc(F)cc2F)cc2c(NCc3ccc(C)nn3)ncnc12] | 6-(2,4-Difluorophenyl)-8-methoxy-N-((6-methylpyridazin-3-yl)methyl)quinazolin-4-amine |
| Example 166 | 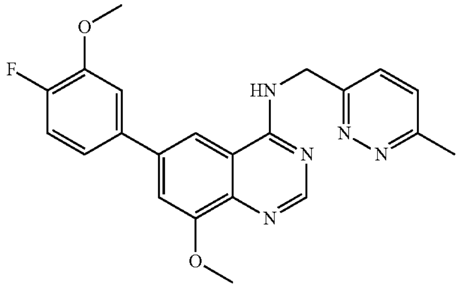 [SMILES: COc1cc(-c2cc(OC)c3ncnc(NCc4ccc(C)nn4)c3c2)ccc1F] | 6-(4-Fluoro-3-methoxyphenyl)-8-methoxy-N-((6-methylpyridazin-3-yl)methyl)quinazolin-4-amine |
| Example 167 | 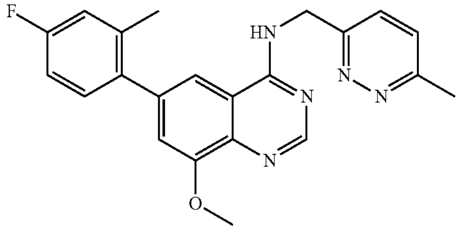 [SMILES: COc1cc(-c2ccc(F)cc2C)cc2c(NCc3ccc(C)nn3)ncnc12] | 6-(4-Fluoro-2-methylphenyl)-8-methoxy-N-((6-methylpyridazin-3-yl)methyl)quinazolin-4-amine |
| Example 168 | 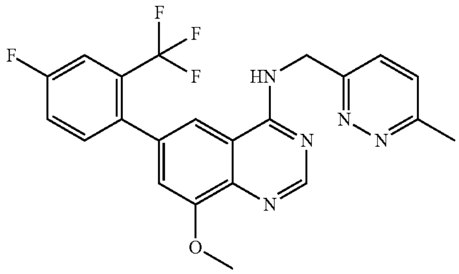 [SMILES: COc1cc(-c2ccc(F)cc2C(F)(F)F)cc2c(NCc3ccc(C)nn3)ncnc12] | 6-(4-Fluoro-2-(trifluoromethyl)phenyl)-8-methoxy-N-((6-methylpyridazin-3-yl)methyl)quinazolin-4-amine |

TABLE 4-continued

List of preferred compounds having Formula (I)

| Ex. N. | Structure | Chemical Name |
|---|---|---|
| Example 169 | 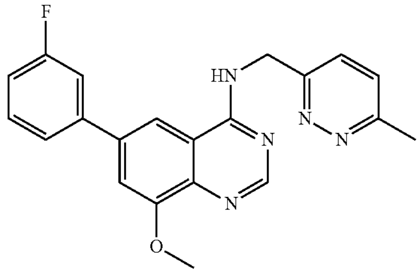 [SMILES: COc1cc(-c2cccc(F)c2)cc2c(NCc3ccc(C)nn3)ncnc12] | 6-(3 -Fluorophenyl)-8-methoxy-N-((6-methylpyridazin-3-yl)methyl)quinazolin-4- |
| Example 170 | 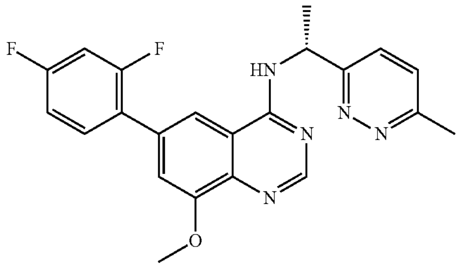 [SMILES: COc1cc(-c2ccc(F)cc2F)cc2c(N[C@H](C)c3ccc(C)nn3)ncnc12] | 6-(2,4-Difluorophenyl)-8-methoxy-N-[(1R)-1-(6-methylpyridazin-3-yl)ethyl]quinazolin-4-amine |
| Example 171 | 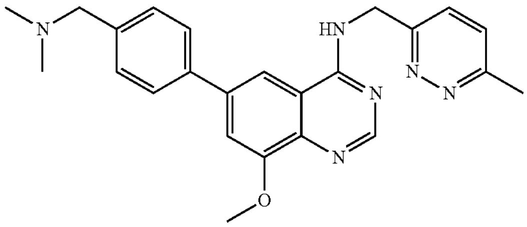 | 6-[4-[(Dimethylamino)methyl]phenyl]-8-methoxy-N-[(6-methylpyridazin-3-yl)methyl]quinazolin-4-amine formate |
| Example 172 | 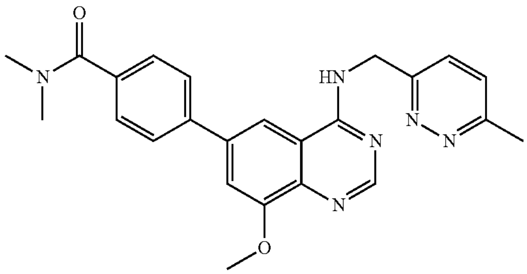 | 4-[8-Methoxy-4-[(6-methylpyridazin-3-yl)methylamino]quinazolin-6-yl]-N,N-dimethyl-benzamide |
| Example 173 | 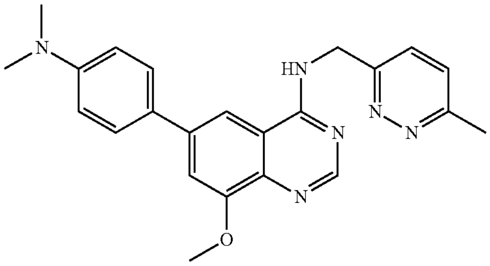 | 6-[4-(Dimethylamino)phenyl]-8-methoxy-N-[(6-methylpyridazin-3-yl)methyl]quinazolin-4-amine |
| Example 174 | 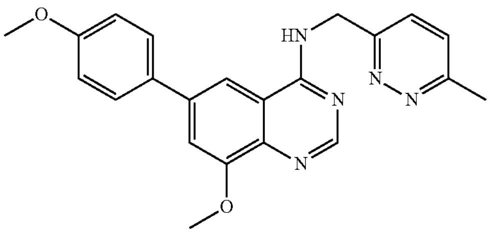 | 8-Methoxy-6-(4-methoxyphenyl)-N-[(6-methylpyridazin-3-yl)methyl]quinazolin-4-amine |

TABLE 4-continued

| List of preferred compounds having Formula (I) | | |
|---|---|---|
| Ex. N. | Structure | Chemical Name |
| Example 175 | 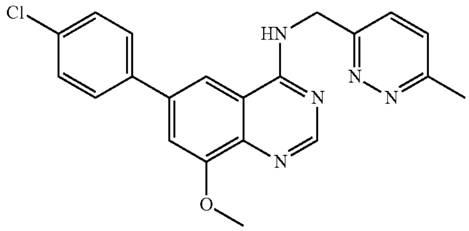 [SMILES: COc1cc(-c2ccc(Cl)cc2)cc2c(NCc3ccc(C)nn3)ncnc12] | 6-(4-chlorophenyl)-8-methoxy-N-((6-methylpyridazin-3-yl)methyl)quinazolin-4-amine |
| Example 176 | 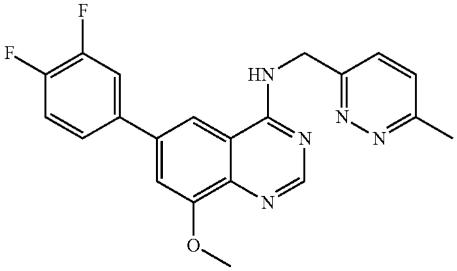 [SMILES: COc1cc(-c2ccc(F)c(F)c2)cc2c(NCc3ccc(C)nn3)ncnc12] | 6-(3,4-Difluorophenyl)-8-methoxy-N-((6-methylpyridazin-3-yl)methyl)quinazolin-4-amine |
| Example 176a | 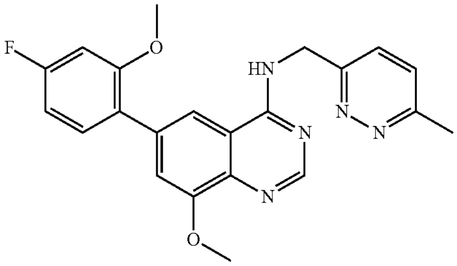 [SMILES: COc1cc(F)ccc1-c1cc(OC)c2ncnc(NCc3ccc(C)nn3)c2c1] | 6-(4-Fluoro-2-methoxyphenyl)-8-methoxy-N-((6-methylpyridazin-3-yl)methyl)quinazolin-4-amine |
| Example 177 | 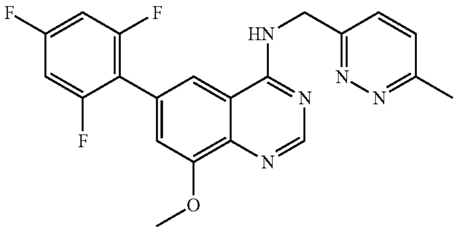 [SMILES: COc1cc(-c2c(F)cc(F)cc2F)cc2c(NCc3ccc(C)nn3)ncnc12] | 8-Methoxy-N-((6-methylpyridazin-3-yl)methyl)-6-(2,4,6-trifluorophenyl)quinazolin-4-amine |
| Example 178 | 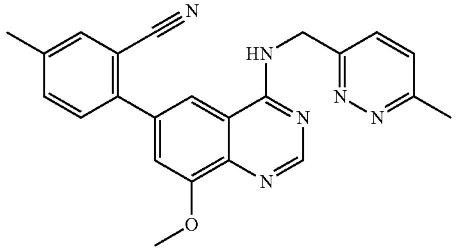 | 2-(8-Methoxy-4-(((6-methylpyridazin-3-yl)methyl)amino)quinazolin-6-yl)-5-methylbenzonitrile |
| Example 179 | 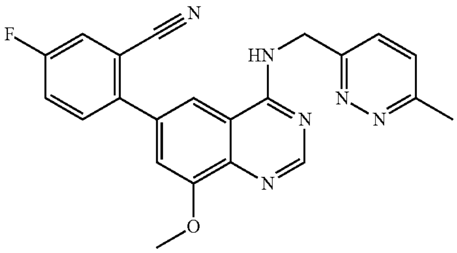 [SMILES: COc1cc(-c2ccc(F)cc2C#N)cc2c(NCc3ccc(C)nn3)ncnc12] | 5-Fluoro-2-(8-methoxy-4-(((6-methylpyridazin-3-yl)methyl)amino)quinazolin-6-yl)benzonitrile |

TABLE 4-continued

| List of preferred compounds having Formula (I) | | |
|---|---|---|
| Ex. N. | Structure | Chemical Name |
| Example 180 | 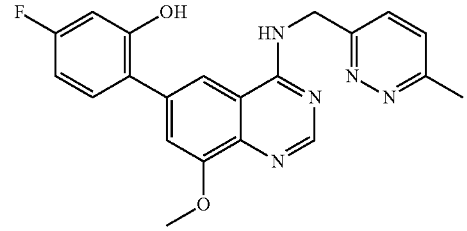 [SMILES: COc1cc(-c2ccc(F)cc2O)cc2c(NCc3ccc(C)nn3)ncnc12] | 5-Fluoro-2-(8-methoxy-4-(((6-methylpyridazin-3-yl)methyl)amino)quinazolin-6-yl)phenol |
| Example 181 | 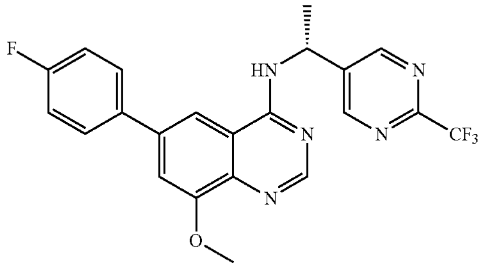 [SMILES: COc1cc(-c2ccc(F)cc2)cc2c(N[C@H](C)c3cnc(C(F)(F)F)nc3)ncnc12] | (R)-6-(4-fluorophenyl)-8-methoxy-N-(1-(2-(trifluoromethyl)pyrimidin-5-yl)ethyl)quinazolin-4-amine |
| Example 182 | 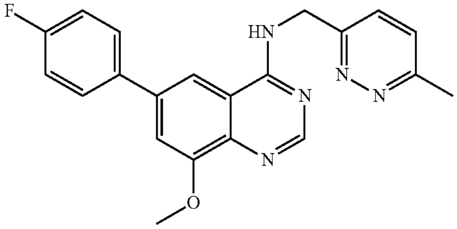 [SMILES: COc1cc(-c2ccc(F)cc2)cc2c(NCc3ccc(C)nn3)ncnc12] | 6-(4-fluorophenyl)-8-methoxy-N-((6-methylpyridazin-3-yl)methyl)quinazolin-4-amine |
| Example 187 | 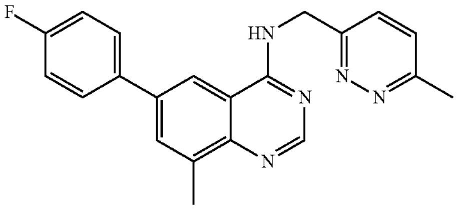 [SMILES: Cc1ccc(CNc2ncnc3c(C)cc(-c4ccc(F)cc4)cc23)nn1] | 6-(4-fluorophenyl)-8-iodo-N-((6-methylpyridazin-3-yl)methyl)quinazolin-4-amine |
| Example 188 | 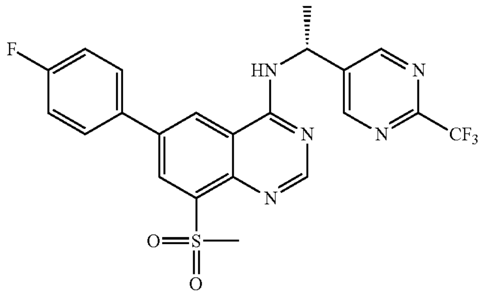 [SMILES: C[C@@H](Nc1ncnc2c(S(C)(=O)=O)cc(-c3ccc(F)cc3)cc12)c1cnc(C(F)(F)F)nc1] | (R)-6-(4-fluorophenyl)-8-(methylsulfonyl)-N-(1-(2-(trifluoromethyl)pyrimidin-5-yl)ethyl)quinazolin-4-amine |
| Example 189 | 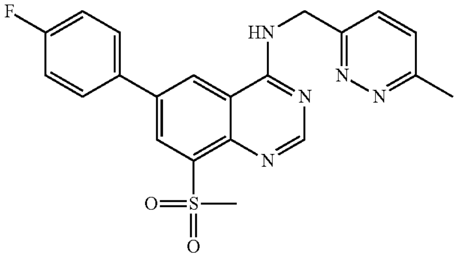 [SMILES: Cc1ccc(CNc2ncnc3c(S(C)(=O)=O)cc(-c4ccc(F)cc4)cc23)nn1] | 6-(4-fluorophenyl)-N-((6-methylpyridazin-3-yl)methyl)-8-(methylsulfonyl)quinazolin-4-amine |

TABLE 4-continued

| List of preferred compounds having Formula (I) | | |
|---|---|---|
| Ex. N. | Structure | Chemical Name |
| Example 190 | 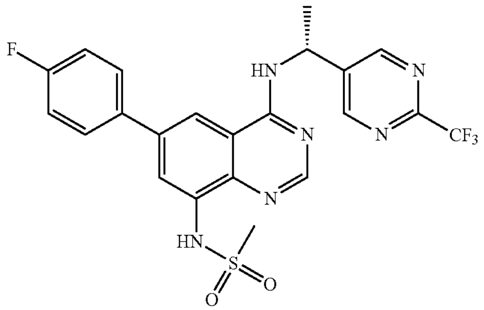 [SMILES: C[C@@H](Nc1ncnc2c(NS(C)(=O)=O)cc(-c3ccc(F)cc3)cc12)c1cnc(C(F)(F)F)nc1] | (R)-N-(6-(4-fluorophenyl)-4-((1-(2-(trifluoromethyl)pyrimidin-5-yl)ethyl)amino)quinazolin-8-yl)methanesulfonamide |
| Example 191 | 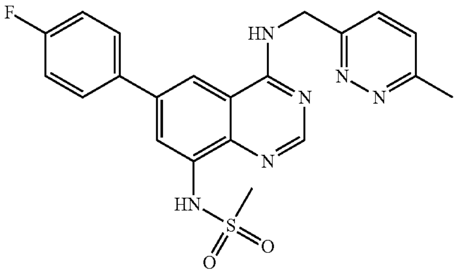 [SMILES: Cc1ccc(CNc2ncnc3c(NS(C)(=O)=O)cc(-c4ccc(F)cc4)cc23)nn1] | N-(6-(4-fluorophenyl)-4-oxo-3,4-dihydroquinazolin-8-yl)methanesulfonamide |
| Example 192 | 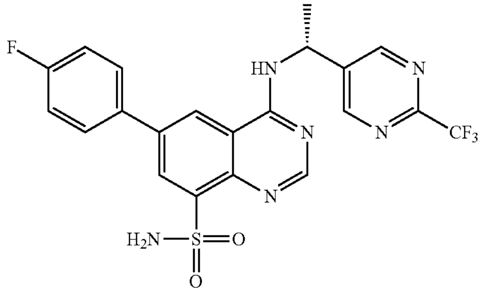 [SMILES: C[C@@H](Nc1ncnc2c(S(N)(=O)=O)cc(-c3ccc(F)cc3)cc12)c1cnc(C(F)(F)F)nc1] | (R)-6-(4-fluorophenyl)-4-((1-(2-(trifluoromethyl)pyrimidin-5-yl)ethyl)amino)quinazoline-8-sulfonamide |
| Example 193 | 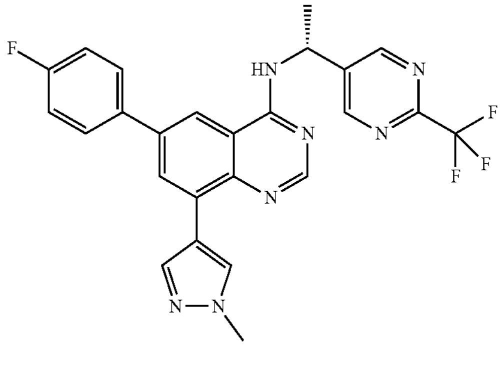 [SMILES: C[C@@H](Nc1ncnc2c(-c3cnn(C)c3)cc(-c3ccc(F)cc3)cc12)c1cnc(C(F)(F)F)nc1] | (R)-6-(4-fluorophenyl)-8-(1-methyl-1H-pyrazol-4-yl)-N-(1-(2-(trifluoromethyl)pyrimidin-5-yl)ethyl)quinazolin-4-amine |

TABLE 4-continued

| List of preferred compounds having Formula (I) | | |
|---|---|---|
| Ex. N. | Structure | Chemical Name |
| Example 194 | 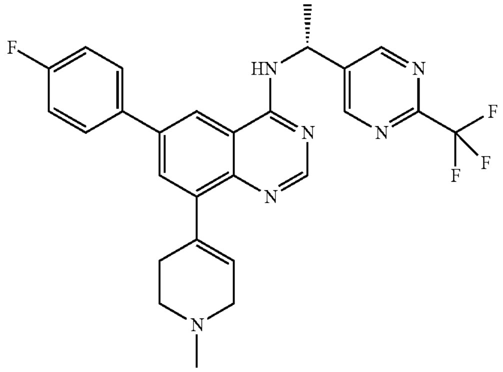 [SMILES: C[C@@H](Nc1ncnc2c(C3=CCN(C)CC3)cc(-c3ccc(F)cc3)cc12)c1cnc(C(F)(F)F)nc1] | (R)-6-(4-Fluorophenyl)-8-(1-methyl-1,2,3,6-tetrahydropyridin-4-yl)-N-(1-(2-(trifluoromethyl)pyrimidin-5-yl)ethyl)quinazolin-4-amine |
| Example 195 | 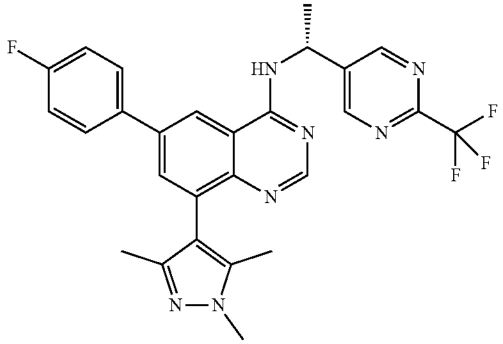 [SMILES: Cc1nn(C)c(C)c1-c1cc(-c2ccc(F)cc2)cc2c(N[C@H](C)c3cnc(C(F)(F)F)nc3)ncnc12] | (R)-6-(4-Fluorophenyl)-N-(1-(2-(trifluoromethyl)pyrimidin-5-yl)ethyl)-8-(1,3,5-trimethyl-1H-pyrazol-4-yl)quinazolin-4-amine |
| Example 196 | 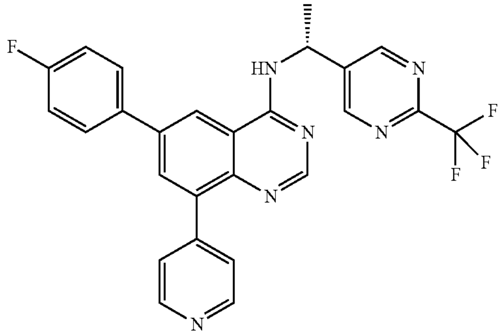 [SMILES: C[C@@H](Nc1ncnc2c(-c3ccncc3)cc(-c3ccc(F)cc3)cc12)c1cnc(C(F)(F)F)nc1] | (R)-6-(4-Fluorophenyl)-8-(pyridin-4-yl)-N-(1-(2-(trifluoromethyl)pyrimidin-5-yl)ethyl)quinazolin-4-amine |
| Example 197 | 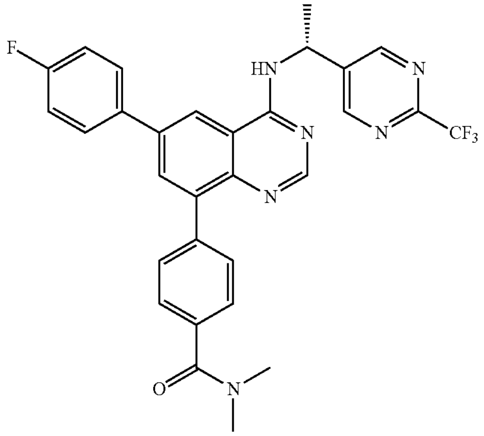 [SMILES: C[C@@H](Nc1ncnc2c(-c3ccc(C(=O)N(C)C)cc3)cc(-c3ccc(F)cc3)cc12)c1cnc(C(F)(F)F)nc1] | (R)-4-(6-(4-Fluorophenyl)-4-((1-(2-(trifluoromethyl)pyrimidin-5-yl)ethyl)amino)quinazolin-8-yl)-N,N-dimethylbenzamide |

TABLE 4-continued

List of preferred compounds having Formula (I)

| Ex. N. | Structure | Chemical Name |
| --- | --- | --- |
| Example 198 | 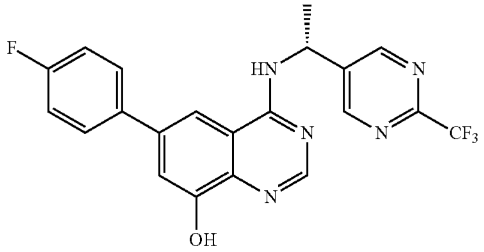 [SMILES: C[C@@H](Nc1ncnc2c(O)cc(-c3ccc(F)cc3)cc12)c1cnc(C(F)(F)F)nc1] | (R)-6-(4-fluorophenyl)-4-((1-(2-(trifluoromethyl)pyrimidin-5-yl)ethyl)amino)-quinazolin-8-ol |
| Example 199 | 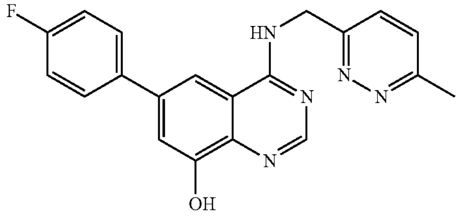 [SMILES: Cc1ccc(CNc2ncnc3c(O)cc(-c4ccc(F)cc4)cc23)nn1] | 6-(4-fluorophenyl)-4-(((6-methylpyridazin-3-yl)methyl)amino)quinazolin-8-ol |
| Example 223 | 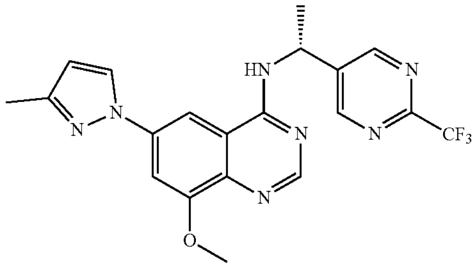 [SMILES: COc1cc(-n2ccc(C)n2)cc2c(N[C@H](C)c3cnc(C(F)(F)F)nc3)ncnc12] | ((R)-8-methoxy-6-(3-methyl-1H-pyrazol-1-yl)-N-(1-(2-(trifluoromethyl)pyrimidin-5-yl)ethyl)quinazolin-4-amine |
| Example 224 | 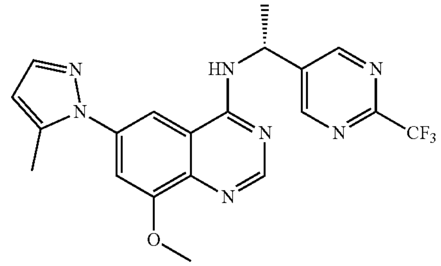 [SMILES: COc1cc(-n2nccc2C)cc2c(N[C@H](C)c3cnc(C(F)(F)F)nc3)ncnc12] | (R)-8-methoxy-6-(5-methyl-1H-pyrazol-1-yl)-N-(1-(2-(trifluoromethyl)pyrimidin-5-yl)ethyl)quinazolin-4-amine |
| Example 225 | 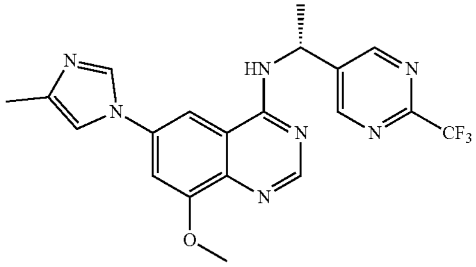 [SMILES: COc1cc(-n2cnc(C)c2)cc2c(N[C@H](C)c3cnc(C(F)(F)F)nc3)ncnc12] | (R)-8-Methoxy-6-(4-methyl-1H-imidazol-1-yl)-N-(1-(2-(trifluoromethyl)pyrimidin-5-yl)ethyl)quinazolin-4-amine |
| Example 226 | 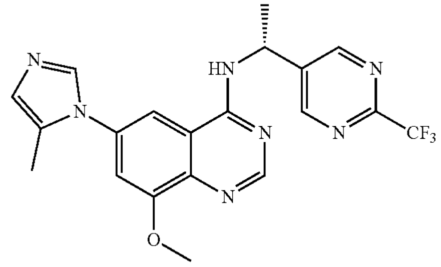 [SMILES: COc1cc(-n2cncc2C)cc2c(N[C@H](C)c3cnc(C(F)(F)F)nc3)ncnc12] | (R)-8-methoxy-6-(5-methyl-1H-imidazol-1-yl)-N-(1-(2-(trifluoromethyl)pyrimidin-5-yl)ethyl)quinazolin-4-amine |

TABLE 4-continued

| List of preferred compounds having Formula (I) | | |
|---|---|---|
| Ex. N. | Structure | Chemical Name |
| Example 227 | 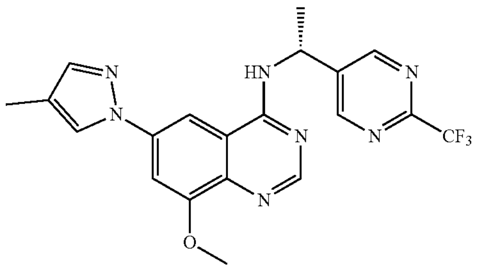 [SMILES: COc1cc(-n2cc(C)cn2)cc2c(N[C@H](C)c3cnc(C(F)(F)F)nc3)ncnc12] | (R)-8-Methoxy-6-(4-methyl-1H-pyrazol-1-yl)-N-(1-(2-(trifluoromethyl)pyrimidin-5-yl)ethyl)quinazolin-4-amine |
| Example 255 | 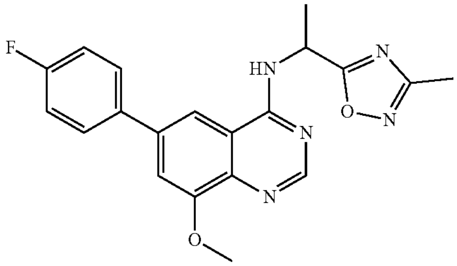 [SMILES: COc1cc(-c2ccc(F)cc2)cc2c(NC(C)c3nc(C)no3)ncnc12] | Single enantiomer 1 of 6-(4-fluorophenyl)-8-methoxy-N-(1-(3-methyl-1,2,4-oxadiazol-5-yl)ethyl)quinazolin-4-amine |
| Example 256 | 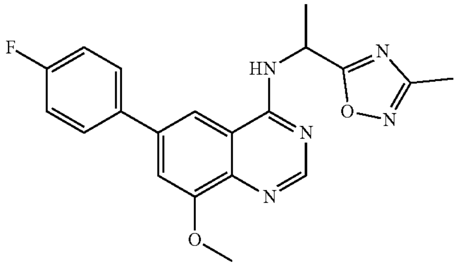 [SMILES: COc1cc(-c2ccc(F)cc2)cc2c(NC(C)c3nc(C)no3)ncnc12] | Single enantiomer 2 of 6-(4-fluorophenyl)-8-methoxy-N-(1-(3-methyl-1,2,4-oxadiazol-5-yl)ethyl)quinazolin-4-amine |
| Example 257 | 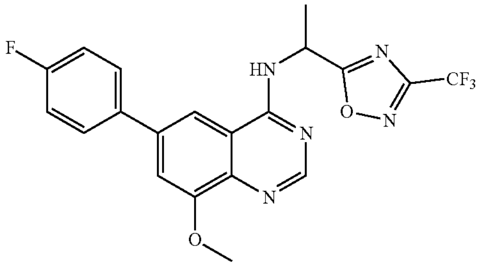 [SMILES: COc1cc(-c2ccc(F)cc2)cc2c(NC(C)c3nc(C(F)(F)F)no3)ncnc12] | Single enantiomer 1 of 6-(4-fluorophenyl)-8-methoxy-N-(1-(3-(trifluoromethyl)-1,2,4-oxadiazol-5-yl)ethyl)quinazolin-4-amine |
| Example 258 | 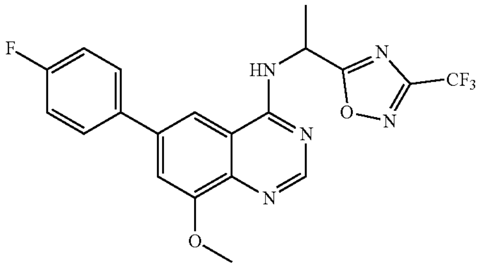 [SMILES: COc1cc(-c2ccc(F)cc2)cc2c(NC(C)c3nc(C(F)(F)F)no3)ncnc12] | Single enantiomer 2 of 6-(4-fluorophenyl)-8-methoxy-N-(1-(3-(trifluorom ethyl)-1,2,4-oxadiazol-5-yl)ethyl)quinazolin-4-amine |

TABLE 4-continued

| List of preferred compounds having Formula (I) | | |
|---|---|---|
| Ex. N. | Structure | Chemical Name |
| Example 259 | 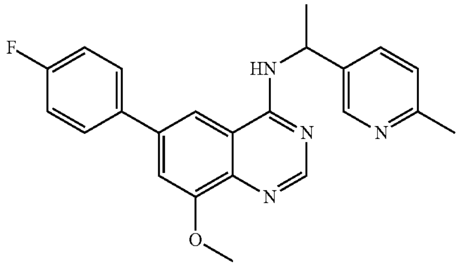 [SMILES: COc1cc(-c2ccc(F)cc2)cc2c(NC(C)c3ccc(C)nc3)ncnc12] | Single enantiomer 1 of 6-(4-fluorophenyl)-8-methoxy-N-(1-(6-methylpyridin-3-yl)ethyl)quinazolin-4-amine |
| Example 260 | 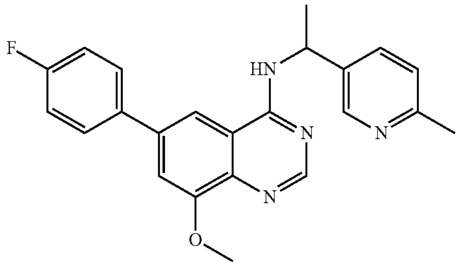 [SMILES: COc1cc(-c2ccc(F)cc2)cc2c(NC(C)c3ccc(C)nc3)ncnc12] | Single enantiomer 2 of 6-(4-fluorophenyl)-8-methoxy-N-(1-(6-methylpyridin-3-yl)ethyl)quinazolin-4-amine |
| Example 261 | 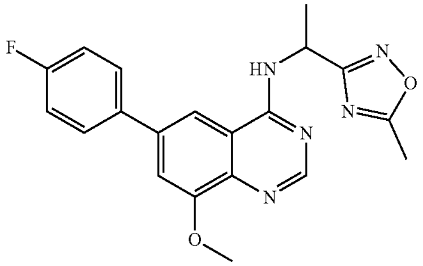 | Single enantiomer 1 of 6-(4-fluorophenyl)-8-methoxy-N-(1-(5-methyl-1,2,4-oxadiazol-3-yl)ethyl)quinazolin-4-amine |
| Example 262 | 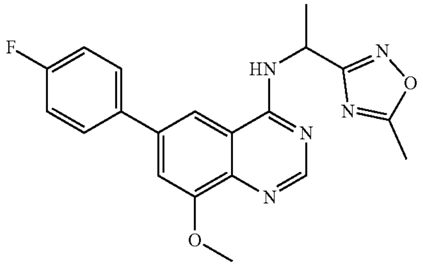 | Single enantiomer 2 of 6-(4-fluorophenyl)-8-methoxy-N-(1-(5-methyl-1,2,4-oxadiazol-3-yl)ethyl)quinazolin-4-amine |
| Example 263 | 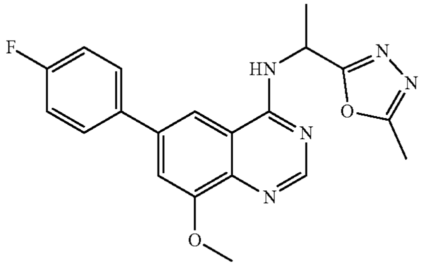 | Single enantiomer 1 of 6-(4-fluorophenyl)-8-methoxy-N-(1-(5-methyl-1,3,4-oxadiazol-2-yl)ethyl)quinazolin-4-amine |

TABLE 4-continued

| List of preferred compounds having Formula (I) | | |
|---|---|---|
| Ex. N. | Structure | Chemical Name |
| Example 264 | 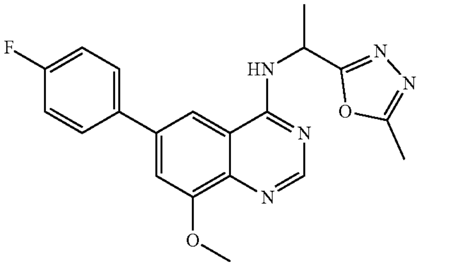 | Single enantiomer 2 of 6-(4-fluorophenyl)-8-methoxy-N-(1-(5-methyl-1,3,4-oxadiazol-2-yl)ethyl)quinazolin-4-amine |
| Example 265 | 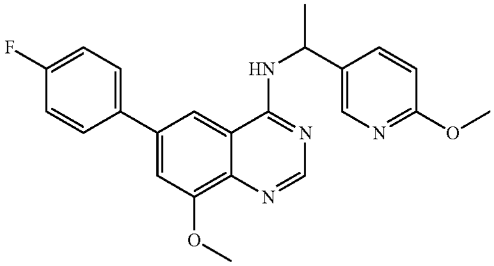 [SMILES: COc1ccc(C(C)Nc2ncnc3c(OC)cc(-c4ccc(F)cc4)cc23)cn1] | Single enantiomer 1 of 6-(4-fluorophenyl)-8-methoxy-N-(1-(6-methoxypyridin-3-yl)ethyl)quinazolin-4-amine |
| Example 266 | 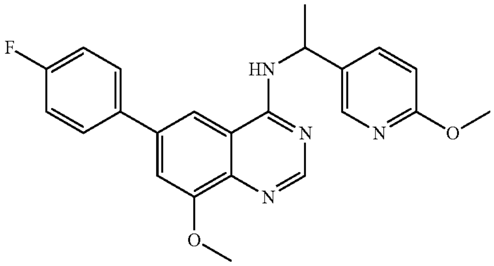 [SMILES: COc1ccc(C(C)Nc2ncnc3c(OC)cc(-c4ccc(F)cc4)cc23)cn1] | Single enantiomer 2 of 6-(4-fluorophenyl)-8-methoxy-N-(1-(6-methoxypyridin-3-yl)ethyl)quinazolin-4-amine |
| Example 267 | 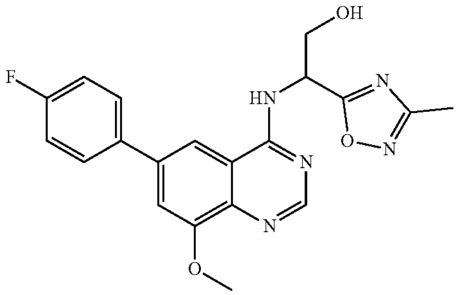 [SMILES: COc1cc(-c2ccc(F)cc2)cc2c(NC(CO)c3nc(C)no3)ncnc12] | Single enantiomer 1 of 2-((6-(4-fluorophenyl)-8-methoxyquinazolin-4-yl)amino)-2-(3-methyl-1,2,4-oxadiazol-5-yl)ethan-1-ol |
| Example 268 | 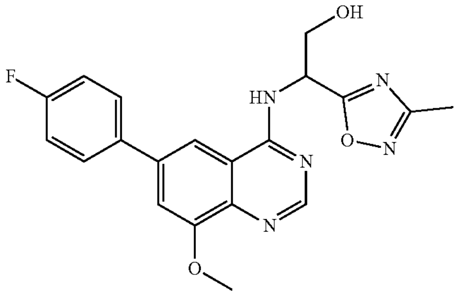 [SMILES: COc1cc(-c2ccc(F)cc2)cc2c(NC(CO)c3nc(C)no3)ncnc12] | Single enantiomer 2 of 2-((6-(4-fluorophenyl)-8-methoxyquinazolin-4-yl)amino)-2-(3-methyl-1,2,4-oxadiazol-5-yl)ethan-1-ol |

TABLE 4-continued

| List of preferred compounds having Formula (I) | | |
|---|---|---|
| Ex. N. | Structure | Chemical Name |
| Example 269 | 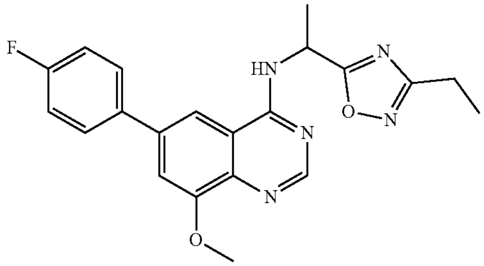 | Single enantiomer 1 of N-(1-(3-ethyl-1,2,4-oxadiazol-5-yl)ethyl)-6-(4-fluorophenyl)-8-methoxyquinazolin-4-amine |
| Example 270 | 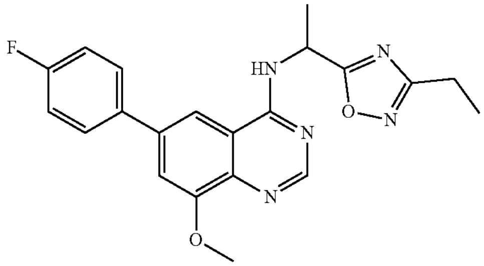 | Single enantiomer 2 of N-(1-(3-ethyl-1,2,4-oxadiazol-5-yl)ethyl)-6-(4-fluorophenyl)-8-methoxyquinazolin-4-amine |
| Example 271 | 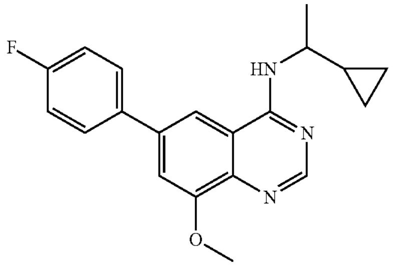 [SMILES: COc1cc(-c2ccc(F)cc2)cc2c(NC(C)C3CC3)ncnc12] | Single enantiomer 1 of N-(1-cyclopropylethyl)-6-(4-fluorophenyl)-8-methoxyquinazolin-4-amine |
| Example 272 | 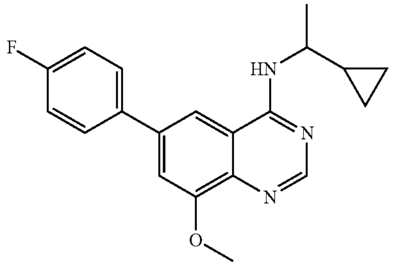 [SMILES: COc1cc(-c2ccc(F)cc2)cc2c(NC(C)C3CC3)ncnc12] | Single enantiomer 2 of N-(1-cyclopropylethyl)-6-(4-fluorophenyl)-8-methoxyquinazolin-4-amine |
| Example 273 | 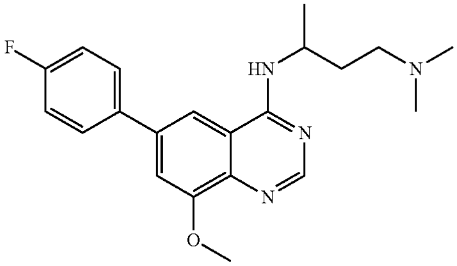 [SMILES: COc1cc(-c2ccc(F)cc2)cc2c(NC(C)CCN(C)C)ncnc12] | Single enantiomer 1 of N3-(6-(4-fluorophenyl)-8-methoxyquinazolin-4-yl)-N1,N1-dimethylbutane-1,3-diamine |

TABLE 4-continued

| List of preferred compounds having Formula (I) | | |
|---|---|---|
| Ex. N. | Structure | Chemical Name |
| Example 274 | 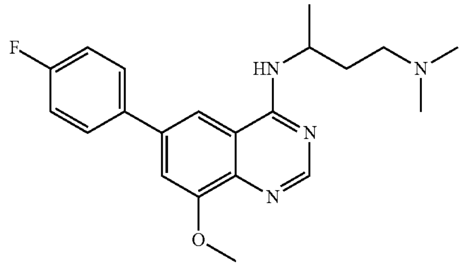 [SMILES: COc1cc(-c2ccc(F)cc2)cc2c(NC(C)CCN(C)C)ncnc12] | Single enantiomer 2 of N3-(6-(4-fluorophenyl)-8-methoxyquinazolin-4-yl)-N1,N1-dimethylbutane-1,3-diamine |
| Example 275 | 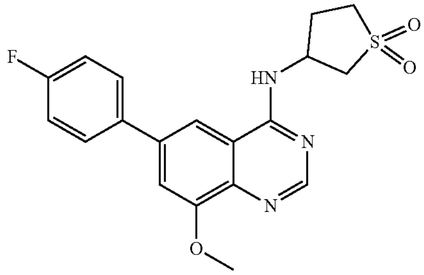 [SMILES: COc1cc(-c2ccc(F)cc2)cc2c(NC3CCS(=O)(=O)C3)ncnc12] | Single enantiomer 1 of 3-((6-(4-fluorophenyl)-8-methoxyquinazolin-4-yl)amino)tetrahydrothiophene 1,1-dioxide |
| Example 276 | 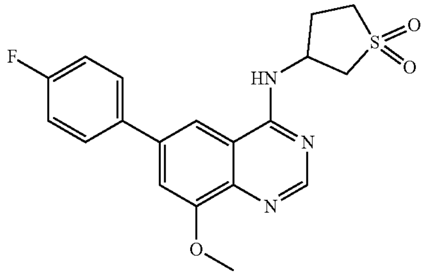 [SMILES: COc1cc(-c2ccc(F)cc2)cc2c(NC3CCS(=O)(=O)C3)ncnc12] | Single enantiomer 2 of 3-((6-(4-fluorophenyl)-8-methoxyquinazolin-4-yl)amino)tetrahydrothiophene 1,1-dioxide |
| Example 277 | 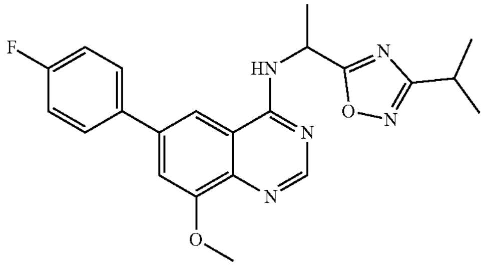 [SMILES: COc1cc(-c2ccc(F)cc2)cc2c(NC(C)c3nc(C(C)C)no3)ncnc12] | Single enantiomer 1 of 6-(4-fluorophenyl)-N-[1-(3-isopropyl-1,2,4-oxadiazol-5-yl)ethyl]-8-methoxy-quinazolin-4-amine |
| Example 278 | 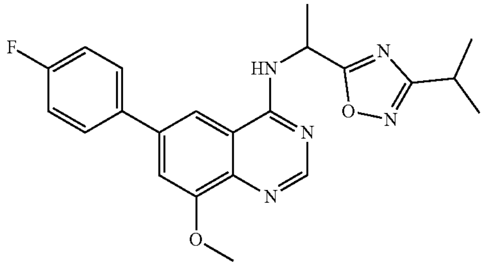 [SMILES: COc1cc(-c2ccc(F)cc2)cc2c(NC(C)c3nc(C(C)C)no3)ncnc12] | Single enantiomer 2 of 6-(4-fluorophenyl)-N-[1-(3-isopropyl-1,2,4-oxadiazol-5-yl)ethyl]-8-methoxy-quinazolin-4-amine |

TABLE 4-continued

| List of preferred compounds having Formula (I) | | |
|---|---|---|
| Ex. N. | Structure | Chemical Name |
| Example 279 | 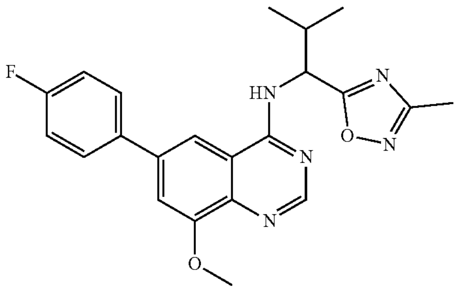 [SMILES: COc1cc(-c2ccc(F)cc2)cc2c(NC(c3nc(C)no3)C(C)C)ncnc12] | Single enantiomer 1 of 6-(4-fluorophenyl)-8-methoxy-N-[2-methyl-1-(3-methyl-1,2,4-oxadiazol-5-yl)propyl]quinazolin-4-amine |
| Example 280 | 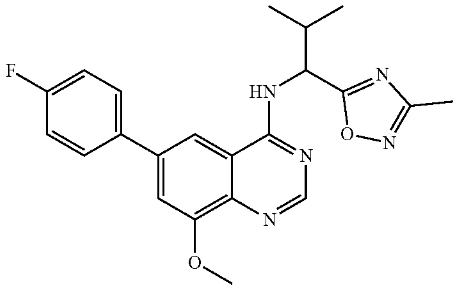 [SMILES: COc1cc(-c2ccc(F)cc2)cc2c(NC(c3nc(C)no3)C(C)C)ncnc12] | Single enantiomer 2 of 6-(4-fluorophenyl)-8-methoxy-N-[2-methyl-1-(3-methyl-1,2,4-oxadiazol-5-yl)propyl]quinazolin-4-amine |
| Example 281 | 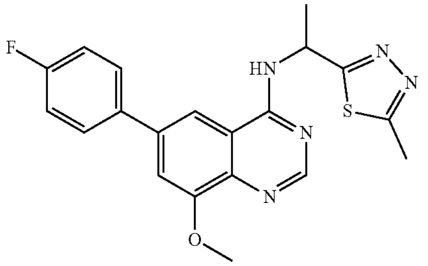 | Single enantiomer 1 of 6-(4-fluorophenyl)-8-methoxy-N-(1-(5-methyl-1,3,4-thiadiazol-2-yl)ethyl)quinazolin-4-amine |
| Example 282 | 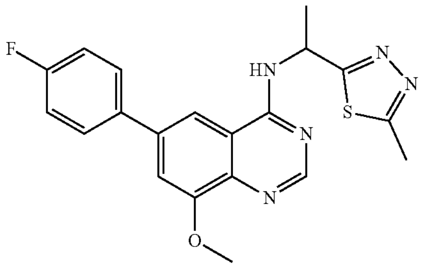 | Single enantiomer 2 of 6-(4-fluorophenyl)-8-methoxy-N-(1-(5-methyl-1,3,4-thiadiazol-2-yl)ethyl)quinazolin-4-amine |
| Example 291 | 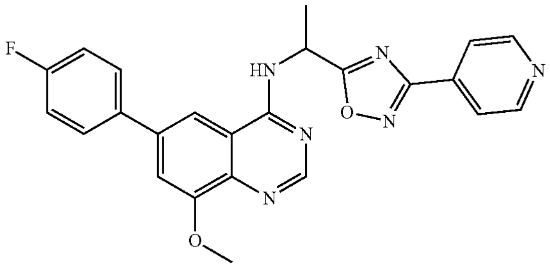 [SMILES: COc1cc(-c2ccc(F)cc2)cc2c(NC(C)c3nc(-c4ccncc4)no3)ncnc12] | 6-(4-Fluorophenyl)-8-methoxy-N-(1-(3-(pyridin-4-yl)-1,2,4-oxadiazol-5-yl)ethyl)quinazolin-4-amine |

TABLE 4-continued

| List of preferred compounds having Formula (I) | | |
|---|---|---|
| Ex. N. | Structure | Chemical Name |
| Example 293 | 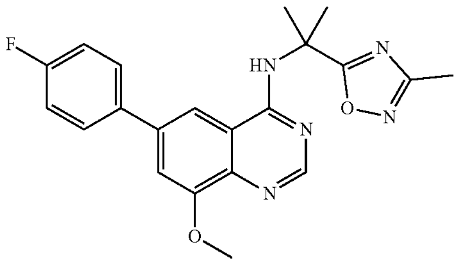 [SMILES: COc1cc(-c2ccc(F)cc2)cc2c(NC(C)(C)c3nc(C)no3)ncnc12] | 6-(4-fluorophenyl)-8-methoxy-N-(2-(3-methyl-1,2,4-oxadiazol-5-yl)propan-2-yl)quinazolin-4-amine |
| Example 294 | 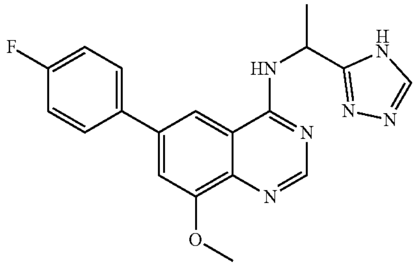 [SMILES: COc1cc(-c2ccc(F)cc2)cc2c(NC(C)c3nnc[nH]3)ncnc12] | (rac)-N-(1-(4H-1,2,4-triazol-3-yl)ethyl)-6-(4-fluorophenyl)-8-methoxyquinazolin-4-amine |
| Example 295 | 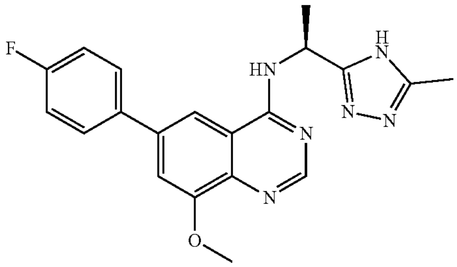 [SMILES: COc1cc(-c2ccc(F)cc2)cc2c(N[C@@H](C)c3nnc(C)[nH]3)ncnc12] | (S)-6-(4-fluorophenyl)-8-methoxy-N-(1-(5-methyl-4H-1,2,4-triazol-3-yl)ethyl)quinazolin-4-amine |
| Example 296 | 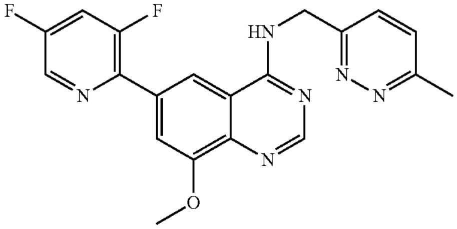 [SMILES: COc1cc(-c2ncc(F)cc2F)cc2c(NCc3ccc(C)nn3)ncnc12] | 6-(3,5-Difluoropyridin-2-yl)-8-methoxy-N-((6-methylpyridazin-3-yl)methyl)quinazolin-4-amine |
| Example 297 | 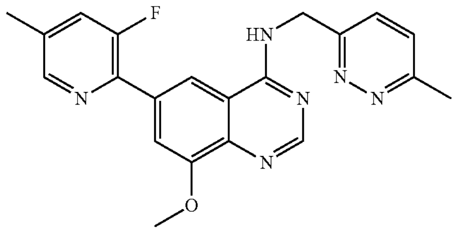 | 6-(3-Fluoro-5-methyl-2-pyridyl)-8-methoxy-N-[(6-methylpyridazin-3-yl)methyl] quinazolin-4-amine |
| Example 298 | 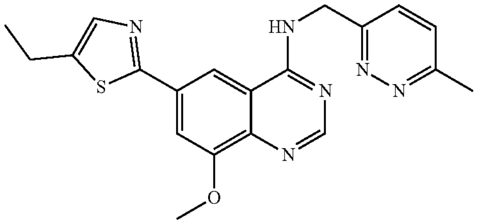 [SMILES: CCc1cnc(-c2cc(OC)c3ncnc(NCc4ccc(C)nn4)c3c2)s1] | 6-(5-Ethylthiazol-2-yl)-8-methoxy-N-[(6-methylpyridazin-3-yl)methyl]quinazolin-4-amine |

TABLE 4-continued

| List of preferred compounds having Formula (I) | | |
|---|---|---|
| Ex. N. | Structure | Chemical Name |
| Example 299 | 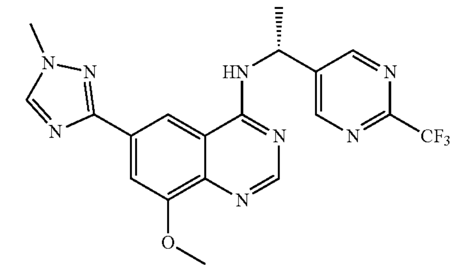 [SMILES: COc1cc(-c2ncn(C)n2)cc2c(N[C@H](C)c3cnc(C(F)(F)F)nc3)ncnc12] | (R)-8-methoxy-6-(1-methyl-1H-1,2,4-triazol-3-yl)-N-(1-(2-(trifluoromethyl)pyrimidin-5-yl)ethyl)quinazolin-4-amine |
| Example 300 | 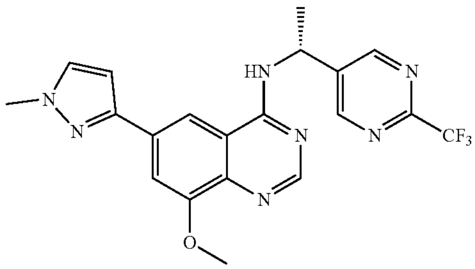 [SMILES: COc1cc(-c2ccn(C)n2)cc2c(N[C@H](C)c3cnc(C(F)(F)F)nc3)ncnc12] | (R)-8-methoxy-6-(1-methyl-1H-pyrazol-3-yl)-N-(1-(2-(trifluoromethyl)pyrimidin-5-yl)ethyl)quinazolin-4-amine |
| Example 301 | 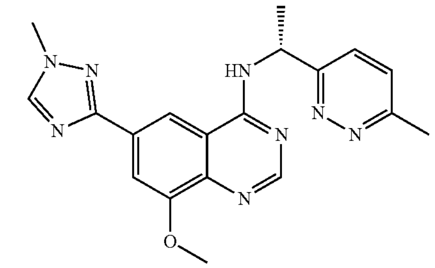 [SMILES: COc1cc(-c2ncn(C)n2)cc2c(N[C@H](C)c3ccc(C)nn3)ncnc12] | (R)-8-methoxy-6-(1-methyl-1H-1,2,4-triazol-3-yl)-N-(1-(6-methylpyridazin-3-yl)ethyl)quinazolin-4-amine |
| Example 315 | 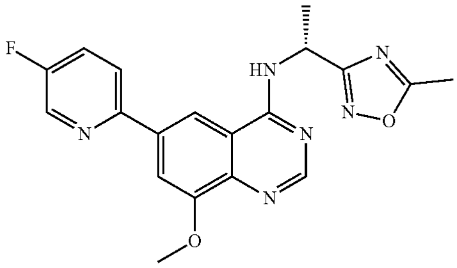 [SMILES: COc1cc(-c2ccc(F)cn2)cc2c(N[C@H](C)c3noc(C)n3)ncnc12] | (R)-6-(5-fluoropyridin-2-yl)-8-methoxy-N-(1-(5-methyl-1,2,4-oxadiazol-3-yl)ethyl)quinazolin-4-amine |
| Example 316 | 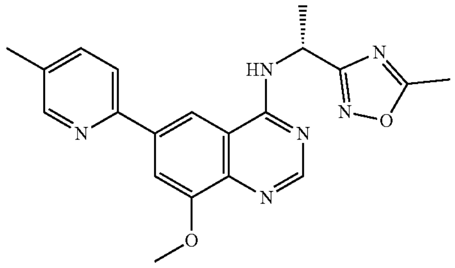 | (R)-8-methoxy-N-(1-(5-methyl-1,2,4-oxadiazol-3-yl)ethyl)-6-(5-methylpyridin-2-yl)quinazolin-4-amine |

TABLE 4-continued

| List of preferred compounds having Formula (I) | | |
|---|---|---|
| Ex. N. | Structure | Chemical Name |
| Example 317 | 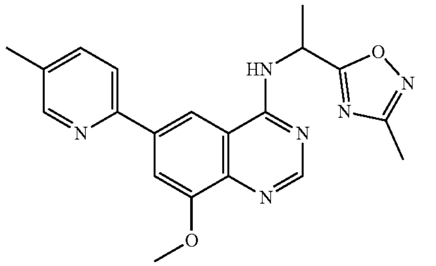 [SMILES: COc1cc(-c2ccc(C)cn2)cc2c(NC(C)c3nc(C)no3)ncnc12] | 8-Methoxy-N-[1-(3-methyl-1,2,4-oxadiazol-5-yl)ethyl]-6-(5-methyl-2-pyridyl)quinazolin-4-amine |
| Example 318 | 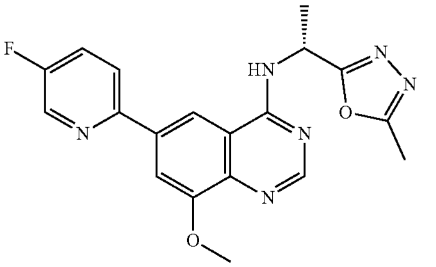 [SMILES: COc1cc(-c2ccc(F)cn2)cc2c(N[C@H](C)c3nnc(C)o3)ncnc12] | 6-(5-fluoro-2-pyridyl)-8-methoxy-N-[(1R)-1-(5-methyl-1,3,4-oxadiazol-2-yl)ethyl]quinazolin-4-amine |
| Example 319 | 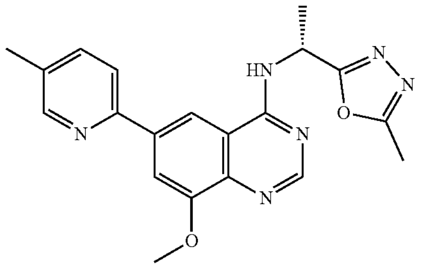 [SMILES: COc1cc(-c2ccc(C)cn2)cc2c(N[C@H](C)c3nnc(C)o3)ncnc12] | 8-methoxy-N-[(1R)-1-(5-methyl-1,3,4-oxadiazol-2-yl)ethyl]-6-(5-methyl-2-pyridyl)quinazolin-4-amine |
| Example 320 | 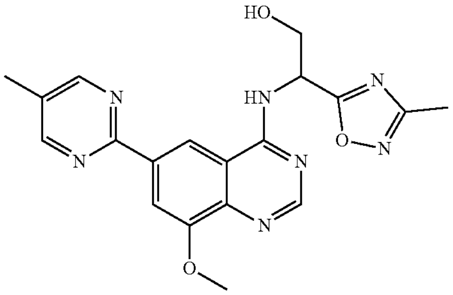 | 2-((8-methoxy-6-(5-methylpyrimidin-2-yl)quinazolin-4-yl)amino)-2-(3-methyl-1,2,4-oxadiazol-5-yl)ethan-1-ol |
| Example 321 | 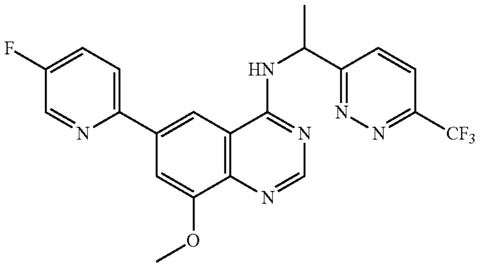 [SMILES: COc1cc(-c2ccc(F)cn2)cc2c(NC(C)c3ccc(C(F)(F)F)nn3)ncnc12] | 6-(5-fluoro-2-pyridyl)-8-methoxy-N-[1-[6-(trifluoromethyl)pyridazin-3-yl]ethyl]quinazolin-4-amine |

TABLE 4-continued

List of preferred compounds having Formula (I)

| Ex. N. | Structure | Chemical Name |
|---|---|---|
| Example 322 | 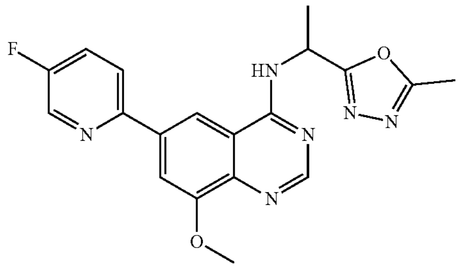 | 6-(5-fluoropyridin-2-yl)-8-methoxy-N-(1-(5-methyl-1,3,4-oxadiazol-2-yl)ethyl)quinazolin-4-amine |
| Example 323 | 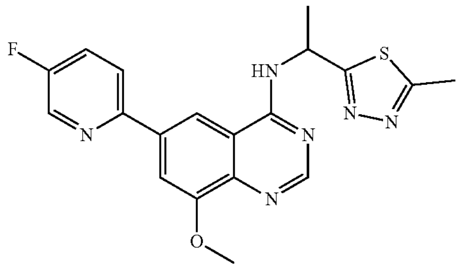 | 6-(5-fluoropyridin-2-yl)-8-methoxy-N-(1-(5-methyl-1,3,4-thiadiazol-2-yl)ethyl)quinazolin-4-amine |
| Example 324 | 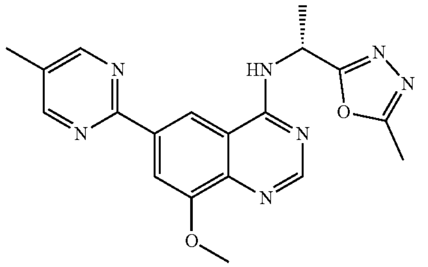 [SMILES: COc1cc(-c2ncc(C)cn2)cc2c(N[C@H](C)c3nnc(C)o3)ncnc12] | 8-methoxy-N-[(1R)-1-(5-methyl-1,3,4-oxadiazol-2-yl)ethyl]-6-(5-methylpyrimidin-2-yl)quinazolin-4-amine |
| Example 325 | 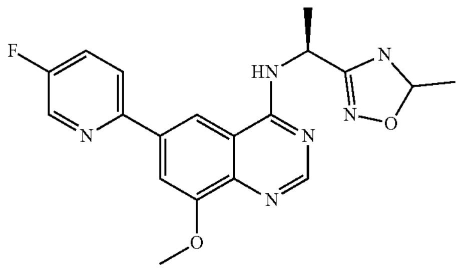 | (S)-6-(5-fluoropyridin-2-yl)-8-methoxy-N-(1-(5-methyl-1,2,4-oxadiazol-3-yl)ethyl)quinazolin-4-amine |
| Example 326 | 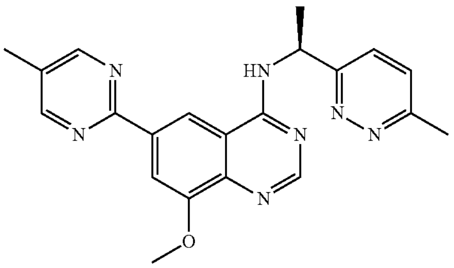 | 8-Methoxy-N-[(1S)-1-(6-methylpyridazin-3-yl)ethyl]-6-(5-methylpyrimidin-2-yl)quinazolin-4-amine |

In a further preferred embodiment, the invention is addressed to compound of formula (I) wherein Z is aryl, wherein any of such aryl may be optionally substituted by one or more groups selected from ($C_1$-$C_3$)alkyl, halo, CN, $R_1$ is H;

$R_2$ is selected from the group consisting of heteroaryl($C_1$-$C_4$)alkyl-, ($C_3$-$C_8$)heterocycloalkyl-($C_1$-$C_6$)alkyl, ($C_3$-$C_8$)heterocycloalkyl, ($C_3$-$C_8$)cycloalkyl-($C_1$-$C_6$)alkyl-, wherein any of such alkyl, heteroaryl may be optionally substituted by one or more groups selected from ($C_1$-$C_3$)alkyl, ($C_1$-$C_6$)haloalkyl, oxo, $R^AO$—, aryl, ($R^AR^B$)N— and halo;

$R^A$ and $R^B$ are at each occurrence independently H or selected from the group consisting of $(C_1-C_4)$alkyl-, $(C_1-C_6)$ haloalkyl;

Y is selected from the group consisting of —$OR^D$, $R^CSO_2$, halo and —$NHSO_2R^C$, heteroaryl, heterocycloalkyl, wherein any of such heteroaryl may be optionally substituted by one or more groups selected from $(C_1-C_3)$alkyl, —$C(O)N(R^AR^B)$;

J is H or selected from the group consisting of $OR^C$;

$R^C$ is H, or selected form the group consisting of $(C_1-C_6)$ alkyl, $(R^AR^B)N$—;

$R^D$ is H or $(C_1-C_6)$alkyl.

According to a preferred embodiment, the invention refers to at least one compound of Table 5, selected from:

TABLE 5

| List of preferred compounds having Formula (I) | | |
|---|---|---|
| Ex. N. | Structure | Chemical Name |
| Example 184 | 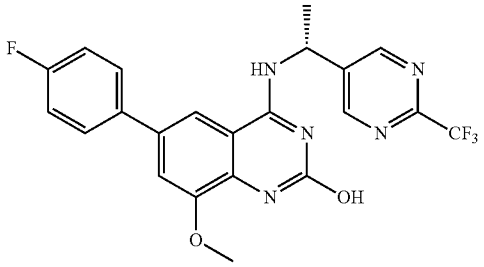 [SMILES: COc1cc(-c2ccc(F)cc2)cc2c(N[C@H](C)c3cnc(C(F)(F)F)nc3)nc(O)nc12] | (R)-6-(4-Fluorophenyl)-8-methoxy-4-((1-(2-(trifluoromethyl)pyrimidin-5-yl)ethyl)-amino)-quinazolin-2-ol |
| Example 185 | 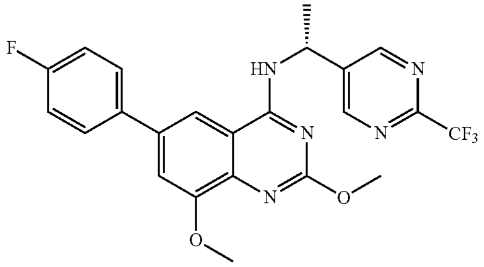 [SMILES: COc1nc(N[C@H](C)c2cnc(C(F)(F)F)nc2)c2cc(-c3ccc(F)cc3)cc(OC)c2n1] | (R)-6-(4-Fluorophenyl)-2,8-dimethoxy-N-(1-(2-(trifluoromethyl)pyrimidin-5-yl)ethyl)quinazolin-4-amine |
| Example 1 | 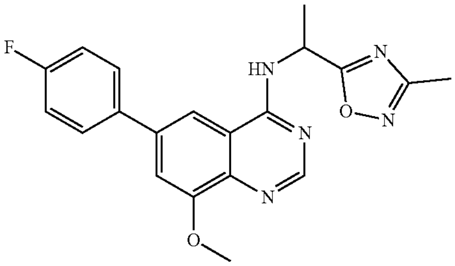 [SMILES: COc1cc(-c2ccc(F)cc2)cc2c(NC(C)c3nc(C)no3)ncnc12] | 6-(4-Fluorophenyl)-8-methoxy-N-(1-(3-methyl-1,2,4-oxadiazol-5-yl)ethyl)quinazolin-4-amine |
| Example 2 | 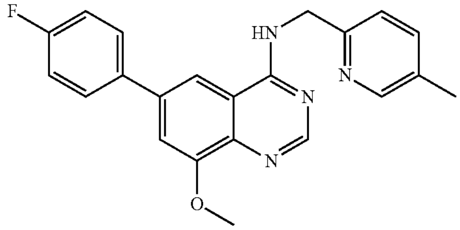 | 6-(4-Fluorophenyl)-8-methoxy-N-((5-methylpyridin-2-yl)methyl)quinazolin-4-amine |
| Example 3 | 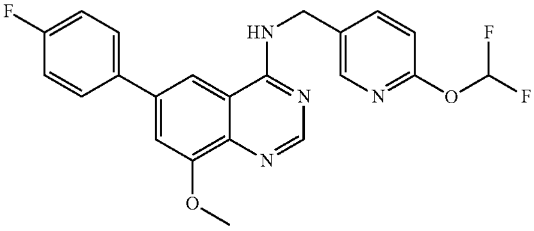 [SMILES: COc1cc(-c2ccc(F)cc2)cc2c(NCc3ccc(OC(F)F)nc3)ncnc12] | N-((6-(Difluoromethoxy)pyridin-3-yl)methyl)-6-(4-fluorophenyl)-8-methoxyquinazolin-4-amine |

TABLE 5-continued

| List of preferred compounds having Formula (I) | | |
|---|---|---|
| Ex. N. | Structure | Chemical Name |
| Example 4 | 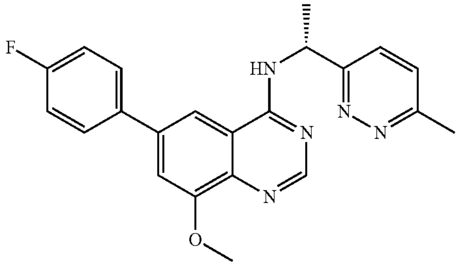 [SMILES: COc1cc(-c2ccc(F)cc2)cc2c(N[C@H](C)c3ccc(C)nn3)ncnc12] | (R)-6-(4-Fluorophenyl)-8-methoxy-N-(1-(6-methylpyridazin-3-yl)ethyl)quinazolin-4-amine |
| Example 5 | 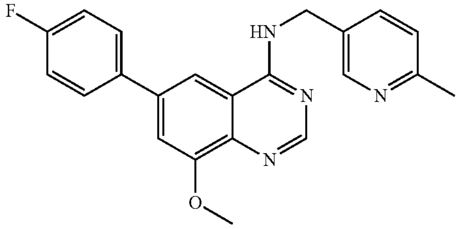 [SMILES: COc1cc(-c2ccc(F)cc2)cc2c(NCc3ccc(C)nc3)ncnc12] | 6-(4-Fluorophenyl)-8-methoxy-N-((6-methylpyridin-3-yl)methyl)quinazolin-4-amine |
| Example 6 | 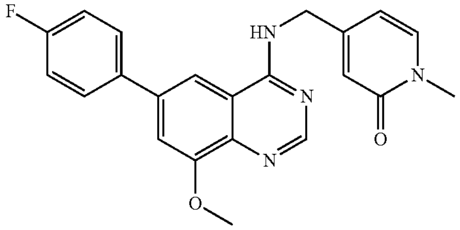 [SMILES: COc1cc(-c2ccc(F)cc2)cc2c(NCc3ccn(C)c(=O)c3)ncnc12] | 4-(((6-(4-Fluorophenyl)-8-methoxyquinazolin-4-yl)amino)methyl)-1-methylpyridin-2(1H)-one |
| Example 7 | 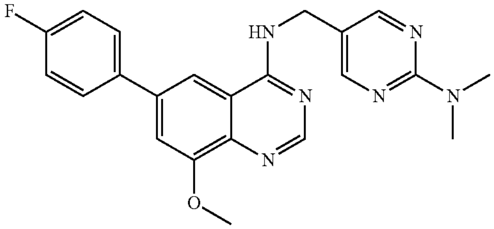 [SMILES: COc1cc(-c2ccc(F)cc2)cc2c(NCc3cnc(N(C)C)nc3)ncnc12] | N-((2-(Dimethylamino)pyrimidin-5-yl)methyl)-6-(4-fluorophenyl)-8-methoxyquinazolin-4-amine |
| Example 8 | 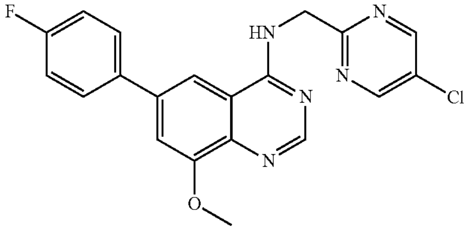 [SMILES: COc1cc(-c2ccc(F)cc2)cc2c(NCc3ncc(Cl)cn3)ncnc12] | N-((5-Chloropyrimidin-2-yl)methyl)-6-(4-fluorophenyl)-8-methoxyquinazolin-4-amine |
| Example 10 | 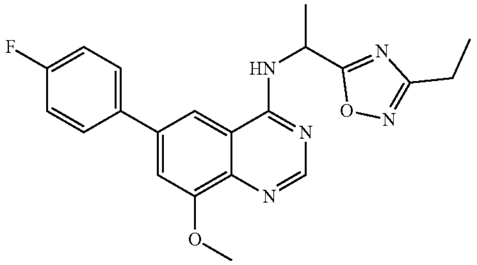 [SMILES: CCc1noc(C(C)Nc2ncnc3c(OC)cc(-c4ccc(F)cc4)cc23)n1] | N-(1-(3-Ethyl-1,2,4-oxadiazol-5-yl)ethyl)-6-(4-fluorophenyl)-8-methoxyquinazolin-4-amine |

TABLE 5-continued

| List of preferred compounds having Formula (I) | | |
|---|---|---|
| Ex. N. | Structure | Chemical Name |
| Example 11 | 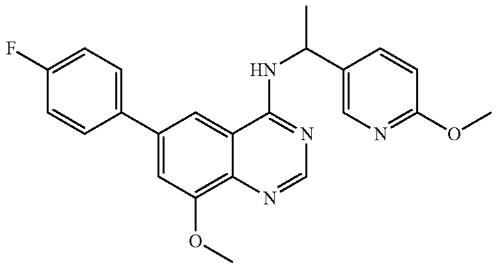 [SMILES: COc1ccc(C(C)Nc2ncnc3c(OC)cc(-c4ccc(F)cc4)cc23)cn1] | 6-(4-Fluorophenyl)-8-methoxy-N-(1-(6-methoxypyridin-3-yl)ethyl)quinazolin-4-amine |
| Example 12 | 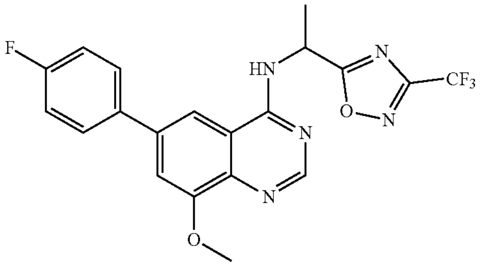 [SMILES: COc1cc(-c2ccc(F)cc2)cc2c(NC(C)c3nc(C(F)(F)F)no3)ncnc12] | 6-(4-Fluorophenyl)-8-methoxy-N-(1-(3-(trifluoromethyl)-1,2,4-oxadiazol-5-yl)ethyl)quinazolin-4-amine |
| Example 14 | 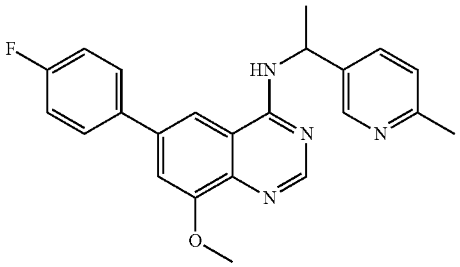 [SMILES: COc1cc(-c2ccc(F)cc2)cc2c(NC(C)c3ccc(C)nc3)ncnc12] | 6-(4-Fluorophenyl)-8-methoxy-N-(1-(6-methylpyridin-3-yl)ethyl)quinazolin-4-amine |
| Example 15 | 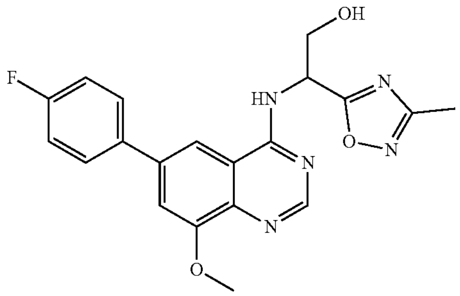 [SMILES: COc1cc(-c2ccc(F)cc2)cc2c(NC(CO)c3nc(C)no3)ncnc12] | 2-((6-(4-Fluorophenyl)-8-methoxyquinazolin-4-yl)amino)-2-(3-methyl-1,2,4-oxadiazol-5-yl)ethan-1-ol |
| Example 16 | 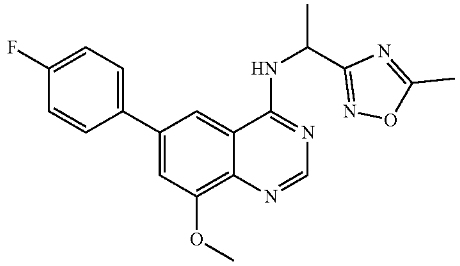 [SMILES: COc1cc(-c2ccc(F)cc2)cc2c(NC(C)c3noc(C)n3)ncnc12] | 6-(4-Fluorophenyl)-8-methoxy-N-(1-(5-methyl-1,2,4-oxadiazol-3-yl)ethyl)quinazolin-4-amine |

TABLE 5-continued

List of preferred compounds having Formula (I)

| Ex. N. | Structure | Chemical Name |
|---|---|---|
| Example 17 | 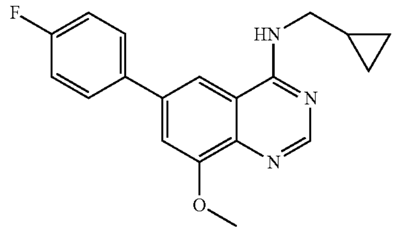 [SMILES: COc1cc(-c2ccc(F)cc2)cc2c(NCC3CC3)ncnc12] | N-(Cyclopropylmethyl)-6-(4-fluorophenyl)-8-methoxyquinazolin-4-amine |
| Example 18 | 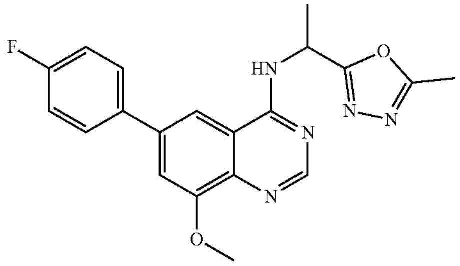 [SMILES: COc1cc(-c2ccc(F)cc2)cc2c(NC(C)c3nnc(C)o3)ncnc12] | 6-(4-Fluorophenyl)-8-methoxy-N-(1-(5-methyl-1,3,4-oxadiazol-2-yl)ethyl)quinazolin-4-amine |
| Example 19 | 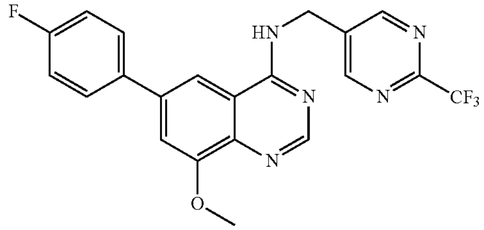 [SMILES: COc1cc(-c2ccc(F)cc2)cc2c(NCc3cnc(C(F)(F)F)nc3)ncnc12] | 6-(4-Fluorophenyl)-8-methoxy-N-((2-(trifluoromethyl)pyrimidin-5-yl)methyl)quinazolin-4-amine |
| Example 20 | 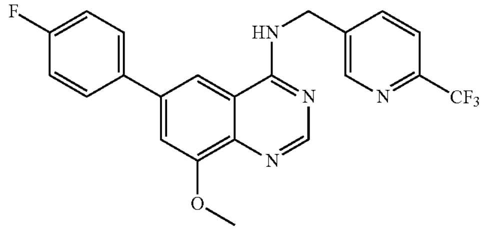 [SMILES: COc1cc(-c2ccc(F)cc2)cc2c(NCc3ccc(C(F)(F)F)nc3)ncnc12] | 6-(4-Fluorophenyl)-8-methoxy-N-((6-(trifluoromethyl)pyridin-3-yl)methyl)quinazolin-4-amine |
| Example 21 | 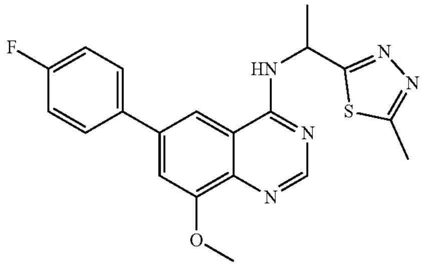 | 6-(4-Fluorophenyl)-8-methoxy-N-(1-(5-methyl-1,3,4-thiadiazol-2-yl)ethyl)quinazolin-4-amine |
| Example 22 | 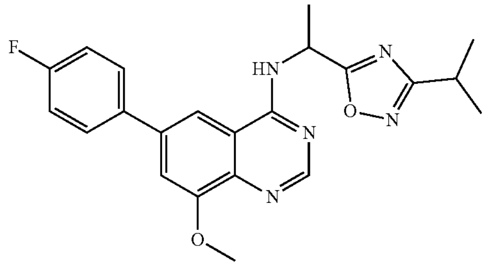 [SMILES: COc1cc(-c2ccc(F)cc2)cc2c(NC(C)c3nc(C(C)C)no3)ncnc12] | 6-(4-Fluorophenyl)-N-(1-(3-isopropyl-1,2,4-oxadiazol-5-yl)ethyl)-8-methoxyquinazolin-4-amine |

TABLE 5-continued

List of preferred compounds having Formula (I)

| Ex. N. | Structure | Chemical Name |
|---|---|---|
| Example 25 | 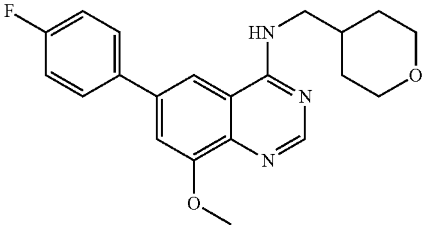 [SMILES: COc1cc(-c2ccc(F)cc2)cc2c(NCC3CCOCC3)ncnc12] | 6-(4-Fluorophenyl)-8-methoxy-N-((tetrahydro-2H-pyran-4-yl)methyl)quinazolin-4-amine |
| Example 31 | 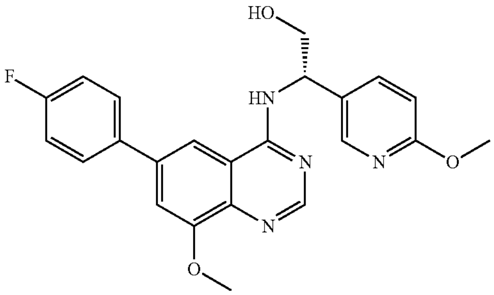 [SMILES: COc1ccc([C@@H](CO)Nc2ncnc3c(OC)cc(-c4ccc(F)cc4)cc23)cn1] | (S)-2-((6-(4-Fluorophenyl)-8-methoxyquinazolin-4-yl)amino)-2-(6-methoxypyridin-3-yl)ethan-1-ol |
| Example 33 | 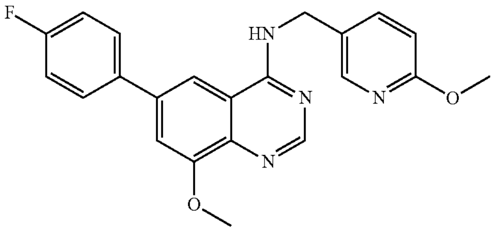 [SMILES: COc1ccc(CNc2ncnc3c(OC)cc(-c4ccc(F)cc4)cc23)cn1] | 6-(4-Fluorophenyl)-8-methoxy-N-((6-methoxypyridin-3-yl)methyl)quinazolin-4-amine |
| Example 39 | 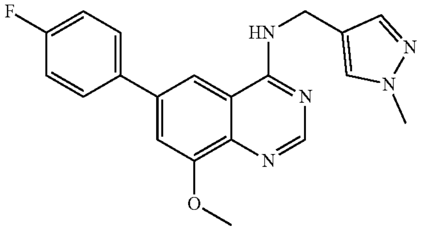 [SMILES: COc1cc(-c2ccc(F)cc2)cc2c(NCc3cnn(C)c3)ncnc12] | 6-(4-Fluorophenyl)-8-methoxy-N-((1-methyl-1H-pyrazol-4-yl)methyl)quinazolin-4-amine |
| Example 45 | 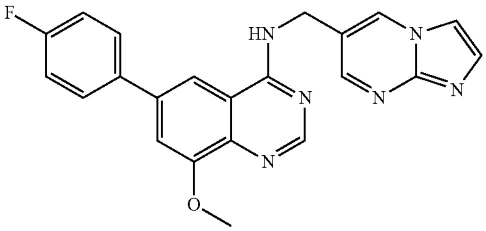 [SMILES: COc1cc(-c2ccc(F)cc2)cc2c(NCc3cnc4nccn4c3)ncnc12] | 6-(4-Fluorophenyl)-N-(imidazo[1,2-a]pyrimidin-6-ylmethyl)-8-methoxyquinazolin-4-amine |
| Example 48 | 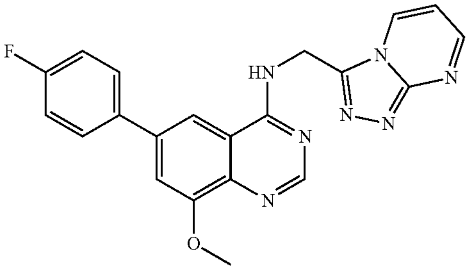 [SMILES: COc1cc(-c2ccc(F)cc2)cc2c(NCc3nnc4ncccn34)ncnc12] | N-([1,2,4]Triazolo[4,3-a]pyrimidin-3-ylmethyl)-6-(4-fluorophenyl)-8-methoxyquinazolin-4-amine |

TABLE 5-continued

List of preferred compounds having Formula (I)

| Ex. N. | Structure | Chemical Name |
|---|---|---|
| Example 49 | 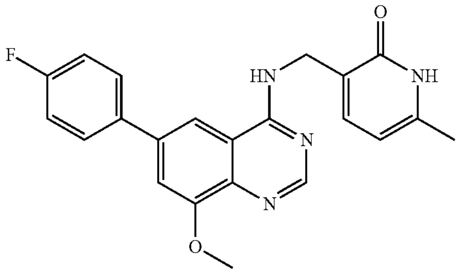 [SMILES: COc1cc(-c2ccc(F)cc2)cc2c(NCc3ccc(C)[nH]c3=O)ncnc12] | 3-(((6-(4-Fluorophenyl)-8-methoxyquinazolin-4-yl)amino)methyl)-6-methylpyridin-2(1H)-one |
| Example 50 | 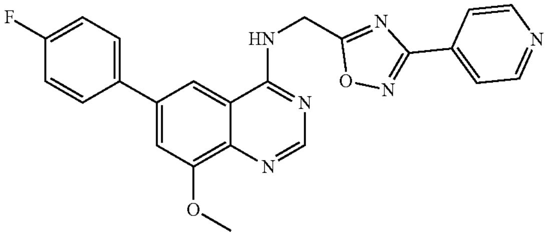 [SMILES: COc1cc(-c2ccc(F)cc2)cc2c(NCc3nc(-c4ccncc4)no3)ncnc12] | 6-(4-Fluorophenyl)-8-methoxy-N-((3-(pyridin-4-yl)-1,2,4-oxadiazol-5-yl)methyl)quinazolin-4-amine |
| Example 64 | 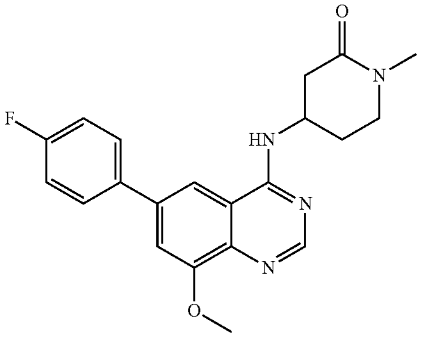 [SMILES: COc1cc(-c2ccc(F)cc2)cc2c(NC3CCN(C)C(=O)C3)ncnc12] | 4-[[6-(4-Fluorophenyl)-8-methoxy-quinazolin-4-yl]amino]-1-methyl-piperidin-2-one |
| Example 112 | 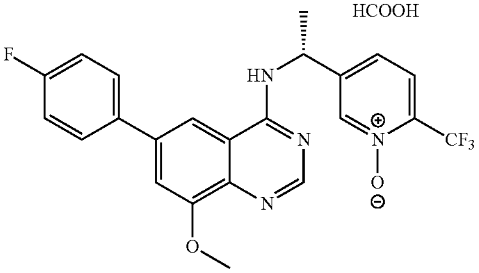 [SMILES: COc1cc(-c2ccc(F)cc2)cc2c(N[C@H](C)c3ccc(C(F)(F)F)[n+]([O-])c3)ncnc12 ; "HCOOH"] HCOOH | (R)-5-(1-((6-(4-fluorophenyl)-8-methoxyquinazolin-4-yl)amino)ethyl)-2-(trifluoromethyl)pyridine 1-oxide formate |
| Example 113 | 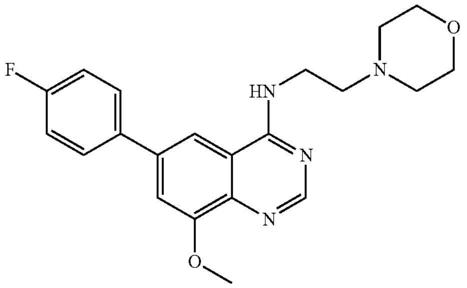 [SMILES: COc1cc(-c2ccc(F)cc2)cc2c(NCCN3CCOCC3)ncnc12] | 6-(4-fluorophenyl)-8-methoxy-N-(2-morpholinoethyl)quinazolin-4-amine |

TABLE 5-continued

| List of preferred compounds having Formula (I) | | |
|---|---|---|
| Ex. N. | Structure | Chemical Name |
| Example 165 | 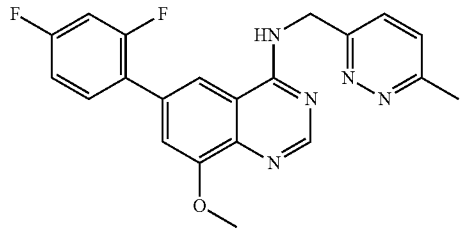 | 6-(2,4-Difluorophenyl)-8-methoxy-N-((6-methylpyridazin-3-yl)methyl)quinazolin-4-amine |
| Example 170 | 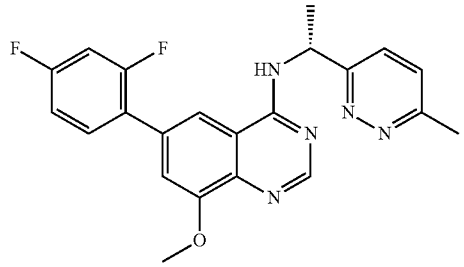 [SMILES: COc1cc(-c2ccc(F)cc2F)cc2c(N[C@H](C)c3ccc(C)nn3)ncnc12] | 6-(2,4-Difluorophenyl)-8-methoxy-N-[(1R)-1-(6-methylpyridazin-3-yl)ethyl]quinazolin-4-amine |
| Example 175 | 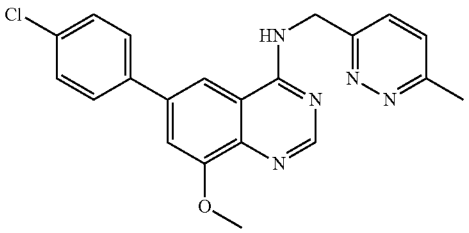 [SMILES: COc1cc(-c2ccc(Cl)cc2)cc2c(NCc3ccc(C)nn3)ncnc12] | 6-(4-chlorophenyl)-8-methoxy-N-((6-methylpyridazin-3-yl)methyl)quinazolin-4-amine |
| Example 178 | 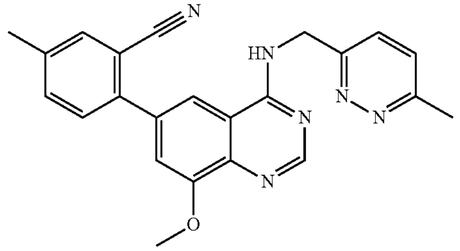 | 2-(8-Methoxy-4-(((6-methylpyridazin-3-yl)methyl)amino)quinazolin-6-yl)-5-methylbenzonitrile |
| Example 181 | 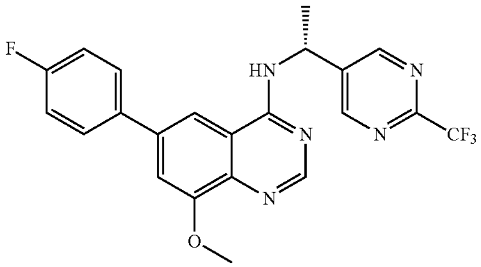 [SMILES: COc1cc(-c2ccc(F)cc2)cc2c(N[C@H](C)c3cnc(C(F)(F)F)nc3)ncnc12] | (R)-6-(4-fluorophenyl)-8-methoxy-N-(1-(2-(trifluoromethyl)pyrimidin-5-yl)ethyl)quinazolin-4-amine |
| Example 182 | 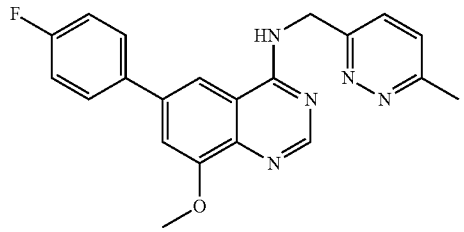 [SMILES: COc1cc(-c2ccc(F)cc2)cc2c(NCc3ccc(C)nn3)ncnc12] | 6-(4-fluorophenyl)-8-methoxy-N-((6-methylpyridazin-3-yl)methyl)quinazolin-4-amine |

TABLE 5-continued

| List of preferred compounds having Formula (I) | | |
|---|---|---|
| Ex. N. | Structure | Chemical Name |
| Example 186 | 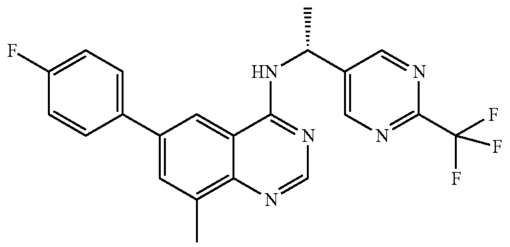 [SMILES: Cc1cc(-c2ccc(F)cc2)cc2c(N[C@H](C)c3cnc(C(F)(F)F)nc3)ncnc12] | (R)-6-(4-Fluorophenyl)-8-iodo-N-(1-(2-(trifluoromethyl)pyrimidin-5-yl)ethyl)quinazolin-4-amine |
| Example 187 | 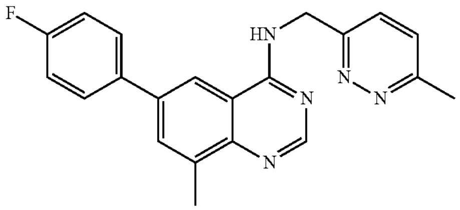 [SMILES: Cc1ccc(CNc2ncnc3c(C)cc(-c4ccc(F)cc4)cc23)nn1] | 6-(4-fluorophenyl)-8-iodo-N-((6-methylpyridazin-3-yl)methyl)quinazolin-4-amine |
| Example 188 | 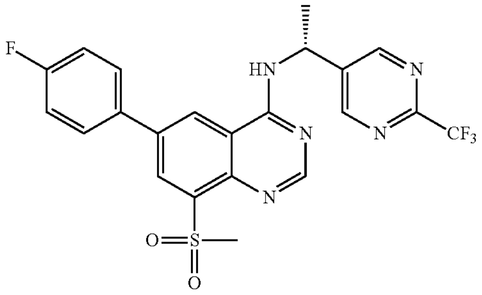 [SMILES: C[C@@H](Nc1ncnc2c(S(C)(=O)=O)cc(-c3ccc(F)cc3)cc12)c1cnc(C(F)(F)F)nc1] | (R)-6-(4-fluorophenyl)-8-(methylsulfonyl)-N-(1-(2-(trifluoromethyl)pyrimidin-5-yl)ethyl)quinazolin-4-amine |
| Example 189 | 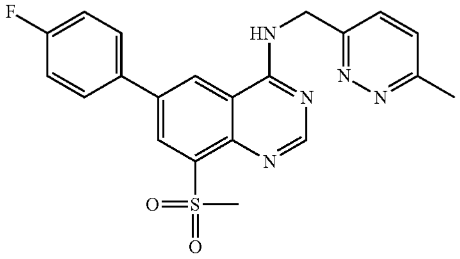 [SMILES: Cc1ccc(CNc2ncnc3c(S(C)(=O)=O)cc(-c4ccc(F)cc4)cc23)nn1] | 6-(4-fluorophenyl)-N-((6-methylpyridazin-3-yl)methyl)-8-(methylsulfonyl)quinazolin-4-amine |
| Example 190 | 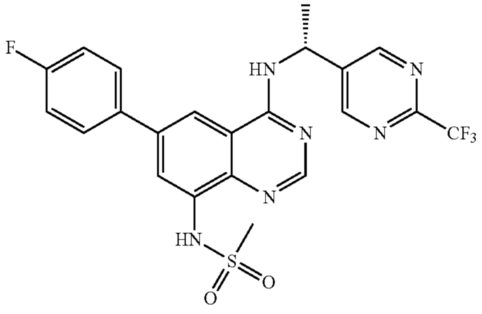 [SMILES: C[C@@H](Nc1ncnc2c(NS(C)(=O)=O)cc(-c3ccc(F)cc3)cc12)c1cnc(C(F)(F)F)nc1] | (R)-N-(6-(4-fluorophenyl)-4-((1-(2-(trifluoromethyl)pyrimidin-5-yl)ethyl)amino)quinazolin-8-yl)methanesulfonamide |

TABLE 5-continued

| List of preferred compounds having Formula (I) | | |
|---|---|---|
| Ex. N. | Structure | Chemical Name |
| Example 191 | 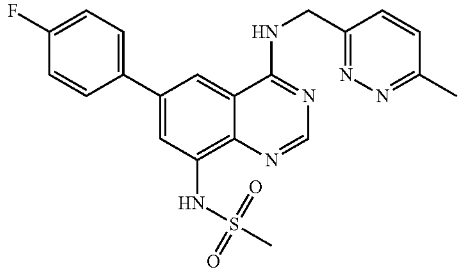 [SMILES: Cc1ccc(CNc2ncnc3c(NS(C)(=O)=O)cc(-c4ccc(F)cc4)cc23)nn1] | N-(6-(4-fluorophenyl)-4-oxo-3,4-dihydroquinazolin-8-yl)methanesulfonamide |
| Example 192 | 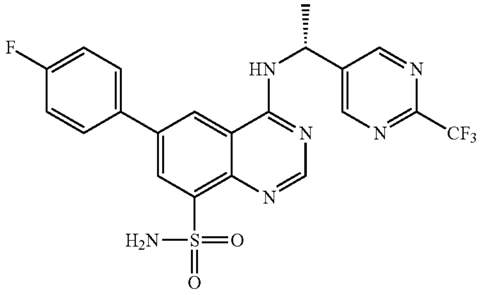 | (R)-6-(4-fluorophenyl)-4-((1-(2-(trifluoromethyl)pyrimidin-5-yl)ethyl)amino)quinazoline-8-sulfonamide |
| Example 195 | 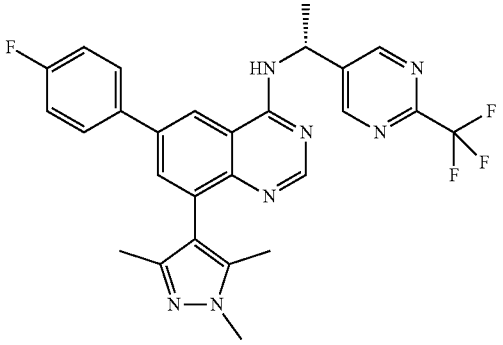 [SMILES: Cc1nn(C)c(C)c1-c1cc(-c2ccc(F)cc2)cc2c(N[C@H](C)c3cnc(C(F)(F)F)nc3)ncnc12] | (R)-6-(4-Fluorophenyl)-N-(1-(2-(trifluoromethyl)pyrimidin-5-yl)ethyl)-8-(1,3,5-trimethyl-1H-pyrazol-4-yl)quinazolin-4-amine |
| Example 196 | 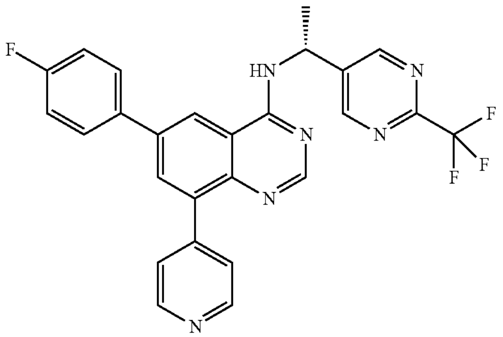 [SMILES: C[C@@H](Nc1ncnc2c(-c3ccncc3)cc(-c3ccc(F)cc3)cc12)c1cnc(C(F)(F)F)nc1] | (R)-6-(4-Fluorophenyl)-8-(pyridin-4-yl)-N-(1-(2-(trifluoromethyl)pyrimidin-5-yl)ethyl)qui azolin-4-amine |
| Example 198 | 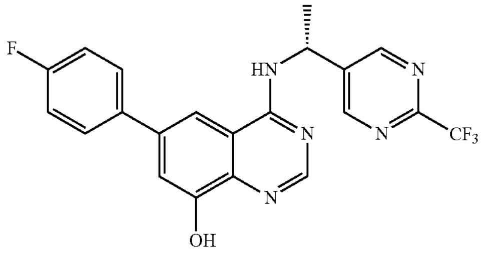 [SMILES: C[C@@H](Nc1ncnc2c(O)cc(-c3ccc(F)cc3)cc12)c1cnc(C(F)(F)F)nc1] | (R)-6-(4-fluorophenyl)-4-((1-(2-(trifluoromethyl)pyrimidin-5-yl)ethyl)amino)-quinazolin-8-ol |

TABLE 5-continued

List of preferred compounds having Formula (I)

| Ex. N. | Structure | Chemical Name |
|---|---|---|
| Example 199 | 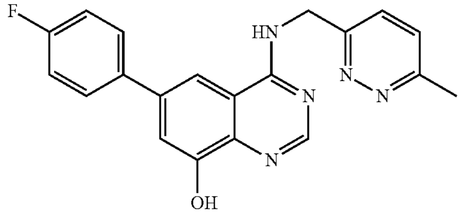 [SMILES: Cc1ccc(CNc2ncnc3c(O)cc(-c4ccc(F)cc4)cc23)nn1] | 6-(4-fluorophenyl)-4-(((6-methylpyridazin-3-yl)methyl)amino)quinazolin-8-ol |
| Example 227 | 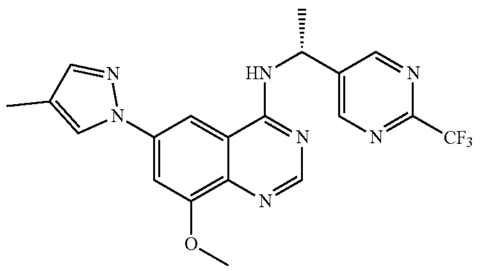 [SMILES: COc1cc(-n2cc(C)cn2)cc2c(N[C@H](C)c3cnc(C(F)(F)F)nc3)ncnc12] | (R)-8-Methoxy-6-(4-methyl-1H-pyrazol-1-yl)-N-(1-(2-(trifluoromethyl)pyrimidin-5-yl)ethyl)quinazolin-4-amine |
| Example 257 | 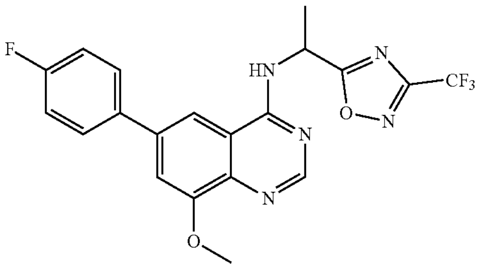 [SMILES: COc1cc(-c2ccc(F)cc2)cc2c(NC(C)c3nc(C(F)(F)F)no3)ncnc12] | Single enantiomer 1 of 6-(4-fluorophenyl)-8-methoxy-N-(1-(3-(trifluoromethyl)-1,2,4-oxadiazol-5-yl)ethyl)quinazolin-4-amine |
| Example 258 | 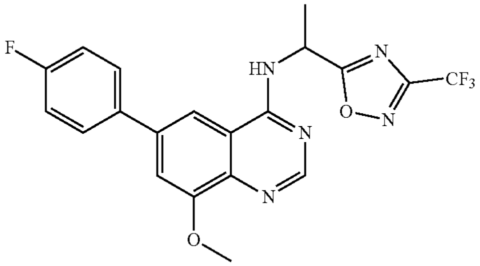 [SMILES: COc1cc(-c2ccc(F)cc2)cc2c(NC(C)c3nc(C(F)(F)F)no3)ncnc12] | Single enantiomer 2 of 6-(4-fluorophenyl)-8-methoxy-N-(1-(3-(trifluoromethyl)-1,2,4-oxadiazol-5-yl)ethyl)quinazolin-4-amine |
| Example 265 | 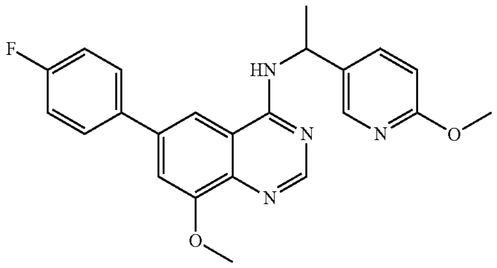 [SMILES: COc1ccc(C(C)Nc2ncnc3c(OC)cc(-c4ccc(F)cc4)cc23)cn1] | Single enantiomer 1 of 6-(4-fluorophenyl)-8-methoxy-N-(1-(6-methoxypyridin-3-yl)ethyl)quinazolin-4-amine |

TABLE 5-continued

| List of preferred compounds having Formula (I) | | |
|---|---|---|
| Ex. N. | Structure | Chemical Name |
| Example 266 | 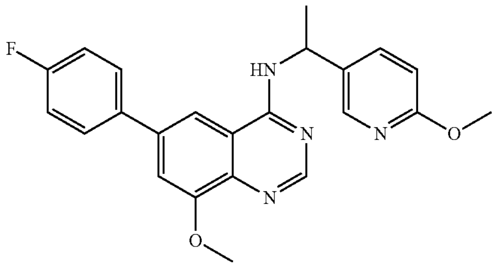 [SMILES: COc1ccc(C(C)Nc2ncnc3c(OC)cc(-c4ccc(F)cc4)cc23)cn1] | Single enantiomer 2 of 6-(4-fluorophenyl)-8-methoxy-N-(1-(6-methoxypyridin-3-yl)ethyl)quinazolin-4-amine |
| Example 269 | 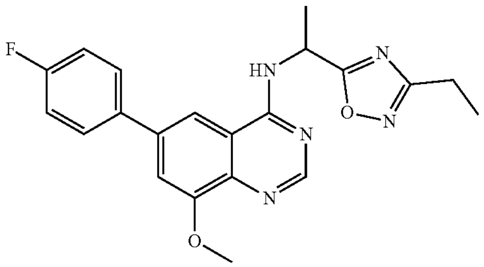 [SMILES: CCc1noc(C(C)Nc2ncnc3c(OC)cc(-c4ccc(F)cc4)cc23)n1] | Single enantiomer 1 of N-(1-(3-ethyl-1,2,4-oxadiazol-5-yl)ethyl)-6-(4-fluorophenyl)-8-methoxyquinazolin-4-amine |
| Example 270 | 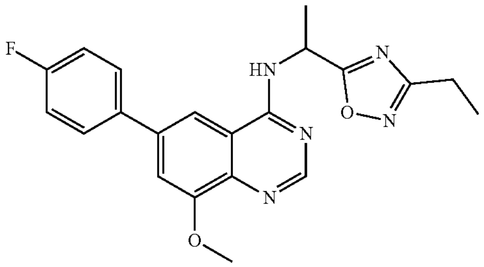 [SMILES: CCc1noc(C(C)Nc2ncnc3c(OC)cc(-c4ccc(F)cc4)cc23)n1] | Single enantiomer 2 of N-(1-(3-ethyl-1,2,4-oxadiazol-5-yl)ethyl)-6-(4-fluorophenyl)-8-methoxyquinazolin-4-amine |
| Example 277 | 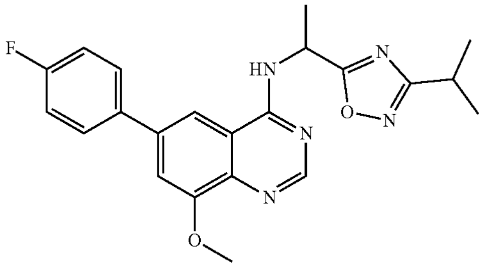 [SMILES: COc1cc(-c2ccc(F)cc2)cc2c(NC(C)c3nc(C(C)C)no3)ncnc12] | Single enantiomer 1 of 6-(4-fluorophenyl)-N-[1-(3-isopropyl-1,2,4-oxadiazol-5-yl)ethyl]-8-methoxy-quinazolin-4-amine |
| Example 278 | 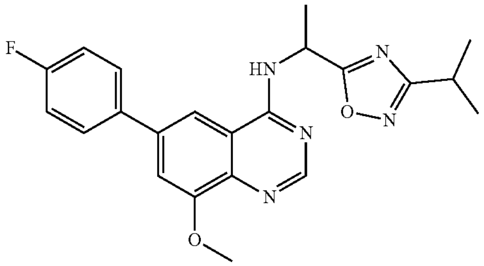 [SMILES: COc1cc(-c2ccc(F)cc2)cc2c(NC(C)c3nc(C(C)C)no3)ncnc12] | Single enantiomer 2 of 6-(4-fluorophenyl)-N-[1-(3-isopropyl-1,2,4-oxadiazol-5-yl)ethyl]-8-methoxy-quinazolin-4-amine |

TABLE 5-continued

| List of preferred compounds having Formula (I) | | |
|---|---|---|
| Ex. N. | Structure | Chemical Name |
| Example 281 | 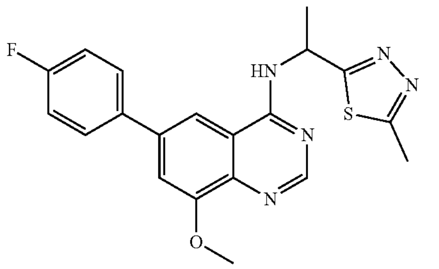 | Single enantiomer 1 of 6-(4-fluorophenyl)-8-methoxy-N-(1-(5-methyl-1,3,4-thiadiazol-2-yl)ethyl)quinazolin-4-amine |
| Example 282 | 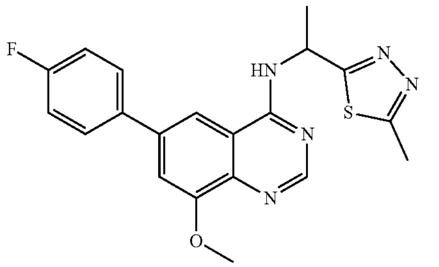 [SMILES: COc1cc(-c2ccc(F)cc2)cc2c(NC(C)c3nnc(C)s3)ncnc12] | Single enantiomer 2 of 6-(4-fluorophenyl)-8-methoxy-N-(1-(5-methyl-1,3,4-thiadiazol-2-yl)ethyl)quinazolin-4-amine |
| Example 294 | 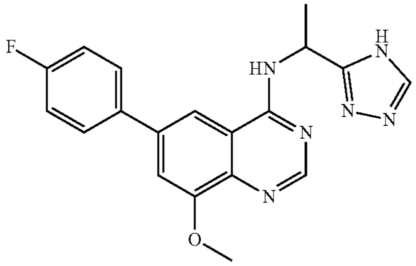 [SMILES: COc1cc(-c2ccc(F)cc2)cc2c(NC(C)c3nnc[nH]3)ncnc12] | (rac)-N-(1-(4H-1,2,4-triazol-3-yl)ethyl)-6-(4-fluorophenyl)-8-methoxyquinazolin-4-amine |
| Example 295 | 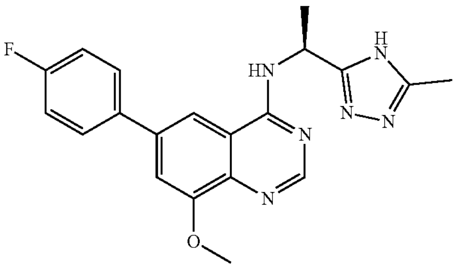 [SMILES: COc1cc(-c2ccc(F)cc2)cc2c(N[C@@H](C)c3nnc(C)[nH]3)ncnc12] | (S)-6-(4-fluorophenyl)-8-methoxy-N-(1-(5-methyl-4H-1,2,4-triazol-3-yl)ethyl)quinazolin-4-amine |

In a further preferred embodiment, the invention is addressed to compound of formula (I) wherein Z is heteroaryl wherein any of such heteroaryl may be optionally substituted by one or more groups selected from ($C_1$-$C_3$)alkyl, halo, CN, ($C_1$-$C_6$)haloalkyl;

$R_1$ is H;

$R_2$ is selected from the group consisting of heteroaryl($C_1$-$C_4$)alkyl-, wherein any of such alkyl, heteroaryl may be optionally substituted by one or more groups selected from ($C_1$-$C_3$)alkyl, ($C_1$-$C_6$)haloalkyl and -oxo;

Y is —$OR^D$;

J is H;

$R^D$ is ($C_1$-$C_6$)alkyl.

According to a preferred embodiment, the invention refers to at least one compound of Table 6, selected from:

TABLE 6

| List of preferred compounds having Formula (I) | | |
|---|---|---|
| Ex. N. | Structure | Chemical Name |
| Example 116 | 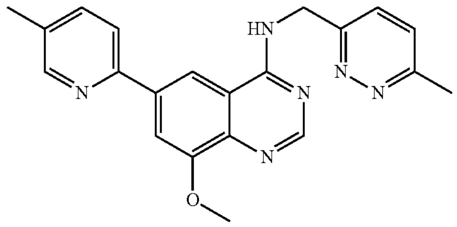 | 8-Methoxy-N-((6-methylpyridazin-3-yl)methyl)-6-(5-methylpyridin-2-yl)quinazolin-4-amine |
| Example 118 | 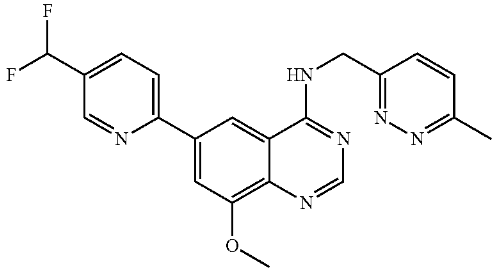 [SMILES: COc1cc(-c2ccc(C(F)F)cn2)cc2c(NCc3ccc(C)nn3)ncnc12] | 6-(5-(Difluoromethyl)pyridin-2-yl)-8-methoxy-N-((6-methylpyridazin-3-yl)methyl)quinazolin-4-amine |
| Example 127 | 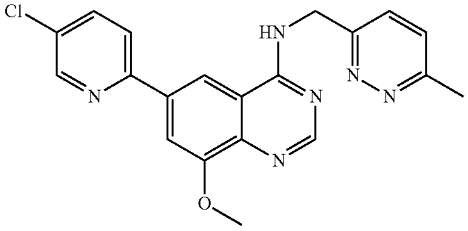 [SMILES: COc1cc(-c2ccc(Cl)cn2)cc2c(NCc3ccc(C)nn3)ncnc12] | 6-(5-Chloropyridin-2-yl)-8-methoxy-N-((6-methylpyridazin-3-yl)methyl)quinazolin-4-amine |
| Example 134 | 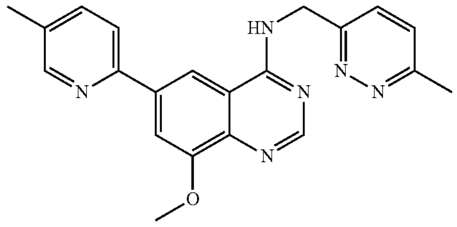 | 8-Methoxy-N-[(6-methylpyridazin-3-yl)methyl]-6-(5-methylpyrimidin-2-yl)quinazolin-4-amine |
| Example 135 | 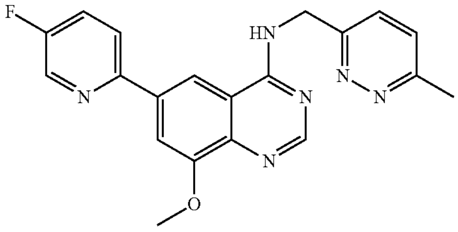 [SMILES: COc1cc(-c2ccc(F)cn2)cc2c(NCc3ccc(C)nn3)ncnc12] | 6-(5-Fluoro-2-pyridyl)-8-methoxy-N-[(6-methylpyridazin-3-yl)methyl]quinazolin-4-amine |
| Example 136 | 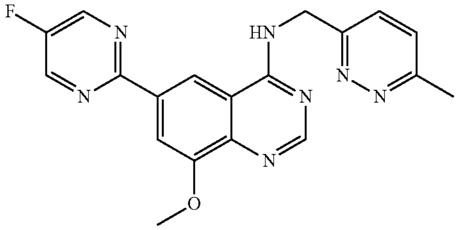 [SMILES: COc1cc(-c2ncc(F)cn2)cc2c(NCc3ccc(C)nn3)ncnc12] | 6-(5-Fluoropyrimidin-2-yl)-8-methoxy-N-[(6-methylpyridazin-3-yl)methyl]quinazolin-4-amine |

TABLE 6-continued

| List of preferred compounds having Formula (I) | | |
|---|---|---|
| Ex. N. | Structure | Chemical Name |
| Example 140 | 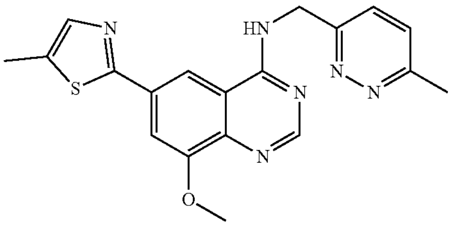 | 8-Methoxy-N-((6-methylpyridazin-3-yl)methyl)-6-(5-methylthiazol-2-yl)quinazolin-4-amine |
| Example 143 | 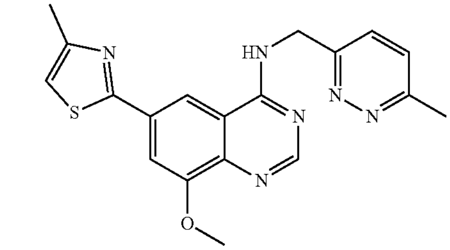 [SMILES: COc1cc(-c2nc(C)cs2)cc2c(NCc3ccc(C)nn3)ncnc12] | 8-Methoxy-N-((6-methylpyridazin-3-yl)methyl)-6-(4-methylthiazol-2-yl)quinazolin-4-amine |
| Example 145 | 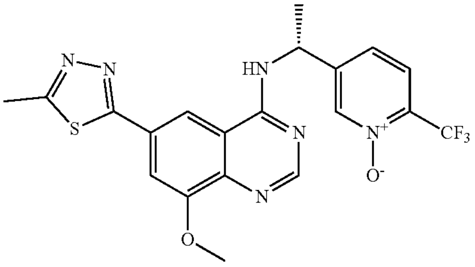 [SMILES: COc1cc(-c2nnc(C)s2)cc2c(N[C@H](C)c3ccc(C(F)(F)F)[n+]([O-])c3)ncnc12] | (R)-5-(1-((8-Methoxy-6-(5-methyl-1,3,4-thiadiazol-2-yl)quinazolin-4-yl)amino)ethyl)-2-(trifluoromethyl)pyridine 1-oxide |
| Example 147 | 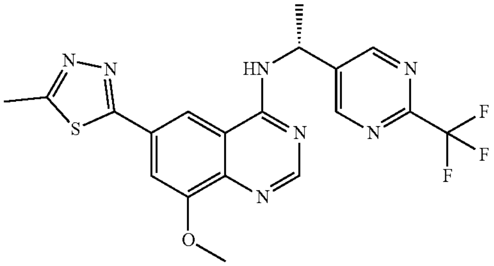 [SMILES: COc1cc(-c2nnc(C)s2)cc2c(N[C@H](C)c3cnc(C(F)(F)F)nc3)ncnc12] | (R)-8-Methoxy-6-(5-methyl-1,3,4-thiadiazol-2-yl)-N-(1-(2-(trifluoromethyl)pyrimidin-5-yl)ethyl)quinazolin-4-amine |
| Example 148 | 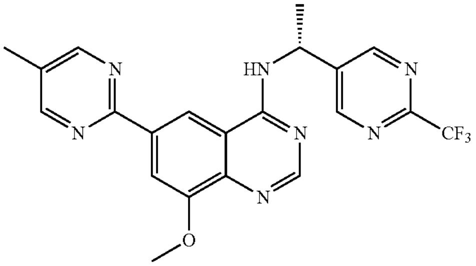 [SMILES: COc1cc(-c2ncc(C)cn2)cc2c(N[C@H](C)c3cnc(C(F)(F)F)nc3)ncnc12] | 8-Methoxy-6-(5-methylpyrimidin-2-yl)-N-[(1R)-1-[2-(trifluoromethyl)pyrimidin-5-yl]ethyl]quinazolin-4-amine |

TABLE 6-continued

| List of preferred compounds having Formula (I) | | |
|---|---|---|
| Ex. N. | Structure | Chemical Name |
| Example 149 | 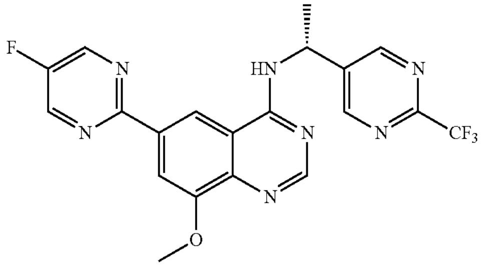 [SMILES: COc1cc(-c2ncc(F)cn2)cc2c(N[C@H](C)c3cnc(C(F)(F)F)nc3)ncnc12] | 6-(5-Fluoropyrimidin-2-yl)-8-methoxy-N-[(1R)-1-[2-(trifluoromethyl)pyrimidin-5-yl]ethyl]quinazolin-4-amine |
| Example 150 | 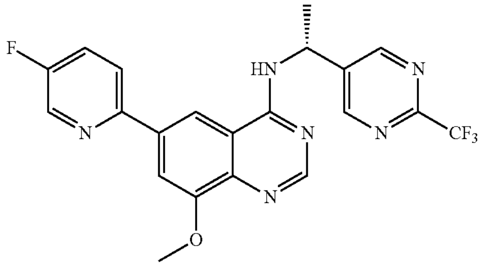 [SMILES: COc1cc(-c2ccc(F)cn2)cc2c(N[C@H](C)c3cnc(C(F)(F)F)nc3)ncnc12] | 6-(5-Fluoro-2-pyridyl)-8-methoxy-N-[(1R)-1-[2-(trifluoromethyl)pyrimidin-5-yl]ethyl]quinazolin-4-amine |
| Example 151 | 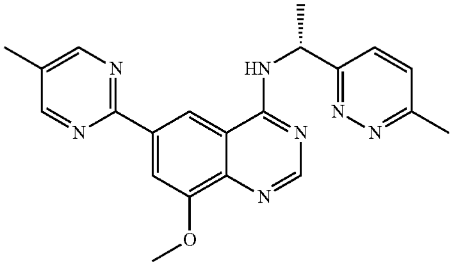 | 8-Methoxy-N-[(1R)-1-(6-methylpyridazin-3-yl)ethyl]-6-(5-methylpyrimidin-2-yl)quinazolin-4-amine |
| Example 152 | 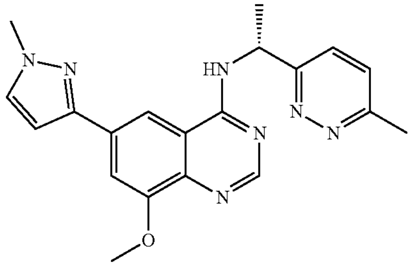 [SMILES: COc1cc(-c2ccn(C)n2)cc2c(N[C@H](C)c3ccc(C)nn3)ncnc12] | 8-Methoxy-6-(1-methylpyrazol-3-yl)-N-[(1R)-1-(6-methylpyridazin-3-yl)ethyl]quinazolin-4-amine |
| Example 153 | 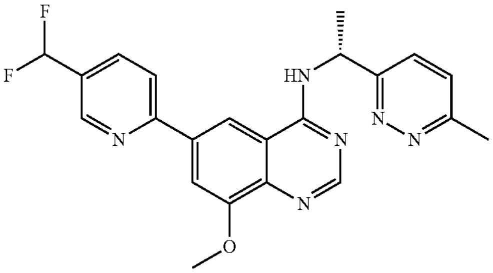 [SMILES: COc1cc(-c2ccc(C(F)F)cn2)cc2c(N[C@H](C)c3ccc(C)nn3)ncnc12] | 6-[5-(Difluoromethyl)-2-pyridyl]-8-methoxy-N-[(1R)-1-(6-methylpyridazin-3-yl)ethyl]quinazolin-4-amine |

TABLE 6-continued

| List of preferred compounds having Formula (I) | | |
|---|---|---|
| Ex. N. | Structure | Chemical Name |
| Example 154 | 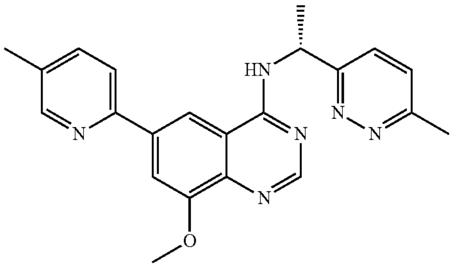 | 8-Methoxy-N-[(1R)-1-(6-methylpyridazin-3-yl)ethyl]-6-(5-methyl-2-pyridyl)quinazolin-4-amine |
| Example 155 | 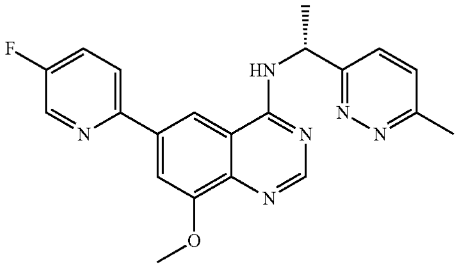 [SMILES: COc1cc(-c2ccc(F)cn2)cc2c(N[C@H](C)c3ccc(C)nn3)ncnc12] | 6-(5-Fluoro-2-pyridyl)-8-methoxy-N-[(1R)-1-(6-methylpyridazin-3-yl)ethyl]quinazolin-4-amine |
| Example 157 | 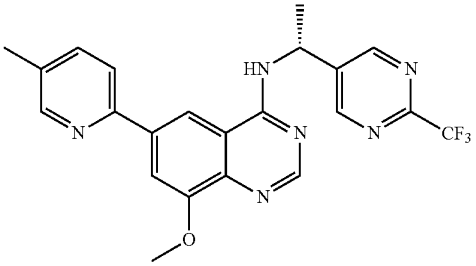 [SMILES: COc1cc(-c2ccc(C)cn2)cc2c(N[C@H](C)c3cnc(C(F)(F)F)nc3)ncnc12] | (R)-8-methoxy-6-(5-methylpyridin-2-yl)-N-(1-(2-(trifluoromethyl)pyrimidin-5-yl)ethyl)quinazolin-4-amine |
| Example 158 | 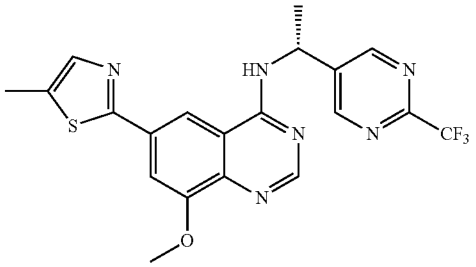 [SMILES: COc1cc(-c2ncc(C)s2)cc2c(N[C@H](C)c3cnc(C(F)(F)F)nc3)ncnc12] | (R)-8-methoxy-6-(5-methylthiazol-2-yl)-N-(1-(2-(trifluoromethyl)pyrimidin-5-yl)ethyl)quinazolin-4-amine |
| Example 161 | 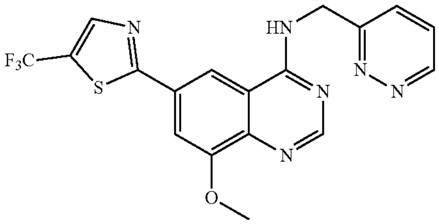 [SMILES: COc1cc(-c2ncc(C(F)(F)F)s2)cc2c(NCc3cccnn3)ncnc12] | 8-Methoxy-N-((6-methylpyridazin-3-yl)methyl)-6-(5-(trifluoromethyl)thiazol-2-yl)quinazolin-4-amine |
| Example 296 | 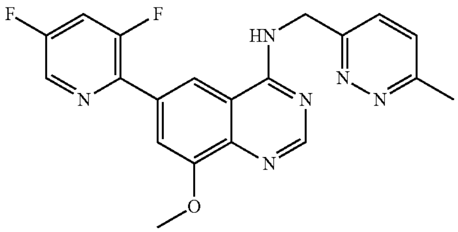 [SMILES: COc1cc(-c2ncc(F)cc2F)cc2c(NCc3ccc(C)nn3)ncnc12] | 6-(3,5-Difluoropyridin-2-yl)-8-methoxy-N-((6-methylpyridazin-3-yl)methyl)quinazolin-4-amine |

TABLE 6-continued

| List of preferred compounds having Formula (I) | | |
|---|---|---|
| Ex. N. | Structure | Chemical Name |
| Example 297 | 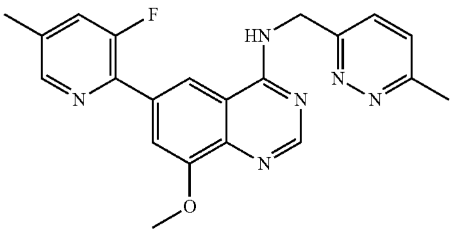 | 6-(3-Fluoro-5-methyl-2-pyridyl)-8-methoxy-N-[(6-methylpyridazin-3-yl)methyl] quinazolin-4-amine |
| Example 298 | 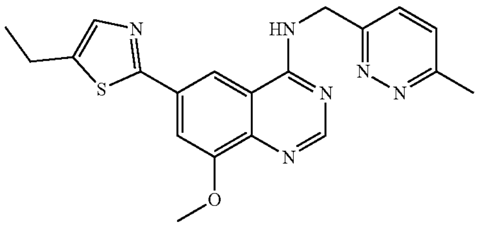 [SMILES: CCc1cnc(-c2cc(OC)c3ncnc(NCc4ccc(C)nn4)c3c2)s1] | 6-(5-Ethylthiazol-2-yl)-8-methoxy-N-[(6-methylpyridazin-3-yl)methyl]quinazolin-4-amine |
| Example 299 | 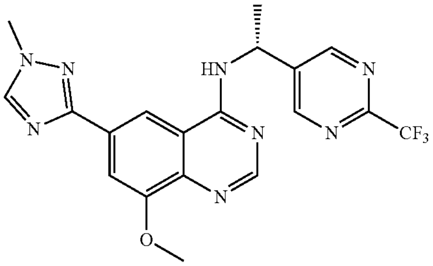 [SMILES: COc1cc(-c2ncn(C)n2)cc2c(N[C@H](C)c3cnc(C(F)(F)F)nc3)ncnc12] | (R)-8-methoxy-6-(1-methyl-1H-1,2,4-triazol-3-yl)-N-(1-(2-(trifluoromethyl)pyrimidin-5-yl)ethyl)quinazolin-4-amine |
| Example 300 | 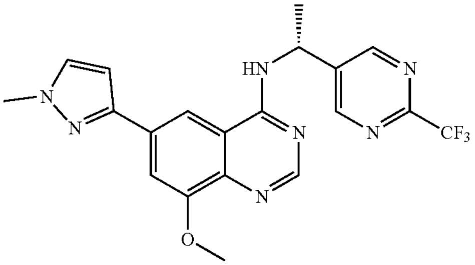 [SMILES: COc1cc(-c2ccn(C)n2)cc2c(N[C@H](C)c3cnc(C(F)(F)F)nc3)ncnc12] | (R)-8-methoxy-6-(1-methyl-1H-pyrazol-3-yl)-N-(1-(2-(trifluoromethyl)pyrimidin-5-yl)ethyl)quinazolin-4-amine |
| Example 301 | 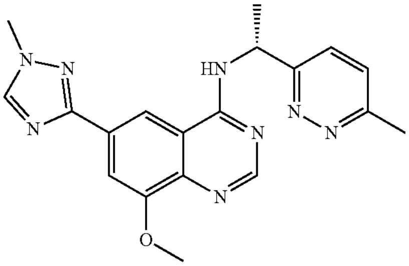 [SMILES: COc1cc(-c2ncn(C)n2)cc2c(N[C@H](C)c3ccc(C)nn3)ncnc12] | (R)-8-methoxy-6-(1-methyl-1H-1,2,4-triazol-3-yl)-N-(1-(6-methylpyridazin-3-yl)ethyl)quinazolin-4-amine |

TABLE 6-continued

| List of preferred compounds having Formula (I) | | |
|---|---|---|
| Ex. N. | Structure | Chemical Name |
| Example 315 | 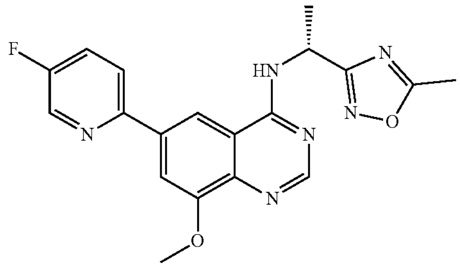 [SMILES: COc1cc(-c2ccc(F)cn2)cc2c(N[C@H](C)c3noc(C)n3)ncnc12] | (R)-6-(5-fluoropyridin-2-yl)-8-methoxy-N-(1-(5-methyl-1,2,4-oxadiazol-3-yl)ethyl)quinazolin-4-amine |
| Example 316 | 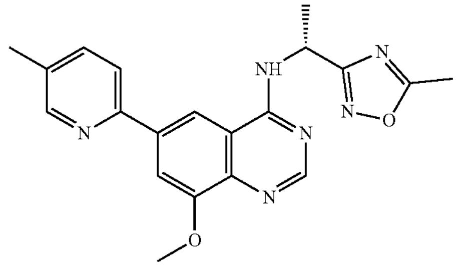 | (R)-8-methoxy-N-(1-(5-methyl-1,2,4-oxadiazol-3-yl)ethyl)-6-(5-methylpyridin-2-yl)quinazolin-4-amine |
| Example 317 | 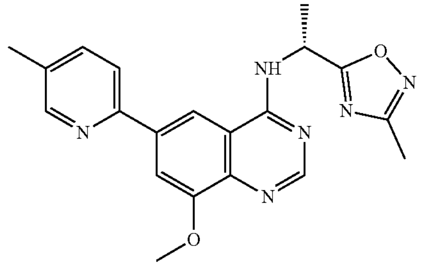 [SMILES: COc1cc(-c2ccc(C)cn2)cc2c(N[C@H](C)c3nc(C)no3)ncnc12] | 8-Methoxy-N-[1-(3-methyl-1,2,4-oxadiazol-5-yl)ethyl]-6-(5-methyl-2-pyridyl)quinazolin-4-amine |
| Example 318 | 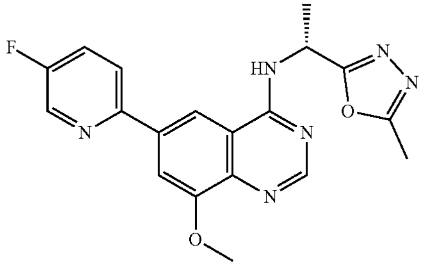 [SMILES: COc1cc(-c2ccc(F)cn2)cc2c(N[C@H](C)c3nnc(C)o3)ncnc12] | 6-(5-fluoro-2-pyridyl)-8-methoxy-N-[(1R)-1-(5-methyl-1,3,4-oxadiazol-2-yl)ethyl]quinazolin-4-amine |
| Example 319 | 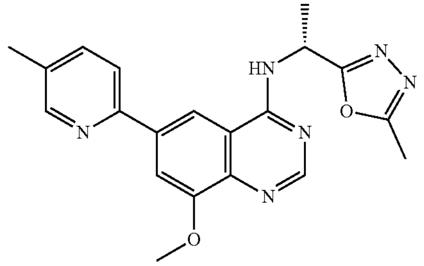 [SMILES: COc1cc(-c2ccc(C)cn2)cc2c(N[C@H](C)c3nnc(C)o3)ncnc12] | 8-methoxy-N-[(1R)-1-(5-methyl-1,3,4-oxadiazol-2-yl)ethyl]-6-(5-methyl-2-pyridyl)quinazolin-4-amine |

TABLE 6-continued

| List of preferred compounds having Formula (I) | | |
|---|---|---|
| Ex. N. | Structure | Chemical Name |
| Example 321 | 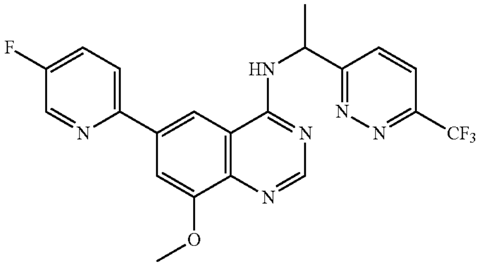 [SMILES: COc1cc(-c2ccc(F)cn2)cc2c(NC(C)c3ccc(C(F)(F)F)nn3)ncnc12] | 6-(5-fluoro-2-pyridyl)-8-methoxy-N-[1-[6-(trifluoromethyl)pyridazin-3-yl]ethyl]quinazolin-4-amine |
| Example 322 | 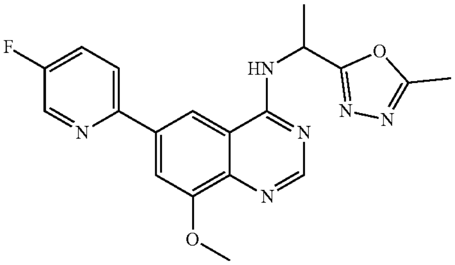 | 6-(5-fluoropyridin-2-yl)-8-methoxy-N-(1-(5-methyl-1,3,4-oxadiazol-2-yl)ethyl)quinazolin-4-amine |
| Example 323 | 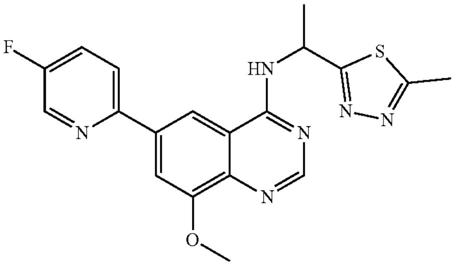 | 6-(5-fluoropyridin-2-yl)-8-methoxy-N-(1-(5-methyl-1,3,4-thiadiazol-2-yl)ethyl)quinazolin-4-amine |
| Example 324 | 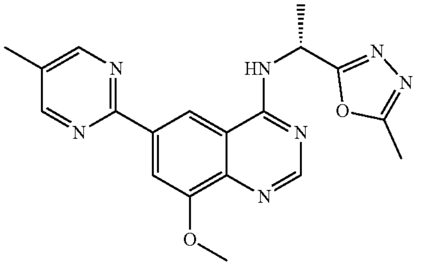 [SMILES: COc1cc(-c2ncc(C)cn2)cc2c(N[C@H](C)c3nnc(C)o3)ncnc12] | 8-methoxy-N-[(1R)-1-(5-methyl-1,3,4-oxadiazol-2-yl)ethyl]-6-(5-methylpyrimidin-2-yl)quinazolin-4-amine |

TABLE 6-continued

List of preferred compounds having Formula (I)

| Ex. N. | Structure | Chemical Name |
| --- | --- | --- |
| Example 325 | 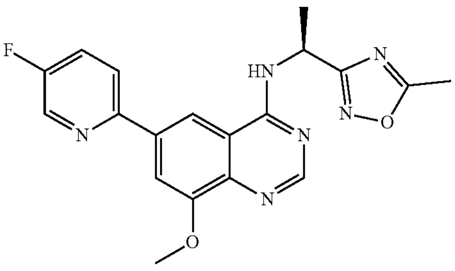 [SMILES: COc1cc(-c2ccc(F)cn2)cc2c(N[C@@H](C)c3noc(C)n3)ncnc12] | (S)-6-(5-fluoropyridin-2-yl)-8-methoxy-N-(1-(5-methyl-1,2,4-oxadiazol-3-yl)ethyl)quinazolin-4-amine |
| Example 326 | 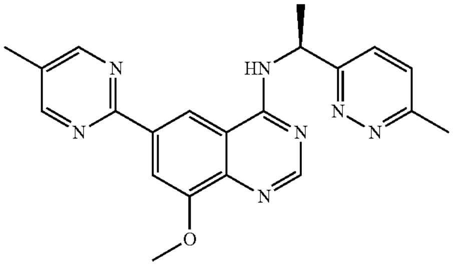 | 8-Methoxy-N-[(1S)-1-(6-methylpyridazin-3-yl)ethyl]-6-(5-methylpyrimidin-2-yl)quinazolin-4-amine |

In a further preferred embodiment, the invention is directed to a compound of formula (I) as defined above, wherein Y is —$OR^D$, represented by formula (Ia)

(Ia)

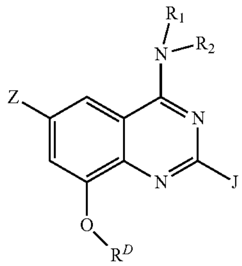

wherein

Z is selected from the group consisting of aryl, wherein any of such aryl may be optionally substituted by one or more groups selected from halo;

$R_1$ is H;

$R_2$ is selected from the group consisting of heteroaryl($C_1$-$C_4$)alkyl-, wherein any of such heteroaryl may be optionally substituted by one or more groups selected from ($C_1$-$C_3$)alkyl, $C_1$-$C_6$)haloalkyl;

$R^A$ and $R^B$ are at each occurrence independently H or selected from the group consisting of ($C_1$-$C_4$)alkyl-;

$R^C$ is at each occurrence H or selected from the group consisting of ($C_1$-$C_6$)alkyl;

$R^D$ is selected in the group consisting of H, ($C_1$-$C_6$)alkyl, ($C_3$-$C_8$)heterocycloalkyl-($C_1$-$C_6$)alkyl-, $R^C$OC(O)($C_1$-$C_4$)alkylene-, ($R^AR^B$)N($C_1$-$C_6$)alkylene-, ($C_3$-$C_8$)heterocycloalkyl, $R^C$O($C_1$-$C_4$)alkylene-, ($R^AR^B$)N(O)C($C_1$-$C_4$)alkylene-, ($C_3$-$C_8$)cycloalkyl-($C_1$-$C_6$)alkyl-, wherein any of such heterocycloalkly may be optionally substituted by one or more groups selected from ($C_1$-$C_3$)alkyl;

J is H.

In a further preferred embodiment, the invention is addressed to compound of formula (Ia) wherein Z is H or selected from the group consisting of
- aryl, preferably phenyl, each of said aryl may be optionally substituted by one or more groups selected from halo, preferably fluorine, $R_1$ is H;

R2 is selected from the group consisting of
- heteroaryl($C_1$-$C_4$)alkyl-, (pyrimidinyl)ethyl, (pyridazinyl)methyl, each of said heteroaryl is optionally further substituted by one or more groups selected from
- ($C_1$-$C_3$)alkyl, preferably methyl
- trifluoromethyl, $R^D$ is H or selected in the group consisting of,
- ($C_1$-$C_6$)alkyl, preferably methyl, propyl,
- ($C_3$-$C_8$)heterocycloalkyl-($C_1$-$C_6$)alkyl-, preferably (azetidinyl)methyl, (morpholinyl)methyl, (morpholinyl)ethyl, (oxetanyl)methyl,
- $R^C$OC(O)($C_1$-$C_4$)alkylene-, wherein $R^C$ is selected form the group of H and ethyl,
- ($R^AR^B$)N($C_1$-$C_6$)alkylene-, preferably dimethylaminopropyl,
- ($C_3$-$C_8$)heterocycloalkyl, preferably tetrahydropyranyl,
- $R^C$O($C_1$-$C_4$)alkylene-, preferably selected from the group of methoxyethyl, propanolyl,
- ($R^AR^B$)N(O)C($C_1$-$C_4$)alkylene-, preferably dimethylacetylamide, tetrahydrofuranyl,
- ($C_3$-$C_8$)cycloalkyl-($C_1$-$C_6$)alkyl-, preferably (cyclopropyl)methyl, each of said heterocycloalkyl may be optionally substituted by one or more groups selected from methyl, ethyl and propyl;

J is H.

According to specific embodiments, the invention provides at least one compound listed in the Table 7 below and pharmaceutical acceptable salts thereof.

TABLE 7

List of preferred compounds having Formula (Ia)

| Ex. N. | Structure | Chemical name |
| --- | --- | --- |
| Example 200 | 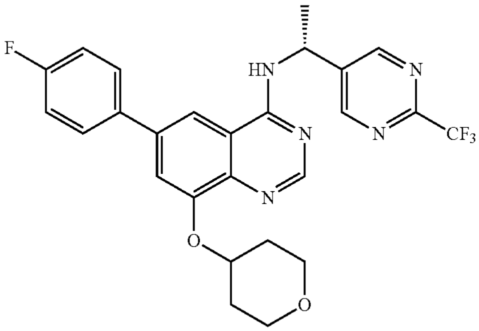 [SMILES: C[C@@H](Nc1ncnc2c(OC3CCOCC3)cc(-c3ccc(F)cc3)cc12)c1cnc(C(F)(F)F)nc1] | (R)-6-(4-Fluorophenyl)-8-((tetrahydro-2H-pyran-4-yl)oxy)-N-(1-(2-(trifluoromethyl)pyrimidin-5-yl)ethyl)quinazolin-4-amine |
| Example 201 | 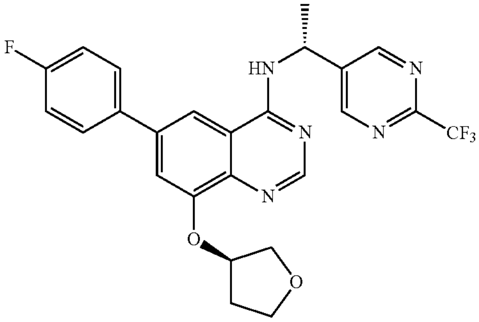 [SMILES: C[C@@H](Nc1ncnc2c(O[C@@H]3CCOC3)cc(-c3ccc(F)cc3)cc12)c1cnc(C(F)(F)F)nc1] | 6-(4-fluorophenyl)-8-(((R)-tetrahydrofuran-3-yl)oxy)-N-((R)-1-(2-(trifluoromethyl)pyrimidin-5-yl)ethyl)quinazolin-4-amine |
| Example 202 | 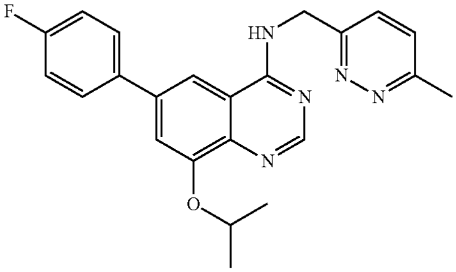 [SMILES: Cc1ccc(CNc2ncnc3c(OC(C)C)cc(-c4ccc(F)cc4)cc23)nn1] | 6-(4-fluorophenyl)-8-isopropoxy-N-[(6-methylpyridazin-3-yl)methyl]quinazolin-4-amine |
| Example 203 | 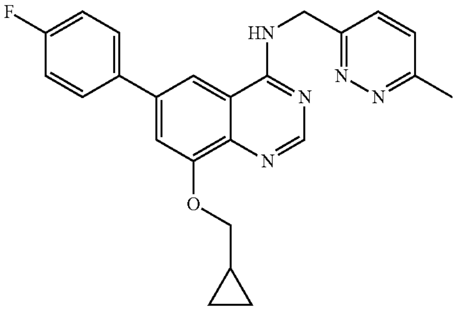 [SMILES: Cc1ccc(CNc2ncnc3c(OCC4CC4)cc(-c4ccc(F)cc4)cc23)nn1] | 8-(cyclopropylmethoxy)-6-(4-fluorophenyl)-N-[(6-methylpyridazin-3-yl)methyl]quinazolin-4-amine |
| Example 204 | 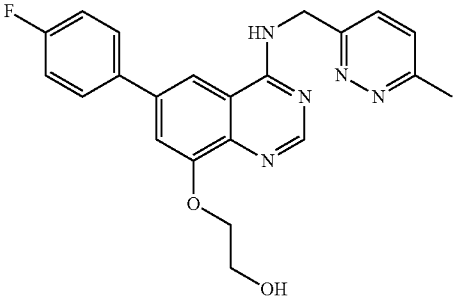 [SMILES: Cc1ccc(CNc2ncnc3c(OCCO)cc(-c4ccc(F)cc4)cc23)nn1] | 2-[6-(4-fluorophenyl)-4-[(6-methylpyridazin-3-yl)methylamino]quinazolin-8-yl]oxyethanol |

TABLE 7-continued

| List of preferred compounds having Formula (Ia) | | |
| --- | --- | --- |
| Ex. N. | Structure | Chemical name |
| Example 205 | 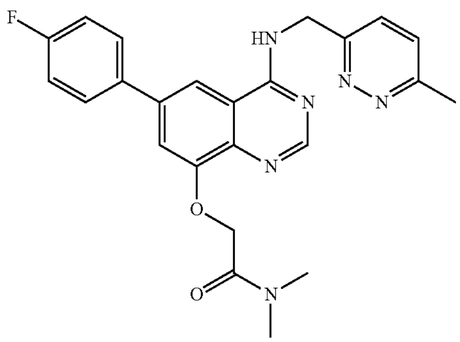 [SMILES: Cc1ccc(CNc2ncnc3c(OCC(=O)N(C)C)cc(-c4ccc(F)cc4)cc23)nn1] | 2-[6-(4-fluorophenyl)-4-[(6-methylpyridazin-3-yl)methylamino]quinazolin-8-yl]oxy-N,N-dimethyl-acetamide |
| Example 206 | 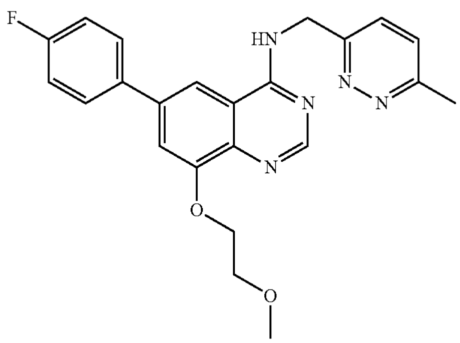 [SMILES: COCCOc1cc(-c2ccc(F)cc2)cc2c(NCc3ccc(C)nn3)ncnc12] | 6-(4-fluorophenyl)-8-(2-methoxyethoxy)-N-[(6-methylpyridazin-3-yl)methyl]quinazolin-4-amine |
| Example 207 | 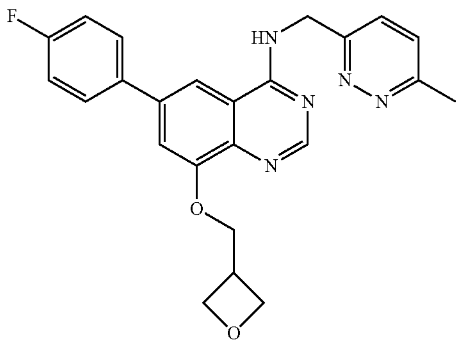 [SMILES: Cc1ccc(CNc2ncnc3c(OCC4COC4)cc(-c4ccc(F)cc4)cc23)nn1] | 6-(4-fluorophenyl)-N-[(6-methylpyridazin-3-yl)methyl]-8-(oxetan-3-ylmethoxy)quinazolin-4-amine |
| Example 208 | 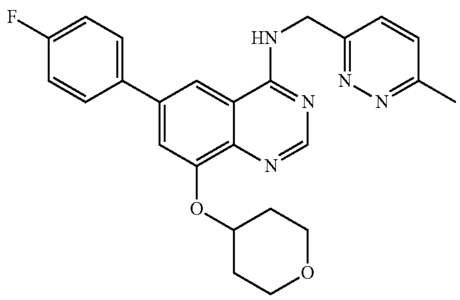 [SMILES: Cc1ccc(CNc2ncnc3c(OC4CCOCC4)cc(-c4ccc(F)cc4)cc23)nn1] | 6-(4-fluorophenyl)-N-[(6-methylpyridazin-3-yl)methyl]-8-tetrahydropyran-4-yloxy-quinazolin-4-amine |

TABLE 7-continued

| List of preferred compounds having Formula (Ia) | | |
|---|---|---|
| Ex. N. | Structure | Chemical name |
| Example 209 | 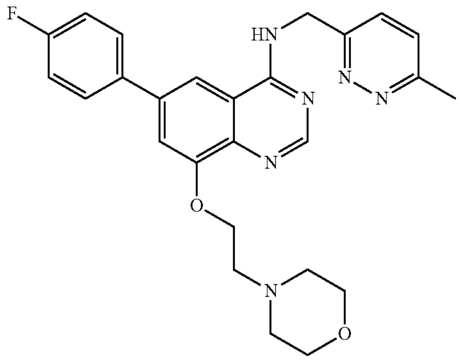 [SMILES: Cc1ccc(CNc2ncnc3c(OCCN4CCOCC4)cc(-c4ccc(F)cc4)cc23)nn1] | 6-(4-fluorophenyl)-N-[(6-methylpyridazin-3-yl)methyl]-8-(2-morpholinoethoxy)quinazolin-4-amine |
| Example 210 | 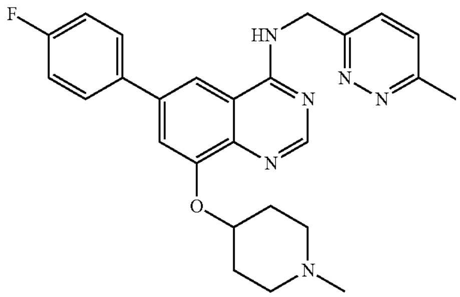 [SMILES: Cc1ccc(CNc2ncnc3c(OC4CCN(C)CC4)cc(-c4ccc(F)cc4)cc23)nn1] | 6-(4-fluorophenyl)-8-[(1-methyl-4-piperidyl)oxy]-N-[(6-methylpyridazin-3-yl)methyl]quinazolin-4-amine |
| Example 211 | 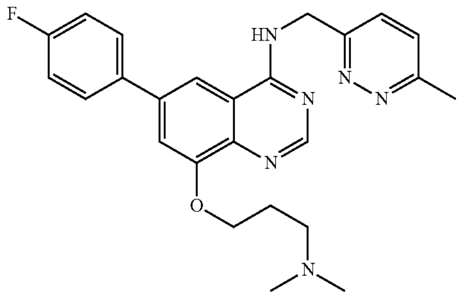 [SMILES: Cc1ccc(CNc2ncnc3c(OCCCN(C)C)cc(-c4ccc(F)cc4)cc23)nn1] | 8-[3-(dimethylamino)propoxy]-6-(4-fluorophenyl)-N-[(6-methylpyridazin-3-yl)methyl]quinazolin-4-amine |
| Example 212 | 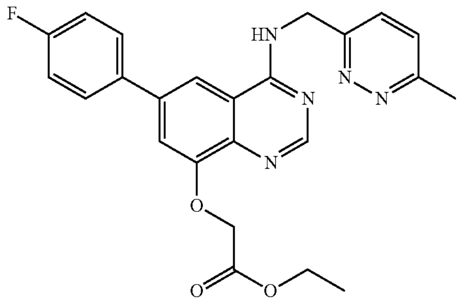 [SMILES: CCOC(=O)COc1cc(-c2ccc(F)cc2)cc2c(NCc3ccc(C)nn3)ncnc12] | ethyl 2-[6-(4-fluorophenyl)-4-[(6-methylpyridazin-3-yl)methylamino]quinazolin-8 yl]oxyacetate |
| Example 213 | 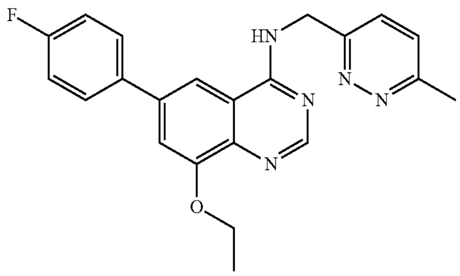 [SMILES: CCOc1cc(-c2ccc(F)cc2)cc2c(NCc3ccc(C)nn3)ncnc12] | 8-ethoxy-6-(4-fluorophenyl)-N-[(6-methylpyridazin-3-yl)methyl]quinazolin-4-amine |

TABLE 7-continued

List of preferred compounds having Formula (Ia)

| Ex. N. | Structure | Chemical name |
|---|---|---|
| Example 214 | 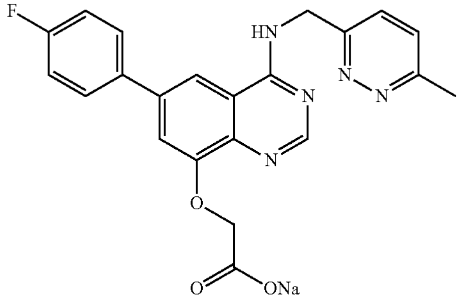 | 2-[6-(4-fluorophenyl)-4-[(6-methylpyridazin-3-yl)methylamino]quinazolin-8-yl]oxyacetic acid, sodium salt |
| Example 215 | 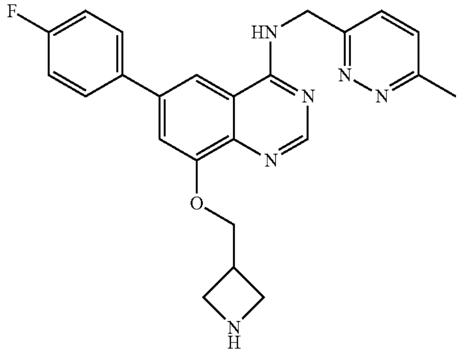 [SMILES: Cc1ccc(CNc2ncnc3c(OCC4CNC4)cc(-c4ccc(F)cc4)cc23)nn1] | 8-(azetidin-3-ylmethoxy)-6-(4-fluorophenyl)-N-[(6-methylpyridazin-3-yl)methyl]quinazolin-4-amine |
| Example 216 | 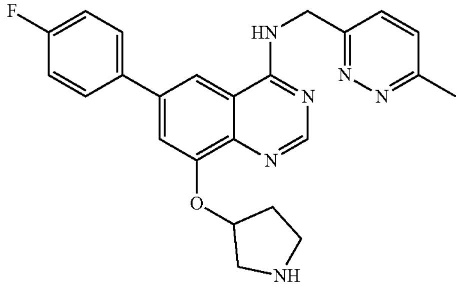 [SMILES: Cc1ccc(CNc2ncnc3c(OC4CCNC4)cc(-c4ccc(F)cc4)cc23)nn1] | 6-(4-fluorophenyl)-N-[(6-methylpyridazin-3-yl)methyl]-8-pyrrolidin-3-yloxy-quinazolin-4-amine |
| Example 217 | 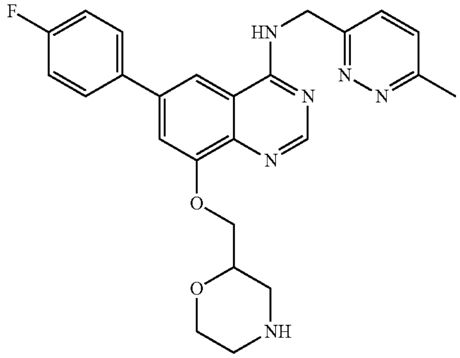 [SMILES: Cc1ccc(CNc2ncnc3c(OCC4CNCCO4)cc(-c4ccc(F)cc4)cc23)nn1] | 6-(4-fluorophenyl)-N-[(6-methylpyridazin-3-yl)methyl]-8-(morpholin-2-ylmethoxy)quinazolin-4-amine |

TABLE 7-continued

| List of preferred compounds having Formula (Ia) | | |
|---|---|---|
| Ex. N. | Structure | Chemical name |
| Example 218 | 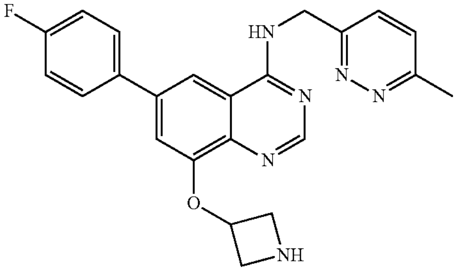 [SMILES: Cc1ccc(CNc2ncnc3c(OC4CNC4)cc(-c4ccc(F)cc4)cc23)nn1] | 8-(azetidin-3-yloxy)-6-(4-fluorophenyl)-N-[(6-methylpyridazin-3-yl)methyl]quinazolin-4-amine |
| Example 219 | 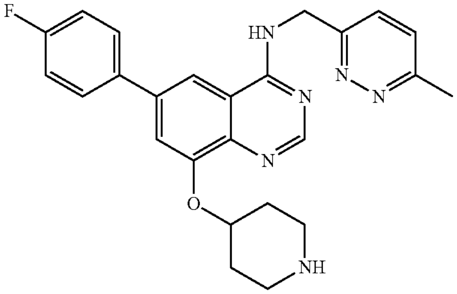 [SMILES: Cc1ccc(CNc2ncnc3c(OC4CCNCC4)cc(-c4ccc(F)cc4)cc23)nn1] | 6-(4-fluorophenyl)-N-[(6-methylpyridazin-3-yl)methyl]-8-(4-piperidyloxy)quinazolin-4-amine |
| Example 220 | 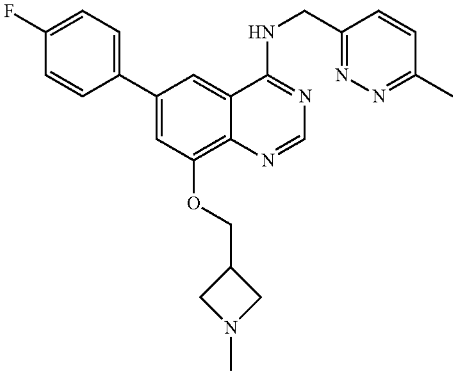 [SMILES: Cc1ccc(CNc2ncnc3c(OCC4CN(C)C4)cc(-c4ccc(F)cc4)cc23)nn1] | 6-(4-fluorophenyl)-8-[(1-methylazetidin-3-yl)methoxy]-N-[(6-methylpyridazin-3-yl)methyl]quinazolin-4-amine |
| Example 221 | 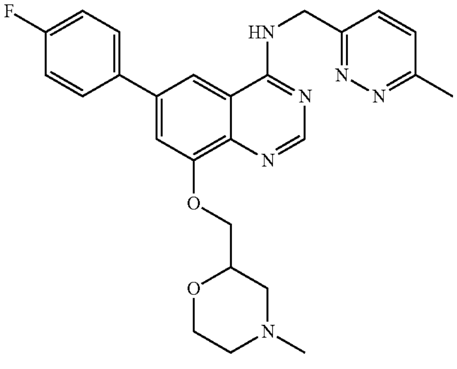 [SMILES: Cc1ccc(CNc2ncnc3c(OCC4CN(C)CCO4)cc(-c4ccc(F)cc4)cc23)nn1] | 6-(4-fluorophenyl)-8-[(4-methylmorpholin-2-yl)methoxy]-N-[(6-methylpyridazin-3-yl)methyl]quinazolin-4-amine |

TABLE 7-continued

| List of preferred compounds having Formula (Ia) | | |
|---|---|---|
| Ex. N. | Structure | Chemical name |
| Example 222 | 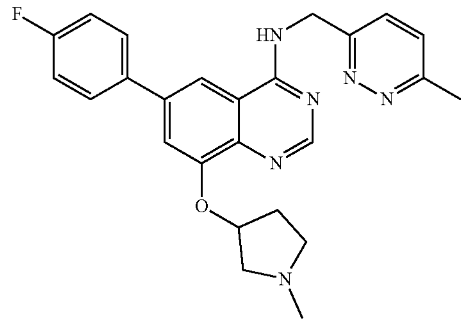 [SMILES: Cc1ccc(CNc2ncnc3c(OC4CCN(C)C4)cc(-c4ccc(F)cc4)cc23)nn1] | 6-(4-fluoropheny1)-N-[(6-methylpyridazin-3-yl)methyl]-8-(1-methylpyrrolidin-3-yl)oxy-quinazolin-4-amine |
| Example 310 | 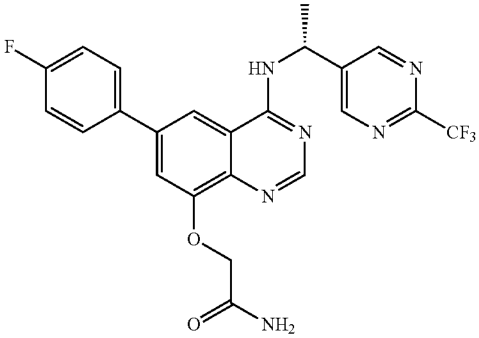 [SMILES: C[C@@H](Nc1ncnc2c(OCC(N)=O)cc(-c3ccc(F)cc3)cc12)c1cnc(C(F)(F)F)nc1] | R)-2-((6-(4-fluorophenyl)-4-((1-(2-(trifluoromethyl)pyrimidin-5-yl)ethyl)amino)quinazolin-8-yl)oxy)acetamide |
| Example 311 | 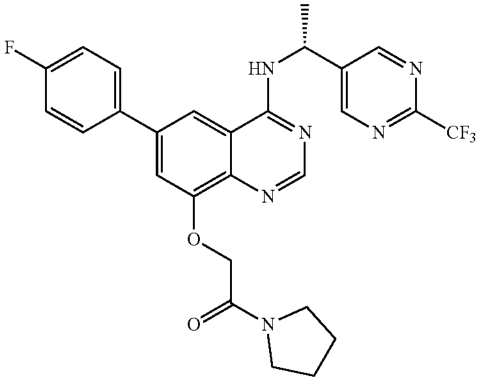 [SMILES: C[C@@H](Nc1ncnc2c(OCC(=O)N3CCCC3)cc(-c3ccc(F)cc3)cc12)c1cnc(C(F)(F)F)nc1] | (R)-2-((6-(4-fluorophenyl)-4-((1-(2-(trifluoromethyl)pyrimidin-5-yl)ethyl)amino)quinazolin-8-yl)oxy)-1-(pyrrolidin-1-yl)ethan-1-one |
| Example 312 | 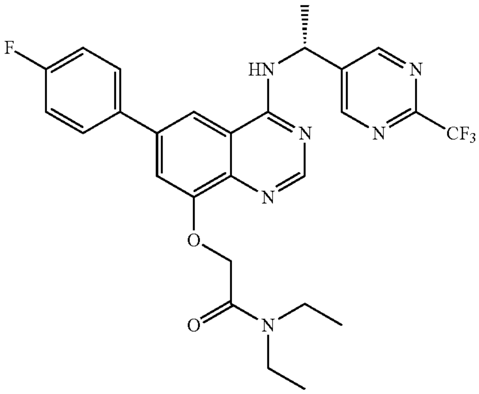 [SMILES: CCN(CC)C(=O)COc1cc(-c2ccc(F)cc2)cc2c(N[C@H](C)c3cnc(C(F)(F)F)nc3)ncnc12] | (R)-N,N-diethyl-2-((6-(4-fluorophenyl)-4-((1-(2-(trifluoromethyl)pyrimidin-5-yl)ethyl)amino)quinazolin-8-yl)oxy)acetamide |

TABLE 7-continued

| List of preferred compounds having Formula (Ia) | | |
|---|---|---|
| Ex. N. | Structure | Chemical name |
| Example 313 | 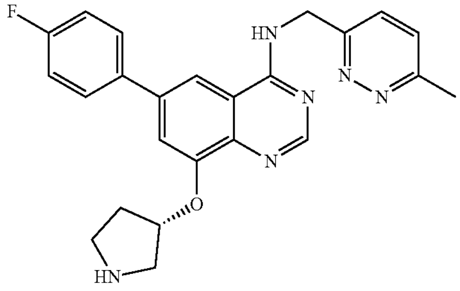 [SMILES: Cc1ccc(CNc2ncnc3c(O[C@H]4CCNC4)cc(-c4ccc(F)cc4)cc23)nn1] | 6-(4-fluorophenyl)-N-[(6-methylpyridazin-3-yl)methyl]-8-[(3S)-pyrrolidin-3-yl]oxy-quinazolin-4-amine |
| Example 314 | 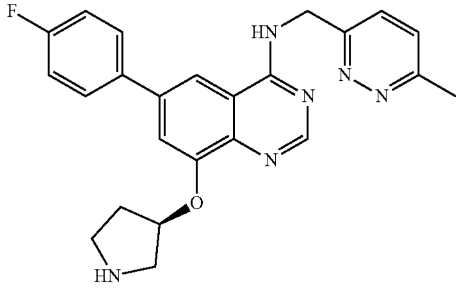 [SMILES: Cc1ccc(CNc2ncnc3c(O[C@@H]4CCNC4)cc(-c4ccc(F)cc4)cc23)nn1] | 6-(4-fluorophenyl)-N-[(6-methylpyridazin-3-yl)methyl]-8-[(3R)-pyrrolidin-3-yl]oxy-quinazolin-4-amine |

The compounds of formula (I) including all the compounds or at least one of the here above listed can be generally prepared according to the procedure outlined in detail in the Schemes shown below using generally known methods.

In one embodiment of the present invention, compound (IA) may be prepared according to SCHEME 1 from compound (II). Compound (II) was prepared following the procedure described in *J. Med Chem.*, 2015, 58 (8), 3548-3571.

Scheme 1

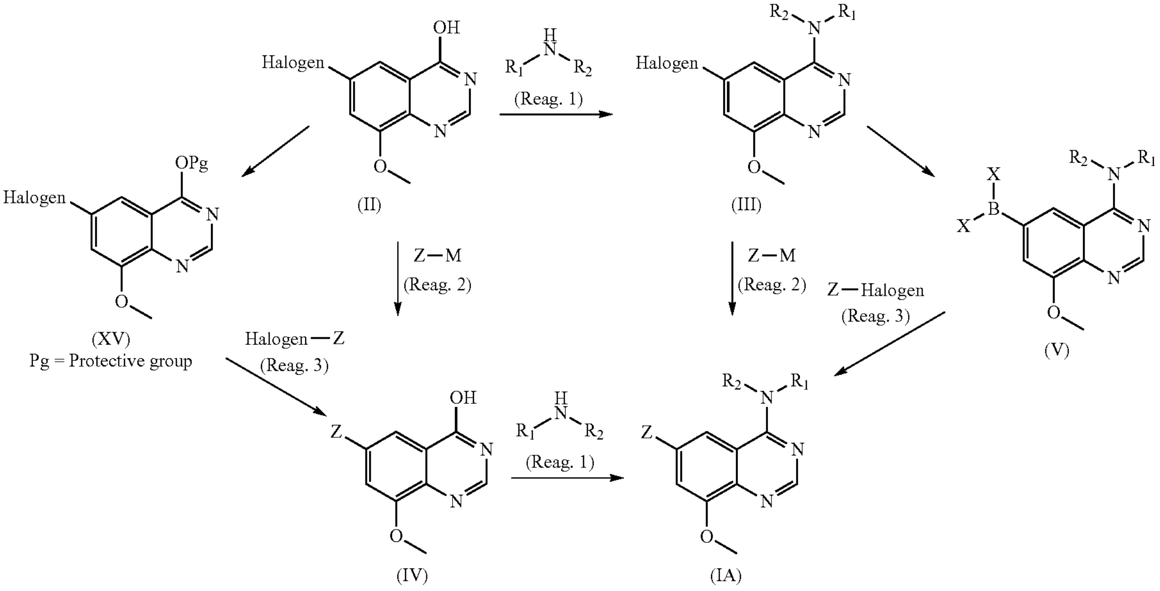

(II) (III) (V) (XV) (IV) (IA)
Pg = Protective group

X = OH, OAlkyl
M = $B(OH)_2$ or
$B(OAlkyl)_2$ or
$SnAlkyl_3$

Compound (III) may be prepared from Compound (II) by a deoxyamination reaction mediated by coupling reagents like PyBOP with a suitable amine (Reag. 1).

Compound (IA) may be prepared from Compound (III) by a metal-catalyzed cross coupling reactions like Stille or Suzuki or similars as described in "Transition Metals for Organic Synthesis", 2nd Ed, 1, 2004 with a suitable reagent like (Reag. 2).

Alternatively Compound (V) may be prepared from Compound (III) by metal-catalyzed Miyaura borylation reaction.

Compound (IA) may be prepared from Compound (V) by a metal-catalyzed cross coupling reactions like Stille, Suzuki or similar as described in "Transition Metals for Organic Synthesis", 2nd Ed, 1, 2004 with a suitable organohalogen compound like (Reag. 3).

In another embodiment, compound (IV) was prepared starting from compound (II) by a metal-catalyzed cross coupling reactions like Stille, Suzuki or similars as described in "Transition Metals for Organic Synthesis", 2nd Ed, 1, 2004 with a suitable Organometallic reagent like (Reag. 2).

Compound (IA) may be prepared from Compound (V) by deoxyamination reaction mediated by reagents like PyBOP or similar with a suitable amine (Reag. 1).

Some compounds (IA) may contain a protected hydroxyl or amino group which were then removed under well known procedures.

Scheme 2

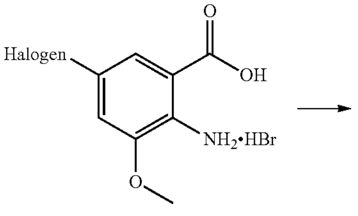

(VI)

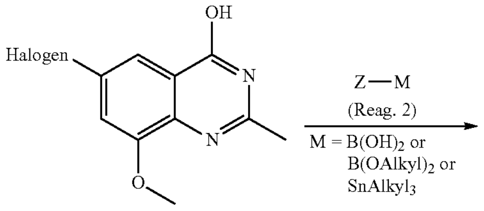

(VII)

-continued

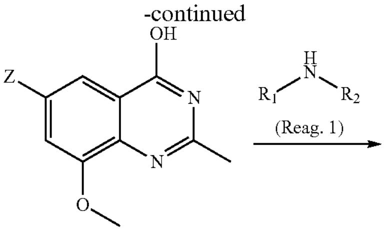

(VIII)

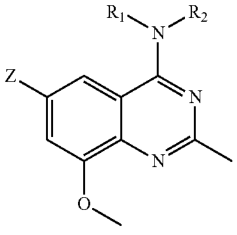

(IB)

In another embodiment of the present invention, compound (IB) may be prepared according to SCHEME 2 from compounds (VI).

Compound (VII) may be prepared from Compound (VI) by means of a quinazoline ring construction reaction mediated by suitable reagents like triethylorthoacetate or similar.

Compound (VIII) may be prepared from Compound (VII) by metal-catalyzed cross coupling reactions like Stille, Suzuki or similar ones with suitable organometallic reagents (Reag. 2) like, for example, organoboron compounds.

Compounds (IB) may be prepared from compound (VIII) by deoxyamination reaction mediated by reagents like PyBOP or similar in the presence of a suitable amine (Reag. 1).

Some compounds (IB) may contain a protected hydroxyl or amino group which were then removed under well known procedures.

Scheme 3

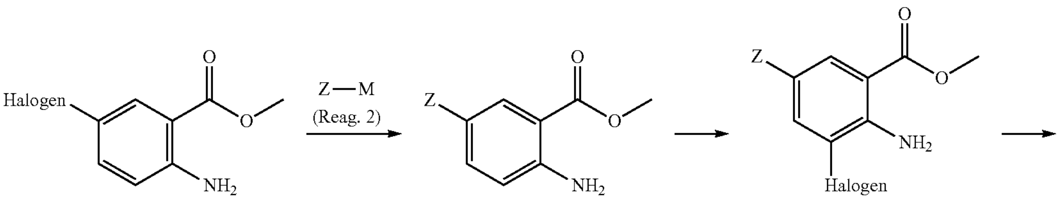

(IX) (X) (XI)

-continued

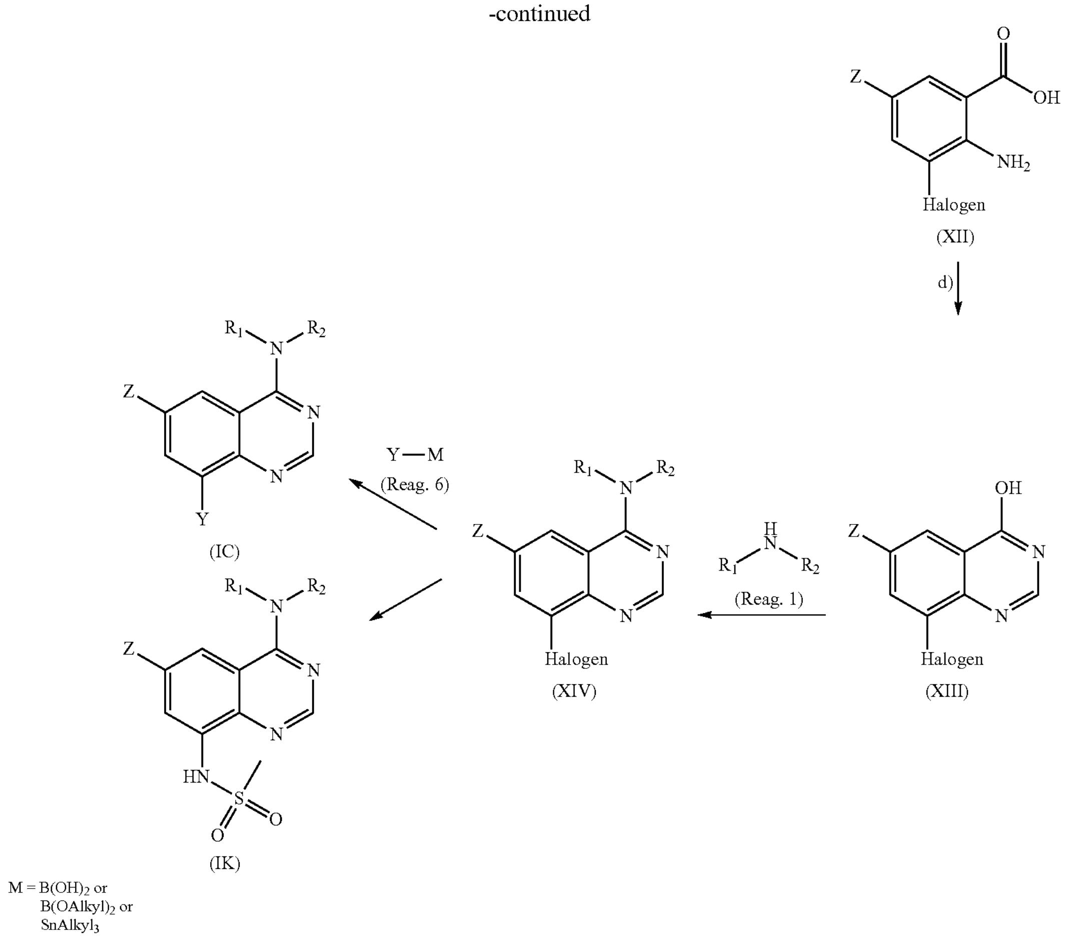

In another embodiment of the present invention, compound (IC) may be prepared according to SCHEME 3 from compound (IX).

Compound (X) may be prepared from Compound (IX) by metal-catalyzed cross coupling reactions like Stille, Suzuki or similar ones with suitable organometallic reagents (Reag. 2) like, for example, organoboron compounds.

Compound (XI) may be prepared from Compound (X) by Halogenation with suitable reagents like Bromine, NBS, NIS, Iodine, iodonium salts or similar.

Compound (XII) may be prepared from Compound (XI) by hydrolysis in a basic or acidic medium.

Compound (XIII) may be prepared from Compound (XII) by quinazoline ring construction reaction with suitable reagents like formamide or similars.

Compound (XIV) may be prepared from Compound (XIII) by deoxyamination reaction mediated by reagents like PyBOP or similar in the presence of a suitable amine (Reag. 1).

Compound (IC) may be prepared from Compound (XIV) by metal-catalyzed cross coupling reactions like Stille, Suzuki or similar ones with suitable organometallic reagents (Reag. 6) like, for example, organoboron compounds. Some compounds (IC) may contain a protected hydroxyl or amino group which were then removed under well known procedures.

Compound (IK) may be prepared from Compound (XIV) by amination reactions in the presence of a suitable reagent like, for example, methanesulfonamide. Some compounds (IK) may contain a protected hydroxyl or amino group which were then removed under well known procedures.

Scheme 4

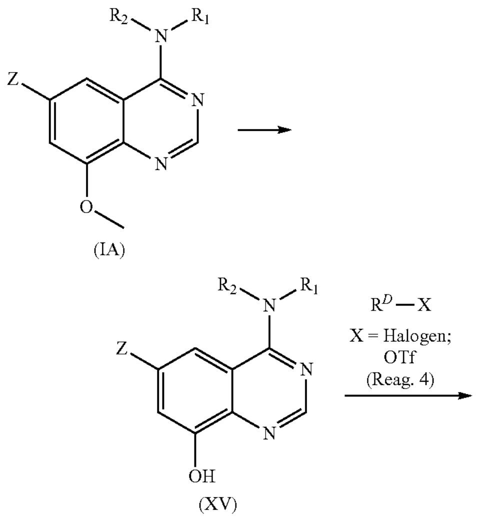

-continued

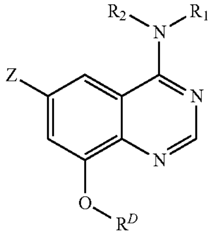

(ID)

In another embodiment of the present invention, compounds (ID) may be prepared according to SCHEME 4 from compounds (IA).

Compound (XV) may be prepared from Compound (IA) by means of dealkylation reactions mediated by strong Lewis acids like $BBr_3$ or similar.

Compounds (ID) were prepared from compounds (XV) by alkylation with a suitable alkylating agent (Reag. 4) like, alkyl chlorides, bromides, iodides, mesylates, tosylates or similar.

Alternatively, compounds (ID) may be prepared from compounds (XV) and a suitable alcohol by Mitsunobu-like reactions mediated, for example, by DEAD/PPh3, DIAD/$PPh_3$ or CMT.

Some compounds (ID) may contain a protected hydroxyl or amino group which were then removed under well-known procedures.

Scheme 5

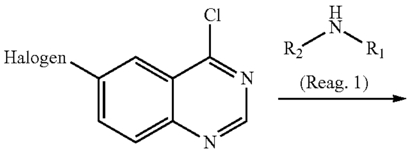

(XVI)

-continued

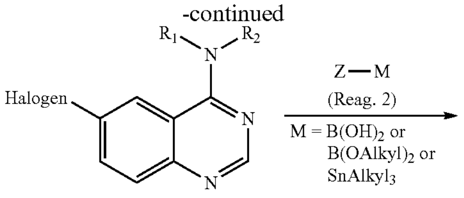

(XVII)

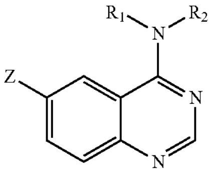

(IE)

In another embodiment of the present invention, compound (IE) may be prepared according to SCHEME 5 from compounds (XVI).

Compound (XVII) may be prepared from Compound (XVI) by deoxyamination reaction mediated by reagents like PyBOP or similar in the presence of a suitable amine (Reag. 1).

Compounds (IE) were prepared from Compounds (XVII) by metal-catalyzed cross coupling reactions like Stille, Suzuki or similar ones with suitable organometallic reagents (Reag. 2) like, for example, organoboron compounds.

Some compounds (IE) may contain a protected hydroxyl or amino group which were then removed under well known procedures.

Scheme 6

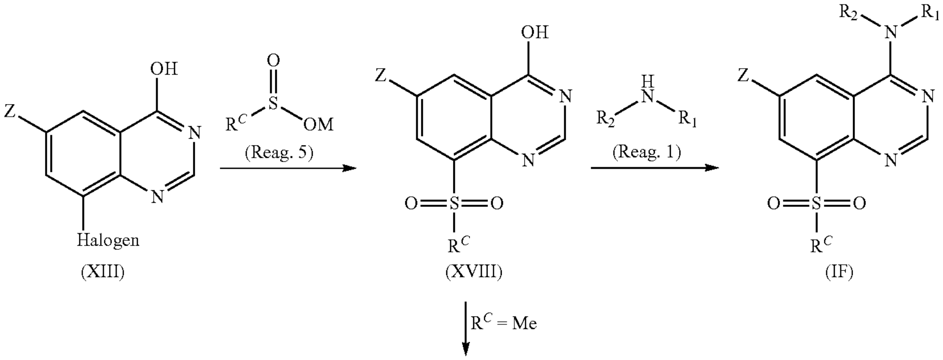

(XIII) (XVIII) (IF)

-continued

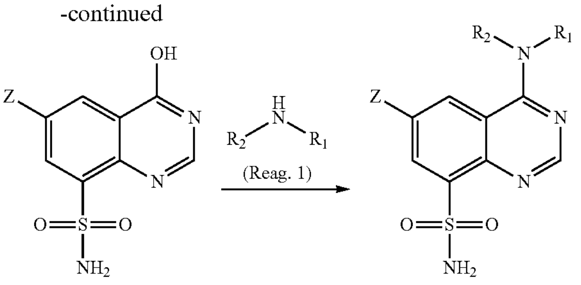

(XIX) (IG)

In another embodiment of the present invention, compound (IF) and (IG) may be prepared according to SCHEME 6 from compounds (XIII).

Compound (XVIII) may be prepared from Compound (XIII) by metal catalyzed sulfenylation reaction with a suitable sulfinate (Reag. 5) like, for example, sodium methanesulfinate.

Compound (IF) may be prepared from Compound (XVIII) by deoxyamination reaction mediated by reagents like PyBOP or similar in the presence of a suitable amine (Reag. 1). Some compounds (IF) may contain a protected hydroxyl or amino group which were then removed under well known procedures.

In another embodiment of the present invention Compound (XIX) may be prepared from Compound (XVIII) by amination with tributylborate and (aminooxy)sulfonic acid as described in Tetr. Lett. 1994, 39, 7201

Compound (IG) may be prepared from Compound (XIX) by deoxyamination reaction mediated by reagents like PyBOP or similar in the presence of a suitable amine (Reag. 1).

Some compounds (IG) may contain a protected hydroxyl or amino group which were then removed under well known procedures.

Scheme 7

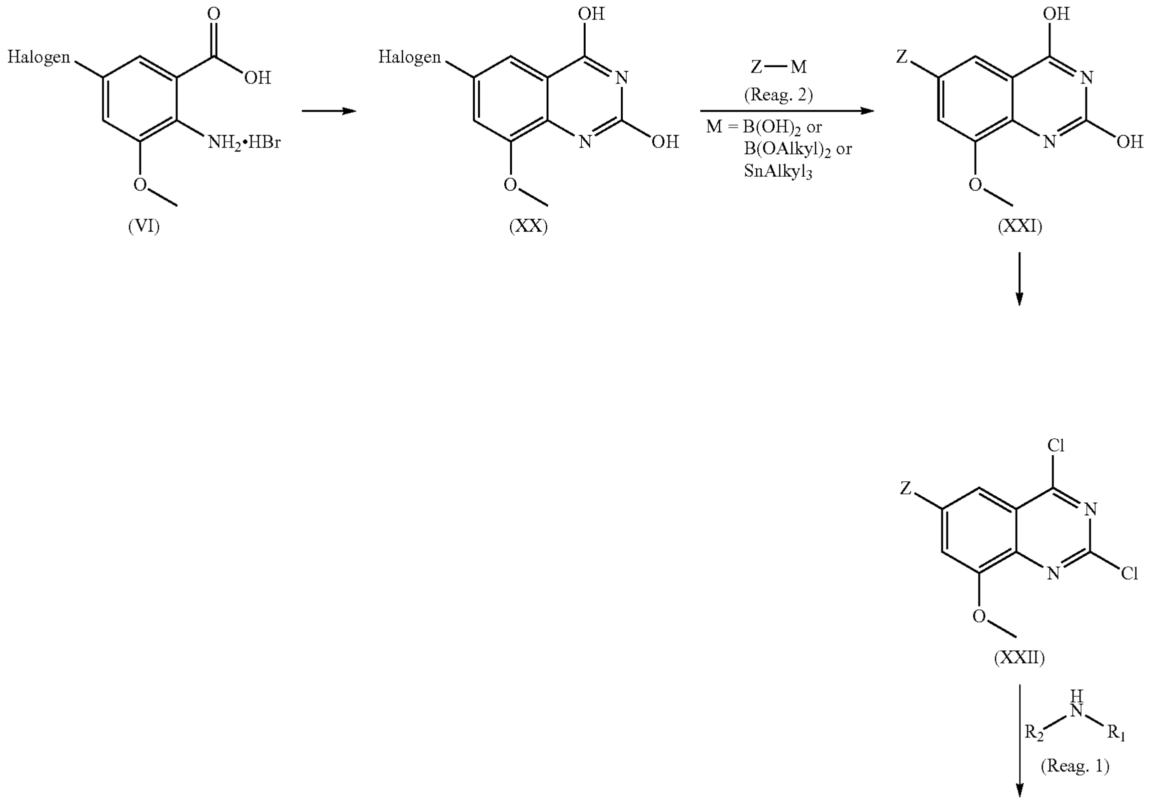

(VI) (XX) (XXI) (XXII)

-continued

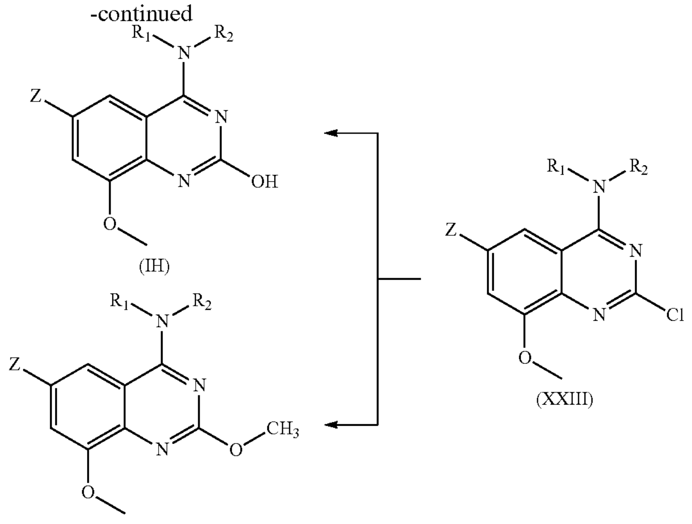

(IH)

(XXIII)

(IJ)

In another embodiment of the present invention, compound (IH) and (IJ) may be prepared according to SCHEME 7 from compounds (VI).

Compound (XX) may be prepared from Compound (VI) by quinazoline ring construction reaction with suitable reagents like Urea or similars.

Compound (XXI) may be prepared from Compound (XX) by metal-catalyzed cross coupling reactions like Stille, Suzuki or similar ones with suitable organometallic reagents (Reag. 2) like, for example, organoboron compounds.

Compound (XXII) may be prepared from Compound (XXI) by chlorination reaction with suitable reagents like phosphorous oxychloride or similar.

Compound (XXIII) may be prepared from Compound (XXII) by amination reaction in the presence of a suitable amine (Reag. 1).

Compound (IH) may be prepared from Compound (XXIII) by hydrolisys with a suitable reagent like, for example, acetic acid.

Some compounds (IH) may contain a protected hydroxyl or amino group which were then removed under well known procedures.

In another embodiment of the present invention Compound (IJ) may be prepared from Compound (XXIII) by reaction with alkoxides, like, for example, Sodium Methoxide.

Some compounds (IJ) may contain a protected hydroxyl or amino group which were then removed under well known procedures.

In a specific aspect the present invention relates to compounds of formula (Ib)

(Ib)

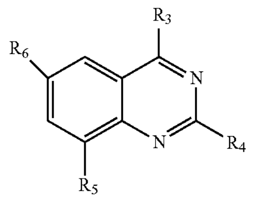

wherein $R_3$ is OH or halo, $R_4$ is H or OH;

$R_5$ is halo or —OMe;

$R_6$ is halo or Z;

Z is as defined above.

In a further aspect the present invention relates to the use of compounds of formula (Ib) as intermediate in the preparation of compounds of formula (I) as above described.

The compounds of the present invention have surprisingly been found to effectively inhibit $P2X_3$ receptor and said compounds are useful for the treatment of respiratory disease.

In one embodiment, representative compounds of formula (I) of the present invention have surprisingly been found to effectively and selectively inhibit $P2X_3$ receptor and said compounds are useful for the treatment of respiratory disease avoiding adverse effect, such as loss of taste response.

In a preferred embodiment, the compound of formula (I) are selective $P2X_3$ antagonist wherein the selective $P2X_3$ antagonist is at least 10-fold selective for $P2X_3$ homomeric receptor antagonism versus $P2X_{2/3}$ heteromeric receptor antagonism.

In a further preferred embodiment, the selective $P2X_3$ antagonist is at least 30-fold selective for $P2X_3$ homomeric receptor antagonism versus $P2X_{2/3}$ heteromeric receptor antagonism.

In a further preferred embodiment, the selective $P2X_3$ antagonist is at least 50-fold selective for $P2X_3$ homomeric receptor antagonism versus $P2X_{2/3}$ heteromeric receptor antagonism.

The present invention also provides a pharmaceutical composition comprising a compound of formula (I) or a pharmaceutically acceptable salt thereof in admixture with one or more pharmaceutically acceptable carrier or excipient, either alone or in combination with one or more further active ingredient.

In one aspect, the invention refers to a compound of formula (I) according to the invention for use as a medicament.

In a further aspect, the invention refers to the use of a compound of formula (I) of the invention, or a pharmaceutically acceptable salt thereof, in the manufacture of a medicament for the treatment of disorders associated with $P2X_3$ receptors mechanism, preferably for the treatment of respiratory diseases.

Preferably, the invention refers to a compound of formula (I) for use in the prevention and/or treatment of respiratory diseases, preferably cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm.

More preferably, the invention refers to a compounds of formula (I) for use in the prevention and/or treatment of chronic cough and cough associated with respiratory diseases such as COPD, asthma and bronchospasm.

The invention also provides a method for the prevention and/or treatment of disorders associated with $P2X_3$ receptors mechanisms, said method comprising administering to a patient in need of such treatment a therapeutically effective amount of a compound of the invention.

In particular the invention refers to a method for the prevention and/or treatment wherein the disorder is cough, sub-acute or chronic cough, treatment-resistant cough, idiopathic chronic cough, post-viral cough, iatrogenic cough, asthma, idiopathic pulmonary fibrosis (IPF), chronic obstructive pulmonary disease (COPD) and cough associated with respiratory diseases such as COPD, asthma and bronchospasm, wherein said method comprises the administration of a proper amount of a compound of formula (I) to a patient in the need thereof.

In a further preferred embodiment, the disorder is chronic cough.

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably the compounds of the present invention may be administered orally or by inhalation.

Various solid oral dosage forms can be used for administering compounds of the invention including such solid forms as tablets, gelcaps, capsules, caplets, granules, lozenges and bulk powders. The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the invention.

Preferably the compounds of the invention are administered in forms of tablets.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the invention may be injected, for example, intravenously, in the form of an isotonic sterile solution.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

Preferably, the compound of the present invention are administered orally.

The compounds of the invention can be administered as the sole active agent or in combination with other pharmaceutical active ingredients.

Preferably, the compound of the present invention can be combined with therapeutic agents or active ingredients useful for the treatment of disease which are related to or mediated by $P2X_3$ receptor.

The dosages of the compounds of the invention depend upon a variety of factors including among others the particular disease to be treated, the severity of the symptoms, the route of administration, and the like.

The invention is also directed to a device comprising a pharmaceutical composition comprising a compound of formula (I) according to the invention, in form of a single- or multi-dose dry powder inhaler or a metered dose inhaler.

The various aspects of the invention described in this application are illustrated buy the following examples which are not meant to limit the invention in any way. following examples illustrate the invention.

The example testing experiments described herein serve to illustrate the present invention and the invention is not limited to the examples given.

PREPARATIONS OF INTERMEDIATES AND EXAMPLES

Chemical names were generated using the Dotmatics software. In some cases generally accepted names of commercially available reagents were used in place of Dotmatics software generated names.

All reagents, for which the synthesis is not described in the experimental part, are either commercially available, or are known compounds or may be formed from known compounds by known methods by a person skilled in the art.

(R)-1-(2-(trifluoromethyl)pyrimidin-5-yl)ethanamine HCl, (R)-1-(6-methylpyridazin-3-yl)ethan-1-amine HCl were prepared accordingly to the procedure described in WO2016/091776.

Abbreviation—Meaning $Et_2O$: diethyl ether;
$Et_3N$: triethyl amine;
TEA: triethyl amine;
DCC: N,N'-Dicyclohexylcarbodiimide;
PyBOP: (benzotriazol-1-yloxy)tripyrrolidinophosphonium hexafluorophosphate;
DMF: dimethylformamide;
EtOAc: Ethyl acetate;
RT: room temperature;
THF: tetrahydrofuran;
DCM: dichloromethane;
MeOH: methyl alcohol;
EtOH: ethylic alcohol;
TFA: Trifluoroacetic acid;
LC-MS: Liquid Chromatography/Mass Spectrometry;
HPLC: high pressure liquid chromatography;
MPLC: medium pressure liquid chromatography;
SFC: Supercritical Fluid Chromatography;
dppf: 1,1'-Bis(diphenylphosphino) ferrocene;
DIEA or DIPEA: N,N-Diisopropylethylamine;
MeCN: Acetonitrile;
MTBE: tert-Butyl methyl ether;
TBDMSCl: tert-Butyl(chloro)dimethylsilane;
DMSO: Dimethylsulfoxide;
$Boc_2O$: di-tert-butyl dicarbonate;
UPLC: Ultra Performance Liquid Chromatography.

General Experimental Details and Methods

Analytical Methods

Liquid Chromatography-Mass Spectrometry

Method 1

UPLC-MS was performed on a Waters Acquity I-Class with Waters Diode Array Detector coupled to a Waters SQD2 single quadrapole mass spectrometer using an Waters HSS C18 column (1.8 μm, 100×2.1 mm) being initially held at 5% acetonitrile/water (with 0.1% formic acid in each mobile phase) for 1.2 minutes, followed by a linear gradient of 5-100% within 3.5 minutes and then held at 100% for 1.5 minutes (F=0.5 mL/min).

Method 2

UPLC-MS was performed on a Waters Acquity I-Class with Waters Diode Array Detector coupled to a Waters SQD2 single quadrapole mass spectrometer using an Waters BEH Shield RP18 column (1.7 μm, 100×2.1 mm) being initially held at 5% acetonitrile/water (with 10 mM ammonium bicarbonate in each mobile phase) for 1.2 minutes, followed by a linear gradient of 5-100% within 3.5 minutes and then held at 100% for 1.5 minutes (F=0.5 mL/min).

Method 3

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% acetonitrile/water (with 10 mM ammonium bicarbonate in each mobile phase) for 0.4 minutes, followed by a linear gradient of 5-95% within 6.4 minutes and then held at 95% for 1.2 minutes (F=0.4 mL/min).

Method 4

UPLC-MS was performed on a Waters DAD+Waters SQD2, single quadrapole UPLC-MS spectrometer using an Acquity UPLC BEH Shield RP18 1.7 um 100×2.1 mm (Plus guard cartridge), maintained at temp column being initially held at 5% Acetonitrile (Far UV grade) with 0.1% (V/V) formic acid/Water (High purity via PureLab Option unit) with 0.1% formic acid for 0.4 minutes, followed by a linear gradient of 5-95% within 6.4 minutes and then held at 95% for 1.2 minutes (F=0.4 mL/min).

Method 5

Aquity UPLC-QDa Mass Spectrometer with a C18-reverse-phase column (50×2.1 mm Acquity CSH with 1.7 μm particle size) maintained at 40° C., elution with A: 95/5 water/acetonitrile+0.05% formic acid; B: 95/5 acetonitrile/water+0.05% formic acid.

Gradient:

| Time [min] | Flow [ml/min] | Mobile phase A [%] | Mobile phase B [%] |
|---|---|---|---|
| 0.0 | 1 | 99.0 | 1.0 |
| 1.50 | 1 | 0.1 | 99.9 |
| 1.90 | 1 | 0.1 | 99.9 |
| 2.00 | 1 | 99.0 | 1.0 |

Detection-MS, UV PDA

MS Ionisation Method-Electrospray (Positive/Negative Ion).

Method 6

Aquity UPLC-QDa Mass Spectrometer with a C18-reverse-phase column (50×2.1 mm Acquity BEH with 1.7 μm particle size) maintained at 40° C., elution with A: 95/5 water/acetonitrile+0.05% conc. ammonia; B: 95/5 acetonitrile/water+0.05% conc. ammonia.

Gradient:

| Time [min] | Flow [ml/min] | Mobile phase A [%] | Mobile phase B [%] |
|---|---|---|---|
| 0.0 | 1 | 99.0 | 1.0 |
| 1.50 | 1 | 0.1 | 99.9 |
| 1.90 | 1 | 0.1 | 99.9 |
| 2.00 | 1 | 99.0 | 1.0 |

Detection-MS, UV PDA

MS Ionisation Method-Electrospray (Positive/Negative Ion)

Method 7

Dionex UHPLC Ultimate 3000 with DAD detector/Thermo Scientific MSQ Pluse quipped with a Kinetex® 2.6 μm XB-C18 (4.6×50 mm), 110 A maintained at 25° C., elution with A: 0.1% v/v water solution of formic acid, B: 0.1% v/v acetonitrile solution of formic acid Gradient:

| Time [min] | Flow [ml/min] | Mobile phase A [%] | Mobile phase B [%] |
|---|---|---|---|
| 0.0 | 1.0 | 95 | 5 |
| 1.0 | 1.0 | 95 | 5 |

-continued

| Time [min] | Flow [ml/min] | Mobile phase A [%] | Mobile phase B [%] |
|---|---|---|---|
| 4.75 | 1.0 | 20 | 80 |
| 5.25 | 1.0 | 20 | 80 |
| 6.0 | 1.0 | 95 | 5 |
| 7.0 | 1.0 | 95 | 5 |

Detection-MS, UV PDA

MS Ionisation Method-Electrospray (Positive/Negative Ion)

NMR $^1H$ Nuclear magnetic resonance (NMR) spectroscopy was carried out using a Bruker or Varian instruments operating at 300 or 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector. The columns used for the preparative purification of the compounds were a Waters Sunfire OBD Phenomenex Luna Phenyl Hexyl or Waters Xbridge Phenyl at 10 μm 19×150 mm or Waters CSH Phenyl Hexyl, 19×150, 5 μm column. Appropriate focused gradients were selected based on acetonitrile and methanol solvent systems under either acidic or basic conditions. The modifiers used under acidic/basic conditions were formic acid or trifluoroacetic acid (0.1% V/V) and ammonium bicarbonate (10 mM) respectively. The purification was controlled by Waters Fractionlynx software through monitoring at 210-400 nm, and triggered a threshold collection value at 260 nm and, when using the Fractionlynx, the presence of target molecular ion as observed under API conditions. Collected fractions were analysed by LCMS (Waters Acquity systems with Waters SQD).

Chiral Supercritical Fluid Chromatography (SFC) Separation Protocol

The diastereomeric separation of compounds was achieved by Supercritical Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector. Appropriate isocratic methods were selected based on methanol, ethanol or isopropanol solvent systems under un-modified or basic conditions. The standard SFC method used was modifier, CO2, 100 mL/min, 120 Bar backpressure, 40° C. column temperature. The modifier used under basic conditions was diethylamine (0.1% V/V). The modifier used under acidic conditions was either formic acid (0.1% V/V) or trifluoroacetic acid (0.1% V/V). The SFC purification was controlled by Waters Fractionlynx software through monitoring at 210-400 nm and triggered at a threshold collection value, typically 260 nm. Collected fractions were analysed by SFC (Waters/Thar SFC systems with Waters SQD). The fractions that contained the desired product were concentrated by vacuum centrifugation.

Supercritical Fluid Chromatography-Mass Spectrometry Analytical Conditions

Method 8

SFC-MS was performed on a Waters/Thar SFC systems with Waters SQD using a Lux Cellulose-3 column with a 15% methyl alcohol/$CO_2$ (with 0.1% diethylamine) isocratic run at 5 mL/min, 120 Bar backpressure, 40° C. column temperature.

Method 9

SFC-MS was performed on a Waters/Thar SFC systems with Waters SQD using a Lux Cellulose-3 column with a 20% methyl alcohol/$CO_2$ (with 0.1% diethylamine) isocratic run at 5 mL/min, 120 Bar backpressure, 40° C. column temperature.

Method 10

SFC-MS was performed on a Waters/Thar SFC systems with Waters SQD using a Lux Cellulose-4 column with a 55% ethyl alcohol/$CO_2$ (with 0.1% diethylamine) isocratic run at 5 mL/min, 120 Bar backpressure, 40° C. column temperature.

Method 11

SFC-MS was performed on a Waters/Thar SFC systems with Waters SQD using a Lux Cellulose-4 column with a 20% iso-propyl alcohol/$CO_2$ (with 0.1% diethylamine) isocratic run at 5 mL/min, 120 Bar backpressure, 40° C. column temperature.

Method 12

SFC-MS was performed on a Waters/Thar SFC systems with Waters SQD using a Lux Cellulose-4 column with a 30% iso-propyl alcohol/$CO_2$ (with 0.1% diethylamine) isocratic run at 5 mL/min, 120 Bar backpressure, 40° C. column temperature.

Method 13

SFC-MS was performed on a Waters/Thar SFC systems with Waters SQD using a Lux Cellulose-4 column with a 50% iso-propyl alcohol/$CO_2$ (with 0.1% diethylamine) isocratic run at 5 mL/min, 120 Bar backpressure, 40° C. column temperature.

Method 14

SFC-MS was performed on a Waters/Thar SFC systems with Waters SQD using a Lux Cellulose-4 column with a 25% methyl alcohol/$CO_2$ (with 0.1% diethylamine) isocratic run at 5 mL/min, 120 Bar backpressure, 40° C. column temperature.

Method 15

SFC-MS was performed on a Waters/Thar SFC systems with Waters SQD using a YMC Amylose-C column with a 15% ethyl alcohol/$CO_2$ (with 0.1% diethylamine) isocratic run at 5 mL/min, 120 Bar backpressure, 40° C. column temperature.

Method 16

SFC-MS was performed on a Waters/Thar SFC systems with Waters SQD using a YMC Amylose-C column with a 25% iso-propyl alcohol/$CO_2$ (with 0.1% diethylamine) isocratic run at 5 mL/min, 120 Bar backpressure, 40° C. column temperature.

Method 17

SFC-MS was performed on a Waters/Thar SFC systems with Waters SQD using a YMC Amylose-C column with a 35% iso-propyl alcohol/$CO_2$ (with 0.1% diethylamine) isocratic run at 5 mL/min, 120 Bar backpressure, 40° C. column temperature.

Method 18

SFC-MS was performed on a Waters/Thar SFC systems with Waters SQD using a YMC Amylose-C column with a 55% iso-propyl alcohol/$CO_2$ (with 0.1% diethylamine) isocratic run at 5 mL/min, 120 Bar backpressure, 40° C. column temperature.

Method 19

SFC-MS was performed on a Waters/Thar SFC systems with Waters SQD using a YMC Amylose-C column with a 15% methyl alcohol/$CO_2$ (with 0.1% diethylamine) isocratic run at 5 mL/min, 120 Bar backpressure, 40° C. column temperature.

Method 20

SFC-MS was performed on a Waters/Thar SFC systems with Waters SQD using a YMC Amylose-C column with a 20% methyl alcohol/$CO_2$ (with 0.1% diethylamine) isocratic run at 5 mL/min, 120 Bar backpressure, 40° C. column temperature.

Method 21

SFC-MS was performed on a Waters/Thar SFC systems with Waters SQD using a YMC Cellulose-C column with a 15% iso-propyl alcohol/$CO_2$ (with 0.1% diethylamine) isocratic run at 5 mL/min, 120 Bar backpressure, 40° C. column temperature.

Method 22

SFC-MS was performed on a Waters/Thar SFC systems with Waters SQD using a YMC Cellulose-C column with a 15% methyl alcohol/$CO_2$ (with 0.1% diethylamine) isocratic run at 5 mL/min, 120 Bar backpressure, 40° C. column temperature.

Method 23

SFC-MS was performed on a Waters/Thar SFC systems with Waters SQD using a YMC Cellulose-C column with a 25% methyl alcohol/$CO_2$ (with 0.1% diethylamine) isocratic run at 5 mL/min, 120 Bar backpressure, 40° C. column temperature.

Method 24

SFC-MS was performed on a Waters/Thar SFC systems with Waters SQD using a YMC Cellulose-SC column with a 55% iso-propyl alcohol/$CO_2$ (with 0.1% diethylamine) isocratic run at 5 mL/min, 120 Bar backpressure, 40° C. column temperature.

Method 25

SFC-MS was performed on a Waters/Thar SFC systems with Waters SQD using a Lux Cellulose-3 column with a 10% methyl alcohol/$CO_2$ (with 0.1% diethylamine) isocratic run at 5 mL/min, 120 Bar backpressure, 40° C. column temperature.

Method 26

SFC-MS was performed on a Waters/Thar SFC systems with Waters SQD using a Lux Cellulose-3 column with a 25% methyl alcohol/$CO_2$ (with 0.1% diethylamine) isocratic run at 5 mL/min, 120 Bar backpressure, 40° C. column temperature.

Method 27

SFC-MS was performed on a Waters/Thar SFC systems with Waters SQD using a Lux Cellulose-3 column with a 30% methyl alcohol/$CO_2$ (with 0.1% diethylamine) isocratic run at 5 mL/min, 120 Bar backpressure, 40° C. column temperature.

Method 28

SFC-MS was performed on a Waters/Thar SFC systems with Waters SQD using a Lux Cellulose-4 column with a 40% iso-propyl alcohol/$CO_2$ (with 0.1% diethylamine) isocratic run at 5 mL/min, 120 Bar backpressure, 40° C. column temperature.

Method 29

SFC-MS was performed on a Waters/Thar SFC systems with Waters SQD using a Lux Cellulose-4 column with a 40% methyl alcohol/$CO_2$ (with 0.1% diethylamine) isocratic run at 5 mL/min, 120 Bar backpressure, 40° C. column temperature.

Method 30

SFC-MS was performed on a Waters/Thar SFC systems with Waters SQD using a Lux Cellulose-4 column with a 50% methyl alcohol/$CO_2$ (with 0.1% diethylamine) isocratic run at 5 mL/min, 120 Bar backpressure, 40° C. column temperature.

Method 31

SFC-MS was performed on a Waters/Thar SFC systems with Waters SQD using a Lux Cellulose-4 column with a 55% iso-propyl alcohol/$CO_2$ (with 0.1% diethylamine) isocratic run at 5 mL/min, 120 Bar backpressure, 40° C. column temperature.

Method 32

SFC-MS was performed on a Waters/Thar SFC systems with Waters SQD using a Lux Cellulose-4 column with a 55% methyl alcohol/$CO_2$ (with 0.1% diethylamine) isocratic run at 5 mL/min, 120 Bar backpressure, 40° C. column temperature.

Method 33

SFC-MS was performed on a Waters/Thar SFC systems with Waters SQD using a YMC Amylose-C column with a 20% ethyl alcohol/$CO_2$ (with 0.1% diethylamine) isocratic run at 5 mL/min, 120 Bar backpressure, 40° C. column temperature.

Method 34

SFC-MS was performed on a Waters/Thar SFC systems with Waters SQD using a YMC Amylose-C column with a 30% iso-propyl alcohol/$CO_2$ (with 0.1% diethylamine) isocratic run at 5 mL/min, 120 Bar backpressure, 40° C. column temperature.

Method 35

SFC-MS was performed on a Waters/Thar SFC systems with Waters SQD using a YMC Amylose-C column with a 30% methyl alcohol/$CO_2$ (with 0.1% diethylamine) isocratic run at 5 mL/min, 120 Bar backpressure, 40° C. column temperature.

Method 36

SFC-MS was performed on a Waters/Thar SFC systems with Waters SQD using a YMC Amylose-C column with a 40% methyl alcohol/$CO_2$ (with 0.1% diethylamine) isocratic run at 5 mL/min, 120 Bar backpressure, 40° C. column temperature.

Method 37

SFC-MS was performed on a Waters/Thar SFC systems with Waters SQD using a YMC Amylose-C column with a 55% methyl alcohol/$CO_2$ (with 0.1% diethylamine) isocratic run at 5 mL/min, 120 Bar backpressure, 40° C. column temperature.

Method 38

SFC-MS was performed on a Waters/Thar SFC systems with Waters SQD using a YMC Cellulose-C column with a 20% methyl alcohol/$CO_2$ (with 0.1% diethylamine) isocratic run at 5 mL/min, 120 Bar backpressure, 40° C. column temperature.

Method 39

SFC-MS was performed on a Waters/Thar SFC systems with Waters SQD using a YMC Cellulose-SC column with a 35% iso-propyl alcohol/$CO_2$ (with 0.1% diethylamine) isocratic run at 5 mL/min, 120 Bar backpressure, 40° C. column temperature.

Method 40

SFC-MS was performed on a Waters/Thar SFC systems with Waters SQD using a YMC Cellulose-SC column with a 45% iso-propyl alcohol/$CO_2$ (with 0.1% diethylamine) isocratic run at 5 mL/min, 120 Bar backpressure, 40° C. column temperature.

Preparation of Intermediates and Examples

Example 1

6-(4-Fluorophenyl)-8-methoxy-N-(1-(3-methyl-1,2,4-oxadiazol-5-yl)ethyl)quinazolin-4-amine Preparation of Intermediate 1, 2-Amino-5-bromo-3-methoxybenzoic acid hydrobromide

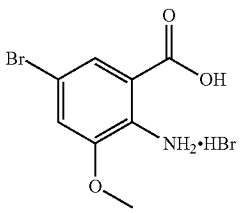

A solution of bromine (6.0 g, 1.9 mL, 37.70 mmol) in chloroform (15 mL) was added dropwise over a period of one hour to a suspension of 2-amino-3-methoxybenzoic acid (6.0 g, 35.90 mmol) in chloroform (180 mL) at 0° C. The reaction was stirred for a further five hours and slowly allowed to warm to room temperature. The solvent was removed in vacuo and the residue was triturated with diethyl ether. The reaction was filtered to give the title compound as a beige solid (11.3 g, 96%).

LCMS (Method 4): [MH+]=247 at 4.07 min.

Preparation of Intermediate 2 6-Bromo-8-methoxyquinazolin-4-ol

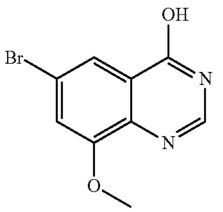

A solution 2-amino-5-bromo-3-methoxybenzoic acid hydrobromide (Intermediate 1) (10.0 g, 30.60 mmol) in formamide (40 mL) was heated to 165° C. for 18 hours. After return to room temperature, the reaction was diluted with water (100 mL) and poured into ice water (400 mL) and filtered. The solid was washed with water (200 mL) and diethyl ether (200 mL) to give the title compound as a light brown solid (5.9 g, 76%).

LCMS (Method 4): [MH+]=255 at 3.07 min.

Preparation of Intermediate 3, 6-(4-Fluorophenyl)-8-methoxyquinazolin-4-ol

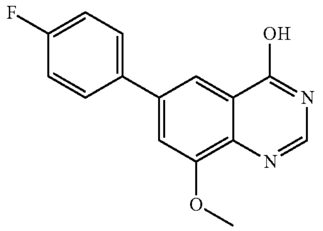 [SMILES: COc1cc(-c2ccc(F)cc2)cc2c(O)ncnc12]

Nitrogen was bubbled for 5 min through a mixture of 6-bromo-8-methoxyquinazolin-4-ol (Intermediate 2) (1.18 g, 4.63 mmol), 4-fluorophenylboronic acid (710 mg, 5.09 mmol) and cesium carbonate (5.73 g, 17.58 mmol) in 1,4-dioxane (30 mL) and water (7.5 mL), then [1,1'-bis(diphenylphosphino)ferrocene]dichloropalladium(II) complex with dichloromethane (190 mg, 0.23 mmol) was added and the reaction was heated to 110° C. for 5 hours. After return to room temperature, the reaction was diluted with water (20 mL), filtered and the solid was washed with 10% methanol in diethyl ether then with diethyl ether to give the title compound (1.0 g, 80%) as a beige solid.

LCMS (Method 5): [MH+]=271.1 at 0.81 min.

6-(4-Fluorophenyl)-8-methoxy-N-(1-(3-methyl-1,2,4-oxadiazol-5-yl)ethyl)quinazolin-4-amine

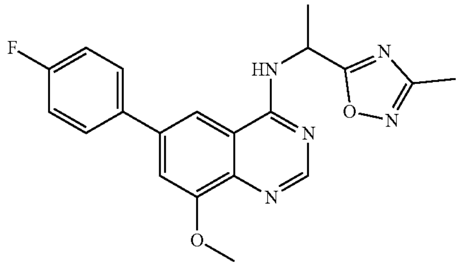 [SMILES: COc1cc(-c2ccc(F)cc2)cc2c(NC(C)c3nc(C)no3)ncnc12]

To a solution of 6-(4-fluorophenyl)-8-methoxyquinazolin-4-ol (Intermediate 3) (100 mg, 0.37 mmol) in N,N-dimethylformamide (2 mL) was successively added (benzotriazol-1-yloxy)tripyrrolidinophosphonium hexafluorophosphate (212 mg, 0.41 mmol) and di-isopropylethylamine (0.32 mL, 1.85 mmol). The resulting mixture was heated to 40° C. and stirred for 20 min, 1-(3-methyl-1,2,4-oxadiazol-5-yl)ethan-1-amine (67 mg, 0.41 mmol) was then added and the heating was maintained at 40° C. for 18 hours. After return to room temperature, the mixture was diluted with ethyl acetate (50 mL) and water (20 mL). The organic phase was washed with brine (2×20 mL), passed through a hydrophobic frit and the solvent was removed in vacuo. The residue was purified by preparative HPLC to give the title compound (43 mg, 31%) as a white solid.

$^1H$ NMR (400 MHz, DMSO): δ 8.85 (d, J=6.8 Hz, 1H), 8.49 (s, 1H), 8.24 (s, 1H), 7.99 (dd, J=5.6, 8.6 Hz, 2H), 7.61 (s, 1H), 7.44 (dd, J=8.8, 8.8 Hz, 2H), 5.88-5.82 (m, 1H), 4.08 (s, 3H), 2.37 (s, 3H), 1.78 (d, J=7.1 Hz, 3H). LCMS (Method 4): [MH+]=375 at 3.29 min.

The compounds reported in the table below were synthesised following the same procedure described for the preparation of 6-(4-Fluorophenyl)-8-methoxy-N-(1-(3-methyl-1,2,4-oxadiazol-5-yl)ethyl)quinazolin-4-amine.

| Example No. | Chemical Name<br>Structure | Analytical Data<br>$^1$H NMR<br>LC-MS |
|---|---|---|
| Example 2 | 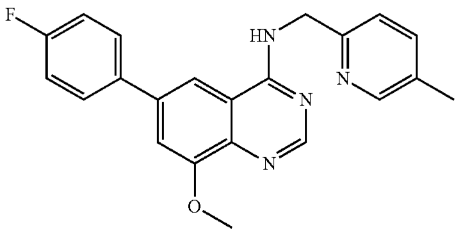 [SMILES: COc1cc(-c2ccc(F)cc2)cc2c(NCc3ccc(C)cn3)ncnc12]<br>6-(4-Fluorophenyl)-8-methoxy-N-((5-methylpyridin-2-yl)methyl)quinazolin-4-amine | $^1$H NMR (400 MHz, DMSO): δ 8.94 (dd, J = 5.9, 5.9 Hz, 1 H), 8.40 (s, 1H), 8.37 (d, J = 1.8 Hz, 1 H), 8.20 (d, J = 1.8 Hz, 1 H), 7.97-7.92 (m, 2 H), 7.56-7.53 (m, 2 H), 7.39 (dd, J = 8.9, 8.9 Hz, 2 H), 7.26 (d, J = 8.0 Hz, 1 H), 4.85 (d, J = 5.9 Hz, 2 H), 4.02 (s, 3 H), 2.28 (s, 3 H). LCMS (Method 4): [MH+] = 375 at 3.10 min. |
| Example 3 | 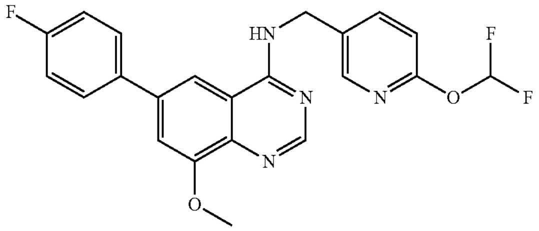 [SMILES: COc1cc(-c2ccc(F)cc2)cc2c(NCc3ccc(OC(F)F)nc3)ncnc12]<br>N-((6-(Difluoromethoxy)pyridin-3-yl)methyl)-6-(4-fluorophenyl)-8-methoxyquinazolin-4-amine | $^1$H NMR (400 MHz, DMSO): δ 8.90 (dd, J = 5.4, 5.4 Hz, 1 H), 8.47 (s, 1 H), 8.33 (d, J = 2.0 Hz, 1 H), 8.11 (d, J = 1.6 Hz, 1 H), 7.97-7.90 (m, 3 H), 7.69 (t, J = 73.0 Hz, 1 H), 7.53 (d, J = 1.7 Hz, 1 H), 7.38 (dd, J = 8.9, 8.9 Hz, 2 H), 7.07 (d, J = 8.8 Hz, 1 H), 4.80 (d, J = 5.6 Hz, 2 H), 4.02 (s, 3 H).<br>LCMS (Method 3): [MH+] = 427 at 4.72 min. |
| Example 4 | 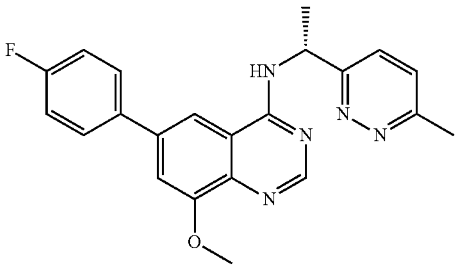<br>(R)-6-(4-Fluorophenyl)-8-methoxy-N-(1-(6-methylpyridazin-3-yl)ethyl)quinazolin-4-amine | $^1$H NMR (400 MHz, DMSO): δ 9.18-9.18 (m, 1 H), 8.47 (s, 1 H), 8.36 (d, J = 1.4 Hz, 1 H), 8.00-7.95 (m, 2 H), 7.65 (d, J = 8.7 Hz, 2 H), 7.53 (d, J = 8.7 Hz, 1 H), 7.42 (dd, J = 8.8, 8.8 Hz, 2 H), 5.88-5.79 (m, 1 H), 4.06 (s, 3 H), 2.60 (s, 3 H), 1.74 (d, J = 7.2 Hz, 3 H). LCMS (Method 3): [MH+] = 390 at 4.13 min. |
| Example 5 | 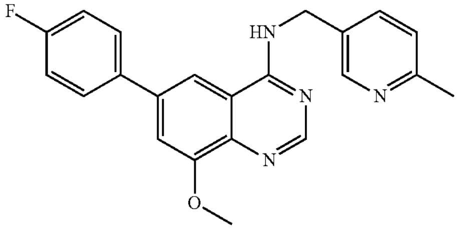 [SMILES: COc1cc(-c2ccc(F)cc2)cc2c(NCc3ccc(C)nc3)ncnc12]<br>6-(4-Fluorophenyl)-8-methoxy-N-((6-methylpyridin-3-yl)methyl)quinazolin-4-amine | $^1$H NMR (400 MHz, DMSO): δ 8.85 (dd, J = 5.7, 5.7 Hz, 1 H), 8.50 (d, J = 1.9 Hz, 1 H), 8.45 (s, 1 H), 8.12 (d, J = 1.6 Hz, 1 H), 7.92 (ddd, J = 3.1, 5.4, 12.1 Hz, 2 H), 7.68 (dd, J = 2.3, 8.0 Hz, 1 H), 7.52 (d, J = 1.6 Hz, 1 H), 7.38 (dd, J = 8.9, 8.9 Hz, 2 H), 7.21 (d, J = 7.9 Hz, 1 H), 4.77 (d, J = 5.5 Hz, 2 H), 2.44 (s, 3 H). LCMS (Method 4): [MH+] = 375 at 2.40 min. |

-continued

| Example No. | Chemical Name<br>Structure | Analytical Data<br>$^1$H NMR<br>LC-MS |
|---|---|---|
| Example 6 | 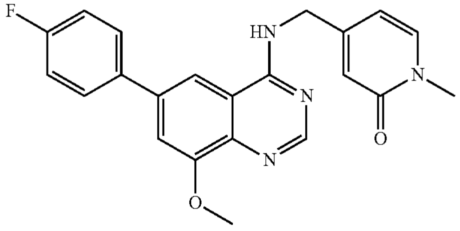 [SMILES: COc1cc(-c2ccc(F)cc2)cc2c(NCc3ccn(C)c(=O)c3)ncnc12]<br>4-(((6-(4-Fluorophenyl)-8-methoxyquinazolin-4-yl)amino)methyl)-1-methylpyridin-2(1H)-one | 1H NMR (400 MHz, DMSO): δ 9.03-8.96 (m, 1 H), 8.46 (s, 1 H), 8.18-8.14 (m, 1 H), 7.95 (ddd, J = 3.2, 5.3, 12.1 Hz, 2 H), 7.63 (d, J = 6.9 Hz, 1 H), 7.58 (d, J = 1.4 Hz, 1 H), 7.40 (dd, J = 8.9, 8.9 Hz, 2 H), 6.27 (s, 1 H), 6.23 (dd, J = 1.9, 7.0 Hz, 1 H), 4.64 (d, J = 5.6 Hz, 2 H), 4.04 (s, 3 H), 3.38 (s, 3 H). LCMS (Method 4): [MH+] = 391 at 2.97 min. |
| Example 7 | 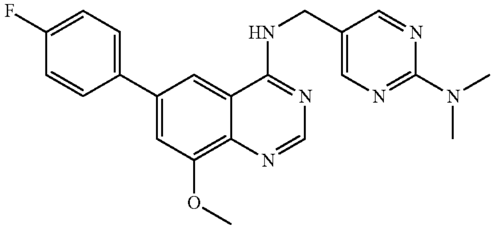 [SMILES: COc1cc(-c2ccc(F)cc2)cc2c(NCc3cnc(N(C)C)nc3)ncnc12]<br>N-((2-(Dimethylamino)pyrimidin-5-yl)methyl)-6-(4-fluorophenyl)-8-methoxyquinazolin-4-amine | $^1$H NMR (400 MHz, DMSO): δ 8.71 (dd, J = 5.1, 5.1 Hz, 1 H), 8.42 (s, 1 H), 8.36 (s, 2 H), 7.99 (d, J = 1.6 Hz, 1 H), 7.83 (ddd, J = 3.2, 5.3, 12.1 Hz, 2 H), 7.44 (d, J = 1.5 Hz, 1 H), 7.29 (dd, J = 8.9, 8.9 Hz, 2 H), 4.51 (d, J = 5.4 Hz, 2 H), 3.94 (s, 3 H), 3.02 (s, 6 H). LCMS (Method 4): [MH+] = 405 at 3.24 min. |
| Example 8 | 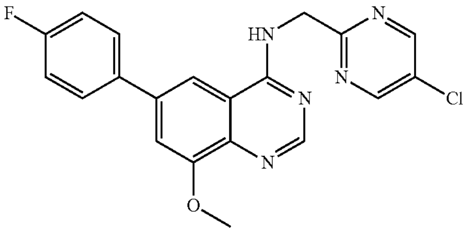 [SMILES: COc1cc(-c2ccc(F)cc2)cc2c(NCc3ncc(Cl)cn3)ncnc12]<br>N-((5-Chloropyrimidin-2-yl)methyl)-6-(4-fluorophenyl)-8-methoxyquinazolin-4-amine | $^1$H NMR (400 MHz, DMSO): δ 9.14-9.06 (m, 1 H), 8.89 (s, 2 H), 8.35 (s, 1 H), 8.21 (d, J = 1.6 Hz, 1 H), 7.97-7.93 (m, 2 H), 7.56 (d, J = 1.5 Hz, 1 H), 7.40 (dd, J = 8.8, 8.8 Hz, 2 H), 4.98 (d, J = 5.9 Hz, 2 H), 4.03 (s, 3 H). LCMS (Method 4): [MH+] = 396 at 3.30 min. |
| Example 9 | 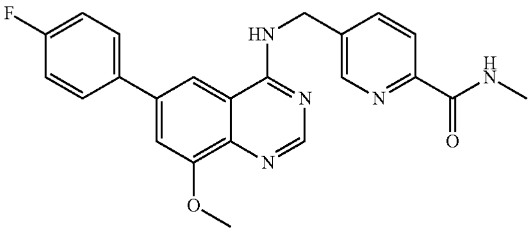 [SMILES: CNC(=O)c1ccc(CNc2ncnc3c(OC)cc(-c4ccc(F)cc4)cc23)cn1]<br>5-(((6-(4-Fluorophenyl)-8-methoxyquinazolin-4-yl)amino)methyl)-N-methylpicolinamide | $^1$H NMR (400 MHz, DMSO): δ 9.18-9.11 (m, 1 H), 8.74-8.69 (m, 2 H), 8.49 (s, 1 H), 8.17-8.15 (m, 2 H), 8.01-7.91 (m, 4 H), 7.58 (d, J = 1.3 Hz, 1H), 7.39 (dd, J = 8.8, 8.8 Hz, 2 H), 4.92 (d, J = 5.5 Hz, 2 H), 4.04 (s, 3 H), 2.82 (d, J = 4.9 Hz, 3 H). LCMS (Method 4): [MH+] = 418 at 3.19 min. |

-continued

| Example No. | Chemical Name Structure | Analytical Data $^1$H NMR LC-MS |
|---|---|---|
| Example 10 | 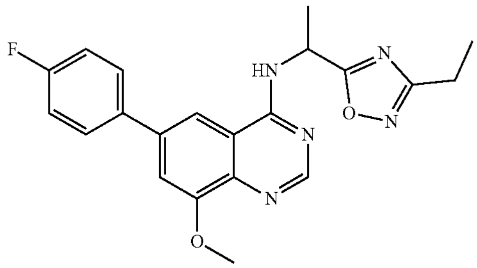 [SMILES: CCc1noc(C(C)Nc2ncnc3c(OC)cc(-c4ccc(F)cc4)cc23)n1] N-(1-(3-Ethyl-1,2,4-oxadiazol-5-yl)ethyl)-6-(4-fluorophenyl)-8-methoxyquinazolin-4-amine | $^1$H NMR (400 MHz, DMSO): δ 8.85 (d, J = 6.8 Hz, 1 H), 8.46 (s, 1 H), 8.21 (d, J = 1.6 Hz, 1 H), 7.95 (ddd, J = 3.2, 5.3, 12.1 Hz, 2 H), 7.58 (d, J = 1.5 Hz, 1 H), 7.40 (dd, J = 8.9, 8.9 Hz, 2 H), 5.86-5.81 (m, 1 H), 4.04 (s, 3 H), 2.71 (q, J = 7.6 Hz, 2 H), 1.74 (d, J = 7.2 Hz, 3 H), 1.22 (dd, J = 7.5, 7.5 Hz, 3 H). LCMS (Method 4): [MH+] = 394 at 3.49 min. |
| Example 11 | 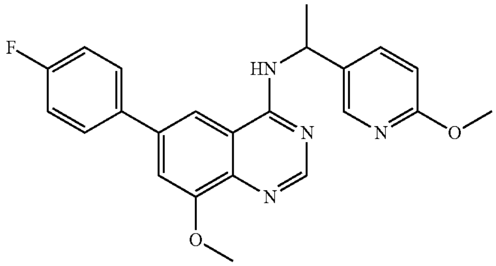 [SMILES: COc1ccc(C(C)Nc2ncnc3c(OC)cc(-c4ccc(F)cc4)cc23)cn1] 6-(4-Fluorophenyl)-8-methoxy-N-(1-(6-methoxypyridin-3-yl)ethyl)quinazolin-4-amine | $^1$H NMR (400 MHz, DMSO): δ 8.45 (d, J = 7.7 Hz, 1 H), 8.42 (s, 1 H), 8.26 (d, J = 2.5 Hz, 1 H), 8.20 (d, J = 1.6 Hz, 1 H), 7.93 (ddd, J = 3.2, 5.5, 12.1 Hz, 2 H), 7.80 (dd, J = 2.5, 8.7 Hz, 1 H), 7.51 (d, J = 1.5 Hz, 1 H), 7.39 (dd, J = 8.9, 8.9 Hz, 2 H), 6.80 (d, J = 8.9 Hz, 1 H), 5.63-5.58 (m, 1 H), 4.01 (s, 3 H), 3.82 (s, 3 H), 1.63 (d, J = 7.0 Hz, 3 H). LCMS (Method 4): [MH+] = 405 at 3.55 min. |
| Example 12 | 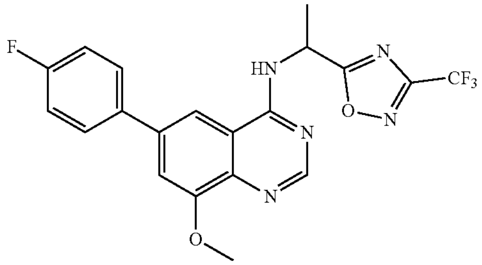 [SMILES: COc1cc(-c2ccc(F)cc2)cc2c(NC(C)c3nc(C(F)(F)F)no3)ncnc12] 6-(4-Fluorophenyl)-8-methoxy-N-(1-(3-(trifluoromethyl)-1,2,4-oxadiazol-5-yl)ethyl)quinazolin-4-amine | $^1$H NMR (400 MHz, DMSO): δ 8.91 (d, J = 6.8 Hz, 1 H), 8.44 (s, 1 H), 8.17 (d, J = 1.6 Hz, 1 H), 7.97-7.92 (m, 2 H), 7.58 (d, J = 1.5 Hz, 1 H), 7.40 (dd, J = 8.8, 8.8 Hz, 2 H), 5.94-5.89 (m, 1 H), 4.04 (s, 3 H), 1.81 (d, J = 7.2 Hz, 3 H). LCMS (Method 4): [MH+] = 434 at 3.90 min. |
| Example 13 | 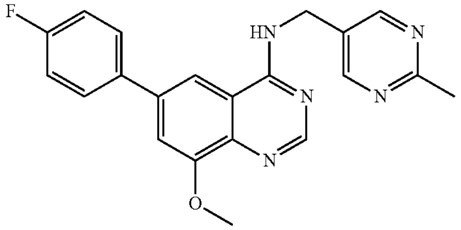 [SMILES: COc1cc(-c2ccc(F)cc2)cc2c(NCc3cnc(C)nc3)ncnc12] 6-(4-Fluorophenyl)-8-methoxy-N-((2-methylpyrimidin-5-yl)methyl)quinazolin-4-amine | $^1$H NMR (400 MHz, DMSO): δ 8.97 (dd, J = 5.8, 5.8 Hz, 1 H), 8.59 (s, 2 H), 8.34 (s, 1 H), 8.21 (d, J = 1.5 Hz, 1 H), 7.98-7.93 (m, 2 H), 7.54 (d, J = 1.3 Hz, 1 H), 7.39 (dd, J = 8.8, 8.8 Hz, 2 H), 4.93 (d, J = 5.6 Hz, 2 H), 4.03 (s, 3 H), 2.25 (s, 3 H). LCMS (Method 4): [MH+] = 376 at 3.08 min. |

-continued

| Example No. | Chemical Name<br>Structure | Analytical Data<br>$^1$H NMR<br>LC-MS |
|---|---|---|
| Example 14 | 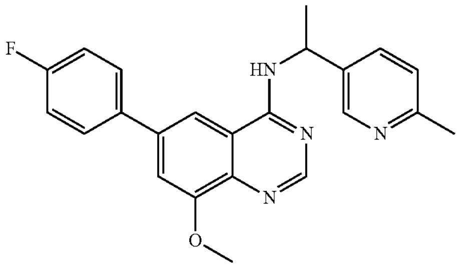<br>6-(4-Fluorophenyl)-8-methoxy-N-(1-(6-methylpyridin-3-yl)ethyl)quinazolin-4-amine | $^1$H NMR (400 MHz, DMSO): δ 8.61-8.54 (m, 2 H), 8.42 (s, 1 H), 8.24 (d, J = 1.5 Hz, 1 H), 7.97-7.92 (m, 2 H), 7.74 (dd, J = 2.3, 8.1 Hz, 1 H), 7.53 (d, J = 1.5 Hz, 1 H), 7.40 (dd, J = 8.8, 8.8 Hz, 2 H), 7.21 (d, J = 8.0 Hz, 1 H), 5.66-5.57 (m, 1 H), 4.02 (s, 3 H), 2.43 (s, 3 H), 1.64 (d, J = 7.0 Hz, 3 H).<br>LCMS (Method 4): [MH+] = 389 at 2.65 min. |
| Example 15 | 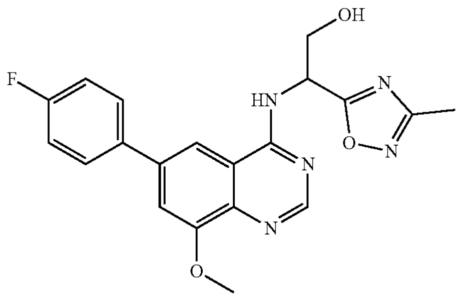 [SMILES: COc1cc(-c2ccc(F)cc2)cc2c(NC(CO)c3nc(C)no3)ncnc12]<br>2-((6-(4-Fluorophenyl)-8-methoxyquinazolin-4-yl)amino)-2-(3-methyl-1,2,4-oxadiazol-5-yl)ethan-1-ol | $^1$H NMR (400 MHz, DMSO): δ 8.92-8.92 (m, 1 H), 8.50 (s, 1 H), 8.28 (d, J = 1.4 Hz, 1 H), 7.99-7.94 (m, 2 H), 7.61 (d, J = 1.1 Hz, 1 H), 7.41 (dd, J = 8.9, 8.9 Hz, 2 H), 5.80 (q, J = 6.7 Hz, 1 H), 5.41 (s, 1 H), 4.05 (s, 6 H), 2.34 (s, 3 H). LCMS (Method 4): [MH+] = 396 at 2.96 min. |
| Example 16 | 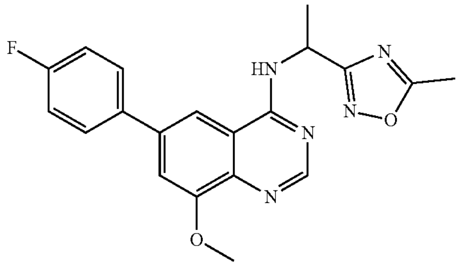 [SMILES: COc1cc(-c2ccc(F)cc2)cc2c(NC(C)c3noc(C)n3)ncnc12]<br>6-(4-Fluorophenyl)-8-methoxy-N-(1-(5-methyl-1,2,4-oxadiazol-3-yl)ethyl)quinazolin-4-amine | $^1$H NMR (400 MHz, DMSO): δ 8.65 (d, J = 7.7 Hz, 1 H), 8.45 (s, 1 H), 8.23 (d, J = 1.6 Hz, 1 H), 7.97-7.93 (m, 2 H), 7.55 (d, J = 1.5 Hz, 1 H), 7.39 (dd, J = 8.9, 8.9 Hz, 2 H), 5.79-5.74 (m, 1 H), 4.03 (s, 3 H), 1.68 (d, J = 7.2 Hz, 3 H).<br>LCMS (Method 4): [MH+] = 380 at 3.32 min. |
| Example 17 | 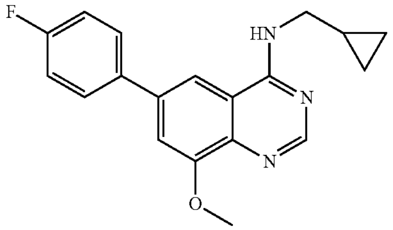 [SMILES: COc1cc(-c2ccc(F)cc2)cc2c(NCC3CC3)ncnc12]<br>N-(Cyclopropylmethyl)-6-(4-fluorophenyl)-8-methoxyquinazolin-4-amine | $^1$H NMR (400 MHz, DMSO): δ 8.43 (s, 2 H), 8.11 (d, J = 1.6 Hz, 1 H), 7.95-7.90 (m, 2 H), 7.50 (d, J = 1.5 Hz, 1 H), 7.39 (dd, J = 8.9, 8.9 Hz, 2 H), 4.01 (s, 3 H), 3.44 (dd, J = 6.1, 6.1 Hz, 2H), 1.27-1.18 (m, 1 H), 0.53-0.47 (m, 2 H), 0.34-0.29 (m, 2 H). LCMS (Method 4): [MH+] = 324 at 3.57 min. |

-continued

| Example No. | Chemical Name<br>Structure | Analytical Data<br>$^1$H NMR<br>LC-MS |
|---|---|---|
| Example 18 | 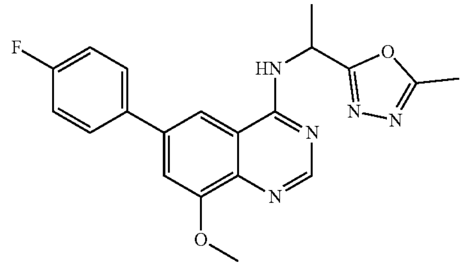 [SMILES: COc1cc(-c2ccc(F)cc2)cc2c(NC(C)c3nnc(C)o3)ncnc12]<br>6-(4-Fluorophenyl)-8-methoxy-N-(1-(5-methyl-1,3,4-oxadiazol-2-yl)ethyl)quinazolin-4-amine | $^1$H NMR (400 MHz, DMSO): δ 9.33-9.33 (m, 1 H), 8.61 (s, 1 H), 8.24 (s, 1 H), 7.95 (ddd, J = 3.2, 5.3, 12.1 Hz, 2 H), 7.69 (s, 1 H), 7.41 (dd, J = 8.8, 8.8 Hz, 2 H), 5.99-5.91 (m, 1 H), 4.09 (s, 3 H), 1.75 (d, J = 7.0 Hz, 3 H). LCMS (Method 4): [MH+] = 380 at 3.08 min. |
| Example 19 | 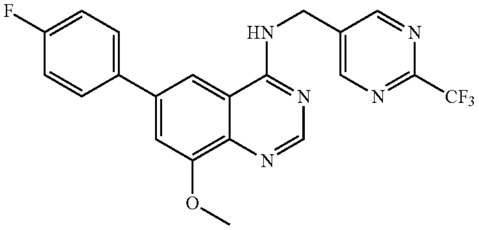<br>6-(4-Fluorophenyl)-8-methoxy-N-((2-(trifluoromethyl)pyrimidin-5-yl)methyl)quinazolin-4-amine | $^1$H NMR (400 MHz, DMSO): δ 9.12 (s, 2 H), 8.96 (dd, J = 5.6, 5.6 Hz, 1 H), 8.47 (s, 1 H), 8.10 (d, J = 1.6 Hz, 1 H), 7.92 (ddd, J = 3.2, 5.3, 12.1 Hz, 2 H), 7.54 (d, J = 1.6 Hz, 1 H), 7.39 (dd, J = 8.9, 8.9 Hz, 2 H), 4.91 (d, J = 5.4 Hz, 2 H), 4.03 (s, 3 H). LCMS (Method 4): [MH+] = 430 at 4.71 min. |
| Example 20 | 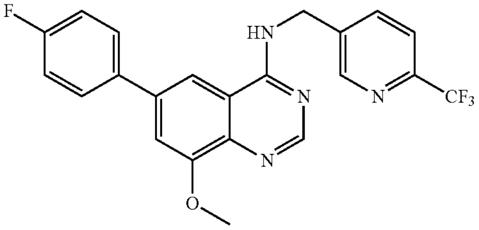<br>6-(4-Fluorophenyl)-8-methoxy-N-((6-(trifluoromethyl)pyridin-3-yl)methyl)quinazolin-4-amine | $^1$H NMR (400 MHz, DMSO): δ 8.97 (dd, J = 5.8, 5.8 Hz, 1 H), 8.84 (d, J = 1.5 Hz, 1 H), 8.45 (s, 1 H), 8.13 (d, J = 1.8 Hz, 1H), 8.06 (dd, J = 1.5, 8.0 Hz, 1 H), 7.95-7.87 (m, 3 H), 7.54 (d, J = 1.6 Hz, 1 H), 7.39 (dd, J = 8.9, 8.9 Hz, 2 H), 4.92 (d, J = 5.5 Hz, 2 H), 4.03 (s, 3 H). LCMS (Method 3): [MH+] = 429 at 4.62 min. |
| Example 21 | 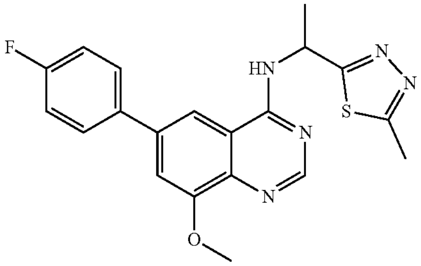 [SMILES: COc1cc(-c2ccc(F)cc2)cc2c(NC(C)c3nnc(C)s3)ncnc12]<br>6-(4-Fluorophenyl)-8-methoxy-N-(1-(5-methyl-1,3,4-thiadiazol-2-yl)ethyl)quinazolin-4-amine | $^1$H NMR (400 MHz, DMSO): δ 8.81 (d, J = 7.7 Hz, 1 H), 8.50 (s, 1 H), 8.20 (d, J = 1.6 Hz, 1 H), 7.94 (ddd, J = 3.2, 5.4, 12.1 Hz, 2 H), 7.56 (d, J = 1.6 Hz, 1 H), 7.39 (dd, J = 8.9, 8.9 Hz, 2 H), 5.99-5.95 (m, 1 H), 4.03 (s, 3 H), 2.66 (s, 3 H), 1.81 (d, J = 7.2 Hz, 3 H). LCMS (Method 4): [MH+] = 396 at 3.13 min. |

-continued

| Example No. | Chemical Name<br>Structure | Analytical Data<br>$^1$H NMR<br>LC-MS |
|---|---|---|
| Example 22 | 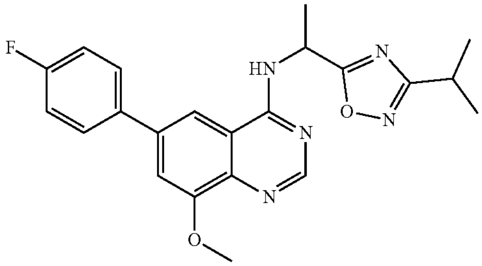<br>6-(4-Fluorophenyl)-N-(1-(3-isopropyl-1,2,4-oxadiazol-5-yl)ethyl)-8-methoxyquinazolin-4-amine | $^1$H NMR (400 MHz, DMSO): δ 8.81 (d, J = 7.3 Hz, 1H), 8.45 (s, 1 H), 8.20 (d, J = 1.8 Hz, 1 H), 7.97-7.93 (m, 2 H), 7.57 (d, J = 1.6 Hz, 1 H), 7.40 (dd, J = 8.8, 8.8 Hz, 2 H), 5.86-5.81 (m, 1 H), 4.04 (s, 3 H), 3.09-3.01 (m, 1 H), 1.74 (d, J = 7.2 Hz, 3 H), 1.25 (dd, J= 1.4, 6.9 Hz, 6 H). LCMS (Method 4): [MH+] = 408 at 3.67 min. |
| Example 23 | 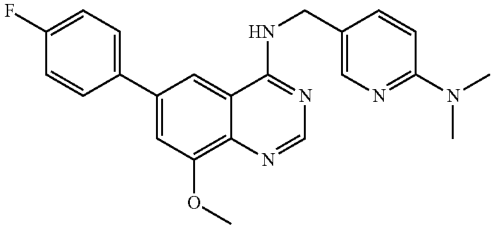 [SMILES: COc1cc(-c2ccc(F)cc2)cc2c(NCc3ccc(N(C)C)nc3)ncnc12]<br>N-((6-(Dimethylamino)pyridin-3-yl)methyl)-6-(4-fluorophenyl)-8-methoxyquinazolin-4-amine | $^1$H NMR (400 MHz, DMSO): δ 8.70 (dd, J = 5.6, 5.6 Hz, 1 H), 8.46 (s, 1 H), 8.16 (d, J = 2.0 Hz, 1 H), 8.10 (d, J = 1.8 Hz, 1 H), 7.94-7.89 (m, 2 H), 7.57 (dd, J = 2.4, 8.7 Hz, 1 H), 7.50 (d, J = 1.5 Hz, 1 H), 7.37 (dd, J = 8.9, 8.9 Hz, 2 H), 6.62 (d, J = 8.4 Hz, 1 H), 4.64 (d, J = 5.5 Hz, 2 H), 4.01 (s, 3 H), 2.99 (s, 6 H). LCMS (Method 4): [MH+] = 404 at 2.41 min. |
| Example 24 | 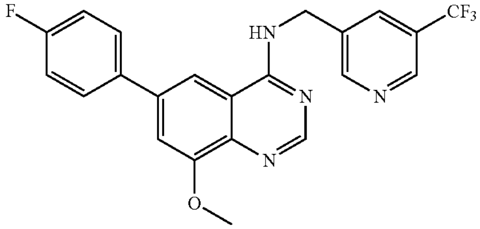 [SMILES: COc1cc(-c2ccc(F)cc2)cc2c(NCc3cncc(C(F)(F)F)c3)ncnc12]<br>6-(4-Fluorophenyl)-8-methoxy-N-[[5-(trifluoromethyl)-3-pyridyl]methyl]quinazolin-4-amine | $^1$H NMR (400 MHz, DMSO): δ 8.94 (dd, J = 2.2, 2.2 Hz, 2 H), 8.89 (d, J = 1.1 Hz, 1 H), 8.46 (s, 1 H), 8.21 (dd, J = 2.2, 2.2 Hz, 1 H), 8.11 (d, J = 1.6 Hz, 1 H), 7.95-7.90 (m, 2 H), 7.54 (d, J = 1.5 Hz, 1 H), 7.39 (dd, J = 8.9, 8.9 Hz, 2 H), 4.92 (d, J = 5.6 Hz, 2 H), 4.02 (s, 3 H). LCMS (Method 4): [MH+] = 429 at 3.55 min. |
| Example 25 | 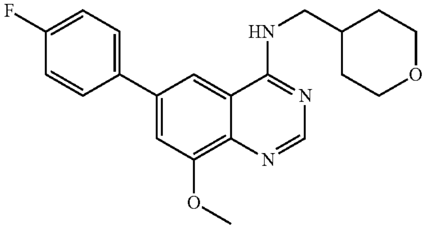 [SMILES: COc1cc(-c2ccc(F)cc2)cc2c(NCC3CCOCC3)ncnc12]<br>6-(4-Fluorophenyl)-8-methoxy-N-((tetrahydro-2H-pyran-4-yl)methyl)quinazolin-4-amine | $^1$H NMR (400 MHz, DMSO): δ 8.46 (s, 2 H), 8.12 (d, J = 1.6 Hz, 1 H), 7.94-7.90 (m, 2 H), 7.52 (d, J = 1.4 Hz, 1 H), 7.39 (dd, J = 8.9, 8.9 Hz, 2 H), 4.02 (s, 3 H), 3.87 (dd, J = 2.5, 11.4 Hz, 2 H), 3.48 (dd, J = 6.3, 6.3 Hz, 2 H), 3.28 (dt, J = 2.0, 11.8 Hz, 2 H), 2.05-1.96 (m, 1 H), 1.67 (dd, J = 1.8, 12.7 Hz, 2 H), 1.34-1.22 (m, 2 H). LCMS (Method 3): [MH+] = 368 at 4.04 min. |

-continued

| Example No. | Chemical Name<br>Structure | Analytical Data<br>$^1$H NMR<br>LC-MS |
|---|---|---|
| Example 26 | 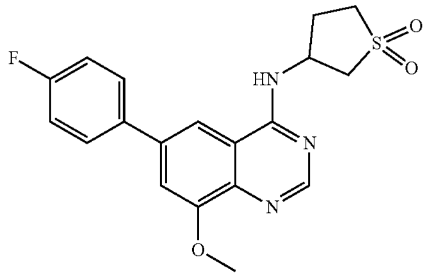 [SMILES: COc1cc(-c2ccc(F)cc2)cc2c(NC3CCS(=O)(=O)C3)ncnc12]<br>3-((6-(4-Fluorophenyl)-8-methoxyquinazolin-4-yl)amino)tetrahydrothiophene 1,1-dioxide | $^1$H NMR (400 MHz, DMSO): δ 8.53 (s, 1 H), 8.38 (d, J = 6.5 Hz, 1 H), 8.09 (d, J = 1.6 Hz, 1 H), 7.94-7.89 (m, 2 H), 7.54 (d, J = 1.6 Hz, 1 H), 7.40 (dd, J = 8.9, 8.9 Hz, 2 H), 5.10 (dd, J = 6.7, 15.6 Hz, 1 H), 4.03 (s, 3 H), 3.69 (dd, J = 8.2, 13.4 Hz, 1 H), 3.50-3.38 (m, 1 H), 3.31-3.23 (m, 1 H), 3.15 (dd, J = 8.1, 13.2 Hz, 1 H), 2.65-2.55 (m, 1 H), 2.41-2.30 (m, 1 H).<br>LCMS (Method 3): [MH+] = 388 at 3.77 min. |
| Example 27 | 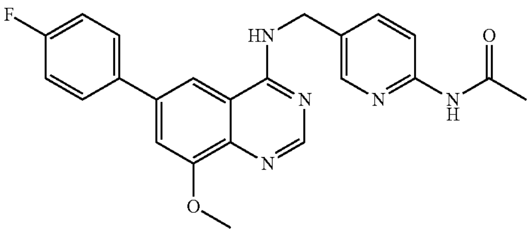 [SMILES: COc1cc(-c2ccc(F)cc2)cc2c(NCc3ccc(NC(C)=O)nc3)ncnc12]<br>N-(5-(((6-(4-Fluorophenyl)-8-methoxyquinazolin-4-yl)amino)methyl)pyridin-2-yl)acetamide | $^1$H NMR (400 MHz, DMSO): δ 10.47 (s, 1 H), 8.82 (dd, J = 5.7, 5.7 Hz, 1 H), 8.46 (s, 1 H), 8.35 (d, J = 1.9 Hz, 1 H), 8.12 (d, J = 1.5 Hz, 1 H), 8.04 (d, J = 8.5 Hz, 1 H), 7.94-7.90 (m, 2 H), 7.80 (dd, J = 2.3, 8.6 Hz, 1 H), 7.52 (d, J = 1.4 Hz, 1 H), 7.38 (dd, J = 8.9, 8.9 Hz, 2 H), 4.76 (d, J = 5.5 Hz, 2 H), 4.02 (s, 3 H), 2.08 (s, 3 H).<br>LCMS (Method 3): [MH+] = 418 at 3.76 min. |
| Example 28 | 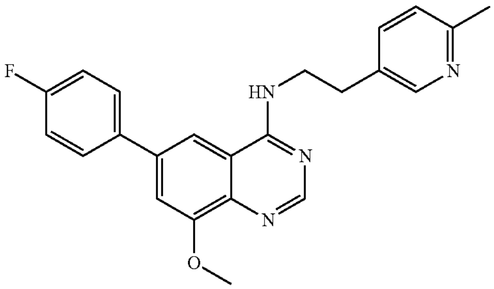 [SMILES: COc1cc(-c2ccc(F)cc2)cc2c(NCCc3ccc(C)nc3)ncnc12]<br>6-(4-Fluorophenyl)-8-methoxy-N-(2-(6-methylpyridin-3-yl)ethyl)quinazolin-4-amine | $^1$H NMR (400 MHz, DMSO): δ 8.47 (s, 1 H), 8.43 (dd, J = 5.5, 5.5 Hz, 1 H), 8.34 (d, J = 1.9 Hz, 1 H), 8.04 (d, J = 1.6 Hz, 1 H), 7.92-7.88 (m, 2 H), 7.57 (dd, J = 2.3, 7.8 Hz, 1 H), 7.51 (d, J = 1.5 Hz, 1 H), 7.39 (dd, J = 8.9, 8.9 Hz, 2 H), 7.18 (d, J = 7.8 Hz, 1 H), 4.02 (s, 3 H), 3.82-3.75 (m, 2 H), 2.97 (dd, J = 7.1, 7.1 Hz, 2 H), 2.42 (s, 3 H). LCMS (Method 4): [MH+] = 389 at 2.40 min. |
| Example 29 | 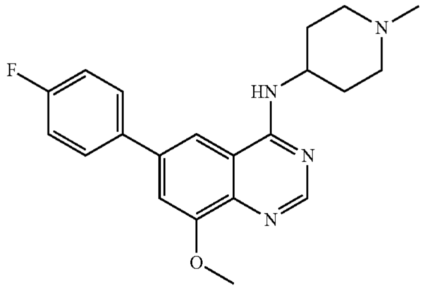 [SMILES: COc1cc(-c2ccc(F)cc2)cc2c(NC3CCN(C)CC3)ncnc12]<br>6-(4-Fluorophenyl)-8-methoxy-N-(1-methylpiperidin-4-yl)quinazolin-4-amine | $^1$H NMR (400 MHz, DMSO): δ 8.43 (s, 1 H), 8.12 (d, J = 1.6 Hz, 1 H), 7.98-7.90 (m, 3 H), 7.49 (d, J = 1.5 Hz, 1 H), 7.38 (dd, J = 8.9, 8.9 Hz, 2 H), 4.22-4.13 (m, 1 H), 4.01 (s, 3 H), 2.85 (dd, J = 2.8, 8.8 Hz, 2 H), 2.21 (s, 3 H), 2.03-1.89 (m, 4 H), 1.74-1.62 (m, 2 H). LCMS (Method 4): [MH+] = 367 at 2.20 min. |

-continued

| Example No. | Chemical Name<br>Structure | Analytical Data<br>$^1$H NMR<br>LC-MS |
|---|---|---|
| Example 30 | 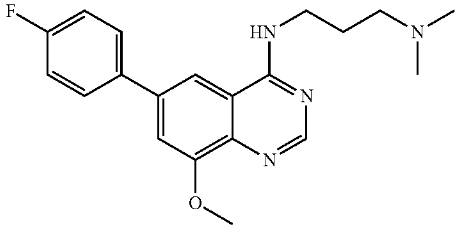 [SMILES: COc1cc(-c2ccc(F)cc2)cc2c(NCCCN(C)C)ncnc12]<br>N[1]-(6-(4-Fluorophenyl)-8-methoxyquinazolin-4-yl)-N[3],N[3]-dimethylpropane-1,3-diamine | $^1$H NMR (400 MHz, DMSO): δ 8.43 (s, 1 H), 8.37 (dd, J = 5.4, 5.4 Hz, 1 H), 8.03 (d, J = 1.6 Hz, 1 H), 7.93-7.89 (m, 2 H), 7.49 (d, J = 1.6 Hz, 1 H), 7.39 (dd, J = 8.9, 8.9 Hz, 2 H), 4.01 (s, 3 H), 3.57 (dd, J = 6.6, 13.1 Hz, 2 H), 2.33 (dd, J = 7.0, 7.0 Hz, 2 H), 2.17 (s, 6 H), 1.85-1.76 (m, 2 H). LCMS (Method 4): [MH+] = 355 at 2.19 min. |
| Example 31 | 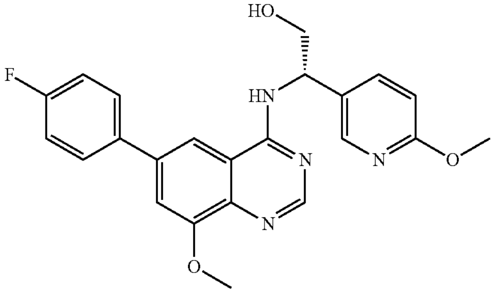 [SMILES: COc1ccc([C@@H](CO)Nc2ncnc3c(OC)cc(-c4ccc(F)cc4)cc23)cn1]<br>(S)-2-((6-(4-Fluorophenyl)-8-methoxyquinazolin-4-yl)amino)-2-(6-methoxypyridin-3-yl)ethan-1-ol | $^1$H NMR (400 MHz, DMSO): δ 8.50 (d, J = 7.5 Hz, 1 H), 8.43 (s, 1 H), 8.25 (dd, J = 1.9, 9.0 Hz, 2 H), 7.97-7.93 (m, 2 H), 7.81 (dd, J = 2.5, 8.7 Hz, 1 H), 7.53 (d, J= 1.4 Hz, 1 H), 7.41 (dd, J = 8.8, 8.8 Hz, 2 H), 6.80 (d, J = 8.5 Hz, 1 H), 5.57-5.49 (m, 1 H), 5.11 (dd, J = 5.5, 5.5 Hz, 1 H), 4.02 (s, 3 H), 3.93-3.87 (m, 1 H), 3.82 (s, 3 H), 3.81-3.75 (m, 1 H). LCMS (Method 3): [MH+] = 421 at 4.15 min. |
| Example 32 | 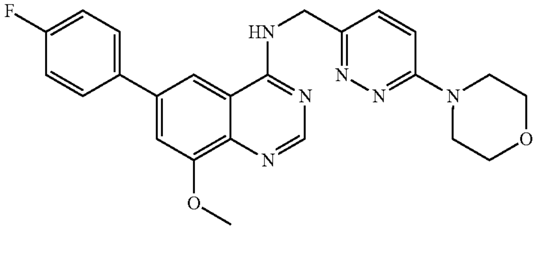 [SMILES: COc1cc(-c2ccc(F)cc2)cc2c(NCc3ccc(N4CCOCC4)nn3)ncnc12]<br>6-(4-Fluorophenyl)-8-methoxy-N-((6-morpholinopyridazin-3-yl)methyl)quinazolin-4-amine | $^1$H NMR (400 MHz, DMSO): δ 8.95-8.94 (m, 1 H), 8.38 (s, 1 H), 8.10-8.06 (m, 2 H), 7.88-7.83 (m, 2 H), 7.47 (d, J = 1.4 Hz, 1 H), 7.37 (d, J = 9.4 Hz, 1 H), 7.30 (dd, J = 8.9, 8.9 Hz, 2 H), 7.17 (d, J = 9.4 Hz, 1 H), 4.85 (d, J = 5.6 Hz, 2 H), 3.95 (s, 3 H), 3.66-3.63 (m, 4 H), 3.45-3.42 (m, 4 H). LCMS (Method 3): [MH+] = 447 at 4.05 min. |
| Example 33 | 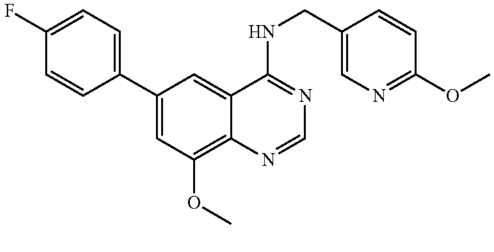<br>6-(4-Fluorophenyl)-8-methoxy-N-((6-methoxypyridin-3-yl)methyl)quinazolin-4-amine | $^1$H NMR (400 MHz, DMSO): δ 8.83 (dd, J = 5.4, 5.4 Hz, 1 H), 8.50 (s, 1 H), 8.27 (d, J = 1.5 Hz, 1 H), 8.14 (s, 1H), 7.95 (dd, J = 5.3, 8.6 Hz, 2 H), 7.79 (dd, J = 2.1, 8.5 Hz, 1H), 7.55 (s, 1H), 7.41 (dd, J = 8.8, 8.8 Hz, 2 H), 6.84 (d, J = 8.6 Hz, 1 H), 4.77 (d, J = 5.6 Hz, 2 H), 4.06 (s, 3 H), 3.87 (s, 3 H). LCMS (Method 4): [MH+] = 398 at 3.38 min. |

-continued

| Example No. | Chemical Name<br>Structure | Analytical Data<br>$^1H$ NMR<br>LC-MS |
|---|---|---|
| Example 34 | 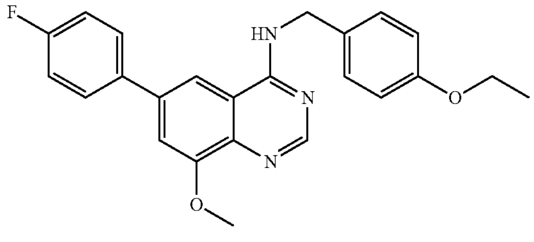 [SMILES: CCOc1ccc(CNc2ncnc3c(OC)cc(-c4ccc(F)cc4)cc23)cc1]<br>N-(4-ethoxybenzyl)-6-(4-fluorophenyl)-8-methoxyquinazolin-4-amine | $^1H$ NMR (400 MHz, DMSO): δ 8.80 (dd, J = 5.9, 5.9 Hz, 1 H), 8.44 (s, 1 H), 8.22 (s, 1 H), 8.14 (d, J = 1.6 Hz, 1 H), 7.92 (ddd, J = 3.2, 5.4, 12.1 Hz, 2 H), 7.52 (d, J = 1.5 Hz, 1 H), 7.37 (dd, J = 8.8, 8.8 Hz, 2 H), 7.31 (d, J = 8.8 Hz, 2 H), 6.88 (d, J = 8.7 Hz, 2 H), 4.74 (d, J = 5.6 Hz, 2 H), 4.02-3.98 (m, 6 H), 1.31 (dd, J = 7.0, 7.0 Hz, 3 H). LCMS (Method 3): [MH+] = 404 at 5.1 min. |
| Example 35 | 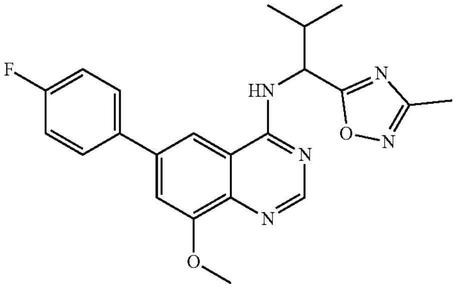 [SMILES: COc1cc(-c2ccc(F)cc2)cc2c(NC(c3nc(C)no3)C(C)C)ncnc12]<br>6-(4-Fluorophenyl)-8-methoxy-N-(2-methyl-1-(3-methyl-1,2,4-oxadiazol-5-yl)propyl)quinazolin-4-amine | $^1H$ NMR (400 MHz, DMSO): δ 8.68 (d, J = 7.9 Hz, 1 H), 8.44 (s, 1 H), 8.31 (d, J = 1.6 Hz, 1H), 7.99-7.94 (m, 2 H), 7.56 (d, J = 1.5 Hz, 1 H), 7.41 (dd, J = 8.9, 8.9 Hz, 2 H), 5.53 (dd, J = 8.5, 8.5 Hz, 1 H), 4.02 (s, 3 H), 2.34 (s, 3 H), 1.13 (d, J = 6.7 Hz, 3 H), 0.95 (d, J = 6.8 Hz, 3 H). LCMS (Method 3): [MH+] = 408 at 4.74 min. |
| Example 36 | 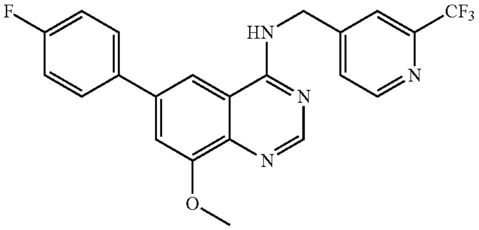 [SMILES: COc1cc(-c2ccc(F)cc2)cc2c(NCc3ccnc(C(F)(F)F)c3)ncnc12]<br>6-(4-Fluorophenyl)-8-methoxy-N-[[2-(trifluoromethyl)-4-pyridyl]methyl]quinazolin-4-amine | $^1H$ NMR (400 MHz, DMSO): δ 9.00 (dd, J = 5.8, 5.8 Hz, 1 H), 8.70 (d, J = 5.0 Hz, 1 H), 8.42 (s, 1 H), 8.16 (d, J = 1.6 Hz, 1 H), 7.97-7.90 (m, 3 H), 7.69 (d, J = 5.0 Hz, 1 H), 7.56 (d, J = 1.5 Hz, 1 H), 7.40 (dd, J = 8.9, 8.9 Hz, 2 H), 4.94 (d, J = 5.8 Hz, 2 H), 4.03 (s, 3 H). LCMS (Method 4): [MH+] = 429 at 3 .57 min. |
| Example 38 | 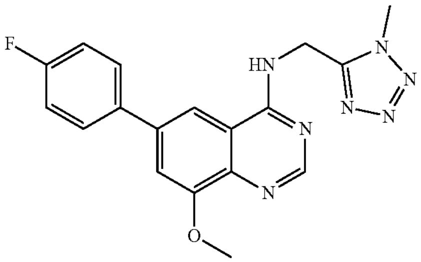 [SMILES: COc1cc(-c2ccc(F)cc2)cc2c(NCc3nnnn3C)ncnc12]<br>6-(4-Fluorophenyl)-8-methoxy-N-((1-methyl-1H-tetrazol-5-yl)methyl)quinazolin-4-amine | $^1H$ NMR (400 MHz, DMSO): δ 9.17-9.16 (m, 1 H), 8.49 (s, 1 H), 8.15 (d, J = 1.6 Hz, 1 H), 7.96-7.91 (m, 2 H), 7.58 (d, J = 1.3 Hz, 1 H), 7.40 (dd, J = 8.9, 8.9 Hz, 2 H), 5.05 (d, J = 5.4 Hz, 2 H), 4.19 (s, 3 H), 4.04 (s, 3 H). LCMS (Method 4): [MH+] = 366 at 2.86 min. |

-continued

| Example No. | Chemical Name<br>Structure | Analytical Data<br>$^1$H NMR<br>LC-MS |
|---|---|---|
| Example 39 | 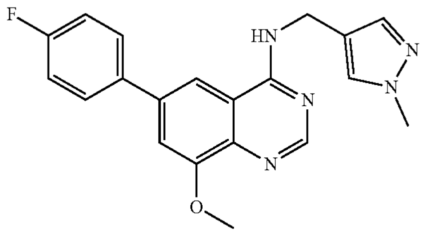 [SMILES: COc1cc(-c2ccc(F)cc2)cc2c(NCc3cnn(C)c3)ncnc12]<br>6-(4-Fluorophenyl)-8-methoxy-N-((1-methyl-1H-pyrazol-4-yl)methyl)quinazolin-4-amine | $^1$H NMR (400 MHz, DMSO): δ 8.61 (dd, J = 5.5, 5.5 Hz, 1 H), 8.48 (s, 1 H), 8.10 (d, J = 1.8 Hz, 1 H), 7.94-7.89 (m, 2 H), 7.68 (s, 1 H), 7.50 (d, J = 1.6 Hz, 1 H), 7.44 (s, 1 H), 7.37 (dd, J = 8.9, 8.9 Hz, 2 H), 4.60 (d, J = 5.5 Hz, 2 H), 4.01 (s, 3 H), 3.38-3.34 (m, 3 H).<br>LCMS (Method 4): [MH+] = 364 at 3.02 min. |
| Example 41 | 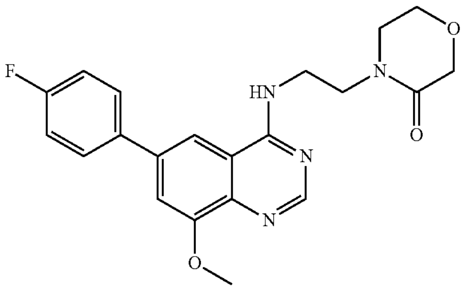 [SMILES: COc1cc(-c2ccc(F)cc2)cc2c(NCCN3CCOCC3=O)ncnc12]<br>4-(2-((6-(4-Fluorophenyl)-8-methoxyquinazolin-4-yl)amino)ethyl)morpholin-3-one | $^1$H NMR (400 MHz, DMSO): δ 8.46 (s, 1 H), 8.03 (d, J = 1.6 Hz, 1 H), 7.91 (ddd, J = 3.2, 5.3, 12.1 Hz, 2 H), 7.51 (d, J = 1.5 Hz, 1 H), 7.39 (dd, J = 8.9, 8.9 Hz, 2 H), 4.01 (d, J = 7.5 Hz, 2 H), 3.81-3.72 (m, 4 H), 3.62 (dd, J = 6.2, 6.2 Hz, 2 H), 3.42 (dd, J = 5.1, 5.1 Hz, 2 H). LCMS (Method 4): [MH+] = 397 at 2.87 |
| Example 42 | 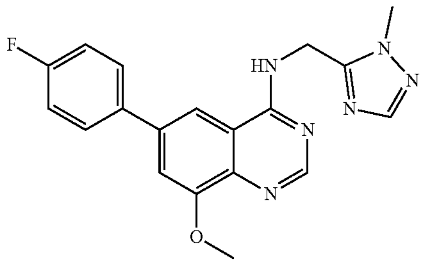 [SMILES: COc1cc(-c2ccc(F)cc2)cc2c(NCc3ncnn3C)ncnc12]<br>6-(4-Fluorophenyl)-8-methoxy-N-((1-methyl-1H-1,2,4-triazol-5-yl)methyl)quinazolin-4-amine | $^1$H NMR (400 MHz, DMSO): δ 9.23-9.23 (m, 1 H), 8.53 (s, 1 H), 8.19 (d, J = 1.6 Hz, 1 H), 7.96-7.91 (m, 2 H), 7.85 (s, 1 H), 7.60 (d, J = 1.3 Hz, 1 H), 7.40 (dd, J = 8.9, 8.9 Hz, 2 H), 4.93 (d, J = 5.4 Hz, 2 H), 4.05 (s, 3 H), 3.98 (s, 3 H). LCMS (Method 3): [MH+] = 365 at 3.77 min. |
| Example 43 | 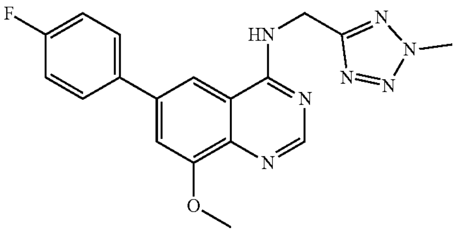 [SMILES: COc1cc(-c2ccc(F)cc2)cc2c(NCc3nnn(C)n3)ncnc12]<br>6-(4-Fluorophenyl)-8-methoxy-N-((2-methyl-2H-tetrazol-5-yl)methyl)quinazolin-4-amine | $^1$H NMR (400 MHz, DMSO): δ 8.99 (dd, J = 5.6, 5.6 Hz, 1 H), 8.44 (s, 1 H), 8.17-8.15 (m, 2 H), 7.96-7.91 (m, 2 H), 7.55 (d, J = 1.5 Hz, 1 H), 7.39 (dd, J = 8.8, 8.8 Hz, 2 H), 5.03 (d, J = 5.6 Hz, 2 H), 4.33 (s, 3 H), 4.03 (s, 3 H) LCMS (Method 4): [MH+] = 366 at 4.01 min. |

-continued

| Example No. | Chemical Name<br>Structure | Analytical Data<br>$^1$H NMR<br>LC-MS |
|---|---|---|
| Example 44 | 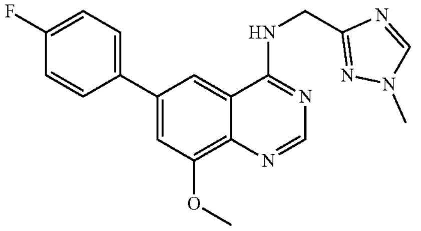 [SMILES: COc1cc(-c2ccc(F)cc2)cc2c(NCc3ncn(C)n3)ncnc12]<br>6-(4-Fluorophenyl)-8-methoxy-N-((1-methyl-1H-1,2,4-triazol-3-yl)methyl)quinazolin-4-amine | $^1$H NMR (400 MHz, DMSO): δ 8.81 (dd, J = 5.6, 5.6 Hz, 1 H), 8.43 (s, 1H), 8.38 (s, 1H), 8.18 (d, J = 1.6 Hz, 1 H), 7.94 (ddd, J = 3.2, 5.4, 12.1 Hz, 2 H), 7.53 (d, J = 1.5 Hz, 1 H), 7.38 (dd, J = 8.9, 8.9 Hz, 2 H), 4.81 (d, J = 5.8 Hz, 2 H), 4.02 (s, 3 H), 3.82 (s, 3 H).<br>LCMS (Method 3): [MH+] = 365 at 3.65 min. |
| Example 45 | 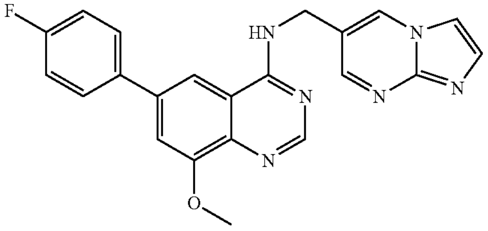 [SMILES: COc1cc(-c2ccc(F)cc2)cc2c(NCc3cnc4nccn4c3)ncnc12]<br>6-(4-Fluorophenyl)-N-(imidazo[1,2-a]pyrimidin-6-ylmethyl)-8-methoxyquinazolin-4-amine | $^1$H NMR (400 MHz, DMSO): δ 9.02 (d, J = 2.0 Hz, 1 H), 8.90 (dd, J = 5.1, 5.1Hz, 1H), 8.70 (d, J = 2.3 Hz, 1H), 8.53 (s, 1 H), 8.14 (s, 1 H), 7.99-7.92 (m, 3 H), 7.75 (d, J = 1.0 Hz, 1 H), 7.57 (s, 1 H), 7.42 (dd, J = 8.8, 8.8 Hz, 2 H), 4.89 (d, J = 5.1 Hz, 2 H), 4.06 (s, 3 H).<br>LCMS (Method 4): [MH+] = 401 at 3.51 min. |
| Example 46 | 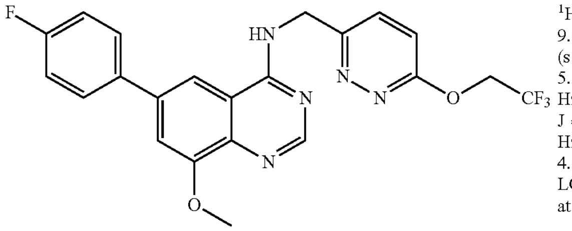<br>6-(4-Fluorophenyl)-8-methoxy-N-((6-(2,2,2-trifluoroethoxy)pyridazin-3-yl)methyl)quinazolin-4-amine | $^1$H NMR (400 MHz, DMSO): δ 9.06 (dd, J = 5.6, 5.6 Hz, 1 H), 8.47 (s, 1 H), 8.20 (s, 1 H), 7.97 (dd, J = 5.3, 8.6 Hz, 2 H), 7.78 (d, J = 9.1 Hz, 1 H), 7.58 (s, 1 H), 7.42 (dd, J = 8.7, 8.7 Hz, 3 H), 5.22 (q, J = 8.9 Hz, 2 H), 5.05 (d, J = 5.6 Hz, 2 H), 4.07 (s, 3 H).<br>LCMS (Method 4): [MH+] = 460 at 3.66 min. |
| Example 47 | 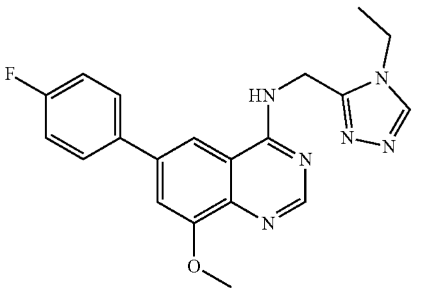 [SMILES: CCn1cnnc1CNc1ncnc2c(OC)cc(-c3ccc(F)cc3)cc12]<br>N-((4-Ethyl-4H-1,2,4-triazol-3-yl)methyl)-6-(4-fluorophenyl)-8-methoxyquinazolin-4-amine | $^1$H NMR (400 MHz, DMSO): δ 8.90 (dd, J = 4.7, 4.7 Hz, 1 H), 8.58 (s, 1 H), 8.53 (s, 1 H), 8.21 (d, J = 7.3 Hz, 1H), 7.96 (dd, J = 5.4, 8.7 Hz, 2 H), 7.58 (s, 1 H), 7.41 (dd, J = 8.7, 8.7 Hz, 2 H), 5.00 (d, J = 5.1 Hz, 2 H), 4.15 (q, J = 7.2 Hz, 2 H), 4.06 (s, 3 H), 1.34 (dd, J = 7.2, 7.2 Hz, 3 H).<br>LCMS (Method 3): [MH+] = 379 at 3.42 min. |

-continued

| Example No. | Chemical Name<br>Structure | Analytical Data<br>$^1$H NMR<br>LC-MS |
|---|---|---|
| Example 48 | 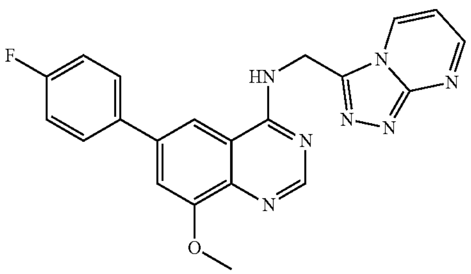 [SMILES: COc1cc(-c2ccc(F)cc2)cc2c(NCc3nnc4ncccn34)ncnc12]<br>N-([1,2,4]Triazolo[4,3-a]pyrimidin-3-ylmethyl)-6-(4-fluorophenyl)-8-methoxyquinazolin-4-amine | $^1$H NMR (400 MHz, DMSO): δ 9.40 (dd, J = 1.5, 6.6 Hz, 1 H), 9.07 (dd, J = 5.3, 5.3 Hz, 1 H), 8.91-8.88 (m, 1 H), 8.46 (s, 1 H), 8.26 (s, 1 H), 7.99 (dd, J = 5.7, 8.5 Hz, 2 H), 7.59 (s, 1 H), 7.46-7.36 (m, 3 H), 5.11 (d, J = 5.3 Hz, 2 H), 4.07 (s, 3 H). LCMS (Method 3): [MH+] = 402 at 3.46 min. |
| Example 49 | 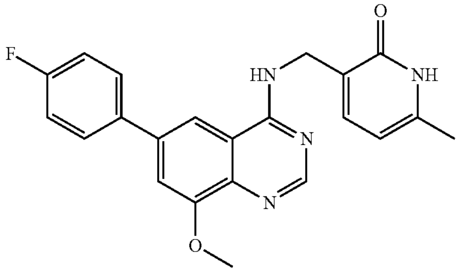 [SMILES: COc1cc(-c2ccc(F)cc2)cc2c(NCc3ccc(C)[nH]c3=O)ncnc12]<br>3-(((6-(4-Fluorophenyl)-8-methoxyquinazolin-4-yl)amino)methyl)-6-methylpyridin-2(1H)-one | $^1$H NMR (400 MHz, DMSO): δ 11.71-11.68 (m, 1 H), 8.66 (dd, J = 5.4, 5.4 Hz, 1 H), 8.45 (s, 1 H), 8.21 (s, 1 H), 7.98 (dd, J = 5.4, 8.7 Hz, 2 H), 7.56 (s, 1 H), 7.42 (dd, J = 8.8, 8.8 Hz, 2 H), 7.25 (d, J = 6.8 Hz, 1 H), 5.98 (d, J = 7.1 Hz, 1 H), 4.55 (d, J = 5.1 Hz, 2 H), 4.06 (s, 3 H), 2.20 (s, 3 H).<br>LCMS (Method 3): [MH+] = 391 at 3.88 min. |
| Example 50 | 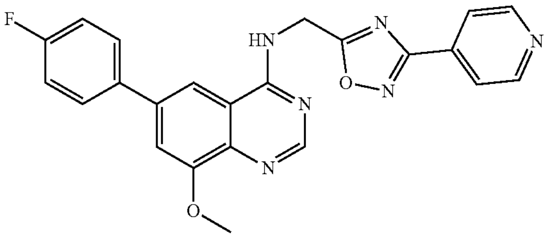 [SMILES: COc1cc(-c2ccc(F)cc2)cc2c(NCc3nc(-c4ccncc4)no3)ncnc12]<br>6-(4-Fluorophenyl)-8-methoxy-N-((3-(pyridin-4-yl)-1,2,4-oxadiazol-5-yl)methyl)quinazolin-4-amine | $^1$H NMR (400 MHz, DMSO): δ 9.28 (dd, J = 4.9, 4.9 Hz, 1 H), 8.83 (d, J = 5.8 Hz, 2 H), 8.48 (s, 1 H), 8.22 (s, 1 H), 8.20 (s, 1 H), 8.03-7.95 (m, 4 H), 7.62 (s, 1 H), 7.45 (dd, J = 8.8, 8.8 Hz, 2 H), 5.19 (d, J = 5.1 Hz, 2 H), 4.08 (s, 3 H).<br>LCMS (Method 3): [MH+] = 429 at 4.31 min. |
| Example 51 | 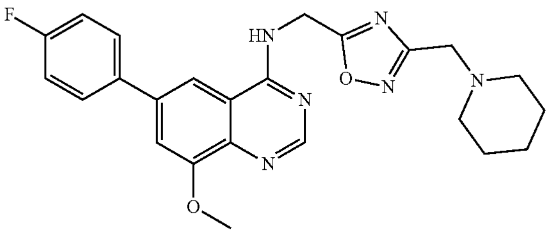 [SMILES: COc1cc(-c2ccc(F)cc2)cc2c(NCc3nc(CN4CCCCC4)no3)ncnc12]<br>6-(4-Fluorophenyl)-8-methoxy-N-((3-(piperidin-1-ylmethyl)-1,2,4-oxadiazol-5-yl)methyl)quinazolin-4-amine | $^1$H NMR (400 MHz, DMSO): δ 9.16 (dd, J = 5.4, 5.4 Hz, 1 H), 8.46 (s, 1 H), 8.19 (s, 1 H), 7.98 (dd, J = 5.6, 8.6 Hz, 2 H), 7.61 (s, 1 H), 7.44 (dd, J = 8.7, 8.7 Hz, 2 H), 5.07 (d, J = 5.6 Hz, 2 H), 4.07 (s, 3 H), 3.60 (s, 2 H), 2.42 (dd, J = 4.9, 4.9 Hz, 4 H), 1.54-1.45 (m, 4 H), 1.38 (d, J = 4.8 Hz, 2 H).<br>LCMS (Method 3): [MH+] = 449 at 4.57 min. |

-continued

| Example No. | Chemical Name<br>Structure | Analytical Data<br>$^1$H NMR<br>LC-MS |
|---|---|---|
| Example 52 | 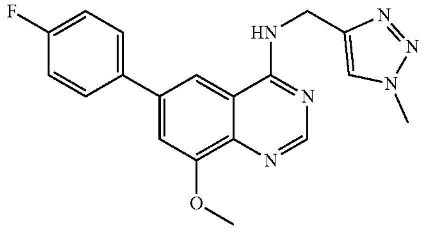 [SMILES: COc1cc(-c2ccc(F)cc2)cc2c(NCc3cn(C)nn3)ncnc12]<br>6-(4-Fluorophenyl)-8-methoxy-N-((1-methyl-1H-1,2,3-triazol-4-yl)methyl)quinazolin-4-amine | $^1$H NMR (400 MHz, DMSO): δ 8.81 (dd, J = 5.6, 5.6 Hz, 1 H), 8.47 (s, 1H), 8.11 (d, J = 1.6 Hz, 1 H), 7.97 (s, 1 H), 7.91 (ddd, J = 3.2, 12.1 Hz, 2 H), 7.51 (d, J = 1.6 Hz, 1 H), 7.36 (dd, J = 8.9, 8.9 Hz, 2 H), 4.79 (d, J = 5.5 Hz, 2 H), 4.00 (s, 3 H), 3.99 (s, 3 H).<br>LCMS (Method 4): [MH+] = 365 at 2.89 min. |
| Example 53 | 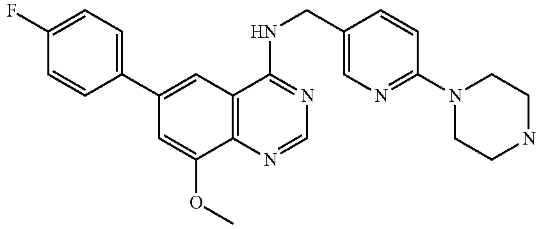<br>6-(4-Fluorophenyl)-8-methoxy-N-((6-(4-methylpiperazin-1-yl)pyridin-3-yl)methyl)quinazolin-4-amine | 1H NMR (400 MHz, DMSO): δ 8.73 (dd, J = 5.6, 5.6 Hz, 1 H), 8.46 (s, 1 H), 8.26 (s, 1 H), 8.19 (d, J = 2.1 Hz, 1 H), 8.10 (d, J = 1.6 Hz, 1 H), 7.94-7.89 (m, 2 H), 7.59 (dd, J = 2.4, 8.7 Hz, 1 H), 7.51 (d, J = 1.6 Hz, 1 H), 7.37 (dd, J = 8.9, 8.9 Hz, 2 H), 6.81 (d, J = 8.7 Hz, 1 H), 4.65 (d, J = 5.5 Hz, 2 H), 4.01 (s, 3 H), 2.38 (dd, J = 5.0, 5.0 Hz, 4 H), 2.21 (s, 3 H), 1.07 (d, J = 6.7 Hz, 3 H).<br>LCMS (Method 4): [MH+] = 458.5 at 2.40 min. |
| Example 54 | 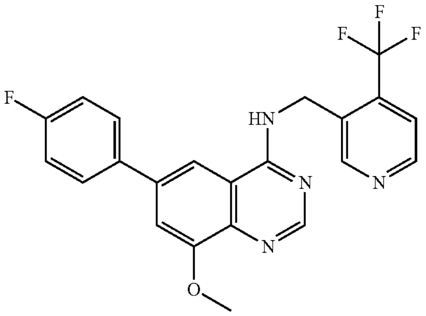 [SMILES: COc1cc(-c2ccc(F)cc2)cc2c(NCc3cnccc3C(F)(F)F)ncnc12]<br>6-(4-Fluorophenyl)-8-methoxy-N-((4-(trifluoromethyl)pyridin-3-yl)methyl)quinazolin-4-amine | $^1$H NMR (400 MHz, DMSO): δ 8.80-8.75 (m, 2 H), 8.42 (s, 1 H), 8.13 (d, J = 8.5 Hz, 2 H), 7.90 (dd, J = 5.5, 8.4 Hz, 2H), 7.77 (d, J = 5.1 Hz, 1 H), 7.53 (s, 1 H), 7.36 (dd, J = 8.8, 8.8 Hz, 2 H), 4.99 (s, 2 H), 4.01 (s, 3 H). LCMS (Method 4): [MH+] = 428.4 at 3.50 min. |
| Example 55 | 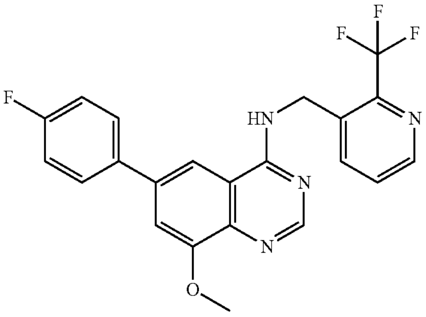 [SMILES: COc1cc(-c2ccc(F)cc2)cc2c(NCc3cccnc3C(F)(F)F)ncnc12]<br>6-(4-Fluorophenyl)-8-methoxy-N-((2-(trifluoromethyl)pyridin-3-yl)methyl)quinazolin-4-amine | $^1$H NMR (400 MHz, DMSO): δ 9.28-9.28 (m, 1 H), 8.66 (d, J = 4.4 Hz, 1 H), 8.50 (s, 1 H), 8.22 (d, J = 1.5 Hz, 1 H), 8.01 (d, J = 8.0 Hz, 1 H), 7.97-7.93 (m, 2 H), 7.70-7.63 (m, 2 H), 7.41 (dd, J = 8.8, 8.8 Hz, 2 H), 5.04 (d, J = 4.8 Hz, 2 H), 4.07 (s, 3 H). LCMS (Method 3): [MH+] = 429.2 at 4.76 min. |

-continued

| Example No. | Chemical Name<br>Structure | Analytical Data<br>$^1$H NMR<br>LC-MS |
|---|---|---|
| Example 56 | 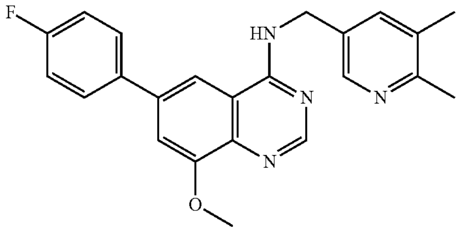 [SMILES: COc1cc(-c2ccc(F)cc2)cc2c(NCc3cnc(C)c(C)c3)ncnc12]<br>N-((5,6-Dimethylpyridin-3-yl)methyl)-6-(4-fluorophenyl)-8-methoxyquinazolin-4-amine | $^1$H NMR (400 MHz, DMSO): δ 8.99 (s, 1 H), 8.48 (s, 1 H), 8.33 (d, J = 1.9 Hz, 1 H), 8.14 (d, J = 1.6 Hz, 1 H), 7.93 (ddd, J = 3.2, 5.4, 12.1 Hz, 2 H), 7.55 (dd, J = 1.5, 8.8 Hz, 2 H), 7.38 (dd, J = 8.9, 8.9 Hz, 2 H), 4.77 (d, J = 5.5 Hz, 2 H), 4.03 (s, 3 H), 2.40 (s, 3 H), 2.23 (s, 3 H). LCMS (Method 4): [MH+] = 389.3 at 2.46 min. |
| Example 57 | 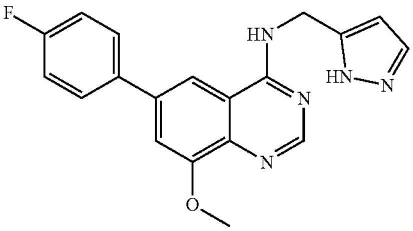 [SMILES: COc1cc(-c2ccc(F)cc2)cc2c(NCc3ccn[nH]3)ncnc12] | $^1$H NMR (400 MHz, DMSO): δ 8.74 (dd, J = 5.6, 5.6 Hz, 1 H), 8.47 (s, 1H), 8.15 (d, J = 1.6 Hz, 1 H), 7.95-7.91 (m, 2 H), 7.58 (s, 1 H), 7.52 (d, J = 1.6 Hz, 1 H), 7.37 (dd, J = 8.9, 8.9 Hz, 2 H), 6.22 (d, J = 2.1 Hz, 1 H), 4.79 (d, J = 5.5 Hz, 2 H), 4.02 (s, 3 H). LCMS (Method 4): [MH+] = 350 at 2.96 min. |
| Example 58 | 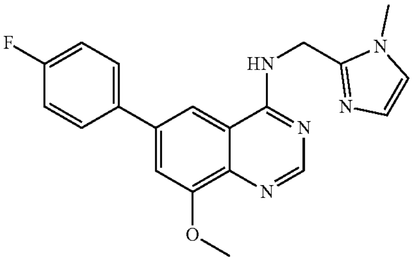 [SMILES: COc1cc(-c2ccc(F)cc2)cc2c(NCc3nccn3C)ncnc12]<br>6-(4-Fluorophenyl)-8-methoxy-N-[(1-methylimidazol-2-yl)methyl]quinazolin-4-amine | $^1$H NMR (400 MHz, DMSO): δ 8.75 (dd, J = 5.1, 5.1 Hz, 1 H), 8.48 (s, 1 H), 8.20-8.17 (m, 1 H), 7.95-7.90 (m, 2 H), 7.53 (d, J = 1.6 Hz, 1 H), 7.37 (dd, J = 8.9, 8.9 Hz, 2 H), 7.12 (s, 2 H), 6.83 (s, 1 H), 4.82 (d, J = 5.1 Hz, 2 H), 4.02 (s, 3 H), 3.71 (s, 3 H). LCMS (Method 4): [MH+] = 364 at 2.23 min. |
| Example 59 | 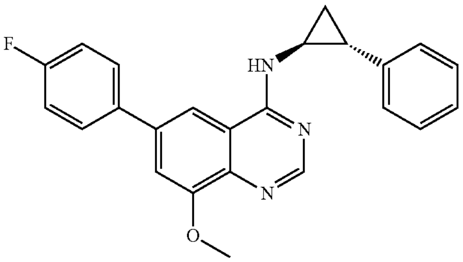 [SMILES: COc1cc(-c2ccc(F)cc2)cc2c(N[C@H]3C[C@@H]3c3ccccc3)ncnc12]<br>6-(4-Fluorophenyl)-8-methoxy-N-(2-phenylcyclopropyl)quinazolin-4-amine | $^1$H NMR (400 MHz, DMSO): δ 8.50-8.47 (m, 2 H), 8.09 (d, J = 1.8 Hz, 1 H), 7.95-7.90 (m, 2 H), 7.51 (d, J = 1.6 Hz, 1H), 7.39 (dd, J = 8.8, 8.8 Hz, 2 H), 7.35-7.30 (m, 2 H), 7.27-7.20 (m, 3 H), 4.02 (s, 3 H), 3.32-3.25 (m, 1 H), 2.22-2.16 (m, 1 H), 1.50-1.34 (m, 2 H). LCMS (Method 3): [MH+] = 386 at 5.1 min. |

-continued

| Example No. | Chemical Name Structure | Analytical Data $^1$H NMR LC-MS |
|---|---|---|
| Example 60 | 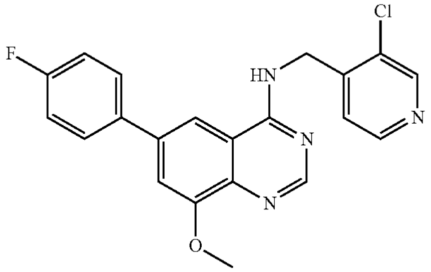 [SMILES: COc1cc(-c2ccc(F)cc2)cc2c(NCc3ccncc3Cl)ncnc12] N-[(3-Chloro-4-pyridyl)methyl]-6-(4-fluorophenyl)-8-methoxy-quinazolin-4-amine | $^1$H NMR (400 MHz, DMSO): δ 8.97 (dd, J = 5.7, 5.7 Hz, 1 H), 8.64 (s, 1 H), 8.45-8.41 (m, 2 H), 8.20 (d, J = 1.5 Hz, 1 H), 7.98-7.93 (m, 2 H), 7.57 (d, J = 1.5 Hz, 1 H), 7.43-7.35 (m, 3 H), 4.87 (d, J = 5.6 Hz, 2 H), 4.04 (s, 3 H). LCMS (Method 3): [MH+] = 395 at 4.48 min. |
| Example 61 | 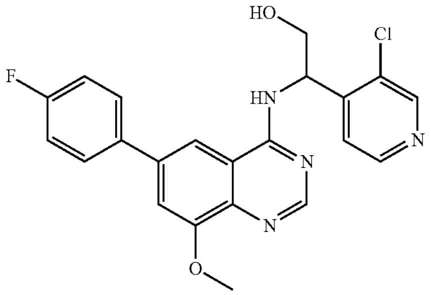 [SMILES: COc1cc(-c2ccc(F)cc2)cc2c(NC(CO)c3ccncc3Cl)ncnc12] 2-(3-Chloro-4-pyridyl)-2-[[6-(4-fluorophenyl)-8-methoxy-quinazolin-4-yl]amino]ethanol | $^1$H NMR (400 MHz, DMSO): δ 8.76 (s, 1H), 8.66 (d, J = 6.5 Hz, 1 H), 8.45-8.42 (m, 2 H), 8.30 (d, J = 1.5 Hz, 1 H), 7.97 (ddd, J = 3.1, 5.4, 12.0 Hz, 2 H), 7.56 (d, J = 5.4 Hz, 2 H), 7.41 (dd, J = 8.9, 8.9 Hz, 2 H), 5.90-5.83 (m, 1 H), 5.32 (dd, J = 5.8, 5.8 Hz, 1 H), 4.03 (s, 3 H), 3.92-3.85 (m, 2 H). LCMS (Method 3): [MH+] = 425 at 4 min. |
| Example 62 | 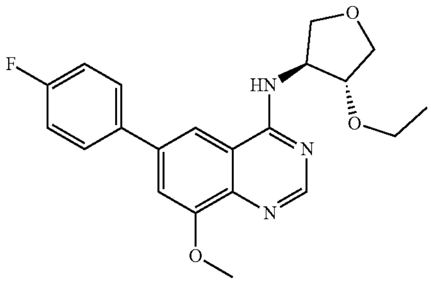 [SMILES: CCO[C@H]1COC[C@@H]1Nc1ncnc2c(OC)cc(-c3ccc(F)cc3)cc12] N-[(3S,4R)-4-Ethoxytetrahydrofuran-3-yl]-6-(4-fluorophenyl)-8-methoxy-quinazolin-4-amine | $^1$H NMR (400 MHz, DMSO): δ 8.50 (s, 1 H), 8.25 (d, J = 6.7 Hz, 1 H), 8.19 (d, J = 1.6 Hz, 1 H), 7.95-7.91 (m, 2 H), 7.52 (d, J = 1.5 Hz, 1H), 7.38 (dd, J = 8.9, 8.9 Hz, 2 H), 4.74 (dd, J = 5.6, 5.6 Hz, 1 H), 4.16-4.12 (m, 1 H), 4.10 (dd, J = 5.9, 9.5 Hz, 1 H), 4.04-3.99 (m, 4 H), 3.85-3.70 (m, 3 H), 3.58 (ddd, J = 7.0, 9.5, 14.0 Hz, 1 H), 1.17 (dd, J = 7.0, 7.0 Hz, 3 H). LCMS (Method 3): [MH+] = 384 at 4.45 min. |
| Example 63 | 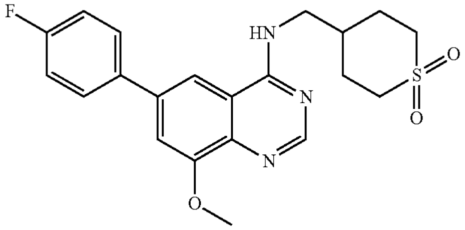 [SMILES: COc1cc(-c2ccc(F)cc2)cc2c(NCC3CCS(=O)(=O)CC3)ncnc12] N-[(1,1-Dioxothian-4-yl)methyl]-6-(4-fluorophenyl)-8-methoxy-quinazolin-4-amine | $^1$H NMR (400 MHz, DMSO): δ 8.45 (s, 2 H), 8.09 (d, J = 1.6 Hz, 1 H), 7.92 (ddd, J = 3.2, 5.4, 12.1 Hz, 2 H), 7.51 (d, J = 1.6 Hz, 1 H), 7.39 (dd, J = 8.9, 8.9 Hz, 2 H), 4.01 (s, 3 H), 3.51 (dd, J = 6.1, 6.1 Hz, 2 H), 3.20-3.01 (m, 4 H), 2.16-2.08 (m, 3 H), 1.77-1.66 (m, 2 H). LCMS (Method 3): [MH+] = 416 at 3.99 min. |

-continued

| Example No. | Chemical Name<br>Structure | Analytical Data<br>$^1$H NMR<br>LC-MS |
|---|---|---|
| Example 64 | 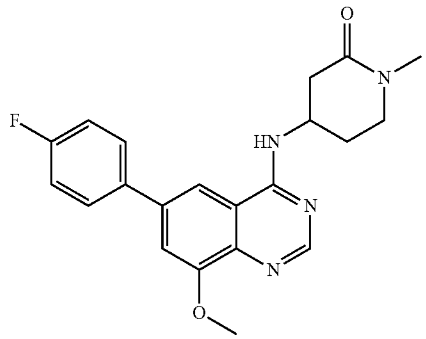 [SMILES: COc1cc(-c2ccc(F)cc2)cc2c(NC3CCN(C)C(=O)C3)ncnc12]<br>4-[[6-(4-Fluorophenyl)-8-methoxy-quinazolin-4-yl]amino]-1-methyl-piperidin-2-one | $^1$H NMR (400 MHz, DMSO): δ 8.47 (s, 1H), 8.12-8.08 (m, 2 H), 7.91 (ddd, J = 3.2, 5.4, 12.1 Hz, 2 H), 7.50 (d, J = 1.6 Hz, 1 H), 7.39 (dd, J = 8.9, 8.9 Hz, 2 H), 4.67-4.56 (m, 1 H), 4.02 (s, 3 H), 2.87 (s, 3 H), 2.75-2.68 (m, 1 H), 2.45 (dd, J = 9.7, 16.9 Hz, 1 H), 2.19 (ddd, J = 1.8, 3.3, 12.8 Hz, 1 H), 2.01-1.89 (m, 1 H). LCMS (Method 4): [MH+] = 381 at 2.9 min. |
| Example 65 | 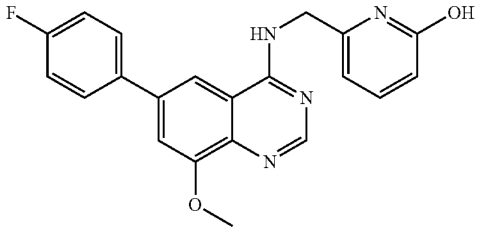<br>6-[[[6-(4-Fluorophenyl)-8-methoxy-quinazolin-4-yl]amino]methyl]-1H-pyridin-2-one | $^1$H NMR (400 MHz, DMSO): δ 8.81 (dd, J = 5.7, 5.7 Hz, 1 H), 8.46 (s, 1H), 8.14 (d, J = 1.6 Hz, 1 H), 7.96-7.92 (m, 2 H), 7.55 (d, J = 1.5 Hz, 1 H), 7.42-7.32 (m, 3 H), 6.21 (d, J = 9.2 Hz, 1 H), 6.10 (d, J = 5.5 Hz, 1 H), 4.63 (d, J = 5.5 Hz, 2 H), 4.03 (s, 3 H). LCMS (Method 4): [MH+] = 377 at 2.84 min. |
| Example 66 | 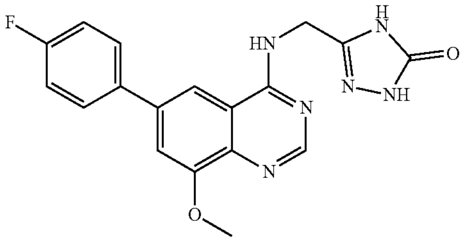 [SMILES: COc1cc(-c2ccc(F)cc2)cc2c(NCc3n[nH]c(=O)[nH]3)ncnc12]<br>3-[[[6-(4-Fluorophenyl)-8-methoxy-quinazolin-4-yl]amino]methyl]-1,4-dihydro-1,2,4-triazol-5-one | $^1$H NMR (400 MHz, DMSO): δ 11.11 (s, 1 H), 8.99 (s, 1H), 8.44 (s, 1H), 8.15 (d, J = 1.6 Hz, 1 H), 7.95-7.90 (m, 2 H), 7.52 (d, J = 1.5 Hz, 1 H), 7.38 (dd, J = 8.9, 8.9 Hz, 2 H), 4.55 (s, 2 H), 4.02 (s, 3 H). LCMS (Method 4): [MH+] = 367 at 2.62 min. |
| Example 67 | 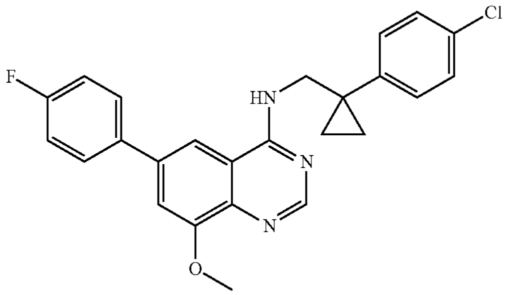 [SMILES: COc1cc(-c2ccc(F)cc2)cc2c(NCC3(c4ccc(Cl)cc4)CC3)ncnc12]<br>N-[[1-(4-Chlorophenyl)cyclopropyl]methyl]-6-(4-fluorophenyl)-8-methoxy-quinazolin-4-amine | $^1$H NMR (400 MHz, DMSO): δ 8.38 (s, 1 H), 8.19 (dd, J = 5.7, 5.7 Hz, 1 H), 8.07 (d, J = 1.6 Hz, 1 H), 7.91-7.87 (m, 2 H), 7.48 (d, J = 1.5 Hz, 1 H), 7.41-7.35 (m, 4 H), 7.31-7.28 (m, 2 H), 4.00 (s, 3 H), 3.90 (d, J = 5.6 Hz, 2 H), 1.11-1.06 (m, 2 H), 0.85-0.80 (m, 2 H). LCMS (Method 4): [MH+] = 434 at 4.17 min. |

-continued

| Example No. | Chemical Name<br>Structure | Analytical Data<br>$^1$H NMR<br>LC-MS |
|---|---|---|
| Example 68 | 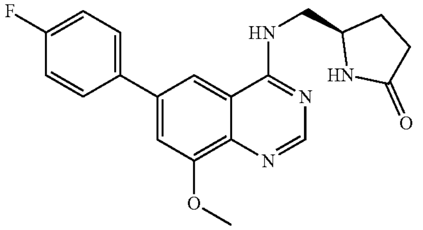 [SMILES: COc1cc(-c2ccc(F)cc2)cc2c(NC[C@H]3CCC(=O)N3)ncnc12]<br>(5R)-5-[[[6-(4-Fluorophenyl)-8-methoxy-quinazolin-4-yl]amino]methyl]pyrrolidin-2-one | $^1$H NMR (400 MHz, DMSO): δ 8.84-8.84 (m, 1 H), 8.53 (s, 1 H), 8.14 (d, J = 1.6 Hz, 1H), 7.96-7.91 (m, 2 H), 7.87 (s, 1 H), 7.61 (s, 1 H), 7.41 (dd, J = 8.9, 8.9 Hz, 2 H), 4.06 (s, 3 H), 3.96-3.88 (m, 1 H), 3.68-3.61 (m, 2 H), 2.28-2.10 (m, 3 H), 1.89-1.81 (m, 1 H). LCMS (Method 4): [MH+] = 367 at 2.78 min. |
| Example 69 | 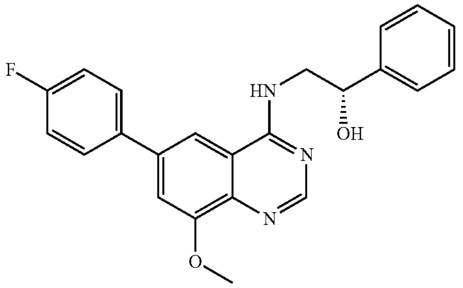 [SMILES: COc1cc(-c2ccc(F)cc2)cc2c(NC[C@@H](O)c3ccccc3)ncnc12]<br>(1S)-2-[[6-(4-Fluorophenyl)-8-methoxy-quinazolin-4-yl]aminol-1-phenyl-ethanol | $^1$H NMR (400 MHz, DMSO): δ 8.52 (dd, J = 5.3, 5.3 Hz, 1H), 8.47 (s, 1H), 8.16-8.13 (m, 2H), 7.96-7.91 (m, 2H), 7.52 (d, J = 1.5 Hz, 1H), 7.44-7.34 (m, 6H), 7.27 (dd, J = 7.2, 7.2 Hz, 1H), 4.98 (dd, J = 4.3, 8.2 Hz, 1H), 4.02 (s, 3H),3.86-3.78 (m, 1H), 3.61-3.52 (m, 1H). LCMS (Method 3): [MH+] = 390 at 4.47 min. |
| Example 70 | 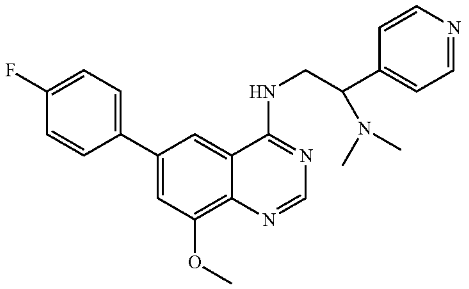 [SMILES: COc1cc(-c2ccc(F)cc2)cc2c(NCC(c3ccncc3)N(C)C)ncnc12]<br>N'-[6-(4-Fluorophenyl)-8-methoxy-quinazolin-4-yl]-N,N-dimethyl-1-(4-pyridyl)ethane-1,2-diamine | $^1$H NMR (400 MHz, DMSO): δ 8.51 (d, J = 5.9 Hz, 2 H), 8.45 (s, 1 H), 8.23 (dd, J = 5.3, 5.3 Hz, 1 H), 7.95 (d, J = 1.6 Hz, 1 H), 7.87 (ddd, J = 3.2, 5.3, 12.1 Hz, 2 H), 7.48 (d, J = 1.5 Hz, 1H), 7.38 (dd, J = 8.8, 8.8 Hz, 2 H), 7.32 (d, J = 5.9 Hz, 2 H), 4.16-4.08 (m, 1 H), 4.00 (s, 3 H), 3.96-3.84 (m, 2 H), 2.20 (s, 6 H). LCMS (Method 3): [MH+] = 418 at 4.05 min. |
| Example 71 | 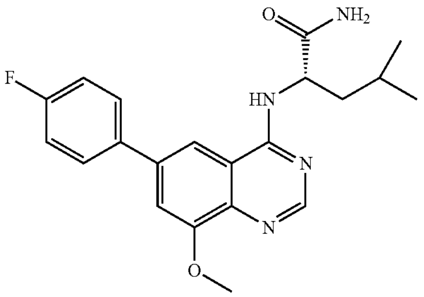 [SMILES: COc1cc(-c2ccc(F)cc2)cc2c(N[C@@H](CC(C)C)C(N)=O)ncnc12]<br>(2S)-2-[[6-(4-fluorophenyl)-8-methoxy-quinazolin-4-yl]amino]-4-methyl-pentanamide | $^1$H NMR (400 MHz, DMSO): δ 8.41 (s, 1H), 8.25 (d, J = 1.6 Hz, 1 H), 8.18 (d, J = 8.0 Hz, 1 H), 7.98-7.94 (m, 2 H), 7.55-7.51 (m, 2 H), 7.39 (dd, J = 8.8, 8.8 Hz, 2 H), 7.01 (s, 1 H), 4.87 (ddd, J = 4.4, 7.9, 10.8 Hz, 1 H), 4.02 (s, 3 H), 1.92-1.62 (m, 3 H), 0.92 (dd, J = 6.5, 26.6 Hz, 6 H). LCMS (Method 4): [MH+] = 383 at 3.31 min. |

-continued

| Example No. | Chemical Name<br>Structure | Analytical Data<br>$^1$H NMR<br>LC-MS |
|---|---|---|
| Example 72 | 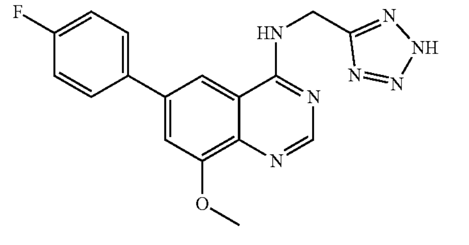 [SMILES: COc1cc(-c2ccc(F)cc2)cc2c(NCc3nn[nH]n3)ncnc12]<br>6-(4-Fluorophenyl)-8-methoxy-N-(2H-tetrazol-5-ylmethyl)quinazolin-4-amine | $^1$H NMR (400 MHz, DMSO): δ 9.09 (s, 1 H), 8.46 (s, 1 H), 8.15 (d, J = 1.5 Hz, 2 H), 7.96-7.92 (m, 2 H), 7.58 (d, J = 1.3 Hz, 2 H), 7.40 (dd, J = 8.8, 8.8 Hz, 2 H), 5.07 (d, J = 5.5 Hz, 2 H), 4.04 (s, 3 H), 2.56 (s, 1 H), 1.28-1.17 (m, 1 H). LCMS (Method 4): [MH+] = 352 at 2.81 min. |
| Example 73 | 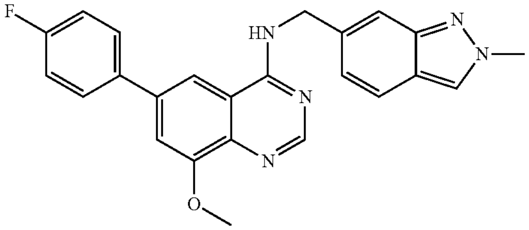 [SMILES: COc1cc(-c2ccc(F)cc2)cc2c(NCc3ccc4cn(C)nc4c3)ncnc12]<br>6-(4-Fluorophenyl)-8-methoxy-N-[(2-methylindazol-6-yl)methyl]quinazolin-4-amine | $^1$H NMR (400 MHz, DMSO): δ 8.86 (dd, J = 5.6, 5.6 Hz, 1 H), 8.46 (s, 1 H), 8.43 (s, 1 H), 8.22-8.18 (m, 1 H), 7.95-7.91 (m, 2 H), 7.54-7.48 (m, 2 H), 7.37 (dd, J = 8.8, 8.8 Hz, 2 H), 7.18 (dd, J = 6.8, 8.7 Hz, 1 H), 7.00 (d, J = 6.8 Hz, 1 H), 5.05 (d, J = 5.4 Hz, 2 H), 4.17 (s, 3 H), 4.03 (s, 3 H). LCMS (Method 4): fMH+1 = 414 at 3.29 min. |
| Example 74 | 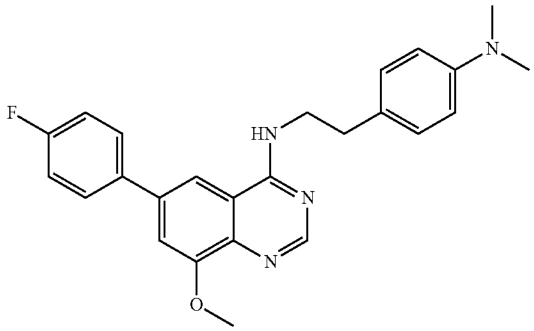 [SMILES: COc1cc(-c2ccc(F)cc2)cc2c(NCCc3ccc(N(C)C)cc3)ncnc12]<br>N-[2-[4-(Dimethylamino)phenyl]ethyl]-6-(4-fluorophenyl)-8-methoxy-quinazolin-4-amine | $^1$H NMR (400 MHz, DMSO): δ 8.47 (s, 1H), 8.39 (dd, J = 5.5, 5.5 Hz, 1 H), 8.07 (d, J = 1.6 Hz, 1 H), 7.94-7.89 (m, 2 H), 7.50 (d, J = 1.6 Hz, 1 H), 7.39 (dd, J = 8.9, 8.9 Hz, 2 H), 7.10 (d, J = 8.8 Hz, 2 H), 6.69 (d, J = 8.7 Hz, 2 H), 4.01 (s, 3 H), 3.71 (dd, J = 5.9, 14.7 Hz, 2 H), 2.88 (app d, J = 8.0 Hz, 2 H), 2.85 (s, 6 H). LCMS (Method 4): [MH+] = 417 at 2.97 min. |
| Example 75 | 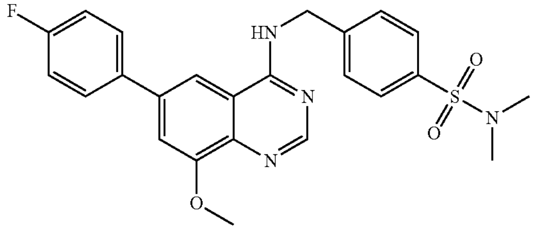 [SMILES: COc1cc(-c2ccc(F)cc2)cc2c(NCc3ccc(S(=O)(=O)N(C)C)cc3)ncnc12]<br>4-[[[6-(4-Fluorophenyl)-8-methoxy-quinazolin-4-yl]amino]methyl]-N,N-dimethyl-benzenesulfonamide | $^1$H NMR (400 MHz, DMSO): δ 8.97 (dd, J = 5.8, 5.8 Hz, 1 H), 8.44 (s, 1 H), 8.17 (d, J = 1.3 Hz, 1 H), 7.94 (dd, J = 5.5, 8.8 Hz, 2 H), 7.73 (d, J = 8.3 Hz, 2 H), 7.64 (d, J = 8.4 Hz, 2 H), 7.55 (d, J = 1.1 Hz, 1 H), 7.39 (dd, J = 8.8, 8.8 Hz, 2 H), 4.93 (d, J = 5.8 Hz, 2 H), 4.03 (s, 3 H), 2.60 (s, 6 H). LCMS (Method 4): [MH+] = 467 at 3.51 min. |

-continued

| Example No. | Chemical Name<br>Structure | Analytical Data<br>$^1H$ NMR<br>LC-MS |
|---|---|---|
| Example 76 | 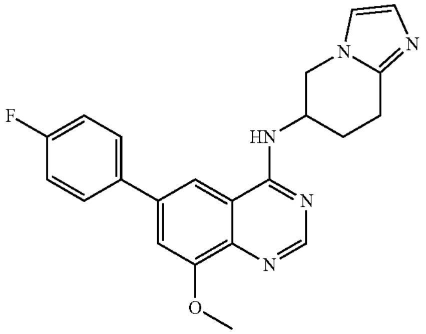 [SMILES: COc1cc(-c2ccc(F)cc2)cc2c(NC3CCc4nccn4C3)ncnc12]<br>6-(4-Fluorophenyl)-8-methoxy-N-(5,6,7,8-tetrahydroimidazo[1,2-a]pyridin-6-yl)quinazolin-4-amine | $^1H$ NMR (400 MHz, DMSO): δ 8.52 (s, 1H), 8.22 (d, J = 6.8 Hz, 1 H), 8.13 (d, J = 2.1 Hz, 1 H), 7.94-7.89 (m, 2 H), 7.53 (d, J = 1.5 Hz, 1 H), 7.39 (dd, J = 8.9, 8.9 Hz, 2 H), 7.12 (s, 1 H), 6.96 (s, 1 H), 4.84-4.78 (m, 1 H), 4.47 (dd, J = 5.2, 12.2 Hz, 1 H), 4.03 (s, 3 H), 3.94 (dd, J = 9.0, 12.2 Hz, 1 H), 3.09-2.87 (m, 2 H), 2.28-2.11 (m, 2 H). LCMS (Method 4): [MH+] = 390 at 2.27 min. |
| Example 77 | 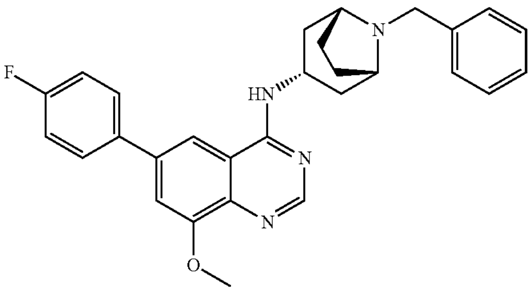 [SMILES: COc1cc(-c2ccc(F)cc2)cc2c(N[C@@H]3C[C@H]4CC[C@@H](C3)N4Cc3ccccc3)ncnc12]<br>N-[(1R,5S)-8-Benzyl-8-azabicyclo[3.2.1]octan-3-yl]-6-(4-fluorophenyl)-8-methoxy-quinazolin-4-amine | $^1H$ NMR (400 MHz, DMSO): δ 8.43 (s, 1 H), 8.11 (d, J = 1.6 Hz, 1 H), 7.96-7.90 (m, 3 H), 7.48 (d, J = 1.5 Hz, 1 H), 7.42-7.32 (m, 6 H), 7.25 (dd, J = 7.2, 7.2 Hz, 1 H), 4.75-4.67 (m, 1 H), 4.00 (s, 3 H), 3.59 (s, 2 H), 3.24 (s, 2 H), 2.12-2.04 (m, 2 H), 1.85-1.79 (m, 4 H), 1.76-1.68 (m, 2 H). LCMS (Method 4): [MH+] = 469 at 2.67 min. |
| Example 78 | 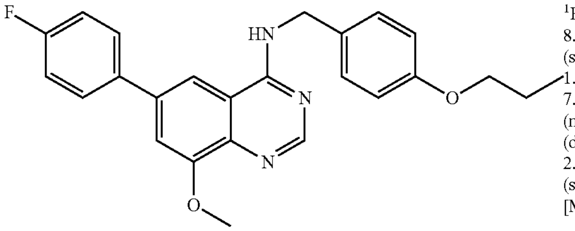<br>N-[[4-[2-(dimethylamino)ethoxy]phenyl]methyl]-6-(4-fluorophenyl)-8-methoxy-quinazolin-4-amine | $^1H$ NMR (400 MHz, DMSO): δ 8.84 (dd, J = 5.8, 5.8 Hz, 1 H), 8.48 (s, 1H), 8.28 (s, 1H), 8.18 (d, J = 1.5 Hz, 1 H), 7.99-7.94 (m, 2 H), 7.55 (d, J = 1.5 Hz, 1 H), 7.44-7.34 (m, 4 H), 6.96-6.92 (m, 2 H), 4.78 (d, J = 5.8 Hz, 2 H), 4.06 (s, 6 H), 2.65 (dd, J = 5.8, 5.8 Hz, 2 H), 2.25 (s, 6 H). LCMS (Method 4): [MH+] = 447 at 2.58 min. |
| Example 79 | 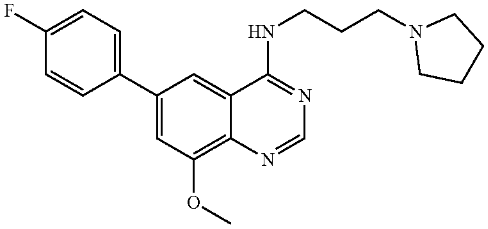 [SMILES: COc1cc(-c2ccc(F)cc2)cc2c(NCCCN3CCCC3)ncnc12]<br>6-(4-Fluorophenyl)-8-methoxy-N-(3-pyrrolidin-1-ylpropyl)quinazolin-4-amine | $^1H$ NMR (400 MHz, DMSO): δ 8.48 (s, 1 H), 8.44 (dd, J = 5.2, 5.2 Hz, 1 H), 8.28 (s, 1 H), 8.07 (d, J = 1.8 Hz, 1 H), 7.97-7.93 (m, 2 H), 7.53 (d, J = 1.5 Hz, 1 H), 7.42 (dd, J = 8.8, 8.8 Hz, 2 H), 4.05 (s, 3 H), 3.64 (ddd, J = 6.5, 6.5, 6.5 Hz, 2 H), 2.74-2.65 (m, 6 H), 1.98-1.88 (m, 2 H), 1.81-1.74 (m, 4 H). LCMS (Method 4): [MH+] = 381 at 2.24 min. |

-continued

| Example No. | Chemical Name<br>Structure | Analytical Data<br>$^1$H NMR<br>LC-MS |
|---|---|---|
| Example 80 | 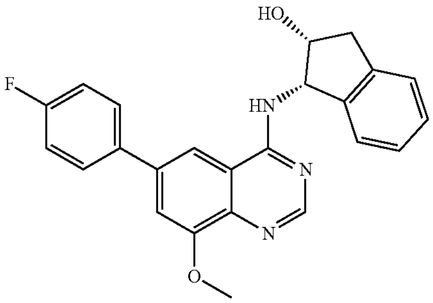 [SMILES: COc1cc(-c2ccc(F)cc2)cc2c(N[C@H]3c4ccccc4C[C@H]3O)ncnc12]<br>(1S,2R)-1-[[6-(4-Fluorophenyl)-8-methoxy-quinazolin-4-yl]amino]indan-2-ol | $^1$H NMR (400 MHz, DMSO): δ 8.48 (s, 1 H), 8.36-8.32 (m, 2 H), 7.98-7.93 (m, 2 H), 7.52 (d, J = 1.5 Hz, 1 H), 7.35-7.20 (m, 6 H), 5.93 (dd, J = 4.9, 8.2 Hz, 1 H), 5.05 (d, J = 3.8 Hz, 1 H), 4.65 (d, J = 3.8 Hz, 1H), 4.02 (s, 3 H), 3.16 (dd, J = 4.9, 16.3 Hz, 1 H), 2.92 (d, J = 15.9 Hz, 1 H). LCMS (Method 4): [MH+] = 402 at 3.56 min. |
| Example 81 | 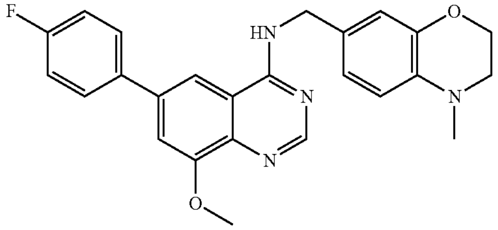 [SMILES: COc1cc(-c2ccc(F)cc2)cc2c(NCc3ccc4c(c3)OCCN4C)ncnc12]<br>6-(4-Fluorophenyl)-8-methoxy-N-[(4-ethyl-2,3-dihydro-1,4-benzoxazin-7-yl)methyl]quinazolin-4-amine | $^1$H NMR (400 MHz, DMSO): δ 8.69 (dd, J = 5.7, 5.7 Hz, 1 H), 8.42 (s, 1H), 8.14-8.11 (m, 1 H), 7.93-7.88 (m, 2 H), 7.49 (d, J = 1.5 Hz, 1H), 7.35 (dd, J = 9.0, 9.0 Hz, 2 H), 6.81 (dd, J = 2.0, 8.1 Hz, 1 H), 6.71 (d, J = 2.0 Hz, 1 H), 6.63 (d, J = 8.3 Hz, 1 H), 4.62 (d, J = 5.6 Hz, 2 H), 4.20-4.17 (m, 2 H), 4.00 (s, 3 H), 3.18-3.15 (m, 2 H), 2.78 (s, 3 H). LCMS (Method 4): [MH+] = 431 at 3.7 min. |
| Example 82 | 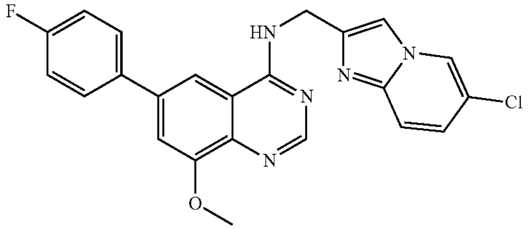 [SMILES: COc1cc(-c2ccc(F)cc2)cc2c(NCc3cn4cc(Cl)ccc4n3)ncnc12]<br>N-[(6-Chloroimidazo[1,2-a]pyridin-2-yl)methyl]-6-(4-fluorophenyl)-8-methoxy-quinazolin-4-amine | $^1$H NMR (400 MHz, DMSO): δ 8.88 (dd, J = 5.8, 5.8 Hz, 1 H), 8.74 (d, J = 1.3 Hz, 1 H), 8.44 (s, 1 H), 8.17 (d, J = 1.8 Hz, 1 H), 7.95-7.90 (m, 2 H), 7.82 (s, 1 H), 7.56-7.51 (m, 2 H), 7.36 (dd, J = 9.0, 9.0 Hz, 2 H), 7.24 (dd, J = 2.0, 9.6 Hz, 1 H), 4.89 (d, J = 5.6 Hz, 2 H), 4.01 (s, 3 H). LCMS (Method 4): [MH+] = 434 at 3.04 min. |
| Example 83 | 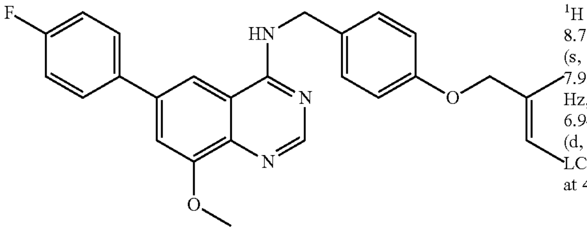<br>N-[(4-Benzyloxyphenyl)methyl]-6-(4-fluorophenyl)-8-methoxy-quinazolin-4-amine | $^1$H NMR (400 MHz, DMSO): δ 8.77 (dd, J = 5.9, 5.9 Hz, 1 H), 8.42 (s, 1H), 8.12 (d, J = 1.5 Hz, 1 H), 7.93-7.88 (m, 2 H), 7.50 (d, J = 1.5 Hz, 1 H), 7.44-7.29 (m, 9 H), 6.98-6.94 (m, 2 H), 5.07 (s, 2 H), 4.72 (d, J = 5.8 Hz, 2 H), 4.00 (s, 3 H). LCMS (Method 4): [MH+] = 466 at 4.23 min. |

-continued

| Example No. | Chemical Name<br>Structure | Analytical Data<br>$^1$H NMR<br>LC-MS |
|---|---|---|
| Example 84 | 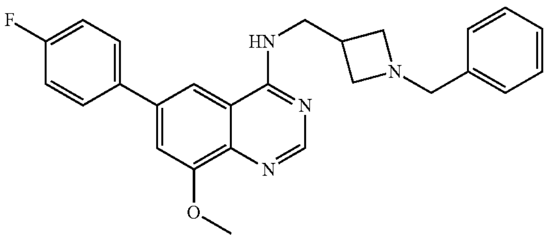 [SMILES: COc1cc(-c2ccc(F)cc2)cc2c(NCC3CN(Cc4ccccc4)C3)ncnc12]<br>N-[(1-Benzylazetidin-3-yl)methyl]-6-(4-fluorophenyl)-8-methoxy-quinazolin-4-amine | $^1$H NMR (400 MHz, MeOD): δ 8.52 (s, 1 H), 8.11 (s, 1 H), 8.02-7.99 (m, 1 H), 7.82-7.77 (m, 2 H), 7.64 (d, J = 1.6 Hz, 1 H), 7.41-7.31 (m, 4 H), 7.28-7.23 (m, 3 H), 4.41 (dd, J = 2.2, 13.0 Hz, 1 H), 4.09 (s, 3 H), 4.09-3.84 (m, 3 H), 3.52-3.38 (m, 1 H), 2.84-2.78 (m, 1 H). LCMS (Method 4): [MH+] = 429 at 2.41 min. |
| Example 85 | 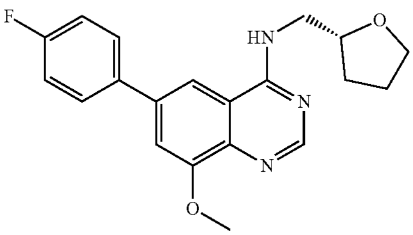 [SMILES: COc1cc(-c2ccc(F)cc2)cc2c(NC[C@H]3CCCO3)ncnc12]<br>6-(4-Fluorophenyl)-8-methoxy-N-[[(2R)-tetrahydrofuran-2-yl]methyl]quinazolin-4-amine | 1H NMR (400 MHz, DMSO): δ 8.41 (s, 2 H), 8.15-8.12 (m, 1 H), 7.94-7.90 (m, 2 H), 7.49 (d, J = 1.8 Hz, 1 H), 7.36 (dd, J = 8.8, 8.8 Hz, 2 H), 4.19-4.11 (m, 1 H), 4.00 (s, 3 H), 3.84-3.78 (m, 1 H), 3.68-3.58 (m, 3 H), 2.00-1.77 (m, 3 H), 1.68-1.58 (m, 1 H). LCMS (Method 3): [MH+] = 354 at 4.36 min. |
| Example 86 | 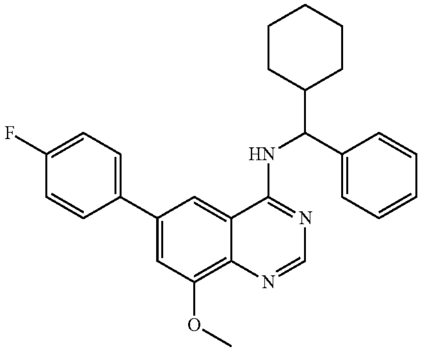 [SMILES: COc1cc(-c2ccc(F)cc2)cc2c(NC(c3ccccc3)C3CCCCC3)ncnc12]<br>N-[Cyclohexyl(phenyl)methyl]-6-(4-fluorophenyl)-8-methoxy-quinazolin-4-amine | $^1$H NMR (400 MHz, DMSO): δ 8.36 (s, 2H), 8.22 (d, J = 1.5 Hz, 1H), 7.94-7.89 (m, 2H), 7.49-7.45 (m, 3H), 7.39 (dd, J = 8.8, 8.8 Hz, 2H), 7.31 (dd, J = 7.6, 7.6 Hz, 2H), 7.20 (dd, J = 7.3, 7.3 Hz, 1H), 5.22 (dd, J = 9.5, 9.5 Hz, 1H), 4.08 (q, J = 5.2 Hz, 1H), 3.97 (s, 3H), 3.17 (d, J = 5.1 Hz, 2H), 2.07 (s, 2H), 2.01-1.91 (m, 1H), 1.70 (d, J = 10.6 Hz, 1H), 1.61 (dd, J = 9.1, 9.1 Hz, 2H), 1.29-0.88 (m, 6H). LCMS (Method 4): [MH+] = 442 at 4.49 min. |

-continued

| Example No. | Chemical Name<br>Structure | Analytical Data<br>$^1$H NMR<br>LC-MS |
|---|---|---|
| Example 87 | 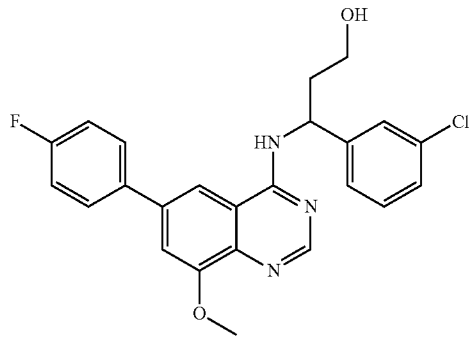 [SMILES: COc1cc(-c2ccc(F)cc2)cc2c(NC(CCO)c3cccc(Cl)c3)ncnc12]<br>3-(3-Chlorophenyl)-3-[[6-(4-fluorophenyl)-8-methoxy-quinazolin-4-yl]amino]propan-1-ol | $^1$H NMR (400 MHz, DMSO): δ 8.48 (d, J = 7.9 Hz, 1 H), 8.38 (s, 1 H), 8.22 (d, J = 1.5 Hz, 1 H), 7.97-7.92 (m, 2 H), 7.51 (s, 2 H),7 .45-7.35 (m, 4 H), 7.29 (d, J = 8.2 Hz, 1 H), 5.61 (dd, J = 8.3, 14.2 Hz, 1 H), 4.01 (s, 3 H), 3.58-3.44 (m, 2 H), 2.25-2.14 (m, 1 H), 2.09-1.98 (m, 1 H). LCMS (Method 4): [MH+] = 438 at 3.69 min. |
| Example 88 | 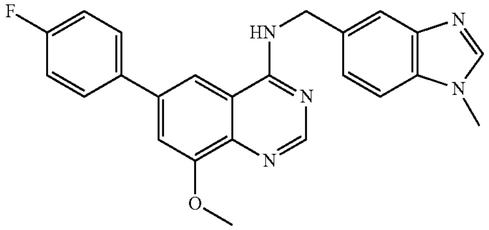 [SMILES: COc1cc(-c2ccc(F)cc2)cc2c(NCc3ccc4c(c3)ncn4C)ncnc12]<br>6-(4-Fluorophenyl)-8-methoxy-N-[(1-methylbenzimidazol-5-yl)methyl]quinazolin-4-amine | $^1$H NMR (400 MHz, DMSO): δ 8.92 (dd, J = 5.7, 5.7 Hz, 1 H), 8.46 (s, 1 H), 8.18 (d, J = 1.6 Hz, 1 H), 8.15 (s, 1 H), 7.95-7.91 (m, 2 H), 7.67 (s, 1 H), 7.54-7.51 (m, 2 H), 7.40-7.33 (m, 3 H), 4.93 (d, J = 5.8 Hz, 2 H), 4.02 (s, 3 H), 3.82 (s, 3 H). LCMS (Method 4): [MH+] = 414 at 2.51 min. |
| Example 89 | 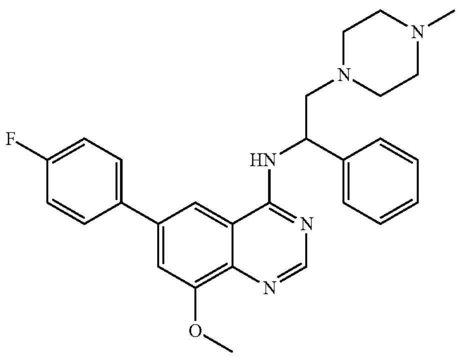 [SMILES: COc1cc(-c2ccc(F)cc2)cc2c(NC(CN3CCN(C)CC3)c3ccccc3)ncnc12]<br>6-(4-Fluorophenyl)-8-methoxy-N-[2-(4-methylpiperazin-1-yl)-1-phenyl-ethyl]quinazolin-4-amine | $^1$H NMR (400 MHz, DMSO): δ 8.45 (d, J = 8.2 Hz, 1 H), 8.38 (s, 1 H), 8.25 (d, J = 1.5 Hz, 1 H), 8.18 (s, 1 H), 7.97-7.93 (m, 2 H), 7.50 (d, J = 7.7 Hz, 3 H), 7.41 (dd, J = 8.9, 8.9 Hz, 2 H), 7.34 (dd, J = 7.5, 7.5 Hz, 2 H), 7.24 (dd, J = 7.3, 7.3 Hz, 1 H), 5.80-5.72 (m, 1 H), 4.01 (s, 3 H), 3.02 (dd, J = 9.8, 12.7 Hz, 1 H), 2.68 (dd, J = 5.2, 12.7 Hz, 1 H), 2.58 (br s, 3 H), 2.35-2.35 (m, 4 H), 2.16 (s, 3 H).<br>LCMS (Method 4): [MH+] = 472 at 2.77 min. |

-continued

| Example No. | Chemical Name<br>Structure | Analytical Data<br>$^1H$ NMR<br>LC-MS |
|---|---|---|
| Example 90 | 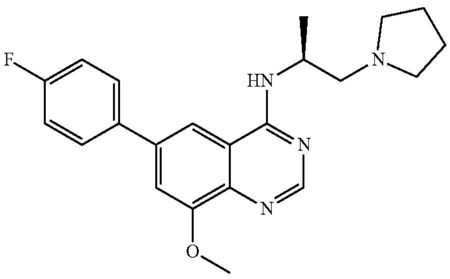 [SMILES: COc1cc(-c2ccc(F)cc2)cc2c(N[C@@H](C)CN3CCCC3)ncnc12]<br>6-(4-Fluorophenyl)-8-methoxy-H-[(1S)-1-methyl-2-pyrrolidin-1-yl-ethyl]quinazolin-4-amine | $^1H$ NMR (400 MHz, DMSO): δ 8.43 (s, 1 H), 8.09 (d, J = 1.6 Hz, 1 H), 7.99-7.89 (m, 3 H), 7.49 (d, J = 1.5 Hz, 1 H), 7.39 (dd, J = 8.9, 8.9 Hz, 2 H), 4.75-4.66 (m, 1 H), 4.01 (s, 3 H), 2.81 (dd, J = 7.6, 12.0 Hz, 1 H), 2.73-2.62 (m, 5 H), 1.70 (s, 4 H), 1.28 (d, J = 6.5 Hz, 3 H). LCMS (Method 4): [MH+] = 381 at 2.34 min. |
| Example 91 | 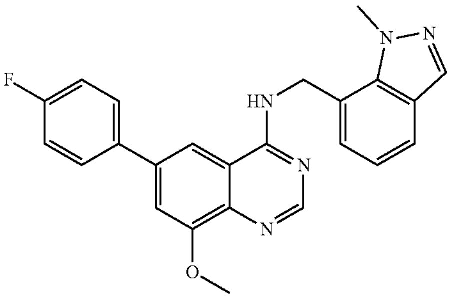 [SMILES: COc1cc(-c2ccc(F)cc2)cc2c(NCc3cccc4cnn(C)c34)ncnc12]<br>6-(4-Fluorophenyl)-8-methoxy-N-[(1-methylindazol-7-yl)methyl]quinazolin-4-amine | $^1H$ NMR (400 MHz, DMSO): δ 8.81 (dd, J = 5.0, 5.0 Hz, 1 H), 8.49 (s, 1 H), 8.24 (d, J = 1.6 Hz, 1 H), 8.07 (s, 1 H), 7.94-7.89 (m, 2 H), 7.71 (d, J = 8.0 Hz, 1 H), 7.54 (d, J = 1.5 Hz, 1 H), 7.38-7.32 (m, 3 H), 7.12-7.07 (m, 1 H), 5.27 (d, J = 4.9 Hz, 2 H), 4.27 (s, 3 H), 4.03 (s, 3 H). LCMS (Method 3): [MH+] = 414 at 4.48 min. |
| Example 92 | 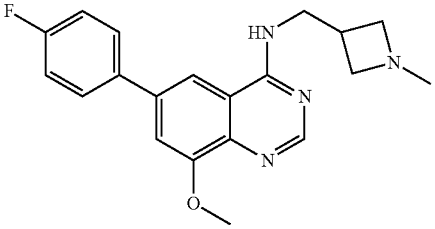 [SMILES: COc1cc(-c2ccc(F)cc2)cc2c(NCC3CN(C)C3)ncnc12]<br>6-(4-Fluorophenyl)-8-methoxy-N-[(1-methylazetidin-3-yl)methyl]quinazolin-4-amine | $^1H$ NMR (400 MHz, DMSO): δ 8.22 (s, 1 H), 7.88 (d, J = 1.8 Hz, 1 H), 7.79 (dd, J = 5.4, 8.8 Hz, 2 H), 7.67 (s, 1 H), 7.39 (d, J = 1.9 Hz, 1 H), 7.32 (dd, J = 8.8, 8.8 Hz, 2 H), 4.11-4.07 (m, 1 H), 3.95 (s, 3 H), 3.76-3.66 (m, 2 H), 3.36-3.29 (m, 1 H), 2.73-2.68 (m, 2 H), 2.46 (s, 3 H), 2.22-2.19 (m, 1 H). LCMS (Method 4): [MH+] = 353 at 2.14 min. |
| Example 93 | 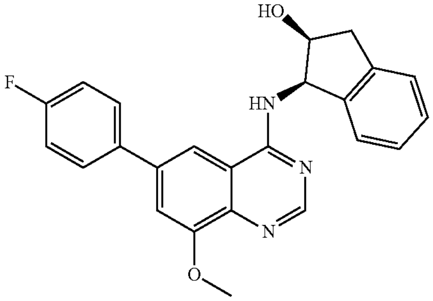 [SMILES: COc1cc(-c2ccc(F)cc2)cc2c(N[C@@H]3c4ccccc4C[C@@H]3O)ncnc12]<br>(1R,2S)-1-[[6-(4-Fluorophenyl)-8-methoxy-quinazolin-4-yl]amino]indan-2-ol | $^1H$ NMR (400 MHz, DMSO): δ 8.50 (s, 1 H), 8.40-8.36 (m, 2 H), 8.00-7.96 (m, 2 H), 7.54 (d, J = 1.5 Hz, 1 H), 7.37-7.21 (m, 6 H), 5.95 (dd, J = 5.0, 8.2 Hz, 1 H), 5.07 (d, J = 3 .6 Hz, 1 H), 4.68 (d, J = 3.3 Hz, 1 H), 4.04 (s, 3 H), 3.17 (dd, J = 5.0, 16.1 Hz, 1 H), 2.94 (d, J = 15.9 Hz, 1 H). LCMS (Method 4): [MH+] = 402 at 3.56 min. |

-continued

| Example No. | Chemical Name<br>Structure | Analytical Data<br>$^1$H NMR<br>LC-MS |
|---|---|---|
| Example 94 | 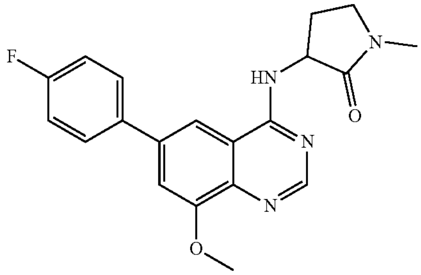 [SMILES: COc1cc(-c2ccc(F)cc2)cc2c(NC3CCN(C)C3=O)ncnc12]<br>3-[[6-(4-Fluorophenyl)-8-methoxy-quinazolin-4-yl]amino]-1-methyl-pyrrolidin-2-one | $^1$H NMR (400 MHz, DMSO): δ 9.10-9.10 (m, 1 H), 8.55 (s, 1 H), 8.19-8.14 (m, 1 H), 7.97-7.92 (m, 2 H), 7.65 (s, 1 H), 7.41 (dd, J = 8.8, 8.8 Hz, 2 H), 5.19 (q, J = 8.9 Hz, 1 H), 4.08 (s, 3 H), 3.47-3.41 (m, 2 H), 2.84 (s, 3 H), 2.50-2.44 (m, 1 H), 2.06 (ddd, J = 9.3, 12.2, 18.7 Hz, 1 H). LCMS (Method 4): [MH+] = 367 at 2.85 min. |
| Example 95 | 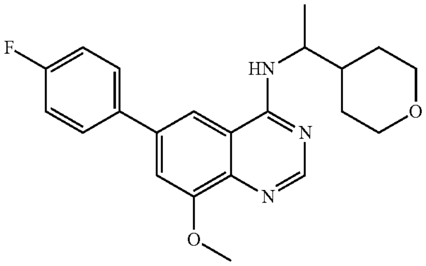 [SMILES: COc1cc(-c2ccc(F)cc2)cc2c(NC(C)C3CCOCC3)ncnc12]<br>6-(4-Fluorophenyl)-8-methoxy-N-(1-tetrahydropyran-4-ylethyl)quinazolin-4-amine | $^1$H NMR (400 MHz, DMSO): δ 8.41 (s, 1H), 8.16-8.12 (m, 2 H), 7.94-7.90 (m, 3 H), 7.49 (d, J = 1.6 Hz, 1 H), 7.38 (dd, J = 8.8, 8.8 Hz, 2 H), 4.38 (dd, J = 8.0, 14.9 Hz, 1 H), 4.01 (s, 3 H), 3.90-3.82 (m, 2 H), 3.33-3.21 (m, 2 H), 1.88-1.78 (m, 1 H), 1.69 (dd, J = 13.0, 13.0 Hz, 2 H), 1.24 (d, J = 6.8 Hz, 5 H). LCMS (Method 4): [MH+] = 382 at 3.32 min. |
| Example 96 | 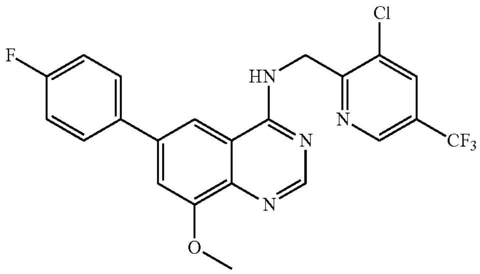 [SMILES: COc1cc(-c2ccc(F)cc2)cc2c(NCc3ncc(C(F)(F)F)cc3Cl)ncnc12]<br>N-[[3-Chloro-5-(trifluoromethyl)-2-pyridyl]methyl]-6-(4-fluorophenyl)-8-methoxy-quinazolin-4-amine | $^1$H NMR (400 MHz, DMSO): δ 8.94 (dd, J = 5.6, 5.6 Hz, 1 H), 8.87 (s, 1 H), 8.50 (d, J = 1.6 Hz, 1 H), 8.36 (s, 1 H), 8.20 (d, J = 1.6 Hz, 1 H), 7.94 (ddd, J = 3.2, 5.5, 12.1 Hz, 2 H), 7.55 (d, J = 1.6 Hz, 1 H), 7.39 (dd, J = 8.8, 8.8 Hz, 2 H), 5.07 (d, J = 5.5 Hz, 2 H), 4.03 (s, 3 H). LCMS (Method 4): [MH+] = 463 at 3.91 min. |
| Example 97 | 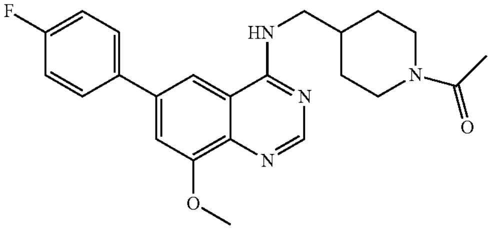 [SMILES: COc1cc(-c2ccc(F)cc2)cc2c(NCC3CCN(C(C)=O)CC3)ncnc12]<br>1-[4-[[[6-(4-Fluorophenyl)-8-methoxy-quinazolin-4-yl]amino]methyl]-1-piperidyl]ethanone | 1H NMR (400 MHz, DMSO): δ 8.96 (s, 1H), 8.54 (s, 1 H), 8.17 (d, J = 1.9 Hz, 1 H), 7.96-7.91 (m, 2 H), 7.63 (s, 1 H), 7.41 (dd, J = 8.9, 8.9 Hz, 2 H), 4.37 (d, J = 12.8 Hz, 1 H), 4.06 (s, 3H), 3.84 (d, J = 13.7 Hz, 1 H), 3.56-3.47 (m, 2 H), 3.04-2.96 (m, 1 H), 2.09 (s, 1 H), 1.99 (s, 4 H), 1.80-1.73 (m, 2 H), 1.26-1.02 (m, 2 H). LCMS (Method 3): [MH+] = 409 at 4.01 |

-continued

| Example No. | Chemical Name<br>Structure | Analytical Data<br>$^1$H NMR<br>LC-MS |
|---|---|---|
| Example 98 | 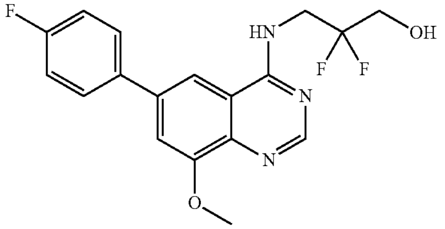 [SMILES: COc1cc(-c2ccc(F)cc2)cc2c(NCC(F)(F)CO)ncnc12]<br>2,2-Difluoro-3-[[6-(4-fluorophenyl)-8-methoxy-quinazolin-4-yl]amino]propan-1-ol | $^1$H NMR (400 MHz, DMSO): δ 8.56 (dd, J = 6.0, 6.0 Hz, 1H), 8.49 (s, 1H), 8.20 (d, J = 1.6 Hz, 1H), 7.97-7.93 (m, 2H), 7.55 (d, J = 1.5 Hz, 1H), 7.39 (dd, J = 8.9, 8.9 Hz, 2H), 5.66-5.65 (m, 1H), 4.23-4.11 (m, 2H), 4.03 (s, 3H), 3.70 (dd, J = 13.7, 13.7 Hz, 2H). LCMS (Method 4): [MH+] = 364 at 3.02 |
| Example 99 | 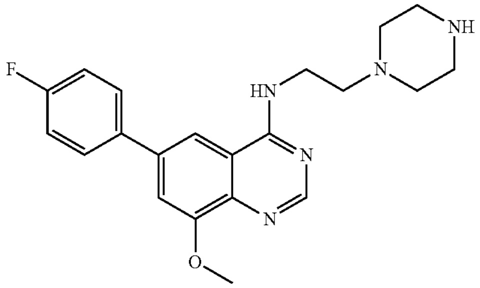 [SMILES: COc1cc(-c2ccc(F)cc2)cc2c(NCCN3CCNCC3)ncnc12]<br>6-(4-Fluorophenyl)-8-methoxy-N-(2-piperazin-1-ylethyl)quinazolin-4-amine | $^1$H NMR (400 MHz, DMSO): δ 8.44 (s, 1 H), 8.32 (s, 1 H), 8.05 (d, J = 1.5 Hz, 1 H), 7.91 (ddd, J = 3.2, 5.3, 12.0 Hz, 2 H), 7.50 (d, J = 1.4 Hz, 1 H), 7.39 (dd, J = 8.9, 8.9 Hz, 2 H), 4.01 (s, 3 H), 3.73-3.66 (m, 2 H), 3.42-3.31 (m, 1 H), 2.90 (dd, J = 4.8, 4.8 Hz, 4 H), 2.67-2.60 (m, 2 H), 2.60-2.54 (m, 3 H). LCMS (Method 4): [MH+] = 382 at 2.18 min. |
| Example 100 | 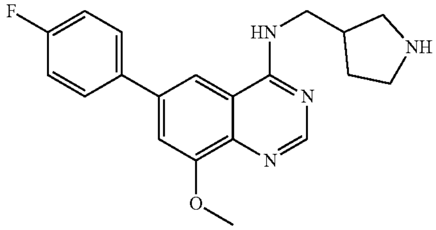 [SMILES: COc1cc(-c2ccc(F)cc2)cc2c(NCC3CCNC3)ncnc12]<br>6-(4-Fluorophenyl)-8-methoxy-N-(pyrrolidin-3-ylmethyl)quinazolin-4-amine | $^1$H NMR (400 MHz, DMSO): δ 8.54 (dd, J = 5.4, 5.4 Hz, 1 H), 8.39 (s, 1 H), 8.10 (d, J = 1.4 Hz, 1 H), 7.95-7.90 (m, 2 H), 7.51 (d, J = 1.5 Hz, 1 H), 7.39 (dd, J = 8.9, 8.9 Hz, 2 H), 4.01 (s, 3 H), 3.69-3.54 (m, 2 H), 3.25-3.16 (m, 1 H), 3.12-3.04 (m, 1 H), 2.95 (dd, J = 7.0, 11.4 Hz, 1 H), 2.76-2.67 (m, 1 H), 2.06-1.93 (m, 1 H), 1.75-1.65 (m, 1 H). LCMS (Method 4): [MH+] = 353 at 2.22 min. |
| Example 101 | 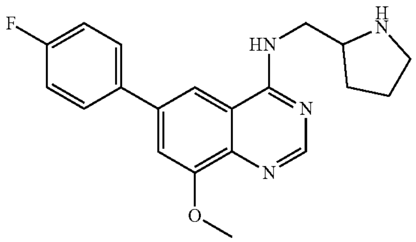 [SMILES: COc1cc(-c2ccc(F)cc2)cc2c(NCC3CCCN3)ncnc12]<br>6-(4-Fluorophenyl)-8-methoxy-N-(pyrrolidin-2-ylmethyl)quinazolin-4-amine | $^1$H NMR (400 MHz, DMSO): δ 9.09 (s, 1 H), 8.46 (s, 1 H), 8.17 (d, J = 1.6 Hz, 1 H), 7.97-7.92 (m, 2 H), 7.52 (d, J = 1.4 Hz, 1 H), 7.37 (dd, J = 8.8, 8.8 Hz, 2 H), 4.02 (s, 3 H), 3.91-3.62 (m, 3 H), 3.18-3.01 (m, 2 H), 2.09-1.99 (m, 1 H), 1.95-1.78 (m, 2 H), 1.65 (ddd, J = 7.8, 12.5, 15.9 Hz, 1 H). LCMS (Method 4): [MH+] = 353 at 2.22 min. |

-continued

| Example No. | Chemical Name<br>Structure | Analytical Data<br>$^1H$ NMR<br>LC-MS |
|---|---|---|
| Example 102 | 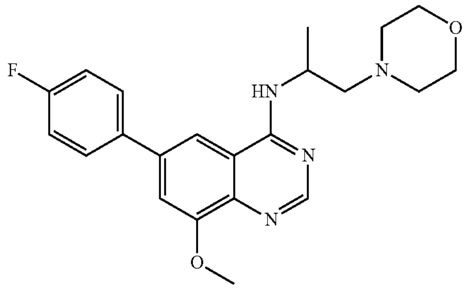 [SMILES: COc1cc(-c2ccc(F)cc2)cc2c(NC(C)CN3CCOCC3)ncnc12]<br>6-(4-Fluorophenyl)-8-methoxy-N-(1-methyl-2-morpholino-ethyl)quinazolin-4-amine | $^1H$ NMR (400 MHz, DMSO): δ 8.42 (s, 1 H), 8.09 (d, J = 1.6 Hz, 1 H), 7.49 (d, J = 1.6 Hz, 1 H), 7.39 (dd, J = 8.9, 8.9 Hz, 2 H), 4.78-4.67 (m, 1 H), 4.01 (s, 3 H), 3.54 (dd, J = 4.6, 4.6 Hz, 4 H), 2.60 (dd, J = 7.3, 12.3 Hz, 1 H), 2.49-2.38 (m, 5 H), 1.27 (d, J = 6.7 Hz, 3 H). LCMS (Method 4): [MH+] = 397 at 2.3 min. |
| Example 103 | 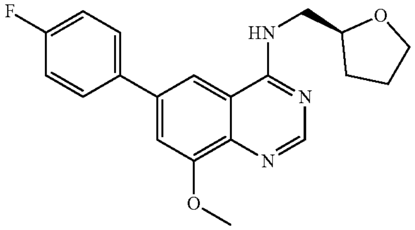 [SMILES: COc1cc(-c2ccc(F)cc2)cc2c(NC[C@@H]3CCCO3)ncnc12]<br>(S)-6-(4-Fluorophenyl)-8-methoxy-N-((tetrahydrofuran-2-yl)methyl)quinazolin-4-amine | 1H NMR (400 MHz, DMSO): δ 8.45-8.42 (m, 2 H), 8.14 (d, J = 1.5 Hz, 1 H), 7.96-7.91 (m, 2 H), 7.51 (d, J = 1.5 Hz, 1 H), 7.38 (dd, J = 8.9, 8.9 Hz, 2 H), 4.20-4.12 (m, 1 H), 4.01 (s, 3 H), 3.86-3.79 (m, 1 H), 3.70-3.59 (m, 3 H), 2.02-1.79 (m, 3 H), 1.70-1.60 (m, 1 H). LCMS (Method 3): [MH+] = 354 at 4.42 min. |
| Example 104 | 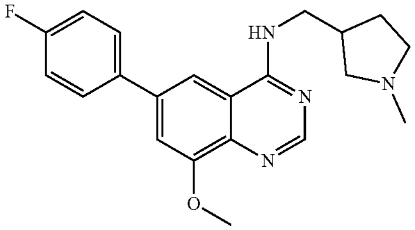 [SMILES: COc1cc(-c2ccc(F)cc2)cc2c(NCC3CCN(C)C3)ncnc12]<br>6-(4-Fluorophenyl)-8-methoxy-N-((1-methylpyrrolidin-3-yl)methyl)quinazolin-4-amine | $^1H$ NMR (400 MHz, DMSO): δ 8.44 (s, 1 H), 8.24 (s, 1 H), 8.08 (d, J = 1.6 Hz, 1 H), 7.92 (ddd, J = 3.2, 5.4, 12.1 Hz, 2 H), 7.50 (d, J = 1.6 Hz, 1 H), 7.39 (dd, J = 8.9, 8.9 Hz, 2 H), 4.01 (s, 3 H), 3.61-3.46 (m, 2 H), 2.78-2.71 (m, 1 H), 2.70-2.64 (m, 2 H), 2.60-2.55 (m, 2 H), 2.37 (s, 3 H), 2.03-1.93 (m, 1 H), 1.64-1.54 (m, 1 H). LCMS (Method 4): [MH+] = 367 at 2.24 min. |
| Example 105 | 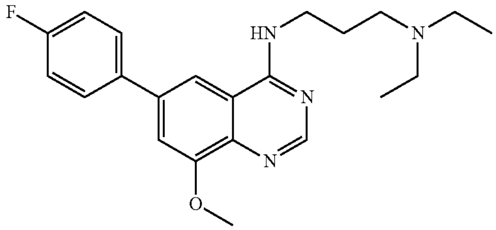 [SMILES: CCN(CC)CCCNc1ncnc2c(OC)cc(-c3ccc(F)cc3)cc12]<br>$N^1$,$N^1$-Diethyl-$N^3$-(6-(4-fluorophenyl)-8-methoxyquinazolin-4-yl)propane-1.3-diamine | $^1H$ NMR (400 MHz, DMSO): δ 8.44 (s, 1 H), 8.39 (dd, J = 5.3, 5.3 Hz, 1 H), 8.02 (d, J = 1.6 Hz, 1 H), 7.93-7.88 (m, 2 H), 7.49 (d, J = 1.5 Hz, 1 H), 7.39 (dd, J = 8.9, 8.9 Hz, 2 H), 4.01 (s, 3H), 3.58 (dd, J = 6.9, 12.4 Hz, 2 H), 2.62-2.54 (m, 6 H), 1.87-1.78 (m, 2 H), 0.99 (dd, J = 7.2, 7.2 Hz, 6 H). LCMS (Method 4): [MH+] = 383 at 2.31 min. |

-continued

| Example No. | Chemical Name Structure | Analytical Data $^1$H NMR LC-MS |
|---|---|---|
| Example 106 | 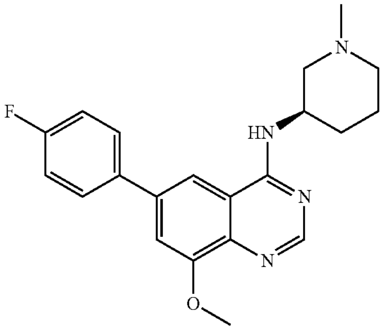 [SMILES: COc1cc(-c2ccc(F)cc2)cc2c(N[C@@H]3CCCN(C)C3)ncnc12] (R)-6-(4-Fluorophenyl)-8-methoxy-N-(1-methylpiperidin-3-yl)quinazolin-4-amine | $^1$H NMR (400 MHz, DMSO): δ 8.45 (s, 1 H), 8.11 (d, J = 1.8 Hz, 1 H), 7.95-7.90 (m, 3 H), 7.50 (d, J = 1.6 Hz, 1 H), 7.38 (dd, J = 8.9, 8.9 Hz, 2 H), 4.47-4.37 (m, 1 H), 4.01 (s, 3 H), 3.05 (dd, J = 3.6, 10.5 Hz, 1 H), 2.81 (d, J = 11.2 Hz, 1 H), 2.28 (s, 3 H), 2.04-1.92 (m, 3 H), 1.82-1.74 (m, 1 H), 1.68-1.57 (m, 1 H), 1.52-1.40 (m, 1 H). LCMS (Method 4): [MH+] = 367 at 2.28 min. |
| Example 107 | 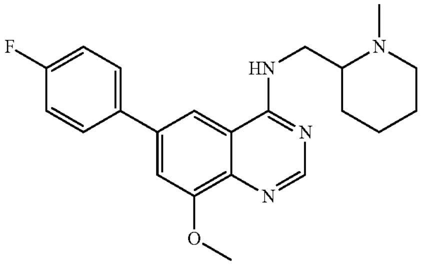 [SMILES: COc1cc(-c2ccc(F)cc2)cc2c(NCC3CCCCN3C)ncnc12] 6-(4-Fluorophenyl)-8-methoxy-N-((1-methylpiperidin-2-yl)methyl)quinazolin-4-amine | $^1$H NMR (400 MHz, DMSO): δ 8.46 (s, 1 H), 8.29 (dd, J = 5.0, 5.0 Hz, 1 H), 8.17 (s, 1 H), 8.08 (d, J = 1.6 Hz, 1 H), 7.94-7.89 (m, 2 H), 7.51 (d, J = 1.4 Hz, 1 H), 7.39 (dd, J = 8.9, 8.9 Hz, 2 H), 4.02 (s, 3 H), 3.98-3.90 (m, 1 H), 3.59-3.53 (m, 1 H), 3.04-2.95 (m, 1 H), 2.69-2.68 (m, 1 H), 2.56 (d, J = 2.6 Hz, 3 H), 2.43-2.41 (m, 1 H), 1.83-1.79 (m, 1 H), 1.75-1.69 (m, 1 H), 1.62-1.52 (m, 2 H), 1.49-1.27 (m, 2 H). LCMS (Method 4): [MH+] = 381 at 2.32 min. |
| Example 108 | 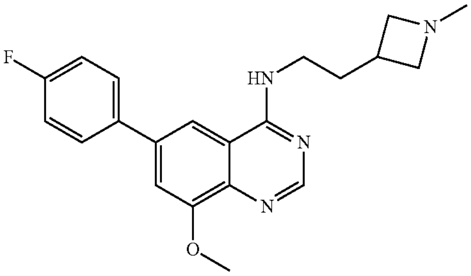 6-(4-Fluorophenyl)-8-methoxy-N-(2-(1-methylazetidin-3-yl)ethyl)quinazolin-4-amine | $^1$H NMR (400 MHz, DMSO): δ 8.44 (s, 1 H), 8.32 (s, 1 H), 7.95 (d, J = 1.4 Hz, 1 H), 7.90-7.86 (m, 2 H), 7.49 (d, J = 1.4 Hz, 1 H), 7.35 (dd, J = 8.8, 8.8 Hz, 2 H), 4.08-3.95 (m, 6 H), 3.70 (dd, J = 7.3, 11.0 Hz, 1H), 2.74-2.68 (m, 1 H), 2.39 (s, 3 H), 2.22-2.11 (m, 1 H), 1.82-1.72 (m, 1 H). LCMS (Method 3): [MH+] = 416 at 3.99 min. |

-continued

| Example No. | Chemical Name Structure | Analytical Data $^1H$ NMR LC-MS |
|---|---|---|
| Example 109 | 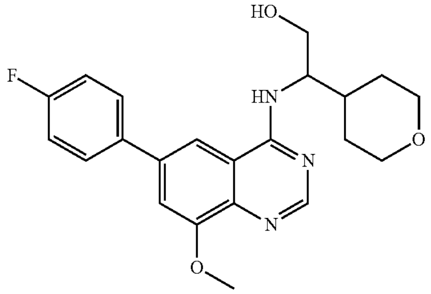 [SMILES: COc1cc(-c2ccc(F)cc2)cc2c(NC(CO)C3CCOCC3)ncnc12] 2-[[6-(4-Fluorophenyl)-8-methoxy-quinazolin-4-yl]amino]-2-tetrahydropyran-4-yl-ethanol formate | $^1H$ NMR (400 MHz, DMSO): δ 8.40 (s, 1 H), 8.21 (d, J = 1.6 Hz, 1 H), 8.16 (s, 1 H), 7.94 (ddd, J = 3.2, 5.4, 12.1 Hz 2 H), 7.87 (d, J = 8.7 Hz, 1 H), 7.50 (d, J = 1.6 Hz, 1 H), 7.38 (dd, J = 8.9, 8.9 Hz, 2 H), 4.76 (s, 1 H), 4.40-4.31 (m, 1 H), 4.01 (s, 3 H), 3.92-3.82 (m, 2 H), 3.70-3.62 (m, 2 H), 3.35-3.24 (m, 2 H), 2.08-1.99 (m, 1 H), 1.71 (dd, J = 11.9, 28.0 Hz, 2 H), 1.39-1.23 (m, 2 H). LCMS (Method 3): [MH+] = 398 at 3.88 min. |
| Example 110 | 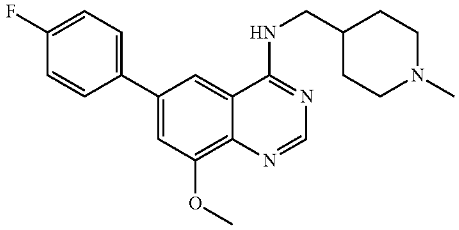 [SMILES: COc1cc(-c2ccc(F)cc2)cc2c(NCC3CCN(C)CC3)ncnc12] 6-(4-Fluorophenyl)-8-methoxy-N-[(1-methyl-4-piperidyl)methyl]quinazolin-4-amine | $^1H$ NMR (400 MHz, DMSO): δ 8.43 (s, 1 H), 8.34 (dd, J = 5.5, 5.5 Hz, 1 H), 8.10 (d, J = 1.6 Hz, 1 H), 7.94-7.89 (m, 2 H), 7.50 (d, J = 1.6 Hz, 1 H), 7.39 (dd, J = 8.8, 8.8 Hz, 2 H), 4.01 (s, 3 H), 3.46 (s, 2 H), 2.89 (d, J = 11.4 Hz, 2 H), 2.27 (s, 3 H), 2.09-2.03 (m, 2 H), 1.76 (dd, J = 10.2, 10.2 Hz, 3 H), 1.34-1.24 (m, 2 H). LCMS (Method 4): [MH+] = 381 at 2.27 min. |
| Example 111 | 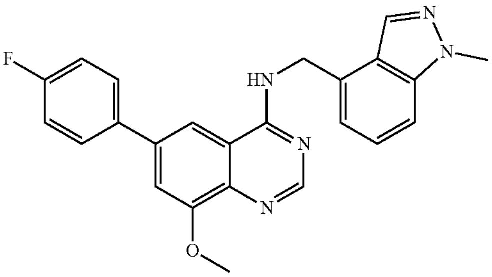 [SMILES: COc1cc(-c2ccc(F)cc2)cc2c(NCc3cccc4c3cnn4C)ncnc12] 6-(4-Fluorophenyl)-8-methoxy-N-[(1-methylindazol-4-yl)methyl]quinazolin-4-amine | $^1H$ NMR (400 MHz, DMSO): δ 10.61 (s, 1 H), 8.78 (s, 1 H), 8.37 (s, 1 H), 8.23 (s, 1 H), 7.95 (dd, J = 5.6, 8.3 Hz, 2 H), 7.87 (s, 1 H), 7.60 (d, J = 8.4 Hz, 1 H), 7.45-7.36 (m, 3 H), 7.17 (d, J = 7.0 Hz, 1 H), 5.31 (s, 2 H), 4.17 (s, 3 H), 4.05 (s, 3 H). LCMS (Method 3): [MH+] = 414 at 4.65 min. |
| Example 112 | 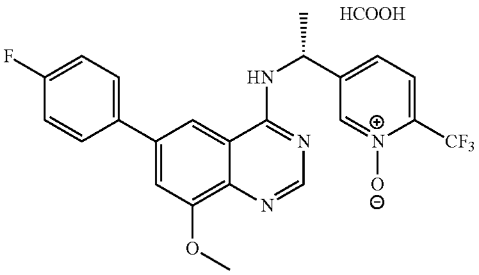 [SMILES: COc1cc(-c2ccc(F)cc2)cc2c(N[C@H](C)c3ccc(C(F)(F)F)[n+]([O-])c3)ncnc12 ; "HCOOH"] (R)-5-(1-((6-(4-fluorophenyl)-8-methoxyquinazolin-4-yl)amino)ethyl)-2-(trifluoromethyl)pyridine 1-oxide formate | LCMS: 0.67 min, 459.1 [M + H]+, Method 5. $^1H$ NMR (400 MHz, DMSO-d6): δ ppm 8.57 (s, 1 H) 8.51 (br d, J = 6.58 Hz, 1 H) 8.37-8.44 (m, 1 H) 8.20 (s, 1 H) 8.17 (s, 1 H) 7.85-7.97 (m, 3 H) 7.55 (br d, J = 8.33 Hz, 1 H) 7.32-7.43 (m, 2 H) 5.55 (br t, J = 6.58 Hz, 1 H) 4.00 (s, 3 H) 1.64 (br d, J = 7.02 Hz, 3 H). |

-continued

| Example No. | Chemical Name Structure | Analytical Data $^1H$ NMR LC-MS |
|---|---|---|
| Example 113 | 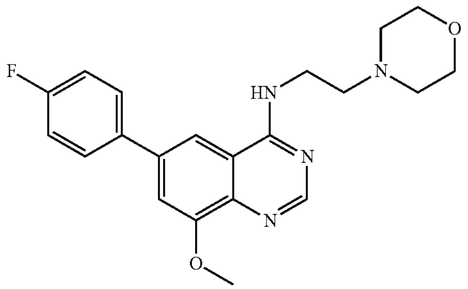 [SMILES: COc1cc(-c2ccc(F)cc2)cc2c(NCCN3CCOCC3)ncnc12] 6-(4-fluorophenyl)-8-methoxy-N-(2-morpholinoethyl)quinazolin-4-amine | LCMS: 0.85 min, 383.2 [M + H]+, Method 5. $^1H$ NMR (400 MHz, DMSO-d6): δ ppm 8.39 (s, 1 H) 8.23 (br t, J = 5.15 Hz, 1 H) 8.00 (d, J = 1.10 Hz, 1 H) 7.78-7.94 (m, 2 H) 7.45 (d, J = 1.10 Hz, 1 H) 7.34 (t, J = 8.88 Hz, 2 H) 3.96 (s, 3 H) 3.61-3.70 (m, 2 H) 3.50-3.57 (m, 4 H) 2.56 (br t, J = 7.02 Hz, 2 H) 2.37-2.44 (m, 4 H). |
| Example 291 | 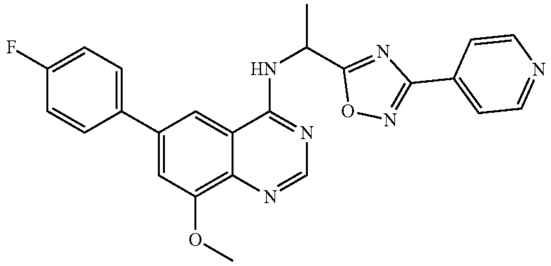 [SMILES: COc1cc(-c2ccc(F)cc2)cc2c(NC(C)c3nc(-c4ccncc4)no3)ncnc12] 6-(4-Fluorophenyl)-8-methoxy-N-(1-(3-(pyridin-4-yl)-1,2,4-oxadiazol-5-yl)ethyl)quinazolin-4-amine | $^1H$ NMR (400 MHz, DMSO): δ 8.95 (d, J = 6.8 Hz, 1 H), 8.85-8.83 (m, 2 H), 8.49 (s, 1 H), 8.27 (d, J = 1.5 Hz, 1 H), 8.02-7.96 (m, 4 H), 7.62 (d, J = 1.5 Hz, 1 H), 7.44 (dd, J = 8.8, 8.8 Hz, 2 H), 5.98-5.93 (m, 1 H), 4.08 (s, 3H), 1.88 (d, J = 7.1 Hz, 3 H). LCMS (Method 4): [MH+] = 443 at 3.32 min. |
| Example 293 | 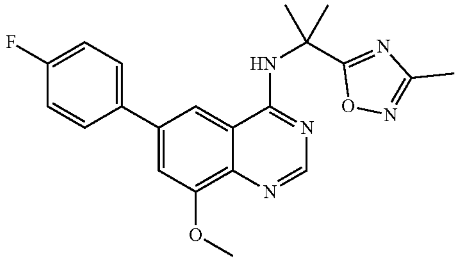 [SMILES: COc1cc(-c2ccc(F)cc2)cc2c(NC(C)(C)c3nc(C)no3)ncnc12] 6-(4-fluorophenyl)-8-methoxy-N-(2-(3-methyl-1,2,4-oxadiazol-5-yl)propan-2-yl)quinazolin-4-amine | $^1H$ NMR (400 MHz, DMSO): δ 8.91 (d, J = 7.0 Hz, 1 H), 8.81-8.79 (m, 2 H), 8.45 (s, 1 H), 8.23 (d, J = 1.8 Hz, 1 H), 7.98-7.92 (m, 4 H), 7.58 (d, J = 1.6 Hz, 1 H), 7.40 (dd, J = 8.9, 8.9 Hz, 2 H), 5.94-5.89 (m, 1 H), 4.04 (s, 3 H), 1.84 (d, J = 7.2 Hz, 3 H). LCMS (Method 3): [MH+] = 392 at 4.41 min. |
| Example 294 | 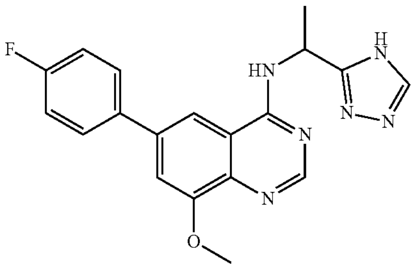 [SMILES: COc1cc(-c2ccc(F)cc2)cc2c(NC(C)c3nnc[nH]3)ncnc12] (rac)-N-(1-(4H-1,2,4-triazol-3-yl)ethyl)-6-(4-fluorophenyl)-8-methoxyquinazolin-4-amine | $^1H$ NMR (400 MHz, DMSO): δ 13.82-13.82 (m, 1 H), 8.62-8.54 (m, 1 H), 8.43-8.40 (m, 1 H), 8.24 (s, 1 H), 7.95-7.95 (m, 2 H), 7.54 (s, 1 H), 7.39-7.38 (m, 2 H), 5.79-5.79 (m, 1 H), 4.03 (s, 3 H), 1.67-1.67 (m, 3 H). 1 NH not observed. LCMS (Method 4): [MH+] = 365 at 2.86 min. |

-continued

| Example No. | Chemical Name<br>Structure | Analytical Data<br>$^1$H NMR<br>LC-MS |
|---|---|---|
| Example 295 | 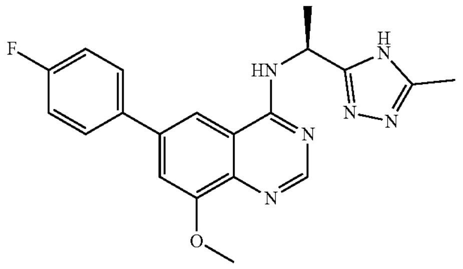 [SMILES: COc1cc(-c2ccc(F)cc2)cc2c(N[C@@H](C)c3nnc(C)[nH]3)ncnc12]<br>(S)-6-(4-fluorophenyl)-8-methoxy-N-(1-(5-methyl-4H-1,2,4-triazol-3-yl)ethyl)quinazolin-4-amine | $^1$H NMR (400 MHz, DMSO): δ 13.37-13.37 (m, 1 H), 8.46-8.46 (m, 1 H), 8.42 (s, 1 H), 8.22 (s, 1 H), 7.95 (s, 2 H), 7.51 (s, 1 H), 7.37 (s, 2 H), 5.73-5.73 (m, 1 H), 4.01 (s, 3 H), 2.31 (s, 3 H), 1.63-1.62 (m, 3 H). LCMS (Method 4): [MH+] = 379 at 2.91 min. Chiral analysis (Method 20) at 2.29 min. |

Example 114

N-(((1r,4r)-4-Aminocyclohexyl)methyl)-6-(4-fluorophenyl)-8-methoxyquinazolin-4-amine

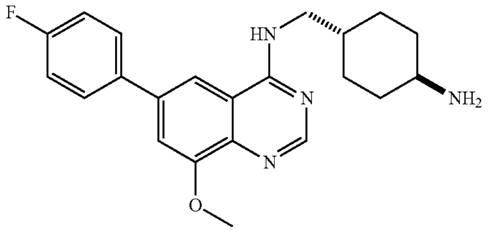

Step 1: Preparation of Benzyl ((1r,4r)-4-(((6-(4-fluorophenyl)-8-methoxyquinazolin-4-yl)amino)methyl)cyclohexyl)carbamate

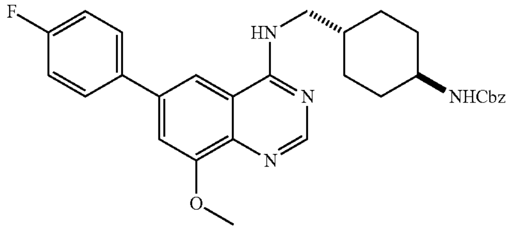

To a solution of 6-(4-fluorophenyl)-8-methoxyquinazolin-4-ol (Intermediate 3) (80 mg, 0.30 mmol) in N,N-dimethylformamide (2 mL) was successively added (benzotriazol-1-yloxy)tripyrrolidinophosphonium hexafluorophosphate (169 mg, 0.32 mmol) and di-isopropylethylamine (0.32 mL, 1.85 mmol). The resulting mixture was heated to 40° C. and stirred for 20 min, benzyl ((1r,4r)-4-(aminomethyl)cyclohexyl)carbamate (93 mg, 0.36 mmol) was then added and the heating was maintained at 40° C. for 18 hours. After return to room temperature, the mixture was diluted with ethyl acetate (50 mL) and water (20 mL). The organic phase was washed with brine (2×20 mL), passed through a hydrophobic frit and the solvent was removed in vacuo. The residue was used directly in the next step without any further purification.

Step 2: Preparation of N-(((1r,4r)-4-aminocyclohexyl)methyl)-6-(4-fluorophenyl)-8-methoxyquinazolin-4-amine

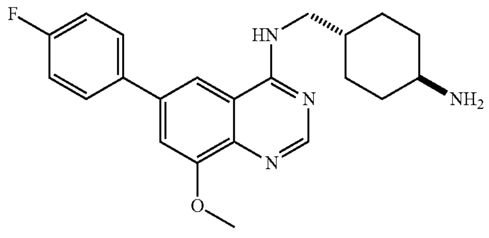

Nitrogen was bubbled for 5 min through a solution of benzyl ((1r,4r)-4-(((6-(4-fluorophenyl)-8-methoxyquinazolin-4-yl)amino)methyl)cyclohexyl)carbamate (152 mg, 0.30 mmol) in MeOH (3.0 mL) then Pd/C (10%) (31 mg, 0.03 mmol) was added followed by portion wise addition of sodium borohydride (88 mg, 2.36 mmol). The resulting mixture was stirred at room temperature for 2 hours. The reaction was filtered through Celite® and then loaded onto an SCX cartridge. The cartridge was washed with methanol and the filtrate was collected when eluting with a 7M solution of ammonia in methanol. The solvent was removed in vacuo and the residue was purified by preparative HPLC to give the title compound (2.0 mg, 1.8%) as a brown solid.

$^1$H NMR (400 MHz, MeOD) δ 8.45 (s, 1H), 8.31 (s, 1H), 7.80 (d, J=1.6 Hz, 1H), 7.72-7.68 (m, 2H), 7.38 (d, J=1.6 Hz, 1H), 7.13 (dd, J=8.8, 8.8 Hz, 2H), 3.98 (s, 3H), 3.41 (d, J=7.0 Hz, 2H), 2.95-2.86 (m, 1H), 1.97-1.87 (m, 4H), 1.80-1.70 (m, 1H), 1.32-1.03 (m, 4H). LCMS (Method 4): [MH+]=381 at 2.43 min.

Intermediate 4

(R)-6-Bromo-8-methoxy-N-(1-(6-methylpyridazin-3-yl)ethyl)quinazolin-4-amine

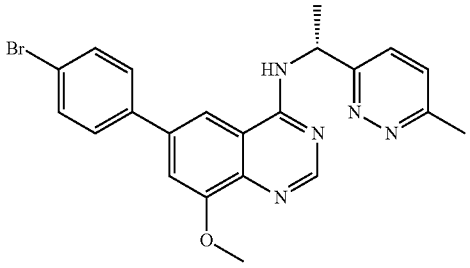 [SMILES: COc1cc(-c2ccc(Br)cc2)cc2c(N[C@H](C)c3ccc(C)nn3)ncnc12]

To a solution of 6-bromo-8-methoxyquinazolin-4-ol (Intermediate 2) (65 mg, 0.27 mmol) in N,N-dimethylformamide (1.5 mL) was successively added (benzotriazol-1-yloxy)tripyrrolidinophosphonium hexafluorophosphate (139 mg, 0.27 mmol) and di-isopropylethylamine (0.2 mL, 0.81 mmol). The resulting mixture was heated to 60° C. for one hour then (R)-1-(6-methylpyridazin-3-yl)ethan-1-amine (65 mg, 0.27 mmol) was added and the heating was maintained at 60° C. for 18 hours. After return to room temperature, the reaction mixture was directly concentrated onto silica gel and purified by chromatography on silica gel eluting with 0-100% (10% MeOH in ethyl acetate) in ethyl acetate to give the title compound as a beige solid (100 mg, quantitative yield).

LCMS (Method 4): [MH+]=374 at 2.42 min.

The following intermediates reported in the table below were synthesised following the same procedure described for the preparation of (R)-6-Bromo-8-methoxy-N-(1-(6-methylpyridazin-3-yl)ethyl)quinazolin-4-amine (Intermediate 4):

| Intermediate No. | Chemical name Structure | Analytical data LC-MS |
|---|---|---|
| Intermediate 5 | 6-Bromo-8-methoxy-N-[(1R)-1-[2-(trifluoromethyl)pyrimidin-5-yl]ethyl]quinazolin-4 amine 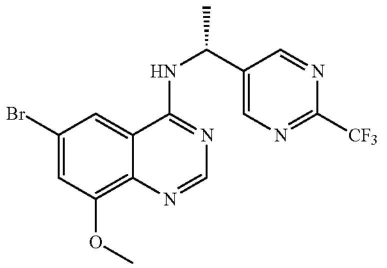 [SMILES: COc1cc(Br)cc2c(N[C@H](C)c3cnc(C(F)(F)F)nc3)ncnc12] | LCMS (Method 4): [MH+] = 428 at 3.19 min |
| Intermediate 6 | 6-Bromo-8-methoxy-N-((6-methylpyridazin-3-yl)methyl)quinazolin-4-amine 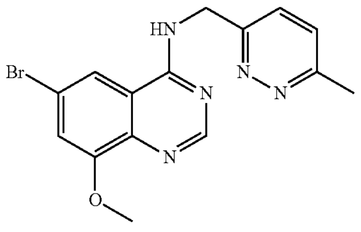 [SMILES: COc1cc(Br)cc2c(NCc3ccc(C)nn3)ncnc12] | LCMS (Method 3): [MH+] = 360 at 3.06 min. |
| Intermediate 7 | (R)-5-(1-((6-Bromo-8-methoxyquinazolin-4-yl)amino)ethyl)-2-(trifluoromethyl) pyridine 1-oxide 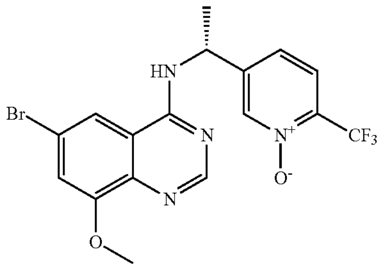 [SMILES: COc1cc(Br)cc2c(N[C@H](C)c3ccc(C(F)(F)F)[n+]([O-])c3)ncnc12] | LCMS (Method 4): [MH+] = 443 at 2.72 min. |

Example 115

8-Methoxy-6-(5-methyl-1,3,4-thiadiazol-2-yl)-N-((6-methylpyridazin-3-yl)methyl)quinazolin-4-amine

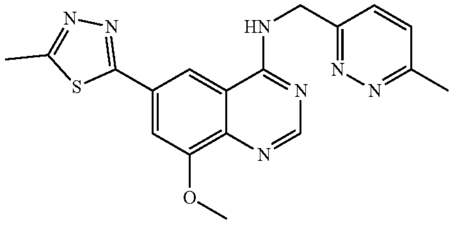

Step 1: Preparation of 8-methoxy-N-((6-methylpyridazin-3-yl)methyl)-6-(4,4,5,5-tetramethyl-1,3,2-dioxaborolan-2-yl)quinazolin-4-amine

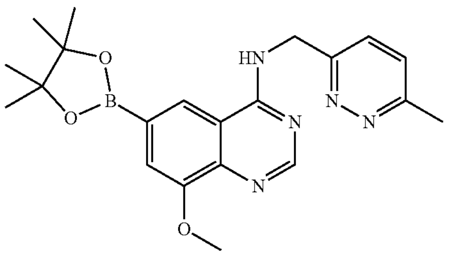

Nitrogen was bubbled for 5 min through a mixture of 6-bromo-8-methoxy-N-((6-methylpyridazin-3-yl)methyl)quinazolin-4-amine (Intermediate 6) (250 mg, 0.69 mmol), bis-(pinacolato)diboron (194 mg, 0.76 mmol), [1,1'-bis-(diphenylphosphino)-ferrocene]dichloropalladium(II) (25 mg, 0.03 mmol) and potassium acetate (204 mg, 2.08 mmol) in 1,4-dioxane (15.0 mL). The mixture was heated at 90° C. for 18 hours. After return to room temperature, the reaction was filtered through Celite® and the solvent was removed in vacuo. The residue was taken on to the next step without further purification.

Step 2: Preparation of 8-methoxy-6-(5-methyl-1,3,4-thiadiazol-2-yl)-N-((6-methylpyridazin-3-yl)methyl)quinazolin-4-amine

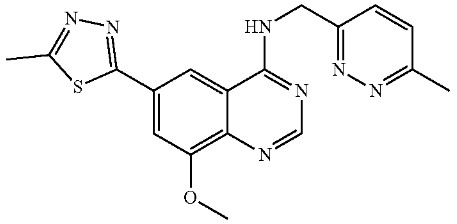

Nitrogen was bubbled for 5 min through a mixture of 2-bromo-5-methyl-1,3,4-thiadiazole (34 mg, 0.19 mmol), 8-methoxy-N-((6-methylpyridazin-3-yl)methyl)-6-(4,4,5,5-tetramethyl-1,3,2-dioxaborolan-2-yl)quinazolin-4-amine (70 mg, 0.17 mmol), potassium carbonate (36 mg, 0.26 mmol) and water (0.5 mL) in 1,4-dioxane (4.0 mL), then tetrakis(triphenylphosphine)palladium(0) (20 mg, 0.02 mmol) was added. The resulting mixture was heated to 95° C. for 16 hours. After return to room temperature, the reaction was filtered through Celite®, rinsed with ethyl acetate (20 mL). The organic phases were combined, passed through a hydrophobic frit and the solvent was removed in vacuo. The residue was purified by preparative HPLC to give the title compound as an off-white solid (21.0 mg, 32%).

$^1$H NMR (400 MHz, DMSO): δ 9.31 (dd, J=5.8, 5.8 Hz, 1H), 8.47 (s, 1H), 8.44 (d, J=1.7 Hz, 1H), 7.80 (d, J=1.4 Hz, 1H), 7.58 (d, J=8.7 Hz, 1H), 7.51 (d, J=8.7 Hz, 1H), 5.03 (d, J=5.8 Hz, 2H), 4.03 (s, 3H), 2.84 (s, 3H), 2.60 (s, 3H). LCMS (Method 3): [MH+]=380 at 2.13 min.

The following compounds reported in the table below were prepared according to the same procedure described for the preparation of 8-methoxy-6-(5-methyl-1,3,4-thiadiazol-2-yl)-N-((6-methylpyridazin-3-yl)methyl)quinazolin-4-amine:

| Example No. | Chemical Name<br>Structure | Analytical data<br>$^1$H NMR<br>LC-MS |
|---|---|---|
| Example 116 | 8-Methoxy-N-((6-methylpyridazin-3-yl)methyl)-6-(5-methylpyridin-2-yl)quinazolin-4-amine<br>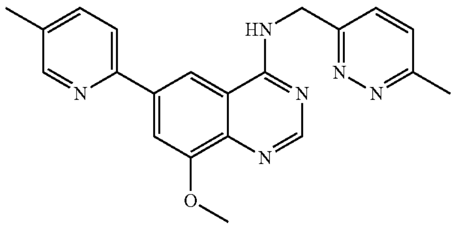 | $^1$H NMR (400 MHz, DMSO): δ 9.11 (dd, J = 5.9, 5.9 Hz, 1 H), 8.57 (dd, J = 1.7, 6.7 Hz, 2 H), 8.43 (s, 1 H), 8.12 (d, J = 8.2 Hz, 1 H), 8.04 (d, J = 1.4 Hz, 1 H), 7.81 (dd, J = 1.9, 8.2 Hz, 1 H), 7.57 (d, J = 8.5 Hz, 1 H), 7.50 (d, J = 8.8 Hz, 1 H), 5.04 (d, J = 5.8 Hz, 2 H), 4.02 (s, 3 H), 2.60 (s, 3 H), 2.39 (s, 3 H). LCMS (Method 4): [MH+] = 373 at 2.46 min. |

-continued

| Example No. | Chemical Name<br>Structure | Analytical data<br>$^1$H NMR<br>LC-MS |
|---|---|---|
| Example 117 | 6-(8-Methoxy-4-(((6-methylpyridazin-3-yl)methyl)amino)quinazolin-6-yl)nicotinonitrile<br>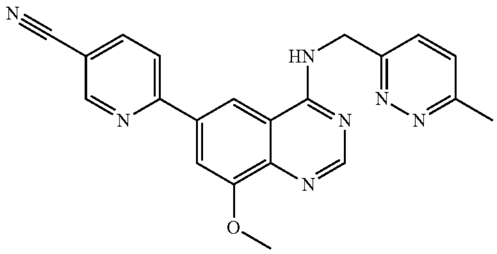 [SMILES: COc1cc(-c2ccc(C#N)cn2)cc2c(NCc3ccc(C)nn3)ncnc12] | $^1$H NMR (400 MHz, DMSO): δ 9.22-9.16 (m, 2 H), 8.72 (d, J = 1.5 Hz, 1 H), 8.55-8.50 (m, 1 H), 8.46 (s, 1 H), 8.39 (d, J = 8.5 Hz, 1 H), 8.05 (d, J = 1.5 Hz, 1 H), 7.56 (d, J = 8.7 Hz, 1 H), 7.49 (d, J = 8.7 Hz, 1 H), 5.04 (d, J = 5.8 Hz, 2 H), 4.02 (s, 3 H), 2.59 (s, 3 H). LCMS (Method 3): [MH+] = 384 at 3.09 min. |
| Example 118 | 6-(5-(Difluoromethyl)pyridin-2-yl)-8-methoxy-N-((6-methylpyridazin-3-yl)methyl)quinazolin-4-amine<br>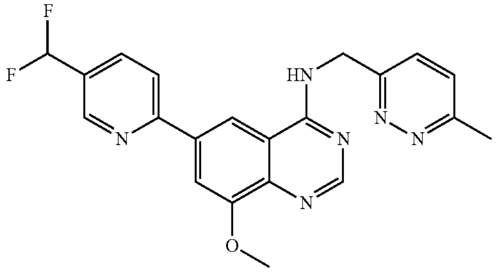 [SMILES: COc1cc(-c2ccc(C(F)F)cn2)cc2c(NCc3ccc(C)nn3)ncnc12] | $^1$H NMR (400 MHz, DMSO): δ 9.19 (dd, J = 5.8, 5.8 Hz, 1 H), 8.95 (s, 1 H), 8.68 (d, J = 1.5 Hz, 1 H), 8.46 (s, 1 H), 8.35 (d, J = 8.4 Hz, 1 H), 8.22 (d, J = 8.4 Hz, 1 H), 8.07 (d, J = 1.4 Hz, 1 H), 7.58 (d, J = 8.7 Hz, 1 H), 7.51 (d, J = 8.7 Hz, 1 H), 7.25 (t, J = 55.4 Hz, 1 H), 5.06 (d, J = 5.8 Hz, 2 H), 4.04 (s, 3 H), 2.61 (s, 3 H). LCMS (Method 3): [MH+] = 409 at 3.33 min. |
| Example 119 | 6-(8-Methoxy-4-(((6-methylpyridazin-3-yl)methyl)amino)quinazolin-6-yl)pyridin-3-ol<br>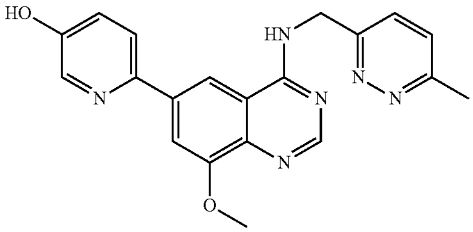 | $^1$H NMR (400 MHz, DMSO): δ 10.74-9.99 (m, 1 H), 9.03 (dd, J = 5.8, 5.8 Hz, 1 H), 8.42 (d, J = 1.4 Hz, 1 H), 8.39 (s, 1 H), 8.27 (d, J = 2.5 Hz, 1 H), 8.02 (d, J = 8.8 Hz, 1 H), 7.94 (d, J = 1.4 Hz, 1 H), 7.54 (d, J = 8.5 Hz, 1 H), 7.48 (d, J = 8.7 Hz, 1 H), 7.30 (dd, J = 2.8, 8.7 Hz, 1 H), 5.02 (d, J = 5.8 Hz, 2 H), 3.98 (s, 3 H), 2.59 (s, 3 H). LCMS (Method 4): [MH+] = 375 at 2.14 min. |
| Example 120 | 6-(5-(Difluoromethoxy)pyridin-2-yl)-8-methoxy-N-((6-methylpyridazin-3-yl)methyl)quinazolin-4-amine<br>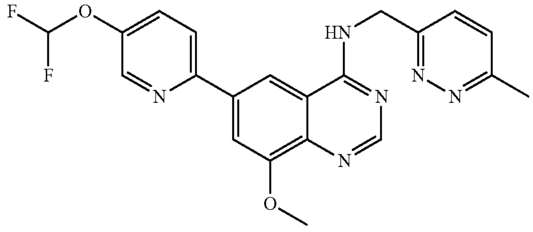 [SMILES: COc1cc(-c2ccc(OC(F)F)cn2)cc2c(NCc3ccc(C)nn3)ncnc12] | $^1$H NMR (400 MHz, DMSO): δ 9.13 (dd, J = 5.8, 5.8 Hz, 1 H), 8.64 (d, J = 2.9 Hz, 1 H), 8.58 (d, J = 1.5 Hz, 1 H), 8.45 (s, 1 H), 8.27 (d, J = 8.9 Hz, 1 H), 8.00 (d, J = 1.4 Hz, 1 H), 7.89 (dd, J = 2.9, 8.8 Hz, 1 H), 7.57 (d, J = 8.8 Hz, 1 H), 7.51 (d, J = 8.7 Hz, 1 H), 7.42 (t, J = 73.4 Hz, 1 H), 5.05 (d, J = 5.8 Hz, 2 H), 4.02 (s, 3 H), 2.61 (s, 3 H). LCMS (Method 4): [MH+] = 425 at 2.78 min. |

-continued

| Example No. | Chemical Name<br>Structure | Analytical data<br>$^1$H NMR<br>LC-MS |
|---|---|---|
| Example 121 | 8-Methoxy-N((6-methylpyridazin-3-yl)methyl)-6-(5-(methylsulfonyl)pyridin-2-yl)quinazolin-4-amine<br>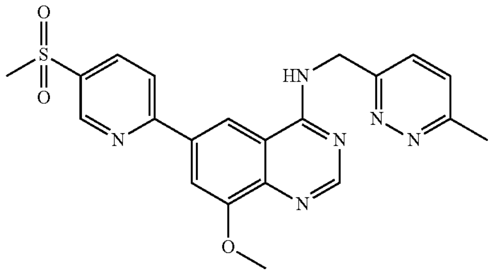 | $^1$H NMR (400 MHz, DMSO): δ 9.26 (dd, J = 5.8, 5.8 Hz, 1 H), 9.20 (d, J = 2.0 Hz, 1 H), 8.75 (d, J = 1.5 Hz, 1 H), 8.53-8.42 (m, 3 H), 8.08 (d, J = 1.4 Hz, 1 H), 7.59 (d, J = 8.7 Hz, 1 H), 7.51 (d, J = 8.8 Hz, 1 H), 5.06 (d, J = 5.8 Hz, 2 H), 4.04 (s, 3 H), 3.40 (s, 3 H), 2.61 (s, 3 H). LCMS (Method 3): [MH+] = 437 at 3.08 min. |
| Example 122 | 6-(8-Methoxy-4-(((6-methylpyridazin-3-yl)methyl)amino)quinazolin-6-yl)nicotinamide<br>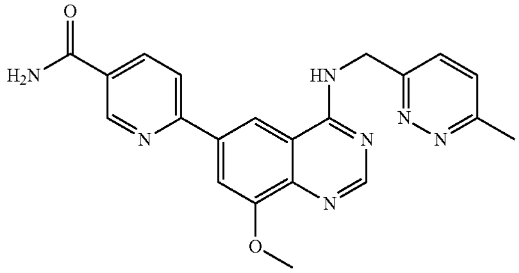 [SMILES: COc1cc(-c2ccc(C(N)=O)cn2)cc2c(NCc3ccc(C)nn3)ncnc12] | $^1$H NMR (400 MHz, DMSO): δ 9.20-9.17 (m, 2 H), 8.69 (d, J = 1.4 Hz, 1 H), 8.46 (s, 1 H), 8.40 (dd, J = 2.3, 8.4 Hz, 1 H), 8.30 (d, J = 8.2 Hz, 1 H), 8.26 (s, 1 H), 8.08 (d, J = 1.4 Hz, 1 H), 7.69-7.67 (m, 1 H), 7.58 (d, J = 8.7 Hz, 1 H), 7.51 (d, J = 8.5 Hz, 1 H), 5.06 (d, J = 5.8 Hz, 2 H), 4.04 (s, 3 H), 2.61 (s, 3 H). LCMS (Method 3): [MH+] = 402 at 2.65 min. |
| Example 123 | 6-(8-Methoxy-4-(((6-methylpyridazin-3-yl)methyl)amino)quinazolin-6-yl)-N-methylnicotinamide<br>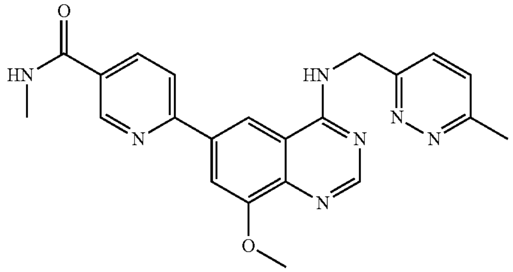 [SMILES: CNC(=O)c1ccc(-c2cc(OC)c3ncnc(NCc4ccc(C)nn4)c3c2)nc1] | $^1$H NMR (400 MHz, DMSO): δ 9.19 (t, J = 5.5 Hz, 1 H), 9.14 (d, J = 2.3 Hz, 1 H), 8.74-8.70 (m, 1 H), 8.68 (d, J = 1.4 Hz, 1 H), 8.46 (s, 1 H), 8.36 (dd, J = 2.3, 8.4 Hz, 1 H), 8.30 (d, J = 8.4 Hz, 1 H), 8.08 (d, J = 1.4 Hz, 1 H), 7.58 (d, J = 8.7 Hz, 1 H), 7.51 (d, J = 8.8 Hz, 1H), 5.06 (d, J = 5.4 Hz, 2 H), 4.04 (s, 3 H), 2.87 (d, J = 4.6 Hz, 3 H), 2.61 (s, 3 H). LCMS (Method 4): [MH+] = 416 at 2.12 min. |
| Example 124 | 8-Methoxy-N-((6-methylpyridazin-3-yl)methyl)-6-(5-(trifluoromethoxy)pyridin-2-yl)quinazolin-4-amine<br>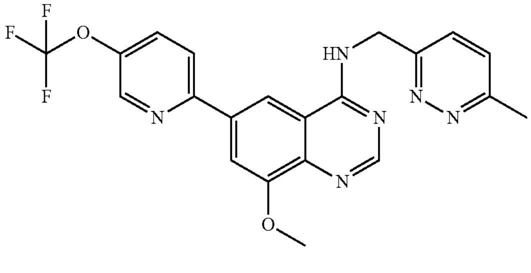 [SMILES: COc1cc(-c2ccc(OC(F)(F)F)cn2)cc2c(NCc3ccc(C)nn3)ncnc12] | $^1$H NMR (400 MHz, DMSO): δ 9.17 (dd, J = 5.9, 5.9 Hz, 1 H), 8.83 (d, J = 2.8 Hz, 1 H), 8.62 (d, J = 1.5 Hz, 1 H), 8.46 (s, 1 H), 8.34 (d, J = 8.9 Hz, 1H) 8.14 (dd, J = 1.9, 8.7 Hz, 1 H), 8.01 (d, J = 1.5 Hz, 1 H), 7.58 (d, J = 8.7 Hz, 1 H), 7.51 (d, J = 8.7 Hz, 1 H), 5.05 (d, J = 5.8 Hz, 2 H), 4.03 (s, 3 H), 2.61 (s, 3 H). LCMS (Method 4): [MH+] = 443 at 3.10 min. |

-continued

| Example No. | Chemical Name<br>Structure | Analytical data<br>$^1$H NMR<br>LC-MS |
|---|---|---|
| Example 125 | 6[5-(Dimethylamino)-2-pyridyl]-8-methoxy-N-[(6-methylpyridazin-3-yl)methyl]quinazolin-4-amine<br>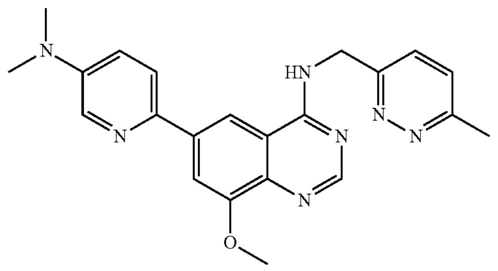 | $^1$H NMR (400 MHz, DMSO): δ 8.43-8.38 (m, 2 H), 8.26 (d, J = 2.9 Hz, 1 H), 8.08-8.01 (m, 2 H), 7.56 (d, J = 8.5 Hz, 1 H), 7.51 (d, J = 8.7 Hz, 1H) 7.27 (dd, J = 3.1, 9.0 Hz, 1 H), 7.22-7.17 (m, 1 H), 5.04 (d, J = 5.8 Hz, 2 H), 4.00 (s, 3 H), 3.03 (s, 6 H), 2.98 (s, 3 H). LCMS (Method 4): [MH+] = 402 at 2.33 min. |
| Example 126 | 6-(5-Cyclopropylpyridin-2-yl)-8-methoxy-N-((6-methylpyridazin-3-yl)methyl)quinazolin-4-amine<br>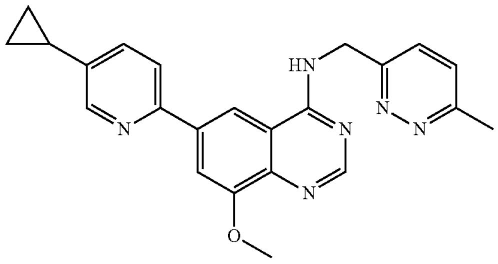 [SMILES: COc1cc(-c2ccc(C3CC3)cn2)cc2c(NCc3ccc(C)nn3)ncnc12] | $^1$H NMR (400 MHz, DMSO): δ 9.11 (dd, J = 5.8, 5.8 Hz, 1 H), 8.55 (dd, J =1.7, 7.2 Hz, 2 H), 8.43 (s, 1 H) 8.09 (d, J = 8.3 Hz, 1 H), 8.03 (d, J = 1.3 Hz, 1 H), 7.61 (dd, J = 2.9, 8.6 Hz, 1 H), 7.57 (d, J = 9.2 Hz, 1H), 7.50 (d, J = 8.7 Hz, 1 H), 5.04 (d, J = 5.6 Hz, 2 H), 4.01 (s, 3 H), 2.60 (s, 3 H), 2.09-2.02 (m, 1 H), 1.11-1.05 (m, 2 H), 0.87-0.82 (m, 2 H). LCMS (Method 3): [MH+] = 399 at 3.82 min. |
| Example 127 | 6-(5-Chloropyridin-2-yl)-8-methoxy-N-((6-methylpyridazin-3-yl)methyl)quinazolin-4-amine<br>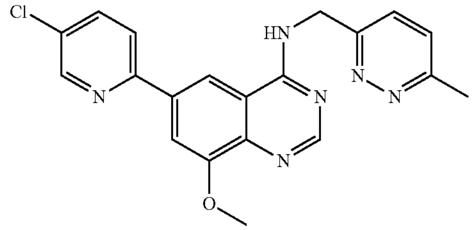 [SMILES: COc1cc(-c2ccc(Cl)cn2)cc2c(NCc3ccc(C)nn3)ncnc12] | $^1$H NMR (400 MHz, DMSO): δ 9.14 (dd, J = 5.8, 5.8 Hz, 1 H), 8.79 (d, J = 2.5 Hz, 1 H), 8.61 (d, J = 1.6 Hz, 1 H), 8.45 (s, 1 H), 8.25 (d, J = 8.7 Hz, 1 H), 8.16 (dd, J = 2.5, 8.7 Hz, 1 H), 8.01 (d, J = 1.4 Hz, 1 H), 7.57 (d, J = 8.7 Hz, 1H), 7.51 (d, J = 8.7 Hz, 1 H), 5.05 (d, J = 5.8 Hz, 2 H), 4.02 (s, 3 H), 2.61 (s, 3 H). LCMS (Method 3): [MH+] = 393 at 3.51 min. |
| Example 128 | 8-Methoxy-N-((6-methylpyridazin-3-yl)methyl)-6-(6-methylpyridin-3-yl)quinazolin-4-amine<br>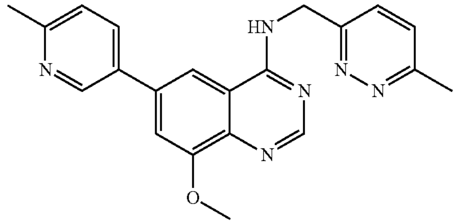 | $^1$H NMR (400 MHz, DMSO): δ 9.05 (t, J = 5.9 Hz, 1 H), 9.00 (d, J = 2.6 Hz, 1 H), 8.43 (s, 1 H), 8.25 (d, J = 1.6 Hz, 1 H), 8.21-8.17 (m, 1 H), 7.61-7.55 (m, 2 H), 7.50 (d, J = 8.7 Hz, 1 H), 7.43 (d, J = 8.2 Hz, 1 H), 5.04 (d, J = 5.8 Hz, 2 H), 4.03 (s, 3 H), 2.61 (s, 3 H), 2.56 (s, 3 H). LCMS (Method 3): [MH+] = 373 at 2.93 min. |

-continued

| Example No. | Chemical Name<br>Structure | Analytical data<br>$^1$H NMR<br>LC-MS |
|---|---|---|
| Example 129 | 8-Methoxy-6-(5-methyl-1,3,4-oxadiazol-2-yl)-N-((6-methylpyridazin-3-yl)methyl)quinazolin-4-amine<br>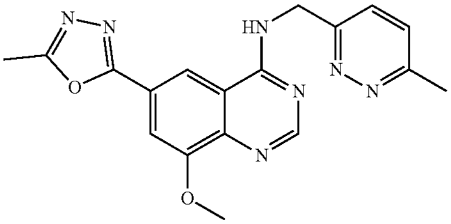 | $^1$H NMR (400 MHz, DMSO): δ 9.37 (s, 1 H), 8.58 (d, J = 1.5 Hz, 1 H), 8.49 (s, 1 H), 7.72 (d, J = 1.5 Hz, 1 H), 7.56 (d, J = 8.5 Hz, 1 H), 7.50 (d, J = 8.7 Hz, 1 H), 5.02 (d, J = 3.6 Hz, 2 H), 4.02 (s, 3 H), 2.65 (s, 3 H), 2.60 (s, 3 H). LCMS (Method 4): [MH+] = 364 at 2.03 min. |
| Example 130 | 8-Methoxy-6-(1-methyl-1H-pyrazol-3-yl)-N((6-methylpyridazin-3-yl)methyl)quinazolin-4-amine<br>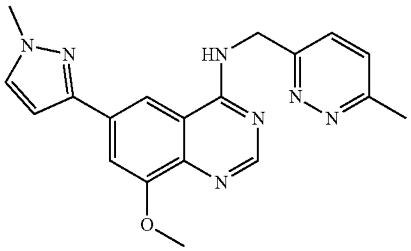 [SMILES: COc1cc(-c2ccn(C)n2)cc2c(NCc3ccc(C)nn3)ncnc12] | $^1$H NMR (400 MHz, DMSO): δ 8.97 (dd, J = 5.8, 5.8 Hz, 1 H), 8.38 (s, 1 H), 8.25 (d, J = 1.4 Hz, 1 H), 7.82 (d, J = 2.3 Hz, 1 H), 7.69 (d, J = 1.3 Hz, 1 H), 7.55 (d, J = 8.7 Hz, 1 H), 7.50 (d, J = 8.7 Hz, 1 H), 6.85 (d, J = 2.3 Hz, 1 H), 5.02 (d, J = 5.6 Hz, 2 H), 3.98 (s, 3 H), 3.95 (s, 3 H), 2.60 (s, 3 H). LCMS (Method 3): [MH+] = 362 at 2.74 min. |
| Example 131 | 6-(1,5-Dimethyl-1H-pyrazol-3-yl)-8-methoxy-N-((6-methylpyridazin-3-yl)methyl)quinazolin-4-amine<br>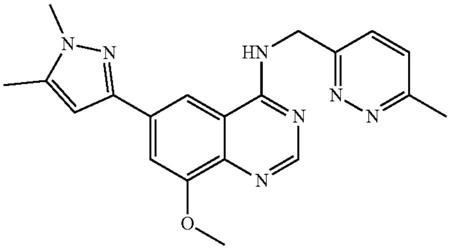 | $^1$H NMR (400 MHz, DMSO): δ 8.95 (dd, J = 5.9, 5.9 Hz, 1 H), 8.37 (s, 1 H), 8.20 (d, J = 1.4 Hz, 1 H), 7.65 (d, J = 1.3 Hz, 1 H), 7.55 (d, J = 8.7 Hz, 1 H), 7.50 (d, J = 8.7 Hz, 1 H), 6.66 (s, 1 H), 5.02 (d, J = 5.8 Hz, 2 H), 3.97 (s, 3 H), 3.82 (s, 3 H), 2.60 (s, 3 H), 2.34 (s, 3 H). LCMS (Method 4): [MH+] = 376 at 2.44 min. |
| Example 132 | 8-Methoxy-6-(6-methoxypyridazin-3-yl)-N-[(6-methylpyridazin-3-yl)methyl]quinazolin-4-amine<br>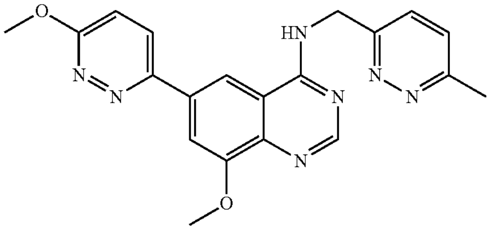 | $^1$H NMR (400 MHz, DMSO): δ 9.07 (dd, J = 5.7, 5.7 Hz, 1 H), 8.46 (s, 1 H), 8.38 (d, J = 1.6 Hz, 1 H), 8.23 (d, J = 9.8 Hz, 1 H), 7.78 (d, J = 1.5 Hz, 1 H), 7.58 (d, J = 8.7 Hz, 1 H), 7.51 (d, J = 8.7 Hz, 1 H), 7.20 (d, J = 9.8 Hz, 1 H), 5.05 (d, J = 5.8 Hz, 2 H), 4.01 (s, 3 H), 3.82 (s, 3 H), 2.61 (s, 3 H). LCMS (Method 3): [MH+] = 390 at 2.84 min. |

-continued

| Example No. | Chemical Name<br>Structure | Analytical data<br>$^1H$ NMR<br>LC-MS |
|---|---|---|
| Example 133 | 8-Methoxy-6-(6-methylpyridazin-3-yl)-N-[(6-methylpyridazin-3-yl)methyl]quinazolin-4-amine<br>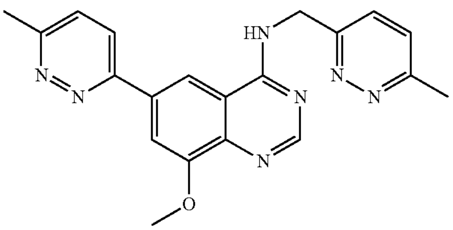 | $^1H$ NMR (400 MHz, DMSO): δ 9.17 (dd, J = 5.6, 5.6 Hz, 1 H), 8.65 (d, J = 1.6 Hz, 1 H), 8.47 (s, 1 H), 8.32 (d, J = 8.8 Hz, 1 H), 8.10 (d, J = 1.5 Hz, 1 H), 7.78 (d, J = 8.8 Hz, 1 H), 7.58 (d, J = 8.7 Hz, 1 H), 7.51 (d, J = 8.7 Hz, 1 H), 5.05 (d, J = 5.5 Hz, 2 H), 4.05 (s, 3 H), 2.71 (s, 3 H), 2.60 (s, 3 H). LCMS (Method 3): [MH+] = 374 at 2.88 min. |
| Example 134 | 8-Methoxy-N-[(6-methylpyridazin-3-yl)methyl]-6-(5-methylpyrimidin-2-yl)quinazolin-4-amine<br>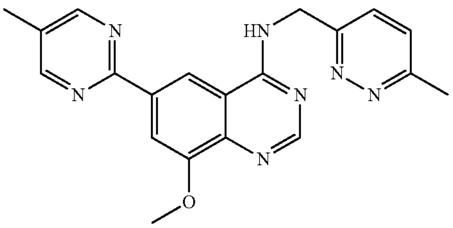 | $^1H$ NMR (400 MHz, DMSO): δ 9.29 (dd, J = 5.7, 5.7 Hz, 1 H), 8.93 (d, J = 1.5 Hz, 1 H), 8.84 (s, 2 H), 8.44 (s, 1 H), 8.22 (d, J = 1.5 Hz, 1H), 7.54 (d, J = 8.7 Hz, 1 H), 7.49 (d, J = 8.7 Hz, 1 H), 5.01 (d, J = 5.8 Hz, 2 H), 4.02 (s, 3 H), 2.60 (s, 3 H), 2.38 (s, 3 H). LCMS (Method 3): [MH+] = 374 at 3.25 min. |
| Example 135 | 6-(5-Fluoro-2-pyridyl)-8-methoxy-N-[(6-methylpyridazin-3-yl)methyl]quinazolin-4-amine<br>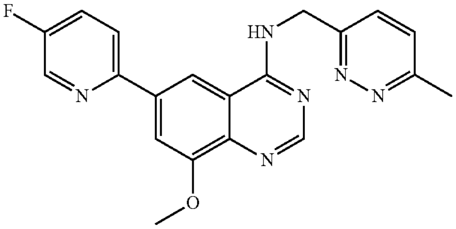 | $^1H$ NMR (400 MHz, DMSO): δ 9.12 (dd, J = 5.9, 5.9 Hz, 1 H), 8.74 (d, J = 3.0 Hz, 1 H), 8.57 (d, J = 1.6 Hz, 1 H), 8.44 (s, 1 H), 8.27 (dd, J = 4.3, 8.9 Hz, 1 H), 8.00-7.94 (m, 2 H), 7.57 (d, J = 8.7 Hz, 1 H), 7.51 (d, J = 8.7 Hz, 1 H), 5.05 (d, J = 5.8 Hz, 2 H), 4.02 (s, 3 H), 2.61 (s, 3 H). LCMS (Method 3): [MH+] = 377 at 3.45 min. |
| Example 136 | 6-(5-Fluoropyrimidin-2-yl)-8-methoxy-N-[(6-methylpyridazin-3-yl)methyl]quinazolin-4-amine<br>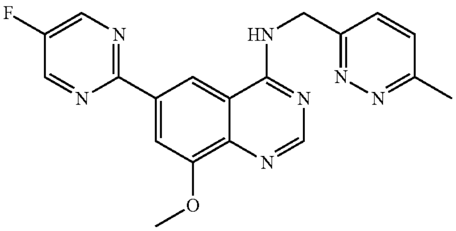 [SMILES: COc1cc(-c2ncc(F)cn2)cc2c(NCc3ccc(C)nn3)ncnc12] | $^1H$ NMR (400 MHz, CDCl3): δ 8.76 (s, 1 H), 8.70 (s, 2 H), 8.61 (d, J = 1.5 Hz, 1 H), 8.21 (d, J = 1.4 Hz, 1 H), 7.57 (dd, J = 4.3, 4.3 Hz, 1 H), 7.51 (d, J = 8.5 Hz, 1 H), 7.37 (d, J = 8.7 Hz, 1 H), 5.13 (d, J = 4.6 Hz, 2 H), 4.17 (s, 3 H), 2.76 (s, 3 H). LCMS (Method 3): [MH+] = 378 at 3.3 min. |

-continued

| Example No. | Chemical Name<br>Structure | Analytical data<br>$^1H$ NMR<br>LC-MS |
|---|---|---|
| Example 137 | 6-[8-Methoxy-4-[(6-methylpyridazin-3-yl)methylamino]quinazolin-6-yl]pyridazin-3-ol<br>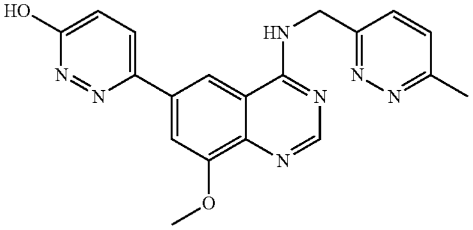 [SMILES: COc1cc(-c2ccc(O)nn2)cc2c(NCc3ccc(C)nn3)ncnc12] | $^1H$ NMR (400 MHz, DMSO): δ 13.32 (s, 1 H), 9.05 (brs, 1 H), 8.44 (s, 1 H), 8.34 (d, J = 1.6 Hz, 1 H), 8.21 (d, J = 10.1 Hz, 1 H), 7.73 (d, J = 1.8 Hz, 1 H), 7.57 (d, J = 8.7 Hz, 1 H), 7.51 (d, J = 8.7 Hz, 1 H), 7.13 (d, J = 9.9 Hz, 1 H), 5.03 (s, 2 H), 3.98 (s, 3 H), 2.60 (s, 3 H). LCMS (Method 3): [MH+] = 376 at 2.33 min. |
| Example 138 | 8-Methoxy-N-((6-methylpyridazin-3-yl)methyl)-6-(5-(trifluoromethyl)pyridin-2-yl)quinazolin-4-amine<br>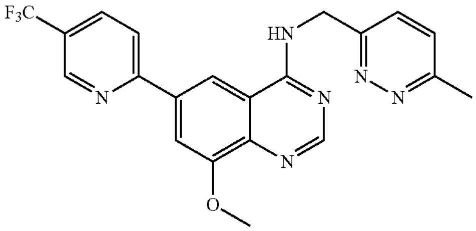 [SMILES: COc1cc(-c2ccc(C(F)(F)F)cn2)cc2c(NCc3ccc(C)nn3)ncnc12] | $^1H$ NMR (400 MHz, DMSO): δ 9.21 (dd, J = 5.7, 5.7 Hz, 1 H), 9.11 (s, 1 H), 8.72 (d, J = 1.5 Hz, 1 H), 8.48 (s, 1 H), 8.43 (s, 2 H), 8.08 (d, J = 1.4 Hz, 1 H), 7.58 (d, J = 8.7 Hz, 1 H), 7.51 (d, J = 8.7 Hz, 1 H), 5.06 (d, J = 5.6 Hz, 2 H), 4.04 (s, 3 H), 2.61 (s, 3 H). LCMS (Method 4): [MH+] = 427 at 3.06 min. |
| Example 139 | 8-Methoxy-6-(5-methoxypyridin-2-yl)-N-((6-methylpyridazin-3-yl)methyl)quinazolin-4-amine<br>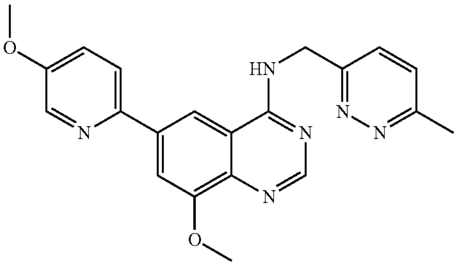 [SMILES: COc1ccc(-c2cc(OC)c3ncnc(NCc4ccc(C)nn4)c3c2)nc1] | $^1H$ NMR (400 MHz, DMSO): δ 9.08 (dd, J = 5.8, 5.8 Hz, 1 H), 8.50 (d, J = 1.4 Hz, 1 H), 8.45 (d, J = 2.6 Hz, 1H) 8.42 (s, 1 H), 8.17 (d, J = 2.8 Hz, 1 H), 8.00 (d, J = 1.4 Hz, 1 H), 7.60 (dd, J = 3.1, 8.9 Hz, 1 H), 7.57 (d, J = 8.8 Hz, 1 H), 7.51 (d, J = 8.5 Hz, 1 H), 5.04 (d, J = 5.6 Hz, 2 H), 4.01 (s, 3 H), 3.93 (s, 3 H), 2.60 (s, 3 H). LCMS (Method 3): [MH+] = 389 at 3.11 min. |

Example 140

8-Methoxy-N-((6-methylpyridazin-3-yl)methyl)-6-(5-methylthiazol-2-yl)quinazolin-4-amine

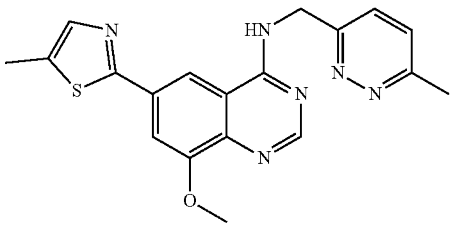

Step 1: Preparation of 6-(5,5-dimethyl-1,3,2-dioxaborinan-2-yl)-8-methoxy-N-((6-methylpyridazin-3-yl)methyl)quinazolin-4-amine

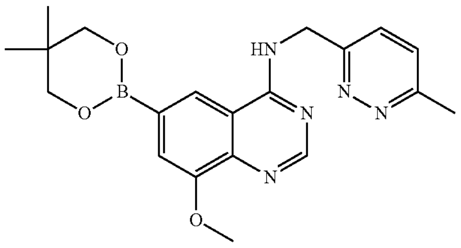

Nitrogen was bubbled for 5 min through a mixture of 6-bromo-8-methoxy-N-((6-methylpyridazin-3-yl)methyl)

quinazolin-4-amine (Intermediate 6) (100 mg, 0.28 mmol), bis(neopentyl glycolato)diboron (66 mg, 0.29 mmol), [1,1'-bis(diphenylphosphino)ferrocene]-dichloropalladium (II) complex with dichloromethane (10 mg, 0.02 mmol) and potassium acetate (54 mg, 0.55 mmol) in 1,4-dioxane (3.0 mL). The mixture was heated to 100° C. for 3 hours. After return to room temperature, the mixture was taken on to the next step as a 1,4-dioxane solution without further purification.

Step 2: Preparation of 8-methoxy-N-((6-methylpyridazin-3-yl)methyl)-6-(5-methylthiazol-2-yl)quinazolin-4-amine

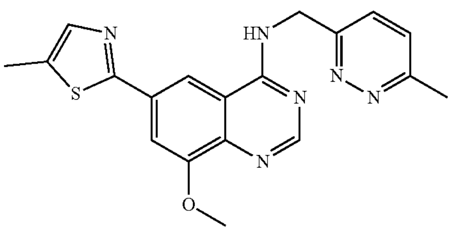

To the above solution of 6-(5,5-dimethyl-1,3,2-dioxaborinan-2-yl)-8-methoxy-N-((6-methylpyridazin-3-yl)methyl)quinazolin-4-amine (100 mg, 0.28 mmol) was added aqueous caesium carbonate (181 mg, 0.56 mmol, 0.4 mL), 2-bromo-5-methylthiazole (64 mg, 0.28 mmol) and tetrakis(triphenylphosphine)palladium(0) (20 mg, 0.02 mmol). The resulting mixture was heated to 95° C. for 16 hours. After return to room temperature, the mixture was filtered through Celite® and the filter cake rinsed with ethyl acetate (2×10 mL). The organic phases were washed with saturated aqueous ammonium chloride (10 mL), passed through a hydrophobic frit and the solvent was removed in vacuo. The residue was purified by preparative HPLC to give the title compound as an off-white solid (25 mg, 24%).

$^1$H NMR (400 MHz, DMSO): δ 9.24 (dd, J=5.7, 5.7 Hz, 1H), 8.43 (s, 1H), 8.37 (d, J=1.5 Hz, 1H), 7.75 (d, J=1.5 Hz, 1H), 7.68 (d, J=1.1 Hz, 1H), 7.57 (d, J=8.7 Hz, 1H), 7.50 (d, J=8.7 Hz, 1H), 5.02 (d, J=5.8 Hz, 2H), 4.00 (s, 3H), 2.60 (s, 3H), 2.50 (s, 3H). LCMS (Method 3): [MH+]=379 at 3.20 min.

The following compounds reported in the table below were prepared according to the same procedure described for the preparation of 8-methoxy-N-((6-methylpyridazin-3-yl)methyl)-6-(5-methylthiazol-2-yl)quinazolin-4-amine:

| Example No. | Chemical Name Structure | Analytical data $^1$H NMR LC-MS |
|---|---|---|
| Example 141 | 8-Methoxy-N-((6-methylpyridazin-3-yl)methyl)-6-(4-(trifluoromethyl)thiazol-2-yl)quinazolin-4-amine 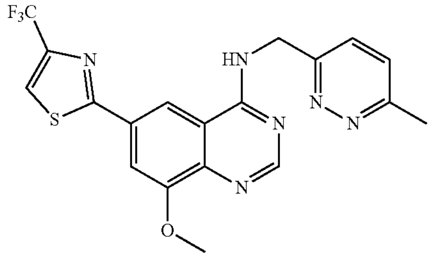 | $^1$H NMR (400 MHz, DMSO): δ 9.37 (dd, J = 5.7, 5.7 Hz, 1 H), 8.64 (s, 1 H), 8.53 (d, J = 1.6 Hz, 1 H), 8.47 (s, 1 H), 7.74 (d, J = 1.5 Hz, 1 H), 7.58 (d, J = 8.7 Hz, 1 H), 7.51 (d, J = 8.7 Hz, 1 H), 5.04 (d, J = 5.8 Hz, 2H), 4.04 (s, 3 H), 2.60 (s, 3 H). LCMS (Method 3): [MH+] = 433 at 2.95 min. |
| Example 142 | 6-(1,3-Dimethyl-1H-pyrazol-4-yl)-8-methoxy-N-((6-methylpyridazin-3-yl)methyl)quinazolin-4-amine 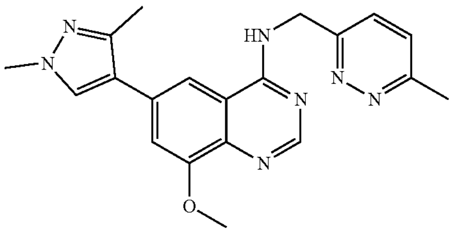 | $^1$H NMR (400 MHz, DMSO): δ 8.96 (dd, J = 5.9, 5.9 Hz, 1 H), 8.39 (s, 1 H), 7.96 (d, J = 1.4 Hz, 1 H), 7.62 (s, 1 H), 7.50 (d, J = 5.6 Hz, 3 H), 5.01 (d, J = 5.9 Hz, 2 H), 3.96 (s, 3 H), 3.88 (s, 3 H), 2.60 (s, 3 H), 2.29 (s, 3 H). LCMS (Method 3): [MH+] = 376 at 2.37 min. |

-continued

| Example No. | Chemical Name Structure | Analytical data $^1H$ NMR LC-MS |
|---|---|---|
| Example 143 | 8-Methoxy-N-((6-methylpyridazin-3-yl)methyl)-6-(4-methylthiazol-2-yl)quinazolin-4-amine 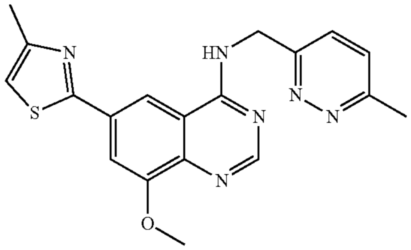 | $^1H$ NMR (400 MHz, DMSO): δ 9.26 (dd, J = 5.8, 5.8 Hz, 1 H), 8.44 - 8.41 (m, 2 H), 7.76 (d, J = 1.5 Hz, 1 H), 7.56 (d, J = 8.7 Hz, 1 H), 7.50 (d, J = 8.7 Hz, 1 H), 7.42 (s, 1 H), 5.03 (d, J = 5.9 Hz, 2 H), 4.01 (s, 3 H), 2.60 (s, 3 H), 2.49 (d, J = 0.7 Hz, 3 H). LCMS (Method 3): [MH+] = 379 at 3.39 min. |
| Example 144 | 8-Methoxy-N-((6-methylpyridazin-3-yl)methyl)-6-(2-methylthiazol-5-yl)quinazolin-4-amine 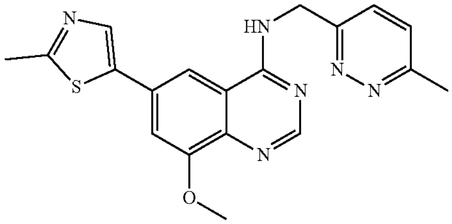 | $^1H$ NMR (400 MHz, DMSO): δ 8.98 (dd, J = 5.8, 5.8 Hz, 1 H), 8.32 (s, 1 H), 8.15 (s, 1 H), 7.98 (d, J = 1.6 Hz, 1 H), 7.47 (d, J = 8.7 Hz, 1 H), 7.42 (d, J = 8.4 Hz, 2 H), 4.94 (d, J = 5.8 Hz, 2 H), 3.92 (s, 3 H), 2.65 (s, 3 H), 2.52 (s, 3 H). LCMS (Method 4): [MH+] = 379 at 2.33 min. |
| Example 145 | (R)-5-(1-((8-Methoxy-6-(5-methyl-1,3,4-thiadiazol-2-yl)quinazolin-4-yl)amino)ethyl)-2-(trifluoromethyl)pyridine 1-oxide 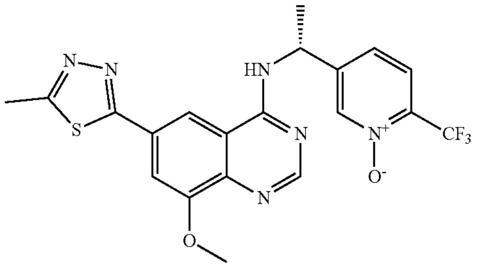 | $^1H$ NMR (400 MHz, DMSO): δ 8.72 (d, J = 7.2 Hz, 1 H), 8.52 (s, 1 H), 8.46 (d, J = 1.6 Hz, 1 H), 8.40 (s, 1 H), 7.84 (d, J = 8.4 Hz, 1 H), 7.67 (d, J = 1.5 Hz, 1 H), 7.50 (d, J = 8.3 Hz, 1 H), 5.52 - 5.46 (m, 1 H), 3.94 (s, 3 H), 2.77 (s, 3 H), 1.59 (d, J = 7.0 Hz, 3 H). LCMS (Method 4): [MH+] = 463 at 2.57 min. |
| Example 146 | (R)-8-Methoxy-6-(5-methyl-1,3,4-thiadiazol-2-yl)-N-(1-(6-methylpyridazin-3-yl)ethyl)quinazolin-4-amine 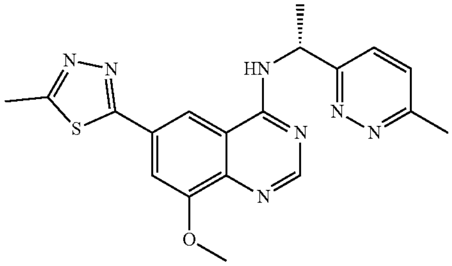 | $^1H$ NMR (400 MHz, DMSO): δ 8.87 (d, J = 7.4 Hz, 1 H), 8.50 (d, J = 1.5 Hz, 1 H), 8.34 (s, 1 H), 7.69 (d, J = 1.5 Hz, 1 H), 7.55 (d, J = 8.7 Hz, 1 H), 7.42 (d, J = 8.7 Hz, 1 H), 5.71 - 5.65 (m, 1 H), 3.93 (s, 3 H), 2.76 (s, 3 H), 2.52 (s, 3 H), 1.64 (d, J = 7.2 Hz, 3 H). LCMS (Method 4): [MH+] = 394 at 2.30 min. |

-continued

| Example No. | Chemical Name Structure | Analytical data $^1$H NMR LC-MS |
|---|---|---|
| Example 147 | (R)-8-Methoxy-6-(5-methyl-1,3,4-thiadiazol-2-yl)-N-(1-(2-(trifluoromethyl)pyrimidin-5-yl)ethyl)quinazolin-4-amine 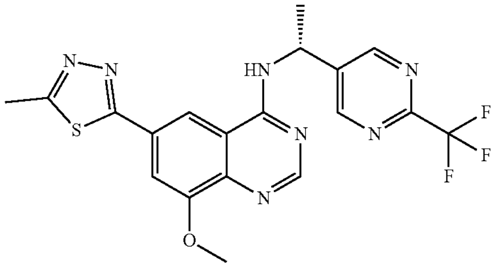 | $^1$H NMR (400 MHz, DMSO): δ 9.18 (s, 2 H), 8.88 (d, J = 6.9 Hz, 1 H), 8.52 (d, J = 1.6 Hz, 1 H), 8.48 (s, 1 H), 7.75 (d, J = 1.5 Hz, 1 H), 5.71 − 5.66 (m, 1 H), 4.02 (s, 3 H), 2.85 (s, 3 H), 1.75 (d, J = 7.2 Hz, 3 H). LCMS (Method 3): [MH+ = 448 at 4.09 min. |
| Example 148 | 8-Methoxy-6-(5-methylpyrimidin-2-yl)-N-[(1R)-1[2-(trifluoromethyl)pyrimidin-5-yl]ethyl]quinazolin-4-amine 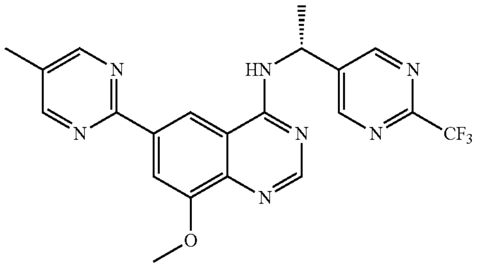 | $^1$H NMR (400 MHz, DMSO): δ 9.20 (s, 2 H), 8.98 − 8.94 (m, 2 H), 8.86 (s, 2 H), 8.46 (s, 1 H), 8.22 (d, J = 1.4 Hz, 1 H), 5.73 − 5.68 (m, 1 H), 4.01 (s, 3 H), 2.38 (s, 3 H), 1.76 (d, J = 7.0 Hz, 3 H). LCMS (Method 3): [MH+] = 442 at 4.13 min. |
| Example 149 | 6-(5-Fluoropyrimidin-2-yl)-8-methoxy-N-[(1R)-1-[2-(trifluoromethyl)pyrimidin-5-yl]ethyl]quinazolin-4-amine 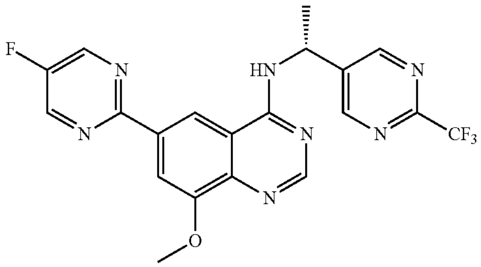 | $^1$H NMR (400 MHz, DMSO): δ 9.20 (s, 2 H), 9.09 (s, 2 H), 9.00 − 8.94 (m, 2 H), 8.48 (s, 1 H), 8.17 (d, J = 1.4 Hz, 1 H), 5.73 − 5.68 (m, 1 H) 4.01 (s, 3H) 1.76 (d J = 7.2 Hz, 3 H). LCMS (Method 4): [MH+] = 446 at 3.48 min. |
| Example 150 | 6-(5-Fluoro-2-pyridyl)-8-methoxy-N-[(1R)-1-[2-(trifluoromethyl)pyrimidin-5-yl]ethyl]quinazolin-4-amine 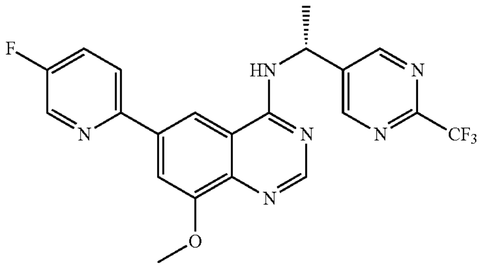 | $^1$H NMR (400 MHz, DMSO): δ 9.19 (s, 2 H), 8.76 − 8.72 (m, 2 H), 8.59 (d, J = 1.5 Hz, 1 H), 8.44 (s, 1 H), 8.31 (dd, J = 4.3, 9.0 Hz, 1 H), 8.02 − 7.97 (m, 2 H), 5.72 − 5.67 (m, 1 H), 4.01 (s, 3 H), 1.76 (d, J = 7.2 Hz, 3 H). LCMS (Method 4): [MH+] = 445 at 3.58 min. |

-continued

| Example No. | Chemical Name Structure | Analytical data $^1H$ NMR LC-MS |
|---|---|---|
| Example 151 | 8-Methoxy-N-[(1R)-1-(6-methylpyridazin-3-yl)ethyl]-6-(5-methylpyrimidin-2-yl)quinazolin-4-amine 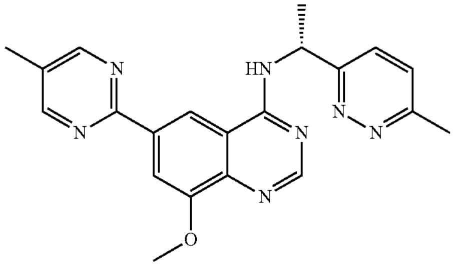 | $^1H$ NMR (400 MHz, DMSO): δ 9.05 (d, J = 1.4 Hz, 1 H), 9.00 (d, J = 7.5 Hz, 1 H), 8.86 (s, 2 H), 8.40 (s, 1 H), 8.21 (d, J = 1.4 Hz, 1 H), 7.64 (d, J = 8.7 Hz, 1 H), 7.50 (d, J = 8.8 Hz, 1 H), 5.81 - 5.76 (m, 1 H), 4.01 (s, 3 H), 2.59 (s, 3 H), 2.39 (s, 3 H), 1.72 (d, J = 7.2 Hz, 3 H). LCMS (Method 3): [MH+] = 388 at 3.64 min. |
| Example 152 | 8-Methoxy-6-(1-methylpyrazol-3-yl)-N-[(1R)-1-(6-methylpyridazin-3-yl)ethyl]quinazolin-4-amine 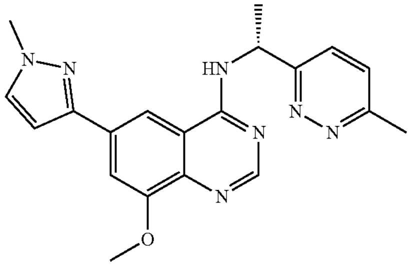 | $^1H$ NMR (400 MHz, DMSO): δ 8.60 (d, J = 7.4 Hz, 1 H), 8.36 - 8.33 (m, 2 H), 7.83 (d, J = 2.1 Hz, 1 H), 7.69 (d, J = 1.3 Hz, 1 H), 7.62 (d, J = 8.7 Hz, 1 H), 7.50 (d, J = 8.7 Hz, 1 H), 6.92 (d, J = 2.4 Hz, 1 H), 5.78 - 5.73 (m, 1 H), 3.97 (s, 3 H), 3.96 (s, 3 H), 2.59 (s, 3 H), 1.72 (d, J = 7.2 Hz, 3 H). LCMS (Method 4): [MH+] = 376 at 2.44 min. |
| Example 153 | 6-[5-(Difluoromethyl)-2-pyridyl]-8-methoxy-N-[(1R)-1-(6-methylpyridazin-3-yl)ethyl]quinazolin-4-amine 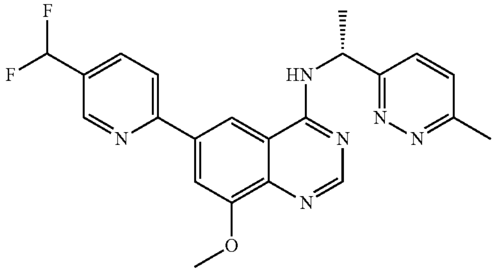 | $^1H$ NMR (400 MHz, DMSO): δ 8.96 (s, 1 H), 8.83 (d, J = 7.4 Hz, 1 H), 8.77 (d, J = 1.5 Hz, 1 H), 8.43 - 8.40 (m, 2 H), 8.23 (d, J = 8.4 Hz, 1 H), 8.07 (d, J = 1.4 Hz, 1 H), 7.64 (d, J = 8.7 Hz, 1 H), 7.51 (d, J = 8.7 Hz, 1 H), 7.26 (t, J = 53.8 Hz, 1 H), 5.82 - 5.76 (m, 1 H), 4.02 (s, 3 H), 2.60 (s, 3 H), 1.74 (d, J = 7.2 Hz, 3 H). LCMS (Method 4): [MH+] = 423 at 3.01 min. |
| Example 154 | 8-Methoxy-N-[(1R)-1-(6-methylpyridazin-3-yl)ethyl]-6-(5-methyl-2-pyridyl)quinazolin-4-amine 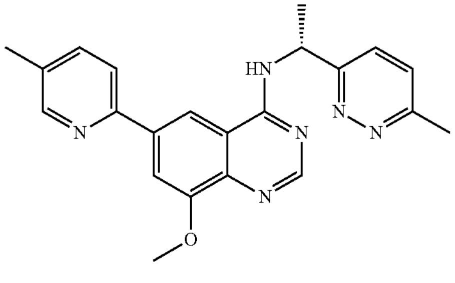 | $^1H$ NMR (400 MHz, DMSO): δ 8.78 (d, J = 6.8 Hz, 1 H), 8.67 (d, J = 1.4 Hz, 1 H), 8.60 (d, J = 1.9 Hz, 1 H), 8.39 (s, 1 H), 8.18 (d, J = 8.2 Hz, 1 H), 8.04 (d, J = 1.3 Hz, 1 H), 7.83 (dd, J = 1.9, 8.2 Hz, 1 H), 7.63 (d, J = 8.7 Hz, 1 H), 7.51 (d, J = 8.8 Hz, 1 H), 5.81 - 5.76 (m, 1 H), 4.01 (s, 3 H), 2.60 (s, 3 H), 2.40 (s, 3 H), 1.74 (d, J = 7.0 Hz, 3 H). LCMS (Method 4): [MH+] = 387 at 2.64 min. |

-continued

| Example No. | Chemical Name Structure | Analytical data $^1$H NMR LC-MS |
|---|---|---|
| Example 155 | 6-(5-Fluoro-2-pyridyl)-8-methoxy-N-[(1R)-1-(6-methylpyridazin-3-yl)ethyl]quinazolin-4-amine 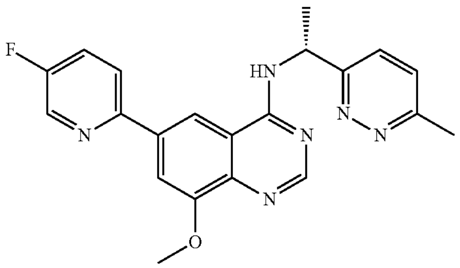 | $^1$H NMR (400 MHz, DMSO): δ 8.72 (d, J = 2.8 Hz, 1 H), 8.62 (s, 1 H), 8.36 (s, 1 H), 8.29 (dd, J = 4.7, 8.9 Hz, 1 H), 7.95 (s, 1 H), 7.96 − 7.89 (m, 1 H), 7.62 (d, J = 8.7 Hz, 1 H), 7.50 (d, J = 8.7 Hz, 1 H), 5.73 (q, J = 7.0 Hz, 1 H), 3.99 (s, 3 H), 1.71 (d, J = 7.2 Hz, 3 H). LCMS (Method 3): [MH+] = 391 at 2.70 min. |
| Example 156 | 8-Methoxy-6-(3-methylisothiazol-5-yl)-N-((6-methylpyridazin-3-yl)methyl)quinazolin-4-amine 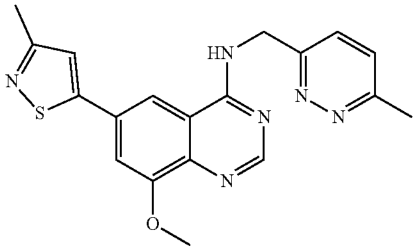 | $^1$H NMR (400 MHz, DMSO): δ 9.14 (dd, J = 5.6, 5.6 Hz, 1 H), 8.44 (s, 1 H), 8.23 (s, 1 H), 8.19 (s, 1 H), 7.77 (s, 1 H), 7.57 (d, J = 8.7 Hz, 1 H), 7.51 (d, J = 8.8 Hz, 2 H), 5.03 (d, J = 5.5 Hz, 2 H), 2.60 (s, 3 H), 2.51 (s, 3 H). LCMS (Method 4): [MH+] = 379 at 2.49 min. |
| Example 157 | (R)-8-methoxy-6-(5-methylpyridin-2-yl)-N-(1-(2-(trifluoromethyl)pyrimidin-5-yl)ethyl)quinazolin-4-amine 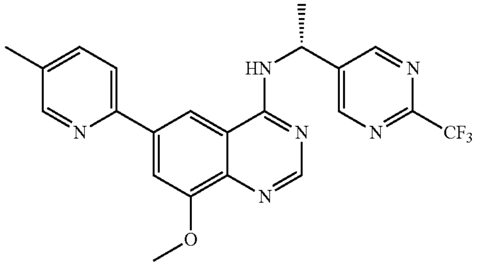 | LCMS: Method 5 0.65 min, 441 [M + H]+, CSH 2 min. $^1$H NMR (400 MHz, DMSO-d6) d ppm 9.17 (s, 2 H), 8.69 (d, J = 6.6 Hz, 1H) 8.53 − 8.60 (m, 2H) 8.42 (s, 1 H), 8.12 (d, J = 8.3 Hz, 1 H), 7.99 (d, J = 1.3 Hz, 1 H), 7.81 (dd, J = 8.3, 1.8 Hz, 1 H), 5.59 − 5.70 (m, 1 H), 4.00 (s, 3 H), 2.38 (s, 3 H), 1.75 (d, J = 7.0 Hz, 3 H) |
| Example 158 | (R)-8-methoxy-6-(5-methylthiazol-2-yl)-N-(1-(2-(trifluoromethyl)pyrimidin-5-yl)ethyl)quinazolin-4-amine 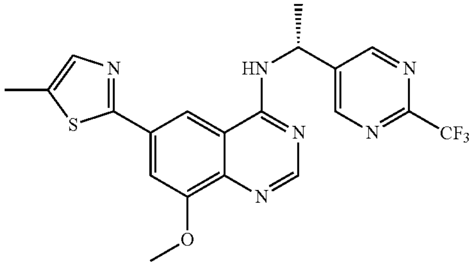 | LCMS: Method 5 0.73 min, 447 [M + H]+, CSH 2 min. $^1$H NMR (400 MHz, DMSO-d6) δ ppm 9.16 (s, 2 H), 8.79 (d, J = 7.0 Hz, 1 H), 8.34 − 8.50 (m, 2 H), 7.69 (dd, J = 5.9, 1.1 Hz, 2 H), 5.67 (t, J = 7.0 Hz, 1 H), 3.98 (s, 3 H), 2.55 (s, 3 H), 1.74 (d, J = 7.0 Hz, 3 H) |

-continued

| Example No. | Chemical Name Structure | Analytical data ¹H NMR LC-MS |
|---|---|---|
| Example 159 | (R)-8-methoxy-4-((1-(2-(trifluoromethyl)pyrimidin-5-yl)ethyl)amino)quinazolin-6-ol 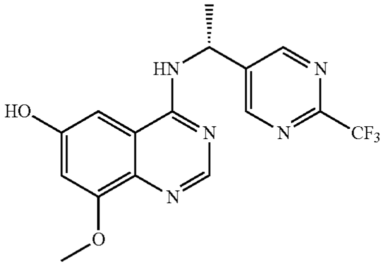 | Compound obtained as a side product in the preparation of Example 156B LCMS: 0.49 min, 366.1 [M + H]+, Method 5. ¹H NMR (400 MHz, DMSO-d6) d ppm 9.87 (s, 1 H), 9.12 (s, 2 H), 8.22 (s, 1 H), 8.13 (d, J = 7.0 Hz, 1 H), 7.13 (d, J = 2.2 Hz, 1 H), 6.83 (d, J = 2.2 Hz, 1 H), 5.50 - 5.60 (m, 1 H), 3.85 (s, 3 H), 1.67 (d, J = 7.5 Hz, 3 H) |
| Example 160 | (R)-8-methoxy-N-(1-(2-(trifluoromethyl)pyrimidin-5-yl)ethyl)quinazolin-4-amine 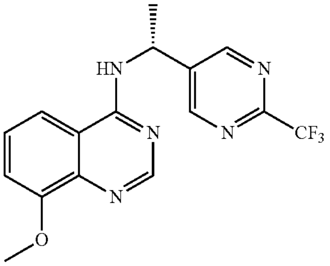 | Compound obtained as a side product in the preparation of Example 156B LCMS: 0.46 min, 350 [M + H]+, Method 5 ¹H NMR (400 MHz, DMSO-d6) d ppm 9.14 (s, 2 H), 8.44 - 8.53 (m, 1 H), 8.40 (s, 1 H), 7.83 - 7.96 (m, 1 H), 7.44 - 7.55 (m, 1 H), 7.23 - 7.35 (m, 1 H), 5.54 - 5.72 (m, 1 H), 3.90 (s, 3 H), 1.69 (d, J = 7.0 Hz, 3 H) |
| Example 161 | 8-Methoxy-N-((6-methylpyridazin-3-yl)methyl)-6-(5-(trifluoromethyl)thiazol-2-yl)quinazolin-4-amine 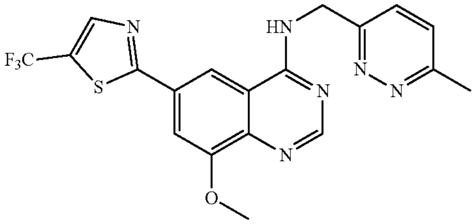 | ¹H NMR (400 MHz, DMSO): δ 9.32 (dd, J = 5.9, 5.9 Hz, 1 H), 8.61 (dd, J = 1.4, 9.9 Hz, 2 H), 8.49 (s, 1 H), 7.81 (d, J = 1.6 Hz, 1 H), 7.59 (d, J = 8.7 Hz, 1 H), 7.51 (d, J = 8.7 Hz, 1 H), 5.04 (d, J = 5.8 Hz, 2 H), 4.03 (s, 3 H), 2.61 (s, 3 H). LCMS (Method 3): [MH+] = 433 at 3.86 min. |
| Example 296 | 6-(3,5-Difluoropyridin-2-yl)-8-methoxy-N-((6-methylpyridazin-3-yl)methyl)quinazolin-4-amine 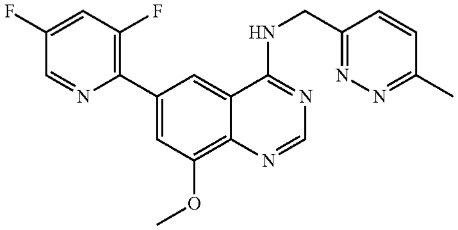 | ¹H NMR (400 MHz, DMSO): δ 8.96 (dd, J = 5.8, 5.8 Hz, 1 H), 8.38 (s, 1 H), 7.86 (d, J = 1.3 Hz, 1 H), 7.55 - 7.48 (m, 2 H), 7.39 (d, J = 1.4 Hz, 1 H), 6.51 (s, 1 H), 5.01 (d, J = 5.9 Hz, 2 H), 4.32 - 4.30 (m, 2 H), 3.96 (s, 3 H), 3.90 (dd, J = 5.5, 5.5 Hz, 2 H), 2.65 - 2.59 (m, 5 H). LCMS (Method 3): $[MH^+]$ = 395 at 2.48 min. |

-continued

| Example No. | Chemical Name Structure | Analytical data $^1H$ NMR LC-MS |
|---|---|---|
| Example 297 | 6-(3-Fluoro-5-methyl-2-pyridyl)-8-methoxy-N-[(6-methylpyridazin-3-yl)methyl] quinazolin-4-amine 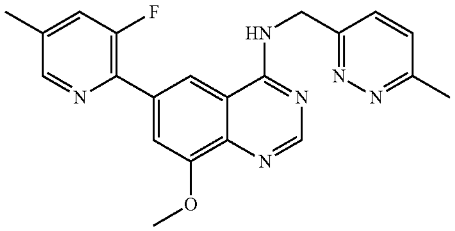 | $^1H$ NMR (400 MHz, DMSO): δ 8.77 (dd, J = 5.9, 5.9 Hz, 1 H), 8.32 (s, 1 H), 7.50 - 7.47 (m, 3 H), 7.07 (d, J = 1.5 Hz, 1 H), 4.98 (d, J = 5.9 Hz, 2 H), 3.92 (s, 3 H), 2.60 (s, 3 H), 2.10 - 2.02 (m, 1 H), 1.07 - 1.02 (m, 2 H), 0.89 - 0.84 (m, 2 H). LCMS (Method 4): [$MH^+$] = 392 at 2.57 min. |
| Example 298 | 6-(5-Ethylthiazol-2-yl)-8-methoxy-N-[(6-methylpyridazin-3-yl)methyl]quinazolin-4-amine 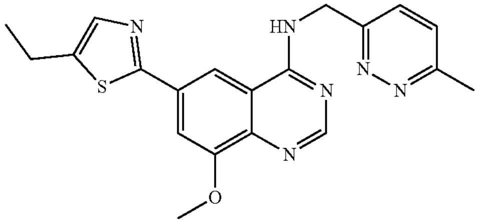 | $^1H$ NMR (400 MHz, DMSO): δ 9.25 (dd, J = 5.8, 5.8 Hz, 1 H), 8.43 (s, 1 H), 8.38 (d, J = 1.6 Hz, 1 H), 7.76 (d, J = 1.5 Hz, 1 H), 7.71 (s, 1 H), 7.56 (d, J = 8.7 Hz, 1 H), 7.50 (d, J = 8.7 Hz, 1 H), 5.02 (d, J = 5.8 Hz, 2 H), 4.00 (s, 3 H), 2.95 (q, J = 7.4 Hz, 2 H), 2.60 (s, 3 H), 1.33 (dd, J = 7.5, 7.5 Hz, 3 H). LCMS (Method 4): [$MH^+$] = 393 at 2.76 min. |
| Example 299 | (R)-8-methoxy-6-(1-methyl-1H-1,2,4-triazol-3-yl)-N-(1-(2-(trifluoromethyl)pyrimidin-5-yl)ethyl)quinazolin-4-amine 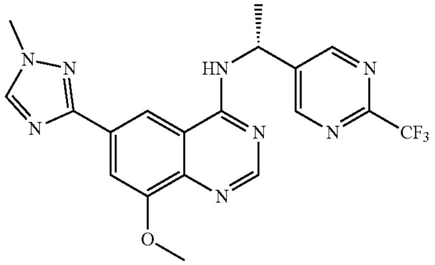 | $^1H$ NMR (400 MHz, DMSO): δ 9.18 (s, 2 H), 8.87 (d, J = 7.3 Hz, 1 H), 8.64 (s, 1 H), 8.58 (d, J = 1.4 Hz, 1 H), 8.43 (s, 1 H), 7.82 (d, J = 1.4 Hz, 1 H), 5.72 - 5.66 (m, 1 H), 3.99 (d, J = 4.9 Hz, 6 H), 1.74 (d, J = 7.2 Hz, 3 H). LCMS (Method 4): [MH+] = 431 at 3.51 min. |
| Example 300 | (R)-8-methoxy-6-(1-methyl-1H-pyrazol-3-yl)-N-(1-(2-(trifluoromethyl)pyrimidin-5-yl)ethyl)quinazolin-4-amine 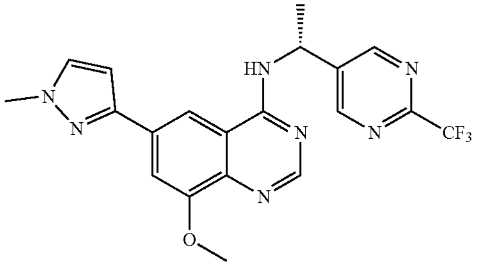 | $^1H$ NMR (400 MHz, DMSO): δ 9.18 (s, 2 H), 8.59 (d, J = 7.0 Hz, 1 H), 8.39 (s, 1 H), 8.28 (d, J = 1.5 Hz, 1 H), 7.84 (d, J = 2.1 Hz, 1 H), 7.67 (d, J = 1.4 Hz, 1 H), 6.90 (d, J = 2.3 Hz, 1 H), 5.70 - 5.65 (m, 1 H), 3.98 (s, 3 H), 3.96 (s, 3 H), 1.75 (d, J = 7.2 Hz, 3 H). LCMS (Method 4): [MH+] = 430 at 4.14 min. |

-continued

| Example No. | Chemical Name Structure | Analytical data $^1H$ NMR LC-MS |
|---|---|---|
| Example 301 | (R)-8-methoxy-6-(1-methyl-1H-1,2,4-triazol-3-yl)-N-(1-(6-methylpyridazin-3-yl)ethyl)quinazolin-4-amine 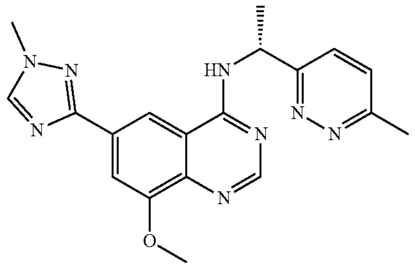 | $^1H$ NMR (400 MHz, DMSO): δ 8.92 (d, J = 7.4 Hz, 1 H), 8.67 (d, J = 1.6 Hz, 1 H), 8.64 (d, J = 0.5 Hz, 1 H), 8.37 (s, 1 H), 7.82 (d, J = 1.4 Hz, 1 H), 7.62 (d, J = 8.7 Hz, 1 H), 7.50 (d, J = 8.7 Hz, 1 H), 5.81 - 5.72 (m, 1 H), 4.00 (s, 3 H), 3.98 (s, 3 H), 2.59 (s, 3 H), 1.71 (d, J = 7.2 Hz, 3 H). LCMS (Method 4): [MH+] = 377 at 2.93 min. |
| Example 326 | 8-Methoxy-N-[(1S)-1-(6-methylpyridazin-3-yl)ethyl]-6-(5-methylpyrimidin-2-yl)quinazolin-4-amine 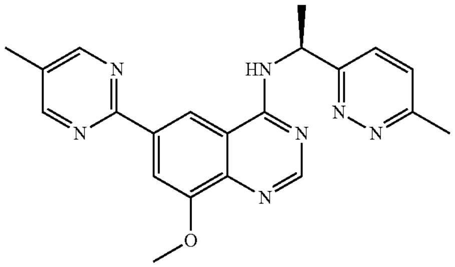 | $^1H$ NMR (400 MHz, DMSO): δ 9.05 (d, J = 1.6 Hz, 1 H), 8.99 (d, J = 7.2 Hz, 1 H), 8.86 (s, 2 H), 8.40 (s, 1 H), 8.21 (d, J = 1.6 Hz, 1 H), 7.63 (d, J = 8.8 Hz, 1 H), 7.50 (d, J = 8.8 Hz, 1 H), 5.81 - 5.76 (m, 1 H), 4.01 (s, 3 H), 2.59 (s, 3 H), 2.38 (s, 3 H), 1.72 (d, J = 7.2 Hz, 3 H). LCMS (Method 3): [MH+] = 388 at 3.64 min. Chiral analysis (Method 37) at 2.21 min. |

Example 163

8-Methoxy-6-(1-methyl-M-pyrazol-4-yl)-N-((6-methylpyridazin-3-yl)methyl)quinazolin-4-amine

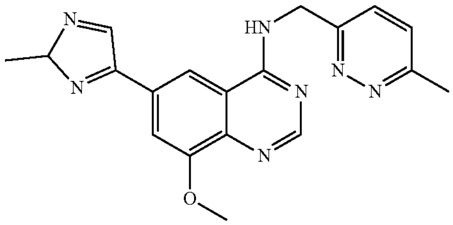

To a solution of 6-bromo-8-methoxy-N-((6-methylpyridazin-3-yl)methyl)quinazolin-4-amine (Intermediate 6) (100 mg, 0.28 mmol) in 1,4-dioxane (2.0 mL) was added 1-methyl-4-(tributylstannyl)-JH-pyrazole (124 mg, 0.33 mmol) and tetrakis(triphenylphosphine)palladium(0) (32 mg, 0.03 mmol). The resulting mixture was heated to 80° C. for 18 h. After return to room temperature, the reaction was filtered through Celite®. The Celite® cake was rinsed with ethyl acetate (2×20 mL). Combined organic phases were washed with 1 N aqueous potassium fluoride (10 mL), filtered through a hydrophobic fit and the solvent was removed in vacuo. The residue was purified by preparative HPLC to give the title compound as an off-white solid (6.7 mg, 7%).

$^1H$ NMR (400 MHz, DMSO): δ 8.83 (dd, J=5.8, 5.8 Hz, 1H), 8.36 (s, 1H), 8.27 (s, 1H), 8.09 (d, J=1.5 Hz, 1H), 8.02 (s, 1H), 7.55 (d, J=8.7 Hz, 1H), 7.52-7.46 (m, 2H), 5.03 (d, J=5.8 Hz, 2H), 3.98 (s, 3H), 3.92 (s, 3H), 2.60 (s, 3H). LCMS (Method 3): [MH+]=362 at 2.64 min.

The following compound reported in the table below was prepared according to the same procedure described for the preparation of 8-Methoxy-6-(1-methyl-1H-pyrazol-4-yl)-N-((6-methylpyridazin-3-yl)methyl)quinazolin-4-amine:

| Example No. | Chemical Name Structure | Analytical data $^1H$ NMR LC-MS |
|---|---|---|
| Example 163a | 6-(4,5-Dimethylthiazol-2-yl)-8-methoxy-N-((6-methylpyridazin-3-yl)methyl)quinazolin-4-amine | $^1H$ NMR (400 MHz, DMSO): δ 9.24 (dd, J =5.8, 5.8 Hz, 1 H), 8.42 (s, 1 H), 8.32 (d, J = 1.6 Hz, 1 H), 7.70 (d, J = 1.6 Hz, 1 H), 7.56 (d, J = 8.7 Hz, |

-continued

| Example No. | Chemical Name<br>Structure | Analytical data<br>$^1$H NMR<br>LC-MS |
|---|---|---|
| | 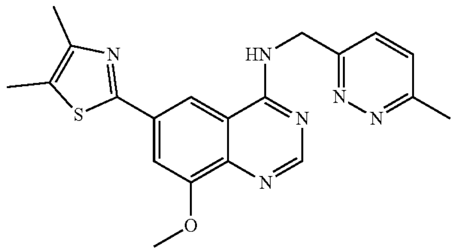 | 1 H), 7.50 (d, J = 8.7 Hz, 1 H) 5.02 (d, J = 5.8 Hz, 2 H), 4.00 (s, 3 H), 2.60 (s, 3 H), 2.44 (s, 3 H), 2.38 (s, 3 H). LCMS (Method 3): [MH+] = 393 at 3.43 min. |

Example 164

6-(4-Fluoro-3-methylphenyl)-8-methoxy-N-((6-methylpyridazin-3-yl)methyl)quinazolin-4-amine

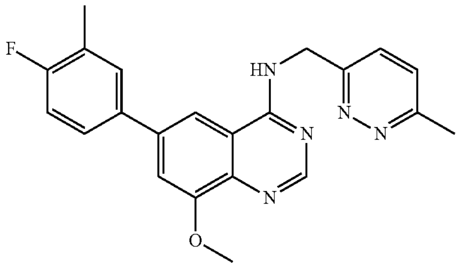 [SMILES: COc1cc(-c2ccc(F)c(C)c2)cc2c(NCc3ccc(C)nn3)ncnc12]

To a solution of 6-bromo-8-methoxy-N-((6-methylpyridazin-3-yl)methyl)quinazolin-4-amine (Intermediate 6) (70 mg, 0.19 mmol) in 1,4-dioxane (4.0 mL) was added 4-fluoro-3-methylphenylboronic acid (33 mg, 0.21 mmol), tetrakis(triphenylphosphine)palladium(0) (20 mg, 0.02 mmol), potassium carbonate (36 mg, 0.26 mmol) and water (0.5 mL). The resulting mixture was heated to 95° C. for 18 h. After return to room temperature, the reaction was filtered through Celite®. The Celite® cake was rinsed with ethyl acetate (2×20 mL). Combined organic phases were washed with brine (2×20 mL), filtered through a hydrophobic frit and the solvent was removed in vacuo. The residue was purified by preparative HPLC to give the title compound as an off-white solid (18 mg, 24%).

$^1$H NMR (400 MHz, DMSO) δ 9.03 (dd, J=5.8, 5.8 Hz, 1H), 8.41 (s, 1H), 8.15 (d, J=1.8 Hz, 1H), 7.82 (dd, J=2.0, 7.4 Hz, 1H), 7.77-7.72 (m, 1H), 7.57-7.49 (m, 3H), 7.31 (dd, J=9.1, 9.1 Hz, 1H), 5.03 (d, J=5.8 Hz, 2H), 4.03 (s, 3H), 2.60 (s, 3H), 2.37 (d, J=1.8 Hz, 3H).

LCMS (Method 4): [MH+]=390 at 3.12 min.

The following compounds reported in the table below were prepared according to the same procedure described for the preparation of 6-(4-Fluoro-3-methylphenyl)-8-methoxy-N-((6-methylpyridazin-3-yl)methyl)quinazolin-4-amine:

| Example No. | Chemical Name<br>Structure | Analytical data<br>$^1$H NMR<br>LC-MS |
|---|---|---|
| Example 165 | 6-(2,4-Difluorophenyl)-8-methoxy-N-((6-methylpyridazin-3-yl)methyl)quinazolin-4-amine 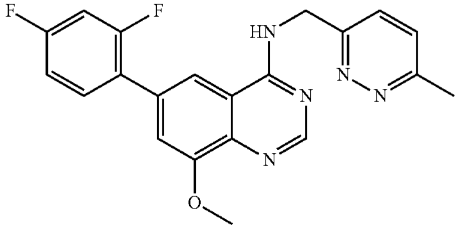 | $^1$H NMR (400 MHz, DMSO): δ 9.00 (dd, J = 5.8, 5.8 Hz, 1 H), 8.43 (s, 1 H), 8.02 (s, 1 H), 7.77 – 7.70 (m, 1 H), 7.50 (dd, J = 8.4, 19.7 Hz, 2 H), 7.45 – 7.41 (m, 1 H), 7.38 (s, 1 H), 7.30 – 7.25 (m, 1 H), 4.99 (d, J = 5.8 Hz, 2 H), 3.95 (s, 3 H), 2.58 (s, 3 H). LCMS (Method 3): [MH+] = 394 at 3.68 min. |

-continued

| Example No. | Chemical Name<br>Structure | Analytical data<br>$^1$H NMR<br>LC-MS |
|---|---|---|
| Example 166 | 6-(4-Fluoro-3-methoxyphenyl)-8-methoxy-N-((6-methylpyridazin-3-yl)methyl)quinazolin-4-amine<br>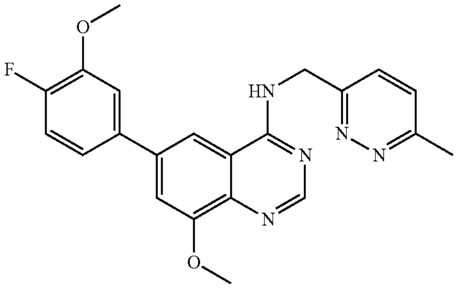 | $^1$H NMR (400 MHz, DMSO): δ 9.03 (dd, J = 5.8, 5.8 Hz, 1 H), 8.42 (s, 1 H), 8.14 (d, J = 1.5 Hz, 1 H), 7.60 - 7.49 (m, 3 H), 7.46 - 7.35 (m, 2 H), 5.04 (d, J = 5.8 Hz, 2 H), 4.04 (s, 3 H), 4.01 (s, 3 H), 2.60 (s, 3 H). LCMS (Method 4): [MH+] = 406 at 2.97 min. |
| Example 167 | 6-(4-Fluoro-2-methylphenyl)-8-methoxy-N-((6-methylpyridazin-3-yl)methyl)quinazolin-4-amine<br>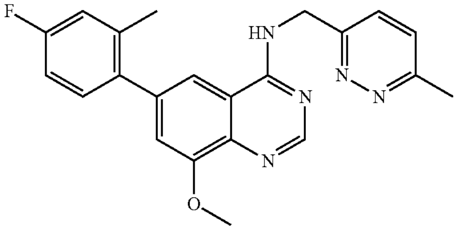 | $^1$H NMR (400 MHz, DMSO): δ 8.91 (dd, J = 5.8, 5.8 Hz, 1 H), 8.43 (s, 1 H), 7.82 (d, J = 1.3 Hz, 1 H), 7.51 (q, J = 8.7 Hz, 2 H), 7.40 (dd, J= 6.1, 8.5 Hz, 1 H), 7.27 - 7.23 (m, 2 H), 7.19 - 7.13 (m, 1 H), 4.98 (d, J = 5.8 Hz, 2 H), 3.95 (s, 3 H), 2.59 (s, 3 H), 2.34 (s, 3 H). LCMS (Method 4): [MH+] = 390 at 3.04 min. |
| Example 168 | 6-(4-Fluoro-2-(trifluoromethyl)phenyl)-8-methoxy-N-((6-methylpyridazin-3-yl)methyl)quinazolin-4-amine<br>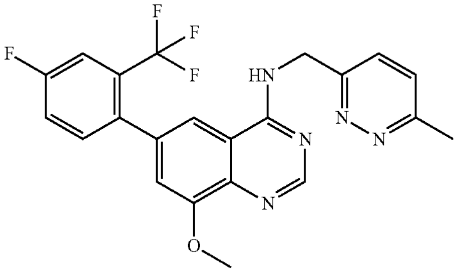 | $^1$H NMR (400 MHz, DMSO): δ 8.91 (dd, J = 5.8, 5.8 Hz, 1 H), 8.46 (s, 1 H), 7.84 - 7.80 (m, 2 H), 7.73 - 7.62 (m, 2 H), 7.51 (dd, J = 8.7, 12.1 Hz, 2 H), 7.22 (s, 1 H), 4.97 (d, J = 5.8 Hz, 2 H), 3.91 (s, 3 H), 2.59 (s, 3 H). LCMS (Method 3): [MH+] = 444 at 4.23 min. |
| Example 169 | 6-(3-Fluorophenyl)-8-methoxy-N-((6-methylpyridazin-3-yl)methyl)quinazolin-4-amine<br>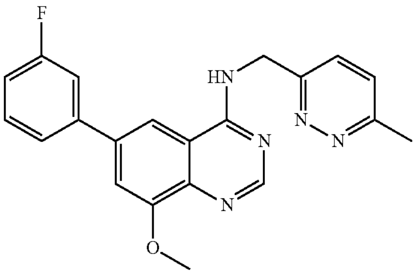 | $^1$H NMR (400 MHz, DMSO): δ 9.06 (dd, J = 5.9, 5.9 Hz, 1 H), 8.43 (s, 1 H), 8.25 (d, J = 1.6 Hz, 1 H), 7.78 (d, J = 7.8 Hz, 2 H), 7.61 - 7.55 (m, 3 H), 7.51 (d, J = 8.7 Hz, 1 H), 7.30 - 7.24 (m, 1 H), 5.04 (d, J = 5.8 Hz, 2 H), 4.04 (s, 3 H), 2.60 (s, 3 H). LCMS (Method 3): [MH+] = 376 at 3.68 min. |

-continued

| Example No. | Chemical Name Structure | Analytical data $^1$H NMR LC-MS |
|---|---|---|
| Example 170 | 6-(2,4-Difluorophenyl)-8-methoxy-N-[(1R)-1-(6-methylpyridazin-3-yl)ethyl]quinazolin-4-amine 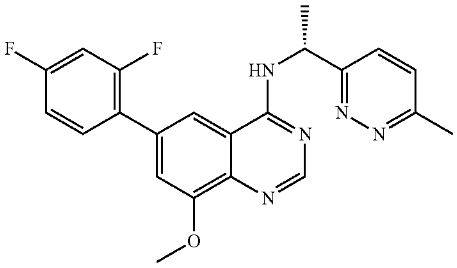 | $^1$H NMR (400 MHz, DMSO): δ 8.35 (s, 1 H), 8.14 (s, 1 H), 7.77 - 7.69 (m, 1 H), 7.59 (d, J = 8.7 Hz, 1 H), 7.49 (d, J = 8.7 Hz, 1 H) 7.43 - 7.35 (m 2H) 7.29 - 7.23 (m, 1 H), 5.69 (d, J = 8.5 Hz, 1 H), 3.93 (s, 3 H), 3.79 (s, 3 H), 1.66 (d, J = 7.2 Hz, 3 H). LCMS (Method 3): [MH+] = 408 at 4.22 min. |
| Example 171 | 6-[4-[(Dimethylamino)methyl]phenyl]-8-methoxy-N-[(6-methylpyridazin-3-yl)methyl]quinazolin-4-amine formate 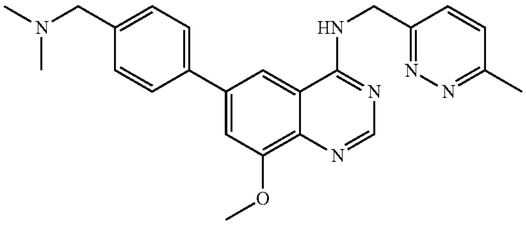 | $^1$H NMR (400 MHz, DMSO): δ 9.04 (brs, 1 H), 8.40 (s, 1 H), 8.21 (s, 1 H), 8.18 (d, J = 1.1 Hz, 1 H), 7.85 (d, J = 8.2 Hz, 2 H), 7.55 (dd, J = 3.5, 5.1 Hz, 2 H), 7.52 - 7.44 (m, 3 H), 5.02 (s, 2 H), 4.02 (s, 3 H), 3.52 (s, 2 H), 2.59 (s, 3 H), 2.22 (s, 6 H). LCMS (Method 3): [MH+] = 415 at 3.24 min. |
| Example 172 | 4-[8-Methoxy-4-[(6-methylpyridazin-3-yl)methylamino]quinazolin-6-yl]-N,N-dimethyl-benzamide 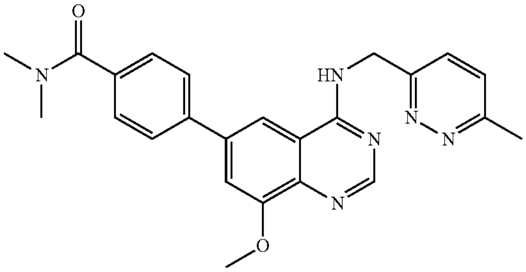 | $^1$H NMR (400 MHz, DMSO): δ 9.11 (dd, J = 5.3, 5.3 Hz, 1 H), 8.46 (s, 1 H), 8.28 (s, 1 H), 7.99 (d, J = 8.3 Hz, 2 H), 7.64 - 7.58 (m, 4 H), 7.54 (d, J = 8.6 Hz, 1 H), 5.07 (d, J = 5.8 Hz, 2 H), 4.07 (s, 3 H), 3.04 (m, 6 H), 2.64 (s, 3 H). LCMS (Method 4): [MH+] = 429 at 2.40 min. |
| Example 173 | 6-[4-(Dimethylamino)phenyl]-8-methoxy-N-[(6-methylpyridazin-3-yl)methyl]quinazolin-4-amine 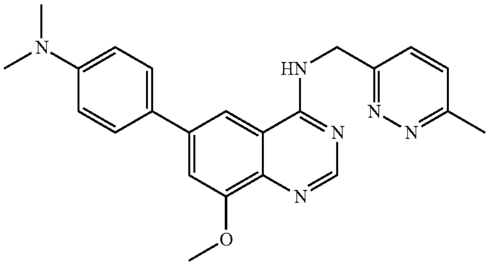 | $^1$H NMR (400 MHz, $CDCl_3$): δ 8.67 (s, 1 H), 7.58 - 7.50 (m, 5 H), 7.38 - 7.32 (m, 2 H), 6.82 (d, J = 8.9 Hz, 2 H), 5.10 (d, J = 4.1 Hz, 2 H), 4.09 (s, 3 H), 3.03 (s, 6 H), 2.74 (s, 3 H). LCMS (Method 4): [MH+] = 401 at 2.78 min. |

-continued

| Example No. | Chemical Name<br>Structure | Analytical data<br>$^1H$ NMR<br>LC-MS |
|---|---|---|
| Example 174 | 8-Methoxy-6-(4-methoxyphenyl)-N-[(6-methylpyridazin-3-yl)methyl]quinazolin-4-amine<br>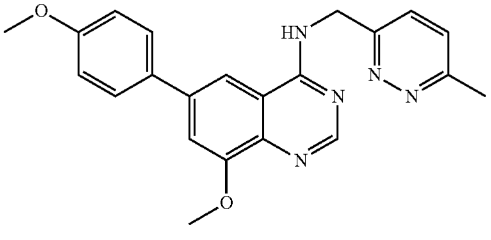 | $^1H$ NMR (400 MHz, DMSO): δ 9.01 (dd, J = 5.9, 5.9 Hz, 1 H), 8.39 (s, 1 H), 8.17 (s, 1 H), 8.14 (d, J = 1.6 Hz, 1 H), 7.86 - 7.83 (m, 2 H), 7.57 - 7.48 (m, 3 H), 7.10 (d, J = 8.9 Hz, 2 H), 5.03 (d, J = 5.8 Hz, 2 H), 4.02 (s, 3 H), 3.84 (s, 3 H), 2.60 (s, 3 H). LCMS (Method 4): [MH+] = 388 at 2.83 min. |
| Example 175 | 6-(4-chlorophenyl)-8-methoxy-N-((6-methylpyridazin-3-yl)methyl)quinazolin-4-amine<br>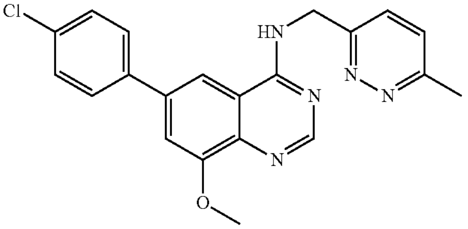 | $^1H$ NMR (400 MHz, DMSO): δ 9.06 (dd, J = 5.9, 5.9 Hz, 1 H), 8.42 (s, 1 H), 8.23 - 8.19 (m, 1 H), 7.95 - 7.92 (m, 2 H), 7.61 (d, J = 8.8 Hz, 2 H), 7.58 - 7.55 (m, 2 H), 7.50 (d, J = 8.7 Hz, 1 H), 5.03 (d, J = 5.8 Hz, 2 H), 4.03 (s, 3 H), 2.60 (s, 3 H). LCMS (Method 4): [MH+] = 392 at 3.18 min. |
| Example 176 | 6-(3,4-Difluorophenyl)-8-methoxy-N-((6-methylpyridazin-3-yl)methyl)quinazolin-4-amine<br>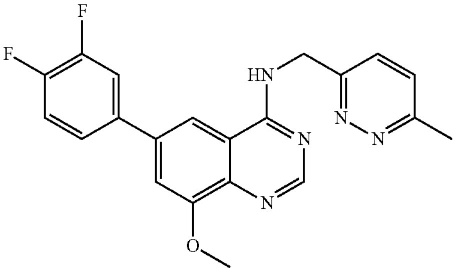 | $^1H$ NMR (400 MHz, DMSO): δ 9.04 (dd, J = 5.9, 5.9 Hz, 1 H), 8.41 (s, 1 H), 8.20 (d, J = 1.6 Hz, 1 H), 8.00 (ddd, J = 2.3, 7.8, 12.5 Hz, 1 H), 7.79 - 7.75 (m, 1 H), 7.65 - 7.59 (m, 1 H), 7.55 (d, J = 8.8 Hz, 2 H), 7.49 (d, J = 8.7 Hz, 1 H), 5.02 (d, J = 5.8 Hz, 2 H), 4.02 (s, 3 H), 2.59 (s, 3 H). LCMS (Method 3): [MH+] =394 at 3.79 min. |

Example 176a

6-(4-Fluoro-2-methoxyphenyl)-8-methoxy-N-((6-methylpyridazin-3-yl)methyl)quinazolin-4-amine

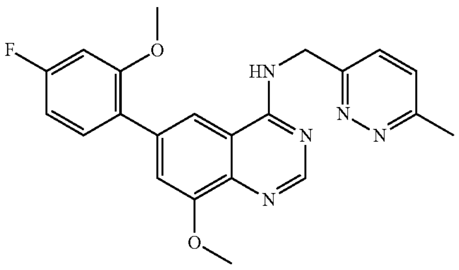 [SMILES: COc1cc(F)ccc1-c1cc(OC)c2ncnc(NCc3ccc(C)nn3)c2c1]

To a solution of 6-bromo-8-methoxy-N-((6-methylpyridazin-3-yl)methyl)quinazolin-4-amine (intermediate 6) (70 mg, 0.19 mmol) in 1,2-dimethoxyethane (3.0 mL) was added (4-fluoro-2-methoxyphenyl)boronic acid (41 mg, 0.24 mmol), [1,1'-bis(diphenylphosphino)ferrocene] dichloropalladium(II) complex with dichloromethane (8.2 mg, 0.01 mmol), caesium carbonate (130 mg, 0.40 mmol) and water (0.3 mL). The resulting mixture was heated to 95° C. for 18 h. After return to room temperature, the reaction was filtered through Celite®. The Celite® cake was rinsed with ethyl acetate (2×20 mL). Combined organic phases were washed with brine (2×20 mL), filtered through a hydrophobic frit and the solvent was removed in vacuo. The residue was purified by preparative HPLC to give the title compound as an off-white solid (35 mg, 45%).

$^1H$ NMR (400 MHz, DMSO): δ 8.92 (dd, J=5.8, 5.8 Hz, 1H), 8.41 (s, 1H), 7.91 (d, J=1.5 Hz, 1H), 7.54-7.46 (m, 3H), 7.37 (d, J=1.4 Hz, 1H), 7.10 (dd, J=2.4, 11.5 Hz, 1H), 6.97-6.91 (m, 1H), 4.99 (d, J=5.6 Hz, 2H), 3.93 (s, 3H), 3.84 (s, 3H), 2.59 (s, 3H). LCMS (Method 3): [MH+]=406 at 3.97 min.

The following compounds reported in the table below were prepared via adaptation of the above procedure starting from appropriate intermediate reported in table.

| Example No. | Chemical Name Structure | Analytical data $^1H$ NMR LC-MS | Starting Intermediate |
|---|---|---|---|
| Example 177 | 8-Methoxy-N-((6-methylpyridazin-3-yl)methyl)-6-(2,4,6-trifluorophenyl)quinazolin-4-amine<br>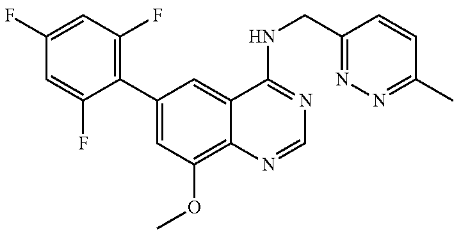 | $^1H$ NMR (400 MHz, DMSO): δ 9.00 (dd, J = 5.8, 5.8 Hz, 1 H), 8.47 (s, 1 H), 7.98 (s, 1 H), 7.54 (d, J = 8.5 Hz, 1 H), 7.49 (d, J = 8.7 Hz, 1 H), 7.43 (dd, J = 8.6, 8.6 Hz, 2 H), 7.33 (s, 1 H), 4.99 (d, J = 5.8 Hz, 2 H), 3.93 (s, 3 H), 2.59 (s, 3 H). LCMS (Method 3): [MH+] = 412 at 3.66 min. | Intermediate 6 |
| Example 178 | 2-(8-Methoxy-4-(((6-methylpyridazin-3-yl)methyl)amino)quinazolin-6-yl)-5-methylbenzonitrile<br>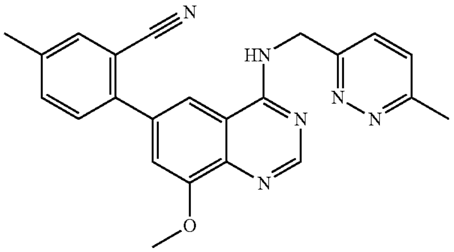 | $^1H$ NMR (400 MHz, DMSO): δ 9.05 (dd, J = 5.7, 5.7 Hz, 1 H), 8.47 (s, 1 H), 8.08 (d, J = 1.8 Hz, 1 H), 7.86 (s, 1 H), 7.69 (s, 2 H), 7.54 (d, J = 8.7 Hz, 1 H), 7.50 - 7.47 (m, 2 H), 5.02 (d, J = 5.6 Hz, 2 H), 3.99 (s, 3 H), 2.60 (s, 3 H), 2.45 (s, 3 H). LCMS (Method 3): [MH+] = 387 at 3.88 min | Intermediate 6 |
| Example 179 | 5-Fluoro-2-(8-methoxy-4-(((6-methylpyridazin-3-yl)methyl)amino)quinazolin-6-yl)benzonitrile<br>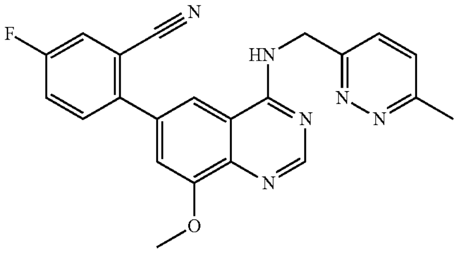 | $^1H$ NMR (400 MHz, DMSO): δ 9.07 (dd, J = 5.8, 5.8 Hz, 1 H), 8.48 (s, 1 H), 8.10 - 8.05 (m, 2 H), 7.87 - 7.76 (m, 2 H), 7.55 - 7.48 (m, 3 H), 5.02 (d, J = 5.8 Hz, 2 H), 3.99 (s, 3 H), 2.60 (s, 3 H). LCMS (Method 4): [MH+] = 401 at 2.71 min. | Intermediate 6 |
| Example 180 | 5-Fluoro-2-(8-methoxy-4-(((6-methylpyridazin-3-yl)methyl)amino)quinazolin-6-yl)phenol<br>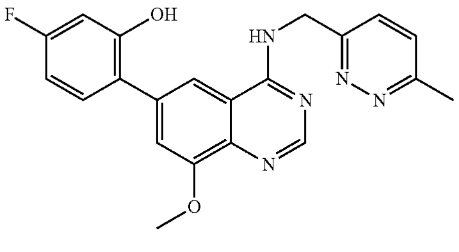 | $^1H$ NMR (400 MHz, DMSO): δ 10.21 (s, 1 H), 8.92 (dd, J = 5.6, 5.6 Hz, 1 H), 8.41 (s, 1 H), 7.94 (d, J = 1.3 Hz, 1 H), 7.54 - 7.44 (m, 4 H), 6.81 - 6.76 (m, 2 H), 4.99 (d, J = 5.6 Hz, 2 H), 3.93 (s, 3 H), 2.60 (s, 3 H). LCMS (Method 3): [MH+] = 392 at 3.27 min. | Intermediate 6 |

-continued

| Example No. | Chemical Name Structure | Analytical data $^1H$ NMR LC-MS | Starting Intermediate |
|---|---|---|---|
| Example 181 | (R)-6-(4-fluorophenyl)-8-methoxy-N-(1-(2-(trifluoromethyl)pyrimidin-5-yl)ethyl)quinazolin-4-amine 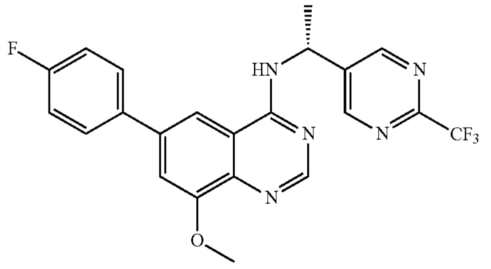 | LCMS (Method 5): 0.79 min, m/z 443.8 [M + 2]+, $^1H$ NMR (400 MHz, DMSO-d6) δ ppm 9.12 (s, 2 H), 8.55 (d, J = 7.0 Hz, 1 H), 8.37 (s, 1 H), 8.14 (d, J = 1.3 Hz, 1 H), 7.83 - 7.96 (m, 2 H), 7.48 (d, J = 1.3 Hz, 1 H), 7.35 (t, J = 8.8 Hz, 2 H), 5.50 - 5.60 (m, 1 H), 3.97 (s, 3 H), 1.69 (d, J = 7.0 Hz, 3 H). | Intermediate 5 |
| Example 182 | 6-(4-fluorophenyl)-8-methoxy-N-((6-methylpyridazin-3-yl)methyl)quinazolin-4-amine 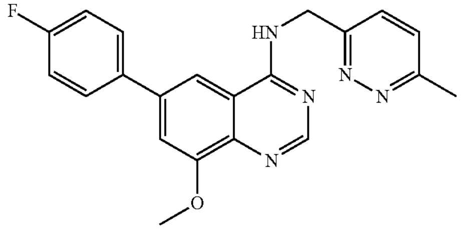 | LCMS (Method 6): 0.88 min, 375.9 m/z [M + H]+, $^1H$ NMR (400 MHz, ACETONITRILE-d3) δ □ ppm 8.43 (s, 1 H), 7.66 - 7.84 (m, 3 H), 7.53 (d, J = 8.8 Hz, 1 H), 7.44 (d, J = 1.3 Hz, 1 H), 7.39 (d, J = 8.8 Hz, 1 H), 7.20 - 7.30 (m, 2 H), 7.00 - 7.15 (m, 1 H), 5.06 (s, 2 H), 4.04 (s, 3 H), 2.62 (s, 3 H). | Intermediate 6 |

Example 183

(R)-6-(4-Fluorophenyl)-8-methoxy-2-methyl-N-(1-(2-(trifluoromethyl)pyrimidin-5 yl)ethyl)quinazolin-4-amine

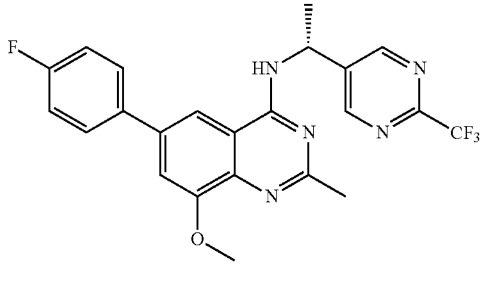 [SMILES: COc1cc(-c2ccc(F)cc2)cc2c(N[C@H](C)c3cnc(C(F)(F)F)nc3)nc(C)nc12]

Step 1: Preparation of 6-bromo-8-methoxy-2-methylquinazolin-4-ol

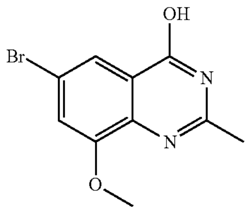

To a solution of 2-amino-5-bromo-3-methoxybenzoic acid hydrobromide (0.5 g, 1.53 mmol) (Intermediate 1) in N,N-dimethylformamide (5 mL) was successively added 1-hydroxybenzotriazole hydrate (0.23 g, 1.68 mmol), N-(3-Dimethylaminopropyl)-N'-ethylcarbodiimide hydrochloride (0.32 g, 1.68 mmol) and N,N-diisopropylethylamine (0.29 mL, 1.68 mmol). The resulting mixture was stirred at room temperature for 2 hours. The reaction was then cooled to 0° C. and 28% aqueous ammonium hydroxide solution (1.5 mL) was added dropwise and the reaction was allowed to warm to room temperature overnight. The reaction was concentrated under reduced pressure and the residue was dissolved in triethyl orthoacetate (3.4 mL, 18.36 mmol), acetic acid (0.84 mL, 14.69 mmol) was added dropwise and the reaction was heated to 120° C. for 2 hours. The reaction was then cooled and concentrated. The crude residue was triturated with iso-propanol and filtered to give the title compound as an off-white solid (0.10 g, 30%).

LCMS (Method 3): [MH+]=268/270 at 3.28 min.

Step 2: Preparation of 6-(4-fluorophenyl)-8-methoxy-2-methylquinazolin-4-ol

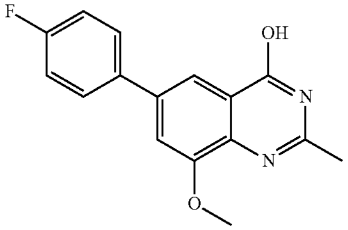 [SMILES: COc1cc(-c2ccc(F)cc2)cc2c(O)nc(C)nc12]

Nitrogen was bubbled for 5 min through a mixture of 6-bromo-8-methoxy-2-methylquinazolin-4-ol (0.10 g, 0.37 mmol), 4-fluorophenylboronic acid (57 mg, 0.409 mmol), cesium carbonate (0.46 g, 1.41 mmol), water (0.5 mL) in 1,4-dioxane (2 mL), then [1,1'-bis(diphenylphosphino)ferrocene]dichloropalladium(II) complex with dichloromethane (15 mg, 0.0186 mmol) was added. The reaction was heated to 120° C. for 4 hours. After return to room temperature, the reaction was diluted with water (10 mL) and ethyl acetate (10 mL), the reaction was then filtered and the collected solid was washed with water (10 mL) and diethyl ether (10 mL) to give the title compound as a grey solid (0.10 g, 94%).

LCMS (Method 3): [MH+]=285 at 3.59 min.

Step 3: Preparation of (R)-6-(4-fluorophenyl)-8-methoxy-2-methyl-N-(1-(2-(trifluoromethyl)pyrimidin-5-yl)ethyl)quinazolin-4-amine

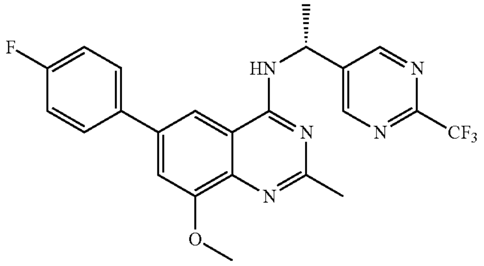 [SMILES: COc1cc(-c2ccc(F)cc2)cc2c(N[C@H](C)c3cnc(C(F)(F)F)nc3)nc(C)nc12]

To a solution of 6-(4-Fluorophenyl)-8-methoxy-2-methylquinazolin-4-ol (100 mg, 0.35 mmol) in N,N-dimethylformamide (2 mL) was successively added (benzotriazol-1-yloxy)tripyrrolidinophosphonium hexafluorophosphate (201 mg, 0.39 mmol) and di-isopropylethylamine (0.31 mL, 1.76 mmol). The resulting mixture was heated to 40° C. and stirred for 20 min, (R)-1-(2-(trifluoromethyl)pyrimidin-5-yl)ethan-1-amine (88 mg, 0.387 mmol) was then added and the heating was maintained at 40° C. for 4 hours. After return to room temperature, the reaction was directly purified by preparative HPLC to give the title compound (15.1 mg, 9%).

$^1$H NMR (400 MHz, DMSO): δ 9.22 (s, 2H), 8.55 (d, J=6.8 Hz, 1H), 8.18 (s, 1H), 7.95 (dd, J=5.6, 8.6 Hz, 2H), 7.51 (s, 1H), 7.42 (dd, J=8.7, 8.7 Hz, 2H), 5.73-5.66 (m, 1H), 4.03 (s, 3H), 2.46 (s, 3H), 1.78 (d, J=7.1 Hz, 3H). LCMS (Method 4): [MH+]=458 at 4.97 min.

Example 184

(R)-6-(4-Fluorophenyl)-8-methoxy-4-((1-(2-(trifluoromethyl)pyrimidin-5-yl)ethyl)-amino)-quinazolin-2-ol

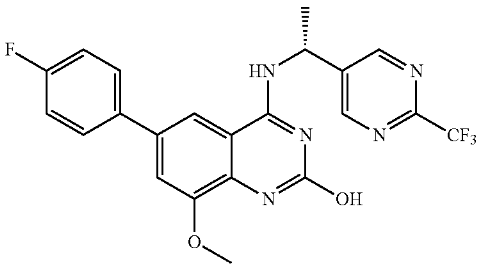 [SMILES: COc1cc(-c2ccc(F)cc2)cc2c(N[C@H](C)c3cnc(C(F)(F)F)nc3)nc(O)nc12]

Step 1: Preparation of 6-bromo-8-methoxyquinazoline-2,4-diol

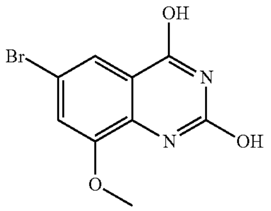

A mixture of 2-amino-5-bromo-3-methoxybenzoic acid hydrobromide (Intermediate 1) (1.0 g, 3.06 mmol) and urea (1.84 g, 30.58 mmol) was heated to 170° C. for 18 hours. After return to room temperature, the reaction was diluted with water (50 mL) and filtered. The collected solid was washed with water (20 mL) and diethyl ether (20 mL) to give the title compound as a light brown solid (0.7 g, 84%) which was taken on to the next step without further purification.

LCMS (Method 4): [MH+]=271 at 3.17 min.

Step 2: Preparation of 2,4-dichloro-6-(4-fluorophenyl)-8-methoxyquinazoline

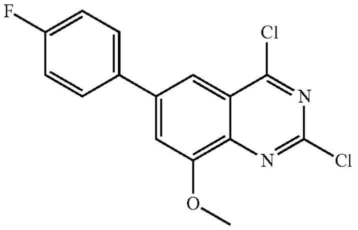 [SMILES: COc1cc(-c2ccc(F)cc2)cc2c(Cl)nc(Cl)nc12]

Nitrogen was bubbled for 5 min through a mixture of 6-bromo-8-methoxyquinazoline-2,4-diol (0.5 g, 1.84 mmol), 4-fluorophenylboronic acid (284 mg, 2.03 mmol), cesium carbonate (2.28 g, 7.01 mmol) and water (2.5 mL) in 1,4-dioxane (10.0 mL), then [1,1'-bis(diphenylphosphino)ferrocene]dichloropalladium(II) complex with dichloromethane (75 mg, 0.09 mmol) was added. The resulting mixture was heated to 120° C. for 4 hours. After return to room temperature, the solvent was removed in vacuo. The residue was dry loaded onto silica gel and purified by chromatography on silica gel, eluting with 0-5% methanol in dichloromethane to give 160 mg of a crude product. This product (68 mg) was suspended in phosphorus oxychloride (1 mL, 10.73 mmol) and N,N-diisopropylethylamine (0.026 mL, 0.147 mmol) was added dropwise followed by a drop of N,N-dimethylformamide. The solution was then heated to 130° C. for 18 hours. After return to room temperature, the solvent was removed in vacuo. The residue was taken up with $H_2O$ (10 mL) and stirred for one hour at room temperature. The reaction was filtered to give the title compound as an off-white solid (44 mg, 65%).

LCMS (Method 4): [MH+]=323 at 5.76 min.

Step 3: Preparation of (R)-6-(4-fluorophenyl)-8-methoxy-4-((1-(2-(trifluoromethyl)pyrimidin-5-yl)ethyl)-amino)-quinazolin-2-ol

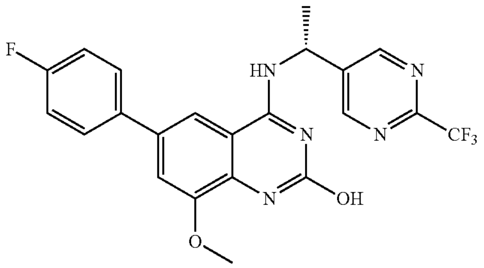 [SMILES: COc1cc(-c2ccc(F)cc2)cc2c(N[C@H](C)c3cnc(C(F)(F)F)nc3)nc(O)nc12]

A mixture of 2,4-dichloro-6-(4-fluorophenyl)-8-methoxyquinazoline (44 mg, 0.13 mmol), (R)-1-(2-(trifluoromethyl)pyrimidin-5-yl)ethan-1-amine (35 mg, 0.13 mmol) and N,N-diisopropylethylamine (0.046 mL, 0.27 mmol) in dichloromethane (2 mL) was stirred at room temperature for 2 hours. The reaction was then diluted with $H_2O$ (10 mL) and extracted with dichloromethane (3×30 mL). The combined organic phases were passed through a hydrophobic frit and concentrated in vacuo. The residue was dissolved in acetic acid (2 mL) and heated to 70° C. for 2 hours. After return to room temperature, the reaction was concentrated in vacuo and the residue was purified by preparative HPLC to give the title compound as an off-white solid (6.1 mg, 10%).

$^1$H NMR (400 MHz, DMSO): δ 10.04 (s, 1H), 9.15 (s, 2H), 8.68 (d, J=7.2 Hz, 1H), 8.04 (s, 1H), 7.87-7.82 (m, 2H), 7.48 (d, J=1.4 Hz, 1H), 7.36 (dd, J=8.9, 8.9 Hz, 2H), 5.66-5.60 (m, 1H), 3.97 (s, 3H), 1.71 (d, J=7.2 Hz, 3H). LCMS (Method 4): [MH+]=460 at 4.5 min.

Example 185

(R)-6-(4-Fluorophenyl)-2,8-dimethoxy-N-(1-(2-(trifluoromethyl)pyrimidin-5-yl)ethyl)quinazolin-4-amine

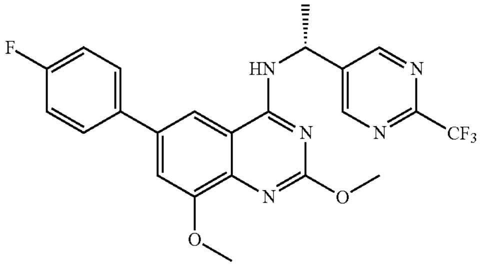 [SMILES: COc1nc(N[C@H](C)c2cnc(C(F)(F)F)nc2)c2cc(-c3ccc(F)cc3)cc(OC)c2n1]

A mixture of 2,4-dichloro-6-(4-fluorophenyl)-8-methoxyquinazoline (143 mg, 0.44 mmol), (R)-1-(2-(trifluoromethyl)pyrimidin-5-yl)ethan-1-amine (117 mg, 0.44 mmol) and N,N-diisopropylethylamine (0.15 mL, 0.89 mmol) in dichloromethane (5 mL) was stirred at room temperature for 2 hours. The reaction was then diluted with $H_2O$ (10 mL) and extracted with dichloromethane (3×30 mL). The combined organic phases were passed through a hydrophobic frit and concentrated in vacuo. The residue was dissolved in methanol (2 mL) and sodium methoxide (25% in methanol) (0.13 mL, 0.58 mmol) was added. The mixture was heated to 80° C. for 2 hours. After return to room temperature, the reaction was concentrated in vacuo and the residue was purified by preparative HPLC to give the title compound as a brown solid (3.5 mg, 3.2%).

$^1$H NMR (400 MHz, DMSO): δ 9.17 (s, 2H), 8.68 (d, J=6.9 Hz, 1H), 8.15 (d, J=1.8 Hz, 1H), 7.93-7.88 (m, 2H), 7.47 (d, J=1.5 Hz, 1H), 7.38 (dd, J=8.9, 8.9 Hz, 2H), 5.61 (dd, J=6.8, 6.8 Hz, 1H), 3.99 (s, 3H), 3.83 (s, 3H), 1.73 (d, J=7.2 Hz, 3H). LCMS (Method 4): [MH+]=474 at 3.87 min.

Example 186

(R)-6-(4-Fluorophenyl)-8-iodo-N-(1-(2-(trifluoromethyl)pyrimidin-5-yl)ethyl)quinazolin-4-amine

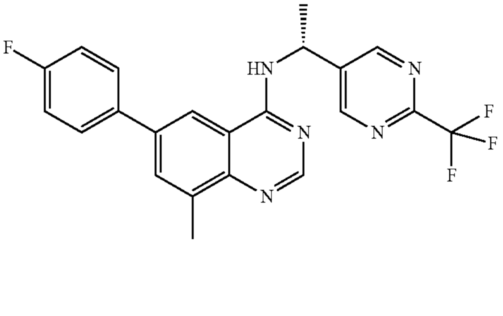 [SMILES: Cc1cc(-c2ccc(F)cc2)cc2c(N[C@H](C)c3cnc(C(F)(F)F)nc3)ncnc12]

Step 1: Preparation of methyl 4-amino-4'-fluoro-[1,1'-biphenyl]-3-carboxylate

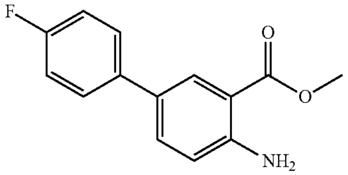 [SMILES: COC(=O)c1cc(-c2ccc(F)cc2)ccc1N]

Nitrogen was bubbled for 5 min through a mixture of methyl 2-amino-5-bromobenzoate (2.00 g, 8.69 mmol), 4-fluorophenylboronic acid, pinacol ester (2.90 g, 12.04 mmol), potassium phosphate tribasic (3.69 g, 17.39 mmol), water (3.5 mL) in N,N-dimethylformamide (10.5 mL), then [1,1'-bis(diphenylphosphino)ferrocene]dichloropalladium (II) complex with dichloromethane (710 mg, 0.87 mmol) was added. The resulting mixture was heated to 100° C. for 1.25 hours. After return to room temperature, the reaction was diluted with water (100 mL) and diethyl ether (100 mL) and the organic phase was separated. The aqueous phase was extracted further with diethyl ether (100 mL) and then Ethyl acetate (100 mL). The organic phases were combined, washed with water (100 mL), dried over $MgSO_4$ and the solvent was removed in vacuo. The residue was purified by chromatography on silica gel eluting with 5-35% Ethyl acetate in cyclohexane to give the title compound as an off-white solid (2.08 g, 97%).

$^1$H NMR (400 MHz, $CDCl_3$): δ 8.06 (d, J=2.3 Hz, 1H), 7.50-7.44 (m, 3H), 7.08 (dd, J=8.7, 8.7 Hz, 2H), 6.74 (d, J=8.6 Hz, 1H), 5.78 (s, 2H), 3.90 (s, 3H).

Step 2: Preparation of methyl 4-amino-4'-fluoro-5-iodo-[1,1'-biphenyl]-3-carboxylate

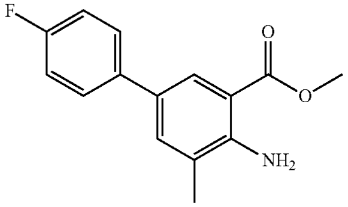 [SMILES: COC(=O)c1cc(-c2ccc(F)cc2)cc(C)c1N]

To a solution of methyl 4-amino-4'-fluoro-[1,1'-biphenyl]-3-carboxylate (2.08 g, 8.48 mmol) in dichloromethane (25 mL) was added bis(pyridine)iodonium tetrafluoroborate (4.73 g, 12.72 mmol) and TFA (2.1 mL, 27.42 mmol). The resulting mixture was stirred at room temperature for 2 days. HPLC analysis showed 70% conversion and further bis (pyridine)iodonium tetrafluoroborate (1.25 g, 3.36 mmol) was added and the stirring was maintained for a further 2.5 hours. The reaction was diluted with dichloromethane (25 mL) and cautiously treated with a solution of $NaHCO_3$ (7 g, 83 mmol) in water (100 mL). The aqueous layer was collected and further extracted with dichloromethane (2×25 mL). The organic phases were combined, washed with an 8% sodium thiosulphate aqueous solution (100 mL), filtered through a hydrophobic fit and the solvent was removed in vacuo. The residue was purified by chromatography on silica gel eluting with 0-25% Ethyl acetate in cyclohexane to give the title compound as an off-white solid (2.71 g, 86%).

$^1$H NMR (400 MHz, $CDCl_3$): δ 8.10-8.07 (m, 1H), 8.04-8.00 (m, 1H), 7.46-7.41 (m, 2H), 7.09 (dd, J=8.6, 8.6 Hz, 2H), 6.48-6.37 (m, 2H), 3.91 (s, 3H).

Step 3: Preparation of 4-amino-4'-fluoro-5-iodo-[1,1'-biphenyl]-3-carboxylic acid

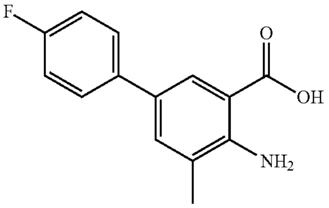 [SMILES: Cc1cc(-c2ccc(F)cc2)cc(C(=O)O)c1N]

To a solution of methyl 4-amino-4'-fluoro-5-iodo-[1,1'-biphenyl]-3-carboxylate (2.59 g, 6.98 mmol) in 1,4-dioxane (25 mL) and water (5 mL) was added lithium hydroxide monohydrate (1.75 g, 41.87 mmol). The mixture was stirred at room temperature for 18 hours. The reaction was diluted with water (100 mL) and diethyl ether (100 mL) and separated. The aqueous phase was acidified with 1N HCl (45 mL) to pH=1 and extracted with dichloromethane (3×50 mL). The organic phases were combined, filtered through a hydrophobic frit and the solvent was removed in vacuo to give the title compound as an off-white solid (2.39 g, 96%).

$^1$H NMR (400 MHz, DMSO): δ 13.17 (s, 1H), 8.18 (d, J=2.0 Hz, 1H), 8.09 (d, J=2.3 Hz, 1H), 7.65 (dd, J=5.4, 8.5 Hz, 2H), 7.27 (dd, J=8.8, 8.8 Hz, 2H), 6.84 (s, 2H).

Step 4: Preparation of 6-(4-fluorophenyl)-8-iodoquinazolin-4(3H)-one

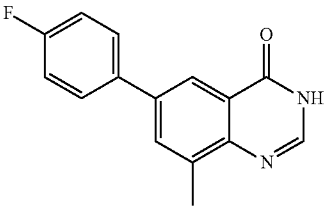 [SMILES: Cc1cc(-c2ccc(F)cc2)cc2c(=O)[nH]cnc12]

A solution of 4-amino-4'-fluoro-5-iodo-[1,1'-biphenyl]-3-carboxylic acid (2.39 g, 6.69 mmol) in formamide (4 mL) was heated to 130° C. for 16 hours. After return to room temperature, the reaction was diluted with water (20 mL) and stirred for 20 minutes before filtering. The solid was washed with water (3×5 mL) then 10% MeOH in diethyl ether (3×5 mL) to give the title compound as an off-white solid (2.14 g, 87%).

$^1$H NMR (400 MHz, DMSO): δ 12.57 (s, 1H), 8.66 (s, 1H), 8.36 (s, 1H), 8.28 (s, 1H), 7.89 (dd, J=5.6, 7.8 Hz, 2H), 7.38 (dd, J=8.6, 8.6 Hz, 2H).

Step 5: Preparation of (R)-6-(4-fluorophenyl)-8-iodo-N-(1-(2-(trifluoromethyl)pyrimidin-5-yl)ethyl)quinazolin-4-amine

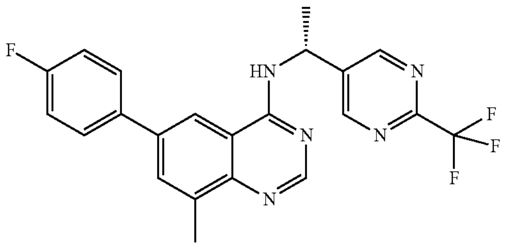 [SMILES: Cc1cc(-c2ccc(F)cc2)cc2c(N[C@H](C)c3cnc(C(F)(F)F)nc3)ncnc12]

To a solution of 6-(4-fluorophenyl)-8-iodoquinazolin-4-(3H)-one (1.14 g, 3.11 mmol) in N,N-dimethylformamide (10 mL) was successively added (benzotriazol-1-yloxy)tripyrrolidinophosphonium hexafluorophosphate (2.03 g, 1.25 mmol) and di-isopropylethylamine (2.7 mL, 15.57 mmol). The resulting mixture was heated to 45° C. for one hour then (R)-1-(2-(trifluoromethyl)pyrimidin-5-yl)ethan-1-amine hydrochloride (0.96 g, 4.2 mmol) was added and the heating was maintained at 45° C. for 2 hours. After return to room temperature, the mixture was diluted with ethyl acetate (75 mL) and water (175 mL). The organic phase was washed with brine (2×20 mL), passed through a hydrophobic frit and the solvent was removed in vacuo. The residue was purified by chromatography on silica gel eluting with 0-15% ethyl acetate in dichloromethane to give the title compound as an off-white solid (1.27 g, 75%).

$^1$H NMR (400 MHz, DMSO): δ 9.18 (s, 2H), 8.88 (d, J=6.9 Hz, 1H), 8.71 (d, J=1.8 Hz, 1H), 8.67 (d, J=1.8 Hz, 1H), 8.51 (s, 1H), 7.95-7.90 (m, 2H), 7.40 (dd, J=8.9, 8.9 Hz, 2H), 5.73-5.67 (m, 1H), 1.75 (d, J=7.2 Hz, 3H).

The following compound reported in the table below was prepared via adaptation of the above procedure using the appropriate amine.

Example 188

(R)-6-(4-fluorophenyl)-8-(methylsulfonyl)-N-(1-(2-(trifluoromethyl)pyrimidin-5-yl)ethyl)quinazolin-4-amine

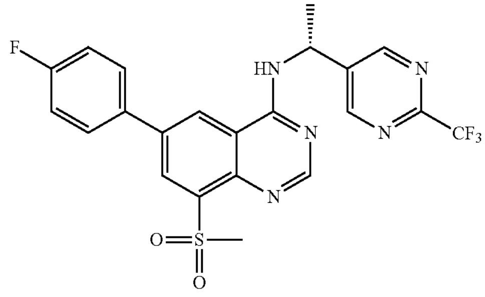 [SMILES: C[C@@H](Nc1ncnc2c(S(C)(=O)=O)cc(-c3ccc(F)cc3)cc12)c1cnc(C(F)(F)F)nc1]

Step 1: Preparation of 6-(4-fluorophenyl)-8-(methylsulfonyl)quinazolin-4(3H)-one

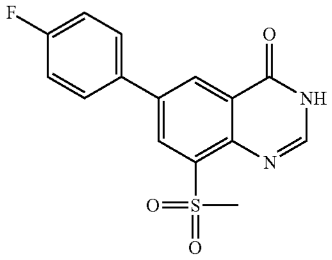 [SMILES: CS(=O)(=O)c1cc(-c2ccc(F)cc2)cc2c(=O)[nH]cnc12]

To a solution of 6-(4-fluorophenyl)-8-iodoquinazolin-4-(3H)-one (200 mg, 0.546 mmol) in dry DMSO (1.5 mL), sodium methanesulfinate (67 mg, 0.655 mmol) was added followed by copper(I) iodide (10.40 mg, 0.055 mmol) and L-proline (13 mg, 0.109 mmol). The reaction was heated to 110° C. and stirred for 18 h. A second addition of all reagents led to complete consumption of the starting material. The reaction mixture was cooled to RT and loaded onto column. Purification by RP flash chromatography (Biotage Isolera, C8 40 g cartridge, gradient elution from 0 to 80% B in A; A: water/MeCN 95:5+0.1% HCOOH, B: MeCN/water 95:5+0.1% HCOOH) yielded the titled compound (52 mg, 0.163 mmol, 30%) as white powder.

LCMS (Method 5): 0.81 min, 319 [M+H]+.

| Example No. | Chemical name Structure | Analytical data $^1$H NMR LC-MS |
|---|---|---|
| Example 187 | 6-(4-fluorophenyl)-8-iodo-N-((6-methylpyridazin-3-yl)methyl)quinazolin-4-amine 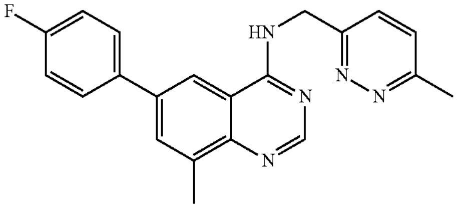 | LCMS (Method 5): 0.96 min, m/z 472.0. $^1$H NMR (400 MHz, DMSO-d6) δ ppm 9.26 (br t, J = 5.62 Hz, 1 H), 8.64 (s, 2 H), 8.47 (s, 1 H), 7.88 (br dd, J = 8.60, 5.51 Hz, 2 H), 7.53 (d, J = 8.60 Hz, 1 H), 7.45 (d, J = 8.60 Hz, 1 H), 7.34 (br t, J = 8.71 Hz, 2 H), 5.02 (br d, J = 5.29 Hz, 2 H), 2.56 (s, 3 H). |

Step 2: Preparation of (R)-6-(4-fluorophenyl)-8-(methyl sulfonyl)-N-(1-(2-(trifluoromethyl)pyrimidin-5-yl)ethyl)quinazolin-4-amine

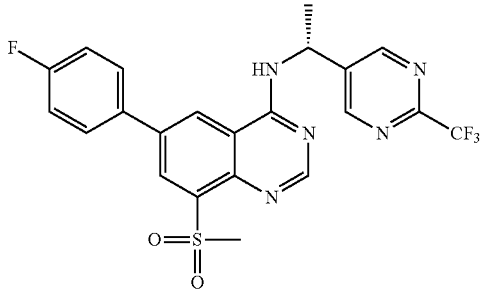 [SMILES: C[C@@H](Nc1ncnc2c(S(C)(=O)=O)cc(-c3ccc(F)cc3)cc12)c1cnc(C(F)(F)F)nc1]

To a suspension of 6-(4-fluorophenyl)-8-(methyl sulfonyl)quinazolin-4(3H)-one (52 mg, 0.163 mmol) in DMF (1 mL), (7-azabenzotriazol-1-yloxy)tripyrrolidinophosphonium hexafluorophosphate (94 mg, 0.180 mmol) and diisopropylethylamine (0.086 mL, 0.490 mmol) were added followed after 10 min by (R)-1-(2-(trifluoromethyl)pyrimidin-5-yl)ethan-1-amine HCl (56 mg, 0.245 mmol). The resulting mixture was stirred at RT for 16 h. Purification by RP flash chromatography (Biotage Isolera, Ultra SNAP 30 g cartridge, gradient elution from 0 to 90% of B in A; A: water/MeCN 95:5+0.1% HCOOH, B: MeCN/water 95:5+0.1% HCOOH) yielded impure titled compound. A second purification by flash chromatography (Biotage Isolera, KP-NH 28 g cartridge, gradient elution from 5% to 100% EtOAc in heptane) yielded the titled compound (20 mg, 0.041 mmol, 25% yield) as pale yellow powder.

LCMS (Method 5): 1.14 min, 492 [M+H]+.

$^1$H NMR (400 MHz, DMSO-d6) δ ppm 9.16 (s, 2H), 9.04 (br d, J=6.61 Hz, 1H), 8.97 (s, 1H), 8.58 (s, 1H), 8.53 (d, J=1.76 Hz, 1H), 7.89 (dd, J=8.60, 5.29 Hz, 2H), 7.41 (t, J=8.82 Hz, 2H), 5.60-5.70 (m, 1H), 3.53 (s, 3H), 1.72 (d, J=7.28 Hz, 3H).

The following compound reported in the table below was prepared via adaptation of the above procedure using the appropriate amine.

Example 190

(R)—N-(6-(4-fluorophenyl)-4-((1-(2-(trifluoromethyl)pyrimidin-5-yl)ethyl)amino)quinazolin-8-yl) methanesulfonamide

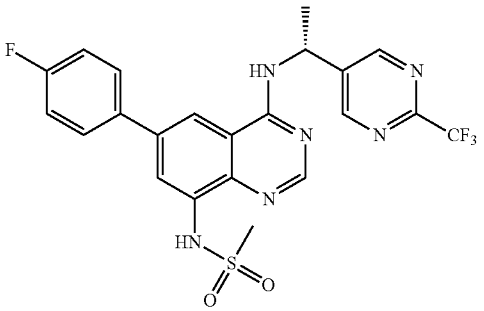

To a solution of (R)-6-(4-fluorophenyl)-8-iodo-N-(1-(2-(trifluoromethyl)pyrimidin-5-yl)ethyl)quinazolin-4-amine (60 mg, 0.111 mmol) in 1,4-Dioxane (1.5 mL), methanesulfonamide (14 mg, 0.145 mmol), copper(I) iodide (2.119 mg, 0.011 mmol), L-proline (2.56 mg, 0.022 mmol) and potassium carbonate (46 mg, 0.334 mmol) were added. The resulting mixture was heated to 150° C. for 6 h. The reaction was diluted with DCM and water was added. The two phases were separated, the aqueous layer was extracted with DCM (2×10 mL) and the combined organic phase was filtered through a PhaseSeparator tube. Volatiles were removed under reduced pressure. Purification by RP flash chromatography (Biotage Isolera, Ultra SNAP 30 g cartridge, gradient elution from 5% to 100% of B in A; A: water/MeCN 95:5+0.1% HCOOH, B: MeCN/water 95:5+0.1% HCOOH) yielded the titled compound (9 mg, 0.018 mmol, 16% yield) as pale beige powder.

LCMS (Method 5): 1.17 min, 507 [M+H]+.

$^1$H NMR (400 MHz, DMSO-d6) δ ppm 9.14 (s, 3H), 8.71-8.86 (m, 1H), 8.47 (s, 1H), 8.36 (br s, 1H), 7.95 (s, 1H), 7.81 (br dd, J=8.16, 5.73 Hz, 2H), 7.37 (br t, J=8.71 Hz, 2H), 5.66 (br s, 1H), 3.12 (s, 3H), 1.71 (br d, J=7.06 Hz, 3H).

The following compound reported in the table below was prepared via adaptation of the above procedure.

| Example No. | Chemical name<br>Structure | Analytical data<br>$^1$H NMR<br>LC-MS |
|---|---|---|
| Example 189 | 6-(4-fluorophenyl)-N-((6-methylpyridazin-3-yl)methyl)-8-(methylsulfonyl)quinazolin-4-amine<br>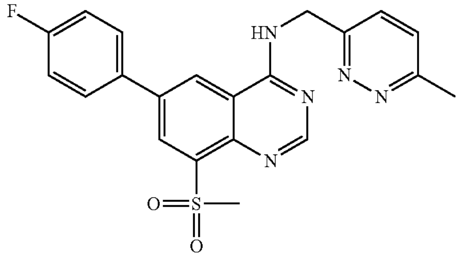 [SMILES: Cc1ccc(CNc2ncnc3c(S(C)(=O)=O)cc(-c4ccc(F)cc4)cc23)nn1] | LCMS (Method 5): 0.82 min, m/z 424.0.<br>$^1$H NMR (400 MHz, DMSO-d6) δ ppm 9.48 (br t, J = 5.18 Hz, 1 H), 8.92 - 9.01 (m, 1 H), 8.58 (s, 1 H), 8.55 (d, J = 1.54 Hz, 1 H), 7.88 (br dd, J = 8.49, 5.40 Hz, 2 H), 7.57 (d, J = 8.60 Hz, 1 H), 7.47 (d, J = 8.60 Hz, 1 H), 7.33 - 7.50 (m, 2 H), 5.04 (br d, J = 4.41 Hz, 2 H), 3.55 (s, 3 H), 2.56 (s, 3 H). |

| Example No. | Chemical name<br>Structure | Analytical data<br>$^1$H NMR<br>LC-MS |
|---|---|---|
| Example 191 | N-(6-(4-fluorophenyl)-4-oxo-3,4-dihydroquinazolin-8-yl)methanesulfonamide<br>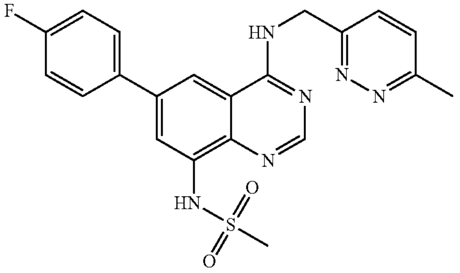 | LCMS (Method 5): 0.79 min, m/z 439.0.<br>$^1$H NMR (400 MHz, DMSO-d6) δ ppm 9.21 (br s, 1 H), 8.47 (s, 1 H), 8.33 (br s, 1 H), 7.97 (s, 1 H), 7.80 (br dd, J = 8.27, 5.62 Hz, 2 H), 7.53 (d, J = 8.60 Hz, 1 H), 7.46 (d, J = 8.60 Hz, 1 H), 7.36 (br t, J = 8.82 Hz, 2 H), 5.01 (br d, J = 5.07 Hz, 2 H), 3.14 (s, 3 H), 2.56 (s, 3 H). |

Example 192

(R)-6-(4-fluorophenyl)-4-((1-(2-(trifluoromethyl)pyrimidin-5-yl)ethyl)amino)quinazoline-8-sulfonamide

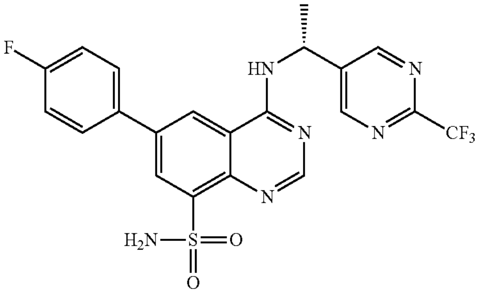 [SMILES: C[C@@H](Nc1ncnc2c(S(N)(=O)=O)cc(-c3ccc(F)cc3)cc12)c1cnc(C(F)(F)F)nc1]

Step 1: Preparation of 6-(4-fluorophenyl)-4-oxo-3,4-dihydroquinazoline-8-sulfonamide

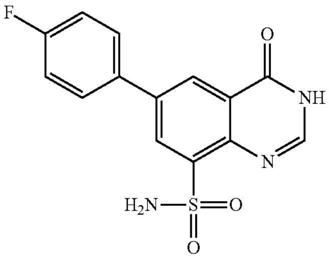 [SMILES: NS(=O)(=O)c1cc(-c2ccc(F)cc2)cc2c(=O)[nH]cnc12]

To a suspension of 6-(4-fluorophenyl)-8-(methyl sulfonyl)quinazolin-4(3H)-one (167 mg, 0.525 mmol) in dry THF (2 mL), cooled to 0° C., lithium diisopropylamide 2.0 M in THF heptane ethylbenzene (1.049 mL, 2.099 mmol) was added. The reaction was warmed to RT and stirred for 30 min until complete dissolution. To the resulting orange solution, tributylborane 1.0 M in THF (2.62 mL, 2.62 mmol) was added and the reaction was heated to 64° C. and stirred for 12 h. A solution of (aminooxy)sulfonic acid (208 mg, 1.836 mmol) and potassium acetate (232 mg, 2.361 mmol) in water (2 mL) was added and the resulting mixture stirred at 65° C. for 6 h. Volatiles were removed under reduced pressure. The crude was taken up with DMF and purified by RP flash chromatography (Biotage Isolera, Ultra SNAP C18 60 g cartridge, gradient elution from 0 to 80% of B in A; A: water/MeCN 95:5+0.1% HCOOH, B: MeCN/water 95:5+0.1% HCOOH). An unseparable mixture of titled compound and starting material was isolated and used as such in the next step.

Step 2: Preparation of (R)-6-(4-fluorophenyl)-4-((1-(2-(trifluoromethyl)pyrimidin-5-yl)ethyl)amino)quinazoline-8-sulfonamide

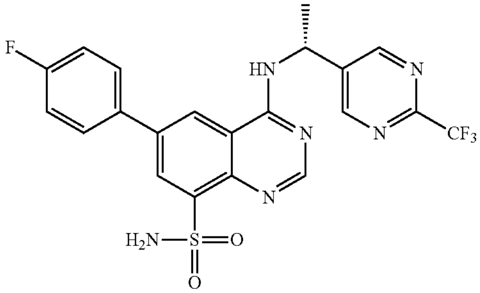 [SMILES: C[C@@H](Nc1ncnc2c(S(N)(=O)=O)cc(-c3ccc(F)cc3)cc12)c1cnc(C(F)(F)F)nc1]

To a suspension of the crude 6-(4-fluorophenyl)-4-hydroxyquinazoline-8-sulfonamide (40 mg, 0.125 mmol) in DMF (1.5 mL), (benzotriazol-1-yloxy)tripyrrolidinophosphonium hexafluorophosphate (78 mg, 0.150 mmol) and di-isopropylethylamine (0.066 mL, 0.376 mmol) were added followed after 5 min by (R)-1-(2-(trifluoromethyl)pyrimidin-5-yl)ethan-1-amine (36 mg, 0.188 mmol). The resulting mixture was stirred at RT for 12 h. The reaction was diluted with DCM and quenched with water. The two phases were separated and the aqueous layer was extracted once with DCM. Combined organic phase was filtered through a PhaseSeparator tube and volatiles removed under reduced pressure. Purification by flash chromatography (Biotage Isolera, Ultra SNAP 25 g cartridge, gradient elution from 5% to 100% EtOAc in heptane) yielded impure titled compound. Second purification by flash chromatography (Biotage Isolera, SNAP NH 28 g cartridge, gradient elution from 5% to 100% EtOAc in heptane) yielded the titled compound (4 mg, 8.12 μmol, 6.48% yield) as white powder.

LCMS (Method 5): 1.08 min, 493 [M+H]+.

$^1$H NMR (400 MHz, DMSO-d6) δ ppm 9.15 (s, 2H), 9.01 (br s, 1H), 8.88 (br d, J=1.98 Hz, 1H), 8.54 (s, 1H), 8.42-8.49 (m, 1H), 7.81-7.96 (m, 2H), 7.40 (br t, J=8.82 Hz, 2H), 7.21 (br s, 2H), 5.67 (br d, J=6.84 Hz, 1H), 1.72 (d, J=7.06 Hz, 3H).

Example 193

(R)-6-(4-fluorophenyl)-8-(1-methyl-JH-pyrazol-4-yl)-N-(1-(2-(trifluoromethyl)pyrimidin-5-yl)ethyl)quinazolin-4-amine

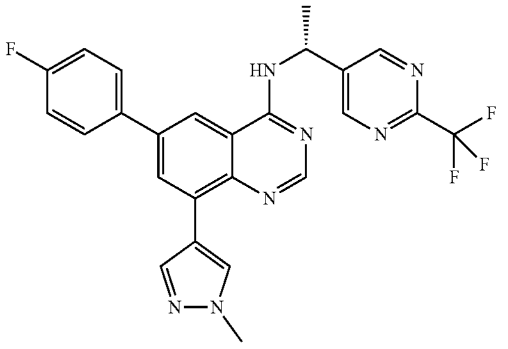 [SMILES: C[C@@H](Nc1ncnc2c(-c3cnn(C)c3)cc(-c3ccc(F)cc3)cc12)c1cnc(C(F)(F)F)nc1]

Nitrogen was bubbled for 15 min through a mixture of (R)-6-(4-Fluorophenyl)-8-iodo-N-(1-(2-(trifluoromethyl)pyrimidin-5-yl)ethyl)quinazolin-4-amine (100 mg, 0.18 mmol), 1-methylpyrazole-4-boronic acid pinacol ester (52 mg, 0.25 mmol), cesium fluoride (85 mg, 0.56 mmol), water (0.5 mL) in N,N-dimethylformamide (2.0 mL), then tetrakis(triphenylphosphine)palladium(0) (21 mg, 0.02 mmol) was added. The resulting mixture was heated to 95° C. for 16 hours. After return to room temperature, the reaction was diluted with water (6 mL) and extracted with ethyl acetate (3×3 mL). The combined organic phases were filtered through a hydrophobic frit and the solvent was removed in vacuo. The residue was purified by preparative HPLC to give the title compound as an off-white solid (63 mg, 69%).

$^1$H NMR (400 MHz, DMSO): δ 9.24 (s, 2H), 8.76 (d, J=6.8 Hz, 1H), 8.71 (s, 1H), 8.59-8.54 (m, 2H), 8.39 (d, J=1.5 Hz, 1H), 8.35 (s, 1H), 8.03 (dd, J=5.4, 8.7 Hz, 2H), 7.45 (dd, J=8.8, 8.8 Hz, 2H), 5.80-5.71 (m, 1H), 3.97 (s, 3H), 1.80 (d, J=7.1 Hz, 3H). LCMS (Method 3): [MH+]=494 at 5.1 min.

The following compounds reported in the table below were prepared according to the same procedure described for the preparation of (R)-6-(4-fluorophenyl)-8-(1-methyl-1H-pyrazol-4-yl)-N-(1-(2-(trifluoromethyl)pyrimidin-5-yl)ethyl)quinazolin-4-amine:

| Example No. | Chemical name<br>Structure | Analytical data<br>$^1$H NMR<br>LC-MS |
|---|---|---|
| Example 194 | (R)-6-(4-Fluorophenyl)-8-(1-methyl-1,2,3,6-tetrahydropyridin-4-yl)-N-(1-(2-(trifluoromethyl)pyrimidin-5-yl)ethyl)quinazolin-4-amine<br>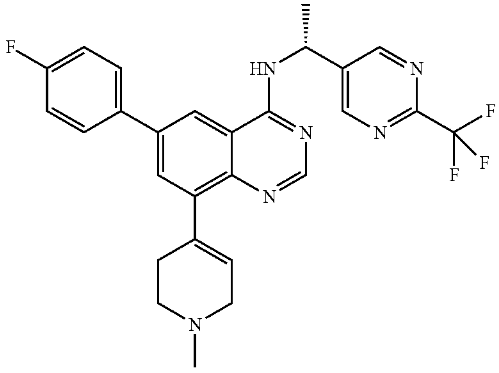 | $^1$H NMR (400 MHz, DMSO): δ 9.22 (s, 2H), 8.74 (d, J = 6.8 Hz, 1 H), 8.62 (d, J = 1.0 Hz, 1 H), 8.49 (s, 1 H), 7.96 (dd, J = 5.6, 8.6 Hz, 2 H), 7.91 (s, 1 H), 7.43 (dd, J = 8.8, 8.8 Hz, 2H) 5.96 (s, 1 H), 5.77 - 5.68 (m, 1 H), 3.12 - 3.05 (m, 2 H), 2.81 - 2.74 (m, 2 H), 2.67 - 2.59 (m, 2 H), 2.35 (s, 3H), 1.78 (d, J = 7.1 Hz, 3 H). LCMS (Method 4): [MH+] = 509 at 3.17 min. |

-continued

| Example No. | Chemical name<br>Structure | Analytical data<br>$^1$H NMR<br>LC-MS |
|---|---|---|
| Example 195 | (R)-6-(4-Fluorophenyl)-N-(1-(2-(trifluoromethyl)pyrimidin-5-yl)ethyl)-8-(1,3,5-trimethyl-1H-pyrazol-4-yl)quinazolin-4-amine<br>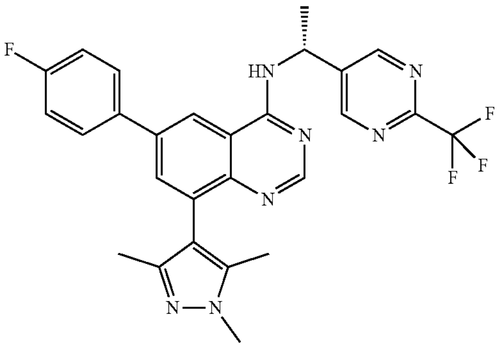 | $^1$H NMR (400 MHz, DMSO): δ 9.12 (s, 2 H), 8.67 (d, J = 6.8 Hz, 1 H), 8.56 (d, J = 1.3 Hz, 1 H), 8.32 (s, 1 H), 7.88 - 7.80 (m, 3 H), 7.31 (dd, J = 8.8, 8.8 Hz, 2 H), 5.65 - 5.57 (m, 1 H), 3.66 (s, 3 H), 1.99 (s, 3 H), 1.92 (s, 3 H), 1.67 (d, J = 7.1 Hz, 3 H). LCMS (Method 4): [MH+] = 522 at 3.77 min. |
| Example 196 | (R)-6-(4-Fluorophenyl)-8-(pyridin-4-yl)-N-(1-(2-(trifluoromethyl)pyrimidin-5-yl)ethyl)quinazolin-4-amine<br>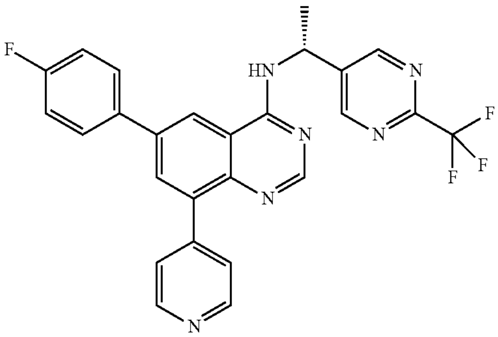 | $^1$H NMR (400 MHz, DMSO): δ 9.21 (s, 2 H), 8.87 (d, J = 6.9 Hz, 1 H), 8.78 (d, J = 2.0 Hz, 1 H), 8.67 (d, J = 6.0 Hz, 2 H), 8.48 (s, 1 H), 8.20 (d, J = 2.0 Hz, 1 H), 8.04 - 7.99 (m, 2 H), 7.78 - 7.75 (m, 2 H), 7.42 (dd, J = 8.9, 8.9 Hz, 2 H), 5.76 - 5.69 (m, 1 H), 1.78 (d, J = 7.2 Hz, 3 H). LCMS (Method 4): [MH+] = 491 at 3.9 min. |
| Example 197 | (R)-4-(6-(4-Fluorophenyl)-4-((1-(2-(trifluoromethyl)pyrimidin-5-yl)ethyl)amino)quinazolin-8-yl)-N,N-dimethylbenzamide<br>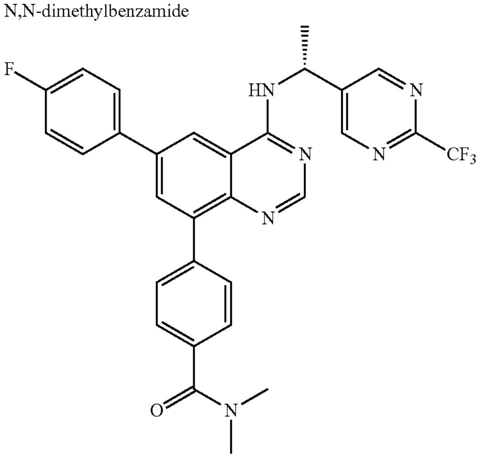 | $^1$H NMR (400 MHz, DMSO): δ 9.22 - 9.18 (m, 5 H), 8.91 (d, J = 6.9 Hz, 1 H), 8.80 (d, J = 2.0 Hz, 1 H), 8.49 (s, 1 H), 8.34 (d, J = 2.0 Hz, 1 H), 8.07 - 8.02 (m, 2 H), 7.43 (dd, J = 8.9, 8.9 Hz, 2 H), 5.75 - 5.69 (m, 1 H), 1.78 (d, J = 7.2 Hz, 3 H). LCMS (Method 3): [MH+] = 561 at 4.09 min. |

Example 198

(R)-6-(4-fluorophenyl)-4-((1-(2-(trifluoromethyl) pyrimidin-5-yl)ethyl)amino)-quinazolin-8-ol

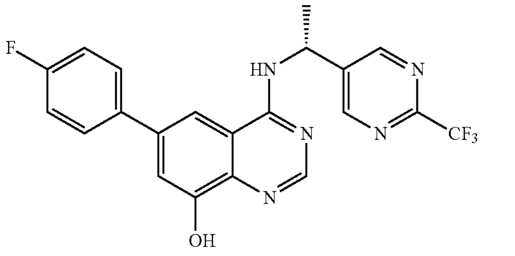 [SMILES: C[C@@H](Nc1ncnc2c(O)cc(-c3ccc(F)cc3)cc12)c1cnc(C(F)(F)F)nc1]

To a solution of 6-(4-fluorophenyl)-8-methoxy-N-[(1R)-1-[2-(trifluoromethyl)-pyrimidin-5-yl]ethyl]quinazolin-4-amine (490 mg, 1.11 mmol) in chloroform (8 mL) at 0° C. was added dropwise boron tribromide (0.32 mL, 3.32 mmol). The reaction was then allowed to warm to room temperature and was heated to 65° C. for 18 hours. After return to room temperature, the reaction was cooled down in an ice-bath and quenched with methanol (2 mL). The solvent was removed in vacuo. The residue was diluted with ethyl acetate (50 mL) and washed with saturated aqueous $NaHCO_3$ solution (50 mL). The aqueous layer was then extracted with ethyl acetate (2×20 mL). The organic phases were combined, passed through a hydrophobic frit and the solvent was removed in vacuo to give the title compound as a grey solid (416 mg, 88%).

$^1H$ NMR (400 MHz, DMSO): δ 9.18 (s, 2H), 8.65 (d, J=7.0 Hz, 1H), 8.46 (s, 1H), 8.09 (s, 1H), 7.86 (dd, J=5.5, 8.7 Hz, 2H), 7.45 (d, J=1.3 Hz, 1H), 7.37 (dd, J=8.8, 8.8 Hz, 2H), 5.71-5.67 (m, 1H), 1.75 (d, J=7.0 Hz, 3H). OH not observed.

The following compounds were prepared via adaptations of the above procedure starting from substrate reported in table.

| Example No. | Structure | Analytical data LC-MS | Substrate |
|---|---|---|---|
| Example 199 | 6-(4-fluorophenyl)-4-(((6-methylpyridazin-3-yl)methyl)amino)quinazolin-8-ol 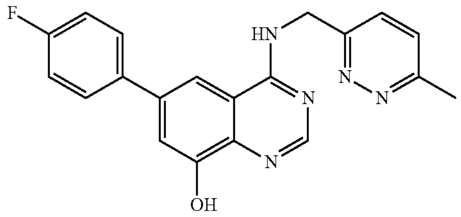 | LCMS: 0.51 min, 362.1 [M + H]+, Method 5method 2 min. | Example 182 |

Example 200

(R)-6-(4-Fluorophenyl)-8-((tetrahydro-2H-pyran-4-yl)oxy)-N-(1-(2-(trifluoromethyl)pyrimidin-5-yl) ethyl)quinazolin-4-amine

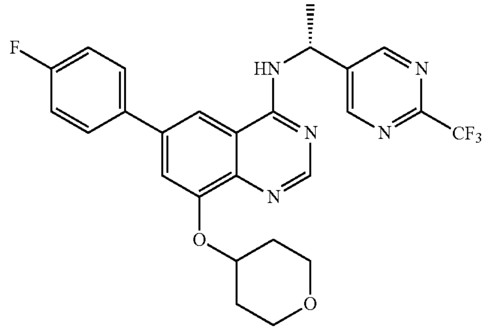 [SMILES: C[C@@H](Nc1ncnc2c(OC3CCOCC3)cc(-c3ccc(F)cc3)cc12)c1cnc(C(F)(F)F)nc1]

Nitrogen was bubbled for 5 min through a mixture of (R)-6-(4-fluorophenyl)-4-((1-(2-(trifluoromethyl)pyrimidin-5-yl)ethyl)amino)quinazolin-8-ol (40 mg, 0.01 mmol), tetrahydro-4-pyranol (10 mg, 0.102 mmol) and cyanomethyltributylphosphorane (1 M in toluene, 0.14 mL, 0.14 mmol) in toluene (3.0 mL). The mixture was heated to 100° C. for 72 hours. After return to room temperature, the solvent was removed in vacuo. The residue was purified by preparative HPLC to give the title compound (17 mg, 38%) as an off white solid.

$^1H$ NMR (400 MHz, DMSO): δ 9.18 (s, 2H), 8.64 (d, J=7.0 Hz, 1H), 8.44 (s, 1H), 8.23 (d, J=1.6 Hz, 1H), 7.94-7.89 (m, 2H), 7.65 (d, J=1.6 Hz, 1H), 7.39 (dd, J=8.8, 8.8 Hz, 2H), 5.71-5.66 (m, 1H) 5.02-4.94 (m, 1H), 3.96-3.88 (m, 2H), 3.51 (dd, J=9.7, 9.7 Hz, 2H), 2.07-2.00 (m, 2H), 1.74 (d, J=7.0 Hz, 5H). LCMS (Method 3): [MH+]=514 at 3.79 min.

Example 201

6-(4-fluorophenyl)-8-(((R)-tetrahydrofuran-3-yl)oxy)-N—((R)-1-(2-(trifluoromethyl)pyrimidin-5-yl)ethyl)quinazolin-4-amine

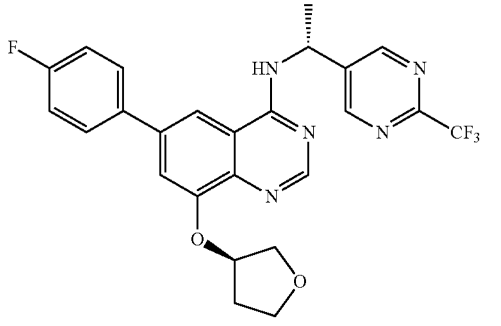 [SMILES: C[C@@H](Nc1ncnc2c(O[C@@H]3CCOC3)cc(-c3ccc(F)cc3)cc12)c1cnc(C(F)(F)F)nc1]

Potassium carbonate (47.7 mg, 0.345 mmol) was added to a mixture of (R)-6-(4-fluorophenyl)-4-((1-(2-(trifluoromethyl)pyrimidin-5-yl)ethyl)amino)quinazolin-8-ol (64.4 mg, 0.150 mmol) and (S)-tetrahydrofuran-3-yl 4-methylbenzenesulfonate (41.8 mg, 0.172 mmol) in DMF (Volume: 3 ml). Stirring went on at 60° C. for 16 h. The reaction mixture was allowed to cool down to rt, then it was quenched by the addition of formic acid (0.017 ml, 0.450 mmol). Purification by RP chromatography (Biotage Isolera, 30 g C18 cartridge, gradient elution from 100:0 to 50:50 A/B, A: water/acetonitrile 95:5+0.1% HCOOH, B: acetonitrile:water 95:5+0.1% HCOOH) then DP chromatography (Biotage Isolera, 11 g NH cartridge, gradient elution from 0 to 40% ethyl acetate in dichloromethane) yielded 6-(4-fluorophenyl)-8-(((R)-tetrahydrofuran-3-yl)oxy)-N—((R)-1-(2-(trifluoromethyl)pyrimidin-5-yl)ethyl)quinazolin-4-amine (8.3 mg, 0.017 mmol, 11.08% yield) as a white powder.

LCMS (Method 5): Method 5 0.74 min, 500.0 [M+H]+, CSH method 2 min.

1H NMR (400 MHz, DMSO-d6) δ ppm 9.16 (s, 2H), 8.61 (d, J=6.6 Hz, 1H), 8.42 (s, 1H), 8.21 (d, J=1.3 Hz, 1H), 7.84-8.01 (m, 2H), 7.51 (d, J=1.3 Hz, 1H), 7.38 (t, J=8.8 Hz, 2H), 5.67 (t, J=7.0 Hz, 1H), 5.35-5.50 (m, 1H), 3.85-4.04 (m, 3H), 3.79 (d, J=4.4 Hz, 1H), 2.19-2.37 (m, 1H), 2.03-2.17 (m, 1H), 1.72 (d, J=7.0 Hz, 3H).

The following compounds were prepared via adaptations of the above procedures starting from substrate reported in table.

| Example No. | Structure | Analytical data $^1$H NMR LC-MS | Reagents |
|---|---|---|---|
| Example 202 | 6-(4-fluorophenyl)-8-isopropoxy-N-[(6-methylpyridazin-3-yl)methyl]quinazolin-4-amine 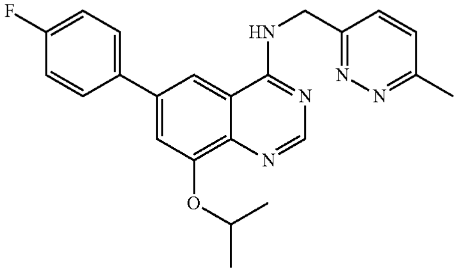 | LCMS (Method 7): 2.50 min, [M + H]+ 404.5 $^1$H NMR (300 MHz, CHLOROFORM-d) δ ppm 8.78 (s, 1 H) 7.69 (br s, 1 H) 7.57 - 7.66 (m, 2 H) 7.50 - 7.57 (m, 2 H) 7.40 (d, J = 8.62 Hz, 1 H) 7.32 (d, J = 1.10 Hz, 1 H) 7.19 (t, J = 8.71 Hz, 2 H) 5.11 (d, J = 4.22 Hz, 2H) 4.91 (spt, J = 6.10 Hz, 1 H) 2.77 (s, 3 H) 1.56 (d, J = 6.05 Hz, 6H) | Example 199, isopropyl iodide, $Cs_2CO_3$, NaI |
| Example 203 | 8-(cyclopropylmethoxy)-6-(4-fluorophenyl)-N-[(6-methylpyridazin-3-yl)methyl]quinazolin-4-amine 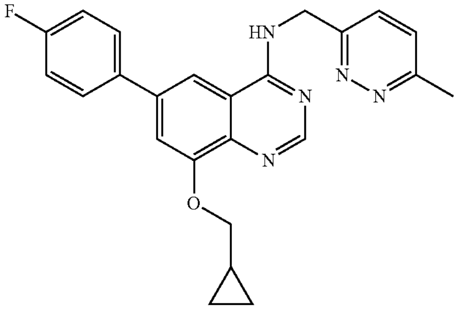 | LCMS (Method 7): 2.89 min, [M + H]+ 416.4 $^1$H NMR (300 MHz, CHLOROFORM-d) δ ppm 8.80 (s, 1 H) 7.70 (br s, 1 H) 7.59 - 7.67 (m, 2 H) 7.55 - 7.58 (m, 1 H) 7.52 (s, 1 H) 7.37 - 7.43 (m, 1 H) 7.29 - 7.31 (m, 1 H) 7.20 (t, J = 8.62 Hz, 2 H) 5.12 (d, J = 4.22 Hz, 2 H) 4.11 (d, J = 6.97 Hz, 2 H) 2.77 (s, 3 H) 2.24 - 2.34 (m, 1 H) 1.47 - 1.55 (m, 1 H) 0.69 - 0.81 (m, 2 H) 0.41 - 0.53 (m, 2 H) | Example 199, (Bromomethyl) cyclopropane, $Cs_2CO_3$, NaI |

-continued

| Example No. | Structure | Analytical data $^1H$ NMR LC-MS | Reagents |
|---|---|---|---|
| Example 204 | 2-[6-(4-fluorophenyl)-4-[(6-methylpyridazin-3-yl)methylamino]quinazolin-8-yl]oxyethanol 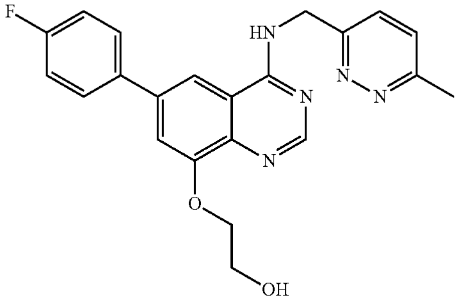 | LCMS (Method 7): 2.24 min, [M + H]+ 406.4 $^1H$ NMR (300 MHz, CHLOROFORM-d) δ ppm 8.57 (s, 1 H) 8.00 - 8.22 (m, 1 H) 7.49 - 7.63 (m, 4 H) 7.36 - 7.47 (m, 2 H) 7.16 (t, J = 8.62 Hz, 2 H) 5.10 (d, J = 4.58 Hz, 2 H) 4.27 - 4.40 (m, 2 H) 4.00 - 4.13 (m, 2 H) 3.52 (br s, 1 H) 2.78 (s, 3 H) | Example 199, 2-bromoethyl benzoate, $Cs_2CO_3$, NaI |
| Example 205 | 2-[6-(4-fluorophenyl)-4-[(6-methylpyridazin-3-yl)methylamino]quinazolin-8-yl]oxy-N,N-dimethyl-acetamide 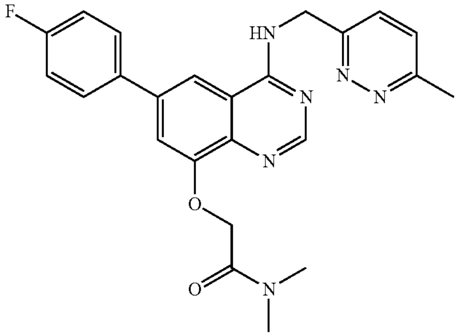 | LCMS (Method 7): 3.22 min, [M + H]+ 447.2 $^1H$ NMR (300 MHz, DMSO-d6) δ ppm 8.99 - 9.14 (m, 1 H) 8.43 (s, 1 H) 8.19 (d, J = 1.47 Hz, 1 H) 7.81 - 7.93 (m, 2 H) 7.45 - 7.60 (m, 3 H) 7.32 - 7.45 (m, 2 H) 5.77 (s, 1 H) 5.11 (s, 2H) 5.03 (d, J = 5.69 Hz, 2 H) 3.08 (s, 3 H) 2.87 (s, 4 H) 2.59 (s, 3 H) | Example 199, 2-Cl-Dimethylacetamide, $Cs_2CO_3$ |
| Example 206 | 6-(4-fluorophenyl)-8-(2-methoxyethoxy)-N-[(6-methylpyridazin-3-yl)methyl]quinazolin-4-amine 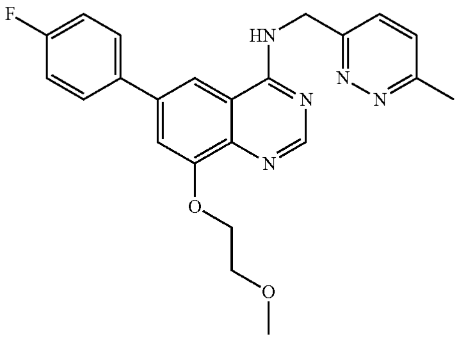 | LCMS (Method 7): 2.42 min, [M + H]+ 420.1 $^1H$ NMR (300 MHz, CHLOROFORM-d) δ ppm 8.73 (s, 1 H), 7.71 - 7.86 (m, 1 H), 7.52 - 7.64 (m, 3H), 7.50 - 7.54 (m, 1 H), 7.38 - 7.42 (m, 2 H), 7.11 - 7.27 (m, 2 H), 5.11 (d, J = 3.12 Hz, 2H), 4.44 (t, J = 5.04 Hz, 2 H), 3.97 (t, J = 5.04 Hz, 2 H), 3.50 (s, 3 H), 2.77 (s, 3 H) | Example 199, 3-MethoxyBromoethane $Cs_2CO_3$ |

-continued

| Example No. | Structure | Analytical data $^1$H NMR LC-MS | Reagents |
|---|---|---|---|
| Example 207 | 6-(4-fluorophenyl)-N-[(6-methylpyridazin-3-yl)methyl]-8-(oxetan-3-ylmethoxy)quinazolin-4-amine 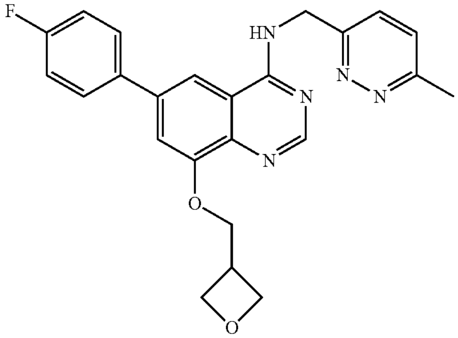 | LCMS (Method 7): 2.47 min, [M + H]+ 432.3 $^1$H NMR (300 MHz, CHLOROFORM-d) δ ppm 8.75 (s, 1 H), 7.70 - 7.78 (m, 1 H), 7.56 - 7.67 (m, 3H), 7.50 - 7.54 (m, 1 H), 7.38 - 7.43 (m, 1 H), 7.36 (d, J = 1.28 Hz, 1 H), 7.15 - 7.27 (m, 2 H), 5.11 (d, J = 4.40 Hz, 2H), 5.02 (t, J = 6.51 Hz, 2 H), 4.63 (t, J = 5.96 Hz, 2 H), 4.56 (d, J = 7.34 Hz, 2 H), 3.61 - 3.79 (m, 1 H), 2.77 (s, 3 H) 3.61 - 3.83 (m, 1 H) 2.77 (s, 3 H) | Example 199, 4-Iodomethyloxethane, $Cs_2CO_3$ |
| Example 208 | 6-(4-fluorophenyl)-N-[(6-methylpyridazin-3-yl)methyl]-8-tetrahydropyran-4-yloxy-quinazolin-4-amine 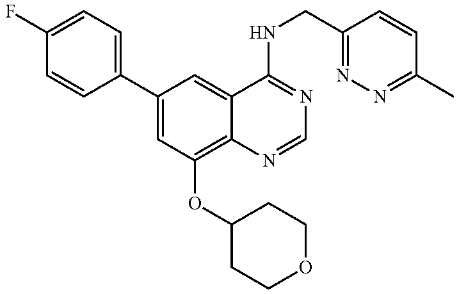 | LCMS (Method 7): 2.50 min, [M + H]+ 446.5 $^1$H NMR (300 MHz, CHLOROFORM-d) δ ppm 8.79 (s, 1 H) 7.68 - 7.78 (m, 1 H) 7.57 - 7.66 (m, 3 H) 7.49 - 7.56 (m, 1 H) 7.33 - 7.46 (m, 2 H) 7.12 - 7.26 (m, 2H) 5.12 (d, J = 4.31 Hz, 2 H) 4.75 - 4.93 (m, 1 H) 4.05 - 4.21 (m, 2 H) 3.62 (ddd, J = 11.85, 9.51, 2.66 Hz, 2 H) 2.77 (s, 3 H) 2.14 - 2.27 (m, 2 H) 1.99 - 2.14 (m, 2 H) | Example 199, 4-Mesyloxytetrahydropyrane, $Cs_2CO_3$ |
| Example 209 | 6-(4-fluorophenyl)-N-[(6-methylpyridazin-3-yl)methyl]-8-(2-morpholinoethoxy)quinazolin-4-amine 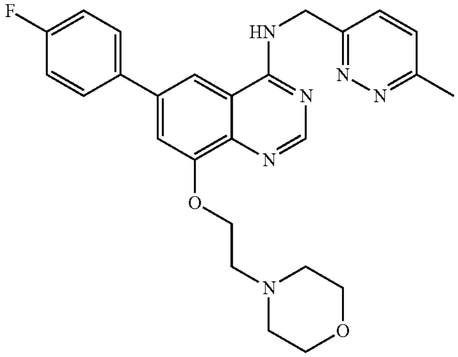 | LCMS (Method 7): 2.25 min, [M + H]+ 475.1 $^1$H NMR (300 MHz, CHLOROFORM-d) δ ppm 8.62 (s, 1 H) 8.11 (br s, 1 H) 7.45 - 7.61 (m, 4 H) 7.40 (d, J = 8.62 Hz, 1 H) 7.25 - 7.28 (m, 1 H) 7.12 (t, J = 8.71 Hz, 2 H) 5.08 (d, J = 4.22 Hz, 2 H) 4.36 (t, J = 6.05 Hz, 2 H) 3.72 - 3.83 (m, 4 H) 3.01 (t, J = 6.05 Hz, 2 H) 2.73 (s, 3 H) 2.57 - 2.70 (m, 4 H) | Example 199, N-(2-Chloroethyl) morpholine, $Cs_2CO_3$ |

-continued

| Example No. | Structure | Analytical data $^1$H NMR LC-MS | Reagents |
|---|---|---|---|
| Example 210 | 6-(4-fluorophenyl)-8-[(1-methyl-4-piperidyl)oxy]-N-[(6-methylpyridazin-3-yl)methyl]quinazolin-4-amine 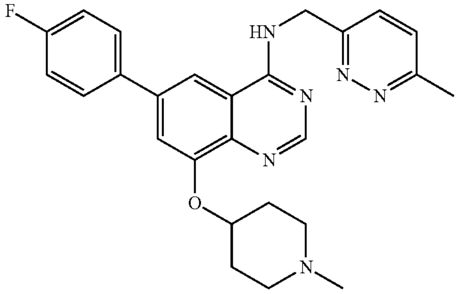 | LCMS (Method 7): 1.97 min, [M + H]+ 459.1 $^1$H NMR (300 MHz, METHANOL-d4) δ ppm 8.48 (s, 1 H), 8.37 (br s, 1 H), 8.04 (d, J = 1.10 Hz, 1 H), 7.73 - 7.81 (m, 2 H), 7.66 - 7.73 (m, 1 H), 7.64 (d, J = 1.28 Hz, 1 H), 7.55 - 7.61 (m, 1 H), 7.22 (t, J = 8.71 Hz, 2 H), 5.05 - 5.17 (m, 3 H), 3.60 - 3.74 (m, 2 H), 3.34 - 3.39 (m, 2 H), 2.92 (s, 3 H), 2.66 (s, 3 H), 2.27 (br s, 4 H) | Example 199, 4-Chloro-1-methylpiper-idine, $Cs_2CO_3$, NaI |
| Example 211 | 8-[3-(dimethylamino)propoxy]-6-(4-fluorophenyl)-N-[(6-methylpyridazin-3-yl)methyl]quinazolin-4-amine 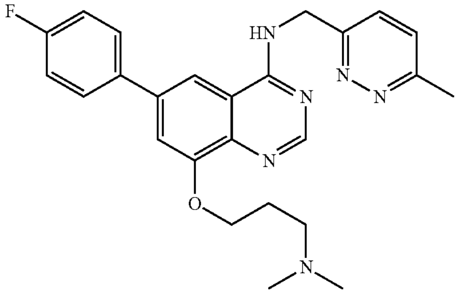 | LCMS (Method 7): 2.30 min, [M + H]+ 447.1 NMR (300 MHz, CHLOROFORM-d) δ ppm 8.71 (s, 1 H), 7.80 - 7.90 (m, 1 H), 7.51 - 7.62 (m, 4 H), 7.40 (d, J = 8.62 Hz, 1 H), 7.34 (d, J = 1.47 Hz, 1 H), 7.12 - 7.21 (m 2 H), 5.10 (d, J = 4.03 Hz, 2 H), 4.33 (t, J = 6.88 Hz, 2 H), 2.75 (s, 3 H), 2.66 t, J = 6.97 Hz, 2 H), 2.27 - 2.36 (m, 8H) | Example 199, 3-Chloro-N,N-Dimethyl aminopropane HCl, $Cs_2CO_3$, NaI |
| Example 212 | ethyl 2-[6-(4-fluorophenyl)-4-[(6-methylpyridazin-3-yl)methylamino]quinazolin-8-yl]oxyacetate 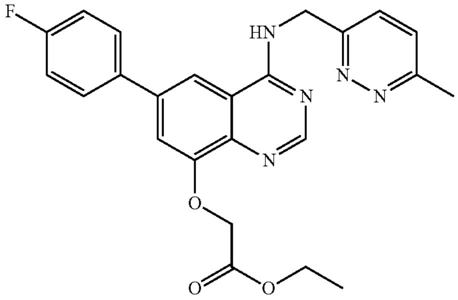 | LCMS (Method 7): 2.69 min, [M + H]+ 448.4 Sel 6 min $^1$H NMR (300 MHz, CHLOROFORM-d) δ ppm 8.69 (s, 1 H), 7.85 (br s, 1 H), 7.50 - 7.61 (m, 4 H), 7.37 - 7.47 (m, 1 H), 7.24 (d, J = 0.92 Hz, 1 H), 7.17 (t, J = 8.62 Hz, 2 H), 5.10 (d, J = 4.03 Hz, 2 H), 5.00 (s, 2 H), 4.30 (q, J = 7.15 Hz, 2 H), 2.77 (s, 3 H), 1.29 (t, J = 7.15 Hz, 3 H) | Example 199, Ethyl 2-Chloroac-etate $Cs_2CO_3$ |

-continued

| Example No. | Structure | Analytical data $^1H$ NMR LC-MS | Reagents |
|---|---|---|---|
| Example 213 | 8-ethoxy-6-(4-fluorophenyl)-N-[(6-methylpyridazin-3-yl)methyl]quinazolin-4-amine 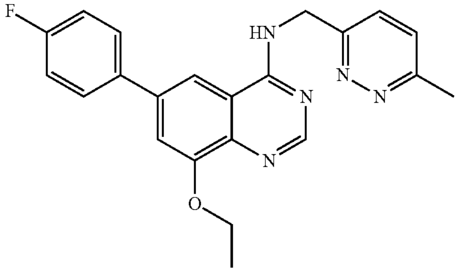 | LCMS (Method 7): 2.43 min, [M + H]+ 390.5 $^1H$ NMR (300 MHz, CHLOROFORM-d) δ ppm 8.75 (s, 1 H) 7.75 (br s, 1 H) 7.50 - 7.64 (m, 4 H) 7.38 - 7.44 (m, 1 H) 7.11 - 7.27(m, 2H) 5.11 (d, J = 4.40 Hz, 2 H) 4.35 (q, J = 6.97 Hz, 2 H) 2.77 (s, 3 H) 1.65 (t, J = 4.30 Hz, 3 H) | Example 199, Ethyl iodide, $Cs_2CO_3$ |
| Example 310 | R)-2-((6-(4-fluorophenyl)-4-((1-(2-(trifluoromethyl)pyrimidin-5-yl)ethyl)amino)quinazolin-8-yl)oxy)acetamide 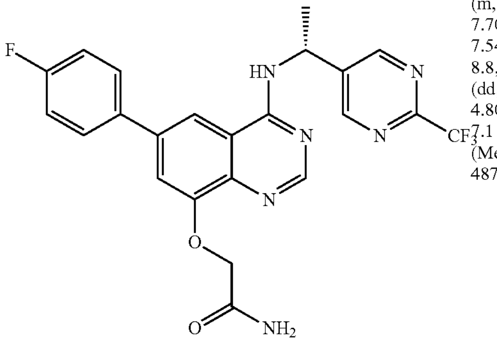 | $^1H$ NMR (400 MHz, DMSO): δ 9.21 (s, 2 H), 8.74 (d, J = 5.6 Hz, 1 H), 8.50 (s, 1 H), 8.33 (d, J = 1.5 Hz, 1 H), 7.98 - 7.93 (m, 2 H), 7.74 (s, 1 H), 7.70 (d, J = 1.5 Hz, 1 H), 7.54 (s, 1 H), 7.44 (dd, J = 8.8, 8.8 Hz, 2 H), 5.73 (dd, J = 6.4, 6.4 Hz, 1H), 4.80 (s, 2 H), 1.78 (d, J = 7.1 Hz, 3 H). LCMS (Method 3): [MH+] = 487.4 at 4.54 min. | Example 198, Bromoacetamide, $K_2CO_3$ |
| Example 311 | (R)-2-((6-(4-fluorophenyl)-4-((1-(2-(trifluoromethyl)pyrimidin-5-yl)ethyl)amino)quinazolin-8-yl)oxy)-1-(pyrrolidin-1-yl)ethan-1-one 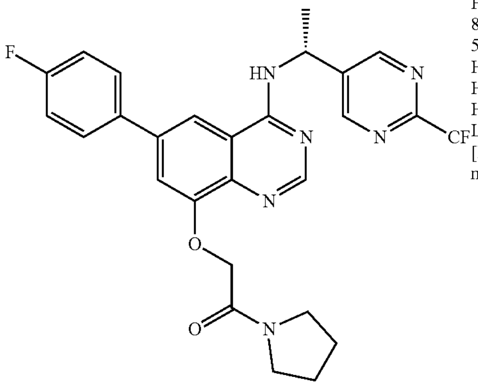 | $^1H$ NMR (400 MHz, DMSO): δ 9.18 (s, 2 H), 8.70 (d, J = 6.9 Hz, 1 H), 8.45 (s, 1 H), 8.23 (d, J = 1.5 Hz, 1 H), 7.91 - 7.86 (m, 2 H), 7.52 (d, J = 1.4 Hz, 1 H), 7.41 (dd, J = 8.8, 8.8 Hz, 2 H), 5.72 - 5.67 (m, 1 H), 5.03 (s, 2 H), 3.56 (dd, J = 6.8, 6.8 Hz, 2 H), 1.93 - 1.73 (m, 6 H). LCMS (Method 3): [MH+] = 541.5 at 4.8 min. | Example 198, 1-(chloroacetyl) pyrrolidine, $K_2CO_3$ |

-continued

| Example No. | Structure | Analytical data $^1H$ NMR LC-MS | Reagents |
|---|---|---|---|
| Example 312 | (R)-N,N-diethyl-2-((6-(4-fluorophenyl)-4-((1-(2-(trifluoromethyl)pyrimidin-5-yl)ethyl)amino)quinazolin-8-yl)oxy)acetamide 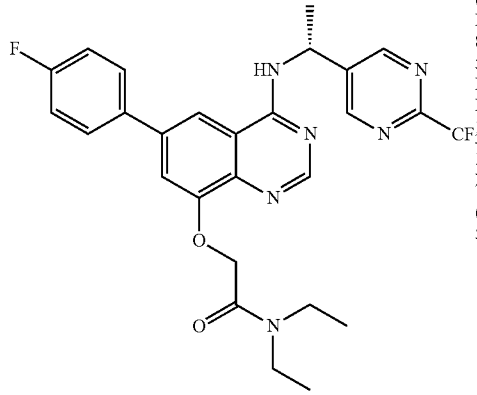 | $^1H$ NMR (400 MHz, DMSO): δ 9.18 (s, 2 H), 8.64 (d, J = 7.0 Hz, 1 H), 8.43 (s, 1 H), 8.22 (d, J = 1.6 Hz, 1 H), 7.89 - 7.85 (m, 2 H), 7.48 (d, J = 1.6 Hz, 1 H), 7.41 (dd, J = 8.9, 8.9 Hz, 2H) 5.72 - 5.66 (m, 1 H), 5.08 (s, 2 H), 3.42 (q, J = 7.1 Hz, 2 H), 3.32 - 3.26 (m, 2 H), 1.74 (d, J = 7.0 Hz, 3 H), 1.17 (dd, J = 7.1, 7.1 Hz, 3H), 1.04 (dd, J = 7.1, 7.1 Hz, 3 H). LCMS (Method 4): [MH+] = 543.5 at 4.8 min. | Example 198, 2-chloro-N,N-diethylacetamide, $K_2CO_3$ |

Example 214

2-[6-(4-fluorophenyl)-4-[(6-methylpyridazin-3-yl)methylamino]quinazolin-8-yl]oxyacetic acid, sodium salt

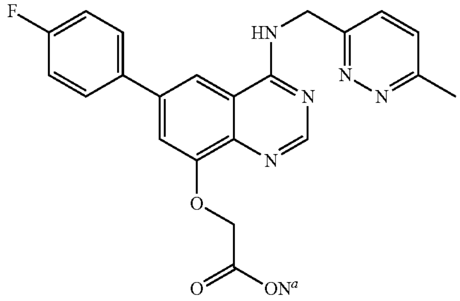

NaOH (10.5 mg, 0.26 mmol) was added to ethyl 2-[6-(4-fluorophenyl)-4-[(6-methylpyridazin-3-yl)methylamino]quinazolin-8-yl]oxyacetate (117 mg, 0.26 mmol) (Example 211) in MeOH (2.2 mL). The mixture was stirred at rt for 3 days then diluted with diethyl ether and filtered to leave 2-[6-(4-fluorophenyl)-4-[(6-methylpyridazin-3-yl)methylamino]quinazolin-8-yl]oxyacetic acid sodium salt (87 mg, 75% yield) as a white powder.

Example 215

8-(azetidin-3-ylmethoxy)-6-(4-fluorophenyl)-N-[(6-methylpyridazin-3-yl)methyl]quinazolin-4-amine

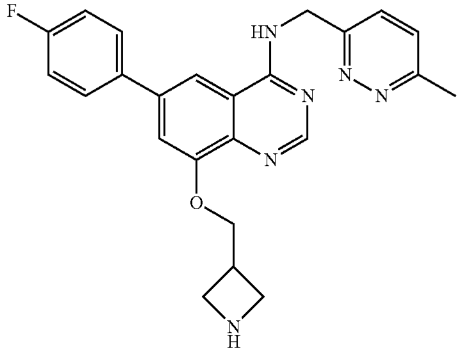 [SMILES: Cc1ccc(CNc2ncnc3c(OCC4CNC4)cc(-c4ccc(F)cc4)cc23)nn1]

Cesium carbonate (360 mg, 1.1 mmol) was added to a mixture of Example 186A (200 mg, 0.55 mmol) and N-Boc-3-(Iodomethyl) azetidine (247 mg, 0.72 mmol) in DMF (Volume: 3 ml). Stirring went on at 25° C. for 48 h. The crude material was purified by chromatography. The intermediate Boc-protected amine (150 mg, 0.28 mmol) was treated with 8N HCl in MeOH at RT for 3 days to leave 8-(azetidin-3-ylmethoxy)-6-(4-fluorophenyl)-N-((6-methylpyridazin-3-yl)methyl) quinazolin-4-amine (122 mg, 87% yield) as a white powder.

LCMS (Method 7): 2.24 min, [M+H]+ 431.1 Sel 6 min $^1H$ NMR (300 MHz, METHANOL-d4) δ ppm 8.80 (s, 1H), 8.49 (d, J=8.80 Hz, 1H), 8.37 (d, J=1.28 Hz, 1H), 8.31 (br d, J=8.44 Hz, 1H), 7.90-7.97 (m, 3H), 7.33 (t, J=8.71 Hz, 2H), 5.43 (s, 2H), 4.60 (d, J=4.95 Hz, 2H), 4.34 (dd, J=8.44, 3.48 Hz, 4H), 2.89 (s, 3H)

The following compounds were prepared via adaptations of the above procedures starting from substrate reported in table.

| Example No. | Chemical Name Structure | Analytical data $^1$H NMR LC-MS | Reagents |
|---|---|---|---|
| Example 216 | 6-(4-fluorophenyl)-N-[(6-methylpyridazin-3-yl)methyl]-8-pyrrolidin-3-yloxy-quinazolin-4-amine 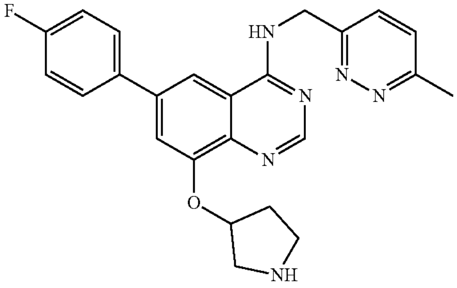 | LCMS (Method 7): 2.17 min, [M + H] + 431.1 Sel 6 min $^1$H NMR (300 MHz, DMSO-d6) δ ppm 11.19 - 11.27 (m, 1 H), 9.84 (br s, 1 H), 9.59 (br s, 1 H), 8.82 (s, 1 H), 8.62 (s, 1 H), 8.00 - 8.09 (m, 3 H), 7.80 d, J = 8.62 Hz, 1 H), 7.67 (d, J = 8.62 Hz, 1 H), 7.45 (t, J = 8.89 Hz, 2H), 5.75 - 5.85 (m, 1 H), 5.26 (br d, J = 4.58 Hz, 2 H), 3.33 - 3.45 (m, 4 H), 2.64 (s, 3 H), 2.23 - 2.32 (m, 2 H) | Example 199, tert-butyl 3-((methylsulfonyl)oxy)pyrrolidine-l-carboxylate, $Cs_2CO_3$ |
| Example 217 | 6-(4-fluorophenyl)-N-[(6-methylpyridazin-3-yl)methyl]-8-(morpholin-2-ylmethoxy)quinazolin-4-amine 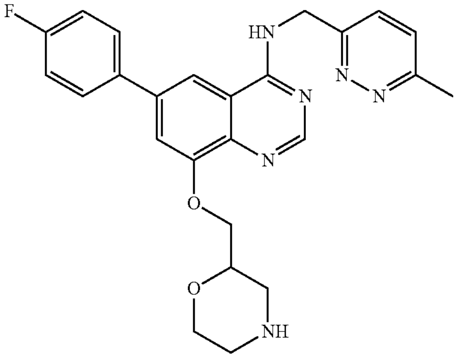 | LCMS (Method 7): 2.23 min, [M + H]+ 461.1 Sel 6 min $^1$H NMR (300 MHz, DMSO-d6) δ ppm 10.96 - 11.49 (m, 1 H) 9.46 - 10.02 (m, 2 H) 8.81 (s, 1 H) 8.62 (s, 1 H) 8.03 (dd, J = 8.71, 5.41 Hz, 2 H) 7.95 (s, 1 H) 7.82 (d, J = 8.80 Hz, 1 H) 7.68 (d, J = 8.80 Hz, 1 H) 7.44 (t, J = 8.80 Hz, 2 H) 5.77 (s, 1 H) 5.25 (br d, J = 5.50 Hz, 2 H) 4.45 - 4.62 (m, 2 H) 4.23 - 4.38 (m, 1 H) 3.99 - 4.11 (m, 1 H) 3.90 (br s, 2 H) 3.53 (br s, 2 H) 3.01 - 3.42 (m, 4 H) 2.64 (s, 3 H) | Example 199, tert-butyl 2-(((methylsulfonyl)oxy)methyl)morpholine-4-carboxylate, $Cs_2CO_3$ |
| Example 218 | 8-(azetidin-3-yloxy)-6-(4-fluorophenyl)-N-[(6-methylpyridazin-3-yl)methyl]quinazolin-4-amine 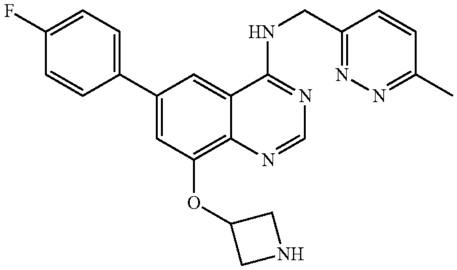 | LCMS (Method 7): 2.07 min, [M + H] + 417.1 $^1$H NMR (300 MHz, DMSO-d6) δ ppm 11.29 (br s, 1 H), 9.51 and 9.65 (br s, 2 H, 1 H each), 8.88 (s, 1 H), 8.67 (s, 1 H), 7.95 - 8.09 (m, 2 H), 7.65 - 7.84 (m, 3 H), 7.44 (t, J = 8.89 Hz, 2 H), 5.50 - 5.64 (m, 1 H), 5.25 (br d, J = 5.69 Hz, 2 H), 4.57 (br dd, J = 11.46, 5.04 Hz, 2 H), 4.05 - 4.32 (m, 2 H), 2.64 (s, 3H) | Example 199, tert-butyl 3-((methylsulfonyl)oxy)azetidine-1-carboxylate, $Cs_2CO_3$ |

-continued

| Example No. | Chemical Name Structure | Analytical data $^1$H NMR LC-MS | Reagents |
|---|---|---|---|
| Example 219 | 6-(4-fluorophenyl)-N-[(6-methylpyridazin-3-yl)methyl]-8-(4-piperidyloxy)quinazolin-4-amine 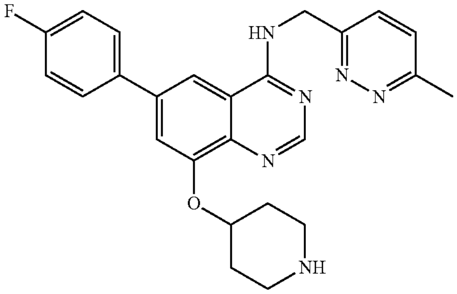 | LCMS (Method 7): 2.17 min, [M + H] + 445.1 Sel 6 min $^1$H NMR (300 MHz, METHANOL-d4) δ ppm 8.77 (s, 1 H), 8.44 (d, J = 8.80 Hz, 1 H), 8.35 (d, J = 1.10 Hz, 1 H), 8.27 (d, J = 8.80 Hz, 1 H), 8.00 (s, 1 H), 7.89 - 7.96 (m, 2 H), 7.33 (t, J = 8.71 Hz, 2 H), 5.42 (s, 2 H), 5.26 - 5.33 (m, 1 H), 3.65 (ddd, J = 12.65, 8.53, 4.13 Hz, 2 H), 3.35 - 3.39 (m, 2 H), 2.88 (s, 3 H), 2.21 - 2.46 (m, 4 H) | Example 199, tert-butyl 4-((methylsulfonyl)oxy)piperidine-1-carboxylate, $Cs_2CO_3$ |
| Example 313 | 6-(4-fluorophenyl)-N-[(6-methylpyridazin-3-yl)methyl]-8-[(3S)-pyrrolidin-3-yl]oxy-quinazolin-4-amine 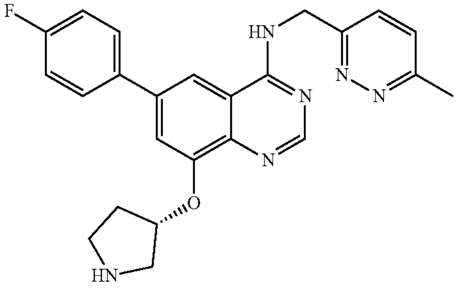 | $^1$H NMR (400 MHz, DMSO): δ 8.42 (s, 1 H), 8.33 (s, 1 H), 8.24 (s, 1 H), 7.93 - 7.90 (m, 2 H), 7.62 - 7.65 (m, 1 H), 7.49 - 7.57 (m, 2 H), 7.36 - 7.49 (m, 2 H), 5.37 (brs, 1 H), 5.02 (s, 2 H), 3.18 - 3.37 (m, 4 H), 3.05 - 3.08 (m, 1 H), 2.59 (s, 3 H), 2.14 - 2.22 (m, 2 H). LCMS (Method 4): [MH+] = 431 at 2.23 min. | Example 199, tert-butyl (R)-3-((methylsulfonyl)oxy)pyrrolidine-1-carboxylate, $Cs_2CO_3$ |
| Example 314 | 6-(4-fluorophenyl)-N-[(6-methylpyridazin-3-yl)methyl]-8-[(3R)-pyrrolidin-3-yl]oxy-quinazolin-4-amine 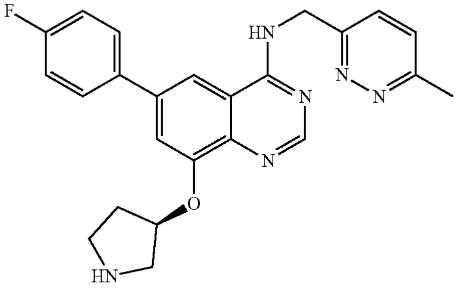 | $^1$H NMR (400 MHz, DMSO): δ 8.42 (s, 1 H), 8.33 (s, 1 H), 8.24 (s, 1 H), 7.93 - 7.90 (m, 2 H), 7.62 - 7.65 (m, 1 H), 7.49 - 7.57 (m, 2 H), 7.36 - 7.49 (m, 2 H), 5.26 - 5.28 (m, 1 H), 5.03 (s, 2 H), 3.05 - 3.33 (m, 4 H), 2.85 - 2.86 (m, 1 H), 2.60 (s, 3 H), 2.08 - 2.13 (m, 1 H), 1.90 - 1.93 (m, 1 H). LCMS (Method 4): [MH+] = 431 at 2.23 min. | Example 199, tert-butyl (S)-3-((methylsulfonyl)oxy)pyrrolidine-1-carboxylate, $Cs_2CO_3$ |

Example 220

6-(4-fluorophenyl)-8-[(1-methylazetidin-3-yl)methoxy]-N-[(6-methylpyridazin-3-yl)methyl]quinazolin-4-amine

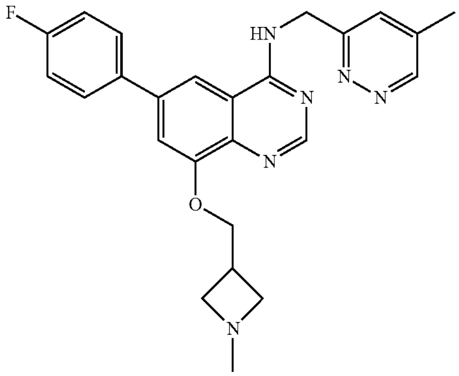 [SMILES: Cc1cnnc(CNc2ncnc3c(OCC4CN(C)C4)cc(-c4ccc(F)cc4)cc23)c1]

8-(azetidin-3-ylmethoxy)-6-(4-fluorophenyl)-N-[(6-methylpyridazin-3-yl)methyl]quinazolin-4-amine (Example 215) (50 mg, 0.1 mmol) was reacted with Sodium carbonate (31.6 mg, 0.3 mmol) dimethylsulfate (247 mg, 0.72 mmol) in DMF (1.65 mL). Stirring went on at 25° C. for 18 h. The crude material was purified by chromatography to leave 6-(4-fluorophenyl)-8-((1-methylazetidin-3-yl)methoxy)-N-((6-methylpyridazin-3-yl)methyl)quinazolin-4-amine (1.9 mg, 4% yield) as a white powder LCMS (Method 7): LCMS (Method 7): 2.09 min, [M+H]+ 445.1

$^1$H NMR (300 MHz, DMSO-d6) $^1$H NMR (300 MHz, CHLOROFORM-d) δ ppm 8.71 (s, 1H), 7.73 (br s, 1H), 7.54-7.63 (m, 3H), 7.51 (d, J=8.80 Hz, 1H), 7.35-7.41 (m, 1H), 7.33 (s, 1H), 7.11-7.22 (m, 2H), 5.09 (d, J=3.85 Hz, 2H), 4.42 (d, J=6.24 Hz, 2H), 3.63-3.70 (m, 2H), 3.34-3.56 (m, 2H), 3.06-3.30 (m, 1H), 2.75 (s, 3H), 2.53 (s, 3H)

The following compounds were prepared via adaptations of the above procedures starting from substrate reported in table.

| Example No. | Chemical Name Structure | Analytical data $^1$H NMR LC-MS | Reagents |
|---|---|---|---|
| Example 221 | 6-(4-fluorophenyl)-8-[(4-methylmorpholin-2-yl)methoxy]-N-[(6-methylpyridazin-3-yl)methyl]quinazolin-4-amine 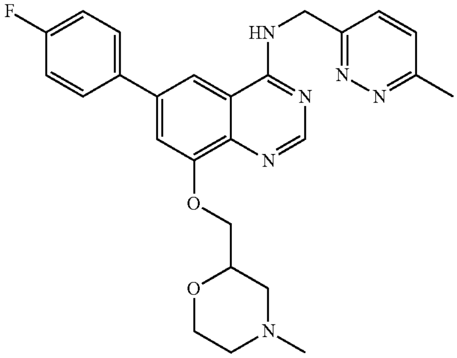 | LCMS (Method 7): 2.10 min, [M + H] + 475.1 Sel 6 min $^1$H NMR (300 MHz, CHLOROFORM-d) δ ppm 8.58 (s, 1 H) 8.21 (br s, 1 H) 7.45 - 7.61 (m, 4 H) 7.41 (d, J = 8.62 Hz, 1 H) 7.31 (d, J = 1.47 Hz, 1 H) 7.11 (t, J = 8.62 Hz, 2 H) 5.08 (d, J = 4.58 Hz, 2 H) 4.28 - 4.39 (m, 1 H) 4.21 (br d, J = 7.52 Hz, 2 H) 3.92 - 4.02 (m, 1 H) 3.81 (td, J = 11.32, 2.29 Hz, 1 H) 3.50 (s, 1 H) 3.01 (br d, J = 11.19 Hz, 1 H) 2.74 (s, 3 H) 2.70 (br s, 1 H) 2.36 (s, 3 H) 2.05 - 2.31 (m, 2H) 1.27 (s, 2 H) | Example 217 |
| Example 222 | 6-(4-fluorophenyl)-N-[(6-methylpyridazin-3-yl)methyl]-8-(1-methylpyrrolidin-3-yl)oxy-quinazolin-4-amine 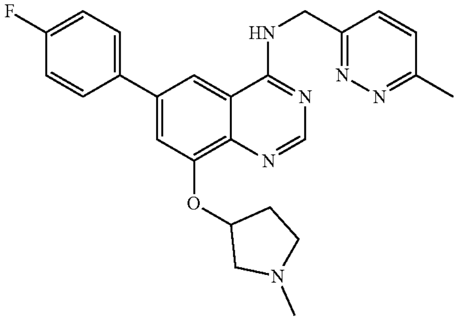 | LCMS (Method 7): 2.02 min, [M + H] + 445.1 Sel 6 min $^1$H NMR (300 MHz, METHANOL-d4) δ ppm 8.45 (s, 1 H), 8.04 (s, 1 H), 7.65 - 7.80 (m, 3 H), 7.58 (br d, J = 8.44 Hz, 2 H), 7.21 (t, J = 8.44 Hz, 2 H) 5.58 (br s, 1 H), 5.10 (s, 2 H), 3.71 - 3.94 (m, 2H), 3.61 (br d, J = 11.19 Hz, 1 H), 3.39 (br d, J = 4.03 Hz, 1 H), 3.08 (s, 3 H), 2.54 - 2.71 (m, 4 H), 2.29 - 2.45 (m, 1H) | |

Example 223 and Example 224

((R)-8-methoxy-6-(3-methyl-M-pyrazol-1-yl)-N-(1-(2-(trifluoromethyl)pyrimidin-5-yl)ethyl)quinazolin-4-amine (Ex. 223) and (R)-8-methoxy-6-(5-methyl-1H-pyrazol-1-yl)-N-(1-(2-(trifluoromethyl) pyrimidin-5-yl)ethyl)quinazolin-4-amine (Ex. 224)

Example 223

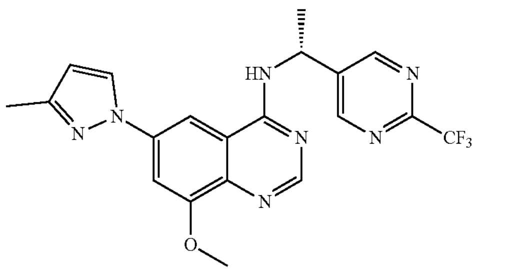

Example 224

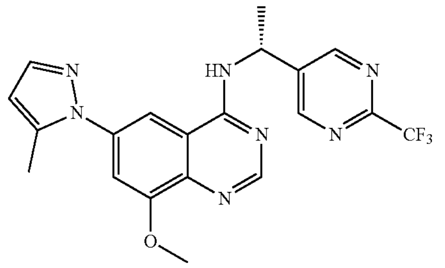

Nitrogen was bubbled for 5 min through a mixture of (R)-6-bromo-8-methoxy-N-(1-(2-(trifluoromethyl)pyrimidin-5-yl)ethyl)quinazolin-4-amine (107 mg, 0.25 mmol), copper (I) iodide (2.4 mg, 0.01 mmol) and potassium carbonate (73 mg, 0.53 mmol). 5-Methyl-1H-pyrazole (20 mg, 0.25 mmol) and (rac)-(+)-N,N'-dimethyl-1,2-cyclohexanediamine (3.6 mg, 0.03 mmol) in toluene (0.5 mL) were added and the reaction mixture was heated to 115° C. for 72 hours. After return to room temperature, the reaction was filtered through Celite® and the filter cake rinsed with toluene (2×5 mL). The organic phases were filtered through a hydrophobic frit and the solvent was removed in vacuo. The residue was purified by preparative HPLC to give the title compounds. The structure of each regioisomer (Example 223 and Example 224) was confirmed by $^1$H NMR studies.

Example 223: 33 mg, 30%, off-white solid $^1$H NMR (400 MHz, DMSO): δ 9.18 (s, 2H), 8.59 (d, J=7.0 Hz, 1H), 8.52 (d, J=2.4 Hz, 1H), 8.39 (s, 1H), 8.23 (d, J=2.1 Hz, 1H), 7.69 (d, J=2.0 Hz, 1H), 6.46 (d, J=2.3 Hz, 1H), 5.69-5.63 (m, 1H), 4.01 (s, 3H), 2.35 (s, 3H), 1.74 (d, J=7.1 Hz, 3H). LCMS (Method 3): [MH+]=430 at 3.30 min.

Example 224: 6 mg, 6%, off-white solid $^1$H NMR (400 MHz, DMSO): δ 9.16 (s, 2H), 8.64 (d, J=7.0 Hz, 1H), 8.08 (d, J=2.0 Hz, 1H), 7.65 (d, J=1.6 Hz, 1H), 7.39 (d, J=2.0 Hz, 1H), 6.77 (s, 1H), 6.37 (s, 1H), 5.69-5.64 (m, 1H), 3.97 (s, 3H), 2.43 (s, 3H), 1.70 (d, J=7.1 Hz, 3H). LCMS (Method 3): [MH+]=430 at 3.18 min.

Example 225 and Example 226

(R)-8-Methoxy-6-(4-methyl-1H-imidazol-1-yl)-N-(1-(2-(trifluoromethyl)pyrimidin-5-yl)ethyl)quinazolin-4-amine (Ex. 225) and (R)-8-methoxy-6-(5-methyl-1H-imidazol-1-yl)-N-(1-(2-(trifluoromethyl) pyrimidin-5-yl)ethyl)quinazolin-4-amine (Ex. 226)

Example 225

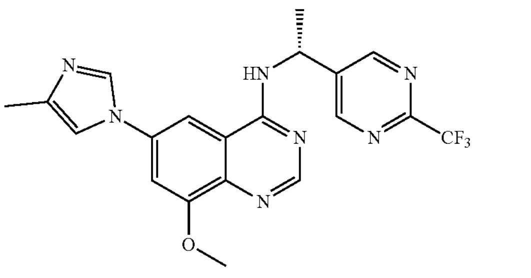

Example 226

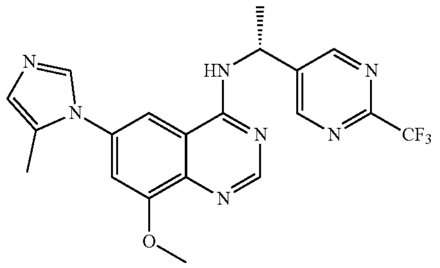

Nitrogen was bubbled for 5 min through a mixture of (R)-6-bromo-8-methoxy-N-(1-(2-(trifluoromethyl)pyrimidin-5-yl)ethyl)quinazolin-4-amine (214 mg, 0.50 mmol), copper (I) iodide (5.0 mg, 0.02 mmol) and caesium carbonate (145 mg, 1.05 mmol). 5-Methyl-1H-imidaozle (50 mg, 0.60 mmol) and (rac)-(+)-N,N-dimethyl-1,2-cyclohexanediamine (3.6 mg, 0.03 mmol) in N,N-dimethylformamide (0.3 mL) were added and the reaction mixture was heated to 115° C. for 72 hours. After return to room temperature, the reaction was filtered through Celite® and the filter cake rinsed with N,N-dimethylformamide (2×3 mL). The organic phases were filtered through a hydrophobic frit and the solvent was removed in vacuo. The residue was purified by preparative HPLC to give the title compounds. The structure of each regioisomer Example 225 and Example 226 was confirmed by $^1$H NMR.

Example 225: 18 mg, 8%, off-white solid $^1$H NMR (400 MHz, DMSO): δ 9.17 (s, 2H), 8.50 (d, J=6.7 Hz, 1H), 8.41 (s, 1H), 8.32 (s, 1H), 8.09 (d, J=1.9 Hz, 1H), 7.62 (s, 1H), 7.53 (d, J=2.1 Hz, 1H), 5.69-5.63 (m, 1H), 4.01 (s, 3H), 2.23 (s, 3H), 1.74 (d, J=7.2 Hz, 3H). LCMS (Method 4): [MH+]=430 at 4.01 min.

Example 226: 14 mg, 7%, off-white solid $^1$H NMR (400 MHz, DMSO): δ 9.40 (s, 1H), 9.33 (s, 1H), 9.18 (s, 2H), 8.70 (s, 1H), 8.26 (s, 1H), 7.74 (d, J=1.5 Hz, 1H), 7.65 (s, 1H), 5.77 (q, J=7.0 Hz, 1H), 4.04 (s, 3H), 2.31 (s, 3H), 1.77-1.72 (m, 3H). LCMS (Method 3): [MH+]=430 at 2.23 min.

Example 227

(R)-8-Methoxy-6-(4-methyl-M-pyrazol-1-yl)-N-(1-(2-(trifluoromethyl)pyrimidin-5-yl)ethyl)quinazolin-4-amine

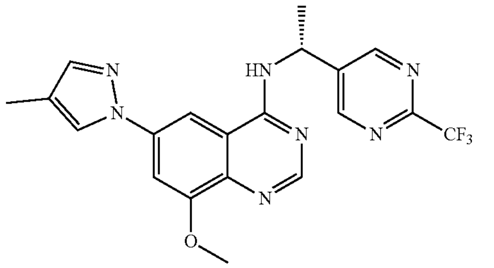 [SMILES: COc1cc(-n2cc(C)cn2)cc2c(N[C@H](C)c3cnc(C(F)(F)F)nc3)ncnc12]

Nitrogen was bubbled for 5 min through a mixture of (R)-6-bromo-8-methoxy-N-(1-(2-(trifluoromethyl)pyrimidin-5-yl)ethyl)quinazolin-4-amine (107 mg, 0.25 mmol), copper (I) iodide (2.4 mg, 0.01 mmol), 4-methyl-1H-pyrazole (25 mg, 0.30 mmol) and potassium carbonate (73 mg, 0.53 mmol). (rac)-(+)-N,N'-dimethyl-1,2-cyclohexanediamine (3.6 mg, 0.03 mmol) in toluene (0.5 mL) was added and the reaction mixture was heated to 115° C. for 72 hours. After return to room temperature, the reaction was filtered through Celite® and the filter cake was rinsed with toluene (2×5 mL). The organic phases were filtered through a hydrophobic frit and the solvent was removed in vacuo. The residue was purified by preparative HPLC to give the title compound (4 mg, 6%) as an off white solid.

$^1$H NMR (400 MHz, DMSO): δ 9.20 (s, 2H), 8.67 (s, 1H), 8.49 (s, 1H), 8.45 (s, 1H), 7.94 (d, J=1.5 Hz, 1H), 7.74 (s, 1H), 5.83 (q, J=6.9 Hz, 1H), 4.13 (s, 3H), 2.17 (s, 3H), 1.80 (d, J=7.2 Hz, 3H). LCMS (Method 3): [MH+]=430 at 4.42 min.

Intermediate 8

6-bromo-N-((6-methylpyridin-3-yl)methyl)quinazolin-4-amine

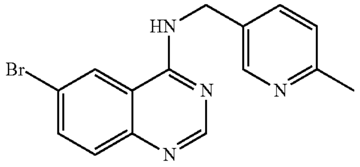 [SMILES: Cc1ccc(CNc2ncnc3ccc(Br)cc23)cn1]

A mixture of 6-bromo-4-chloroquinazoline (1 g, 4.11 mmol), (6-methylpyridin-3-yl)methanamine (0.500 g, 4.09 mmol) and triethylamine (3 ml, 21.52 mmol) in 1,4-Dioxane/DMF 5:1 (Volume: 12 ml) was stirred at 100° C. for 16 h. The reaction mixture was concentrated under reduced pressure. Purification by column chromatography (Biotage Isolere, 55 g NH cartridge, gradient elution from 0 to 50% Acetone in heptane) yielded 6-bromo-N-((6-methylpyridin-3-yl)methyl)quinazolin-4-amine (1.35 g, 4.10 mmol, 100% yield) as a pale yellow powder.

LCMS (Method 6): 0.82 min, m/z 328.8 [M]+ and 330.8 [M+2]+,

The following intermediates were synthesised via adaptations of the same procedure by reacting suitable amines with substrate reported in the table.

| Intermediate No. | Chemical Name Structure | Analytical data LC-MS | Substrate |
|---|---|---|---|
| Intermediate 9 | 6-bromo-N-((6-methylpyridazin-3-yl)methyl)quinazolin-4-amine 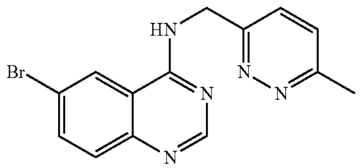 | LCMS (Method 5): 0.38 min, m/z 330 [M]+ and 332 [M + 2]+. | 6-bromo-4-chloroquinazoline |
| Intermediate 10 | (R)-6-bromo-N-(1-(2-(trifluoromethyl)pyrimidin-5-yl)ethyl)quinazolin-4-amine 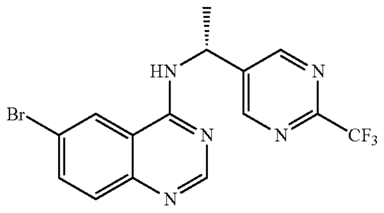 | LCMS (Method 5): 0.70 min, m/z 399 [M]+ and 401 [M + 2]+. | 6-bromo-4-chloroquinazoline |

-continued

| Intermediate No. | Chemical Name Structure | Analytical data LC-MS | Substrate |
|---|---|---|---|
| Intermediate 11 | 6-bromo-N-(1-(3-methyl-1,2,4-oxadiazol-5-yl)ethyl)quinazolin-4-amine 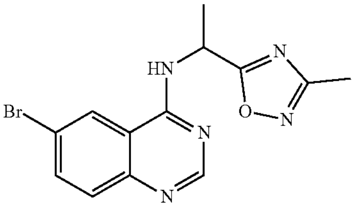 | LCMS (Method 5): 0.54 min, m/z 334 [M]+ and 336 [M + 2]+. | 6-bromo-4-chloroquinazoline |
| Intermediate 12 | 6-bromo-2-methyl-N-((6-methylpyridazin-3-yl)methyl)quinazolin-4-amine 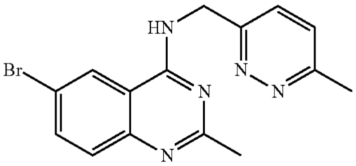 | LCMS (Method 5): : 0.36 min, m/z 343.8 [M]+ and 345.8 [M + 2]+, | 6-bromo-4-chloro-2-methylquinazoline |
| Intermediate 13 | 6-chloro-N-((6-methylpyridazin-3-yl)methyl)-2-(trifluoromethyl)quinazolin-4-amine 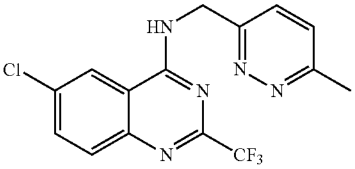 | LCMS (Method 6): : 0.95 min, m/z 354 [M + H]+, | 4,6-dichloro-2-(trifluoromethyl)quinazoline |
| Intermediate 14 | 6-bromo-2-chloro-N-(1-(3-methyl-1,2,4-oxadiazol-5-yl)ethyl)quinazolin-4-amine 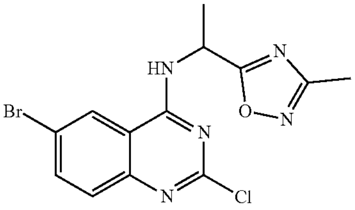 | LCMS (Method 5): : 1.06 min, 367.8 [M]+, 369.7 [M + 2]+, 371.6 [M + 4]+, | 6-bromo-2,4-dichloro quinazoline |

Example 228

6-(5-methylpyridin-2-yl)-N-((6-methylpyridin-3-yl)methyl)quinazolin-4-amine

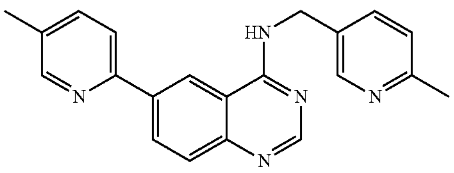

Tetrakis(triphenylphosphine)palladium(0) (70.2 mg, 0.061 mmol) was added to a mixture of 6-bromo-N-((6-methylpyridin-3-yl)methyl)quinazolin-4-amine (Intermediate 8) (100 mg, 0.304 mmol) and 5-methyl-2-(tributylstannyl)pyridine (0.315 ml, 0.911 mmol) in DMF (Volume: 2 ml). Stirring went on for 16 h at 80° C. Purification by DP chromatography (Biotage Isolera, 28 g NH cartridge, gradient elution from 0 to 100% EtOAC in dichloromethane in 20 CV) yielded 6-(5-methylpyridin-2-yl)-N-((6-methylpyridin-3-yl)methyl)quinazolin-4-amine (69.8 mg, 0.204 mmol, 67.3% yield) as a white powder.

LCMS: 0.33 min, 341.9 m/z [M+H]+, CSH 2 min.

$^1$H NMR (400 MHz, DMSO-d6) δ ppm 9.02 (t, J=5.7 Hz, 1H), 8.93-8.96 (m, 1H), 8.55-8.58 (m, 1H), 8.49-8.54 (m, 2H), 8.48 (s, 1H), 8.00-8.09 (m, 1H), 7.73-7.82 (m, 2H), 7.66-7.72 (m, 1H), 7.16-7.22 (m, 1H), 4.76-4.82 (m, 2H), 2.43 (s, 3H), 2.37 (s, 3H).

The following compounds were synthesised via adaptation of the above procedure using the appropriate stannane reagent and starting from substrate reported in table:

| Example No. | Chemical Name Structure | Analytical data $^1$H NMR LC-MS | Starting Intermediate |
|---|---|---|---|
| Example 229 | N-(1-(3-methyl-1,2,4-oxadiazol-5-yl)ethyl)-6-(5-methylpyridin-2-yl)quinazolin-4-amine 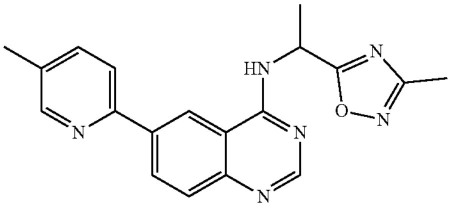 | LCMS (Method 5): 0.54 min, m/z 347.0 [M + H]+. $^1$H NMR (400 MHz, DMSO-d6) δ ppm 9.04 (d, J = 1.54 Hz, 1 H), 9.01 (d, J = 7.06 Hz, 1 H), 8.53 - 8.61 (m, 2 H), 8.47 (s, 1 H), 8.08 (d, J = 7.94 Hz, 1 H), 7.78 - 7.85 (m, 2 H), 5.83 (quin, J = 7.11 Hz, 1 H), 2.38 (s, 3 H), 2.32 (s, 3 H), 1.75 (d, J = 7.06 Hz, 3 H). | Intermediate 11 |
| Example 230 | N-((6-methylpyridazin-3-yl)methyl)-6-(5-methylpyridin-2-yl)-2-(trifluoromethyl)quinazolin-4-amine 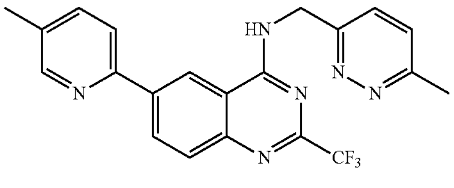 | LCMS (Method 2): [MH+] = 411 at 4.36 min $^1$H NMR (400 MHz, $CDCl_3$): δ 8.54 (d, J = 4.4 Hz, 2 H), 8.42-8.39 (m, 1 H), 8.02-7.99 (m, 2 H), 7.68 (d, J = 8.0 Hz, 1 H), 7.62-7.52 (m, 2 H), 7.39 (d, J = 8.4 Hz, 1 H), 5.15-5.08 (m, 2 H), 2.78 (s, 3 H), 2.74 (s, 3 H). | Intermediate 13 |
| Example 231 | N-((6-methylpyridazin-3-yl)methyl)-6-(5-methylpyridin-2-yl)quinazolin-4-amine 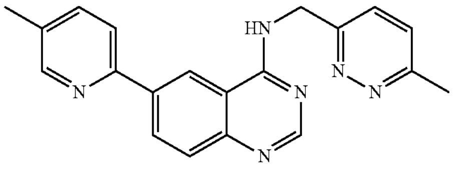 | LCMS (Method 6): 0.75 min, 342.9 m/z [M + H]+, $^1$H NMR (400 MHz, DMSO-d6) δ ppm 9.20 (t, J = 5.9 Hz, 1 H), 9.00 (d, J = 1.3 Hz, 1H), 8.50 - 8.60 (s, 2 H), 8.44 (s, 1 H), 8.06 (d, J = 8.3 Hz, 1 H), 7.78 (d, J = 8.8 Hz, 2 H), 7.45 - 7.60 (m, 2 H), 5.04 (d, J = 6.1 Hz, 2 H), 2.59 (s, 3 H), 2.37 (s, 3 H). | Intermediate 9 |

-continued

| Example No. | Chemical Name Structure | Analytical data $^1$H NMR LC-MS | Starting Intermediate |
|---|---|---|---|
| Example 232 | N-(1-(3-methyl-1,2,4-oxadiazol-5-yl)ethyl)-6-(5-methylthiazol-2-yl)quinazolin-4-amine 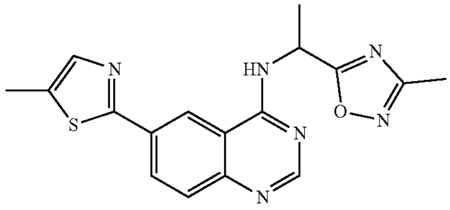 | LCMS (Method 2): [MH+] = 353 at 3.86 min. $^1$H NMR (400 MHz, $CDCl_3$): δ 9.22-9.20 (m, 1 H), 8.95 (s, 1 H), 8.54 (s, 1 H), 8.37-8.35 (m, 1 H), 7.68 (d, J = 8.0 Hz, 1 H), 7.67 (s, 1 H), 5.88-5.84 (m, 1 H), 2.60 (s, 3 H), 2.37 (s, 3 H), 1.79 (d, J = 8.0 Hz, 3H). | Intermediate 11 |
| Example 233 | 2-chloro-6-(4-fluorophenyl)-N-(1-(3-methyl-1,2,4-oxadiazol-5-yl)ethyl)quinazolin-4-amine 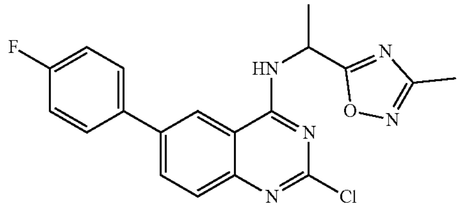 [SMILES: Cc1noc(C(C)Nc2nc(Cl)nc3ccc(-c4ccc(F)cc4)cc23)n1] | LCMS (Method 5): : 1.20 min, m/z 383.9 [M]+ and 385.7 [M + 2]+, $^1$H NMR (400 MHz, DMSO-d6) d ppm 9.33 (d, J = 7.0 Hz, 1 H), 8.69 (d, J = 1.8 Hz, 1 H), 8.19 (dd, J = 8.6, 2.0 Hz, 1 H), 7.84 - 7.95 (m, 2 H), 7.76 (d, J = 8.8 Hz, 1 H), 7.40 - 7.45 (m, 2 H), 5.75 - 5.80 (m, 1 H), 2.37 (br. s., 3 H), 1.77 (d, J = 1.0 Hz, 3 H). | Intermediate 14 |

Example 234

6-(4-fluorophenyl)-N2,N2-dimethyl-N4-(1-(3-methyl-1,2,4-oxadiazol-5-yl)ethyl)quinazoline-2,4-diamine

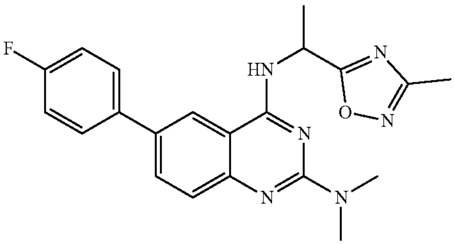 [SMILES: Cc1noc(C(C)Nc2nc(N(C)C)nc3ccc(-c4ccc(F)cc4)cc23)n1]

A solution of 2-chloro-6-(4-fluorophenyl)-N-(1-(3-methyl-1,2,4-oxadiazol-5-yl)ethyl)quinazolin-4-amine (Example 223) (80 mg, 0.208 mmol) and dimethylamine 2.0 M in THF (0.625 ml, 1.251 mmol) in 1,4-dioxane (Volume: 3 ml) was stirred at 100° C. for 16 h. The reaction mixture was partitioned between saturated aqueous ammonium chloride and dichloromethane. The organic layer was concentrated under reduced pressure. Purification by DP chromatography (Biotage Isolera, 10 g KP-Sil cartridge, gradient elution from 0 to 70% [dichloromethane/MeOH 9:1] in dichloromethane in 15 CV) yielded 6-(4-fluorophenyl)-N2,N2-dimethyl-N4-(1-(3-methyl-1,2,4-oxadiazol-5-yl)ethyl)quinazoline-2,4-diamine (73.5 mg, 0.187 mmol, 90% yield) as a pale yellow powder.

LCMS: 0.71 min, m/z 393.0 [M+H]+, Method 5 acidic method.

1H NMR (400 MHz, DMSO-d6) δ ppm 8.51-8.84 (m, 1H), 8.45 (d, J=1.8 Hz, 1H), 7.81 (dd, J=8.8, 5.7 Hz, 3H), 7.32 (t, J=8.8 Hz, 3H), 5.45-5.55 (m, 1H), 3.02 (s, 6H), 2.30 (s, 3H), 1.72 (d, J=7.0 Hz, 3H).

The following compounds were synthesised via adaptation of the above procedure. Example 237 was obtained using the same reaction conditions as Example 235, Example 238 was obtained using the same reaction conditions as Example 236

| Example No. | Chemical Name<br>Structure | Analytical data<br>$^{1}$H NMR<br>LC-MS |
|---|---|---|
| Example 235 | N2-cyclopropyl-6-(4-fluorophenyl)-N4-(1-(3-methyl-1,2,4-oxadiazol-5-yl)ethyl)quinazoline-2,4-diamine<br>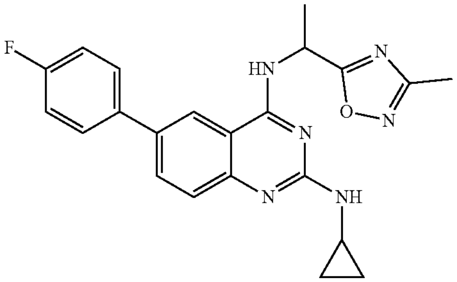 | LCMS (Method 5): 0.78 min, m/z 405.1 [M + H]+, $^{1}$H NMR (400 MHz, DMSO-d6) δ ppm 8.48 - 8.64 (m, 1 H), 8.42 (d, J = 1.8 Hz, 1 H), 7.70 - 7.93 (m, 3 H), 7.25 - 7.35 (m, 3 H), 6.82 (s, 1 H), 5.60 - 5.81 (m, 1 H), 2.58 - 2.77 (m, 1 H), 2.31 (s, 3 H), 1.71 (d, J = 7.0 Hz, 3 H), 0.17 - 0.70 (m, 4H). |
| Example 236 | 6-(4-fluorophenyl)-N-(1-(3-methyl-1,2,4-oxadiazol-5-yl)ethyl)-2-morpholinoquinazolin-4-amine<br>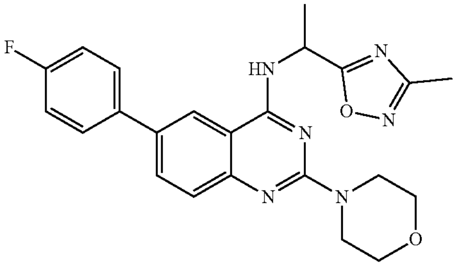 | LCMS (Method 5): 0.67 min, m/z 435 [M + H]+, $^{1}$H NMR (400 MHz, DMSO-d6) δ pm 8.69 (d, J = 6.1 Hz, 1 H), 8.47 (d, J = 1.8 Hz, 1 H), 7.90 (dd, J = 8.8, 2.2 Hz, 1 H), 7.82 (dd, J = 8.8, 5.3 Hz, 2 H), 7.27 - 7.43 (m, 3 H), 5.40 - 5.50 (s, 1 H), 3.46 - 3.80 (m, H), 2.31 (s, 3 H), 1.72 (d, J = 7.5 Hz, 3 H). |
| Example 237 | 2-((2-(cyclopropylamino)-6-(4-fluorophenyl)quinazolin-4-yl)amino)propanamide<br>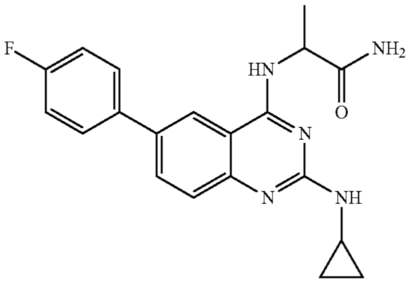 | LCMS (Method 5):: 0.72 min, m/z 406.1 [M + H]+, $^{1}$H NMR (400 MHz, DMSO-d6) d ppm 8.43 (s, 1 H), 7.92 - 8.07 (m, 1 H), 7.72 - 7.92 (m, 3 H), 7.21 - 7.43 (m, 3 H), 4.60 - 4.77 (m, 1 H), 2.85 - 2.70 (m, 1 H), 2.70 - 2.55 (m, 1 H), 1.41 (d, J = 7.0 Hz, 3 H), 0.40 - 0.47 (m, 4 H), 0.32 - 0.50 (m, 4 H). |
| Example 238 | N-cyclopropyl-2-((2-(cyclopropylamino)-6-(4-fluorophenyl)quinazolin-4-yl)amino)propenamide<br>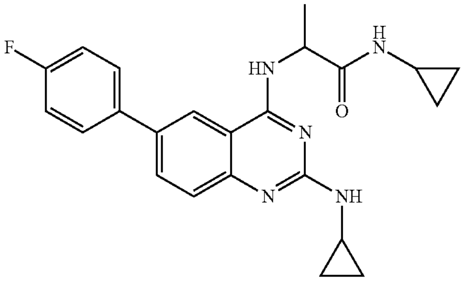 | LCMS (Method 5):: 0.61 min, m/z 366.0 [M + H]+, $^{1}$H NMR (400 MHz, DMSO-d6) δ ppm 8.43 (s, 1 H), 8.11 (bs, 1 H), 7.69 - 7.91 (m, 3 H), 7.18 - 7.42 (m, 4 H), 6.96 (br s, 2 H), 4.73 (br t, J = 7.23 Hz, 1 H), 2.75 - 2.94 (m, 1 H), 1.41 (d, J = 7.23 Hz, 3 H), 0.55 - 0.71 (m, 2 H), 0.42 - 0.53 (m, 2 H). |

Example 239

6-(4-fluorophenyl)-2-methyl-N-((6-methylpyridazin-3-yl)methyl)quinazolin-4-amine

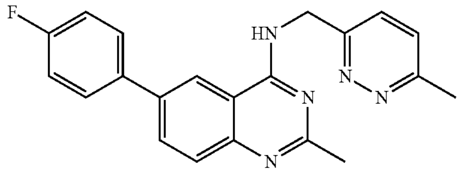 [SMILES: Cc1ccc(CNc2nc(C)nc3ccc(-c4ccc(F)cc4)cc23)nn1]

$Pd(dppf)Cl_2 \cdot CH_2Cl_2$ (11.86 mg, 0.015 mmol) was added to a mixture of 6-bromo-2-methyl-N-((6-methylpyridazin-3-yl)methyl)quinazolin-4-amine (Intermediate 9) (50 mg, 0.145 mmol), (4-fluorophenyl)boronic acid (30.5 mg, 0.218 mmol) and potassium phosphate (61.7 mg, 0.291 mmol) in DMF/water 2:1 (Volume: 3 ml). Stirring went on for 16 h at 80° C. Purification by RP chromatography (Biotage Isolera, 30 g C18 cartridge, gradient elution from 0 to 65% B in A, A: water/acetonitrile 95:5+0.1% conc ammonia, B: acetonitrile:water 95:5+0.1% conc ammonia in 20 CV) then by RP chromatography (Biotage Isolera, 30 g C18 cartridge, gradient elution from 0 to 50% B in A, A: water/acetonitrile 95:5+0.1% HCOOH, B: acetonitrile:water 95:5+0.1% HCOOH in 15 CV) yielded 6-(4-fluorophenyl)-2-methyl-N-((6-methylpyridazin-3-yl)methyl)quinazolin-4-amine (35.9 mg, 0.100 mmol, 68.8% yield) as an off-white powder.

LCMS (Method 5): 0.53 min, m/z 360 [M+H]+.

1H NMR (400 MHz, DMSO-d6) δ ppm 12.17-13.22 (bs, 1H), 9.00 (br. s., 1H), 8.60 (d, J=1.8 Hz, 1H), 8.07 (dd, J=8.8, 1.8 Hz, 1H), 7.87 (dd, J=8.8, 5.7 Hz, 2H), 7.69 (d, J=8.3 Hz, 1H), 7.46-7.61 (m, 2H), 7.35 (t, J=8.8 Hz, 2H), 5.03 (d, J=5.3 Hz, 2H), 2.59 (s, 3H), 2.43 (s, 3H).

The following intermediates were synthesised via adaptations of the same procedure starting from suitable intermediates reported in table.

Example 246 was obtained with the same conditions used for Example 245.

| Example No. | Chemical Name Structure | Analytical data $^1H$ NMR LC-MS | Starting Intermediate |
|---|---|---|---|
| Example 240 | N-((6-methylpyridin-3-yl)methyl)-6-(5-methylthiophen-2-yl)quinazolin-4-amine 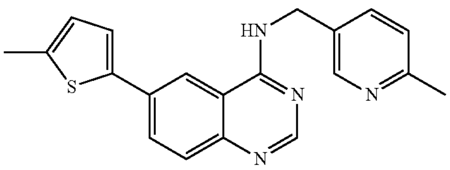 | LCMS (Method 5): 0.42 min, m/z 346.9 [M + H]+. $^1H$ NMR (400 MHz, DMSO-d6) δ ppm 8.91 (s, 1 H), 8.48 (dd, J = 12.28, 1.75 Hz, 1 H), 8.45 (dd, J = 12.28 1.75 Hz, 1 H), 8.43 (s, 1 H), 7.99 (dd, J = 8.55, 1.97 Hz, 1 H), 7.63 – 7.73 (m, 2 H), 7.44 (d, J = 3.51 Hz, 1 H), 7.20 (d, J = 7.89 Hz, 1 H), 6.88 (d, J = 2.63 Hz, 1 H), 4.77 (br d, J = 5.70 Hz, 2 H), 2.51 (s, 3 H), 2.43 (s, 3 H). | Intermediate 8 |
| Example 241 | N-((6-methylpyridin-3-yl)methyl)-6-(p-tolyl)quinazolin-4-amine 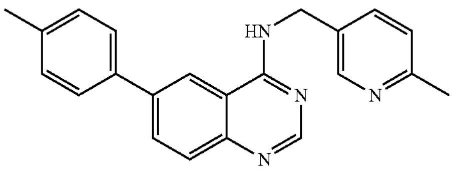 | LCMS (Method 5): 0.40 min, 341.0 m/z [M + H]+. $^1H$ NMR (400 MHz, DMSO-d6) δ ppm 8.89 – 9.01 (m, 1 H), H), 8.50 (d, J = 1.8 Hz, 1 H), 8.46 (s, 1 H), 8.10 (s, 1 H), 7.75 (dd, J = 8.6, 2.4 Hz, 3 H), 7.68 (dd, J = 8.3, 2.2 Hz, 1 H), 7.33 (d, J = 7.9 Hz, 2 H), 7.20 (d, J = 7.9 Hz, 1 H), 4.78 (d, J = 5.7 Hz, 2 H), 2.43 (s, 3 H), 2.37 (s, 3 H). | Intermediate 8 |
| Example 242 | N-((6-methylpyridazin-3-yl)methyl)-6-(2-methylpyrimidin-5-yl)quinazolin-4-amine | LCMS (Method 5): 0.35 min, m/z 344.0. $^1H$ NMR (400 MHz, DMSO-d6) δ ppm | Intermediate 9 |

-continued

| Example No. | Chemical Name Structure | Analytical data $^1$H NMR LC-MS | Starting Intermediate |
|---|---|---|---|
| | 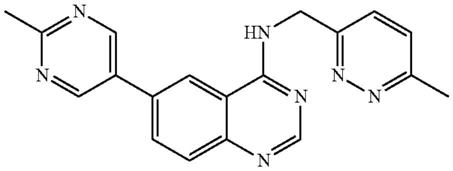 | 9.19 (s, 2 H), 9.06 – 9.16 (m, 1 H), 8.79 (d, J = 2.2 Hz, 1 H), 8.48 (s, 1 H), 8.25 (d, J = 1.8 Hz, 1 H), 7.83 (d, J = 8.8 Hz, 1 H), 7.58 (d, J = 8.4 Hz, 1 H), 7.50 (d, J = 8.4 Hz, 1 H), 5.05 (d, J = 5.7 Hz, 2 H), 2.70 (s, 3 H), 2.59 (s, 3H). | |
| Example 243 | (R)-6-(4-fluorophenyl)-N-(1-(2-(trifluoromethyl)pyrimidin-5-yl)ethyl)quinazolin-4-amine 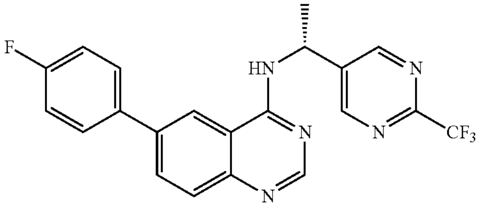 [SMILES: C[C@@H](Nc1ncnc2ccc(-c3ccc(F)cc3)cc12)c1cnc(C(F)(F)F)nc1] | LCMS (Method 5): 0.77 min, m/z 414.0. $^1$H NMR (400 MHz, DMSO-d6) δ ppm 9.17 (s, 2 H), 8.72 (d, J = 7.1 Hz, 1 H), 8.67 (d, J = 1.8 Hz, 1 H), 8.44 (s, 1 H), 8.12 (dd, J = 8.6, 2.0 Hz, 1 H), 7.84 – 7.96 (m, 2 H), 7.78 (d, J = 8.8 Hz, 1 H), 7.39 (t, J = 8.8 Hz, 2 H), 5.69 (t, J = 7.1 Hz, 1 H), 1.74 (d, J = 7.1 Hz, 3 H). | Intermediate 10 |
| Example 244 | 6-(4-fluorophenyl)-N-(1-(3-methyl-1,2,4-oxadiazol-5-yl)ethyl)quinazolin-4-amine 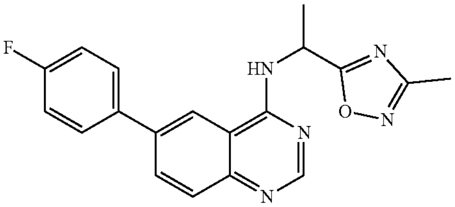 [SMILES: Cc1noc(C(C)Nc2ncnc3ccc(-c4ccc(F)cc4)cc23)n1] | LCMS (Method 5): 0.72 min, m/z 350.0. $^1$H NMR (400 MHz, DMSO-d6) δ ppm 8.86 (d, J = 7.0 Hz, 1 H), 8.65 (d, J = 1.3 Hz, 1 H), 8.43 (s, 1 H), 8.12 (dd, J = 8.6, 1.5 Hz, 1 H), 7.87 (dd, J = 8.6, 5.5 Hz, 2 H), 7.78 (d, J = 8.8 Hz, 1 H), 7.35 (t, J = 8.8 Hz, 2 H), 5.77 (t, J = 7.2 Hz, 1 H), 2.28 (s, 3 H), 1.70 (d, J = 7.0 Hz, 3 H). | Intermediate 11 |
| Example 245 | 2-(4-(((6-methylpyridin-3-yl)methyl)amino)quinazolin-6-yl)benzonitrile 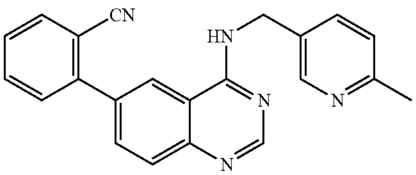 [SMILES: Cc1ccc(CNc2ncnc3ccc(-c4ccccc4C#N)cc23)cn1] | LCMS (Method 5): : 0.34 min, 351.9 m/z [M + H]+. $^1$H NMR (400 MHz, DMSO-d6) δ ppm 8.97 (t, J = 5.5 Hz, 1 H), 8.53 (s, 2 H), 8.49 (d, J = 1.3 Hz, 1 H), 7.95 – 8.05 (m, 2 H), 7.79 – 7.90 (m, 2 H), 7.75 (d, J = 7.5 Hz, 1 H), 7.59 – 7.71 (m, 2 H), 7.19 (d, J = 7.9 Hz, 1 H), 4.76 (d, J = 5.7 Hz, 2 H), 2.42 (s, 3 H). | Intermediate 8 |
| Example 246 | 2-(4-(((6-methylpyridin-3-yl)methyl)amino)quinazolin-6-yl)benzamide 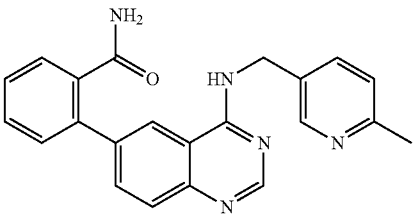 [SMILES: Cc1ccc(CNc2ncnc3ccc(-c4ccccc4C(N)=O)cc23)cn1] | LCMS (Method 6): 0.68 min, 369.9 m/z [M + H]+. $^1$H NMR (400 MHz, DMSO-d6) δ ppm 8.88 (t, J = 5.7 Hz, 1 H), 8.43 – 8.53 (m, 2 H), 8.33 (d, J = 1.3 Hz, 1 H), 7.76 (d, J = 1.8 Hz, 1 H), 7.60 – 7.70 (m, 3 H), 7.42 – 7.58 (m, 4 H), 7.33 (bs, 1 H), 7.19 (d, J = 7.9 Hz, 1 H), 4.75 (d, J = 5.7 Hz, 2 H) ,2.42 (s, 3 H). | Intermediate 8 |

-continued

| Example No. | Chemical Name Structure | Analytical data $^1H$ NMR LC-MS | Starting Intermediate |
|---|---|---|---|
| Example 247 | 6-(4-fluorophenyl)-N-((6-methylpyridin-3-yl)methyl)quinazolin-4-amine formate 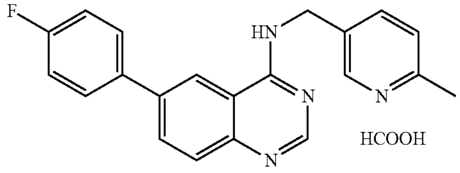 [SMILES: Cc1ccc(CNc2ncnc3ccc(-c4ccc(F)cc4)cc23)cn1 ; "HCOOH"] | LCMS (Method 5): : 0.45 min, m/z 345.0 [M + H]+. $^1H$ NMR (400 MHz, DMSO-d6) δ ppm 8.95 (t, 1 H), 8.59 (d, J = 1.8 Hz, 1 H), 8.42-8.54(m, 2H) 8.02 − 8.19 (m, 2 H), 7.81 − 7.93 (m, 2 H), 7.77 (d, J = 8.8 Hz, 1 H), 7.68 (dd, J = 7.9, 2.2 Hz, 1 H), 7.36 (t, J = 8.8 Hz, 2 H), 7.20 (d, J = 7.9 Hz, 1 H), 4.78 (d, J = 5.7 Hz, 2 H), 2.43 (s, 3 H). | Intermediate 8 |
| Example 248 | 6-(4-fluorophenyl)-N-((6-methylpyridazin-3-yl)methyl)quinazolin-4-amine 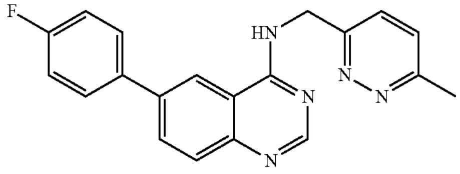 | LCMS (Method 5): : 0.53 min, m/z 345.9 [M + H]+. $^1H$ NMR (400 MHz, DMSO-d6) δ ppm 9.13 (t J = 5.9 Hz 1 H), 8.65 (d, J = 1.8 Hz, 1 H), 8.45 (s, 1 H), 8.13 (dd, J = 8.8, 1.8 Hz, 1 H), 7.90 (dd, J = 8.8, 5.3 Hz, 2 H), 7.78 (d, J = 8.8 Hz, 1 H), 7.44 − 7.62 (m, 2 H), 7.37 (t, J = 8.8 Hz, 2 H), 5.04 (d, J = 5.7 Hz, 2 H), 2.59 (s, 3 H). | Intermediate 9 |

Example 249

N-((3,5-difluoropyridin-2-yl)methyl)-6-(4-fluorophenyl)quinazolin-4-amine hydrochloride

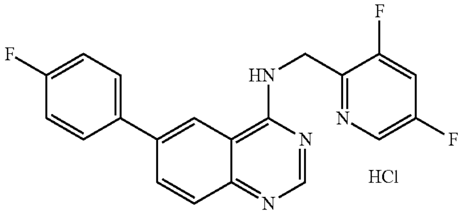 [SMILES: Fc1ccc(-c2ccc3ncnc(NCc4ncc(F)cc4F)c3c2)cc1 ; Cl]

DIPEA (0.15 mL, 0.861 mmol) was added to a mixture of 6-bromo-4-chloroquinazoline (100 mg, 0.411 mmol) and (3,5-difluoropyridin-2-yl)methanamine hydrochloride (74.2 mg, 0.411 mmol) in DMF (Volume: 2 ml). Stirring went on for 6 h at 80° C. Upon completion of conversion of starting materials to 6-bromo-N-((3,5-difluoropyridin-2-yl)methyl) quinazolin-4-amine, water (1 mL) was added to the reaction mixture followed by 4-fluorophenylboronic acid (86 mg, 0.614 mmol), potassium phosphate (174 mg, 0.818 mmol) and Pd(dppf)$Cl_2$·$CH_2Cl_2$ (33.5 mg, 0.041 mmol). Stirring went on for 16 h at 80° C. The mixture was allowed to cool down to rt, then formic acid (150 μL, 3.98 mmol) was added. Purification by RP chromatography (Biotage Isolera, 30 g C18 cartridge, gradient elution from 100:0 to 65:35 A/B, A: water/acetonitrile 95:5+0.1% HCOOH, B: acetonitrile:water 95:5+0.1% HCOOH in 15 CV) yielded N-((3,5-difluoropyridin-2-yl)methyl)-6-(4-fluorophenyl)quinazolin-4-amine hydrochloride (98.4 mg, 0.244 mmol, 59.5% yield) as an off-white powder.

LCMS (Method 5): 0.67 min, 366.9 m/z [M+H]+, $^1H$ NMR (400 MHz, DMSO-d6) δ ppm 10.82 (br s, 1H), 8.92-9.00 (m, 1H), 8.84-8.91 (m, 1H), 8.44-8.50 (m, 1H), 8.34-8.44 (m, 1H), 7.98-8.07 (m, 1H), 7.87-7.97 (m, 3H), 7.43 (t, J=8.88 Hz, 2H), 5.13 (br d, J=5.26 Hz, 2H).

Example 250

6-(4-fluorophenyl)-N-methyl-N-(1-(3-methyl-1,2,4-oxadiazol-5-yl)ethyl) quinazolin-4-amine

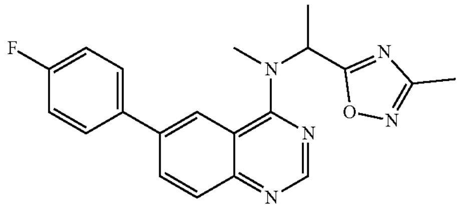 [SMILES: Cc1noc(C(C)N(C)c2ncnc3ccc(-c4ccc(F)cc4)cc23)n1]

To a solution of 6-(4-fluorophenyl)-N-(1-(3-methyl-1,2,4-oxadiazol-5-yl)ethyl)quinazolin-4-amine (30 g, 0.086 mmol) in DMF (1 mL), cooled to 0° C., NaH (6.07 mg, 0.240 mmol) was added and the reaction stirred for 30 min before adding MeI (10.74 μL, 0.172 mmol). After 20 h, the crude mixture was directly loaded onto column and purified by RP flash chromatography (Biotage Isolera, 12 g C18 cartridge, gradient elution from 0 to 80% B in A; A: water/MeCN 95:5+0.1% HCOOH, B: MeCN/water 95:5+0.1% HCOOH) yielded the titled compound (16 mg, 0.044 mmol, 51.3% yield) as pale beige powder.

LCMS (Method 5): 0.57 min, 364.0 [M+H]+.

$^{1}$H NMR (400 MHz, DMSO-d6) δ □ ppm 8.33 (d, J=2.2 Hz, 1H), 8.08 (s, 1H), 7.98 (dd, J=8.4, 2.2 Hz, 1H), 7.69-7.77 (m, 2H), 7.51 (d, J=8.8 Hz, 1H), 7.32 (t, J=8.8 Hz, 2H), 5.72 (d, J=6.6 Hz, 1H), 3.63 (s, 3H), 2.31 (s, 3H), 1.53 (d, J=7.1 Hz, 3H).

Example 251

(R)-6-(3,3-difluoropyrrolidin-1-yl)-N-(1-(2-(trifluoromethyl)pyrimidin-5-yl)ethyl)quinazolin-4-amine

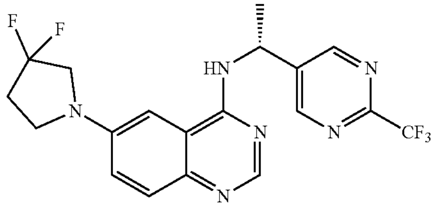 [SMILES: C[C@@H](Nc1ncnc2ccc(N3CCC(F)(F)C3)cc12)c1cnc(C(F)(F)F)nc1]

To a suspension of (R)-6-bromo-N-(1-(2-(trifluoromethyl)pyrimidin-5-yl)ethyl)quinazolin-4-amine (40 mg, 0.100 mmol) in Toluene (1.5 mL), 3,3-difluoropyrrolidine hydrochloride (36 mg, 0.251 mmol) and cesium carbonate (82 mg, 0.251 mmol) were added, followed by (R)-(+)-2,2'-bis(diphenylphoshino)-1,1'-binaphthyl (13 mg, 0.020 mmol) and tris(dibenylideneacetone)dipalladium (0) (9.20 mg, 10.05 μmol). The resulting mixture was heated to 100° C. and stirred for 7 h. The mixture was cooled to RT and filtered. Volatiles were removed under reduced pressure. Purification by RP flash chromatography (Biotage Isolera, 30 g C18 cartridge, gradient elution from 0 to 90% B in A; A: water/MeCN 95:5+0.1% HCOOH, B: MeCN/water 95:5+0.1% HCOOH) yielded impure product. A second purification by flash chromatography (Biotage Isolera, 11 g NH cartridge, gradient elution from 5% to 100% EtOAc in heptane) yielded the titled compound (21 mg, 4.95 μmol, 5% yield) as white powder.

LCMS (Method 5): 0.68 min, 425.0 [M+H]+.

$^{1}$H NMR (400 MHz, DMSO-d6) δ 9.13 (s, 2H), 8.31 (d, J=7.06 Hz, 1H), 8.27 (s, 1H), 7.55-7.62 (m, 3H), 5.66 (quin, J=6.89 Hz, 1H), 3.76 (t, J=13.89 Hz, 2H), 3.51 (t, J=7.06 Hz, 2H), 2.39-2.49 (m, 2H), 1.72 (d, J=7.06 Hz, 3H).

The following Examples were synthesised via adaptations of the above procedure.

| Example No. | Chemical Name<br>Structure | Analytical data<br>$^{1}$H NMR<br>LC-MS |
|---|---|---|
| Example 252 | (R)-6-morpholino-N-(1-(2-(trifluoromethyl)pyrimidin-5-yl)ethyl)quinazolin-4-amine<br>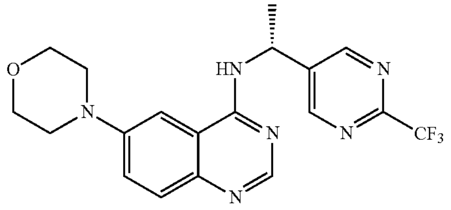 [SMILES: C[C@@H](Nc1ncnc2ccc(N3CCOCC3)cc12)c1cnc(C(F)(F)F)nc1] | LCMS (Method 5): 0.53 min, 405.0 [M + H]$^{+}$.<br>$^{1}$H NMR (400 MHz, DMSO-d6) δ ppm 9.13 (s, 2 H), 8.29 - 8.34 (m, 1 H), 8.27 (s, 1 H), 7.53 - 7.65 (m, 2 H), 7.35 - 7.47 (m, 1 H), 5.56 - 5.75 (m, 1 H), 3.75 - 3.94 (m, 4 H), 3.20 - 3.30 (m, 4 H), 1.71 (d, J = 7.0 Hz, 3 H). |
| Example 253 | (R)-1-methyl-4-(4-((1-(2-(trifluoromethyl)pyrimidin-5-yl)ethyl)amino) quinazolin-6-yl)piperazin-2-one<br>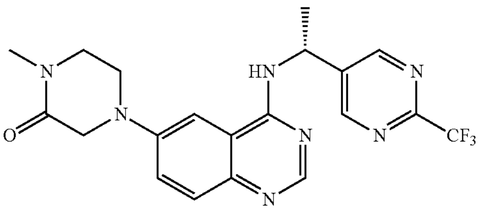 [SMILES: C[C@@H](Nc1ncnc2ccc(N3CCN(C)C(=O)C3)cc12)c1cnc(C(F)(F)F)nc1] | LCMS (Method 5): 0.48 min, 432 [M + H]$^{+}$.<br>$^{1}$H NMR (400 MHz, DMSO-d6) δ ppm 9.13 (s, 2 H), 8.38 (d, J = 6.6 Hz, 1 H), 8.26 (s, 1 H), 7.56 - 7.73 (m, 2 H), 7.53 (d, J = 2.2 Hz, 1 H), 5.51 - 5.77 (m, 1 H), 3.95 (s, 2 H), 3.59 - 3.70 (m, 2 H), 3.45 - 3.57 (m, 2 H), 2.94 (s, 3 H), 1.73 (d, J = 7.1 Hz, 3 H). |
| Example 254 | N-((6-methylpyridazin-3-yl)methyl)-6-morpholinoquinazolin-4-amine<br>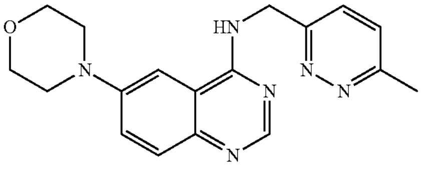 [SMILES: Cc1ccc(CNc2ncnc3ccc(N4CCOCC4)cc23)nn1] | LCMS (Method 5): 0.34 min, 337 [M + H]$^{+}$.<br>$^{1}$H NMR (400 MHz, CDCb) δ □ppm 8.68 - 8.77 (m, 1 H), 8.22 - 8.32 (m, 1 H), 7.37 - 7.64 (m,5H), 4.91 - 5.04 (m, 2 H), 3.72 - 3.87 (m,4H), 3.17 - 3.27 (m, 4 H), 2.58 (s, 3 H). |

The following compounds reported in the table below were obtained as single isomers by chiral preparative SFC purification of the appropriate racemic mixture hereinabove described.

| Example No. | Chemical Name Structure | Analytical data $^1$H NMR LC-MS |
|---|---|---|
| Example 255 | Single enantiomer 1 of 6-(4-fluorophenyl)-8-methoxy-N-(1-(3-methyl-1,2,4-oxadiazol-5-yl)ethyl)quinazolin-4-amine 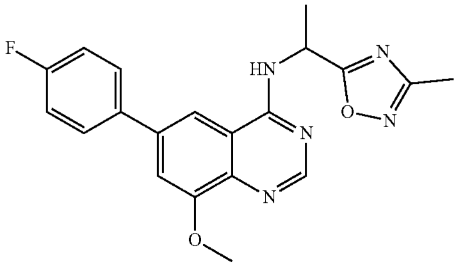 [SMILES: COc1cc(-c2ccc(F)cc2)cc2c(NC(C)c3nc(C)no3)ncnc12] | $^1$H NMR (400 MHz, DMSO): δ 8.79 (d, J = 6.8 Hz, 1 H), 8.44 (s, 1 H), 8.20 (d, J = 1.5 Hz, 1 H), 7.97-7.93 (m, 2 H), 7.56 (d, J = 1.3 Hz, 1 H), 7.40 (dd, J = 8.9, 8.9 Hz, 2 H), 5.83-5.78 (m, (s, 3 H), 2.33 (s, 3 H), 1.74 (d, J = 7.2 Hz, 3 H). LCMS (Method 4): [MH+] = 380 at 3.27 min. Chiral analysis (Method 9) at 2.7 min. |
| Example 256 | Single enantiomer 2 of 6-(4-fluorophenyl)-8-methoxy-N-(1-(3-methyl-1,2,4-oxadiazol-5-yl)ethyl)quinazolin-4-amine 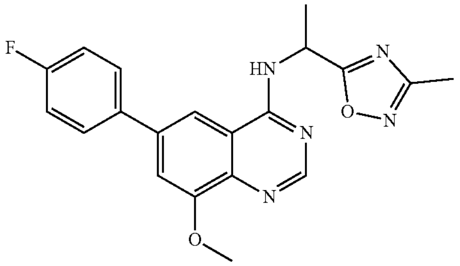 [SMILES: COc1cc(-c2ccc(F)cc2)cc2c(NC(C)c3nc(C)no3)ncnc12] | $^1$H NMR (400 MHz, DMSO): δ 8.79 (d, J = 7.3 Hz, 1 H), 8.44 (s, 1 H), 8.21 (d, J = 1.6 Hz, 1 H), 7.97-7.93 (m, 2 H), 7.56 (d, J = 1.5 Hz, 1 H), 7.40 (dd, J = 8.9, 8.9 Hz, 2 H), 5.83-5.78 (m, 1 H), 4.03 (s, 3 H), 2.33 (s, 3 H), 1.74 (d, J = 7.2 Hz, 3 H). LCMS (Method 4): [MH+] = 380 at 3.27 min. Chiral analysis (Method 9) at 3.27 min. |
| Example 257 | Single enantiomer 1 of 6-(4-fluorophenyl)-8-methoxy-N-(1-(3-(trifluoromethyl)-1,2,4-oxadiazol-5-yl)ethyl)quinazolin-4-amine 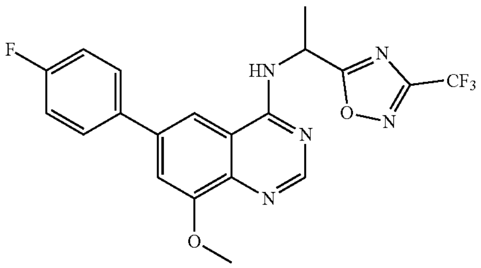 [SMILES: COc1cc(-c2ccc(F)cc2)cc2c(NC(C)c3nc(C(F)(F)F)no3)ncnc12] | $^1$H NMR (400 MHz, DMSO): δ 8.91 (d, J = 6.8 Hz, 1 H), 8.44 (s, 1 H), 8.17 (d, J = 1.6 Hz, 1 H), 7.97-7.92 (m, 2 H), 7.58 (d, J = 1.5 Hz, 1 H), 7.40 (dd, J = 8.9, 8.9 Hz, 2 H), 5.94-5.89 (m, 1 H), 4.04 (s, 3 H), 1.81 (d, J = 7.0 Hz, 3 H). LCMS (Method 3): [MH+] = 434 at 4.96 min. Chiral analysis (Method 8) at 2.6 min. |
| Example 258 | Single enantiomer 2 of 6-(4-fluorophenyl)-8-methoxy-N-(1-(3-(trifluoromethyl)-1,2,4-oxadiazol-5-yl)ethyl)quinazolin-4-amine | $^1$H NMR (400 MHz, DMSO): δ 8.91 (d, J = 7.4 Hz, 1 H), 8.44 (s, 1 H), 8.17 (d, J = 1.4 Hz, 1 H), 7.97-7.91 (m, 2 H), 7.58 (d, J = 1.5 Hz, 1 H), 7.43-7.38 (m, 2 H), 5.95-5.88 (m, 1 H), 4.04 |

-continued

| Example No. | Chemical Name Structure | Analytical data $^1$H NMR LC-MS |
|---|---|---|
| | 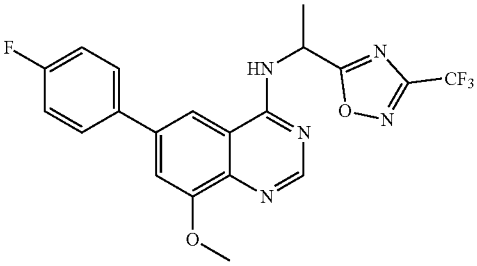 [SMILES: COc1cc(-c2ccc(F)cc2)cc2c(NC(C)c3nc(C(F)(F)F)no3)ncnc12] | (s, 4H) 1.81 (d, J = 7.0 Hz, 3 H). LCMS (Method 3): [MH+] = 434 at 4.95 min. Chiral analysis (Method 8) at 3.6 min. |
| Example 259 | Single enantiomer 1 of 6-(4-fluorophenyl)-8-methoxy-N-(1-(6-methylpyridin-3-yl)ethyl)quinazolin-4-amine 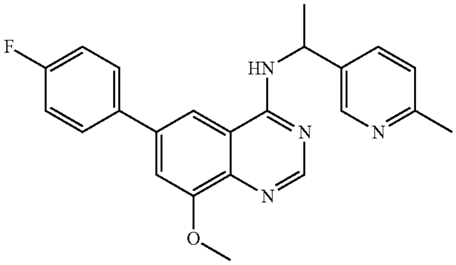 [SMILES: COc1cc(-c2ccc(F)cc2)cc2c(NC(C)c3ccc(C)nc3)ncnc12] | $^1$H NMR (400 MHz, DMSO): δ 8.54 (d, J = 2.4 Hz, 1 H), 8.52-8.47 (m, 1 H), 8.40 (s, 1 H), 8.22 (d, J = 1.6 Hz, 1 H), 7.97-7.92 (m, 2 H), 7.73 (dd, J = 2.3, 8.1 Hz, 1H) 7.51(d J = 1.5 Hz, 1 H), 7.40 (dd, J = 8.8, 8.8 Hz, 2 H), 7.21 (d, J = 8.0 Hz, 1 H), 5.63-5.58 (m, 1 H), 4.01 (s, 3 H), 2.43 (s, 3 H), 1.64 (d, J = 7.2 Hz, 3 H). LCMS (Method 4): [MH+] = 389 at 2.55 min. Chiral analysis (Method 5) at 1.9 min. |
| Example 260 | Single enantiomer 2 of 6-(4-fluorophenyl)-8-methoxy-N-(1-(6-methylpyridin-3-yl)ethyl)quinazolin-4-amine 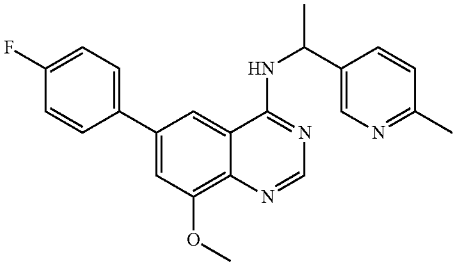 [SMILES: COc1cc(-c2ccc(F)cc2)cc2c(NC(C)c3ccc(C)nc3)ncnc12] | $^1$H NMR (400 MHz, DMSO): δ 8.54 (d, J = 2.4 Hz, 1 H), 8.52-8.47 (m, 1 H), 8.40 (s, 1 H), 8.22 (d, J = 1.6 Hz, 1 H), 7.97-7.92 (m, 2 H), 7.73 (dd, J = 2.3, 8.1 Hz, 1H) 7.51 (d, J = 1.5 Hz, 1 H), 7.40 (dd, J = 8.8, 8.8 Hz, 2 H), 7.21 (d, J = 8.0 Hz, 1 H), 5.63-5.58 (m, 1 H), 4.01 (s, 3 H), 2.43 (s, 3 H), 1.64 (d, J = 7.2 Hz, 3 H). LCMS (Method 4): [MH+] = 389 at 2.55 min. Chiral analysis (Method 5) at 2.6 min. |
| Example 261 | Single enantiomer 1 of 6-(4-fluorophenyl)-8-methoxy-N-(1-(5-methyl-1,2,4-oxadiazol-3-yl)ethyl)quinazolin-4-amine 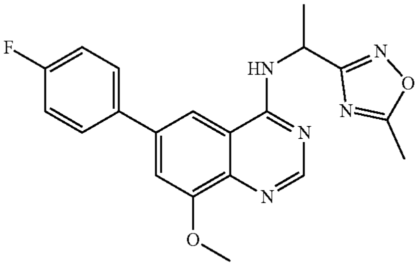 | $^1$H NMR (400 MHz, DMSO): δ 8.64 (d, J = 7.8 Hz, 1 H), 8.44 (s, 1 H), 8.23 (d, J = 1.6 Hz, 1 H), 7.97-7.93 (m, 2 H), 7.54 (d, J = 1.5 Hz, 1 H), 7.39 (dd, J = 8.9, 8.9 Hz, 2 H), 5.79-5.74 (m, 1 H), 4.03 (s, 3 H), 2.57 (s, 3 H), 1.68 (d, J = 7.0 Hz, 3 H). LCMS (Method 3): [MH+] = 380 at 4.14 min. Chiral analysis (Method 14) at 2.0 min. |
| Example 262 Single enantiomer 2 | Single enantiomer of 6-(4-fluorophenyl)-8-methoxy-N-(1-(5-methyl-1,2,4-oxadiazol-3-yl)ethyl)quinazolin-4-amine | $^1$H NMR (400 MHz, DMSO): δ 8.64 (d, J = 7.8 Hz, 1 H), 8.44 (s, 1 H), 8.23 (d, J = 1.6 Hz, 1 H), 7.97-7.93 (m, 2 H), 7.54 (d, J = 1.5 Hz, 1 H), 7.39 (dd, J = |

-continued

| Example No. | Chemical Name Structure | Analytical data $^1$H NMR LC-MS |
|---|---|---|
| | 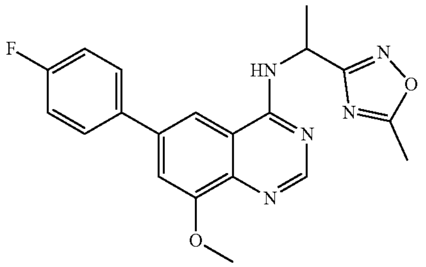 | 8.8, 8.8 Hz, 2 H), 5.79-5.74 (m, 1 H), 4.03 (s, 3 H), 2.58 (s, 3 H), 1.68 (d, J = 7.0 Hz, 3 H). LCMS (Method 3): [MH+] = 380 at 4.15 min. Chiral analysis (Method 14) at 3.1 min. |
| Example 263 | Single enantiomer 1 of 6-(4-fluorophenyl)-8-methoxy-N-(1-(5-methyl-1,3,4-oxadiazol-2-yl)ethyl)quinazolin-4-amine 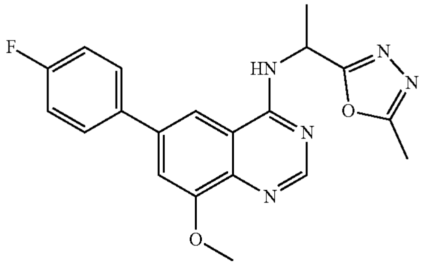 | $^1$H NMR (400 MHz, DMSO): δ 8.73 (d, J = 7.5 Hz, 1 H), 8.48 (s, 1 H), 8.17 (d, J = 1.8 Hz, 1 H), 7.96-7.91 (m, 2 H), 7.56 (d, J = 1.5 Hz, 1 H), 7.39 (dd, J = 8.9, 8.9 Hz, 2 H), 5.90-5.85 (m, 1 H), 4.03 (s, 3 H), 2.48 (s, 3 H), 1.72 (d, J = 7.0 Hz, 3 H). LCMS (Method 4): [MH+] 380 at 3.06 min. Chiral analysis (Method 19) at 2.63 min. |
| Example 264 | Single enantiomer 2 of 6-(4-fluorophenyl)-8-methoxy-N-(1-(5-methyl-1,3,4-oxadiazol-2-yl)ethyl)quinazolin-4-amine 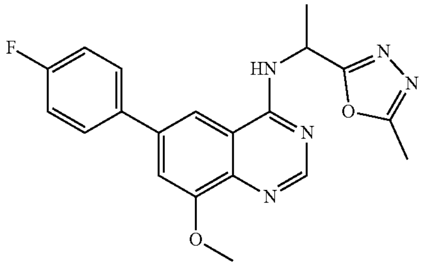 | $^1$H NMR (400 MHz, DMSO): δ 8.80 (br s, 1 H), 8.50 (s, 1 H), 8.18 (d, J = 1.5 Hz, 1 H), 7.96-7.92 (m, 2 H), 7.57 (s, 1 H), 7.39 (dd, J = 8.9, 8.9 Hz, 2 H), 5.91-5.86 (m, 1 H), 4.04 (s, 3 H), 3.44-3.38 (m, 1 H), 2.48 (s, 3H), 1.72 (d, J = 7.0 Hz, 3 H). LCMS (Method 4): [MH+] = 380 at 3.02 min. Chiral analysis (Method 19) at 3.57 min. |
| Example 265 | Single enantiomer 1 of 6-(4-fluorophenyl)-8-methoxy-N-(1-(6-methoxypyridin-3-yl)ethyl)quinazolin-4-amine 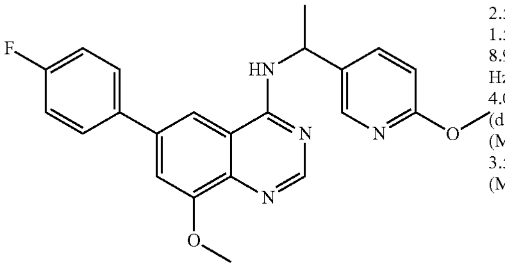 | $^1$H NMR (400 MHz, DMSO): δ 8.46 (d, J = 7.7 Hz, 1 H), 8.42 (s, 1 H), 8.26 (d, J = 2.5 Hz, 1 H), 8.20 (d, J = 1.6 Hz, 1 H), 7.96-7.91 (m, 2 H), 7.80 (dd, J = 2.5, 8.7 Hz, 1 H), 7.51 (d, J = 1.5 Hz, 1 H), 7.39 (dd, J = 8.9, 8.9 Hz, 2 H), 6.80 (d, J = 8.7 Hz, 1 H), 5.63-5.58 (m, 1 H), 4.01 (s, 3 H), 3.82 (s, 3 H), 1.63 (d, J = 7.0 Hz, 3 H). LCMS (Method 4): [MH+] = 405 at 3.57 min. Chiral analysis (Method 20) at 1.68 min. |
| Example 266 | Single enantiomer 2 of 6-(4-fluorophenyl)-8-methoxy-N-(1-(6-methoxypyridin-3-yl)ethyl)quinazolin-4-amine | $^1$H NMR (400 MHz, DMSO): δ 8.45 (d, J = 7.7 Hz, 1 H), 8.42 (s, 1 H), 8.26 (d, J = 2.5 Hz, 1 H), 8.20 (d, J = 1.6 Hz, 1 H), 7.96-7.91 (m, 2 H), 7.80 (dd, J = |

-continued

| Example No. | Chemical Name Structure | Analytical data $^1$H NMR LC-MS |
|---|---|---|
| | 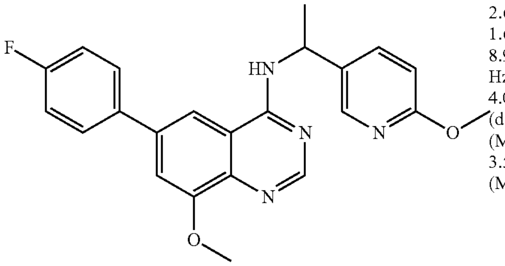 | 2.6, 8.6 Hz, 1 H), 7.51 (d, J = 1.6 Hz, 1 H), 7.39 (dd, J = 8.9, 8.9 Hz, 2 H), 6.80 (d, J = 8.5 Hz, 1 H), 5.63-5.58 (m, 1 H), 4.01 (s, 3 H), 3.82 (s, 3 H), 1.63 (d, J = 7.2 Hz, 3 H). LCMS (Method 3): [MH+] = 405 at 3.58 min. Chiral analysis (Method 20) at 2.68 min. |
| Example 267 | Single enantiomer 1 of 2-((6-(4-fluorophenyl)-8-methoxyquinazolin-4-yl)amino)-2-(3-methyl-1,2,4-oxadiazol-5-yl)ethan-1-ol 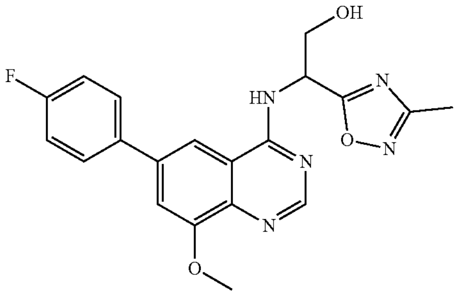 | $^1$H NMR (400 MHz, DMSO): δ 8.71 (d, J = 7.4 Hz, 1 H), 8.45 (s, 1 H), 8.25 (d, J = 1.6 Hz, 1 H), 7.99-7.94 (m, 2 H), 7.57 (d, J = 1.5 Hz, 1 H), 7.40 (dd, J = 8.9, 8.9 Hz, 2 H), 5.80-5.74 (m, 1 H), 5.38 (dd, J = 6.0, 6.0 Hz, 1 H), 4.03 (s, δ H), 2.33 (s, 3 H). LCMS (Method 3): [MH+] = 389 at 2.55 min. Chiral analysis (Method 12) at 3.6 min. |
| Example 268 | Single enantiomer 2 of 2-((6-(4-fluorophenyl)-8-methoxyquinazolin-4-yl)amino)-2-(3-methyl-1,2,4-oxadiazol-5-yl)ethan-1-ol 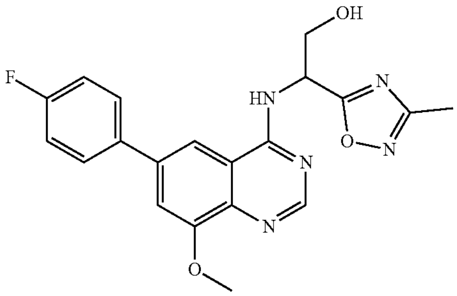 [SMILES: COc1cc(-c2ccc(F)cc2)cc2c(NC(CO)c3nc(C)no3)ncnc12] | $^1$H NMR (400 MHz, DMSO): δ 8.71 (d, J = 7.4 Hz, 1 H), 8.45 (s, 1 H), 8.25 (d, J = 1.6 Hz, 1 H), 7.99-7.94 (m, 2 H), 7.57 (d, J = 1.6 Hz, 1 H), 7.40 (dd, J = 8.9, 8.9 Hz, 2 H), 5.80-5.74 (m, 1 H), 5.39 (dd, J = 6.0, 6.0 Hz, 1 H), 4.03 (s, 5 H), 3.44-3.38 (m, 1 H), 3.31 (s, 2 H), 2.33 (s, 3 H). LCMS (Method 4): [MH+] = 396 at 2.97 min. Chiral analysis (Method 12) at 4.85 min. |
| Example 269 | Single enantiomer 1 of N-(1-(3-ethyl-1,2,4-oxadiazol-5-yl)ethyl)-6-(4-fluorophenyl)-8-methoxyquinazolin-4-amine 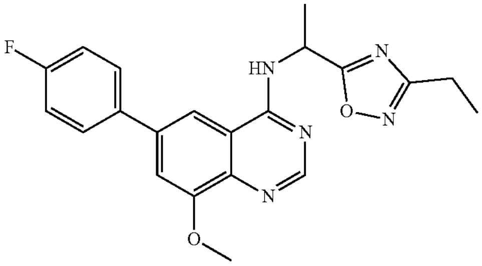 [SMILES: CCc1noc(C(C)Nc2ncnc3c(OC)cc(-c4ccc(F)cc4)cc23)n1] | $^1$H NMR (400 MHz, DMSO): δ 8.80 (d, J = 7.2 Hz, 1 H), 8.45 (s, 1 H), 8.21 (d, J = 1.5 Hz, 1 H), 7.97-7.92 (m, 2 H), 7.56 (d, J = 1.4 Hz, 1 H), 7.40 (dd, J = 8.9, 8.9 Hz, 2 H), 5.85-5.79 (m, 1 H), 4.03 (s, 3 H), 2.71 (q, J = 7.6 Hz, 2 H), 1.74 (d, J = 7.2 Hz, 3 H), 1.22 (dd, J = 7.6, 7.6 Hz, 3 H). LCMS (Method 4): [MH+] = 394 at 3.47 min. Chiral analysis (Method 9) at 2.61 min. |

-continued

| Example No. | Chemical Name Structure | Analytical data $^1H$ NMR LC-MS |
|---|---|---|
| Example 270 | Single enantiomer 2 of N-(1-(3-ethyl-1,2,4-oxadiazol-5-yl)ethyl)-6-(4-fluorophenyl)-8-methoxyquinazolin-4-amine<br>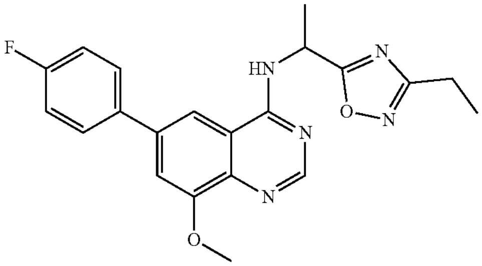 [SMILES: CCc1noc(C(C)Nc2ncnc3c(OC)cc(-c4ccc(F)cc4)cc23)n1] | $^1H$ NMR (400 MHz, DMSO): δ 8.80 (d, J = 7.3 Hz, 1 H), 8.45 (s, 1 H), 8.21 (d, J = 1.6 Hz, 1 H), 7.97-7.93 (m, 2 H), 7.57 (d, J = 1.6 Hz, 1 H), 7.40 (dd, J = 8.8, 8.8 Hz, 2 H), 5.85-5.80 (m, 1 H), 4.03 (s, 3 H), 2.71 (q, J = 7.5 Hz, 2 H), 1.74 (d, J = 7.2 Hz, 3 H), 1.22 (dd, J = 7.5, 7.5 Hz, 3 H). LCMS (Method 3): [MH+] = 394 at 4.68 min. Chiral analysis (Method 9) at 3.46 min. |
| Example 271 | Single enantiomer 1 of N-(1-cyclopropylethyl)-6-(4-fluorophenyl)-8-methoxyquinazolin-4-amine<br>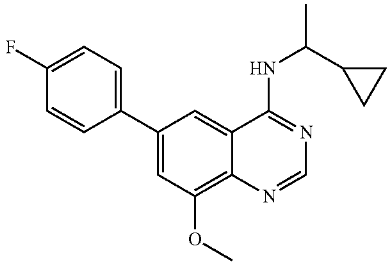 [SMILES: COc1cc(-c2ccc(F)cc2)cc2c(NC(C)C3CC3)ncnc12] | $^1H$ NMR (400 MHz, DMSO): δ 8.36 (s, 1 H), 8.13-8.08 (m, 2 H), 7.94-7.89 (m, 2 H), 7.47 (d, J = 1.5 Hz, 1 H), 7.37 (dd, J = 8.9, 8.9 Hz, 2 H), 3.99 (s, 3 H), 3.94 (dd, J = 8.2, 14.9 Hz, 1 H), 1.32 (d, J = 6.7 Hz, 3 H), 1.17-1.08 (m, 1 H), 0.55-0.22 (m, 1 H). LCMS (Method 4): [MH+] = 338 at 3.67 min. Chiral analysis (Method 14) at 6.55 min. |
| Example 272 | Single enantiomer 2 of N-(1-cyclopropylethyl)-6-(4-fluorophenyl)-8-methoxyquinazolin-4-amine<br>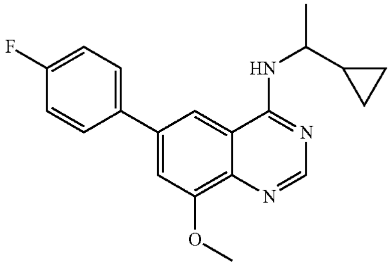 [SMILES: COc1cc(-c2ccc(F)cc2)cc2c(NC(C)C3CC3)ncnc12] | $^1H$ NMR (400 MHz, DMSO): δ 8.36 (s, 1 H), 8.13-8.08 (m, 2 H), 7.94-7.89 (m, 2 H), 7.47 (d, J = 1.5 Hz, 1 H), 7.37 (dd, J = 8.9, 8.9 Hz, 2 H), 3.99 (s, 3 H), 3.94 (dd J = 8.3 14.9 Hz 1 H) 1.32 (d, J = 6.5 Hz, 3 H), 1.16-1.08 (m, 1 H), 0.55-0.23 (m, 1 H). LCMS (Method 3): [MH+] = 338 at 3.68 min. Chiral analysis (Method 14) at 7.91 min. |
| Example 273 | Single enantiomer 1 of $N^3$-(6-(4-fluorophenyl)-8-methoxyquinazolin-4-yl)-$N^1$,$N^1$-dimethylbutane-1,3-diamine<br>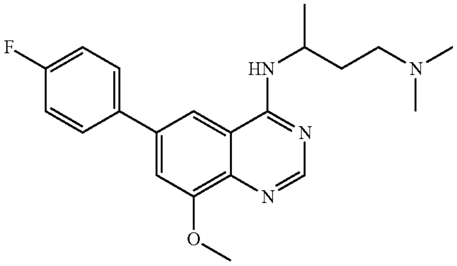 [SMILES: COc1cc(-c2ccc(F)cc2)cc2c(NC(C)CCN(C)C)ncnc12] | $^1H$ NMR (400 MHz, DMSO): δ 8.42 (s, 1 H), 8.09-8.04 (m, 2 H), 7.94-7.89 (m, 2 H), 7.48 (d, J = 1.5 Hz, 1 H), 7.39 (dd, J = 8.9, 8.9 Hz, 2 H), 4.56-4.48 (m, 1 H), 4.01 (s, 3 H), 2.35-2.28 (m, 2 H), 2.14 (s, δ H), 1.89-1.67 (m, 1 H), 1.27 (d, J = 6.7 Hz, 3 H). LCMS (Method 4): [MH+] = 369 at 2.37 min. Chiral analysis (Method 7) at 1.62 min. |

-continued

| Example No. | Chemical Name Structure | Analytical data $^1H$ NMR LC-MS |
|---|---|---|
| Example 274 | Single enantiomer 2 of $N^3$-(6-(4-fluorophenyl)-8-methoxyquinazolin-4-yl)-$N^1$,$N^1$-dimethylbutane-1,3-diamine 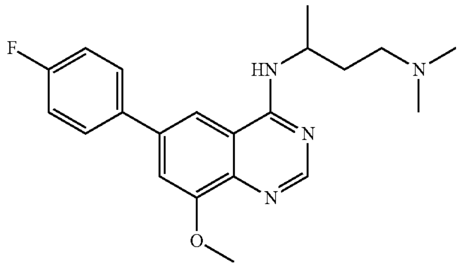 [SMILES: COc1cc(-c2ccc(F)cc2)cc2c(NC(C)CCN(C)C)ncnc12] | $^1H$ NMR (400 MHz, DMSO): δ 8.42 (s, 1 H), 8.09-8.04 (m, 2 H), 7.94-7.89 (m, 2 H), 7.48 (d, J = 1.5 Hz, 1 H), 7.39 (dd, J = 8.9, 8.9 Hz, 2 H), 4.56-4.48 (m, 1 H), 4.01 (s, 3 H), 2.35-2.28 (m, 2 H), 2.14 (s, δ H), 1.88-1.68 (m, 1H), 1.27 (d, J = 6.5 Hz, 3 H). LCMS (Method 4): [MH+] = 369 at 2.37 min. Chiral analysis (Method 7) at 2.4 min. |
| Example 275 | Single enantiomer 1 of 3-((6-(4-fluorophenyl)-8-methoxyquinazolin-4-yl)amino)tetrahydrothiophene 1,1-dioxide 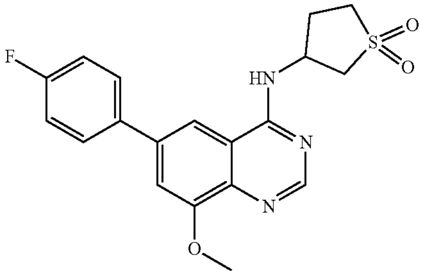 [SMILES: COc1cc(-c2ccc(F)cc2)cc2c(NC3CCS(=O)(=O)C3)ncnc12] | $^1H$ NMR (400 MHz, DMSO): δ 8.57 (s, 1 H), 8.43-8.38 (m, 1 H), 8.13 (d, J = 1.6 Hz, 1 H), 7.98-7.94 (m, 2 H), 7.58 (d, J = 1.6 Hz, 1 H), 7.45 (dd, J = 8.9, 8.9 Hz, 2 H), 5.14 (dd, J = 7.2, 15.8 Hz, 1 H), 4.07 (s, 3 H), 3.73 (dd, J = 8.2, 13.3 Hz, 1 H), 3.53-3.46 (m, 1 H), 3.35-3.28 (m, 1 H), 3.19 (dd, J = 8.0, 13.2 Hz, 1 H), 2.67-2.61 (m, 1 H), 2.45-2.36 (m, 1 H). LCMS (Method 4): [MH+] = 388 at 2.97 min. Chiral analysis (Method 15) at 4.5 min. |
| Example 276 | Single enantiomer 2 of 3-((6-(4-fluorophenyl)-8-methoxyquinazolin-4-yl)amino)tetrahydrothiophene 1,1-dioxide 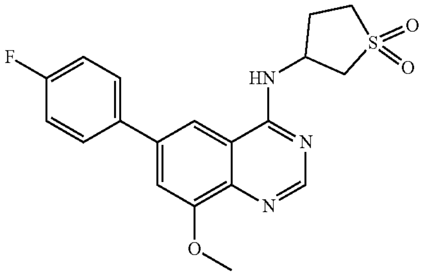 [SMILES: COc1cc(-c2ccc(F)cc2)cc2c(NC3CCS(=O)(=O)C3)ncnc12] | $^1H$ NMR (400 MHz, DMSO): δ 8.64 (d, J = 7.8 Hz, 1 H), 8.44 (s, 1 H), 8.23 (d, J = 1.6 Hz, 1 H), 7.97-7.93 (m, 2 H), 7.54 (d, J = 1.5 Hz, 1 H), 7.39 (dd, J = 8.8, 8.8 Hz, 2 H), 5.79-5.74 (m, 1 H), 4.03 (s, 3 H), 2.58 (s, 3 H), 1.68 (d, J = 7.0 Hz, 3 H). LCMS (Method 4): [MH+] = 388 at 2.98 min. Chiral analysis (Method 15) at 6.86 min. |
| Example 277 | Single enantiomer 1 of 6-(4-fluorophenyl)-N-[1-(3-isopropyl-1,2,4-oxadiazol-5-yl)ethyl]-8-methoxy-quinazolin-4-amine | $^1H$ NMR (400 MHz, DMSO): δ 8.79 (d, J = 7.3 Hz, 1 H), 8.45 (s, 1 H), 8.20 (d, J = 1.8 Hz, 1 H), 7.97-7.93 (m, 2 H), 7.56 (d, J = 1.6 Hz, 1 H), 7.40 (dd, J = |

-continued

| Example No. | Chemical Name Structure | Analytical data $^1H$ NMR LC-MS |
|---|---|---|
| | 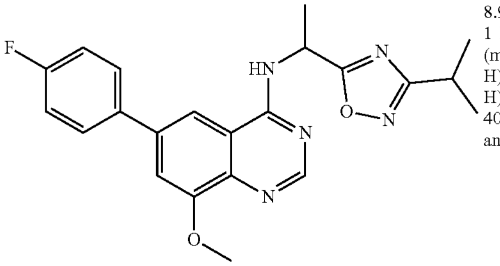 | 8.9, 8.9 Hz, 2 H), 5.86-5.81 (m, 1 H), 4.03 (s, 3 H), 3.09-3.01 (m, 1 H), 1.74 (d, J = 7.2 Hz, 3 H), 1.25 (dd, J = 1.3, 7.0 Hz, δ H). LCMS (Method 4): [MH+] = 408 at 3.66 min. Chiral analysis (Method 11) at 2.52 min. |
| Example 278 | Single enantiomer 2 of 6-(4-fluorophenyl)-N-[1-(3-isopropyl-1,2,4-oxadiazol-5-yl)ethyl]-8-methoxy-quinazolin-4-amine 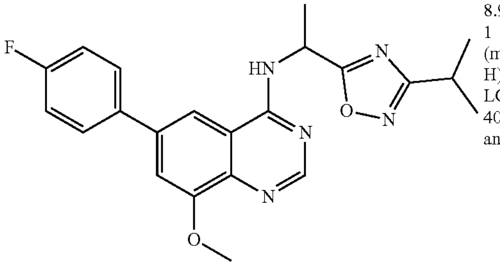 | $^1H$ NMR (400 MHz, DMSO): δ 8.79 (d, J = 7.3 Hz, 1 H), 8.45 (s, 1 H), 8.20 (d, J = 1.8 Hz, 1 H), 7.97-7.93 (m, 2 H), 7.56 (d, J = 1.6 Hz, 1 H), 7.40 (dd, J = 8.9, 8.9 Hz, 2 H), 5.86-5.81 (m, 1 H), 4.03 (s, 3 H), 3.09-3.01 (m, 1H), 1.74 (d, J = 7.2 Hz, 3 H), 1.25 (dd, J = 1.3, 7.0 Hz, δ H). LCMS (Method 4): [[MH+] = 408 at 3.73 min. Chiral analysis (Method 11) at 3.23 min. |
| Example 279 | Single enantiomer 1 of 6-(4-fluorophenyl)-8-methoxy-N-[2-methyl-1-(3-methyl-1,2,4-oxadiazol-5-yl)propyl]quinazolin-4-amine 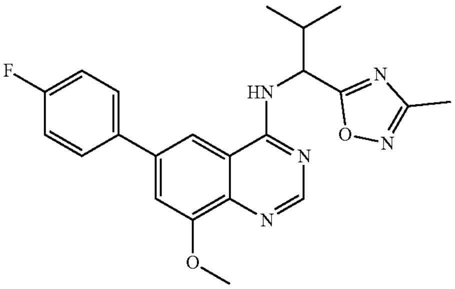 [SMILES: COc1cc(-c2ccc(F)cc2)cc2c(NC(c3nc(C)no3)C(C)C)ncnc12] | $^1H$ NMR (400 MHz, DMSO): δ 8.68 (d, J = 7.8 Hz, 1 H), 8.44 (s, 1 H), 8.31 (d, J = 1.6 Hz, 1 H), 7.96 (ddd, J = 3.2, 5.4, 12.1 Hz, 2 H), 7.56 (d, J = 1.5 Hz, 1 H), 7.41 (dd, J = 8.9, 8.9 Hz, 2 H), 5.53 (dd, J = 8.5, 8.5 Hz, 1 H), 4.02 (s, 3 H), 2.34 (s, 3 H), 1.13 (d, J = 6.7 Hz, 3 H), 0.95 (d, J = 6.8 Hz, 3 H). LCMS (Method 4): [MH+] = 408 at 3.67 min. Chiral analysis (Method 13) at 3.68 min. |
| Example 280 | Single enantiomer 2 of 6-(4-fluorophenyl)-8-methoxy-N-[2-methyl-1-(3-methyl-1,2,4-oxadiazol-5-yl)propyl]quinazolin-4-amine 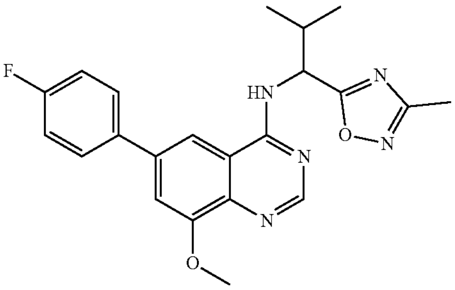 [SMILES: COc1cc(-c2ccc(F)cc2)cc2c(NC(c3nc(C)no3)C(C)C)ncnc12] | $^1H$ NMR (400 MHz, DMSO): δ 8.68 (d, J = 7.8 Hz, 1 H), 8.44 (s, 1 H), 8.31 (d, J = 1.6 Hz, 1 H), 7.99-7.94 (m, 2 H), 7.56 (d, J = 1.5 Hz, 1 H), 7.41 (dd, J = 8.8, 8.8 Hz, 2 H), 5.53 (dd, J = 8.4, 8.4 Hz, 1 H), 4.02 (s, 3 H), 2.34 (s, 3 H), 1.13 (d, J = 6.7 Hz, 3 H), 0.95 (d, J = 6.7 Hz, 3 H). LCMS (Method 4): [MH+] = 408 at 3.68 min. Chiral analysis (Method 13) at 1.62 min. |

-continued

| Example No. | Chemical Name<br>Structure | Analytical data<br>$^{1}$H NMR<br>LC-MS |
|---|---|---|
| Example 281 | Single enantiomer 1 of 6-(4-fluorophenyl)-8-methoxy-N-(1-(5-methyl-1,3,4-thiadiazol-2-yl)ethyl)quinazolin-4-amine<br>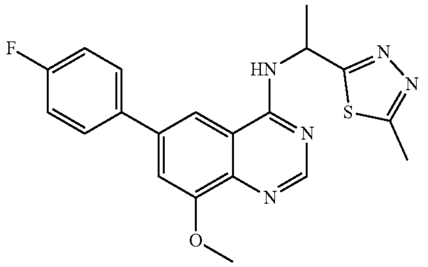 | $^{1}$H NMR (400 MHz, DMSO): δ 8.82 (d, J = 7.5 Hz, 1 H), 8.50 (s, 1 H), 8.20 (d, J = 1.6 Hz, 1 H), 7.96-7.92 (m, 2 H), 7.56 (d, J = 1.5 Hz, 1 H), 7.39 (dd, J = 8.8, 8.8 Hz, 2 H), 6.00-5.94 (m, 1 H), 4.03 (s, 3 H), 2.66 (s, 3 H), 1.81 (d, J = 7.0 Hz, 3 H). LCMS (Method 4): [MH+] = 396 at 3.12 min. Chiral analysis (Method 6) at 1.8 min. |
| Example 282 | Single enantiomer 2 of 6-(4-fluorophenyl)-8-methoxy-N-(1-(5-methyl-1,3,4-thiadiazol-2-yl)ethyl)quinazolin-4-amine<br>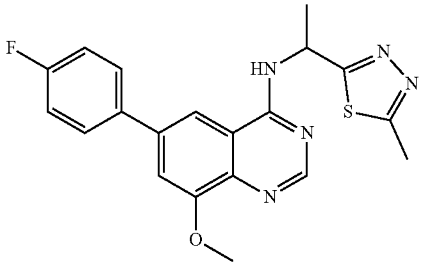 [SMILES: COc1cc(-c2ccc(F)cc2)cc2c(NC(C)c3nnc(C)s3)ncnc12] | $^{1}$H NMR (400 MHz, DMSO): δ 8.83 (d, J = 7.5 Hz, 1 H), 8.50 (s, 1 H), 8.20 (d, J = 1.8 Hz, 1 H), 7.96-7.92 (m, 2 H), 7.56 (d, J = 1.6 Hz, 1H) 7.39 (dd, J = 8.9, 8.9 Hz, 2 H), 5.99-5.94 (m, 1 H), 4.03 (s, 3 H), 2.66 (s, 3 H), 1.80 (d, J = 7.0 Hz, 3 H). LCMS (Method 4): [MH+] = 396 at 3.11 min. Chiral analysis (Method 6) at 3.03 min. |
| Example 283 | Single enantiomer 1 of 6-(4-fluorophenyl)-N-[1-(3-methyl-1,2,4-oxadiazol-5-yl)ethyl]quinazolin-4-amine<br>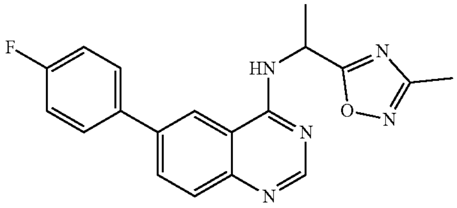 [SMILES: Cc1noc(C(C)Nc2ncnc3ccc(-c4ccc(F)cc4)cc23)n1] | $^{1}$H NMR (400 MHz, DMSO): δ 8.95 (d, J = 7.1 Hz, 1 H), 8.74 (d, J = 1.3 Hz, 1 H), 8.52 (s, 1 H), 8.21 (dd, J = 1.6, 8.7 Hz, 1 H), 7.96 (dd, J = 5.6, 8.6 Hz, 2 H), 7.87 (d, J = 8.6 Hz, 1 H), 7.45 (dd, J = 8.8, 8.8 Hz, 2 H), 5.89-5.83 (m, 1 H), 2.37 (s, 3 H), 1.79 (d, J = 7.3 Hz, 3 H). LCMS (Method 3): [MH+] = 350 at 4.31 min. Chiral analysis (Method 8) at 1.92 min. |
| Example 284 | Single enantiomer 2 of 6-(4-fluorophenyl)-N-[1-(3-methyl-1,2,4-oxadiazol-5-yl)ethyl]quinazolin-4-amine<br>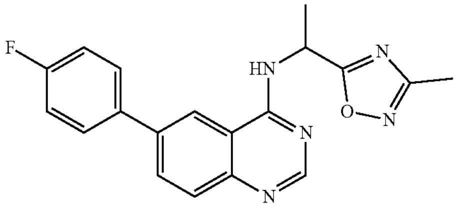 [SMILES: Cc1noc(C(C)Nc2ncnc3ccc(-c4ccc(F)cc4)cc23)n1] | $^{1}$H NMR (400 MHz, DMSO): δ 8.83 (d, J = 7.1 Hz, 1 H), 8.61 (s, 1 H), 8.40 (s, 1 H), 8.09 (dd, J = 1.5, 8.6 Hz, 1 H), 7.83 (dd, J = 5.6, 8.6 Hz, 2 H), 7.74 (d, J = 8.6 Hz, 1 H), 7.32 (dd, J = 8.8, 8.8 Hz, 2 H), 5.77-5.71 (m, 1 H), 2.25 (s, 3 H), 1.67 (d, J = 7.1 Hz, 3 H). LCMS (Method 8): [MH+] = 350 at 2.45 min. |
| Example 285 | Single enantiomer 1 of $N^2$-cyclopropyl-6-(4-fluorophenyl)-$N^4$-[1-(3-methyl-1,2,4-oxadiazol-5-yl)ethyl]quinazoline-2,4-diamine | $^{1}$H NMR (400 MHz, DMSO): δ 8.47-8.47 (m, 1 H), 8.36 (s, 1 H), 7.80 (dd, J = 1.5, 8.6 Hz, 1 H), 7.74 (dd, J = 5.6, 8.6 Hz, 2 H), 7.31-7.22 (m, 3 H), 6.76 (d, J = 1.3 Hz, 1 H), 5.63-5.62 (m, |

-continued

| Example No. | Chemical Name Structure | Analytical data $^1H$ NMR LC-MS |
|---|---|---|
| | 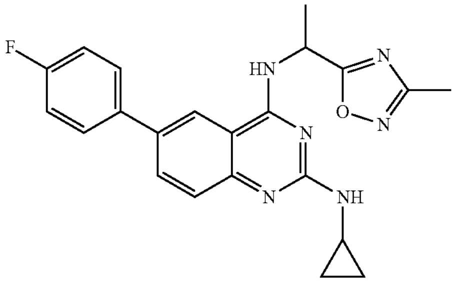 [SMILES: Cc1noc(C(C)Nc2nc(NC3CC3)nc3ccc(-c4ccc(F)cc4)cc23)n1] | 1 H), 2.69-2.54 (m, 1 H), 2.24 (s, 3 H), 1.65 (d, J = 7.1 Hz, 3 H), 0.55-0.52 (m, 2 H), 0.41-0.37 (m, 1 H), 0.26-0.26 (m, 1 H). LCMS (Method 4): [MH+] = 405 at 3.61 min. Chiral analysis (Method 16) at 1.86 min. |
| Example 286 | Single enantiomer 2 of $N^2$-cyclopropyl-6-(4-fluorophenyl)-$N^4$-[1-(3-methyl-1,2,4-oxadiazol-5-yl)ethyl]quinazoline-2,4-diamine 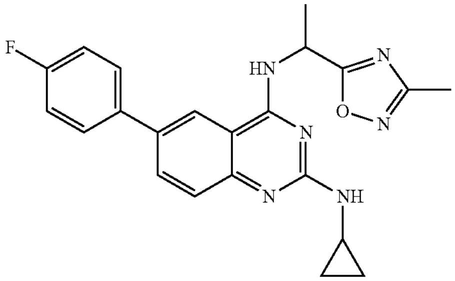 [SMILES: Cc1noc(C(C)Nc2nc(NC3CC3)nc3ccc(-c4ccc(F)cc4)cc23)n1] | $^1H$ NMR (400 MHz, DMSO): δ 8.41-8.38 (m, 1 H), 7.88 (dd, J = 1.8, 8.8 Hz, 1 H), 7.79 (dd, J = 5.5, 8.5 Hz, 2 H), 7.45-7.38 (m, 1 H), 7.30 (dd, J = 8.8, 8.8 Hz, 2 H), 5.71-5.60 (m, 1 H), 2.72-2.59 (m, 1 H), 2.29 (s, 3 H), 1.70 (d, J = 7.2 Hz, 3 H), 0.64-0.58 (m, 2 H), 0.45-0.42 (m, 1 H), 0.37-0.28 (m, 1 H). NH not observed. LCMS (Method 3): [MH+] = 405 at 4.77 min. Chiral analysis (Method 16) at 2.41 min. |
| Example 287 | Single enantiomer 1 of 6-(4-fluorophenyl)-N-[1-(3-methyl-1,2,4-oxadiazol-5-yl)ethyl]-2-morpholino-quinazolin-4-amine 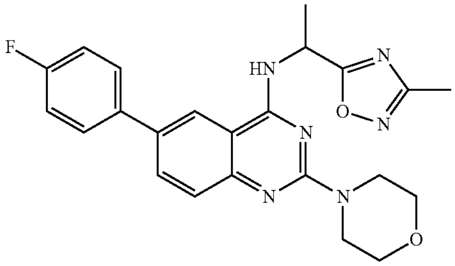 [SMILES: Cc1noc(C(C)Nc2nc(N3CCOCC3)nc3ccc(-c4ccc(F)cc4)cc23)n1] | $^1H$ NMR (400 MHz, DMSO): δ 8.76 (d, J = 5.8 Hz, 1 H), 8.53 (s, 1 H), 7.97 (d, J = 8.8 Hz, 1 H), 7.88 (dd, J = 5.4, 8.5 Hz, 2 H), 7.46-7.35 (m, 3 H), 5.59-5.51 (m, 1 H), 3.69-3.59 (m, 8 H), 2.36 (s, 3 H), 1.77 (d, J = 7.1 Hz, 3 H). LCMS (Method 3): [MH+] = 435 at 4.95 min. Chiral analysis (Method 17) at 1.17 min. |
| Example 288 | Single enantiomer 2 of 6-(4-fluorophenyl)-N-[1-(3-methyl-1,2,4-oxadiazol-5-yl)ethyl]-2-morpholino-quinazolin-4-amine 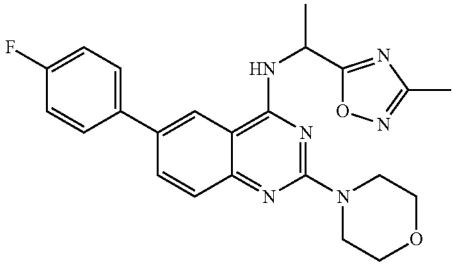 [SMILES: Cc1noc(C(C)Nc2nc(N3CCOCC3)nc3ccc(-c4ccc(F)cc4)cc23)n1] | $^1H$ NMR (400 MHz, DMSO): δ 7.22 (d, J = 1.5 Hz, 1 H), 6.69 (dd, J = 2.0, 8.8 Hz, 1 H), 6.59 (dd, J = 5.6, 8.6 Hz, 2 H), 6.20 (d, J = 8.6 Hz, 1 H), 6.10 (dd, J = 8.8, 8.8 Hz, 2 H), 4.22 (q, J = 7.1 Hz, 1 H), 2.44-2.30 (m, 8 H), 1.08 (s, 3 H), 0.50 (d, J = 7.1 Hz, 3 H). NH not observed. (Method 3): [MH+] = LCMS 435 at 4.94 min.Chiral analysis (Method 17) at 1.89 min. |

-continued

| Example No. | Chemical Name Structure | Analytical data $^1H$ NMR LC-MS |
|---|---|---|
| Example 289 | Single enantiomer 1 of 6-(4-fluorophenyl)-$N^2$,$N^2$-dimethyl-$N^4$-[1-(3-methyl-1,2,4-oxadiazol-5-yl)ethyl]quinazoline-2,4-diamine 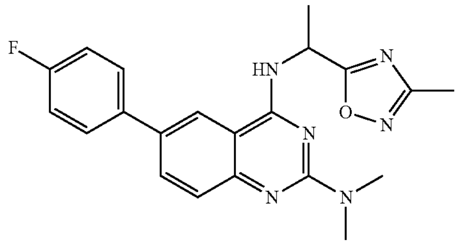 [SMILES: Cc1noc(C(C)Nc2nc(N(C)C)nc3ccc(-c4ccc(F)cc4)cc23)n1] | $^1H$ NMR (400 MHz, DMSO): δ 8.40-8.37 (m, 1 H), 7.85 (d, J = 8.8 Hz, 1 H), 7.77 (dd, J = 5.7, 8.2 Hz, 2 H), 7.38 (d, J = 8.8 Hz, 1 H), 7.28 (dd, J = 8.7, 8.7 Hz, 2 H), 5.44 (q, J = 7.0 Hz, 1 H), 2.97 (s, δ H), 2.27 (s, 3 H), 1.69 (d, J = 7.1 Hz, 3 H). NH not observed. LCMS (Method 3): [MH+] = 393 at 5.11 min. Chiral analysis (Method 18) at 3.65 min. |
| Example 290 | Single enantiomer 2 of 6-(4-fluorophenyl)-$N^2$,$N^2$-dimethyl-$N^4$-[1-(3-methyl-1,2,4-oxadiazol-5-yl)ethyl]quinazoline-2,4-diamine 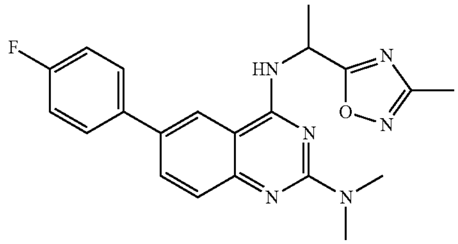 [SMILES: Cc1noc(C(C)Nc2nc(N(C)C)nc3ccc(-c4ccc(F)cc4)cc23)n1] | $^1H$ NMR (400 MHz, DMSO): δ 8.65 (d, J = 5.6 Hz, 1 H), 8.49 (d, J = 1.3 Hz, 1 H), 7.92 (dd, J = 1.6, 8.7 Hz, 1 H), 7.86 (dd, J = 5.6, 8.6 Hz, 2 H), 7.43-7.34 (m, 3 H), 5.60-5.51 (m, 1 H), 3.07 (s, δ H), 2.35 (s, 3 H), 1.77 d, J = 7.1 Hz, 3 H). LCMS (Method 3): [MH+] = 393 at 5.12 min. Chiral analysis (Method 18) at 5.26 min. |

Intermediate 15

6-bromo-8-methoxy-4-((2-(trimethylsilyl)ethoxy) methoxy)quinazoline

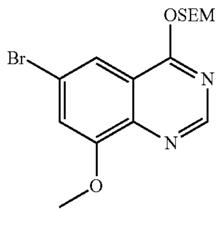

6-Bromo-8-methoxyquinazolin-4-ol (200 mg, 0.78 mmol) (intermediate 2) was dissolved in N,N-dimethylformamide (10 mL) and the reaction mixture cooled to 0° C. Sodium hydride (60% dispersion in mineral oil, 38 mg, 0.94 mmol) was added portion-wise and the reaction mixture stirred for 30 min. (2-Chloromethoxyethyl)trimethylsilane (0.21 ml, 1.18 mmol) was then added dropwise. The reaction was then stirred at 0° C. for 1 hour and then allowed to warm to room temperature. The reaction mixture was quenched with water (5 mL) and partitioned with ethyl acetate (15 mL). The phases were separated and the aqueous layer washed with ethyl acetate (2×10 mL). The combined organic phases were dried (MgSO4), filtered and concentrated in vacuo. The crude product was purified by column chromatography on silica gel, eluting with 0-40% ethyl acetate in cyclohexane to give the title compound (181 mg, 60%) as a colourless solid.

$^1H$ NMR (400 MHz, $CDCl_3$): δ 8.17 (s, 1H), 8.04 (d, J=2.0 Hz, 1H), 7.3 (d, J=2.0 Hz, 1H), 5.43 (s, 2H), 4.02 (s. 3H), 3.66 (m, J=4.1 Hz, 2H), 0.95 (m, J=4.1 Hz, 2H)), 0.02 (s, 9H). LCMS (Method 3): [MH+]=385 at 5.24 min.

Intermediate 16

8-methoxy-6-(4,4,5,5-tetramethyl-1,3,2-dioxaborolan-2-yl)-4-((2-(trimethylsilyl)ethoxy) methoxy) quinazoline

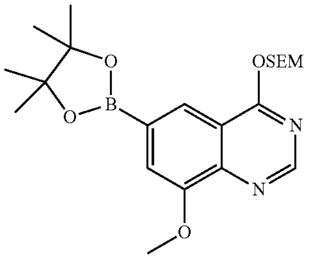

Nitrogen was bubbled for 10 minutes through a mixture of 6-bromo-8-methoxy-4-((2-(trimethylsilyl)ethoxy)methoxy)

quinazoline (190 mg, 0.49 mmol), bis(pinacolato)diboron (150 mg, 0.59 mmol) and potassium acetate (97 mg, 0.99 mmol) in 1,4-dioxane (5 mL), then [1,1'-bis(diphenylphosphino)ferrocene]dichloropalladium(II) (36 mg, 0.05 mmol) was added. The reaction mixture was then heated at 95° C. for 2 hours. After this time the reaction was cooled to room temperature and filtered through Celite®. The title compound was used directly as a solution in 1,4-dioxane, assuming a quantitative yield.

Intermediate 17

6-(5-Fluoropyridin-2-yl)-8-methoxy-4-((2-(trimethylsilyl)ethoxy)-methoxy)-quinazoline

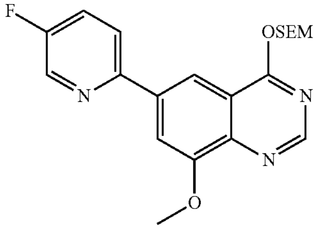

To 8-methoxy-6-(4,4,5,5-tetramethyl-1,3,2-dioxaborolan-2-yl)-4-((2-(trimethylsilyl) ethoxy)methoxy) quinazoline (330 mg, 0.78 mmol) was added 2-bromo-5-fluropyridine (137 mg, 0.78 mmol), cesium carbonate (508 mg, 1.56 mmol), 1,4-dioxane (8 mL) and water (1 mL). Nitrogen was bubbled through the reaction mixture for 10 minutes before tetrakis(triphenylphosphine)palladium(0) (90 mg, 0.078 mmol) was added. The reaction was then heated at 90° C. for 16 hours. After this time the reaction mixture was cooled to room temperature, filtered through Celite® and concentrated in vacuo. The residue was purified by column chromatography on silica gel eluting with 0-60% ethyl acetate in cyclohexane to give the title compound (226 mg, 72%) as a pale yellow solid.

$^1$H NMR (400 MHz, DMSO): δ 8.76 (d, J=2.4 Hz, 1H), 8.46 (s, 1H), 8.42 (d, J=1.7 Hz, 1H), 8.30 (dd, J=9.1 Hz, 4.4 Hz, 1H), 8.06 (d, J=1.7 Hz, 1H), 7.91 (dt, J=2.4, 9.1 Hz, 1H), 5.44 (s, 2H), 4.06 (s, 3H), 3.64 (t, J=8.1 Hz, 2H), 0.97 (t, J=8.1 Hz, 2H), 0.01 (s, 9H). LCMS (Method 3): [MH+]=402 at 5.43 min.

The following intermediates reported in the table below were synthesised following the same procedure described for the preparation of 6-(5-Fluoropyridin-2-yl)-8-methoxy-4-((2-(trimethyl silyl)ethoxy)-methoxy)-quinazoline (Intermediate 17):

| Intermediate No. | Chemical Name<br>Structure | Analytical data<br>$^1$H NMR<br>LC-MS |
|---|---|---|
| Intermediate 21 | 6-(5-methylpyridin-2-yl)-8-methoxy-4-((2-(trimethylsilyl)ethoxy) methoxy)quinazoline<br>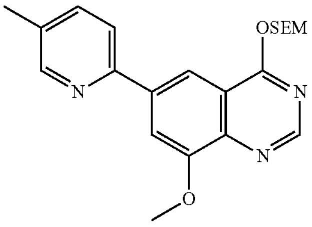 | $^1$H NMR (400 MHz, DMSO): δ 8.60-8.59 (m, 1 H), 8.43 (d, J = 2.0 Hz, 2 H), 8.10-8.08 (m, 2 H), 7.80-7.78 (m, 1 H), 5.44 (s, 2 H), 4.05 (s, 3 H), 3.70-3.64 (m, 2 H), 3.36 (s, 3 H), 0.94-0.90 (m, 2 H), 0.01 (s, 9 H). LCMS (Method 4): [MH+] = 398 at 5.12 min. |
| Intermediate 22 | 6-(5-Methylpyrimidin-2-yl)-8-methoxy-4-((2-(trimethylsilyl)ethoxy)methoxy) quinazoline<br>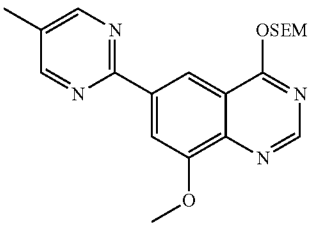 | $^1$H NMR (400 MHz, $CDCl_3$): δ 9.00 (d, J = 2.0 Hz, 1 H), 8.68 (s, 2 H), 8.33 (d, J = 1.6 Hz, 1 H), 8.22 (s, 1 H), 5.48 (s, 2 H), 4.17 (s, 3 H), 3.71-3.67 (m, 2 H), 2.38 (s, 3 H), 0.99-0.97 (m, 2 H), 0.01 (s, 9 H). LCMS (Method 4): [MH+] = 399 at 5.18 min. |

Intermediate 23

6-(5-fluoropyridin-2-yl)-8-methoxyquinazolin-4-ol

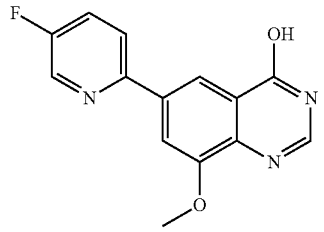 [SMILES: COc1cc(-c2ccc(F)cn2)cc2c(O)ncnc12]

6-(5-Fluoropyridin-2-yl)-8-methoxy-4-((2-(trimethylsilyl)ethoxy)methoxy)quinazoline (225 mg, 0.56 mmol) was dissolved in dichloromethane (5 mL) and trifluoroacetic acid (0.21 mL, 2.81 mmol). The reaction mixture was stirred for 16 hours. The reaction mixture was concentrated in vacuo to yield the title compound (142 mg, 93%) as a pale orange solid.

$^1$H NMR (400 MHz, DMSO): δ 8.76 (d, J=2.4 Hz, 1H), 8.39 (d, J=1.7 Hz, 1H), 8.29 (dd, J=9.0 Hz, 4.6 Hz, 1H), 8.13 (s, 1H) 8.05 (d, J=1.7 Hz, 1H), 7.92 (dt, J=2.4, 9.1 Hz, 1H), 5.69 (br s, 1H), 4.06 (s, 3H). LCMS (Method 3): [MH+] =272 at 3.08 min.

The following intermediates reported in the table below were synthesised following the same procedure described for the preparation of 6-(5-fluoropyridin-2-yl)-8-methoxyquinazolin-4-ol (Intermediate 23):

| Intermediate No. | Chemical Name<br>Structure | Analytical data<br>$^1$H NMR<br>LC-MS |
|---|---|---|
| Intermediate 26 | 8-Methoxy-6-(5-methylpyridin-2-yl)quinazolin-4-ol<br>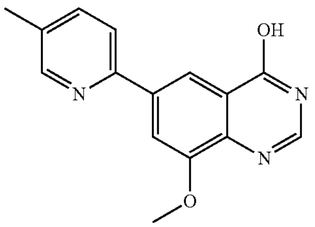 [SMILES: COc1cc(-c2ccc(C)cn2)cc2c(O)ncnc12] | $^1$H NMR (400 MHz, DMSO): δ 8.56 (s, 1 H), 8.33 (s, 1 H), 8.12 (s, 1 H), 7.99-7.93 (m, 1 H), 7.92 (s, 1 H), 7.76-7.73 (m, 1 H), 4.02 (s, 3 H), 2.38 (s, 3 H). LCMS (Method 4): [MH+] = 268 at 2.39 min. |
| Intermediate 27 | 6-(5-methylpyrimidin-2-yl)-8-methoxyquinazolin-4-ol<br>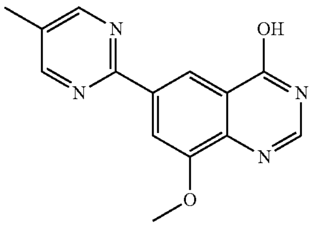 [SMILES: COc1cc(-c2ncc(C)cn2)cc2c(O)ncnc12] | LCMS (Method 4): [MH+] = 269 at 2.89 min. |

Example 315

(R)-6-(5-fluoropyridin-2-yl)-8-methoxy-N-(1-(5-methyl-1,2,4-oxadiazol-3-yl)ethyl)quinazolin-4-amine

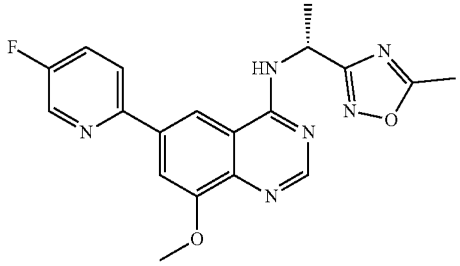 [SMILES: COc1cc(-c2ccc(F)cn2)cc2c(N[C@H](C)c3noc(C)n3)ncnc12]

Example 325

(S)-6-(5-fluoropyridin-2-yl)-8-methoxy-N-(1-(5-methyl-1,2,4-oxadiazol-3-yl)ethyl)quinazolin-4-amine

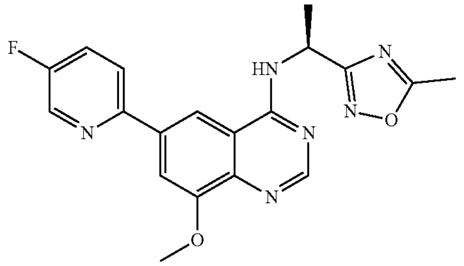 [SMILES: COc1cc(-c2ccc(F)cn2)cc2c(N[C@@H](C)c3noc(C)n3)ncnc12]

Step 1: Preparation of 4-Chloro-6-(5-fluoropyridin-2-yl)-8-methoxyquinazoline

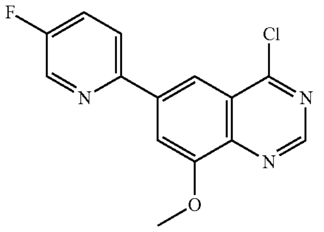 [SMILES: COc1cc(-c2ccc(F)cn2)cc2c(Cl)ncnc12]

8-Methoxy-6-(5-fluoropyridin-2-yl)quinazolin-4-ol (750 mg, 2.81 mmol) was suspended in thionyl chloride (4.1 mL, 56.12 mmol) and DMF (0.0005 mL, 0.006 mmol) was added. The reaction mixture was heated at 95° C. for 4 hours. The reaction was cooled to room temperature and the solvent was removed in vacuo to give 4-chloro-6-(5-fluoropyridin-2-yl)-8-methoxyquinazoline (800 mg, 98%). The crude residue was taken on directly to the next step without further purification.

Step 2: Preparation of (R)-6-(5-fluoropyridin-2-yl)-8-methoxy-N-(1-(5-methyl-1,2,4-oxadiazol-3-yl)ethyl)quinazolin-4-amine and

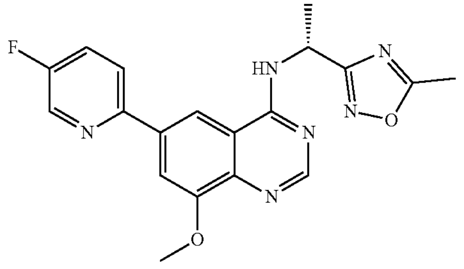 [SMILES: COc1cc(-c2ccc(F)cn2)cc2c(N[C@H](C)c3noc(C)n3)ncnc12]

and (S)-6-(5-fluoropyridin-2-yl)-8-methoxy-N-(1-(5-methyl-1,2,4-oxadiazol-3-yl)ethyl)quinazolin-4-amine

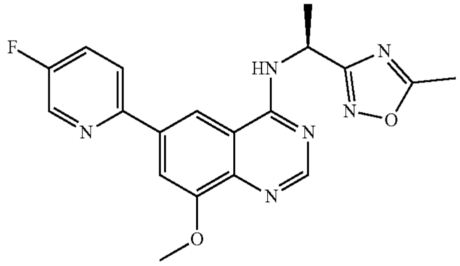 [SMILES: COc1cc(-c2ccc(F)cn2)cc2c(N[C@@H](C)c3noc(C)n3)ncnc12]

To a mixture of 4-chloro-6-(5-fluoropyridin-2-yl)-8-methoxyquinazoline (100 mg, 0.367 mmol) and N,N-diisopropylethylamine (0.32 mL, 1.84 mmol) in 1,4-dioxane (5 mL) was added (R)-1-(5-methyl-1,2,4-oxadiazol-3-yl)ethan-1-amine (93 mg, 0.735 mmol). The resulting mixture was stirred at 50° C. for 5 days. The reaction mixture was cooled to room temperature and concentrated in vacuo. The residue was purified by preparative HPLC to give the title compound (25 mg, 19%) as an off white solid.

Example 315

(R)-6-(5-fluoropyridin-2-yl)-8-methoxy-N-(1-(5-methyl-1,2,4-oxadiazol-3-yl)ethyl)quinazolin-4-amine: $^{1}H$ NMR (400 MHz, $CDCl_3$) δ 8.57 (s, 1H), 8.54 (d, J=3.8 Hz, 1H), 7.88 (s, 2H), 7.69 (s, 1H), 7.54 (ddd, J=8.6, 8.6, 2.9 Hz, 1H), 6.82 (s, 1H), 5.92-5.84 (m, 1H), 4.13 (s, 3H), 2.65 (s, 3H), 1.77 (d, J=6.1 Hz, 3H). LCMS (Method 3): [MH+]=381 at 2.90 min. Chiral analysis (Method 31) at 2.24 min.

Example 325

(S)-6-(5-fluoropyridin-2-yl)-8-methoxy-N-(1-(5-methyl-1,2,4-oxadiazol-3-yl)ethyl)quinazolin-4-amine Chiral analysis (Method 31) at 0.58 min.

The following compounds reported in the table below were prepared according to the same procedure described for the preparation of (R)-6-(5-fluoropyridin-2-yl)-8-methoxy-N-(1-(5-methyl-1,2,4-oxadiazol-3-yl)ethyl)quinazolin-4-amine.

Some compounds were further purified by preparative chiral SFC to obtain the pure enantiomers.

| Example No. | Chemical Name<br>Structure | Analytical data<br>$^1$H NMR<br>LC-MS |
|---|---|---|
| Example 316 (From Intermediate 26) | (R)-8-methoxy-N-(1-(5-methyl-1,2,4-oxadiazol-3-yl)ethyl)-6-(5-methylpyridin-2-yl)quinazolin-4-amine<br>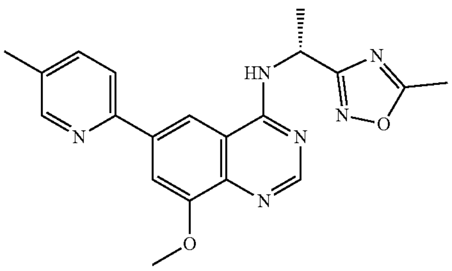 | $^1$H NMR (400 MHz, DMSO): δ 8.75-8.71 (m, 1 H), 8.59 (s, 2 H), 8.46-8.45 (m, 1 H), 8.21-8.14 (m, 1 H), 8.05 (d, J = 1.4 Hz, 1 H), 7.82 (dd, J = 1.6, 8.2 Hz, 1 H), 5.82-5.74 (m, 1 H), 4.02 (s, 3 H), 2.58 (s, 3 H), 2.39 (s, 3 H), 1.71-1.68 (m, 3 H). LCMS (Method 3): [MH+] = 377 at 3.64 min. Chiral analysis (Method 38) at 3.10 min. |
| Example 317 (From Intermediate 26) | 8-Methoxy-N-[1-(3-methyl-1,2,4-oxadiazol-5-yl)ethyl]-6-(5-methyl-2-pyridyl)quinazolin-4-amine<br>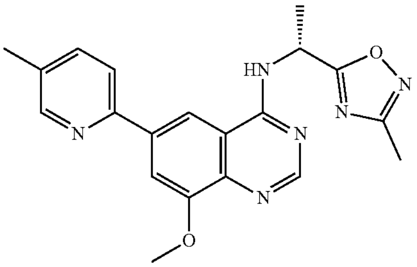 [SMILES: COc1cc(-c2ccc(C)cn2)cc2c(N[C@H](C)c3nc(C)no3)ncnc12] | $^1$H NMR (400 MHz, DMSO): δ 8.89 (d, J = 7.2 Hz, 1 H), 8.59 (s, 2 H), 8.46 (s, 1 H), 8.15-8.12 (m, 1 H), 8.05 (d, J = 1.5 Hz, 1 H), 7.82 (dd, J = 1.6, 8.2 Hz, 1 H), 5.87-5.78 (m, 1 H), 4.03 (s, 3 H), 2.40 (s, 3 H), 2.33 (s, 3 H), 1.76 (d, J = 7.2 Hz, 3 H). LCMS (Method 4): [MH+] = 377 at 2.91 min. |
| Example 318 (From Intermediate 23) | 6-(5-fluoro-2-pyridyl)-8-methoxy-N-[(1R)-1-(5-methyl-1,3,4-oxadiazol-2-yl)ethyl]quinazolin-4-amine<br>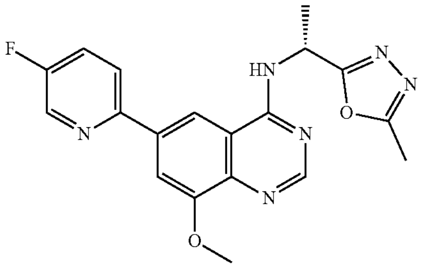 [SMILES: COc1cc(-c2ccc(F)cn2)cc2c(N[C@H](C)c3nnc(C)o3)ncnc12] | $^1$H NMR (400 MHz, DMSO): δ 8.84 (d, J = 7.7 Hz, 1 H), 8.75-8.73 (m, 1 H), 8.55 (d, J = 1.5 Hz, 1 H), 8.51 (s, 1 H), 8.28 (dd, J = 4.4, 8.9 Hz, 1 H), 8.01-7.94 (m, 2 H), 5.94-5.85 (m, 1 H), 4.03 (s, 3 H), 2.48 (s, 3 H), 1.74 (d, J = 7.0 Hz, 3H). LCMS (Method 3): [$MH^+$] = 381 at 3.8 min. Chiral analysis (Method 28) at 3.17 min. |
| Example 319 (From Intermediate 26) | 8-methoxy-N-[(1R)-1-(5-methyl-1,3,4-oxadiazol-2-yl)ethyl]-6-(5-methyl-2-pyridyl)quinazolin-4-amine<br>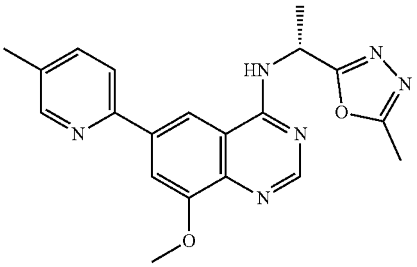 [SMILES: COc1cc(-c2ccc(C)cn2)cc2c(N[C@H](C)c3nnc(C)o3)ncnc12] | $^1$H NMR (400 MHz, DMSO): δ 8.85-8.81 (m, 1 H), 8.58 (d, J = 2.2 Hz, 1 H), 8.55 (d, J = 1.5 Hz, 1 H), 8.49-8.49 (m, 1 H), 8.14-8.10 (m, 1 H), 8.05-8.04 (m, 1 H), 7.81 (dd, J = 1.5, 8.2 Hz, 1 H), 5.94-5.85 (m, 1 H), 4.03-4.02 (m, 3 H), 2.40-2.38 (m, 3 H), 1.74 (d, J = 7.0 Hz, 3 H). LCMS (Method 4): [$MH^+$] = 377 at 2.55 min. Chiral analysis (Method 38) at 1.98 min. |

-continued

| Example No. | Chemical Name Structure | Analytical data $^1$H NMR LC-MS |
|---|---|---|
| Example 320 (From Intermediate 27) | 2-((8-methoxy-6-(5-methylpyrimidin-2-yl)quinazolin-4-yl)amino)-2-(3-methyl-1,2,4-oxadiazol-5-yl)ethan-1-ol 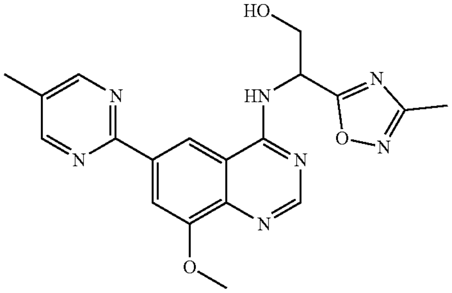 | $^1$H NMR (400 MHz, DMSO): δ 9.01-8.96 (m, 2 H), 8.86 (s, 2 H), 8.48 (s, 1 H), 8.24 (d, J = 1.2 Hz, 1 H), 5.75 (q, J = 6.5 Hz, 1 H), 5.38 (dd, J = 5.9, 5.9 Hz, 1 H), 4.15-4.06 (m, 2 H), 4.03 (s, 3 H), 2.38 (s, 3 H), 2.33 (s, 3 H). LCMS (Method 3): [MH+] = 394 at 3.38 min. |
| Example 321 (From Intermediate 23) | 6-(5-fluoro-2-pyridyl)-8-methoxy-N-[1-[6-(trifluoromethyl)pyridazin-3-yl]ethyl]quinazolin-4-amine 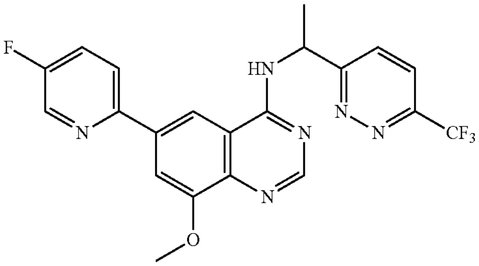 [SMILES: COc1cc(-c2ccc(F)cn2)cc2c(NC(C)c3ccc(C(F)(F)F)nn3)ncnc12] | $^1$H NMR (400 MHz, DMSO): δ 8.87 (d, J = 7.0 Hz, 1 H), 8.76 (d, J = 3.0 Hz, 1 H), 8.68 (d, J = 1.5 Hz, 1 H), 8.38 (s, 1 H), 8.34 (dd, J = 4.3, 8.9 Hz, 1 H), 8.21 (d, J = 8.8 Hz, 1 H), 8.07 (d, J = 8.8 Hz, 1 H), 8.02-7.96 (m, 2 H), 5.91-5.86 (m, 1 H), 4.01 (s, 3H), 1.80 (d, J = 7.2 Hz, 3 H). LCMS (Method 4): [$MH^+$] = 445 at 3.35 min. |
| Example 322 (From Intermediate 23) | 6-(5-fluoropyridin-2-yl)-8-methoxy-N-(1-(5-methyl-1,3,4-oxadiazol-2-yl)ethyl)quinazolin-4-amine 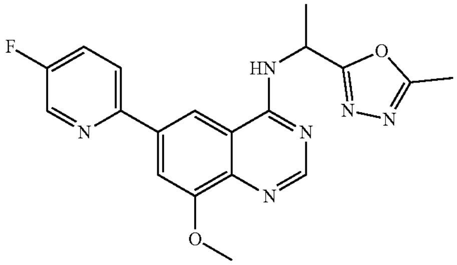 | $^1$H NMR (400 MHz, $CDCl_3$) δ 8.55 (d, J = 2.8 Hz, 1 H), 8.49 (s, 1 H), 7.86 (d, J = 1.9 Hz, 1 H), 7.74 (s, 2 H), 7.48 (ddd, J = 8.4, 8.4, 3.1 Hz, 1 H), 7.05 (s, 1 H), 5.85-5.90 (m, 1 H), 4.13 (s, 3 H), 2.60 (s, 3 H), 1.79 (d, J = 7.9 Hz, 3 H); LCMS (Method 4): [$MH^+$] = 381 at 3.37 min. |
| Example 323 (From Intermediate 23) | 6-(5-fluoropyridin-2-yl)-8-methoxy-N-(1-(5-methyl-1,3,4-thiadiazol-2-yl)ethyl)quinazolin-4-amine 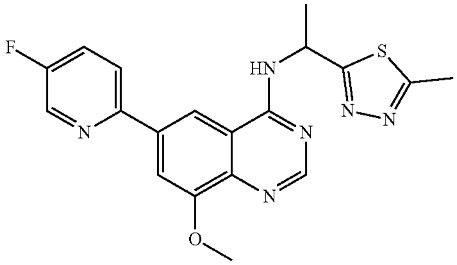 [SMILES: COc1cc(-c2ccc(F)cn2)cc2c(NC(C)c3nnc(C)s3)ncnc12] | $^1$H NMR (400 MHz, $CDCl_3$) δ 8.67 (s, 1 H), 8.56 (d, J = 3.3 Hz, 1 H), 7.93 (s, 1 H), 7.86 (dd, J = 4.1, 8.7 Hz, 1 H), 7.78 (d, J = 2.5 Hz, 1 H), 7.52 (ddd, J = 8.6, 8.6, 2.8 Hz, 1 H), 7.05 (s, 1 H), 6.09-6.00 (m, 1 H), 4.14 (s, 3 H), 2.78 (s, 3 H), 1.89 (d, J = 7.5 Hz, 3 H). LCMS (Method 4): [$MH^+$] = 397 at 3.83 min. |

-continued

| Example No. | Chemical Name<br>Structure | Analytical data<br>$^1$H NMR<br>LC-MS |
|---|---|---|
| Example 324 (From Intermediate 27) | 8-methoxy-N-[(1R)-1-(5-methyl-1,3,4-oxadiazol-2-yl)ethyl]-6-(5-methylpyrimidin-2-yl)quinazolin-4-amine<br>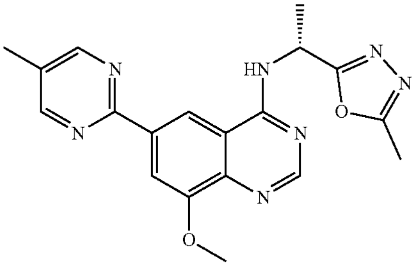 [SMILES: COc1cc(-c2ncc(C)cn2)cc2c(N[C@H](C)c3nnc(C)o3)ncnc12] | $^1$H NMR (400 MHz, DMSO): δ 9.11 (d, J = 7.7 Hz, 1 H), 8.95 (d, J = 1.4 Hz, 1 H), 8.85 (s, 2 H), 8.51 (s, 1 H), 8.23 (d, J = 1.5 Hz, 1H) 5.91-5.86 (m, 1 H), 4.03 (s, 3 H), 2.38 (s, 3 H), 1.73 (d, J = 7.0 Hz, 3 H). LCMS (Method 4): [MH$^+$] = 378 at 2.53 min. Chiral analysis (Method 13) at 1.83 min. |

Pharmacological Activity of the Compounds of the Invention.

In Vitro Electrophysiology Assay for $P2X_3$

Cells expressing $P2X_3$ receptors were grown according to standard practice and maintained at 37° C. in a 5% humidified $CO_2$ atmosphere. The cells were seeded into T175 flask 2 days prior to the day of the assay and dissociated from the flasks using TrypLE when grown to confluence of 80-90%. The dissociated cells were resuspended in serum free media at a cell density of $3\times10^6$ cells/ml and loaded onto the Sophion Qube automated patch-clamp system. The extracellular assay buffer contained 145 mM NaCl, 4 mM KCl, 2 mM $CaCl_2$), 1 mM $MgCl_2$, 10 mM HEPES, and 10 mM glucose at pH 7.4. The intracellular assay solution contained 140 mM CsF, 10 mM NaCl, 10 mM EGTA, 10 mM HEPES at pH 7.2. Agonist stock solutions were prepared in $H_2O$ and diluted in bath solution prior to use. All antagonists were prepared as 10 mM stock solutions in DMSO and diluted in bath solution prior to use. All experiments were performed under the whole-cell patch clamp configuration at room temperature with 384 individual cells being voltage clamped at −60 mV simultaneously on the Sophion Qube instrument. Two baseline responses were established with the application of α,β-MeATP (800 nM), with the subsequent agonist applications being washed out using extracellular assay buffer containing 0.5 U/ml apyrase. Following the second agonist application, antagonist was incubated in the absence of α,β-MeATP for 10 minutes. After antagonist preincubation, 800 nM α,β-MeATP and antagonist were co-administered to determine the inhibitory effect of the antagonist. One concentration of an antagonist was assessed against a single cell, with different concentrations of the antagonist applied to other cells on the 384 recording substrate. The control $P2X_3$ current amplitude was taken from the peak current amplitude from the second agonist response prior to preincubation with antagonist. The peak $P2X_3$ current amplitude in the presence of antagonist was used to calculate the inhibitory effect at each concentration of the antagonist according to the following equation:

$$\text{Percentage inhibition of } P2X_3 = (P2X_3 \text{ control peak amplitude} - P2X_3 \text{ antagonist peak amplitude}) / P2X_3 \text{ control peak amplitude}) * 100$$

Concentration-response curves were constructed from ten different concentrations with each concentration of antagonist tested on at least two individual cells. The concentration of the antagonist to inhibit $P2X_3$ current by 50% ($IC_{50}$) was determined by fitting the data with the following equation:

$$Y = a + [(b - a)/(1 + 10\,\hat{}\,((\log c - x)d)]$$

Where 'a' is minimum response, 'b' is maximum response, 'c' is $IC_{50}$ and 'd' is Hill slope.

The results for individual compounds are provided below in Table 8 and are expressed as range of activity.

TABLE 8

| Example No. | h $P2X_3$ |
|---|---|
| 1 | +++ |
| 2 | +++ |
| 3 | +++ |
| 5 | +++ |
| 6 | +++ |
| 7 | +++ |
| 8 | +++ |
| 9 | ++ |
| 10 | +++ |
| 11 | +++ |
| 12 | +++ |
| 13 | ++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | ++ |
| 24 | ++ |
| 25 | +++ |
| 26 | ++ |
| 27 | ++ |
| 28 | ++ |
| 29 | + |
| 30 | + |
| 31 | +++ |
| 32 | ++ |
| 33 | +++ |

TABLE 8-continued

| Example No. | h $P2X_3$ |
|---|---|
| 34 | ++ |
| 35 | ++ |
| 36 | ++ |
| 37 | ++ |
| 38 | ++ |
| 39 | +++ |
| 40 | ++ |
| 41 | ++ |
| 42 | ++ |
| 43 | ++ |
| 44 | ++ |
| 45 | +++ |
| 46 | ++ |
| 47 | ++ |
| 48 | +++ |
| 49 | +++ |
| 50 | +++ |
| 51 | ++ |
| 52 | ++ |
| 53 | + |
| 54 | ++ |
| 55 | ++ |
| 56 | ++ |
| 57 | ++ |
| 58 | ++ |
| 59 | ++ |
| 60 | ++ |
| 61 | ++ |
| 62 | ++ |
| 63 | ++ |
| 64 | +++ |
| 65 | ++ |
| 66 | ++ |
| 67 | ++ |
| 68 | ++ |
| 69 | ++ |
| 70 | ++ |
| 71 | + |
| 72 | + |
| 73 | + |
| 74 | + |
| 75 | ++ |
| 76 | ++ |
| 77 | + |
| 78 | + |
| 79 | ++ |
| 80 | + |
| 81 | + |
| 82 | + |
| 83 | + |
| 84 | + |
| 85 | + |
| 86 | + |
| 87 | + |
| 88 | ++ |
| 89 | + |
| 90 | + |
| 91 | + |
| 92 | + |
| 93 | + |
| 94 | + |
| 95 | ++ |
| 96 | ++ |
| 97 | ++ |
| 98 | ++ |
| 99 | ++ |
| 100 | + |
| 101 | + |
| 102 | ++ |
| 103 | + |
| 104 | ++ |
| 105 | ++ |
| 106 | + |
| 107 | + |
| 108 | + |
| 109 | + |
| 110 | ++ |
| 111 | + |

TABLE 8-continued

| Example No. | h $P2X_3$ |
|---|---|
| 113 | +++ |
| 114 | ++ |
| 115 | ++ |
| 116 | +++ |
| 117 | ++ |
| 118 | +++ |
| 119 | ++ |
| 120 | ++ |
| 121 | + |
| 122 | + |
| 123 | + |
| 124 | + |
| 125 | ++ |
| 126 | ++ |
| 127 | +++ |
| 128 | ++ |
| 129 | + |
| 130 | ++ |
| 131 | ++ |
| 132 | + |
| 133 | ++ |
| 134 | +++ |
| 135 | +++ |
| 136 | +++ |
| 137 | + |
| 138 | ++ |
| 139 | ++ |
| 140 | +++ |
| 141 | ++ |
| 142 | + |
| 143 | +++ |
| 144 | ++ |
| 145 | +++ |
| 146 | ++ |
| 147 | +++ |
| 149 | +++ |
| 153 | +++ |
| 154 | +++ |
| 156 | ++ |
| 157 | +++ |
| 158 | +++ |
| 159 | + |
| 160 | + |
| 161 | +++ |
| 163 | ++ |
| 163a | ++ |
| 164 | ++ |
| 165 | +++ |
| 166 | ++ |
| 167 | ++ |
| 168 | + |
| 169 | ++ |
| 170 | +++ |
| 171 | + |
| 172 | + |
| 173 | ++ |
| 174 | ++ |
| 175 | +++ |
| 176 | ++ |
| 176a | ++ |
| 177 | ++ |
| 178 | +++ |
| 179 | ++ |
| 180 | + |
| 183 | ++ |
| 185 | +++ |
| 186 | ++ |
| 187 | +++ |
| 188 | +++ |
| 189 | +++ |
| 190 | +++ |
| 191 | +++ |
| 192 | +++ |
| 193 | ++ |
| 194 | ++ |
| 195 | +++ |
| 196 | +++ |
| 197 | ++ |

TABLE 8-continued

| Example No. | h $P2X_3$ |
|---|---|
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 209 | +++ |
| 210 | +++ |
| 211 | +++ |
| 212 | +++ |
| 213 | +++ |
| 214 | +++ |
| 215 | +++ |
| 216 | +++ |
| 217 | +++ |
| 218 | ++ |
| 219 | ++ |
| 220 | ++ |
| 221 | +++ |
| 222 | +++ |
| 223 | +++ |
| 224 | ++ |
| 225 | + |
| 226 | + |
| 227 | +++ |
| 229 | +++ |
| 230 | ++ |
| 232 | +++ |
| 233 | +++ |
| 234 | ++ |
| 235 | ++ |
| 236 | ++ |
| 237 | + |
| 238 | + |
| 239 | ++ |
| 242 | + |
| 245 | ++ |
| 246 | ++ |
| 248 | +++ |
| 249 | ++ |
| 250 | + |
| 251 | ++ |
| 252 | + |
| 253 | + |
| 254 | + |
| 255 | ++ |
| 256 | ++ |
| 257 | +++ |
| 258 | ++ |
| 259 | + |
| 260 | ++ |
| 261 | + |
| 262 | + |
| 263 | ++ |
| 264 | + |
| 265 | +++ |
| 266 | + |
| 267 | ++ |
| 269 | +++ |
| 270 | +++ |
| 271 | + |
| 272 | + |
| 273 | + |
| 274 | + |
| 275 | ++ |
| 276 | ++ |
| 277 | +++ |
| 278 | ++ |
| 279 | ++ |
| 280 | + |
| 281 | ++ |
| 282 | +++ |
| 283 | + |
| 284 | +++ |

TABLE 8-continued

| Example No. | h $P2X_3$ |
|---|---|
| 285 | ++ |
| 286 | ++ |
| 287 | ++ |
| 288 | + |
| 289 | + |
| 290 | ++ |
| 291 | ++ |
| 293 | ++ |
| 294 | ++ |
| 295 | + |
| 296 | +++ |
| 297 | +++ |
| 298 | +++ |
| 299 | ++ |
| 300 | +++ |
| 301 | ++ |
| 310 | +++ |
| 311 | ++ |
| 312 | ++ |
| 313 | +++ |
| 314 | +++ |
| 315 | +++ |
| 316 | +++ |
| 317 | +++ |
| 318 | ++ |
| 319 | +++ |
| 320 | ++ |
| 321 | ++ |
| 322 | ++ |
| 323 | +++ |
| 324 | +++ |
| 325 | + |
| 326 | ++ |

wherein the compounds are classified in term of potency with respect to their inhibitory activity on $P2X_3$ according to the following classification criterion:

$$+++: pIC_{50}\ h\ P2X_3 > 6.5$$

$$++: 6.5 < pIC_{50}\ h\ P2X_3 > 55$$

$$+: 5.5 < pIC_{50}\ h\ P2X_3 > 4.5$$

In Vitro Electrophysiology Assay for $P2X_{2/3}$

Representative compound of the present invention have been also tested for $P2X_{2/3}$ receptor.

The same assay protocol was used for the $P2X_{2/3}$ assay as the $P2X_3$ assay with two modifications: 1) 10 μM ATP was used as the agonist; and 2) the mean current amplitude was measured seven seconds after the application of agonist.

The results of Table 9 indicate that representative compounds of the present invention are selective $P2X_3$ antagonist.

TABLE 9

| Example No. | h $P2X_3$ | h $P2X_{2/3}$ |
|---|---|---|
| 4 | +++ | + |
| 19 | +++ | + |
| 28 | ++ | + |
| 48 | +++ | + |
| 65 | ++ | + |
| 110 | ++ | + |
| 112 | +++ | + |
| 116 | +++ | + |
| 134 | +++ | + |
| 140 | +++ | + |
| 145 | +++ | + |

TABLE 9-continued

| Example No. | h $P2X_3$ | h $P2X_{2/3}$ |
|---|---|---|
| 148 | +++ | ++ |
| 149 | +++ | + |
| 150 | +++ | + |
| 151 | +++ | + |
| 152 | ++ | + |
| 155 | +++ | + |
| 175 | +++ | ++ |
| 181 | +++ | ++ |
| 182 | +++ | + |
| 184 | +++ | + |
| 206 | +++ | + |
| 207 | +++ | + |
| 208 | +++ | + |
| 214 | +++ | + |
| 216 | +++ | + |
| 217 | +++ | + |
| 228 | +++ | + |
| 231 | +++ | + |
| 240 | +++ | + |
| 241 | +++ | ++ |
| 243 | +++ | + |
| 244 | +++ | ++ |
| 247 | +++ | + |
| 256 | ++ | + |
| 258 | ++ | + |
| 268 | +++ | + |
| 282 | +++ | + |
| 293 | ++ | + |
| 298 | +++ | + |
| 300 | +++ | + |
| 314 | +++ | + |
| 315 | +++ | + |
| 317 | +++ | + |
| 319 | +++ | + |
| 322 | ++ | ++ |
| 323 | +++ | + |
| 324 | +++ | + |

wherein the compounds are classified in term of potency with respect to their inhibitory activity on $P2X_3$ or $P2X_{2/3}$ isoforms according to the following classification criterion:

+++: $pIC_{50}$ $h\ P2X_3$ or $h\ P2X_{2/3} > 6.5$

++: $6.5 < pIC_{50}$ $h\ P2X_3$ or $h\ P2X_{2/3} > 5.5$

+: $5.5 < pIC_{50}$ $h\ P2X_3$ or $h\ P2X_{2/3} > 4.5$

Comparative Example A 6-(4-fluorophenyl)-4-[(6-methyl-3-pyridyl)methoxy]pyrido[2,3-d]pyrimidine

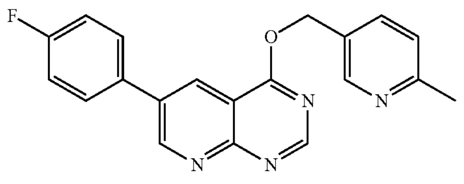 [SMILES: Cc1ccc(COc2ncnc3ncc(-c4ccc(F)cc4)cc23)cn1]

Step 1: Synthesis of 6-bromo-4-((6-methylpyridin-3-yl)methoxy)pyrido[2,3-d]pyrimidine

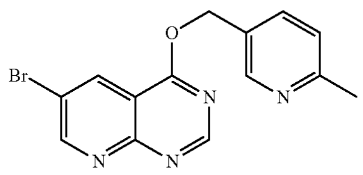 [SMILES: Cc1ccc(COc2ncnc3ncc(Br)cc23)cn1]

6-Bromopyrido[2,3-d]pyrimidin-4(3H)-one (202 mg, 0.89 mmol) (Intermediate 1), 5-hydroxymethyl-2-methylpyridine (110 mg, 0.89 mmol) and triphenylphosphine (328 mg, 1.25 mmol) were stirred in dry THF (7 mL) and a solution of diisopropyl azodicarboxylate (229 μL, 1.16 mmol) in dry THF (3 mL) was added dropwise and stirred at room temperature for 6 hours. The reaction was filtered and the precipitate was washed with (2:1) DCM/MeOH (20 mL). The filtrates were combined and the solvent was removed in vacuo. The residue was purified by chromatography on silica gel eluting with 0-100% EtOAc in DCM to give 6-bromo-4-((6-methylpyridin-3-yl)methoxy)pyrido[2,3-d]pyrimidine (164 mg, 55%).

$^1$H NMR (400 MHz, DMSO): δ 9.08 (d, J=2.6 Hz, 1H), 8.89 (s, 1H), 8.67 (d, J=2.6 Hz, 1H), 8.55 (d, J=2.1 Hz, 1H), 7.72 (dd, J=2.4, 8.0 Hz, 1H), 7.24 (d, J=8.0 Hz, 1H), 5.20 (s, 2H), 2.44 (s, 3H).

Step 2: Synthesis of 6-(4-fluorophenyl)-4-[(6-methyl-3-pyridyl)methoxy]pyrido[2,3-d]pyrimidine

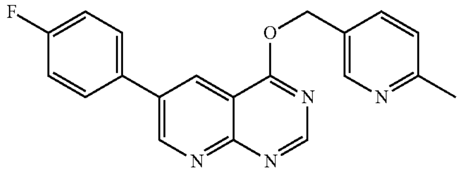 [SMILES: Cc1ccc(COc2ncnc3ncc(-c4ccc(F)cc4)cc23)cn1]

Nitrogen gas was bubbled through a mixture of 6-bromo-4-((6-methylpyridin-3-yl)methoxy)pyrido[2,3-d]pyrimidine (84 mg, 0.254 mmol), 4-fluorophenylboronic acid, pinacol ester (76 mg, 0.342 mmol) and cesium fluoride (116 mg, 0.761 mmol) in DMF (1 mL) and water (0.3 mL). After 5 min, tetrakis(triphenylphosphine)palladium(0) (29 mg, 0.025 mmol) was added and the resulting mixture was heated at 95° C. for 16 hours. The reaction was diluted with water (6 mL) and EtOAc (3 mL). The aqueous phase was extracted EtOAc (2×10 mL). The combined organic phases were passed through a hydrophobic frit, combined and the solvent was removed in vacuo. Purification by reverse phase preparative HPLC afforded 6-(4-fluorophenyl)-4-[(6-methyl-3-pyridyl)methoxy]pyrido[2,3-d]pyrimidine (52 mg, 59%) as a 0.5 eq formate salt.

$^1$H NMR (400 MHz, DMSO): δ 9.35 (d, J=2.8 Hz, 1H), 8.92 (s, 1H), 8.73 (d, J=2.5 Hz, 1H), 8.61 (d, J=1.5 Hz, 1H), 8.32 (s, 0.5H), 7.97 (dd, J=5.3, 8.6 Hz, 2H), 7.77 (dd, J=2.1, 8.0 Hz, 1H), 7.42 (dd, J=8.8, 8.8 Hz, 2H), 7.29 (d, J=8.1 Hz, 1H), 5.27 (s, 2H), 2.49 (s, 3H).

LCMS (Method 4): [MH+]=347 at 2.82 min.

The following compound reported in the table below was prepared according to the same procedure described for the preparation of 6-(4-fluorophenyl)-4-[(6-methyl-3-pyridyl)methoxy]pyrido[2,3-d]pyrimidine.

| Example No. | Chemical Name Structure | Analytical data $^1H$ NMR LC-MS |
|---|---|---|
| Comparative Example B | 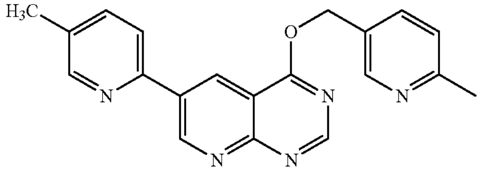 6-(5-methylpyridin-2-yl)-4-((6-methylpyridin-3-yl)methoxy)pyrido[2,3-d]pyrimidine | $^1H$ NMR (400 MHz, DMSO): δ 9.70 (d, J = 2.3 Hz, 1 H), 9.14 (d, J = 2.3 Hz, 1 H), 8.92 (s, 1 H), 8.66-8.60 (m, 2 H), 8.18 (d, J = 8.1 Hz, 1 H), 7.83 (d, J = 6.8 Hz, 1 H), 7.78 (dd, J = 1.9, 8.0 Hz, 1 H), 7.29 (d, J = 8.1 Hz, 1 H), 5.27 (s, 2 H), 2.49 (s, 3 H), 2.42 (s, 3 H). LCMS (Method 3): [MH+] = 344 at 3.31 m |

The activity of the comparative examples A and B have been tested in the in vitro Electrophysiology Assay for $P2X_3$ as described above.

Results for individual compounds are provided below in Table 10 and are expressed as range of activity.

TABLE 10

| Comparative Example No. | h $P2X_3$ |
|---|---|
| A | inactive |
| B | inactive |

Inactive: $pIC_{50}$ h $P2X_3$ < 4.5.

The invention claimed is:

1. A compound of formula (I)

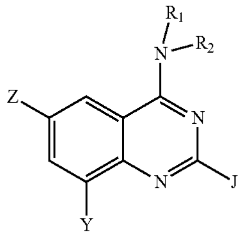

(I)

wherein

Z is selected from the group consisting of $(C_3-C_8)$ heterocycloalkyl, $(R^AR^B)N$—, heteroaryl, aryl, wherein any of such alkyl, heteroaryl, heterocycloalkyl and aryl may be optionally substituted by one or more groups selected from $(C_1-C_3)$alkyl-, halo, CN, $(R^AR^B)NC(O)$—, $(C_1-C_6)$haloalkyl-, $R^AO$—, $(R^AR^B)N(C_1-C_6)$alkylene-, $(C_3-C_7)$cycloalkyl-, $R^CSO_2$—, $(R^AR^B)N$—;

$R_1$ is H or $(C_1-C_4)$alkyl;

$R_2$ is selected from the group consisting of heteroaryl $(C_1-C_4)$alkyl-, $(C_3-C_8)$heterocycloalkyl-$(C_1-C_6)$alkyl-, heteroaryl-$(C_1-C_6)$hydroxyalkyl-, $(C_3-C_8)$heterocycloalkyl, $(C_3-C_8)$cycloalkyl-$(C_1-C_6)$alkyl-, aryl-$(C_1-C_4)$alkyl-, $(R^AR^B)N(C_1-C_6)$alkylene-, $(R^AR^B)N(O)C(C_1-C_4)$alkylene- and $R^AO(C_1-C_4)$alkylene- wherein any of such alkyl, alkylene, aryl, heteroaryl and heterocycloalkyl may be optionally substituted by one or more groups selected from $(C_1-C_3)$alkyl, $R^AO(C_1-C_4)$alkylene-, $(C_1-C_6)$haloalkyl, halo, oxo, $R^AO$—, $(C_3-C_8)$heterocycloalkyl-$(C_1-C_6)$alkyl-, heteroaryl, $(R^AR^B)N$—, —$NHC(O)R^C$, —$C(O)N(R^AR^B)$, —$SO_2N(R^AR^B)$, —$O(C_1-C_4)$alkylene-$N(R^AR^B)$, aryl optionally substituted by halo, —$OR^C$, aryl-$(C_1-C_4)$alkyl-, —$C(O)R^A$;

$R^A$ and $R^B$ are at each occurrence independently H or selected from the group consisting of $(C_1-C_4)$alkyl-, $(C_3-C_8)$cycloalkyl-, $(C_1-C_6)$ haloalkyl, or $R^A$ and $R^B$ may form together with the nitrogen atom to which they are attached a 5- or 6-membered saturated heterocyclic monocyclic ring system optionally containing a further heteroatom which is nitrogen or oxygen, which may be optionally substituted by one or more groups selected from $(C_1-C_4)$alkyl and oxo;

$R^C$ is at each occurrence H or selected from the group consisting of $(C_1-C_6)$alkyl, $(R^AR^B)N$—, aryl-$(C_1-C_4)$alkyl-;

Y is selected from the group consisting of —$OR^D$, $R^CSO_2$, —$NHSO_2R^C$, heteroaryl, $(C_3-C_8)$heterocycloalkyl, wherein any of such heteroaryl and heterocycloalkyl may be optionally substituted by one or more groups selected from $(C_1-C_3)$alkyl, —$C(O)N(R^AR^B)$;

$R^D$ is selected from the group consisting of H, $(C_1-C_6)$ alkyl, $(C_3-C_8)$heterocycloalkyl-$(C_1-C_6)$alkyl-, $R^COC(O)(C_1-C_4)$alkylene-, $(R^AR^B)N(C_1-C_6)$alkylene-, $(C_3-C_8)$heterocycloalkyl, $(C_3-C_8)$cycloalkyl-$(C_1-C_6)$alkyl-, $R^CO(C_1-C_4)$alkylene-, $(R^AR^B)N(O)C(C_1-C_4)$alkylene-, wherein any of such heterocycloalkyl may be optionally substituted by one or more groups selected from $(C_1-C_3)$alkyl-;

J is H or selected from the group consisting of $(C_1-C_6)$ alkyl, $(R^AR^B)N$—, $(C_1-C_6)$haloalkyl, —$OR^C$ and halo.

2. A compound of formula I according to claim 1 selected from the group consisting of:

(R)-6-(4-Fluorophenyl)-8-methoxy-N-(1-(6-methylpyridazin-3-yl)ethyl)quinazolin-4-amine, 6-(4-Fluorophenyl)-8-methoxy-N-((2-(trifluoromethyl)pyrimidin-5-yl)methyl)quinazolin-4-amine, 6-(4-Fluorophenyl)-8-methoxy-N-(2-(6-methylpyridin-3-yl)ethyl)quinazolin-4-amine, N-([1,2,4]Triazolo[4,3-a]pyrimidin-3-ylmethyl)-6-(4-fluorophenyl)-8-methoxyquinazolin-4-amine, 6-[[[6-(4-Fluorophenyl)-8-methoxy-quinazolin-4-yl]amino]methyl]-1H-pyridin-2-one, 6-(4-Fluorophenyl)-8-methoxy-N-[(1-methyl-4-piperidyl)methyl]quinazolin-4-amine, (R)-5-(1-((6-(4-fluorophenyl)-8-methoxyquinazolin-4-yl)amino)ethyl)-2-(trifluoromethyl)pyridine 1-oxide formate, 8-Methoxy-N-((6-methylpyridazin-3-yl)methyl)-6-(5-methylpyridin-2-yl)quinazolin-4-amine, 8-Methoxy-N-[(6-methylpyridazin-3-yl)methyl]-6-(5-methylpyrimidin-2-yl)quinazolin-4-amine, 8-Methoxy-N-((6-methylpyridazin-3-yl)methyl)-6-(5-methylthiazol-2-yl)quinazolin-4-amine, (R)-5-(1-((8-Methoxy-6-(5-methyl-1,3,4-thiadiazol-2-yl)quinazolin-4-yl)amino)ethyl)-2-(trifluoromethyl)pyridine 1-oxide, 8-Methoxy-6-(5-methylpyrimidin-2-yl)-N-[(1R)-1-[2-(trifluoromethyl)pyrimidin-5-yl]ethyl]quinazolin-4-amine, 6-(5-Fluoropyrimidin-2-yl)-8-methoxy-N-[(1R)-1-[2-(trifluoromethyl)pyrimidin-5-yl]ethyl]quinazolin-4-amine, 6-(5-Fluoro-2-pyridyl)-8-methoxy-N-[(1R)-1-[2-(trifluoromethyl)pyrimidin-5-yl]ethyl]quinazolin-4-amine, 8-Methoxy-N-[(1R)-1-(6-methylpyridazin-3-yl)ethyl]-6-(5-methylpyrimidin-2-yl)quinazolin-4-amine, 8-Methoxy-6-(1-methylpyrazol-3-yl)-N-[(1R)-1-(6-methylpyridazin-3-yl)ethyl]quinazolin-4-amine, 6-(5-Fluoro-2-pyridyl)-8-methoxy-N-[(1R)-1-(6-methylpyridazin-3-yl)ethyl]quinazolin-4-amine, 6-(5-Chloropyridin-2-yl)-8-methoxy-N-((6-methylpyridazin-3-yl)methyl)quinazolin-4-amine, (R)-6-(4-fluorophenyl)-8-methoxy-N-(1-(2-(trifluoromethyl)pyrimidin-5-yl)ethyl)quinazolin-4-amine, 6-(4-fluorophenyl)-8-methoxy-N-((6-methylpyridazin-3-yl)methyl)quinazolin-4-amine, (R)-6-(4-Fluorophenyl)-8-methoxy-4-((1-(2-(trifluoromethyl)pyrimidin-5yl)ethyl)-amino)-quinazolin-2-ol, 6-(4-fluorophenyl)-8-(2-methoxyethoxy)-N-[(6-methylpyridazin-3-yl)methyl]quinazolin-4-amine, 6-(4-fluorophenyl)-N-[(6-methylpyridazin-3-yl)methyl]-8-(oxetan-3-ylmethoxy)quinazolin-4-amine, 6-(4-fluorophenyl)-N-[(6-methylpyridazin-3-yl)methyl]-8-tetrahydropyran-4-yloxy-quinazolin-4-amine, 2-[6-(4-fluorophenyl)-4-[(6-methylpyridazin-3-yl)methylamino]quinazolin-8-yl]oxyacetic acid, sodium salt, 6-(4-fluorophenyl)-N-[(6-methylpyridazin-3-yl)methyl]-8-pyrrolidin-3-yloxy-quinazolin-4-amine, 6-(4-fluorophenyl)-N-[(6-methylpyridazin-3-yl)methyl]-8-(morpholin-2-ylmethoxy)quinazolin-4-amine, Single enantiomer 1 of 6-(4-fluorophenyl)-8-methoxy-N-(1-(3-(trifluoromethyl)-1,2,4-oxadiazol-5-yl)ethyl)quinazolin-4-amine Single enantiomer 2 of 6-(4-fluorophenyl)-8-methoxy-N-(1-(3-(trifluoromethyl)-1,2,4-oxadiazol-5-yl)ethyl)quinazolin-4-amine, Single enantiomer 1 of 2-((6-(4-fluorophenyl)-8-methoxyquinazolin-4-yl)amino)-2-(3-methyl-1,2,4-oxadiazol-5-yl)ethan-1-ol, Single enantiomer 2 of 2-((6-(4-fluorophenyl)-8-methoxyquinazolin-4-yl)amino)-2-(3-methyl-1,2,4-oxadiazol-5-yl)ethan-1-ol, Single enantiomer 1 of 6-(4-fluorophenyl)-8-methoxy-N-(1-(5-methyl-1,3,4-thiadiazol-2-yl)ethyl)quinazolin-4-amine, Single enantiomer 2 of 6-(4-fluorophenyl)-8-methoxy-N-(1-(5-methyl-1,3,4-thiadiazol-2-yl)ethyl)quinazolin-4-amine, Single enantiomer 1 of 6-(4-fluorophenyl)-8-methoxy-N-(1-(3-methyl-1,2,4-oxadiazol-5-yl)ethyl)quinazolin-4-amine, Single enantiomer 2 of 6-(4-fluorophenyl)-8-methoxy-N-(1-(3-methyl-1,2,4-oxadiazol-5-yl)ethyl)quinazolin-4-amine, 6-(3,5-Difluoropyridin-2-yl)-8-methoxy-N-((6-methylpyridazin-3-yl)methyl)quinazolin-4-amine, 6-(3-Fluoro-5-methyl-2-pyridyl)-8-methoxy-N-[(6-methylpyridazin-3-yl)methyl]quinazolin-4-amine, 6-(5-Ethylthiazol-2-yl)-8-methoxy-N-[(6-methylpyridazin-3-yl)methyl]quinazolin-4-amine, (R)-8-methoxy-6-(1-methyl-1H-1,2,4-triazol-3-yl)-N-(1-(2-(trifluoromethyl)pyrimidin-5-yl)ethyl)quinazolin-4-amine, (R)-8-methoxy-6-(1-methyl-1H-pyrazol-3-yl)-N-(1-(2-(trifluoromethyl)pyrimidin-5-yl)ethyl)quinazolin-4-amine, (R)-8-methoxy-6-(1-methyl-1H-1,2,4-triazol-3-yl)-N-(1-(6-methylpyridazin-3-yl)ethyl)quinazolin-4-amine, (R)-6-(5-fluoropyridin-2-yl)-8-methoxy-N-(1-(5-methyl-1,2,4-oxadiazol-3-yl)ethyl)quinazolin-4-amine, (R)-8-methoxy-N-(1-(5-methyl-1,2,4-oxadiazol-3-yl)ethyl)-6-(5-methylpyridin-2-yl)quinazolin-4-amine, 8-Methoxy-N-[1-(3-methyl-1,2,4-oxadiazol-5-yl)ethyl]-6-(5-methyl-2-pyridyl)quinazolin-4-amine, 6-(5-fluoro-2-pyridyl)-8-methoxy-N-[(1R)-1-(5-methyl-1,3,4-oxadiazol-2-yl)ethyl]quinazolin-4-amine, 8-methoxy-N-[(1R)-1-(5-methyl-1,3,4-oxadiazol-2-yl)ethyl]-6-(5-methyl-2-pyridyl)quinazolin-4-amine, 6-(5-fluoro-2-pyridyl)-8-methoxy-N-[1-[6-(trifluoromethyl)pyridazin-3-yl]ethyl]quinazolin-4-amine, 6-(5-fluoropyridin-2-yl)-8-methoxy-N-(1-(5-methyl-1,3,4-oxadiazol-2-yl)ethyl)quinazolin-4-amine, 6-(5-fluoropyridin-2-yl)-8-methoxy-N-(1-(5-methyl-1,3,4-thiadiazol-2-yl)ethyl)quinazolin-4-amine, 8-methoxy-N-[(1R)-1-(5-methyl-1,3,4-oxadiazol-2-yl)ethyl]-6-(5-methylpyrimidin-2-yl)quinazolin-4-amine, (S)-6-(5-fluoropyridin-2-yl)-8-methoxy-N-(1-(5-methyl-1,2,4-oxadiazol-3-yl)ethyl)quinazolin-4-amine, and 8-Methoxy-N-[(1S)-1-(6-methylpyridazin-3-yl)ethyl]-6-(5-methylpyrimidin-2-yl)quinazolin-4-amine.

3. A compound of formula I according to claim 1,

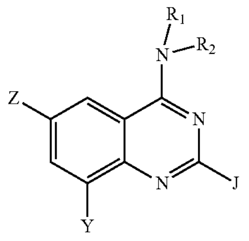

(I)

wherein

Z is selected from the group consisting of heteroaryl and aryl, wherein any of such heteroaryl and aryl may be optionally substituted by one or more groups selected from $(C_1\text{-}C_3)$alkyl, halo, CN, $(R^AR^B)NC(O)$—, $(C_1\text{-}C_6)$haloalkyl, $R^AO$—, $(R^AR^B)N(C_1\text{-}C_6)$alkylene-, $(C_3\text{-}C_7)$cycloalkyl-, $R^CSO_2$—, $(R^AR^B)N$—;

$R_1$ is H or $(C_1\text{-}C_4)$alkyl, $R_2$ is selected from the group consisting of heteroaryl $(C_1\text{-}C_4)$alkyl-, $(C_3\text{-}C_8)$heterocycloalkyl-$(C_1\text{-}C_6)$alkyl, heteroaryl-$(C_1\text{-}C_6)$hydroxyalkyl, aryl-$(C_1\text{-}C_4)$alkyl-, $(C_3\text{-}C_8)$heterocycloalkyl, $(C_3\text{-}C_8)$cycloalkyl-$(C_1\text{-}C_6)$alkyl-, $(R^AR^B)N(C_1\text{-}C_6)$alkylene-;

$R^AO(C_1\text{-}C_4)$alkylene, wherein any of such alkyl, alkylene, aryl, heteroaryl, cycloalkyl and heterocycloalkyl may be optionally substituted by one or more groups selected from ($C_1$-$C_3$) alkyl, $R^AO$($C_1$-$C_4$)alkylene, ($C_1$-$C_6$)haloalkyl, oxo, $R^AO$—, ($C_3$-$C_8$)heterocycloalkyl-($C_1$-$C_6$)alkyl, heteroaryl, aryl optionally substituted by halo, $R^CO$—, ($R^AR^B$)N—, —NHC(O)$R^C$, —C(O)N($R^AR^B$) halo, —$SO_2$N($R^AR^B$), —O($R^A$O($C_1$-$C_4$)alkylene-N($R^AR^B$), aryl-($C_1$-$C_4$)alkyl-, —C(O)$R^A$, $R^A$ and $R^B$ are at each occurrence independently H or selected from the group consisting of ($C_1$-$C_4$)alkyl-, aryl, ($C_1$-$C_6$) haloalkyl, or $R^A$ and $R^B$ may form together with the nitrogen atom to which they are attached a 6-membered saturated heterocyclic monocyclic ring system optionally containing a further heteroatom which is nitrogen or oxygen, which may be optionally substituted by ($C_1$-$C_4$)alkyl- and oxo;

$R^C$ is H or selected from the group consisting of ($C_1$-$C_6$)alkyl, ($R^AR^B$)N—, aryl-($C_1$-$C_4$)alkyl-, Y is selected from the group consisting of —$OR^D$, $R^CSO_2$—, —$NHSO_2R^C$, heteroaryl, ($C_3$-$C_8$)heterocycloalkyl, wherein any of such heteroaryl and heterocycloalkyl may be optionally substituted by one or more groups selected from ($C_1$-$C_3$)alkyl, —C(O)N($R^AR^B$);

J is H or selected from the group consisting of ($C_1$-$C_6$) alkyl, —$OR^C$, $R^D$ is H or ($C_1$-$C_6$)alkyl.

4. A compound of formula I according to claim 3, selected from the group consisting of:

(R)-6-(4-Fluorophenyl)-8-methoxy-2-methyl-N-(1-(2-(trifluoromethyl)pyrimidin-5 yl)ethyl)quinazolin-4-amine, (R)-6-(4-Fluorophenyl)-8-methoxy-4-((1-(2-(trifluoromethyl)pyrimidin-5-yl)ethyl)-amino)-quinazolin-2-ol, (R)-6-(4-Fluorophenyl)-2,8-dimethoxy-N-(1-(2-(trifluoromethyl)pyrimidin-5-yl)ethyl)quinazolin-4-amine, 6-(4-Fluorophenyl)-8-methoxy-N-(1-(3-methyl-1,2,4-oxadiazol-5-yl)ethyl)quinazolin-4-amine, 6-(4-Fluorophenyl)-8-methoxy-N-((5-methylpyridin-2-yl)methyl)quinazolin-4-amine, N-((6-(Difluoromethoxy)pyridin-3-yl)methyl)-6-(4-fluorophenyl)-8-methoxyquinazolin-4-amine, (R)-6-(4-Fluorophenyl)-8-methoxy-N-(1-(6-methylpyridazin-3-yl)ethyl)quinazolin-4-amine, 6-(4-Fluorophenyl)-8-methoxy-N-((6-methylpyridin-3-yl)methyl)quinazolin-4-amine, 4-(((6-(4-Fluorophenyl)-8-methoxyquinazolin-4-yl)amino)methyl)-1-methylpyridin-2(1H)-one, N-((2-(Dimethylamino)pyrimidin-5-yl)methyl)-6-(4-fluorophenyl)-8-methoxyquinazolin-4-amine, N-((5-Chloropyrimidin-2-yl)methyl)-6-(4-fluorophenyl)-8-methoxyquinazolin-4-amine, 5-(((6-(4-Fluorophenyl)-8-methoxyquinazolin-4-yl)amino)methyl)-N-methylpicolinamide, 6-(4-Fluorophenyl)-8-methoxy-N-((2-methylpyrimidin-5-yl)methyl)quinazolin-4-amine, N-(1-(3-Ethyl-1,2,4-oxadiazol-5-yl)ethyl)-6-(4-fluorophenyl)-8-methoxyquinazolin-4-amine, 6-(4-Fluorophenyl)-8-methoxy-N-(1-(6-methoxypyridin-3-yl)ethyl)quinazolin-4-amine, 6-(4-Fluorophenyl)-8-methoxy-N-(1-(3-(trifluoromethyl)-1,2,4-oxadiazol-5-yl)ethyl)quinazolin-4-amine, 6-(4-Fluorophenyl)-8-methoxy-N-(1-(6-methylpyridin-3-yl)ethyl)quinazolin-4-amine, 2-((6-(4-Fluorophenyl)-8-methoxyquinazolin-4-yl)amino)-2-(3-methyl-1,2,4-oxadiazol-5-yl)ethan-1-ol, 6-(4-Fluorophenyl)-8-methoxy-N-(1-(5-methyl-1,2,4-oxadiazol-3-yl)ethyl)quinazolin-4-amine, N-(Cyclopropylmethyl)-6-(4-fluorophenyl)-8-methoxyquinazolin-4-amine, 6-(4-Fluorophenyl)-8-methoxy-N-(1-(5-methyl-1,3,4-oxadiazol-2-yl)ethyl)quinazolin-4-amine, 6-(4-Fluorophenyl)-8-methoxy-N-((2-(trifluoromethyl)pyrimidin-5-yl)methyl)quinazolin-4-amine, 6-(4-Fluorophenyl)-8-methoxy-N-((6-(trifluoromethyl)pyridin-3-yl)methyl)quinazolin-4-amine, 6-(4-Fluorophenyl)-8-methoxy-N-(1-(5-methyl-1,3,4-thiadiazol-2-yl)ethyl)quinazolin-4-amine, 6-(4-Fluorophenyl)-N-(1-(3-isopropyl-1,2,4-oxadiazol-5-yl)ethyl)-8-methoxyquinazolin-4-amine, N-((6-(Dimethylamino)pyridin-3-yl)methyl)-6-(4-fluorophenyl)-8-methoxyquinazolin-4-amine, 6-(4-Fluorophenyl)-8-methoxy-N-[[5-(trifluoromethyl)-3-pyridyl]methyl]quinazolin-4-amine, 3-((6-(4-Fluorophenyl)-8-methoxyquinazolin-4-yl)amino)tetrahydrothiophene 1,1-dioxide, 6-(4-Fluorophenyl)-8-methoxy-N-((tetrahydro-2H-pyran-4-yl)methyl)quinazolin-4-amine, Single enantiomer 1 of 3-((6-(4-Fluorophenyl)-8-methoxyquinazolin-4-yl)amino)tetrahydrothiophene 1,1-dioxide, Single enantiomer 2 of 3-((6-(4-Fluorophenyl)-8-methoxyquinazolin-4-yl)amino)tetrahydrothiophene 1,1-dioxide, N-(5-(((6-(4-Fluorophenyl)-8-methoxyquinazolin-4-yl)amino)methyl)pyridin-2-yl)acetamide, 6-(4-Fluorophenyl)-8-methoxy-N-(2-(6-methylpyridin-3-yl)ethyl)quinazolin-4-amine, 6-(4-Fluorophenyl)-8-methoxy-N-(1-methylpiperidin-4-yl)quinazolin-4-amine, N1-(6-(4-Fluorophenyl)-8-methoxyquinazolin-4-yl)-N3,N3-dimethylpropane-1,3-diamine, (S)-2-((6-(4-Fluorophenyl)-8-methoxyquinazolin-4-yl)amino)-2-(6-methoxypyridin-3-yl)ethan-1-ol, 6-(4-Fluorophenyl)-8-methoxy-N-((6-morpholinopyridazin-3-yl)methyl)quinazolin-4-amine, 6-(4-Fluorophenyl)-8-methoxy-N-((6-methoxypyridin-3-yl)methyl)quinazolin-4-amine, N-(4-ethoxybenzyl)-6-(4-fluorophenyl)-8-methoxyquinazolin-4-amine, 6-(4-Fluorophenyl)-8-methoxy-N-(2-methyl-1-(3-methyl-1,2,4-oxadiazol-5-yl)propyl)quinazolin-4-amine, 6-(4-Fluorophenyl)-8-methoxy-N-[[2-(trifluoromethyl)-4-pyridyl]methyl]quinazolin-4-amine, 6-(4-Fluorophenyl)-8-methoxy-N-((1-methyl-1H-tetrazol-5-yl)methyl)quinazolin-4-amine, 6-(4-Fluorophenyl)-8-methoxy-N-((1-methyl-1H-pyrazol-4-yl)methyl)quinazolin-4-amine, 4-(2-((6-(4-Fluorophenyl)-8-methoxyquinazolin-4-yl)amino)ethyl)morpholin-3-one, 6-(4-Fluorophenyl)-8-methoxy-N-((1-methyl-1H-1,2,4-triazol-5-yl)methyl)quinazolin-4-amine, 6-(4-Fluorophenyl)-8-methoxy-N-((2-methyl-2H-tetrazol-5-yl)methyl)quinazolin-4-amine, 6-(4-Fluorophenyl)-8-methoxy-N-((1-methyl-1H-1,2,4-triazol-3-yl)methyl)quinazolin-4-amine, 6-(4-Fluorophenyl)-N-(imidazo[1,2-a]pyrimidin-6-ylmethyl)-8-methoxyquinazolin-4-amine, 6-(4-Fluorophenyl)-8-methoxy-N-((6-(2,2,2-trifluoroethoxy)pyridazin-3-yl)methyl)quinazolin-4-amine, N-((4-Ethyl-4H-1,2,4-triazol-3-yl)methyl)-6-(4-fluorophenyl)-8-methoxyquinazolin-4-amine, N-([1,2,4]Triazolo[4,3-a]pyrimidin-3-ylmethyl)-6-(4-fluorophenyl)-8-methoxyquinazolin-4-amine,
3-(((6-(4-Fluorophenyl)-8-methoxyquinazolin-4-yl)amino)methyl)-6-methylpyridin-2(1H)-one,
6-(4-Fluorophenyl)-8-methoxy-N-((3-(pyridin-4-yl)-1,2,4-oxadiazol-5-yl)methyl)quinazolin-4-amine,
6-(4-Fluorophenyl)-8-methoxy-N-((3-(piperidin-1-ylmethyl)-1,2,4-oxadiazol-5-yl)methyl)quinazolin-4-amine,
6-(4-Fluorophenyl)-8-methoxy-N-((1-methyl-1H-1,2,3-triazol-4-yl)methyl)quinazolin-4-amine,
6-(4-Fluorophenyl)-8-methoxy-N-((6-(4-methylpiperazin-1-yl)pyridin-3-yl)methyl)quinazolin-4-amine,
6-(4-Fluorophenyl)-8-methoxy-N-((4-(trifluoromethyl)pyridin-3-yl)methyl)quinazolin-4-amine,
6-(4-Fluorophenyl)-8-methoxy-N-((2-(trifluoromethyl)pyridin-3-yl)methyl)quinazolin-4-amine,
N-((5,6-Dimethylpyridin-3-yl)methyl)-6-(4-fluorophenyl)-8-methoxyquinazolin-4-amine,
6-(4-Fluorophenyl)-8-methoxy-N-[(1-methylimidazol-2-yl)methyl]quinazolin-4-amine,
6-(4-Fluorophenyl)-8-methoxy-N-(2-phenylcyclopropyl)quinazolin-4-amine,
N-[(3-Chloro-4-pyridyl)methyl]-6-(4-fluorophenyl)-8-methoxy-quinazolin-4-amine,
2-(3-Chloro-4-pyridyl)-2-[[6-(4-fluorophenyl)-8-methoxy-quinazolin-4-yl]amino]ethanol,
N-[(3S,4R)-4-Ethoxytetrahydrofuran-3-yl]-6-(4-fluorophenyl)-8-methoxy-quinazolin-4-amine,
N-[(1,1-Dioxothian-4-yl)methyl]-6-(4-fluorophenyl)-8-methoxy-quinazolin-4-amine,
4-[[6-(4-Fluorophenyl)-8-methoxy-quinazolin-4-yl]amino]-1-methyl-piperidin-2-one,
6-[[[6-(4-Fluorophenyl)-8-methoxy-quinazolin-4-yl]amino]methyl]-1H-pyridin-2-one,
3-[[[6-(4-Fluorophenyl)-8-methoxy-quinazolin-4-yl]amino]methyl]-1,4-dihydro-1,2,4-triazol-5-one,
N-[[1-(4-Chlorophenyl)cyclopropyl]methyl]-6-(4-fluorophenyl)-8-methoxy-quinazolin-4-amine,
(5R)-5-[[[6-(4-Fluorophenyl)-8-methoxy-quinazolin-4-yl]amino]methyl]pyrrolidin-2-one,
(1S)-2-[[6-(4-Fluorophenyl)-8-methoxy-quinazolin-4-yl]amino]-1-phenyl-ethanol,
N'-[6-(4-Fluorophenyl)-8-methoxy-quinazolin-4-yl]-N,N-dimethyl-1-(4-pyridyl)ethane-1,2-diamine,
(2S)-2-[[6-(4-fluorophenyl)-8-methoxy-quinazolin-4-yl]amino]-4-methyl-pentanamide,
6-(4-Fluorophenyl)-8-methoxy-N-(2H-tetrazol-5-ylmethyl)quinazolin-4-amine,
6-(4-Fluorophenyl)-8-methoxy-N-[(2-methylindazol-6-yl)methyl]quinazolin-4-amine,
N-[2-[4-(Dimethylamino)phenyl]ethyl]-6-(4-fluorophenyl)-8-methoxy-quinazolin-4-amine,
4-[[[6-(4-Fluorophenyl)-8-methoxy-quinazolin-4-yl]amino]methyl]-N,N-dimethyl-benzenesulfonamide,
6-(4-Fluorophenyl)-8-methoxy-N-(5,6,7,8-tetrahydroimidazo[1,2-a]pyridin-6-yl)quinazolin-4-amine,
N-[(1R,5S)-8-Benzyl-8-azabicyclo[3.2.1]octan-3-yl]-6-(4-fluorophenyl)-8-methoxy-quinazolin-4-amine,
N-[[4-[2-(dimethylamino)ethoxy]phenyl]methyl]-6-(4-fluorophenyl)-8-methoxy-quinazolin-4-amine,
6-(4-Fluorophenyl)-8-methoxy-N-(3-pyrrolidin-1-ylpropyl)quinazolin-4-amine,
(1S,2R)-1-[[6-(4-Fluorophenyl)-8-methoxy-quinazolin-4-yl]amino]indan-2-ol,
6-(4-Fluorophenyl)-8-methoxy-N-[(4-methyl-2,3-dihydro-1,4-benzoxazin-7-yl)methyl]quinazolin-4-amine,
N-[(6-Chloroimidazo[1,2-a]pyridin-2-yl)methyl]-6-(4-fluorophenyl)-8-methoxy-quinazolin-4-amine,
N-[(4-Benzyloxyphenyl)methyl]-6-(4-fluorophenyl)-8-methoxy-quinazolin-4-amine,
N-[(1-Benzylazetidin-3-yl)methyl]-6-(4-fluorophenyl)-8-methoxy-quinazolin-4-amine,
6-(4-Fluorophenyl)-8-methoxy-N-[[(2R)-tetrahydrofuran-2-yl]methyl]quinazolin-4-amine,
N-[Cyclohexyl(phenyl)methyl]-6-(4-fluorophenyl)-8-methoxy-quinazolin-4-amine,
3-(3-Chlorophenyl)-3-[[6-(4-fluorophenyl)-8-methoxy-quinazolin-4-yl]amino]propan-1-ol,
6-(4-Fluorophenyl)-8-methoxy-N-[(1-methylbenzimidazol-5-yl)methyl]quinazolin-4-amine,
6-(4-Fluorophenyl)-8-methoxy-N-[2-(4-methylpiperazin-1-yl)-1-phenyl-ethyl]quinazolin-4-amine,
6-(4-Fluorophenyl)-8-methoxy-N-[(1S)-1-methyl-2-pyrrolidin-1-yl-ethyl]quinazolin-4-amine,
6-(4-Fluorophenyl)-8-methoxy-N-[(1-methylindazol-7-yl)methyl]quinazolin-4-amine,
6-(4-Fluorophenyl)-8-methoxy-N-[(1-methylazetidin-3-yl)methyl]quinazolin-4-amine,
(1R,2S)-1-[[6-(4-Fluorophenyl)-8-methoxy-quinazolin-4-yl]amino]indan-2-ol,
3-[[6-(4-Fluorophenyl)-8-methoxy-quinazolin-4-yl]amino]-1-methyl-pyrrolidin-2-one,
6-(4-Fluorophenyl)-8-methoxy-N-(1-tetrahydropyran-4-ylethyl)quinazolin-4-amine,
N-[[3-Chloro-5-(trifluoromethyl)-2-pyridyl]methyl]-6-(4-fluorophenyl)-8-methoxy-quinazolin-4-amine,
1-[4-[[[6-(4-Fluorophenyl)-8-methoxy-quinazolin-4-yl]amino]methyl]-1-piperidyl]ethanone,
2,2-Difluoro-3-[[6-(4-fluorophenyl)-8-methoxy-quinazolin-4-yl]amino]propan-1-ol,
6-(4-Fluorophenyl)-8-methoxy-N-(2-piperazin-1-ylethyl)quinazolin-4-amine,
6-(4-Fluorophenyl)-8-methoxy-N-(pyrrolidin-3-ylmethyl)quinazolin-4-amine,
6-(4-Fluorophenyl)-8-methoxy-N-(pyrrolidin-2-ylmethyl)quinazolin-4-amine,
6-(4-Fluorophenyl)-8-methoxy-N-(1-methyl-2-morpholino-ethyl)quinazolin-4-amine,
(S)-6-(4-Fluorophenyl)-8-methoxy-N-((tetrahydrofuran-2-yl)methyl)quinazolin-4-amine,
6-(4-Fluorophenyl)-8-methoxy-N-((1-methylpyrrolidin-3-yl)methyl)quinazolin-4-amine,
N1,N1-Diethyl-N3-(6-(4-fluorophenyl)-8-methoxyquinazolin-4-yl)propane-1,3-diamine,
(R)-6-(4-Fluorophenyl)-8-methoxy-N-(1-methylpiperidin-3-yl)quinazolin-4-amine,
6-(4-Fluorophenyl)-8-methoxy-N-((1-methylpiperidin-2-yl)methyl)quinazolin-4-amine,
6-(4-Fluorophenyl)-8-methoxy-N-(2-(1-methylazetidin-3-yl)ethyl)quinazolin-4-amine,
2-[[6-(4-Fluorophenyl)-8-methoxy-quinazolin-4-yl]amino]-2-tetrahydropyran-4-yl-ethanol formate,
6-(4-Fluorophenyl)-8-methoxy-N-[(1-methyl-4-piperidyl)methyl]quinazolin-4-amine,
6-(4-Fluorophenyl)-8-methoxy-N-[(1-methylindazol-4-yl)methyl]quinazolin-4-amine,
(R)-5-(1-((6-(4-fluorophenyl)-8-methoxyquinazolin-4-yl)amino)ethyl)-2-(trifluoromethyl)pyridine 1-oxide formate, 6-(4-fluorophenyl)-8-methoxy-N-(2-morpholinoethyl) quinazolin-4-amine, N-(((1r,4r)-4-Aminocyclohexyl)methyl)-6-(4-fluorophenyl)-8-methoxyquinazolin-4-amine, 8-Methoxy-6-(5-methyl-1,3,4-thiadiazol-2-yl)-N-((6-methylpyridazin-3-yl)methyl)quinazolin-4-amine, 8-Methoxy-N-((6-methylpyridazin-3-yl)methyl)-6-(5-methylpyridin-2-yl)quinazolin-4-amine, 6-(8-Methoxy-4-(((6-methylpyridazin-3-yl)methyl) amino)quinazolin-6-yl)nicotinonitrile, 6-(5-(Difluoromethyl)pyridin-2-yl)-8-methoxy-N-((6-methylpyridazin-3-yl)methyl)quinazolin-4-amine, 6-(8-Methoxy-4-(((6-methylpyridazin-3-yl)methyl) amino)quinazolin-6-yl)pyridin-3-ol, 6-(5-(Difluoromethoxy)pyridin-2-yl)-8-methoxy-N-((6-methylpyridazin-3-yl)methyl)quinazolin-4-amine, 8-Methoxy-N-((6-methylpyridazin-3-yl)methyl)-6-(5-(methylsulfonyl)pyridin-2-yl)quinazolin-4-amine, 6-(8-Methoxy-4-(((6-methylpyridazin-3-yl)methyl) amino)quinazolin-6-yl)nicotinamide, 6-(8-Methoxy-4-(((6-methylpyridazin-3-yl)methyl) amino)quinazolin-6-yl)-N-methylnicotinamide, 8-Methoxy-N-((6-methylpyridazin-3-yl)methyl)-6-(5-(trifluoromethoxy)pyridin-2-yl)quinazolin-4-amine, 6-[5-(Dimethylamino)-2-pyridyl]-8-methoxy-N-[(6-methylpyridazin-3-yl)methyl]quinazolin-4-amine, 6-(5-Cyclopropylpyridin-2-yl)-8-methoxy-N-((6-methylpyridazin-3-yl)methyl)quinazolin-4-amine, 6-(5-Chloropyridin-2-yl)-8-methoxy-N-((6-methylpyridazin-3-yl)methyl)quinazolin-4-amine, 8-Methoxy-N-((6-methylpyridazin-3-yl)methyl)-6-(6-methylpyridin-3-yl)quinazolin-4-amine, 8-Methoxy-6-(5-methyl-1,3,4-oxadiazol-2-yl)-N-((6-methylpyridazin-3-yl)methyl)quinazolin-4-amine, 8-Methoxy-6-(1-methyl-IH-pyrazol-3-yl)-N-((6-methylpyridazin-3-yl)methyl)quinazolin-4-amine, 6-(1,5-Dimethyl-1H-pyrazol-3-yl)-8-methoxy-N-((6-methylpyridazin-3-yl)methyl)quinazolin-4-amine, 8-Methoxy-6-(6-methoxypyridazin-3-yl)-N-[(6-methylpyridazin-3-yl)methyl]quinazolin-4-amine, 8-Methoxy-6-(6-methylpyridazin-3-yl)-N-[(6-methylpyridazin-3-yl)methyl]quinazolin-4-amine, 8-Methoxy-N-[(6-methylpyridazin-3-yl)methyl]-6-(5-methylpyrimidin-2-yl)quinazolin-4-amine, 6-(5-Fluoro-2-pyridyl)-8-methoxy-N-[(6-methylpyridazin-3-yl)methyl]quinazolin-4-amine, 6-(5-Fluoropyrimidin-2-yl)-8-methoxy-N-[(6-methylpyridazin-3-yl)methyl]quinazolin-4-amine, 6-[8-Methoxy-4-[(6-methylpyridazin-3-yl)methylamino] quinazolin-6-yl]pyridazin-3-ol, 8-Methoxy-N-((6-methylpyridazin-3-yl)methyl)-6-(5-(trifluoromethyl)pyridin-2-yl)quinazolin-4-amine, 8-Methoxy-6-(5-methoxypyridin-2-yl)-N-((6-methylpyridazin-3-yl)methyl)quinazolin-4-amine, 8-Methoxy-N-((6-methylpyridazin-3-yl)methyl)-6-(5-methylthiazol-2-yl)quinazolin-4-amine, 8-Methoxy-N-((6-methylpyridazin-3-yl)methyl)-6-(4-(trifluoromethyl)thiazol-2-yl)quinazolin-4-amine, 6-(1,3-Dimethyl-1H-pyrazol-4-yl)-8-methoxy-N-((6-methylpyridazin-3-yl)methyl)quinazolin-4-amine, 8-Methoxy-N-((6-methylpyridazin-3-yl)methyl)-6-(4-methylthiazol-2-yl)quinazolin-4-amine, 8-Methoxy-N-((6-methylpyridazin-3-yl)methyl)-6-(2-methylthiazol-5-yl)quinazolin-4-amine, (R)-5-(1-((8-Methoxy-6-(5-methyl-1,3,4-thiadiazol-2-yl) quinazolin-4-yl)amino)ethyl)-2-(trifluoromethyl)pyridine 1-oxide, (R)-8-Methoxy-6-(5-methyl-1,3,4-thiadiazol-2-yl)-N-(1-(6-methylpyridazin-3-yl)ethyl)quinazolin-4-amine, (R)-8-Methoxy-6-(5-methyl-1,3,4-thiadiazol-2-yl)-N-(1-(2-(trifluoromethyl)pyrimidin-5-yl)ethyl)quinazolin-4-amine, 8-Methoxy-6-(5-methylpyrimidin-2-yl)-N-[(1R)-1-[2-(trifluoromethyl)pyrimidin-5-yl]ethyl]quinazolin-4-amine, 6-(5-Fluoropyrimidin-2-yl)-8-methoxy-N-[(1R)-1-[2-(trifluoromethyl)pyrimidin-5-yl]ethyl]quinazolin-4-amine, 6-(5-Fluoro-2-pyridyl)-8-methoxy-N-[(1R)-1-[2-(trifluoromethyl)pyrimidin-5-yl]ethyl]quinazolin-4-amine, 8-Methoxy-N-[(1R)-1-(6-methylpyridazin-3-yl)ethyl]-6-(5-methylpyrimidin-2-yl)quinazolin-4-amine, 8-Methoxy-6-(1-methylpyrazol-3-yl)-N-[(1R)-1-(6-methylpyridazin-3-yl)ethyl]quinazolin-4-amine, 6-[5-(Difluoromethyl)-2-pyridyl]-8-methoxy-N-[(1R)-1-(6-methylpyridazin-3-yl)ethyl]quinazolin-4-amine, 8-Methoxy-N-[(1R)-1-(6-methylpyridazin-3-yl)ethyl]-6-(5-methyl-2-pyridyl)quinazolin-4-amine, 6-(5-Fluoro-2-pyridyl)-8-methoxy-N-[(1R)-1-(6-methylpyridazin-3-yl)ethyl]quinazolin-4-amine, 8-Methoxy-6-(3-methylisothiazol-5-yl)-N-((6-methylpyridazin-3-yl)methyl)quinazolin-4-amine, (R)-8-methoxy-6-(5-methylpyridin-2-yl)-N-(1-(2-(trifluoromethyl)pyrimidin-5-yl)ethyl)quinazolin-4-amine, (R)-8-methoxy-6-(5-methylthiazol-2-yl)-N-(1-(2-(trifluoromethyl)pyrimidin-5-yl)ethyl)quinazolin-4-amine, (R)-8-methoxy-4-((1-(2-(trifluoromethyl)pyrimidin-5-yl) ethyl)amino)quinazolin-6-ol, (R)-8-methoxy-N-(1-(2-(trifluoromethyl)pyrimidin-5-yl) ethyl)quinazolin-4-amine, 8-Methoxy-N-((6-methylpyridazin-3-yl)methyl)-6-(5-(trifluoromethyl)thiazol-2-yl)quinazolin-4-amine, 8-Methoxy-6-(1-methyl-1H-pyrazol-4-yl)-N-((6-methylpyridazin-3-yl)methyl)quinazolin-4-amine, 6-(4,5-Dimethylthiazol-2-yl)-8-methoxy-N-((6-methylpyridazin-3-yl)methyl)quinazolin-4-amine, 6-(4-Fluoro-3-methylphenyl)-8-methoxy-N-((6-methylpyridazin-3-yl)methyl)quinazolin-4-amine, 6-(2,4-Difluorophenyl)-8-methoxy-N-((6-methylpyridazin-3-yl)methyl)quinazolin-4-amine, 6-(4-Fluoro-3-methoxyphenyl)-8-methoxy-N-((6-methylpyridazin-3-yl)methyl)quinazolin-4-amine, 6-(4-Fluoro-2-methylphenyl)-8-methoxy-N-((6-methylpyridazin-3-yl)methyl)quinazolin-4-amine, 6-(4-Fluoro-2-(trifluoromethyl)phenyl)-8-methoxy-N-((6-methylpyridazin-3-yl)methyl)quinazolin-4-amine, 6-(3-Fluorophenyl)-8-methoxy-N-((6-methylpyridazin-3-yl)methyl)quinazolin-4-amine, 6-(2,4-Difluorophenyl)-8-methoxy-N-[(1R)-1-(6-methylpyridazin-3-yl)ethyl]quinazolin-4-amine, 6-[4-[(Dimethylamino)methyl]phenyl]-8-methoxy-N-[(6-methylpyridazin-3-yl)methyl]quinazolin-4-amine formate, 4-[8-Methoxy-4-[(6-methylpyridazin-3-yl)methylamino] quinazolin-6-yl]-N,N-dimethyl-benzamide, 6-[4-(Dimethylamino)phenyl]-8-methoxy-N-[(6-methylpyridazin-3-yl)methyl]quinazolin-4-amine, 8-Methoxy-6-(4-methoxyphenyl)-N-[(6-methylpyridazin-3-yl)methyl]quinazolin-4-amine, Single enantiomer 1 of 6-(4-fluorophenyl)-8-methoxy-N-(1-(3-methyl-1,2,4-oxadiazol-5-yl)ethyl)quinazolin-4-amine, Single enantiomer 2 of 6-(4-fluorophenyl)-8-methoxy-N-(1-(3-methyl-1,2,4-oxadiazol-5-yl)ethyl)quinazolin-4- amine,6-(3,4-Difluorophenyl)-8-methoxy-N-((6-methylpyridazin-3-yl)methyl)quinazolin-4-amine, 6-(4-Fluoro-2-methoxyphenyl)-8-methoxy-N-((6-methylpyridazin-3-yl)methyl)quinazolin-4-amine, 8-Methoxy-N-((6-methylpyridazin-3-yl)methyl)-6-(2,4,6-trifluorophenyl)quinazolin-4-amine, 2-(8-Methoxy-4-(((6-methylpyridazin-3-yl)methyl)amino)quinazolin-6-yl)-5-methylbenzonitrile, 5-Fluoro-2-(8-methoxy-4-(((6-methylpyridazin-3-yl)methyl)amino)quinazolin-6-yl)benzonitrile, 5-Fluoro-2-(8-methoxy-4-(((6-methylpyridazin-3-yl)methyl)amino)quinazolin-6-yl)phenol, (R)-6-(4-fluorophenyl)-8-methoxy-N-(1-(2-(trifluoromethyl)pyrimidin-5-yl)ethyl)quinazolin-4-amine, 6-(4-fluorophenyl)-8-methoxy-N-((6-methylpyridazin-3-yl)methyl)quinazolin-4-amine, (R)-6-(4-Fluorophenyl)-8-methoxy-2-methyl-N-(1-(2-(trifluoromethyl)pyrimidin-5 yl)ethyl)quinazolin-4-amine, (R)-6-(4-Fluorophenyl)-8-methoxy 4-((1-(2 (trifluoromethyl)pyrimidin-5 yl)ethyl)-amino)-quinazolin-2-ol, 6-(4-fluorophenyl)-8-iodo-N-((6-methylpyridazin-3-yl)methyl)quinazolin-4-amine, 6-(4-fluorophenyl)-N-((6-methylpyridazin-3-yl)methyl)-8-(methylsulfonyl)quinazolin-4-amine, (R)—N-(6-(4-fluorophenyl)-4-((1-(2-(trifluoromethyl)pyrimidin-5-yl)ethyl)amino)quinazolin-8-yl)methanesulfonamide, N-(6-(4-fluorophenyl)-4-oxo-3,4-dihydroquinazolin-8-yl)methanesulfonamide, (R)-6-(4-fluorophenyl)-4-((1-(2-(trifluoromethyl)pyrimidin-5-yl)ethyl)amino)quinazoline-8-sulfonamide, (R)-6-(4-fluorophenyl)-8-(1-methyl-IH-pyrazol-4-yl)-N-(1-(2-(trifluoromethyl)pyrimidin-5-yl)ethyl)quinazolin-4-amine, (R)-6-(4-Fluorophenyl)-8-(1-methyl-1,2,3,6-tetrahydropyridin-4-yl)-N-(1-(2-(trifluoromethyl)pyrimidin-5-yl)ethyl)quinazolin-4-amine, (R)-6-(4-Fluorophenyl)-N-(1-(2-(trifluoromethyl)pyrimidin-5-yl)ethyl)-8-(1,3,5-trimethyl-1H-pyrazol-4-yl)quinazolin-4-amine, (R)-6-(4-Fluorophenyl)-8-(pyridin-4-yl)-N-(1-(2-(trifluoromethyl)pyrimidin-5-yl)ethyl)quinazolin-4-amine, (R)-4-(6-(4-Fluorophenyl)-4-((1-(2-(trifluoromethyl)pyrimidin-5-yl)ethyl)amino)quinazolin-8-yl)-N,N-dimethylbenzamide, (R)-6-(4-fluorophenyl)-4-((1-(2-(trifluoromethyl)pyrimidin-5-yl)ethyl)amino)-quinazolin-8-ol, 6-(4-fluorophenyl)-4-(((6-methylpyridazin-3-yl)methyl)amino)quinazolin-8-ol, ((R)-8-methoxy-6-(3-methyl-IH-pyrazol-1-yl)-N-(1-(2-(trifluoromethyl)pyrimidin-5-yl)ethyl)quinazolin-4-amine, (R)-8-methoxy-6-(5-methyl-IH-pyrazol-1-yl)-N-(1-(2-(trifluoromethyl)pyrimidin-5-yl)ethyl)quinazolin-4-amine, (R)-8-Methoxy-6-(4-methyl-1H-imidazol-1-yl)-N-(1-(2-(trifluoromethyl)pyrimidin-5-yl)ethyl)quinazolin-4-amine, (R)-8-methoxy-6-(5-methyl-1H-imidazol-1-yl)-N-(1-(2-(trifluoromethyl)pyrimidin-5-yl)ethyl)quinazolin-4-amine, (R)-8-Methoxy-6-(4-methyl-1H-pyrazol-1-yl)-N-(1-(2-(trifluoromethyl)pyrimidin-5-yl)ethyl)quinazolin-4-amine, Single enantiomer 1 of 6-(4-fluorophenyl)-8-methoxy-N-(1-(3-(trifluoromethyl)-1,2,4-oxadiazol-5-yl)ethyl)quinazolin-4-amine, Single enantiomer 2 of 6-(4-fluorophenyl)-8-methoxy-N-(1-(3-(trifluoromethyl)-1,2,4-oxadiazol-5-yl)ethyl)quinazolin-4-amine, Single enantiomer 1 6-(4-fluorophenyl)-8-methoxy-N-(1-(6-methylpyridin-3-yl)ethyl)quinazolin-4-amine, Single enantiomer 2 6-(4-fluorophenyl)-8-methoxy-N-(1-(6-methylpyridin-3-yl)ethyl)quinazolin-4-amine, Single enantiomer 1 6-(4-fluorophenyl)-8-methoxy-N-(1-(5-methyl-1,2,4-oxadiazol-3-yl)ethyl)quinazolin-4-amine, Single enantiomer 2 6-(4-fluorophenyl)-8-methoxy-N-(1-(5-methyl-1,2,4-oxadiazol-3-yl)ethyl)quinazolin-4-amine, Single enantiomer 1 of 6-(4-fluorophenyl)-8-methoxy-N-(1-(5-methyl-1,3,4-oxadiazol-2-yl)ethyl)quinazolin-4-amine, Single enantiomer 2 of 6-(4-fluorophenyl)-8-methoxy-N-(1-(5-methyl-1,3,4-oxadiazol-2-yl)ethyl)quinazolin-4-amine, Single enantiomer 1 of 6-(4-fluorophenyl)-8-methoxy-N-(1-(6-methoxypyridin-3-yl)ethyl)quinazolin-4-amine, Single enantiomer 2 of 6-(4-fluorophenyl)-8-methoxy-N-(1-(6-methoxypyridin-3-yl)ethyl)quinazolin-4-amine, Single enantiomer 1 of 2-((6-(4-fluorophenyl)-8-methoxyquinazolin-4-yl)amino)-2-(3-methyl-1,2,4-oxadiazol-5-yl)ethan-1-ol, Single enantiomer 2 of 2-((6-(4-fluorophenyl)-8-methoxyquinazolin-4-yl)amino)-2-(3-methyl-1,2,4-oxadiazol-5-yl)ethan-1-ol, Single enantiomer 1 of N-(1-(3-ethyl-1,2,4-oxadiazol-5-yl)ethyl)-6-(4-fluorophenyl)-8-methoxyquinazolin-4-amine, Single enantiomer 2 of N-(1-(3-ethyl-1,2,4-oxadiazol-5-yl)ethyl)-6-(4-fluorophenyl)-8-methoxyquinazolin-4-amine, Single enantiomer 1 of N-(1-cyclopropylethyl)-6-(4-fluorophenyl)-8-methoxyquinazolin-4-amine, Single enantiomer 2 of N-(1-cyclopropylethyl)-6-(4-fluorophenyl)-8-methoxyquinazolin-4-amine, Single enantiomer of N3-(6-(4-fluorophenyl)-8-methoxyquinazolin-4-yl)-N1,N1-dimethylbutane-1,3-diamine, Single enantiomer 2 of N3-(6-(4-fluorophenyl)-8-methoxyquinazolin-4-yl)-N1,N1-dimethylbutane-1,3-diamine, Single enantiomer 1 of 6-(4-fluorophenyl)-N-[1-(3-isopropyl-1,2,4-oxadiazol-5-yl)ethyl]-8-methoxy-quinazolin-4-amine, Single enantiomer 2 of 6-(4-fluorophenyl)-N-[1-(3-isopropyl-1,2,4-oxadiazol-5-yl)ethyl]-8-methoxy-quinazolin-4-amine, Single enantiomer 1 of 6-(4-fluorophenyl)-8-methoxy-N-[2-methyl-1-(3-methyl-1,2,4-oxadiazol-5-yl)propyl]quinazolin-4-amine, Single enantiomer 2 of 6-(4-fluorophenyl)-8-methoxy-N-[2-methyl-1-(3-methyl-1,2,4-oxadiazol-5-yl)propyl]quinazolin-4-amine, Single enantiomer 1 of 6-(4-fluorophenyl)-8-methoxy-N-(1-(5-methyl-1,3,4-thiadiazol-2-yl)ethyl)quinazolin-4-amine, Single enantiomer 2 of 6-(4-fluorophenyl)-8-methoxy-N-(1-(5-methyl-1,3,4-thiadiazol-2-yl)ethyl)quinazolin-4-amine, (R)-6-(4-Fluorophenyl)-8-iodo-N-(1-(2-(trifluoromethyl)pyrimidin-5-yl)ethyl)quinazolin-4-amine, (R)-6-(4-fluorophenyl)-8-(methylsulfonyl)-N-(1-(2-(trifluoromethyl)pyrimidin-5-yl)ethyl)quinazolin-4-amine,
6-(4-Fluorophenyl)-8-methoxy-N-(1-(3-(pyridin-4-yl)-1,2,4-oxadiazol-5-yl)ethyl)quinazolin-4-amine,
6-(4-fluorophenyl)-8-methoxy-N-(2-(3-methyl-1,2,4-oxadiazol-5-yl)propan-2-yl)quinazolin-4-amine,
(rac)-N-(1-(4H-1,2,4-triazol-3-yl)ethyl)-6-(4-fluorophenyl)-8-methoxyquinazolin-4-amine,
(S)-6-(4-fluorophenyl)-8-methoxy-N-(1-(5-methyl-4H-1,2,4-triazol-3-yl)ethyl)quinazolin-4-amine,
6-(3,5-Difluoropyridin-2-yl)-8-methoxy-N-((6-methylpyridazin-3-yl)methyl)quinazolin-4-amine,
6-(3-Fluoro-5-methyl-2-pyridyl)-8-methoxy-N-[(6-methylpyridazin-3-yl)methyl]quinazolin-4-amine,
6-(5-Ethylthiazol-2-yl)-8-methoxy-N-[(6-methylpyridazin-3-yl)methyl]quinazolin-4-amine,(R)-8-methoxy-6-(1-methyl-1H-1,2,4-triazol-3-yl)-N-(1-(2-(trifluoromethyl)pyrimidin-5-yl)ethyl)quinazolin-4-amine,(R)-8-methoxy-6-(1-methyl-1H-pyrazol-3-yl)-N-(1-(2-(trifluoromethyl)pyrimidin-5-yl)ethyl)quinazolin-4-amine,
(R)-8-methoxy-6-(1-methyl-1H-1,2,4-triazol-3-yl)-N-(1-(6-methylpyridazin-3-yl)ethyl)quinazolin-4-amine,
(R)-6-(5-fluoropyridin-2-yl)-8-methoxy-N-(1-(5-methyl-1,2,4-oxadiazol-3-yl)ethyl)quinazolin-4-amine,
(R)-8-methoxy-N-(1-(5-methyl-1,2,4-oxadiazol-3-yl)ethyl)-6-(5-methylpyridin-2-yl)quinazolin-4-amine,
8-Methoxy-N-[1-(3-methyl-1,2,4-oxadiazol-5-yl)ethyl]-6-(5-methyl-2-pyridyl)quinazolin-4-amine,
6-(5-fluoro-2-pyridyl)-8-methoxy-N-[(1R)-1-(5-methyl-1,3,4-oxadiazol-2-yl)ethyl]quinazolin-4-amine,
8-methoxy-N-[(1R)-1-(5-methyl-1,3,4-oxadiazol-2-yl)ethyl]-6-(5-methyl-2-pyridyl)quinazolin-4-amine,
2-((8-methoxy-6-(5-methylpyrimidin-2-yl)quinazolin-4-yl)amino)-2-(3-methyl-1,2,4-oxadiazol-5-yl)ethan-1-ol,
6-(5-fluoro-2-pyridyl)-8-methoxy-N-[1-[6-(trifluoromethyl)pyridazin-3-yl]ethyl]quinazolin-4-amine,
6-(5-fluoropyridin-2-yl)-8-methoxy-N-(1-(5-methyl-1,3,4-oxadiazol-2-yl)ethyl)quinazolin-4-amine,
6-(5-fluoropyridin-2-yl)-8-methoxy-N-(1-(5-methyl-1,3,4-thiadiazol-2-yl)ethyl)quinazolin-4-amine,
8-methoxy-N-[(1R)-1-(5-methyl-1,3,4-oxadiazol-2-yl)ethyl]-6-(5-methylpyrimidin-2-yl)quinazolin-4-amine,
(S)-6-(5-fluoropyridin-2-yl)-8-methoxy-N-(1-(5-methyl-1,2,4-oxadiazol-3-yl)ethyl)quinazolin-4-amine, and
8-Methoxy-N-[(1S)-1-(6-methylpyridazin-3-yl)ethyl]-6-(5-methylpyrimidin-2-yl)quinazolin-4-amine.

5. A compound of formula I according to claim 1, (I)

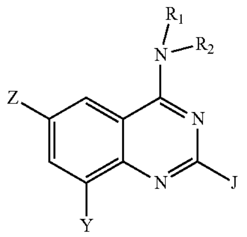

wherein

Z is selected from the group consisting of heteroaryl and aryl, wherein any of such heteroaryl and aryl may be optionally substituted by one or more groups selected from $(C_1-C_3)$alkyl, halo, CN, $(R^AR^B)$NC(O)—, $(C_1-C_6)$haloalkyl, $R^A$O—, $(R^AR^B)N(C_1-C_6)$alkylene-, $(C_3-C_7)$cycloalkyl-, $R^CSO_2$—, $(R^AR^B)$N—;

$R_1$ is H, $R_2$ is selected from the group consisting of heteroaryl $(C_1-C_4)$alkyl-, $(C_3-C_8)$heterocycloalkyl-$(C_1-C_6)$alkyl, heteroaryl-$(C_1-C_6)$hydroxyalkyl, aryl-$(C_1-C_4)$alkyl-, $(C_3-C_8)$heterocycloalkyl, $(C_3-C_8)$cycloalkyl-$(C_1-C_6)$alkyl-, $(R^AR^B)N(C_1-C_6)$alkylene-;

$R^AO(C_1-C_4)$alkylene, wherein any of such alkyl, alkylene, aryl, heteroaryl, cycloalkyl and heterocycloalkyl may be optionally substituted by one or more groups selected from $(C_1-C_3)$alkyl, $R^AO(C_1-C_4)$alkylene, $(C_1-C_6)$haloalkyl, oxo, $R^A$O—, $(C_3-C_8)$heterocycloalkyl-$(C_1-C_6)$alkyl, heteroaryl, aryl optionally substituted by halo, $R^C$O—, $(R^AR^B)$N—, —NHC(O)$R^C$, —C(O)N$(R^AR^B)$, halo, —$SO_2N(R^AR^B)$, —$O(R^AO(C_1-C_4)$alkylene-N$(R^AR^B)$, aryl-$(C_1-C_4)$alkyl-, —C(O)$R^A$, $R^A$ and $R^B$ are at each occurrence independently H or selected from the group consisting of $(C_1-C_4)$alkyl-, aryl, $(C_1-C_6)$ haloalkyl, or $R^A$ and $R^B$ may form together with the nitrogen atom to which they are attached a 6-membered saturated heterocyclic monocyclic ring system optionally containing a further heteroatom which is nitrogen or oxygen, which may be optionally substituted by $(C_1-C_4)$alkyl- and oxo;

$R^C$ is H or selected from the group consisting of $(C_1-C_6)$alkyl, $(R^AR^B)$N—, aryl-$(C_1-C_4)$alkyl-, Y is selected from the group consisting of —$OR^D$, $R^CSO_2$—, —$NHSO_2R^C$, heteroaryl, $(C_3-C_8)$heterocycloalkyl, wherein any of such heteroaryl and heterocycloalkyl may be optionally substituted by one or more groups selected from $(C_1-C_3)$alkyl, —C(O)N$(R^AR^B)$;

J is H or selected from the group consisting of $(C_1-C_6)$ alkyl, —$OR^C$, $R^D$ is H or $(C_1-C_6)$alkyl.

6. A compound of formula (I) according to claim 1, wherein Y is —$OR^D$, represented by formula (Ia)

(Ia)

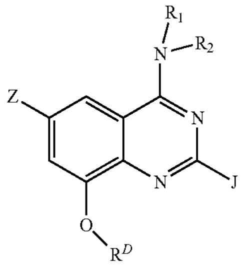

wherein

Z is selected from the group consisting of aryl, wherein any of such aryl may be optionally substituted by one or more groups selected from halo;

$R_1$ is H, $R_2$ is selected from the group consisting of heteroaryl $(C_1-C_4)$alkyl-, wherein any of such heteroaryl may be optionally substituted by one or more groups selected from $(C_1-C_3)$alkyl, $C_1-C_6$)haloalkyl;

$R^A$ and $R^B$ are at each occurrence independently H or selected from the group consisting of $(C_1-C_4)$alkyl-;

$R^C$ is at each occurrence H or selected from the group consisting of $(C_1-C_6)$alkyl;

$R^D$ is selected in the group consisting of H, $(C_1-C_6)$ alkyl, $(C_3-C_8)$heterocycloalkyl-$(C_1-C_6)$alkyl-, $R^C$OC(O)$(C_1-C_4)$alkylene-, $(R^AR^B)$N$(C_1-C_6)$alkylene-, $(C_3-C_8)$heterocycloalkyl, $R^C$O$(C_1-C_4)$alkylene-, $(R^AR^B)$N(O)C$(C_1-C_4)$alkylene-, $(C_3-C_8)$cycloalkyl-$(C_1-C_6)$alkyl-, wherein any of such heterocycloalkyl may be optionally substituted by one or more groups selected from $(C_1-C_3)$alkyl;

J is H.

7. A compound of formula I according to claim 1, selected from:

(R)-6-(4-Fluorophenyl)-8-((tetrahydro-2H-pyran-4-yl) oxy)-N-(1-(2-(trifluoromethyl) pyrimidin-5-yl)ethyl) quinazolin-4-amine, 6-(4-fluorophenyl)-8-(((R)-tetrahydrofuran-3-yl)oxy)-N—((R)-1-(2-(trifluoromethyl)pyrimidin-5-yl)ethyl) quinazolin-4-amine, 6-(4-fluorophenyl)-8-isopropoxy-N-[(6-methylpyridazin-3-yl)methyl]quinazolin-4-amine, 8-(cyclopropylmethoxy)-6-(4-fluorophenyl)-N-[(6-methylpyridazin-3-yl)methyl]quinazolin-4-amine, 2-[6-(4-fluorophenyl)-4-[(6-methylpyridazin-3-yl)methylamino]quinazolin-8-yl]oxyethanol, 2-[6-(4-fluorophenyl)-4-[(6-methylpyridazin-3-yl)methylamino]quinazolin-8-yl]oxy-N,N-dimethyl-acetamide, 6-(4-fluorophenyl)-8-(2-methoxyethoxy)-N-[(6-methylpyridazin-3-yl)methyl]quinazolin-4-amine, 6-(4-fluorophenyl)-N-[(6-methylpyridazin-3-yl)methyl]-8-(oxetan-3-ylmethoxy)quinazolin-4-amine, 6-(4-fluorophenyl)-N-[(6-methylpyridazin-3-yl)methyl]-8-tetrahydropyran-4-yloxy-quinazolin-4-amine, 6-(4-fluorophenyl)-N-[(6-methylpyridazin-3-yl)methyl]-8-(2-morpholinoethoxy)quinazolin-4-amine, 6-(4-fluorophenyl)-8-[(1-methyl-4-piperidyl)oxy]-N-[(6-methylpyridazin-3-yl)methyl]quinazolin-4-amine, 8-[3-(dimethylamino)propoxy]-6-(4-fluorophenyl)-N-[(6-methylpyridazin-3-yl)methyl]quinazolin-4-amine, ethyl 2-[6-(4-fluorophenyl)-4-[(6-methylpyridazin-3-yl) methylamino]quinazolin-8-yl]oxyacetate, 8-ethoxy-6-(4-fluorophenyl)-N-[(6-methylpyridazin-3-yl)methyl]quinazolin-4-amine, 2-[6-(4-fluorophenyl)-4-[(6-methylpyridazin-3-yl)methylamino]quinazolin-8-yl]oxyacetic acid, sodium salt, 8-(azetidin-3-ylmethoxy)-6-(4-fluorophenyl)-N-[(6-methylpyridazin-3-yl)methyl]quinazolin-4-amine, 6-(4-fluorophenyl)-N-[(6-methylpyridazin-3-yl)methyl]-8-pyrrolidin-3-yloxy-quinazolin-4-amine, 6-(4-fluorophenyl)-N-[(6-methylpyridazin-3-yl)methyl]-8-(morpholin-2-ylmethoxy)quinazolin-4-amine, 8-(azetidin-3-yloxy)-6-(4-fluorophenyl)-N-[(6-methylpyridazin-3-yl)methyl]quinazolin-4-amine, 6-(4-fluorophenyl)-N-[(6-methylpyridazin-3-yl)methyl]-8-(4-piperidyloxy)quinazolin-4-amine, 6-(4-fluorophenyl)-8-[(1-methylazetidin-3-yl)methoxy]-N-[(6-methylpyridazin-3-yl)methyl]quinazolin-4-amine, 6-(4-fluorophenyl)-8-[(4-methylmorpholin-2-yl) methoxy]-N-[(6-methylpyridazin-3-yl)methyl]quinazolin-4-amine, 6-(4-fluorophenyl)-N-[(6-methylpyridazin-3-yl)methyl]-8-(1-methylpyrrolidin-3-yl)oxy-quinazolin-4-amine, R)-2-((6-(4-fluorophenyl)-4-((1-(2-(trifluoromethyl)pyrimidin-5-yl)ethyl)amino)quinazolin-8-yl)oxy)acetamide, (R)-2-((6-(4-fluorophenyl)-4-((1-(2-(trifluoromethyl)pyrimidin-5-yl)ethyl)amino)quinazolin-8-yl)oxy)-1-(pyrrolidin-1-yl)ethan-1-one, (R)—N,N-diethyl-2-((6-(4-fluorophenyl)-4-((1-(2-(trifluoromethyl)pyrimidin-5-yl)ethyl)amino)quinazolin-8-yl)oxy)acetamide, 6-(4-fluorophenyl)-N-[(6-methylpyridazin-3-yl)methyl]-8-[(3S)-pyrrolidin-3-yl]oxy-quinazolin-4-amine, 6-(4-fluorophenyl)-N-[(6-methylpyridazin-3-yl)methyl]-8-[(3R)-pyrrolidin-3-yl]oxy-quinazolin-4-amine.

8. A pharmaceutical composition comprising a compound as defined in claim 1, or a pharmaceutically acceptable salt thereof, either alone or in combination with another one or more active ingredient, in admixture with one or more pharmaceutically acceptable carrier or excipient.

9. The pharmaceutical composition according to claim 8 for oral administration.

10. A method of preparing the compounds of formula (I) as described in claim 1, comprising using the compound of formula (Ib) as an intermediate:

(Ib)

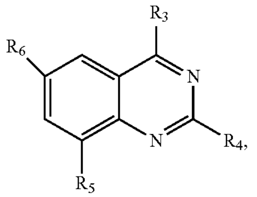

wherein $R_3$ is OH or halo, $R_4$ is H or OH, $R_5$ is —OMe, $R_6$ is Z, wherein Z is selected from the group consisting of $(C_3-C_8)$heterocycloalkyl, $(R^AR^B)$N—, heteroaryl, aryl, wherein any of such alkyl, heteroaryl, heterocycloalkyl and aryl may be optionally substituted by one or more groups selected from $(C_1-C_3)$alkyl-, halo, CN, $(R^AR^B)$NC(O)—, $(C_1-C_6)$haloalkyl-, $R^A$O—, $(R^AR^B)$N$(C_1-C_6)$alkylene-, $(C_3-C_7)$cycloalkyl-, $R^C$$SO_2$—, $(R^AR^B)$N—; and wherein $R^A$ and $R^B$ are at each occurrence independently H or selected from the group consisting of $(C_1-C_4)$ alkyl-, $(C_3-C_8)$cycloalkyl-, $(C_1-C_6)$ haloalkyl, or $R^A$ and $R^B$ may form together with the nitrogen atom to which they are attached a 5- or 6-membered saturated heterocyclic monocyclic ring system optionally containing a further heteroatom which is nitrogen or oxygen, which may be optionally substituted by one or more groups selected from $(C_1-C_4)$alkyl and oxo.

11. A compound selected from the group consisting of 6-(5-methylpyridin-2-yl)-N-((6-methylpyridin-3-yl) methyl)quinazolin-4-amine, N-(1-(3-methyl-1,2,4-oxadiazol-5-yl)ethyl)-6-(5-methylpyridin-2-yl)quinazolin-4-amine, N-((6-methylpyridazin-3-yl)methyl)-6-(5-methylpyridin-2-yl)-2-(trifluoromethyl)quinazolin-4-amine, N-((6-methylpyridazin-3-yl)methyl)-6-(5-methylpyridin-2-yl)quinazolin-4-amine, N-(1-(3-methyl-1,2,4-oxadiazol-5-yl)ethyl)-6-(5-methylthiazol-2-yl)quinazolin-4-amine, 2-chloro-6-(4-fluorophenyl)-N-(1-(3-methyl-1,2,4-oxadiazol-5-yl)ethyl)quinazolin-4-amine, N2-cyclopropyl-6-(4-fluorophenyl)-N4-(1-(3-methyl-1,2,4-oxadiazol-5-yl)ethyl)quinazoline-2,4-diamine, 6-(4-fluorophenyl)-N-(1-(3-methyl-1,2,4-oxadiazol-5-yl)ethyl)-2-morpholinoquinazolin-4-amine, 2-((2-(cyclopropylamino)-6-(4-fluorophenyl)quinazolin-4-yl)amino)propanamide, N-cyclopropyl-2-((2-(cyclopropylamino)-6-(4-fluorophenyl)quinazolin-4-yl)amino)propanamide, 6-(4-fluorophenyl)-2-methyl-N-((6-methylpyridazin-3-yl)methyl)quinazolin-4-amine, N-((6-methylpyridin-3-yl)methyl)-6-(5-methylthiophen-2-yl)quinazolin-4-amine, N-((6-methylpyridin-3-yl)methyl)-6-(p-tolyl)quinazolin-4-amine, N-((6-methylpyridazin-3-yl)methyl)-6-(2-methylpyrimidin-5-yl)quinazolin-4-amine, (R)-6-(4-fluorophenyl)-N-(1-(2-(trifluoromethyl)pyrimidin-5-yl)ethyl)quinazolin-4-amine, 6-(4-fluorophenyl)-N-(1-(3-methyl-1,2,4-oxadiazol-5-yl)ethyl)quinazolin-4-amine, 2-(4-(((6-methylpyridin-3-yl)methyl)amino)quinazolin-6-yl)benzonitrile, 2-(4-(((6-methylpyridin-3-yl)methyl)amino)quinazolin-6-yl)benzamide, 6-(4-fluorophenyl)-N-((6-methylpyridin-3-yl)methyl)quinazolin-4-amine formate, 6-(4-fluorophenyl)-N-((6-methylpyridazin-3-yl)methyl)quinazolin-4-amine, N-((3,5-difluoropyridin-2-yl)methyl)-6-(4-fluorophenyl)quinazolin-4-amine hydrochloride, 6-(4-fluorophenyl)-N-methyl-N-(1-(3-methyl-1,2,4-oxadiazol-5-yl)ethyl) quinazolin-4-amine, (R)-6-(3,3 difluoropyrrolidin-1-yl)-N-(1-(2-(trifluoromethyl)pyrimidin-5-yl)ethyl)quinazolin-4-amine, (R)-6-morpholino-N-(1-(2-(trifluoromethyl)pyrimidin-5-yl)ethyl)quinazolin-4-amine, (R)-1-methyl-4-(4-((1-(2-(trifluoromethyl)pyrimidin-5-yl)ethyl)amino) quinazolin-6-yl)piperazin-2-one, N-((6-methylpyridazin-3-yl)methyl)-6-morpholinoquinazolin-4-amine, Single enantiomer 1 of 6-(4-fluorophenyl)-N-[1-(3-methyl-1,2,4-oxadiazol-5-yl)ethyl]quinazolin-4-amine, Single enantiomer 2 of 6-(4-fluorophenyl)-N-[1-(3-methyl-1,2,4-oxadiazol-5-yl)ethyl]quinazolin-4-amine, Single enantiomer 1 of N2-cyclopropyl-6-(4-fluorophenyl)-N4-[1-(3-methyl-1,2,4-oxadiazol-5-yl)ethyl]quinazoline-2,4-diamine, Single enantiomer 2 of N2-cyclopropyl-6-(4-fluorophenyl)-N4-[1-(3-methyl-1,2,4-oxadiazol-5-yl)ethyl]quinazoline-2,4-diamine, Single enantiomer 1 of 6-(4-fluorophenyl)-N-[1-(3-methyl-1,2,4-oxadiazol-5-yl)ethyl]-2-morpholino-quinazolin-4-amine, Single enantiomer 2 of 6-(4-fluorophenyl)-N-[1-(3-methyl-1,2,4-oxadiazol-5-yl)ethyl]-2-morpholino-quinazolin-4-amine, Single enantiomer 1 of 6-(4-fluorophenyl)-N2,N2-dimethyl-N4-[1-(3-methyl-1,2,4-oxadiazol-5-yl)ethyl]quinazoline-2,4-diamine, and Single enantiomer 2 of 6-(4-fluorophenyl)-N2,N2-dimethyl-N4-[1-(3-methyl-1,2,4-oxadiazol-5-yl)ethyl]quinazoline-2,4-diamine.

* * * * *